(12) United States Patent
Reeves et al.

(10) Patent No.: US 7,714,118 B2
(45) Date of Patent: May 11, 2010

(54) POLYNUCLEOTIDES ENCODING THE FKBB GENE OF THE FK-520 POLYKETIDE SYNTHASE GENE CLUSTER

(75) Inventors: Christopher Reeves, Orinda, CA (US); Kai Wu, Foster City, CA (US)

(73) Assignee: Kosan Biosciences Incorporated, Hayward, CA (US)

( * ) Notice: Subject to any disclaimer, the term of this patent is extended or adjusted under 35 U.S.C. 154(b) by 1636 days.

(21) Appl. No.: 10/885,305

(22) Filed: Jul. 6, 2004

(65) Prior Publication Data

US 2009/0186378 A1 Jul. 23, 2009

Related U.S. Application Data

(62) Division of application No. 09/940,316, filed on Aug. 27, 2001, now Pat. No. 6,759,536, which is a division of application No. 09/410,551, filed on Oct. 1, 1999, now Pat. No. 6,503,737.

(60) Provisional application No. 60/102,748, filed on Oct. 2, 1998, provisional application No. 60/139,650, filed on Jun. 17, 1999, provisional application No. 60/123,810, filed on Mar. 11, 1999.

(51) Int. Cl.
| | |
|---|---|
| C12P 19/62 | (2006.01) |
| C12P 17/18 | (2006.01) |
| C12P 19/00 | (2006.01) |
| C12P 19/32 | (2006.01) |
| C12N 15/31 | (2006.01) |
| C12N 15/52 | (2006.01) |
| C12N 15/60 | (2006.01) |
| C12N 15/79 | (2006.01) |

(52) U.S. Cl. ............... 536/23.2; 435/76; 435/232; 435/252.3; 435/252.35; 435/320.1; 536/23.1; 536/23.7

(58) Field of Classification Search .............. None
See application file for complete search history.

(56) References Cited

U.S. PATENT DOCUMENTS

| 4,874,748 A | 10/1989 | Katz et al. |
| 5,063,155 A | 11/1991 | Cox et al. |

(Continued)

FOREIGN PATENT DOCUMENTS

| EP | 0 184 162 | 6/1986 |

(Continued)

OTHER PUBLICATIONS

Caffrey et al., FEBS Letters (1992) 304:205.

(Continued)

*Primary Examiner*—Nashaat T Nashed
*Assistant Examiner*—William W Moore
(74) *Attorney, Agent, or Firm*—Stephen C. D'Amico

(57) ABSTRACT

Host cells comprising recombinant vectors encoding the FK-520 polyketide synthase and FK-520 modification enzymes can be used to produce the FK-520 polyketide. Recombinant DNA constructs comprising one or more FK-520 polyketide synthase domains, modules, open reading frames, and variants thereof can be used to produce recombinant polyketide synthases and a variety of different polyketides with application as pharmaceutical and veterinary products.

19 Claims, 9 Drawing Sheets

U.S. PATENT DOCUMENTS

| | | | |
|---|---|---|---|
| 5,098,837 | A | 3/1992 | Beckmann et al. |
| 5,149,639 | A | 9/1992 | Katz et al. |
| 5,189,042 | A | 2/1993 | Goulet et al. |
| 5,672,491 | A | 9/1997 | Khosla et al. |
| 5,712,146 | A | 1/1998 | Khosla et al. |
| 5,824,513 | A | 10/1998 | Katz et al. |
| 5,830,750 | A | 11/1998 | Khosla et al. |
| 5,843,718 | A | 12/1998 | Khosla et al. |
| 5,962,290 | A | 10/1999 | Khosla et al. |
| 5,968,921 | A | 10/1999 | Gold |
| 6,022,731 | A | 2/2000 | Khosla et al. |
| 6,077,696 | A | 6/2000 | Khosla et al. |
| 6,150,513 | A | 11/2000 | Wu |
| 6,210,974 | B1 | 4/2001 | Gold |
| 6,503,737 | B1 * | 1/2003 | Reeves et al. .............. 435/76 |
| 6,759,536 | B2 * | 7/2004 | Reeves et al. .............. 546/71 |

FOREIGN PATENT DOCUMENTS

| | | |
|---|---|---|
| EP | 0 323 042 | 7/1989 |
| EP | 0 356 399 | 2/1990 |
| EP | 0 463 690 | 1/1992 |
| WO | WO-93/13663 | 7/1993 |
| WO | WO-95/08548 | 3/1995 |
| WO | WO-96/40968 | 12/1996 |
| WO | WO-97/02358 | 1/1997 |
| WO | WO-98/27203 | 6/1998 |
| WO | WO-98/49315 | 11/1998 |
| WO | WO-00/20601 | 4/2000 |

OTHER PUBLICATIONS

Chen et al., J. Antibit. (1992) 45:577-580.
Dumont et al., J. Exp. Med. (1992) 176:751-760.
Fu et al., Biochemistry (1994) 33:9321-9326.
Gold et al., Journal of Neuroscience (1995) 15:7509-7516.
Gold et al., J. Pharm. Exp. Ther. (1999) 289:1202-1210.
Iwasaki et al., Drug Metabolism and Disposition (1995) 23:28-34.
Iwasaki et al., Drug Metabolism and Disposition (1993) 21:971-977.
Kawai et al., FEBS Letters (1993) 316:107-113.
Khosla, Chemical Reviews (1997) 97:2577-2590.
Lyons et al., PNAS USA (1994) 91:3191-3195.
McDaniel et al., Science (1993) 262:1546-1550.
Motamedi and Shafiee, Eur. J. Biochem. (1998) 256:528.
Motamedi et al., Eur. J. Biochem. (1997) 244:78-80.
Motamedi et al., J. Bacteriol. (1996) 178:5243-5248.
Reynolds et al., Drugs Pharm. Sci. (1997) 82:497-520.
Rohr, Angew. Chem. Int. Ed. Engl. (1995) 262:1546-1550.
Shafiee et al., J. Antibiot. (1993) 46:1397-1405.
Shiraga et al., Biochem. Pharmacol. (1994) 47:727-735.
Stassi et al., PNAS USA (1998) 95:7305-7309.
Steiner et al., PNAS USA (1997) 94:2019-2024.
Vincent et al., Arch. Biochem. Biophys. (1992) 294:454-460.
Wu et al., Gene (2000) 251:81-90.

* cited by examiner

SEQUENCE LISTING

```
<160> NUMBER OF SEQ ID NOS: 96

<210> SEQ ID NO 1
<211> LENGTH: 77536
<212> TYPE: DNA
<213> ORGANISM: Streptomyces hygroscopicus

<400> SEQUENCE: 1
gatctcaggc atgaagtcct ccaggcgagg cgccgaggtg gtgaacacct cgccgctgct      60
tgtacggacc acttcagtca gcggcgattg cggaaccaag tcatccggaa taaagggcgg    120
```

```
ttacaagatc ctcacattgc gcgaccgcca gcatacgctg agttgcctca gaggcaaacc     180
gaaagggcgc gggcggtccg caccagggcg gagtacgcga cgagagtggc gcacccgcgc     240
accgtcacct ctctccccg ccggcgggat gccggcgtg acacggttgg gctctcctcg       300
acgctgaaca cccgcgcggt gtggcgtcgg ggacaccgcc tggcatcggc cgggtgacgg    360
tacggggagg gcgtacggcg gccgtggctc gtgctcacgg ccgccgggcg gtcatccgtc    420
gagacggcac tcggcgagca gggacgcctg gtcggcacct gcgggccgga cgaccgtgtg    480
gttcgcgggc gggcggtggc cggtggtgag ccagctctcc agggcggtga aggctgagcg    540
gtgacacggc agcaaaggcc ggagtcggtc ggggaaggtg tcgacgaggg cgtcggtgtg    600
cgtgccgtcc tcgatgcggt agtagcggta ccggccgcca ggccgctgcc ggacatacgc    660
gcgtacacgt cggagcccgg gcggcaggca gcagcacgtc gagagtgcct ggatggtgat    720
cagcggcttg ccgatacgac cggtcaacgc gatgcgttcc acggccgcgt ggacgccgga    780
ggagcgggtg gcgtagtcgt agtcggcatc gcagcccggg accgtccccg ggcgcaata    840
cggtgtgccg gcttccttct ccccatcgaa gccggggtcg aactcctcgc ggtagacgcg    900
ctgcgtcaga tcccagtaga cctcgtggtg gtacggccac aagaactcgg agtcggccgg    960
gaacccggcg cggagcagcg cctcgcgcgc ctggccggct gcggggccgc ctgccgcgta    1020
ggtggggtag tcgcgcaggg cggccggcag gaaggtgaag aggttgggac cctccgcgcg    1080
ccacagggtg ccttcccagt cgactcctcc gtcgtacagc tcgggatggt tctccagctg    1140
ccagcgcacg aggtagccgc cgttggacat cccggtgacc agggtgcgct cgagcggccg    1200
gtggtagcgc tgggcgaccg acgcgcgggc ggcccgggtc agctgggtga ggcgggtgtt    1260
ccactcggcg acggcgtcgc ccggccggga gccatcacgg tagaacgcgg ggccggtgtt    1320
gcccttgtcg gtggcggcgt aggcgtaacc gcgggcgagc acccagtcgg cgatggcccg    1380
gtcgttggcg tactgctcgc ggttaccggg ggtgccggcc acgaccaggc caccgttcca    1440
gcggtcgggc agccggatga cgaactgggc gtcgtggttc cacccgtggt tggtgttggt    1500
ggtgaggtg tcgggaagt agccgtcgat ctggatcccg ggcactccgg tgggagtggc    1560
caggttcttg ggcgtcagcc ctgcccagtc cgccgggtcg gtgtggccgg tggccgccgt    1620
tcccgccgtg gtcagctcgt ccaggcagtc ggcctgctga cgtgccgccg ccgggacacg    1680
cagctgggac agacgggcgc agtgaccgtc cggggcatcg ggagcaggcc gggccgtggc    1740
cggtgagggg agcaggacgg cgactgcggc caggtgaga cgccgaggc cggtgcgtct     1800
tctcggggcc cgtccgacac cgaggggcag aaccatggag agcctccaga cgtgcggatg    1860
gatgacggac tggaggctag gtcgcgcacg gtggagacga acatgggtgc gcccgccatg    1920
actgaggccc ctcagaggtg ggccgccgcc atgacgggcg cgggaccgcg ggcgctccgg    1980
ggcggtgccc gcggccgcca ccggttccgg gtccccgggt cagggacagg tgtcgttcgc    2040
gacggtgaag tagccggtcg gcgactcttt caaggtggtc gtgacgaagg tgttgtacag    2100
gcccatgttc tggccggagc ccttggcgta ggtgtaaccg gcgctcgtcg tggcgcggcc    2160
cgcctggacg tgagcgtagt tgccggcggt ccagcagacg gccgtggcac cggtcgtctg    2220
cgcggtgacc gcgcccgaga gcggtccggc cttgccgtcc gcgtcccggg cggcgaccgc    2280
gtaggtgtgc gatgtgcccg ccctcaggcc ggtgtccgtg tacgacgtcg tggcggacgt    2340
ggtgatctgg gcaccgtcgc ggtggacggc gtagtcggtg gcgccgtcga cgggtttcca    2400
ggtcaggctg atggtggtgt cggtggcgcc ggtggcggcc aggccggacg gagcgggcag    2460
```

```
cgaaccgggg tcggaggcgg atccgctcag gccgaagaac tgcgtgatcc agtagctgga   2520
acagatcgag tccaggaagt aggcggcgcc ggtgctgccg cactgctgtg ctccggtgcc   2580
gggatcgacc ggggtgccgt gcccgatgcc cggcacccgg ttcacctcca cggccaccga   2640
tccgtccgcg gccaggtact cctcgtgccg ggtggagttc gggccgatca ccgaggtacg   2700
gtccggcgtc tgggacacgc cgtgcacagc ggtccactgg tcgcgcaact cgtcggcgtt   2760
gcgcggcgcg acggtggtgt ccttgtcgcc gtgccagatg ccacgcgcg gccacggggcc   2820 cgaccacgag gggtagccgt cacggacccg ccgcgcccac tggtccgcgg tcaggtcggt   2880 cccgggggttc atgcacaggt acgcgctgct gacgtcggtg gcacagccga agggcaggcc   2940
ggcgacgacc gcgccggcct ggaagacgtc cggataggtg gcgagcatca ccgacgtcat   3000
ggcaccgccg gcgacagcc cggtgatgta gtgcgctgg gggtccgcgc cgtaggcgga   3060
gacggtgtga gcggccatct gccggatcga cgcggcttcg ccctggcccc tgcggttgtc   3120
gctgctctgg aaccagttga agcacctgtt cgcgttgttc gacacgtgg tctcggcgaa   3180 cacgagcagg aagccatagc ggtccgcgaa tgagagcagg ccggagttgt cggcgtagcc   3240
ctgggcgtcc tgggtgcaac cgtgcagggc gaacaccacc gccggctccg cgggcaggga   3300
cgcgggccgg tagacgtaca tgttcagccg gcccgggttc gtgccgaagt ccgcgacctc   3360
ggtcaggtcc gccttggtca gacccgggctt ggccaggccc ccgcggcgt gggccgtcgg   3420 cgccgggccg agcagggccg ctccgagtac gagggccacg acggccacga gacgggtgag   3480
caccccccgc cgtcccggac gcgacaacga cccgaccggc ggcgaggagg agagggggaa   3540
cagcggggtg aggattcccc ggaacggcgg cggctgcatg gcggctccct cgatgtcgtg   3600
ggggggacac ggagggctcc ctgacgtcga tcagtgggag cgccccggtg cccggcaccg   3660
taggggtggt tcaacccgca acggtatggc ccggagcacc acaccccgca ccgcgcgatg   3720
tgcgcccgga cggattgtgt cgccttgcgg aatctgatac ccggacgcga cgaacgcccc   3780
acccgacacg ggtagggcgt catggtgtcc gactcggccg gtcggccttg cctgccctgg   3840
acggaccggg cgtcggcgga ccgggcgtcg gcgggctggg cggtatggcg ccgaggacg   3900 ccagccgcgt ggggcggccg cgcccaagtg cagtacgccg accgtggccg gcgggagggc   3960
cggaccggtc agtgcagtcc cgcggccctg cgggaccgct cgtcccagac gggttccacc   4020
gcggcgaacc ggggtccgtg tccgcggcgg tagaccatca gtgtccgctc gaaggtgatg   4080
acgatgacac cgtcctggtt gtagccgatg gtgcgcacgc tgatgatgcc tacgtcaggt   4140
cggctggcgg actcccgggt gttcaggacc tcggactgcg agtagatggt gtcgccctcg   4200
aagaccgggt tcggcagcct gaccggtcc cagccgaggt tggccatcac atgctgggag   4260
atgtcggtga cgctctgccc ggtgaccagg gcgagggtga aggtggagtc caccagcggc   4320
ttgccccagg tggtgcccgc cgagtagtgg cggtcgaagt gcagcggcgc ggtgttctgc   4380
gtcaggagcg tgagccagga gttgtcggtc tccaggaccg tgcggcccag ggggtggcgg   4440
tacacgtcgc cggtggtgaa gtcctcgaag tagcggccct gccagccctc gaccacagcg   4500
gtgcgggtgg cgtcctggtc cgggttctca gtcgtcatgg cgctcattct gggaagtccc   4560
cggtccgctg tgaaatgccg aaccttcacc gggctcatac gtgcggcgca tgagccctgg   4620
accgtacgta gtcgtagaac ctcgccacca ctggcgcgcg tggtcctccg gcgagtgtga   4680
ccacgccgac cgtgcgccgc gcctgcgggt cgtcgagcgg cacggcgacg cgtggtcac   4740 cgggcccgga cgggctgccg gtgagggggg cgacggccac accgaggccg gcggcgacca   4800
gggcccgcag cgtgctcagc tcggtgctct ccaggacgac ccgcggcacg aatccggccg   4860
```

```
cggcgcacag ccggtcggtg atctggcgca gtccgaagac cggctccagt gccacgaacg   4920
cctcatcggc cagctccgcg gtccgcaccc ggcggcgtct ggccagccgg tgtccgggtg   4980
ggacgagcag gcacagtgcc tcgtcccgca gtggtgtcca ctccacatcg tccccggcgg   5040
gtcgtgggct ggtcagcccc aggtccagcc tgctgttgcg gacgtcgtcg accacggcgt   5100
cggcggcgtc gccgcgcagt tcgaaggtgg tgccgggagc cagccggcgg tacccggcga   5160
ggaggtcggg caccagccag gtgccgtagg agtgcaggaa acccagtgcc acggtgccgg   5220
tgtcggggtc gatcagggcg gtgatgcgct gctcggcgcc ggagacctca ctgatcgcgc   5280
gcagggcgtg ggcgcggaag acctcgccgt acttgttgag ccggagccgg ttctggtgcc   5340
ggtcgaacag cggcacgccc actcgtcgct ccagccgccg gatggccctg gacagggtcg   5400
gctgggagat gttgagccgt tccgcggtga tcgtcacgtg ctcgtgctcg gccaaggccg   5460
tgaaccactg caactcccgt atctccatgc agggactata cgtaccgggc atggtcctgg   5520
cgaggtttcg tcatttcaca gcggccgggc ggcggcccac agtgagtcct caccaaccag   5580
gaccccatgg gagggacccc atgtccgagc cgcatcctcg ccctgaacag gaacgccccg   5640
ccgggcccct gtccggtctg ctcgtggttt ctttggagca ggccgtcgcc gctccgttcg   5700
ccacccgcca cctggcggac ctgggcgccc gtgtcatcaa gatcgaacgc cccggcagcg   5760
gcgacctcgc ccgcggctac gaccgcacgg tgcgtggcat gtccagccac ttcgtctggc   5820
tgaaccgggg gaaggagagc gtccagctcg atgtgcgctc gccggagggc aaccggcacc   5880
tgcacgcctt ggtggaccgg gccgatgtcc tggtgcagaa tctggcaccc ggcgccgcgg   5940
gccgcctggc atcggccacc aggtcctcgc gcggagccac cgaggctgat cacctgcgga   6000
catatccggc tacggcagta ccggctgcta ccgcggaccg caaggcgtac gacctcctgg   6060
tccagtgcga agcggggctg gtctccatca ccggcacccc cgagacccg tccaaggtgg   6120 gcctgtccat cgcggacatc tgtgcgggga tgtacgcgta ctccggcatc ctcacggccc   6180
tgctgaagcg ggcccgcacc ggccggggct cgcagttgga ggtctcgatg ctcgaagccc   6240
tcggtgaatg gatgggatac gccgagtact acacgcgcta cggcggcacc gctccggccc   6300
gcgccggcgc cagccacgcg acgatcgccc cctacggccc gttcaccacg cgcgacgggc   6360
agacgatcaa tctcgggctc cagaacgagc gggagtgggc ttccttctgc ggtgtcgtgc   6420
tacaacgccc cggtctctgc gacgacccgc gcttttccgg caacgccgac cgggtggcgc   6480
accgcaccga gctcgacgcc ctggtgagcg aggtgacggg cacgctcacc ggcgaggaac   6540
tggtggcgcg gctggaggag gcgtcgatcg cctacgcacg ccagcgcacc gtgcgggagt   6600
tcagcgaaca ccccccaactg cgtgaccgtg gacgctgggc tccgttcgac agccggtcg   6660 gtgcgctgga gggcctgatc ccccggtca ccttccacgg cgagcacccg cggcggctgg   6720
gccgggtccc ggagctgggc gagcataccg agtccgtcct ggcgtggctg gccgcgcccc   6780
acagcgccga ccgcgaagag gccggccatg ccgaatgaac tcaccggagt cctgatcctg   6840
gccgccgtgt tcctgctcgc cggcgtacgg gggctgaaca tgggcctgct cgcgctggtc   6900
gccacctttc tgctcggggt ggtcgcactc gaccgaacgc cggacgaggt gctggcgggt   6960
ttccccgcga gcatgttcct ggtgctggtc gccgtcacgt tcctcttcgg gatcgcccgc   7020
gtcaacggca cggtggactg gctggtacgt gtcgcggtgc gggcggtggg ggcccgggtg   7080
ggagccgtcc cctgggtgct cttcggcctg gcggcactgc tctgcgcgac aggcgcggcc   7140
tcgcccgcgg cggtggcgat cgtggcgccg atcagcgtcg cgttcgccgt caggcaccgc   7200
```

-continued

```
atcgatccgc tgtacgccgg actgatggcg gtgaacgggg ccgcagccgg cagtttcgcc   7260
ccctccggga tcctgggcgg catcgtccac tcggcgctgg agaagaacca tctgcccgtc   7320
agcggcgggc tgctcttcgc aggcaccttc gccttcaacc tggcggtcgc cgcggtgtca   7380
tggctcgtcc tcgggcgcag gcgcctcgaa ccacatgacc tggacgagga caccgatccc   7440
acggaagggg acccggcttc ccgccccggc gcggaacacg tgatgacgct gaccgcgatg   7500
gccgcgctgg tgctgggaac cacggtcctc tccctggaca ccggcttcct ggccctcacc   7560
ttggcggcgt tgctggcgct gctcttcccg cgcacctccc agcaggccac caaggagatc   7620
gcctggcccg tggtgctgct ggtatgcggg atcgtgacct acgtcgccct gctccaggag   7680
ctgggcatcg tggactccct ggggaagatg atcgcggcga tcggcacccc gctgctggcc   7740
gccctggtga tctgctacgt gggcggtgtc gtctcggcct tcgcctcgac caccgggatc   7800
ctcggtgccc tgatgccgct gtccgagccg ttcctgaagt ccggtgccat cgggacgacc   7860
ggcatggtga tggccctggc ggccgcgcg accgtggtgg acgcgagtcc cttctccacc   7920
aatggtgctc tggtggtggc caacgctccc gagcggctgc ggcccggcgt gtaccagggg   7980
ttgctgtggt ggggcgccgg ggtgtgcgca ctggctcccg cggccgcctg gcggccttc    8040
gtggtggcgt gagcgcagcg gagcgggaat ccctggagc ccgtttcccg tgctgtgtcg    8100
ctgacgtagc gtcaagtcca cgtgccggc gggcagtacg cctagcatgt cgggcatggc    8160
taatcagata ccctgtccg acacgctgct cgcttacgta cggaaggtgt ccctgcgcga    8220
tgacgaggtg ctgagccggc tgcgcgcgca gacggccgag ctgccgggcg gtggcgtact    8280
gccggtgcag gccgaggagg acagttcct cgagttcctg gtgcggttga ccggcgcgcg    8340
tcaggtgctg gagatcggga cgtacaccgg ctacagcacg ctctgcctgg cccgcggatt    8400
ggcgcccggg ggccgtgtgg tgacgtgcga tgtcatgccg aagtggcccg aggtgggcga    8460
gcggtactgg gaggaggccg gggttgccga ccggatcgac gtccggatcg gcgacgcccg    8520
gaccgtcctc accgggctgc tcgacgaggc gggcgcgggg ccggagtcgt tcgacatggt    8580
gttcatcgac gccgacaagg ccggctaccc cgcctactac gaggcggcgc tgccgctggt    8640
acgccgcggc gggctgatcg tcgtcgacaa cacgctgttc ttcggccggg tggccgacga    8700
agcggtgcag gacccggaca cggtcgcggt acgcgaactc aacgcggcac tgcgcgacga    8760
cgaccgggtg gacctggcga tgctgacgac ggccgacggc gtcaccctgc tgcggaaacg    8820
gtgaccgggg cgatgtcggc ggcggtcagc gtcagcgtcg tcggcgcggg cctcgcggag    8880
ggctccagat gcaggcgttc gacgccggcg gcggaagcgc ccgccacctc ggacacgcag    8940
gggcagtcgg agtccgcgaa gcccgcgaac cggtaggcga tctccatcat gcggttgcgg    9000
tccgtacgcc ggaagtccgc caccaggtgc gcccccgcgc gggcgccctg gtccgtgagc    9060
cagttcagga tcgtcgcacc ggcaccgaac gacacgaccc ggcaggacgt ggcgagcagt    9120
ttcaggtgcc acgtcgacgg cttcttctcc agcaggatga tgccgacggc gccgtgcggg    9180
ccgaagcggt cgcccatggt gacgacgagg acctcatggg cgggatcggt gagcacgcgc    9240
gcaggtcggt gtcggagtag tgcacgccgg tcgcgttcat ctggctggtc cgcagcgtca    9300
gttcctcgac gcggctgagt tcctcctccc ccgcgggtgc gatcgtcatg gagaggtcga    9360
gcgagcgcag gaagtcctcg tcgggaccgg agtacgcctc ccgggcctgg tcgcgcgcga    9420
aacccgcctg gtacatcagg cggcgccgac gcgagtcgac cgtggacacc ggcgggctga    9480
actccggcag cgacaggagc gtggccgcct gctcggccgg gtagcaccgc acctcggcca    9540
ggtggaacgc cacctcggca cgctcggcgg gctggtcgtc gatgaacgcg atcgtggtcg    9600
```

```
gtgcgaagtt cagctccgtg gcgatctcgc ggacggactg cgacttcggc ccccatccga   9660
tgcgggccag cacgaagtac tccgccacac cgaggcgttc cagacgctcc cacgcgaggt   9720
cgtggtcgtt cttgctcgcc accgcctgga ggatgccgcg gtcgtcgagc gtggtgatca   9780
cctcgcggat ctcgtcggtg aggaccacct cgtcgtcctc cagcacggtg ccccgccaca   9840
aggtgttgtc caggtcccag accagacact tgacaatggt catggctgtc ctctcaagcc   9900
gggagcgcca gcgcgtgctg ggccagcatc acccggcaca tctcgctgct gccctcgatg   9960
atctccatga gcttggcgtc gcggtacgcc cgttcgacga cgtgtccctc tctcgcgcct  10020
gccgacgcga gcacctgtgc ggcggtcgcg gccccggcgg cggctcgttc ggcggcgacg  10080
tgcttggcca ggatcgtcgc gggcaccatc tcgggcgagc cctcgtccca gtggtcgctg  10140
gcgtactcgc acacgcgggc cgcgatctgc tccgcggtcc acaggtcggc gatgtgcccg  10200
gcgacgagtt ggtggtcgcc gagcggccgg ccgaactgct cccgggtccg ggcgtgggcc  10260
accgcggcgg tgcggcaggc ccgcaggatc ccgacgcagc cccaggcgac cgacttgcgc  10320
ccgtaggcga gtgacgccgc gaccagcatc ggcagtgacg cgccggagcc ggccaggacc  10380
gcgccggccg gcacacgcac ctggtccagg tgcagatcgg cgtggccggc ggcgcggcag  10440
ccggacggct cgggacgcg ctcgacgcgt acgccggggg tgtcggcggg cacgaccacc  10500
accgcaccgg aaccatcctc ctggagaccg aagacgacca ggtggtccgc gtaggcggcg  10560
gcagtcgtcc agaccttgtg gccgtcgacg acagcggtgt ccccgtcgag ccgaacccgc  10620
gtccgcatcg ccgacagatc gctgcccgcc tgccgctcac tgaagccgac ggccgcgagt  10680
ttcccgctgg tcagctcctt caggaaggtc gcccgctgac cggcgtcgcc gagccgctgc  10740
acggtccacg cggccatgcc ctgcgacgtc atgacactgc gcagcgaact gcagaggctg  10800
ccgacgtgtg cggtgaactc gccgttctcc cggctgccga gtcccagacc gccgtgctcg  10860
gccgccactt ccgcgcagag caggccgtcg gcgccgagcc ggacgagcag gtcgcgcggc  10920
agttcgccgg acgtgtccca ctcggcggcc cggtcaccga caaggtcggt cagcagcgcg  10980
tcacgctcag gcatcgacgg cccgcagccg gtggacgagt gcgaccatgg actcgacggt  11040
acggaagttc gcgagctgga ggtccgggcc ggcgatcgtg acgtcgaacg tcttctccag  11100
gtacacgacc agttccatcg cgaacagcga cgtgaggccg ccctccgcga acaggtcgcg  11160
gtccacgggc cagtccgacc tggtcttcgt cttgaggaac gcgaccaacg cgtgcgcgac  11220
ggggtcgtcc ttgacgggtg cggtcatgag aacaccttct cgtattcgta gaagcccgg  11280
ccggtcttcc ggccgtggtg tccctcgcgg accttgccca gcagcaggtc acaggggcgg  11340
ctgcgctcgt cgccggtgcg tttgtgcagc acccacagcg cgtcgacgag gttgtcgatg  11400
ccgatcaggt ccgcggtgcg cagcggcccg gtcggatggc cgaggcaccc cgtcatgagc  11460
gcgtcgacgt cctcgacgga cgcggtgccc tcctgcacga tccgcgccgc gtcgttgatc  11520
atcgggtgga gcagccggct cgtgacgaag ccgggcgcgt cccggacgac gatcggcttg  11580
cgccgcagcg ccgcgagcag gtccccggcg gcggccatgg ccttctcacc ggtccggggt  11640
ccgcggatca cctcgaccgt cgggatcagg tacgacgggt tcatgaagtg cgtgccgagc  11700
aggtcctcgg gccgggccac ggagtcggcc agttcgtcaa ccgggatcga cgacgtgttc  11760
gtgatgaccg ggataccggg cgccgctgcc gagaccgtgg cgagtacctc cgccttgacc  11820
tcggcgtcct cgacgacggc ctcgatcacc gcggtggccg taccgatcgc gggcagcgcg  11880
gacgtggccg tccgcagcac accggggtcg gcctcggcgg gcccggccac gagttgtgcc  11940
```

```
gtccgcagtt cggtggcgat ccgcgcccgc gccgccgtaa ggatctcctc ggacgtgtcg   12000
acgagtgtca ccgggacgcc gtggcgcagc gcgagcgtgg tgatgccggt gcccatcact   12060
cccgcgccga gcacgatcag ctggtggtcc acgctgtttc ctccctccgg ggtcaccatg   12120
gcagcgagta cgggtcgagg acgtcttccg gggtcgaccc gatcgcgtcc ttgcggccga   12180
ggccgagttc gtcggcgaag ccgagcagca cgtcgaacgc gatgtggtcg gcgaacgcgc   12240
tgcccgtcga gtcgaggacg ctcaggctgt cccggtggtc cgccgcggtg tccggtgccg   12300
cgcacagggc cgccagcgac gggccgagct cgcggtccgg cagttgctgg tactcgccct   12360
cggcgcgggc ctgccccgga tggtcgacgc agatgaacgc gtcgtcgagc agggtcttcg   12420
gcagttcggt cttgcccggc tcgtcggcgc cgatggcgtt cacatgcagg tgcggcagcc   12480
gcggctcggg gggcagcacc ggcccttgc ccgagggcac cgaggtgacg gtggacagga   12540
catccgcggc ggcggcggcc tccgccggat cggtcacctt gaccggcagt ccgaggaacg   12600
cgatgcggtc cgcgaacgac gccgcgtggc cggggtcggt gtcgctgacc aggatccgct   12660
cgatgggcag gaccctgctg agcgcgtgcg cctgggtcac cgcctgtgcg cccgcgccga   12720
tcagcgtgag cgtggcgctg tcggaccggg ccagcagccg gctcgcgacg gcggcgaccg   12780
cgccggtccg catcgcggtg atcacgcctg cgtcggcgag ggcggtcaga ctgccgctgt   12840
cgtcgtcgag gcgcgacatc gtgccgacga tcgtcggcag ccggaagcgc ggatagttgt   12900
gcggactgta cgaaaccgtc ttcatggtca cgccgacacc ggggaccgg tacggcatga   12960 actcgatgac gccgggaatg tcgccgccgc ggacgaatcc ggtacgcggc ggcgcctcgg   13020
cgaactcgcc gcggccgagc gcggcgaacc cgtcgtgcag ctcgctgatc agccggtcca   13080
tcatcacgtc gcggccgatc acggagagaa tccgcttgat gtcacgttgg cgcaggaccc   13140
tggtctgcat gtgtcacctc cctttcgtgg ccggagctgt cttggtggtg ccgctcgggg   13200
cggcttccgt tctcatcgca gctccctgtc gatgaggtcg aaaatctcgt ccgcggtcgc   13260
gtccgcggac agcacgccgg ccggcgtggt cgggcgggtc tcccgccgcc agcggttgag   13320
cagggcgtcc agccgggttc cgatcgcgtc cgcctggcgg gcgccgggt cgacaccggc   13380 aacgagtgct tccagccggt cgagctgcgc gagcaccacg gtcaccgggt cgtccgggga   13440
cagcagttca ccgatgcggt cggcgagtgc gcgcggcgac gggtagtcga agacgagcgt   13500
ggcggacagt cgcagaccgg tcgcctcgtt gaggccgttg cgcagctgca ccgcgatgag   13560
cgagtccaca ccgagttccc ggaacgccgc gtcctccggg atgtcctccg ggtcggcgtg   13620
gcccaggacg gccgctgcct tctgccggac gagggcgagc aggtcggtgg ggcgttcctg   13680
ctcgttgcgg gcgctccggc gggccgacgg cttgggccgg ccacgcagca gcggaggtc   13740 cggcggcagg tcgcccgcca cggcgacgac actgcccgtt ccggtgtgga cggcggcgtc   13800
gtacatgcgc atgccctgtt cggcggtgag cgcgctcgcc ccaccttgc gcatacggcg   13860 ccggtcggcg tcggtcaggt ccgcggtcag gccactcgcc tggtcccaca gccccacgcc   13920
gatcgacagc cctggcagcc cttgtgcacg ccggtgttcg gcgagcgcgt cgaggaacgc   13980
gttcgccgcc gcgtagttgc cctgaccggg ggtgcccagc acaccggccg ccgacgagta   14040
gacgacgaat gcggcgaggt cggtgtcgcg ggtgagccgg tgcaggtgcc aggcggcgtc   14100
ggccttgggt ttgaggacgg tgtcgatgcg gtcggggtg aggttgtcga gcagggcgtc   14160
gtcgagggtt ccggcggtgt ggaagacggc ggtgaggggt tgaggatgt gggcgagggt   14220 ggtgcgagt tggtgggggt cgccgacgtc gcagggagg tgggtgccgg gggtggtgtc   14280 gggggggtggg gtgcgggaga ggaggtaggt gtgggggtgg ttcaggtggc gggcgaggat   14340
```

```
gccggcgagg gtgccggagc cgccggtgat gacgacggcc ccctcggggt ccagcggccg   14400
cgggaccgtg aggacgatct tgccggtgtg ctcgccgcgg ctcatggtcg ccagcgcctc   14460
gcggacctgc cgcatgtcgt gcaccgtcac cggcagcggg tgcagcacac cgcgcgcgaa   14520
caggccgagc agctccgcga tgatctcctt gagccggtcg ggccccgcgt ccatcaggtc   14580
gaacggtcgc tggacggcgt gccggatgtc cgtcttcccc atctcgatga accggccacc   14640
cggcgcgagc aggccgacgg acgcgtcgag gagttcaccg gtgagcgagt tgagcacgac   14700
gtcgaccggc gggaacgcgt cggcgaacgc ggtgctgcgg gaatcggcca gatgcgctcc   14760
gtccaggtcc accagatggc gcttcgcggc gctggtggtc gcgtacacct ccgcgcccag   14820
gtgccgcgcg atctgccggg cggcggaacc gacaccgccg gtggccgcgt ggatcaggac   14880
cttctcgccg gggcgcagcc cggcgaggtc gaccaggccg taccacgcgg tcgcgaacgc   14940
ggtcatcacg gacgccgcct gcgggaacgt ccagccgtcc ggcatccggc cgagcatccg   15000
gtggtcggcg atgaccgtgg ggccgaagcc ggtgccgacg aggccgaaga cgcggtcgcc   15060
cggtgccaga ccggagacgt cggcgccggt ctccaggacg atgcccgcgg cctcgccgcc   15120
gagcacgccc tgaccggggt aggtgccgag cgcgatcagc acatcgcgga agttgaggcc   15180
cgccgcacgc acaccgatcc ggacctcggc cggggcgagg gggcgccggg gctccgccga   15240
gtcggccgcg gtgaggccgt cgagggtgcc cgtccgcgcc ggccggatca gccacgtgtc   15300
gctgtccggc acggtgagcg gctccggcac ccgggtgagg cgggccgcct cgaaccggcc   15360
gccgcgcagc cgcagacgcg gctcgccgag tgcgacggcg atgcgctgct gctcgggggc   15420
gagcgtgacg ccggactcgg tctcgacgtg gacgaaccgg ccgggctgct cggcctgggc   15480
ggcgcgcagc agtccggccg ccgcgccggt ggcgaggccc gcgtggtgt gcacgagcag   15540 atccccgccg gagccggtca gggcggtcag cagccgggtg gtgagcgcac gcgtctcggc   15600
caccgggtcg tcgccatcag cggcaggcaa cgtgatgacg tccacgtcgg tcgcggggac   15660
atccgtgggt gcggcgacct cgatccaggt gagacgcatc aggccggtgc cgacgggtgg   15720
ggacagcggg cgggtgcgga ccgtccggat ctcggcgacg agttggccgg cggagtcggc   15780
gacgcgcaga ctcagctcgt cgccgtcacg agtgatcacg gctcggagca tggccgagcc   15840
cgtggcgacg aaccgggccc ccttccaggc gaacggcaga cccgcagcgc tgtcgtccgg   15900
cgtggtgagg gcgacggcgt gcagggccgc gtcgagcagc gccggatgca caccgaaacc   15960
gtccgcctcg gcggcctgct cgtcgggcag cgccacctcg gcatacacgg tgtcaccatc   16020
acgccaggca gcccgcaacc cctggaacgc cgacccgtac tcataaccgg catcccgcag   16080
ttcgtcatag aaccccgaga cgtcgacggc cacggccgtg accggcggcc actgcgagaa   16140
cggctccaca ccgacaacac cgggggtgtc ggggggtgtcg ggggtcaggg tgccgctggc   16200
gtgccgggtc cagctgcccg tgccctcggt acgcgcgtgg acggtcaccg gccgccgtcc   16260
ggcctcatca gccccttcca cggtcaccga cacatccacc gctgcggtca ccggcaccac   16320
aaggggggat tcgatgacca gctcgtccac tatcccgcaa ccggtctcgt caccggcccg   16380
gatgaccagc tccacaaacg ccgtacccgg cagcaggacc gtgccccgca ccgcgtgatc   16440
agccagccag gggtgagtgc gcaatgagat ccggccagtg agaacaacac caccatcgtc   16500
ggcgggcagc gctgtgacag cggccagcat cggatgcgcc gcaccgtca ccccgccgc   16560 cgacagatcg gtggcaccgg ccgcctccag ccagtaccgc ctgtgctcga acgcgtacgt   16620
gggcagatcc agcagccgtc ccggcaccgg ttcgaccacc gtgtcccagt ccactgccgt   16680
```

-continued

```
gcccagggtc cacgcctgcg ccaacgccgt cagccaccgc tcccagccgc cgtcaccggt    16740
ccgcaacgac gccaccgtgt gagcctgctc catcgccggc agcagcaccg gatgggcact    16800
gcactccacg aacaccgacc catccagctc cgccaccgcc gcgtccaacg ccaccggacg    16860
acgcagattc cggtaccagt acccctcatc caccggctcc gtcacccagg cgctgtccac    16920
ggtcgaccac cacgccaccg acgcggcctt ccctgccacc ccctccagta ccttggccag    16980
ttcatcctcg atggcttcca cgtggggcgt gtgggaggcg tagtcgaccg cgatacgacg    17040
cacccgcacg ccttcggcct cataccgcgc caccacctcc tccaccgccg acgggtcccc    17100
cgccaccacc gtcgaagccg ggccgttacg cgccgcgatc cacacaccct cgaccagacc    17160
gacctcaccg gccggcaacg ccaccgaagc catcgctccc cgcccggcca gtcgcgccgc    17220
gatgacctga ctgcgcaatg ccaccacgcg ggcggcgtcc tcgaggctga gggctccggc    17280
cacgcacgcc gccgcgatct cgccctggga gtgtccgatc accgcgtccg gcacgacccc    17340
atgcgcctgc cacagcgcgg ccaggctcac cgcgaccgcc cagctggccg gctggaccac    17400
ctccacccgc tccgccacat ccggccgcgc caacatctcc cgcacatccc agcccgtgtg    17460
cggcagcaac gcctgagcgc actcctccat acgcgcggcg aacaccgcgg agtgggccat    17520
gagttccacg cccatgccga cccactgggc gccctggccg gggaagacga acaccgtacg    17580
cggctggtcc accgccacac ccgtcacccg ggcatcgccc agcagcaccg cacggtgacc    17640
gaagacagca cgctcccgca ccaaccctg cgcgaccgcg gccacatcca caccacccc    17700
gcgcagatac ccctccagcc gctccacctg ccccgcaga ctcacctcac cacgagccga    17760
caccggcaac ggcaccaacc cgtcaacaac cgactcccca cgcgacggcc caggaacacc    17820
ctcaaggatc acgtgcgcgt tcgtaccgct caccccgaac gacgacacac ccgcatgcgg    17880
tgcccgatcc gactcgggcc acggcctcgc ctcggtgagc agctccaccg caccggccga    17940
ccagtccaca tgcgacgacg gctcgtccac atgcagcgtc ttcggcgcga tcccgtaccg    18000
catcgccatg accatcttga tcacaccggc gacacccgcc gccgcctgcg catgaccgat    18060
gttcgacttc aacgaaccca gcagcagcgg aacctcacgc tcctgcccgt acgtcgccag    18120
aatggcctgc gcctcgatgg gatcgcccag cgtcgtcccc gtcccgtgcg cctccaccac    18180
gtccacatcg gcggcgcgca gtccggcgtt caccaacgcc tgctggatga cacgctgctg    18240
ggacgggccg ttgggggcgg acagcccgtt ggaggcaccg tcctggttca ccgccgaccc    18300
gcggacgacc gcgagaacgg tgtgtccgtt gcgctcggcg tcggagagcc gctccagcac    18360
aagaacgccg gcgccctccg cccagccggt gccgttggcg gcgtccgcga acgcgcggca    18420
gcggccgtcg ggggagagtc cgccctgctg ctggaattcc acgaacccgg tcggggtcgc    18480
catgacggta acaccgccga ccagccccag cgagcactcc ccgtgcgca gtgcgtgccc    18540
ggcctggtgc agcgcgacca gcgacgacga gcacgccgtg tccaccgtga acgccggtcc    18600
ctggagccca tagaagtacg agatccggcc ggtgagcacg ctgggctgca tgccgatcga    18660
gccgaacccg tccaggtccg cgccgacgcc gtacccgtac gagaaggcgc ccatgaacac    18720
gccggtgtcg ctgccgcgca gtgtgcccgg cacgatgccc gcgctctcga acgcctccca    18780
tgtcgttttc cagcaggatcc gctgctgggg gtccatggcc cgtgcctcac gggggctgat    18840
gccgaagaac gcggcatcga agccggcggc gtcgagagg aagccgccgc ggtccgtgtc    18900
cgatccgccg gtgaggccgg acgggtccca gccacggtcg gccgggaagc cggtgaccgc    18960
gtcgccgcca ctgtccacca tgcgccacag gtcgtcgggc gaggtgacgc cgcccggcag    19020
tcggcaggcc atgcccacga tggccagcgg ttcgtcacgg gtcgcggcgg ctgtgggaac    19080
```

```
agcgaccggt gcggcaccac cgaccagagc ctcgtccaac cgcgacgcga tggcccgcgg   19140
cgtcgggtag tcgaagacaa gcgtggcggg cagtcggaca ccggtcgccg cggcgagtcg   19200
gttccgcagt tcgacggcgg tcagcgagtc gatacccagt tccttgaagg ccgcgtccgc   19260
ggacacgtcc gcggcgtccg cgtggccgag caccgccgcc gcgttgtcgc ggaccagtgc   19320
cagcagcgcg gtgtcccgct cagcgccgga catggtgccg agccggtcgg cgagcggaac   19380
ggcggtggcc gccgccgggc gcgatacggc gcggcgcaga tcggcgaaaa gcggcgatgt   19440
gtgcgcggtg aggtccatcg tggccgccac ggcgaacgcg gtgccggttc cggccgcggc   19500
ttccagcagg cgcatgccca caccggccga catggggcgg aaaccgccgc ggcggacacg   19560
ggtgcggttg gtgccgctca tgctgccggt gagtccgctg tcatcggccc agaggcccca   19620
ggccagcgac agcgcgggca gtccttcggc atggcgcagc gtcgcgagtc cgtcgaggaa   19680
cccgttcgcc gccgagtagt tgccctggcc gcggccgccc atgatgcccg cgacggacga   19740
gtagaggacg aacgagcgca ggtccgcgtc ccgggtcagc tcgtgcaggt gccaggcgcc   19800
gtcggctttg gggcgcagtg tggtggcgag ccgctccggg gtgagtgccg tggtcacgcc   19860
gtcgtcgagc acggctgccg tgtggaagac cgccgtgagc ggcctgccgg cggcggcgag   19920
cgcggcggcg agctggtccc ggtcggcgac gtcacagcgg atgtggacac cgggagtgtc   19980
cgccggcggt tcgctgcgcg acagcaacag gaggtggcgg gcgccatgct cggcgacgag   20040
atgccgggcg aggagacctg ccagcacacc cgagccgccg gtgatgacca ccgtgccgtc   20100
cgggtcgagc agcggttcgg gcgtttccgc ggcggccgtg cgggtgaacc gcggcgcttc   20160
gtaccgcccg tcggtgacgc ggacgtacgg ctcggccagt gtcgtggcgg cggccagcgc   20220
ctcgatgggg gtgtcggtgc cggtctccac cagcacgaac cggcccgggt gctcggcctg   20280
ggcggaccgg acgaggccgg cgaccgctcc tccgaccggt cccgcgtcga tccggacgac   20340
gagggtggtc tccgcagggc cgtcctcggc gatcacccgg tgcagctcgc cgagcacgaa   20400
ctcggtgagc cggtacgtct cgtcgaggac atccgcgccc ggttccggga gcgcggagac   20460
gatgtggacc gcgtccgcag gaccgggccc gggagtgggc agctcggtcc aggagaggcc   20520
gtacaaggag ttccgtacga cggcggcgtc gccgtcgacg ttcaccggtc gcgcggtcag   20580
cgcggcgacg gtcaccaccg gttggccgac cgggtccgtc gcatgcacgg cagcgccgtc   20640
cgggccctga gtgatcgtga cgcgcagcgt ggtggccccg gtcgtgtgga accgcacgcc   20700
gctccacgag aacggcagcc gcacctccgc ttcctgttcc gcgagcagcg gcaggcaggt   20760
gacgtgcaag gccgcgtcga acagcgccgg gtggacgcca tagtgcggcg tgtcgtccgc   20820
ctgttccccg gcgatctcca cctcggcgta cagggtttcg ccgtcgcgcc aggcggtgcg   20880
cagtccctgg aacgctgggc cgtagctgta gccggtctcg gccagccgct cgtagaacgc   20940
gctcacgtcg acgcgtcgcg cgcccggcgg cggccacgcg ggcggcggga ccgccgcgac   21000
gcttccggcc cggccgaggg tgccgctggc gtgccgggtc cagctgtccg tgccctcggt   21060
acgcgcgtgg acggtcactc gccgccgtcc ggcctcatcg gccccttcga cggtcaccga   21120
cacatccacc gcgccggtca ccggcaccac gagcggggtc tcgatgacca gttcatccac   21180
caccccgcaa ccggtctcgt caccggcccg gatgaccagc tccacaaacg ccgtacccgg   21240
cagcagaacc gtgcccgca ccgcgtgatc agccagccag gatgcgtac gcaacgagat   21300 ccggccagtg agaacaacac caccaccgtc gtcggcggc agtgctgtga cggcggccag   21360
catcggatgc gccgccccgg tcagcccggc cgcggacaga tcggtggcac cggccgcctc   21420
```

```
cagccagtac cgcctgtgct cgaacgcgta ggtgggcaga tcgagcagcc gtcccggcac  21480
cggttcgacc accgtgtccc agtccactgc cgtgcccagg gtccacgcct gcgccaacgc  21540
cgtcagccac cgctcccagc cgccgtcacc ggtccgcaac gacgccaccg tgtgagcctg  21600
ttccatcgcc ggcagcagca ccggatgggc gctgcactcc acgaacacgg acccgtccag  21660
ctccgccacc gccgcgtcca gcgcgacggg gcgacgcagg ttccggtacc agtagccctc  21720
atccaccggc tcggtcaccc aggcgctgtc caccgtggac caccaggcca ccgacccggt  21780
cccgccggaa atcccctcca gtacctcggc caactcgtcc tcgatggctt ccacgtgggg  21840
cgtgtgggag gcgtagtcga ccgcgatacg gcgcactcgc acgccttcgg cctcgtaccg  21900
cgtcaccact tcttccaccg cggacgggtc ccccgccacc acagtcgaag acgggccgtt  21960 acgccgcgc atccacacgc cctcgaccag gtccacctca ccggccggca acgccaccga  22020
agccatcgcc ccccgcccgg ccagccgccc ggcgatcacc tggctgcgca aggccaccac  22080
gcgggcggcc tcctcaaggc tgagggctcc ggccacacac gccgccgcga tctcgccctg  22140
ggagtgtccg accaccgcgt ccggcacgac cccatgcgcc tgccacagcg cggccaggct  22200
caccgcgacc gcccagctgg ccggctggac cacctccacc cgctccgcca catccggccg  22260
cgccaacatc tcccgcacat cccagcccgt gtgcggcaac aacgcccgcg cacactcctc  22320
catacgagcc gcgaacaccg cagaacacgc catcaactcc acaccatgc ccacccactg  22380 agcaccctgc ccgggaaaga cgaacaccgt acgcggctga tccaccgcca cacccatcac  22440
ccgggcatcg cccaacaaca ccgcacggtg accgaagaca gcacgctcac gcaccaaccc  22500
ctgcgcgacc gcggccacat ccacaccacc cccgcgcaga taccctcca gccgctccac  22560 ctgcccccgc agactcacct cactccgagc cgacaccggc aacggcacca acccatcgac  22620
agccgactcc ccacgcgacg gcccgggaac accctcaagg atcacgtgcg cgttcgtacc  22680
gctcaccccg aaagcggaga caccggcccg gcgcggacgt cccgcgtcgg gccacgcccg  22740
cgcctcggtg agcagttcca ccgcgccctc ggtccagtcc acatgcgacg acggctcgtc  22800
cacatgcagc gtcttcggcg cgatgccata ccgcatcgcc atgaccatct tgatgacacc  22860
ggcgacaccc gcagccgcct gcgcatgacc gatgttcgac ttcaacgaac ccagcagcag  22920
cggaacctca cgctcctgcc cgtacgtcgc cagaatcgcg tgcgcctcga tgggatcgcc  22980
cagcgtcgtc cccgtcccgt gcgcctccac cacgtccacg tcggcggggg cgagcccgc  23040 cttgtggagg gcctggcgga tgacgcgctg ctgggagggg ccgttgggtg cggagatgcc  23100
gttggaggcg ccgtcctggt tgacggcgga ggagcggacg accgcgagga cggtgtgtcc  23160
gttgcgctcg gcgtcggaga gcttttcgac gacgaggacg ccggccccct cggcgaaacc  23220
ggtgccgtcc gccgcgtcag cgaacgcctt gcaccgtccg tccggcgcga cgccgccctg  23280
ccgggagaac tccacgaagg tctgtggtga tgccatcact gtgacaccac cgaccagcgc  23340
cagcgagcac tccccggtcc gcagcgcctg cccggcctgg tgcagcgcga ccagcgacga  23400
cgaacacgcc gtgtcgaccg tgaccgccgg accctccatg ccgaagaagt acgacagccg  23460
tccggcgagc accgcgggct gtgtgctgta ggcgccgaat ccgcccaggt ccgcgcccgt  23520
gccgtagccg tagtagaagc cgccgacgaa gacgccggtg tcgctgccgc gcagggtgtc  23580
cggcacgatg ccggcgtgtt cgagcgcctc ccaggcgatt tcgaggagga tccgctgctg  23640
cgggtcgagt gcggtggcct cgcgcggact gatgccgaag aacgcggcat cgaagtcggc  23700
ggcgcccgca gtgcgccgg cccgcccggt ggcggactcg gcggcggcgt gcagcgcggc  23760
cacgtcccag ccgcggtcgg tggggaagtc gccgatcgcg tcgcggccgt ccgcgacgag  23820
```

```
ctgccacagc tcttccggtg aggtgacgcc gcccggcagt cggcaggcca tgccgacgac   23880
ggcgagcggc tcgttcgccg cggcgcgcag cgcggtgttc tcccggcgga gctgcgcgtt   23940
gtccttgacc gacgtccgca gcgcctcgat caggtcgttc tcggccatcg cctcatccct   24000
tcagcacgtg cgcgatgagc gcgtctgcgt ccatgtcgtc gaacagttcg tcgtccggct   24060
ccgcggtcgt ggtgctcgcg ggtgcctgtg ccggtggttc accgccgtcc ggggtcccgt   24120
tgtcgtccgg ggtcccgttg acgtccgggg ccaggagggt cagcagatga cgggtgagcg   24180 cgccggcgg gggatagtcg aagacgagcg tggccggcag cggaatgccg agggcctcgg   24240
agagccggtt gcgcaggccg agcgcggtga gcgagtcgac cccgaggtcc ttgaacgccg   24300
tggtggccgt gaccgccgcc gcgtcggtgt ggcccagcag ggtggcggcg tgtcgcggga   24360
cgacgccgag cagcacctgt tcccgttcct tgtggggcag gtccggcagg cgttccagca   24420
gggagccgcc gtcggtcgcg gagcgccggg tggggcgctg gatcggtcgc cacagcggtg   24480
acgggtcgcc gggcccgggt ggggcggtcg ccacgaccac ggcttccccg gtggcgcacg   24540
cggcgtcgag gaggtcggtc agccggtccg ccgcggcggt gaacgccacg gccggcaggc   24600
cttgtgcccg gcgcaggtcg gccagggcct ggagcggtcc ggccgcctcg ccggacggaa   24660
cggcgagaac gaacgcggtc aggtcgaggt cgcgggtcag gcggtgcagt tcccaggccg   24720
actcggcggt gccgtccgcg tggacgaccg cggtcaccgg ggtttccggc actgtgcccg   24780
gctcgtaccg gatcacttcg gcgccgtgtc cgccgaggtg tccggcgagt tcctccgaac   24840
cgcccgcgag gaggacggtg tcgccgtacg aggccgcggc cgtggtgggc gcggcggga   24900 cgaggcgggg cgcttcgagg cgcccgtcgg ccaggcgcag gtgcggttcg tcgaggcggg   24960
agagggcggc ggcgcggcgg ggggtgaccg tgtcggtggt ctccacgagc acgagccggc   25020
ccggttccgc ggtgtcgagc agtgcggcga cggcaccggc gacgggcccg gcctcggcgg   25080
acaccaccag cgtggcgccg gcggtcctcg ggtcgtccag tgcggtacgg acctcgtcgg   25140
gaccggatac cgggacgacg atgacgtcgg gcgtggcgtc gtcgccgagg tcggtgtacc   25200
ggcgggccgt ggtgccgggt gccgccgggg cccggacgcc ggtccaggtg cgccggaaca   25260
gccgcacgtc cccgtccggg cccgtcgtgg cgggggccg ggtgatgagc gagccgatct   25320
gagccaccgg ccgtcccagt tcgtcggcga ggtgcacgcg ggcgccgccc tcgccctcgc   25380
cgtggacgaa ggtgacgcgc agtttcgtgg cgccgctggt gtggacacgg acgccggtga   25440
acgcgaacgg caaccgtacc cccgcgttct cggcggccgc gccgatgctg cccgcttgca   25500
gcgcggtgac gagcagcgcc gggtgcagtg tgtagcgggc ggcgtccctg gcgagggcgc   25560
cgtcgagggc gacttcggcg cagacggtgt ctccgtggct ccacgcggcg gacatgccgc   25620
ggaactcggg gccgaactcg tatcccgcgt cgtcgagtcg ctggtagaag ccgcgacgt   25680 cgaccggttc cgcgtgctcg gcggccagg gccccggcgt ggtggccggt tcggtggtgg   25740
cgatgccggc gaagccggag gcgtggcggg tccatgtccg gtcgccgtcc gtccgggcgt   25800
ggacgcgcac ggcacggcgt ccggtgtcgt cgggcgcggc gacggtcacg cgcacctgga   25860
cggcgccggt ggcgggcagg accagcggtg tctcgacgac cagttcgtcg agcaggtcgc   25920
agcctgcctc gtcggcgccg cgtccggcca attccaggaa ggcgggtccg ggcagcagta   25980
cggcgccgtc gacggagtga ccggccagcc atgggtgggt ggcagcgag aaccggccgg   26040 tgagcagcac ctcgtcggag tcggggagcc ccaccgacgc ggcgagcagc gggtggtcga   26100
cggcgtcgag tccgaggccg gaagcgtccg tgccggccgc ggtctcgatc cagtagcgct   26160
```

-continued

```
catggtggaa ggcgtatgtg ggcaggtcgt gtgccgtcgc cgtcgcgggg acgaccgccg    26220
cccagtcgac gggcacgccg gttgtgtgcg cctcggccag cgcggtgagc agccggtgga    26280
ctcccccgcc gcggcggagc gtggcgacgg tcgcgccgtc gatcgcgggc agcagcacgg    26340
ggtgcgcgct gacctcgacg aacacggtgt cacccggctc gcgggcagcg gtcacggccg    26400
tggcgaagcc tacggggtgg cgcatgttgc ggaaccagta ctcgtcgtcg agcggcgcgt    26460
cgatccagcg ttcgtcggcg gtggagaacc acgggatctc gggcgtgcgc gaggtggtgt    26520
ccgcgacgat ccgctggagt tcgtcgtaca gcgggtcgac gaacggggtg tgggtcgggc    26580
agtcgacggg gatgcggcgc acccagacgc gcgggcctc gtagtcggcg atcagcgttt    26640
cgacggcgtc cgggcgcccg gcgacggtcg tggtggtggc gccgttgcgg cccgcgaccc    26700
agacgccgtc gatccgggcg gcatccgcct cgacgtcggc ggccgggagc gcgaccgagc    26760
ccatcgcgcc gcgtccggcg agttcgcgca ggagcaggag aacgctgcgc agcgcgacga    26820
ggcgggcacc gtcctccagg gtgagcgctc cggcgacaca ggccgcggcg atctcgccct    26880
gggagtgtcc gatgacggcg tccgggcgta cgcccgcggc ctcccacacg gcggccagcg    26940
acaccatgac ggcccagcag acggggtgca cgacgtcgac gcggcgggtc acctccgggt    27000
cgtcgagcat ggcgatgggg tcccagcccg tgtgcgggat cagcgcgtcg gcgcattggc    27060
gcatcctggc ggcgaacacc ggggaggccg ccatcagttc gacgcccatg ccgcgccact    27120
gcggtccttg tccggggaag acgaagacgg tgcgcggctc ggtgagcgcc gtgccggtga    27180
cgacgtcgtc gtcgagcagc acggcgcggt gcgggaacgt cgtacgcctg gcgagcaggc    27240
ccgcggcgat ggcgcgcggg tcgtggccgg gacgggcggc gaggtgctcg cggagtcggc    27300
ggacctggcc gtcgagggcc gtggcggtcc gcgccgagac gggcagtggt gtgagcggcg    27360
tggcgatcag cggctcaccg ggcttcgagg ccgacggctc ctcggccggc ggctccccgg    27420
ccgggtgggc ttccagcagg acgtgggcgt tggtgccgct gacgccgaag gaggacacac    27480
cggcgcgccg cgggcggtcg gtctcgggcc agggccgggc atcggtgagg agttcgacgg    27540
cgccggccgt ccagtcgacg tgcgaggacg gcgtgtccac gtgcagggtg cgcggcaggg    27600
tgccgtgccg catggcgagg accatcttga tgacaccggc gacacccgcg gcggcctgag    27660
tgtggccgat gttggacttc agcgagccca gcagcaccgg ggtgtcgcgc ccctgcccgt    27720
aggtggccag caccgcctgt gcctcgatgg gatcgcccag cctggtgccg gtgccgtgcg    27780
cctccacggc gtccacgtcc gccggggtga gcccggcgtt ggccagggcc tgccggatca    27840
cccgctcctg cgagggcccg ttcggcgccg acaacccgtt ggaagcaccg tcctggttga    27900
ccgccgaacc ccggacaacc gccagcacac ggtggccgtt gcgctcggca tcggagagcc    27960
tctcgacgat cagcacaccg gaccccctcgg cgaaaccggt gccgtcagcc gcatccgcga    28020
acgccttgca gcgcgcgtcg ggcgcgagac cccgctgctg ggagaactcg acgaagccgg    28080
acggcgaggc catcaccgtg acgccgccga ccagggcgag cgagcattcg ccggagcgca    28140
gtgactgccc ggcctggtgc agcgccacca gcgacgacga acacgccgtg tcgaccgtga    28200
ccgccggacc ctccagaccg tagaagtacg acagccgacc ggacagcaca ctggtctggg    28260
tgccggtcgc gccgaaaccg cccaggtcgg tgccgagtcc gtaccgtcg gagaaggcgc    28320 ccatgaacac gccggtgtcg cttccgcgca gcgactccgg gaggatcccg gcgtgttcca    28380
gcgcctccca cgaggtctcc aggaccagac gctgctgcgg gtccatcgcc agcgcctcac    28440
gcggactgat cccgaagaac gccgcgtcga agtccgccac cccggcgagg aagccaccat    28500
gacgcacggt cgacgtgccc ggatgatccg gatcgggatc gtacagcccg tccacgtccc    28560
```

```
aaccacggtc cgtcggaaac gccgtgatcc cgtcaccacc cgactccagc agccgccaca   28620
agtcctccgg cgacgcgacc ccacccggca gccggcaggc catccccacg atcgccaacg   28680
gctcgtcctg ccggacggcc gcggtcgtgg tgcgggtcgg cgatgccgtc cggccggaca   28740
gcgccgcggt gagcttcgcc gcgacggcgc gcggcgtcgg gaagtcgaag accgcggtgg   28800
cgggcagccg tacgcccgtc gcctcggtga aggcgttgcg cagccggatc gccatgagcg   28860
agtcgacgcc gagttccttg aacgtggcgg tcgcctcgac ccgtgcggca ccgtcgtggc   28920
cgagtacggc cgcggtgcac tgccggacga cggcgagcac gtccttttcg gcgtccgcgg   28980
cggagagccg cgcgatccgg tcggcgaggg tggtggcgcc ggccgcccgg cgccgcggct   29040
cccgcgcgcg tgcgcgcagc aggggcgagc tgccgaggcc ggccgggtcg gcggcgacca   29100
gcgccgggtc cgaggaccgc aacgccgcgt cgaacagcgt cagtccgcct tcggcggtca   29160
gcgccgtcac gccgtcgcgg cgcatgcggg cgccggtgcc gaccgtcagc ccgctctccg   29220
gttcccacag gccccaggcc acggacaacg cgggcagtcc ggctgccgg cgctgttcgg   29280
ccagcgcgtc gaggaacgcg ttcgcggccg cgtagttgcc ctgtccgggg ctgccgagca   29340
caccggcggc cgacgagtag aggacgaacg cggccagttc cgtgtcctgg gtgagttcgt   29400
gcaggtgcca cgcggcgtcc accttcgggc gcagcaccgt ctcgagccgg tcggggtga   29460
gcgcggtgag gacgccgtcg tcgaggacgg ccgcggtgtg cacgacggcc gtgagcgggt   29520
gcgccgggtc gatccccgcc agtacgagg cgagttcgtc ccggtcggcg acgtcgcagg   29580
cgatcgccgt gacctcggcg ccgggcacgt cgctcgccgt gccgctgcgc gacagcatca   29640
gcagccggcg cacgccgtgg cgttcgacga ggtggcggct gatgatgccg gccagcgtcc   29700
cggagccacc ggtgacgagc acggtgccgt ccgggtcgag cgccgagcg tcacccgccg   29760
ggaccgccgg ggccagacgg cgggcgtaca cctggccgtc acgcagcacc acctggggct   29820
catcgagcgc ggtggccgct gcgagcagcg gctcggcggt gtccggggcg cgtcgacga   29880
ggacgatccg gccggggtgt tcggcctgcg cggtccgcac cagtccggcg gccgcggccg   29940
acgcgagacc gggcccggtg tggacggcca ggaccgcgtc ggcgtaccgg tcgtcggtga   30000
ggaagcgctg cacggcggtc aggacgccgg cgcccagttc gcgggtgtcg tcgagcgggg   30060
caccgccgcc gccgtgcgcg gggaggatca ccacgtccgg gaccgtcggg tcgtcgaggc   30120
ggccggtcgt cgcggtcgtg ggcggcagct ccgggagctc ggccagcacc gggcgcagca   30180
ggcccggaac ggctcccgtg atcgtcaggg ggcgcctgcg cacggcgccg atggtggcga   30240
cgggcccgcc ggtctcgtcc gcgaggtgta cgccgtcagc ggtgacggcg acgcgtaccg   30300
ccgtggcgcc ggtggcgtgg acgcggacgt cgtcgaacgc gtacggaagg tggtcccctt   30360
ccgcggcgag gcggagtgcg gcgccgagca gcgccgggtg caggccgtac cgtccggcgt   30420
cggcgagctg tccgtcggcg agggccactt ccgcccagac ggcgtcgtcg tcggcccaga   30480
cggcgcgcgg gcggggcagc gcgggcccgt ccgtgtaccc ggctcgggcc agacggtcgg   30540
cgatgtcgtc ggggtccacc ggccgggccg tggcgggcgg ccacgtcgac ggcatctccc   30600
gcacggccgg ggccgtccgc gggtcggggg cgaggattcc gtgcgcgtgc tcggtccact   30660
cccccgccgc gtgccgcgtg tgcacggtga ccgcgcggcg gccgtccgcc ccgggcgcgc   30720
tcaccgtgac ggagagcgcg agcgcaccgg accgcggcag cgtgagggg gtgtccacgg   30780
tgaacgtgtc gagggcgccg cagccggctt cgtcgcccgc ccggatcgcc agatccagga   30840
gggccgcggc gggcagcacc gcgaggccgt gcagggagtg cgccagcgga tcggcggcgt   30900
```

```
cgacccggcc ggtgagcacc aggtcgccgg tgccgggcag ggtgaccgcc gcggtcagcg   30960
ccgggtgcgc gaccggcgtc tgtccggccg gggccgcgtc cccgcggtc tgggtgccga    31020
gccagtagcg gacccgctcg aacgggtacg tcggcgggtg cgaggcgcgt gccggcgcgg   31080
ggtcgatgac cttcggccag tcgaccgtga cgccgtcggt gtgcagccgg gcgagcgcgg   31140
tcagggcgga tcgcggttcg tcgtcggcgt gcagcatcgg gatgccgtcg acgagtcggg   31200
tcaggctccg gtccgggccg atctccagga gcaccgcccc gtcgtgcgcg cgacctgtt   31260
ccccgaaccg gacggtgtcg cggacctgtc gtacccagta ctccggcgtg gtgcaggcgg   31320
cgcccgcggc catcgggatc ctcggctcgt ggtacgtcag gctctccgcg accttgcgga  31380
actcctcgag catcggctcc atccgcgccg agtggaacgc gtggctggtc cgcaggcggg   31440
tgaagcggcc gagccgggcc gcgacgtcga gcaccgcctc ctcgtcaccg gagagcacga   31500
tcgacgcggg cccgttgacc gcggcgatct ccacgccgtc ccgcagcagc ggcagcgcgt   31560
cccgttccga cgcgatcacg gcggccatcg ccccgccgga cggcagcgcc tgcatcaggc   31620
gggcccgtgc ggacaccagc ctgcacgcgt cctccaggga ccagacgccg gcgacgtacg   31680
cggcggccag ctcgccgatc gaatggccca cgaaggcgtc cgggcgtacg ccccacgcct   31740
cgagctgtgc gccgagtgcg acctggagcg cgaacaccgc gggctgggcg tacccggtgt   31800
cgtggaggtc gagcccggcg ggcacgtcga gggcgtccag cacctcgcgg cgagtgcggg   31860
cgaagacgtc gtaggcggcg gccagtccgt cgcccatgcc gggacgttgt gagccctgtc   31920
cggagaagag ccacacgagg cggcggtccg gttctgcggc gccggtgacc gtgtcggtgc   31980
cgatcagcgc ggcccggtgc gggaaggccg tgcgggcgag cagggccgcg gccaccgcgc   32040
gctcgtcctc ctcgccggtg gcgaggtggg cgcgcaggcg gtgtacctgt gcgtcgagtg   32100
cctgcggggt gcgtgccgag agcagcaggg gcagcggtcc ggtgtcgggt gccggggcgg   32160
gttcgggggc cggtcggggg tggctttcga ggatgatgtg agcgttggtg ccgctaacgc   32220
cgaaggagga caccccggcg cgccgtgggc ggtcggtttc gggccagggg cgggcgtcgg   32280
tgaggagttc gacggcgccg gccgtccagt cgacgtgcga ggacggcgtg tccacgtgca   32340
gggtgcgcgg cagggtgccg tgccgcatgg cgaggaccat cttgatgaca ccggcgacgc   32400
ccgcggcggc ctgagtgtgg ccgatgttgg acttcagcga gcccagcagc accgggtgt    32460
cgcgatgctg cccgtaggtg gccagtaccg cctgcgcctc gatggggtcg cccagcctgg   32520
tcccggtgcc atgcgcctcg acagcgtcca catccgccgg ggtgagcccg gcgttggcca   32580
gcgcctgccg gatcacccgc tcctgcgacg gcccgttcgg cgccgacaac ccgttggaag   32640
caccgtcctg gttgaccgcc gaaccacgca cgaccgccag gacattgtgg ccgtgccgct   32700
cggcgtcgga gagcctctcg acgatcagca caccggatcc ctcggcgaaa ccggtgccat   32760
cagccgcatc cgcgaacgcc ttgcagcggc cgtccgggga gaggccccgc tgctgggaga   32820
agtccacgaa gccggacggc gaggccatca ccgtgacgcc gccgaccacg cgagcgagc    32880
actcccccga gcgcagcgac tgcccggcct ggtgcagcgc caccagcgac gacgaacacg   32940
ccgtgtccac cgtgaccgcc ggaccctcca aaccgtagaa gtacgacagc cgaccggaca   33000
gcacactggt ctgggtgctg gtggcaccga aaccgccgcg gtcggctcca gtgccgtacc   33060
cgtagaagta gccgcccatg aacacgccgg tgtcgcttcc gcgcagcgac tccggaggga   33120
tcccggcgtg ttccagcgcc tcccacgagg tctccaggac cagacgctgc tgcgggtcca   33180
tcgccagcgc ctcacgcgga ctgatcccga agaacgccgc gtcgaagtcc gccaccccgg   33240
cgaggaagcc accatgacgc acggtcgacg tgcccggatg atccggatcg ggatcgtaca   33300
```

```
gcccgtccac gtcccaacca cggtccgtcg gaaacgccgt gatcccgtca ccacccgact   33360
ccagcagccg ccacaagtcc tccggcgacg cgaccccacc cggcagccgg caggccatcc   33420
ccacgatcgc caacggctcg tcctgccgga cggccgcgt cggggtacgc cgccgggtgg   33480
tggcccgcgc gccggccagt tcgtccaggt gggcggcgag cgcctgcgcc gtggggtggt   33540
cgaagacgag cgtagcgggc agcgtcaggc ccgtcgcgtc ggccagccgg ttgcgcagtt   33600
cgacgccggt cagcgagtcg aagcccactt ccctgaacgc gcgcgcgggt gcgatggcgt   33660
gggcgtcgcg gtggccgagc accgcggcag cgctggtacg gacgaggtcg agcatgtcgc   33720
gcgcggccgg aggtgcggac gtgcgccgga cggccggcac gagggtgcgt aggaccggcg   33780
ggacccggtc ggacgcggcg acggcggcga ggtcgagccg gatcggcacg agcgcgggcc   33840
ggtcggtgtg cagggccgcg tcgaacaggg cgagcccctg tgcggccgtc atcggggtca   33900
tgccgttgcg ggcgatgcgg gccaggtcgg tggcggtcag ccgcccgccc atcccgtccg   33960
ccgcgtccca cagtccccag gcgagcgaga cggcgggcag ccctggtgg tgccggtggc   34020
gggcgagcgc gtcgaggaac gcgttgccgg tcgcgtagtt ggcctgaccc cgccgccga   34080
acgtggcgga tatggacgag tacaggacga acgcggccag gtcgagatcg cgcgtcagct   34140
cgtgcaggtg ccaggcgacg tccgccttga cccgcagcac ggcgtccac tgctccggcc   34200
gcatggtcgt cacggccgcg tcgtcgacga tcccggccat gtgcacgacg gcgcgcagcc   34260
gctgggcgac gtcggcgacg actgcggcca gctcgtcgcg gtcgacgacg tcggcggcca   34320
cgtaccgcac gcggtcgtcc tccggcgtgt cgccggccg gccgttgcgg gacaccacga   34380
cgacctcggc ggcctcgtgc acggtgagca ggtggtccac gaggaggcgg ccgagcccgc   34440
cggtgccgcc ggtgacgagg acggtcccgc cggtcagcgg ggaggttccg gtggccgcgg   34500
cgacacggcg cagacgggcc gcacgcgctg tgccgtcggc gacccggacg tgcggctcgt   34560
cgccggcggc gagcccggcc gctatggcgg cgggcgtgat ctcgtccgct tcgatcaggg   34620
cgacgcggcc gggatgctcc gtctccgccg tccggaccag gccgccgagc gcttcctgcg   34680
cgggatcgcc ggtacgggtg gccacgatga gccgggatcg cgcccagcgc ggctcggcga   34740
gccaggtctg cacggtggtg agcaggtcgc ggcccagctc ccgggtccgg gcgccgggcg   34800
aggtgcccgg gtcgccgggt tccacggcca ggaccacgac cggggggtgc tcgccgtcgg   34860
gcacgtcggc gaggtacgtc cagtcgggga cgggtgacgc gggcacgggc acccaggcga   34920
tctcgaacag cgcctcggca tcggggtcgg cggcccgcac ggtcaggctg tcgacgtcaa   34980
ggaccggtga gccgtgctcg tccgtggcga cgatgcggac catgtcgggg ccgacgcgtt   35040
ccagcagcac gcgcagcgcg gtcgcggcgc gcgcgtggat cctcacgccg gaccaggaga   35100
acgccagccg gcgccgctcc gggtccgtga agaccgtccc gagggcgtgc agggccgcgt   35160
cgagcagcac ggggtgcagc ccgtaccggg cgtcggtgag ctgttcggcg aggcggaccg   35220
acgcgtaggc gcggccctcc cccgtccaca tcgcggtcat ggcccggaac gcgggcccgt   35280
acgagagcgg cagcgcgtcg tagaagccgg tcaggtcggc cgggtcggcg tcggcgggcg   35340
gccagtccac gggctccgcc ggaccgccag tgtccacgct cagcgctccg gtcgcactga   35400
gcgcccaggg gcccgtgccg gtacggctgt gcagactcac cgaccgccgt ccggacacct   35460
cggttccgac ggtggcctgg atctccgtgt cgccgtcgcc gtcgaccacc accggcgcga   35520
cgatggtcag ctccgcgatc tccggcgtgc cgagccgggc tcccgcttcg gcgagcagtt   35580
ccacgagcgc cgagccgggc acgatgaccc ggccgtccac ctcgtggtcg gcgagccagg   35640
```

```
gctgacggcg taccgagaca ccgcggtggc cagcgcgccc tcgccgtcgg gcgaggtcga   35700
cccacgagcc gagcagcggg tggccggacg ttcccgccgg ttccgcgtcg atccagtagc   35760
ggtcacggcg gaacgggtac gtgggcagcg gcaccacccg acgcgtcgcg aacgaccagg   35820
tgacgggcac gccccggacc cagagcgcgg cgagcgaccg agtgaagcgg tccaggccgc   35880
cctcgcctcg ccgcagtgtg ccggtgacga ccgtatgcgc atgcccggcg agcgtgtcct   35940
ccagtgcggt ggtgagcacg ggatgcgcgc tgacctcgac gaacgcgcgg tatccgcggt   36000
ccgccaggtg gccggtcgcg gcggcgaacc gaacggtgcg gcgcaggttg tcgtaccagt   36060
aggcggcgtc cgcgggccgg tccagccacg cctcgtccac ggtggagaag aacgggacgt   36120
ccggcgtgcg cggagtgatg ccggcgagag cgtcgagcag cgcgccgcgg atcgtttcga   36180
catgcgcggt gtgcgacgcg tagtcgacgg cgatccggcg ggcgcggggg gtggcggcca   36240
gcagctcctc cacggcgtcg gccgcaccgg cgacaacgat cgacgcgggt ccgttgaccg   36300
cggcgacctc caggcgcccg gcccacacgg cggcgtcgaa gtcggcgggc ggcaccgaga   36360
ccatgccgcc ctgcccggcc agttcggtgg cgacgagtcg gctgcgcacc gcgacgacct   36420
tcgcggcgtc gtccagggtg agcaccccgg cgacgcaggc cgcggcgact tcgccctggg   36480
agtggccgac gaccgcggcc ggggcgaccc cgtgcgcacg ccacagctcc gccagcgcca   36540
ccatcaccgc gaacgacgcg ggctgcacga catcgacccg gtcgaacgcg ggcgctccgg   36600
gccgctgggc gatgacgtcc agcaggtccc atccggtgtg cggggcgagc gccgtggcgc   36660
actcgcggag ccgccgggcg aacacgggct cggtggcgag cagttcggca cccatgccgg   36720
cccactggga gccctgcccg gggaacgcga acacgacacg tgtgtcggtg acgtcggcgg   36780
ttcccgtcac ggcccccggc acttcggcac cacgggcgaa cgcctccgcc tctcgggccg   36840
gcacgaccgc ccggtggcgc atggccgtcc gggtggtggc gagcgagtgg ccgaccgcgg   36900
ccgcggcgcc agtgagcggg gccagctgtc ccgcgacgtc ccgcagtccc tccggggtcc   36960
gggccgacat cggccagacc acgtcctcgg gcaccggctc ggcttcgggt gcggacacgg   37020
gtgcgggcgc ggcgggggc ccggcctcca ggacgacatg ggcgttggtg ccgctgatgc   37080
cgaacgacga gacacccgca cgccgggcgc gcccggtgac cggccacggc tcactgcggt   37140
gcagcagccg gatgtcgccg tcccagtcga cgtgccggga cggctcgtcg acgtgcagcg   37200
tgcgcggcag gacgccgtgc cgcatcgcca tgaccatctt gatgacgccg gcgacgccgg   37260
ccgcggcctg ggtgtggccg atgttcgact tgagcgagcc gatcagcagc ggatgcacgc   37320
gttcgcgccc gtaggccact tgcagggcct gggcctcgac ggggtcgccg agacgggtgc   37380
cggtgccgtg tgcctccacg gcgtcgacgt cacccggcgc caggccggcg tcggcgagcg   37440
cacgctggat gacgcgctgc tgcgcaggcc cgttcggggc ggacagcccg ttcgacgcgc   37500
cgtcggagtt gaccgcggag ccgcgcacca gcgccagcac ggggtggccg tggcgggtgg   37560
cgtcggagag ccgctccagc accaggacac cggcgccctc ggcgaagctc gtgccgtccg   37620
cggtgtccgc gaaggccttg gcacggccgt cggggcgag cccgcgctgc cgggagaact   37680
cgacgaaccc ggtcgtcgtc gccatcaccg tgacaccgcc gaccagggcg agcgagcact   37740
cccccgagcg cagcgaccgc gcggcctggt gcagcgccac cagcgacgac gaacacgccg   37800
tgtcgacggt gaccgacggg ccctccagac cgaagtagta cgagagccgc ccggagagaa   37860
cgctggtcgg cgtgccggtc gccccgaaac cgcccaggtc cacgcccgcg ccgtagccct   37920
gggtgaacgc gcccatgaat acgcggtgt cgctgccgcg gacgctttcg ggcaggatgc   37980
ccgctcgttc gaacgcctcc cacgacgctt cgaggaccag acgctgctgc gggtccatcg   38040
```

```
ccagcgcctc acgcgggctg atcccgaaga acgcggcgtc gaagtcggcg gcgccggtga    38100
ggaagccgcc gtgacgcacg gaaaccttgc cgaccgcgtc ggggttcggg tcgtagagcg    38160
cggcgaggtc ccagccgcgg tcggcgggga actcggtgat cgcgtccccg ccggagtcga    38220
ccagccgcca caggtcctcc ggtgaccgca cgccaccggg catccggcac gccatggcca    38280
cgatcgccag cggctcgttc cccgccaccg tcggtgcggg cactgtcgcc gccggagcgg    38340
caggggccgg ctcaccccgc cgttcctcat ccaggcgggc ggcgagcgcg gccggtgtcg    38400
ggtggtcgaa gacggccgtc gcggagagcc gtaccccgt cgtctcggcg aggctgttgc    38460
gcaaccggac accgctgagc gagtcgatgc cgaggtcctt gaacgccgtc gtgggcgtga    38520
tctcggaggc gtcggcgtgg ccgagcacgg cggccgtggc cgcacacacg atggccagca    38580
ggtcacgatc gcggtcgcgg tcgcggtcgc ggttgtcctc cgcacgggcg gcgatgcggc    38640
gctcggtccg ctgccggacg ggctcggtgg gaatcgccgc gaccatgaac ggcacgtccg    38700
cggcgaggct cgcgtcgatg aagtgggtgc cctcggcctc ggtgagcggc cggaacccgt    38760
cgcgcacccg ctgccggtcg gcgtcgtcaa gttgtccggt gagggtgctg gtggtgtgcc    38820
acatgcccca ggcgatggag gtggcgggtt ggccgagggt gtggcggtgg gtggcgaggg    38880
cgtcgaggaa ggcgttggcg gcggcgtagt ttccttgtcc ggggctgccg aggacggcgg    38940
cggcgctgga gtagaggacg aagtgggtga ggggttggtt ttgggtgagg tggtgcaggt    39000
gccaggcggc gttggctttg ggtggagga cggtggtgag gcggtcgggg gtgagggcgt    39060
cgaggatgcc gtcgtcgagg gtggcggcgg tgtggaagac ggcggtgagg ggttggggga    39120
tgtgggcgag ggtggtggcg agttggtggg ggtcgccgac gtcgcagggg aggtgggtgc    39180
cgggggtggt gtcgggggt gggtgcggg agaggaggta ggtgtggggg tggttcaggt    39240
ggcgggcgag gatgccggcg agggtgccgg agccgccggt gatgatgatg cgtgttcgg    39300 ggttgagggg ggtggtggtg ggtggggtgg tggtgtggag ggggtgagg tggggtcggt    39360 ggagggtgtg gtgggtgagg cggaggtggg ggtggtcgag ggtggcgagt tgggccaggg    39420
ggaggggagt gtggggggtgg tcggtttcga tgaggcggat gcggtggggg tgttcgttct    39480
gggcggtgcg ggtgaggccg gtgacggtgg cgccggcggg gtcggtggtg gtgtggacga    39540
tgagggtgtg gtcggtggtg gtgaggtggt gttgcagggc ggtcaggacg cgggtggcgc    39600
gggtgtgggc gcgggtgggt atgtcctcgg ggtcgtcggg gtgggcggcg gtgatcagga    39660
cgtgtccctc gggcaggtca ccgtcgtaga ccgcctcggc gaccgcgagc cactccaacc    39720
ggagcgggtt cggccccgac ggggtgtcgg cccgctccct cagcaccagc gagtccaccg    39780
acacgacagg acgccatcc gggtcggcca cgcgcacggc gacgccggcc tccccccggg    39840
tgagggcgac gcgcaccgcg gcggcccggg tggcgttcag gcgcacgccc gtccaggaga    39900
acggcagctc gatcccgccg cccgcgtcga ggcgcccggc gtgcagggcc gcgtcgagca    39960
gtgccggatg cacaccgaaa ccgtccgcct cggcggcctg ctcgtcgggc agcgccacct    40020
cggcatacac ggtgtcacca tcacgccagg cagcccgcaa cccctggaac gccgacccgt    40080
actcataacc ggcatcccgc agttcgtcat agaaccccga gacgtcgacg gccgcggccg    40140
tggccggcgg ccactgcgag aacggctcac cggaagcgtt ggaggtatcc ggggtgtcgg    40200
gggtcagggt gccgctggcg tgccgggtcc agctgcccgt gccctcggta cgcgcgtgga    40260
cggtcaccgg ccgccgtccg gcctcatcgg ccccttccac ggtcaccgac acatccaccg    40320
ctgcggtcac cggcaccacg agcggggatt cgatgaccag ttcatccacc accccgcaac    40380
```

```
cggtctcgtc accggcccgg atgaccagct ccacaaacgc cgtacccggc agcagaaccg    40440
tgccccgcac cgcgtgatca gccagccagg gatgcgtacg caatgagatc cggccggtga    40500
gaacaacacc accaccgtcg tcggcgggca gtgctgtgac ggcggccagc atcggatgcg    40560 ccgcccggt cagcccggcc gcggacaggt cggtggcacc ggccgcctcc agccagtacc     40620
gcctgtgctc gaacgcgtag gtgggcagat ccagcagccg ccccggcacc ggttcgacca    40680
ccgtgcccca gtccaccccc gcacccgag tccacgcctg cgccaacgcc cccagccacc     40740
gctcccagcc accgtcacca gtccgcaacg acgccaccgt gcgggcctgt tccatcgccg    40800
gcagcagcac cggatgggca ctgcactcca cgaacaccga cccgtccagc tccgccaccg    40860
ccgcatccag cgcgacaggg cgacgcaggt tccggtacca gtacccctca tccaccggct    40920
cggtcaccca ggcgctgtcc acggtcgacc accacgccac cgacccggtc ccgccggaaa    40980
ttcccttcag tacctcagcg agttcgtcct cgatggcctc cacgtgaggc gtgtgggagg    41040
cgtagtcgac cgcgatacga cgcacccgca ccccatcagc ctcataccgc gccaccacct    41100
cctccaccgc cgacgggtcc cccgccacca ccgtcgaagc cggaccatta cgcgccgcga    41160
tccacacacc ctcgaccaga cccacctcac cggccggcaa cgccaccgaa gccatcgccc    41220
cccggccggc cagccgcgcc gcgatcaccc gactgcgcaa cgccaccacg cgggcggcgt    41280
cctccaggct gagggctccg gccacacacg ccgccgcgat ctcccctgc gagtgtccga     41340 ccacagcgtc cggcacgacc ccatgcgcct gccacagcgc ggccaggctc accgcgaccg    41400
cccagctggc cggctggacc acctccaccc gctccgccac atccgaccgc gacaacatct    41460
cccgcacatc ccagcccgtg tgcggcaaca acgcccgcgc acactcctcc atacgagccg    41520
cgaacaccgc ggaacggtcc atgagttcca cgcccatgcc cacccactgg gcaccctgcc    41580
cggggaagac gaacaccgta cgcggctgat ccaccgccac acccatcacc cgggcatcac    41640
ccagcagcac cgcacggtga ccgaagacag cacgctcacg caccaacccc tgcgcgaccg    41700
cggccacatc cacccaccc ccgcgcagat accctccag ccgctccacc tgccccgca       41760 gactcacctc accacgagcc gacaccggca acggcaccaa cccatcacca cccgactcca    41820
cacgcgacgg cccaggaaca ccctccagga tcacgtgcgc gttcgtaccg ctcacccga     41880 acgacgacac cccgcatgc ggtgcccgat ccgactcggg ccacggcctc gcctcggtga     41940
gcagctccac cgcaccggcc gaccagtcca catgcgacga cggctcgtcc acgtgcagcg    42000
tcttcggcgc gatcccatgc cgcatcgcca tgaccatctt gatgacaccg gcgacacccg    42060
cagccgcctg cgcatgaccg atgttcgact tgaccgaacc gaggtagagc ggcgtgtcgc    42120
ggtcctgccc gtaggccgcg aggacggcct gcgcctcgat cgggtcgccc agccgcgtgc    42180
cggtgccgtg cgcctccacc acgtccacat cggcggcgcg cagtccggcg ttgaccaacg    42240
cctgccggat cacgcgctgc tgggcgacgc cgttgggggc ggacagtccg ttggaggcac    42300
cgtcctggtt caccgccgag ccgcggacga ccgcgagaac ggtgtgcccg ttgcgctcgg    42360
cgtcggagag ccgctccagc acgagaacgc cgacgccctc ggcgaagccg gtcccgtccg    42420
ccgcgtcggc gaacgccttg caccgtccgt ccggggagag tccgcgctgc cgggagaact    42480
ccacgagctc tgcggtgttc gccatgacgg tgacaccgcc gaccagcgcc agggagcact    42540
ccccggcccg cagtgcctgt gccgcctggt gcagggcgac cagcgacgac gagcacgccg    42600
tgtcgaccgt gaccgccggg ccctgaagtc cgtacacgta cgagaggcgc ccggacagga    42660
cgctcgtctg cgtcgccgtg acaccgagcc cgcccaggtc ccggccgacg ccgtagccct    42720
ggttgaacgc gcccatgaac acgccggtgt cgctctcccg gagcctgtcc ggcacgatgc    42780
```

```
cggcgttctc gaacgcctcc caggaggtct ccaggatcag gcgctgctgg gggtccatcg   42840
ccagcgcctc gttcggactg atgccgaaga acgcggcgtc gaacccggcg ccggccagga   42900
atccgccgtg gcgtgtcgtg gagcggccgg ccgcgtccgg gtccgggtcg tacagcgcgt   42960
cgacgtccca gccccggtcg gtggggaact cggtgatcgc ctcggtaccg gcggcgacga   43020
gccgccacag gtcctccggc gaggcgaccc cgccgggcag tcggcacgcc atgccgacga   43080
tcgcgacggg gtcgccggag ccgagggtct gggcggtcgc gggtgccgct gtcgcggagc   43140
cggcgaggtg ggcggcgaac gcacgcggag tggggtggtc gaacgcggtt gacgcgggca   43200
cccgcagacc cgtccgcgcg gcgacggtgt tggtgaactc gacggtggtg agcgagtcga   43260
ggccgttctc gcggaacgtg cggtccgggg agcagtgtcc ggcgcccggc aggcccagga   43320
cggtggcgac gctgtcgcgg accaggtcga gcagtacgtc ctcccggccc gcacgggccg   43380
cggcgaggcg gttcgcccac tcctgttccg tggcgtcggg ctcggccggt ccggtcagtg   43440
cggtgaggat cggcggcgtg gcgcccgcca tcgtcgcggc ccgcgccccg gcggaaccgg   43500
tccgggccac gatgtacgag ccgccgcccg cgatggcctt ctcgatcagg tcgccggtga   43560
gcgccggccg ttcgatgccg ggcagcgcgc ggacggtgac ggtggggagt ccctccgcgg   43620
cccgtggccg ggtgtgggcg tcggcgccgg ccgggccgtc gagcaggacg tgcacgagcg   43680
cgccggggtt cgcggcttcc tcggctgcgg tggtcacgtg ggtgaggccg gtctcgtcgc   43740
ggagcaggcc ggcgacggtg tcggcgtcct ccccggtgac caggaccggc gcgtccgggc   43800
cgatcggagg cggcacggtg aggaccatct tgccggtgtg ccgggcgtgg ctcatccacg   43860
cgaacgcgtc ccgcgcacgg cggatgtccc acggctgcac cggcagcggg cacagctcac   43920
cgcggtcgaa caggtcgagg agcagttcga ggatctcccg caggcgcgcg ggatccacgt   43980
cggccaggtc gaacggctgc tgggcggcgt ggcggatgtc ggtcttgccc atctcgacga   44040
accggccgcc cggtgcgagc aggccgatgg acgcgtcgag gagttcaccg gtgagcgagt   44100
tgagcacgac gtcgaccggc gggaaggtgt cggcgaacgc ggcgctgcgg gagttcgcca   44160
catggtcggt gtcgaagccg tcggcgtgca gcaggtgttg tttggcggga ctggcggtgg   44220
cgtacacctc ggcgccgagg tggcgggcga tccgggtcgc cgccatgccg acaccgcccg   44280
tcgcggcgtg gaccaggacc ttctggccgg gtcgcagctc gcccgcgtcg acgaggccgt   44340
accaggcggt ggcgaacacg atgggcacgg acgcggcgat ggggaacgac catcccgtg   44400
ggatccgtgc gaccagccgc cggtccgcga ccacgctgcg ccgaacgcg tcctgcacga   44460
gaccgaacac gcggtcgccg ggggccaggt cgtcgacgcc gggtccgact tcggtcacga   44520
tgcccgcggc ctccccgccc atctcgccct cgcccgggta ggtgccgagc gcgatcagca   44580
cgtcgcggaa gttcagcccc gcggcgcgga cgtcgatgcg gacctcgccg gcggccaggg   44640
gcgcggcggg acgtcgagcg gggcgacgac gaggtcgcgg agcgttccgg aggcgggcgg   44700
gcgcagcgcc cactggcgcg gtcggcaggg gggtggtgtc cgcgcgtacc agccggggca   44760
cgtaggccac gccggcccgc agcgcgatct ggggttcgcc gagcgaggcc gcggcgggga   44820
cgaggtcgtc atcgccgtcc gtgtccacca gcacgaacga tccgggttcg gcggcctggc   44880
ggcgcagcgc ctcgtcccag agccgggcct ggtccgcgtc cggatctcg gccgggccga   44940
cgcccaccgc gcggcgggtg acgaccgtcc ggcggggtga cggggtgccg ggcaggtcgc   45000
gccgctccca gaccagttcg cacagcgtgg cctcgccact gccggtggcg accagatggg   45060
ccggcagccc cgcgagccgc gcgcgctgga ccttgcccga cgcggtgcgg gggatcgtgg   45120
```

```
tgacgtgcca gatctcgtcg ggcaccttga agtaggcgag ccggcggcgg cactcggcga   45180
ggatcgcctc ggcggggacg cggggggccgt cggaaacgac gtagagcacg ggtatgtcgc   45240
cgaggacggg gtgcgggcgg cccgccgcgg cggcgtcccg gacaccggcc acctcctggg   45300
cgacggtctc gatctcccgg gggtggatgt tctccccgcc gcggatgatc agctccttga   45360
cccggccggt gatcgtcacg tgtccggtct cggcctgacg tgcgaggtcc ccggtgcggt   45420
accagccgtc cacgagcacc tgggcggtcg cctccggctg ggcgtggtag ccgagcatga   45480
ggctcggccc gctcgcccac agctcgccct cctcgccggg tgccacgtcg gcgccggaca   45540
ccgggtcgac gaaccgcagc gacaggcccg gcacgggcag cccgcacgag ccgggaaccc   45600
gcgcatcctc cagggtgttg gcggtgagcg agccggtcgt ctcggtgcag ccgtacgtgt   45660
cgagcagggg cacgccgaac gtcgcctcga aatccctggt gagcgacgcc ggcgaggtgg   45720
atccggcgac cagcgccacg cgcagcgcgc gagcccgcgg ctcgccggac acggcgccga   45780
ggaggtagcg gtacatcgtc ggcacgccga cgagcacggt gctggagtgt tcggccaggg   45840
cgtcgaggac gtcacgcgcg acgaagccgc ccaggatacg ggcggacgcg ccgaccgtga   45900
ggacggcgag caggcagagg tggtggccga ggctgtggaa cagcggggcg ggccagagca   45960
gttcgtcgtc ctcggtcagc cgccaggacg gcacgtcgca gtgcatcgcg gaccacaggc   46020
cgctgcgctg tgcggaaacc acgcccttgg gacggccggt ggtgccggag gtgtagagca   46080
tccaggcggg ttcgtccagg ccgaggtcgt cgcggggcgg gcacggcggc tcggtcccgg   46140
cgaggtcctc gtaggagacg cagtccggtg cccggcgccc gacgagcacg acggtggcgt   46200
cggtgccggt gcggcgcacc tggtcgaggt gggtttcgtc ggtgaccagc acggtcgcgc   46260
cggagtccgt caggaagtgg gcgagttcgg cgtcggcggc gtccggggttg agcgggacgg   46320 cgacggcggc ggcgcgggcg gcggcgaggt agacctcgat ggtctcgatc cggttgccga   46380
gcagcatcgc gacccggtcg ccgcggtcga cgccggacgc ggcgaggtgt ccggcgagcc   46440
ggccggcccg gagccggagt tgcgtgtacg tcacggcgcg ttgggaatcc gtgtaggcga   46500
tccggtcgcc gcgtcgctcg gcatggatgc ggagcaattc gtgcaacggc cggattggtt   46560
ccacacgcgc catggaaaca cctttctctc gaccaaccgc acaacagcac ggaaccggcc   46620
acgagtagac gccggcgacg ctagcagcgt tttccggacc gccacccccct gaagatcccc   46680 ctaccgtggc cggcctcccc ggacgctcat ctagggggtt gcacgcatac cgccgtgcgt   46740
aattgccttc ctgatgaccg atgccggacg ccagggaagg gtggaggcgt tgtccatatc   46800
tgtcacggcg ccgtattgcc gcttcgagaa gaccggatca ccggacctcg agggtgacga   46860
gacggtgctc ggcctgatcg agcacggcac cggccacacc gacgtgtcgc tggtggacgg   46920
tgctccccgg accgccgtgc acaccacgac ccgtgacgac gaggcgttca ccgaggtctg   46980
gcacgcacag cgccctgtcg agtccggcat ggacaacggc atcgcctggg cccgcaccga   47040
cgcgtacctg ttcggtgtcg tgcgcaccgg cgagagcggc aggtacgccg atgccaccgc   47100
ggccctctac acgaacgtct tccagctcac ccggtcgctg gggtatcccc tgctcgcccg   47160
gacctggaac tacgtcagcg gtatcaacac gacgaacgcg gacgggctgg aggtgtaccg   47220
ggacttctgc gtgggccgcg cccaggcgct cgacgagggc gggatcgacc cggccaccat   47280
gcccgcggcc accggtatcg gcgcccacgg gggcggcatc acctgcgtgt tcctcgcgc   47340 ccggggcgga gtgcggatca acatcgagaa ccccgccgtc ctcacggccc accactaccc   47400
gacgacgtac ggtccgcggc ccccggtctt cgcacgggcc acctggctgg gcccgccgga   47460 gggggggccgg ctgttcatct ccgcgacggc cggcatcctc ggacaccgaa cggtgcacca   47520
```

```
cggtgatgtg accggccagt gcgaggtcgc cctcgacaac atggcccggg tcatcggcgc   47580
ggagaacctg cggcgccacg gcgtccagcg ggggcacgtc ctcgccgacg tggaccacct   47640
caaggtctac gtccgccgcc gcgaggatct cgatacggtc cgccgggtct gcgccgcacg   47700
cctgtcgagc accgcggccg tcgccctttt gcacaccgac atagcccgcg aggatctgct   47760
cgtcgaaatc gaaggcatgg tggcgtgaca atacccggta aaaggcccgc gacgctgcgc   47820
ctcggcggat ccgcgaagag aaagaagagc gtcaccgcac agcgcggcag cccggtcctt   47880
tcgtccttcg cacagcggcg gatctggttt ctccagcaat tggacccgga gagcaacgcc   47940
tataatctcc cgctcgtgca acgcctgcgc ggtctattgg acgcgccggc cctggagcgt   48000
gcgctggcgc tcgtcgtcgc gcgccacgag gcgttgcgga cggtgttcga caccgccgac   48060
ggcgagcccc tccagcgggt gcttcccgcc ccggaacacc tcctgcgcca cgcgcgggcg   48120
ggcagcgagg aggacgccgc ccggctcgtc cgcgacgaga tcgccgcgcc gttcgacctc   48180
gccaccgggc cgttgatcag ggccctgctg atccgcctcg gtgacgacga ccacgttctc   48240
gcggtgaccg tgcaccatgt cgccggcgac ggctggtcgt tcgggctcct ccaacatgaa   48300
ctcgcagccc actacacggc gctgcgcgac actgcccgcc ctgccgaact gccgccgttg   48360
ccggtgcagt acgccgactt cgccgcctgg gagcggcgcg aactcaccgg cgccggactg   48420
gacaggcgtc tggcctactg gcgcgagcaa ctccggggcg ccccggcgcg gctcgccctc   48480
cccaccgacc gtccccgccc gccggtcgcc gacgcggacg cgggcatggc cgagtggcgg   48540
ccgccggccg cgctggccac cgcggtcctc acgctcgcgc gcgactccgg tgcgtccgtg   48600
ttcatgaccc tgctggcggc cttccaagcg gtcctcgccc ggcaggcggg cacgcgggac   48660
gtgctggtcg gcacgcccgt ggcgaaccgt acgcgggcgg cgtacgaggg cctgatcggc   48720
atgttcgtca acacgctcgc gctgcgcggc gacctctcgg gcgatccgtc gttccgggaa   48780
ctcctcgacc gctgccgggc cacgaccacg gacgcgttcg cccacgccga cctgccgttc   48840
gagaacgtca tcgaactcgt cgcaccggaa cgcgacctgt cggtcaaccc ggtcgtccag   48900
gtgctgttgc aggtgctgcg gcgcgacgcg gcgacgccg cgctgccgg catcgcggcc   48960
gaaccgttcc gcaccggacg ctggttcacc cgcttcgacc tcgaattcca tgtgtacgag   49020
gagccgggtg gcgcgctgac cggcgaactg ctctacagcc gtgcgctgtt cgacgagcca   49080
cggatcacgg ggttgctgga ggagttcacg gcggtgcttc aggcggtcac cgccgacccg   49140
gacgtacggg tgtcgcggct gccggccggc gacgcgacgg cggcagcgcc cgtggtgccc   49200
tcgaacgaca cggcgcggga cctgcccgtc gacacgctgc cgggcctgct ggcccggtac   49260
gccgcacgca ccccggcgc cgtggccgtc accgacccgc acatctccct cacctacgcg   49320
cagctggacc ggcgggcgaa ccgcctcgcg cacctgctcc gcgcgcgcgg caccgccacc   49380
ggcgacctgg tcgggatctg cgccgatcgc ggcgccgacc tgatcgtcgg catcgtgggg   49440
atcctcaagg cgggcgccgc ttatgtgccg ctggaccccg aacatcctcc ggagcgcacg   49500
gcgttcgtgc tggccgacgc gcagctgacc acggtggtgg cgcacgaggt ctaccgttcc   49560
cggttccccg atgtgccgca cgtggtggcg ttggacgacc cggagctgga ccggcagccg   49620
gacgacacgg cgccggacgt cgagctggac cgggacagcc tcgcctacgc gatctacacg   49680
tccgggtcga ccggcaggcc gaaggccgtg ctcatgccgg gtgtcagcgc cgtcaacctg   49740
ctgtctctgg caggagcgcac gatgggccgc gagccggcca gccgcaccgt ccagttcgtg   49800
acgcccacgt tcgactactc ggtgcaggag atcttttccg cgctgctggg cggcacgctc   49860
```

```
gtcatcccgc cggacgaggt gcggttcgac ccgcccgggac tcgcccggtg gatggacgaa   49920
caggcgatta cccggatcta cgcgccgacg gccgtactgc gcgcgctgat cgagcacgtc   49980
gatccgcaca gcgaccagct cgccgccctg cggcacctgt gccagggcgg cgaggcgctg   50040
atcctcgacg cgcggttgcg cgagctgtgc cggcaccggc cccacctgcg cgtgcacaat   50100
cactacggtc cggccgaaag ccagctcatc accgggtaca cgctgcccgc cgaccccgac   50160
gcgtggcccg ccaccgcacc gatcggcccg ccgatcgaca acacccgcat ccatctgctc   50220
gacgaggcga tgcggccggt tccggacggt atgccggggc agctctgcgt cgccggcgtc   50280
ggcctcgccc gtgggtacct ggcccgtccc gagctgaccg ccgagcgctg ggtgccggga   50340
gatgcggtcg gcgaggagcg catgtacctc accggcgacc tggcccgccg cgcgcccgac   50400
ggcgacctgg aattcctcgg ccggatcgac gaccaggtca agatccgcgg catccgcgtc   50460
gaaccgggtg agatcgagag cctgctcgcc gaggacgccc gcgtcacgca ggcggcggtg   50520
tccgtgcgcg aggaccggcg gggcgagaag ttcctggccg cgtacgtcgt accggtggcc   50580
ggccggcacg gcgacgactt cgccgcgtcg ctgcgcgcgg gactggccgc ccggctgccc   50640
gccgcgctcg tgccctccgc cgtcgtcctg gtggagcgac tgccgaggac cacgagcggc   50700
aaggtggacc ggcgcgcgct gcccgacccg gagccgggcc cggcgtcgac cggggcggtt   50760
acgccccgca ccgatgccga gcggacggtg tgccggatct tccaggaggt gctcgacgtc   50820
ccgcgggtcg gtgccgacga cgacttcttc acgctcggcg ggcactccct gctcgccacc   50880
cgggtcgtct cccgcatccg cgccgagctg ggtgccgatg tcccgctgcg tacgctcttc   50940
gacgggcgga cgcccgccgc gctcgcccgt gcggcggacg aggccggccc ggccgccctg   51000
ccccgatcg cgccctccgc ggagaacggg ccggcccccc tcaccgcggc acaggaacag   51060
atgctgcact cgcacggctc gctgctcgcc gcgccctcct acacggtcgc cccgtacggg   51120
ttccggctgc gcgggccact cgaccgcgaa gcgctcgacg cggcactgac ccggatcgcc   51180
gcgcgccacg agccgctgcg gaccgggttc cgcgatcggg aacaggtcgt ccggccgccc   51240
gctccggtgc gcgccgaggt ggttccggtg ccggtcggcg acgtcgacgc gcgggtccgg   51300
gtcgcccacc gggagctgac ccggccgttc gacctcgtga acgggtcgtt gctgcgtgcc   51360
gtgctgctgc cgctgggcgc cgaggatcac gtgctgctgc tgatgctgca ccacctcgcc   51420
ggtgacggat ggtccttcga cctcctggtc cgggagttgt cggggacgca accggacctt   51480
ccggtgtcct acacgacgt ggccggtgg gaacggagtc cggccgtgat cgcggccagg   51540
gagaacgacc gggcctactg cgcgccggcg ctggggggcg ccaccgcgcc ggagctgccc   51600
gcggtccggc ccggcgggc accgaccggg cgggcgttcc tgtggacgct caaggacacc   51660
gccgtcctgg cggcacgccg ggtcgcggac gcccacgacg cgacgttgca cgaaaccgtg   51720
ctcggcgcct tcgccctggt cgtggcggag accgccgaca ccgacgacgt gctcgtcgcg   51780
acgccgttcg cggaccgggg gtacgccggg accgaccacc tcatcggctt cttcgcgaag   51840
gtcctcgcgc tgcgcctcga cctcggcggc acgccgtcgt tccccgaggt gctgcgccgg   51900
gtgcacaccg cgatggtggg cgcgcacgcc caccaggcgg tgccctactc cgcgctgcgc   51960
gccgaggacc ccgcgctgcc gccggccccc gtgtcgttcc agctcatcag cgcgctcagc   52020
gcggaactgc ggctgcccgg catgcacacc gagccgttcc ccgtcgtcgc cgagaccgtc   52080
gacgagatga ccggcgaact gtcgatcaac ctcttcgacg acggtcgcac cgtctccggc   52140
gcggtggtcc acgatgccgc gctgctcgac cgtgccaccg tcgacgattt gctcacccgg   52200
gtggaggcga cgctgcgtgc cgccgcgggc gacctcaccg tacgcgtcac cggttacgtg   52260
```

```
gaaagcgagt agccatgccc gagcaggaca agacagtcga gtaccttcgc tgggcgaccg    52320
cggaactcca gaagacccgt gcggaactcg ccgcgcacag cgagccgttg gcgatcgtgg    52380
ggatggcctg ccggctgccc ggcggggtcg cgtcgccgga ggacctgtgg cagttgctgg    52440
agtccggtgg cgacggcatc accgcgttcc ccacggaccg gggctgggag accaccgccg    52500
acggtcgcgg cggcttcctc accggggcgg ccggcttcga cgcggcgttc ttcggcatca    52560
gcccgcgcga ggcgctggcg atggacccgc agcagcgcct ggccctggag acctcgtggg    52620
aggcgttcga gcacgcgggc atcgatccgc agacgctgcg gggcagtgac acggggggtgt    52680 tcctcggcgc gttcttccag gggtacggca tcggcgccga cttcgacggt tacggcacca    52740
cgagcattca cacgagcgtg ctctccggcc gcctcgcgta cttctacggt ctggagggtc    52800
cggcggtcac ggtcgacacg gcgtgttcgt cgtcgctggt ggcgctgcac caggccgggc    52860
agtcgctgcg ctccgcgaa tgctcgctcg ccctggtcgg cggcgtcacg gtgatggcct    52920
cgccggcggg gttcgcggac ttctccgagc agggcggcct ggccccgac gcgcgctgca    52980 aggccttcgc ggaagcggct gacggcaccg gtttcgccga ggggtccggc gtcctgatcg    53040
tcgagaagct ctccgacgcc gagcgcaacg gccaccgcgt gctggcggtc gtccggggtt    53100
ccgccgtcaa ccaggacggt gcctccaacg ggctgtccgc gccgaacggg ccgtcgcagg    53160
agcgggtgat ccggcaggcc ctggccaacg ccggactcac cccggcggac gtggacgccg    53220
tcgaggccca cggcaccggc accaggctgg gcgaccccat cgaggcacag gccgtgctgg    53280
ccacctacgg gcaggggcgc gacacccctg tgctgctggg ctcgctgaag tccaacatcg    53340
gccacaccca ggccgccgcg ggcgtcgccg gtgtcatcaa gatggtcctc gccatgcggc    53400
acggcaccct gccccgcacc ctgcacgtgg acacgccgtc ctcgcacgtc gactggacgg    53460
ccggcgccgt cgaactcctc accgacgccc ggcctggcc cgaaaccgac cgcccacggc    53520
gcgccggtgt ctcctccttc ggcgtcagcg gcaccaacgc ccacatcatc ctcgaaagcc    53580
acccccgacc ggccccgaa cccgccccgg cacccgacac cggaccgctg ccgctgctgc    53640
tctcggcccg caccccgcag gcactcgacg cacaggtaca ccgcctgcgc gcgttcctcg    53700
acgacaaccc cggcgcggac cgggtcgccg tcgcgcagac actcgcccgg cgcacccagt    53760
tcgagcaccg cgccgtgctg ctcggcgaca cgctcatcac cgtgagcccg aacgccggcc    53820
gcggaccggt ggtcttcgtc tactcggggc aaagcacgct gcacccgcac accgggcggc    53880
aactcgcgtc cacctacccc gtgttcgccg aagcgtggcg cgaggccctc gaccacctcg    53940
accccaccca gggcccggcc acgcacttcg cccaccagac cgcgctcacc gcgctcctgc    54000
ggtcctgggg catcacccg cacgcggtca tcggccactc cctcggtgag atcaccgccg    54060
cgcacgccgc cggtgtcctg tccctgaggg acgcgggcgc gctcctcacc acccgcaccc    54120
gcctgatgga ccaactgccg tcgggcgcg cgatggtcac cgtcctgacc agcgaggaaa    54180
aggcacgcca ggtgctgcgg ccgggcgtgg agatcgccgc cgtcaacggc ccccactccc    54240
tcgtgctgtc cggggacgag gaagccgtac tcgaagccgc ccggcagctc ggcatccacc    54300
accgcctgcc gacccgccac gccggccact ccgagcgcat gcagccactc gtcgcccccc    54360
tcctcgacgt cgcccggacc ctgacgtacc accagcccca caccgccatc cccggcgacc    54420
ccaccaccgc cgaatactgg gcgcaccagg tccgcgacca agtacgtttc caggcgcaca    54480
ccgagcagta cccgggcgcg acgttcctcg agatcggccc caaccaggac ctctcgccgc    54540
tcgtcgacgg cgttgccgcc cagaccggta cgcccgacga ggtgcgggcg ctgcacaccg    54600
```

```
cgctcgcgca gctccacgtc cgcggcgtcg cgatcgactg gacgctcgtc ctcggcgggg    54660
accgcgcgcc cgtcacgctg cccacgtatc cgttccagca caaggactac tggctgcggc    54720
ccacctcccg ggccgatgtg accgcgcgcg ggcaggagca ggtggcgcac ccgctgctcg    54780
gcgccgcggt cgcgctgccc ggcacgggcg gagtcgtcct gaccggccgc ctgtcgctgg    54840
cctcccatcc gtggctcggc gagcacgcgg tcgacggcac cgtgctcctg cccggcgcgg    54900
ccttcctcga actcgcggcg cgcgccgcg acgaggtcgg ctgcgacctg ctgcacgaac     54960
tcgtcatcga gacgccgctc gtgctgcccg cgaccggcgg tgtggcggtc tccgtcgaga    55020
tcgccgaacc cgacgacacg gggcggcggg cggtcaccgt ccacgcgcgg gccgacggct    55080
cgggcctgtg gacccgacac gccggcggat cctcggcac ggcaccggca ccggccacgg     55140
ccacggaccc ggcaccctgg ccgcccgcgg aagccggacc ggtcgacgtc gccgacgtct    55200
acgaccggtt cgaggacatc gggtactcct acggaccggg cttccggggg ctgcgggccg    55260
cctggcgcgc cggcgacacc gtgtacgccg aggtcgcgct ccccgacgag cagagccgcg    55320
acgccgcccg tttcacgctg caccccgcgc tgctcgacgc cgcgttccag gccggcgcgc    55380
tggccgcgct cgacgcaccc ggcggggcgg cccgactgcc gttctcgttc caggacgtcc    55440
gcatccacgc ggccggggcg acgcggctgc gggtcacggt cggccgcgac ggcgagcgca    55500
gcaccgtccg catgaccggc ccggacgggc agctggtggc cgtggtcggt gccgtgctgt    55560
cgcgcccgta cgcggaaggc tccggtgacg gcctgctgcg cccggtctgg accgagctgc    55620
cgatgcccgt cccgtccgcg gacgatccgc gcgtggaggt cctcggcgcc gacccggggcg    55680
acggcgacgt tccggcggcc acccgggagc tgaccgcccg cgtcctcggc gcgctccagc    55740
gccacctgtc cgccgccgag gacaccacct tggtggtacg gaccggcacc ggcccggccg    55800
ctgccgccgc cgcgggtctg gtccgctcgg cgcaggcgga gaaccccggc cgcgtcgtgc    55860
tcgtcgaggc gtccccggac acctcggtgg agctgctcgc cgcgtgcgcc cgcgctggacg    55920
aaccgcagct ggccgtccgg gacggcgtgc tcttcgcgcc gcggctggtc cggatgtccg    55980
accccgcgca cggcccgctg tccctgccgg acgcgactg gctgctcacc cggtccgcct     56040
ccggcacgtt gcacgacgtc gcgctcatag ccgacgacac gccccggcgg gcgctcgaag    56100
ccggcgaggt ccgcatcgac gtccgcgcgg ccggactgaa cttccgcgat gtgctgatcg    56160
cgctcgggac gtacaccggg gccacggcca tgggcggcga ggccgcgggc gtcgtggtgg    56220
agaccgggcc cggcgtggac gacctgtccc ccggcgaccg ggtgttcggc ctgacccggg    56280
gcggcatcgg cccgacggcc gtcaccgacc ggcgctggct ggcccggatc cccgacggct    56340
ggagcttcac cacggcggcg tccgtcccga tcgtgttcgc gaccgcgtgg tacggcctgg    56400
tcgacctcgg cacactgcgc gccggcgaga aggtcctcgt ccacgcggcc accggcgtg    56460
tcggcatggc cgccgcacag atcgcccgcc acctgggcgc cgagctctac gccaccgcca    56520
gtaccggcaa gcagcacgtc ctgcgcgccg ccgggctgcc cgacacgcac atcgccgact    56580
ctcggacgac cgcgttccgg accgctttcc cgcgcatgga cgtcgtcctg aacgcgctga    56640
ccggcgagtt catcgacgcg tcgctcgacc tgctggacgc cgacgccgg ttcgtcgaga     56700
tgggccgcac cgagctgcgc gaccggccg cgatcgtccc cgcctacctg ccgttcgacc     56760
tgctggacgc gggcgccgac cgcatcgcg agatcctggg cgaactgctc cggctgttcg    56820
acgggggcgc gctggagccg ctgccggtcc gtgcctggga cgtccggcag gcacgcgacg    56880
cgctcggctg gatgagccgc gcccgccaca tcggcaagaa cgtcctgacg ctgccccggc    56940
cgctcgaccc ggagggcgcc gtcgtcctca ccggcggctc cggcacgctc gccggcatcc    57000
```

```
tcgcccgcca cctgcgcgaa cggcatgtct acctgctgtc ccggacggca ccgcccgagg   57060
ggacgcccgg cgtccacctg ccctgcgacg tcggtgaccg ggaccagctg gcggcggccc   57120
tggagcgggt ggaccggccg atcaccgccg tggtgcacct cgccggtgcg ctggacgacg   57180
gcaccgtcgc gtcgctcacc cccgagcgtt tcgacacggt gctgcgcccg aaggccgacg   57240
gcgcctggta cctgcacgag ctgacgaagg agcaggacct cgccgcgttc gtgctctact   57300
cgtcggccgc cggcgtgctc ggcaacgccg gccagggcaa ctacgtcgcc gcgaacgcgt   57360
tcctcgacgc gctcgccgag ctgcgccacg gttcccggct gccggccctc tccatcgcct   57420
gggggctctg ggaggacgtg agcgggctca ccgcggcgct cggcgaagcc gaccgggacc   57480
ggatgcggcg cagcggtttc cgggccatca ccgcgcaaca gggcatgcac ctgtacgagg   57540
cggccggccg caccggaagt cccgtggtgg tcgcggcggc gctcgacgac gcgccggacg   57600
tgccgctgct cgcgcggcctg cggcggacga ccgtccggcg ggccgccgtc cgggagtgtt   57660
cgtccgccga ccggctcgcc gcgctgaccg gcgacgagct cgccgaagcg ctgctgacgc   57720
tcgtccggga gagcaccgcc gccgtgctcg gccacgtggg tggcgaggac atccccgcga   57780
cggcggcgtt caaggacctc ggcatcgact cgctcaccgc ggtccagctg cgcaacgccc   57840
tcaccgaggc gaccggtgtg cggctgaacg ccacggcggt cttcgacttc ccgaccccgc   57900
acgtgctcgc cgggaagctc ggcgacgaac tgaccggcac ccgcgcgccc gtcgtgcccc   57960
ggaccgcggc cacggccggt gcgcacgacg agccgctggc gatcgtggga atggcctgcc   58020 ggctgccccgg cggggtcgcg tcacccgagg agctgtggca cctcgtggca tccggcaccg   58080
acgccatcac ggagttcccg acggaccgcg gctgggacgt cgacgcgatc tacgacccgg   58140
accccgacgg gatcggcaag accttcgtcc ggcacggtgg cttcctcacc ggcgcgacag   58200
gcttcgacgc ggcgttcttc ggcatcagcc cgcgcgaggc cctcgcgatg acccgcagc   58260 agcgggtgct cctggagacg tcgtgggagg cgttcgaaag cgccggcatc accccggact   58320
cgacccgcgg cagcgacacc ggcgtgttcg tcggcgcctt ctcctacggt tacggcaccg   58380
gtgcggacac cgacgcgttc ggcgcgaccg gctcgcagac cagtgtgctc tccggccggc   58440
tgtcgtactt ctacggtctg gagggtccgg cggtcacggt cgacacggcg tgttcgtcgt   58500
cgctggtggc gctgcaccag gccgggcagt cgctgcgctc cggcgaatgc tcgctcgccc   58560
tggtcggcgg cgtcacggtg atggcgtctc ccggcggctt cgtggagttc tcccggcagc   58620
gcggcctcgc gccggacggc cgggcgaagg cgttcggcgc gggtgcggac ggcacgagct   58680
tcgccgaggg tgccggtgtg ctgatcgtcg agaggctctc cgacgccgaa cgcaacggtc   58740
acaccgtcct ggcggtcgtc cgtggttcgg cggtcaacca ggatggtgcc tccaacgggc   58800
tgtcggcgcc gaacgggccg tcgcaggagc gggtgatccg gcaggccctg ccaacgccg   58860 ggctcacccc ggcggacgtg gacgccgtcg aggcccacgg caccggcacc aggctgggcg   58920
accccatcga ggcacaggcg gtactggcca cctacggaca ggagcgcgcc acccccctgc   58980
tgctgggctc gctgaagtcc aacatcggcc acgcccaggc cgcgtccggc gtcgccggca   59040
tcatcaagat ggtgcaggcc ctccggcacg gggagctgcc gccgacgctg cacgccgacg   59100
agccgtcgcc gcacgtcgac tggacggccg gcgccgtcga actgctgacg tcggcccggc   59160
cgtggcccga gaccgaccgg ccacggcgtg ccgccgtctc ctcgttcggg gtgagcgcga   59220
ccaacgccca cgtcatcctg gaggccgac cggtaacgga gacgcccgcg gcatcgcctt   59280
ccggtgacct tcccctgctg gtgtcggcac gctcaccgga agcgctcgac gagcagatcc   59340
```

```
gccgactgcg cgcctacctg gacaccaccc cggacgtcga ccgggtggcc gtggcacaga   59400
cgctggcccg gcgcacacac ttcgcccacc gcgccgtgct gctcggtgac accgtcatca   59460
ccacaccccc cgcggaccgg cccgacgaac tcgtcttcgt ctactccggc cagggcaccc   59520
agcatcccgc gatgggcgag cagctcgccg ccgcccatcc cgtgttcgcc gacgcctggc   59580
atgaagcgct ccgccgcctt gacaacccc g accccacga ccccacgcac agccagcatg   59640
tgctcttcgc ccaccaggcg gcgttcaccg ccctcctgcg gtcctggggc atcccccgc    59700 acgcggtcat cggccactcg ctgggcgaga tcaccgcggc gcacgccgcc ggcatcctgt   59760
cgctggacga cgcgtgcacc ctgatcacca cgcgcgcccg cctcatgcac acgctcccgc   59820
cacccggtgc catggtcacc gtactgacca gcgaagagaa ggcacgccag gcgttgcggc   59880
cgggcgtgga gatcgccgcc gtcaacgggc cccactccat cgtgctgtcc ggggacgagg   59940
acgccgtgct caccgtcgcc gggcagctcg gcatccacca ccgcctgccc gccccgcacg   60000
ccgggcactc cgcgcacatg gagcccgtgg ccgccgagct gctcgccacc acccgcgggc   60060
tccgctacca ccctcccca c acctccattc cgaacgaccc caccaccgct gagtactggg   60120
ccgagcaggt ccgcaagccc gtgctgttcc acgcccacgc gcagcagtac ccggacgccg   60180
tgttcgtgga gatcggcccc gcccaggacc tctccccgct cgtcgacggg atcccgctgc   60240
agaacggcac cgcggacgag gtgcacgcgc tgcacaccgc gctcgcgcac ctctacgcgc   60300
gcggtgccac gctcgactgg ccccgcatcc tcggggctgg gtcacggcac gacgcggatg   60360
tgcccgcgta cgcgttccaa cggcggcact actggatcga gtcggcacgc ccggccgcat   60420
ccgacgcggg ccaccccgtg ctgggctccg gtatcgccct cgccgggtcg ccgggccggg   60480
tgttcacggg ttccgtgccg accggtgcgg accgcgcggt gttcgtcgcc gagctggcgc   60540
tggccgccgc ggacgcggtc gactgcgcca cggtcgagcg gctcgacatc gcctccgtgc   60600
ccggccggcc gggccatggc cggacgaccg tacagacctg ggtcgacgag ccggcggacg   60660
acggccggcg ccggttcacc gtgcacaccc gcaccggcga cgccccgtgg acgctgcacg   60720 ccgaggggg t gctgcgcccc catgcacgg ccctgcccga tgcggccgac gccgagtggc   60780
ccccaccggg cgcggtgccc gcggacgggc tgccgggtgt gtggcgccgg ggggaccagg   60840
tcttcgccga ggccgaggtg gacgaccgg acgtttcgt ggtgcaccc c gacctgctcg   60900 acgcggtctt ctccgcggtc ggcgacggaa gccgccagcc ggccggatgg cgcgacctga   60960
cggtgcacgc gtcggacgcc accgtactgc gcgcctgcct cacccggcgc accgacggag   61020
ccatgggatt cgccgccttc gacggcgccg gcctgccggt actcaccgcg gaggcggtga   61080
cgctgcggga ggtggcgtca ccgtccggct ccgaggagtc ggacggcctg caccggttgg   61140
agtggctcgg ggtcgccgag gcggtctacg acggtgacct gcccgaggga catgtcctga   61200
tcaccgccgc ccaccccgac gaccccgagg acatacccac ccgcgccac acccgcgcca   61260 cccgcgtcct gaccgcccg caacaccacc tcaccaccac cgaccacacc ctcatcgtcc   61320
acaccaccac cgaccccgcc ggcgccaccg tcaccggcct cacccgcacc gcccagaacg   61380
aacaccccca ccgcatccgc ctcatcgaaa ccgaccaccc ccacaccccc ctcccccctgg   61440 cccaactcgc caccctcgac caccccacc tccgcctcac ccaccacacc ctccaccacc   61500
cccacctcac cccctccac accaccaccc cacccaccac caccccctc aacccgaac    61560 acgccatcat catcaccggc ggctccggca ccctcgccgg catcctcgcc cgccacctga   61620
accaccccca cacctacctc ctctcccgca cccacccc c gacgccacc cccggcaccc   61680 acctccctg cgacgtcggc gaccccacc aactcgccac caccctcacc cacatccccc   61740
```

```
aaccccucac cgccatcttc cacaccgccg ccaccctcga cgacggcatc ctccacgccc   61800 tcaccccga ccgcctcacc accgtcctcc accccaaagc caacgccgcc tggcacctgc     61860
accacctcac ccaaaaccaa cccctcaccc acttcgtcct ctactccagc gccgccgccg   61920
tcctcggcag ccccggacaa ggaaactacg ccgccgccaa cgccttcctc gacgccctcg   61980
ccacccaccg ccacaccctc ggccaacccg ccacctccat cgcctggggc atgtggcaca   62040
ccaccagcac cctcaccgga caactcgacg acgccgaccg ggaccgcatc cgccgcggcg   62100
gtttcctccc gatcacggac gacgagggca tgcgcctcta cgaggcggcc gtcggctccg   62160
gcgaggactt cgtcatggcc gccgcgatgg acccggcaca gccgatgacc ggctccgtac   62220
cgcccatcct gagcggcctg cgcaggagcg gcgggcgcgt cgcccgtgcc gggcagacgt   62280
tcgcccagcg gctcgccgag ctgcccgacg ccgaccgcgg cgcggcgctg accaccctcg   62340
tctcggacgc cacggccgcc gtgctcggcc acgccgacgc ctccgagatc gcgccgacca   62400
cgacgttcaa ggacctcggc atcgactcgc tcaccgcgat cgagctgcgc aaccggctcg   62460
cggaggcgac cgggctgcgg ctgagtgcca cgctggtgtt cgaccacccg acacctcggg   62520
tcctcgccgc caagctccgc accgatctgt tcggcacggc cgtgcccacg cccgcgcgga   62580
cggcacggac ccaccacgac gagccactcg cgatcgtcgg catggcgtgc cgactgcccg   62640
gcggggtcgc ctcgccggag gacctgtggc agctcgtggc gtccggcacc gacgcgatca   62700
ccgagttccc caccgaccgc ggctgggaca tcgaccggct gttcgacccg gacccggacg   62760
cccccggcaa gacctacgtc cggcacgcg gcttcctcgc cgaggccgcc ggcttcgatg   62820
ccgcgttctt cggcatcagc ccgcgcgagg cacgggccat ggacccgcag cagcgcgtca   62880
tcctcgaaac ctcctgggag gcgttcgaga acgcgggcat cgtgccggac acgctgcgcg   62940
gcagcgacac cggcgtgttc atgggcgcgt ctcccatgg gtacggcgcc ggcgtcgacc   63000
tgggcgggtt cggcgccacc gccacgcaga acagcgtgct ctccggccgg ttgtcgtact   63060
tcttcggcat ggagggcccg gccgtcaccg tcgacaccgc ctgctcgtcg tcgctggtcg   63120
ccctgcacca ggcggcacag gcgctgcgga ctggagaatg ctcgctggcg ctcgccggcg   63180
gtgtcacggt gatgcccacc ccgctgggct acgtcgagtt ctgccgccag cggggactcg   63240
cccccgacgg ccgttgccag gccttcgcgg aaggcgccga cggcacgagc ttctcggagg   63300
gcgccggcgt tcttgtgctg gagcggctct ccgacgccga gcgcaacgga cacaccgtcc   63360
tcgcggtcgt ccgctcctcc gccgtcaacc aggacgcgc ctccaacggc atctccgcac   63420
ccaacggccc ctcccagcag cgcgtcatcc gccaggccct cgacaaggcc gggctcgccc   63480
ccgccgacgt ggacgtggtg gaggcccacg gcaccgaaac cccgctgggc gacccgatcg   63540
aggcacaggc catcatcgcg acctacggcc aggaccgcga cacccgctc tacctcggtt   63600 cggtcaagtc gaacatcgga cacacccaga ccaccgccgg tgtcgccggc gtcatcaaga   63660
tggtcatggc gatgcgccac ggcatcgcgc cgaagacact gcacgtggac gagccgtcgt   63720
cgcatgtgga ctggaccgag ggtgcggtgg aactgctcac cgaggcgagg ccgtggcccg   63780
acgcgggacg cccgcgccgc gcgggcgtgt cgtcgctcgg tatcagcggt acgaacgccc   63840
acgtgatcct tgagggtgtt cccgggccgt cgcgtgtgga gccgtctgtt gacgggttgg   63900
tgccgttgcc ggtgtcggct cggagtgagg cgagtctgcg ggggcaggtg gagcggctgg   63960
aggggtatct gcgcgggagt gtggatgtgt ccgcggtcgc gcaggggttg gtgcgtgagc   64020
gtgctgtctt cggtcaccgt gcggtactgc tgggtgatgc ccgggtgatg ggtgtggcgg   64080
```

```
tggatcagcc gcgtacggtg ttcgtctttc ccgggcaggg tgctcagtgg gtgggcatgg   64140
gtgtggagtt gatggaccgt tctgcggtgt tcgcggctcg tatggaggag tgtgcgcggg   64200
cgttgttgcc gcacacgggc tgggatgtgc gggagatgtt ggcgcggccg gatgtggcgg   64260
agcgggtgga ggtggtccag ccggccagct gggcggtcgc ggtcagcctg gccgcactgt   64320
ggcaggccca cggggtcgta cccgacgcgg tgatcggaca ctcccagggc gagatcgcgg   64380
cggcgtgcgt ggccggggcc ctcagccttg aggacgccgc ccgcgtggtg gccttgcgca   64440
gccaggtcat cgcggcgcga ctggccgggc ggggagcgat ggcttcggtg cattgccgg    64500 ccggtgaggt cggtctggtc gagggcgtgt ggatcgcggc gcgtaacggc cccgcctcga   64560
cagtcgtggc cggcgagccg tcggcggtgg aggacgtggt gacgcggtat gagaccgaag   64620
gcgtgcgagt gcgtcgtatc gccgtcgact acgcctccca cacgcccac gtggaagcca    64680 tcgaggacga actcgctgag gtactgaagg gagttgcagg gaaggccgcg tcggtggcgt   64740
ggtggtcgac cgtggacagc gcctgggtga ccgagccggt ggatgagagt tactggtacc   64800
ggaacctgcg tcgccccgtc gcgctggacg cggcggtggc ggagctggac gggtccgtgt   64860
tcgtggagtg cagcgcccat ccggtgctgc tgccggcgat ggaacaggcc cacacggtgg   64920
cgtcgttgcg caccggtgac ggcggctggg agcgatggct gacggcgttg gcgcaggcgt   64980
ggaccctggg cgcggcagtg gactgggaca cggtggtcga accggtgcca gggcggctgc   65040
tcgatctgcc cacctacgcg ttcgagcgcc ggcgctactg gctggaagcg gccggtgcca   65100 ccgaccgtc cgcggccggg ctgacagggg cagcacatcc catgctggcc gccatcacgg    65160
cactacccgc cgacgacggt ggtgttgttc tcaccggccg gatctcgttg cgcacgcatc   65220
cctggctggt gatcacgcg gtgcggggca cggtcctgct gccgggcacg gcctttgtgg    65280
agctggtcat ccgggccggt gacgagaccg gttgcgggat agtggatgaa ctggtcatcg   65340
aatcccccct cgtggtgccg gcgaccgcag ccgtggatct gtcggtgacc gtggaaggag   65400
ctgacgaggc cggacggcgg cgagtgaccg tccacgcccg caccgaaggc accggcagct   65460 ggaccccggca cgccagcggc accctgaccc ccgacacccc cgacaccccc aacgcttccg   65520
gtgttgtcgg tgcggagccg ttctcgcagt ggccacctgc cactgccgcg gccgtcgaca   65580
cctcggagtt ctacttgcgc ctggacgcgc tgggctaccg gttcggaccc atgttccgcg   65640
gaatgcgggc tgcctggcgt gatggtgaca ccgtgtacgc cgaggtcgcg ctccccgagg   65700
accgtgccgc cgacgcggac ggtttcggca tgcacccggc gctgctcgac gcggccttgc   65760
agagcggcag cctgctcatg ctggaatcgg acggcgagca gagcgtgcaa ctgccgttct   65820
cctggcacgg cgtccggttc cacgcgacgg gcgcgaccat gctgcgggtg gcggtcgtac   65880
cgggcccgga cggcctccgg ctgcatgccg cggacagcgg gaaccgtccc gtcgcgacga   65940
tcgacgcgct cgtgacccgg tccccggaag cggacctcgc gcccgccgat ccgatgctgc   66000
gggtcgggtg ggccccggtg cccgtacctg ccggggccgg tccgtccgac gcggacgtgc   66060
tgacgctgcg cggcgacgac gccgacccgc tcggggagac ccgggacctg accacccgtg   66120
ttctcgacgc gctgctccgg gccgaccggc cggtgatctt ccaggtgacc ggtggcctcg   66180
ccgccaaggc ggccgcaggc ctggtccgca ccgctcagaa cgagcagccc ggccgcttct   66240
tcctcgtcga aacggacccg ggagaggtcc tggacgcgc gaagcgcgac gcgatcgcgg    66300
cactcggcga gccccatgtg cggctgcgcg acggcctctt cgaggcagcc cggctgatgc   66360
gggccacgcc gtccctgacg ctcccggaca ccgggtcgtg gcagctgcgg ccgtccgcca   66420
ccggttccct cgacgacctt gccgtcgtcc ccaccgacgc cccggaccgg ccgctcgcgg   66480
```

```
ccggcgaggt gcggatcgcg gtacgcgcgg cgggcctgaa cttccgggat gtcacggtcg   66540
cgctcggtgt ggtcgccgat gcgcgtccgc tcggcagcga ggccgcgggt gtcgtcctgg   66600
agaccggccc cggtgtgcac gacctggcgc ccggcgaccg ggtcctgggg atgctcgcgg   66660
gcgccttcgg accggtcgcg atcaccgacc ggcggctgct cggccggatg ccggacggct   66720
ggacgttccc gcaggcggcg tccgtgatga ccgcgttcgc gaccgcgtgg tacgcctgg    66780 tcgacctggc cgggctgcgc cccggcgaga aggtcctgat ccacgcggcg cgaccggtg    66840 tcggcgcggc ggccgtccag atcgcgcggc atctgggcgc ggaggtgtac gcgaccacca   66900
gcgccgcgaa gcgccatctg gtggacctgg acggagcgca tctggccgat tcccgcagca   66960
ccgcgttcgc cgacgcgttc ccgccggtcg atgtcgtgct caactcgctc accggtgaat   67020
tcctcgacgc gtccgtcggc ctgctcgcgg cgggtggccg gttcatcgag atggggaaga   67080
cggacatccg gcacgccgtc cagcagccgt tcgacctgat ggacgccggc cccgaccgga   67140
tgcagcggat catcgtcgag ctgctcggcc tgttcgcgcg cgacgtgctg cacccgctgc   67200
cggtccacgc ctgggacgtg cggcaggcgc gggaggcgtt cggctggatg agcagcgggc   67260
gtcacaccgg caagctggtg ctgacggtcc cgcggccgct ggatcccgag ggggccgtcg   67320
tcatcaccgg cggctccggc accctcgccg gcatcctcgc ccgccacctg gccacccccc   67380
acacctacct gctctcccgc accccacccc ccgacaccac cccggcacc cacctcccct   67440 gcgacgtcgg cgaccccac caactcgcca cccctcgc ccgcatcccc caaccctca    67500 ccgccgtctt ccacaccgcc ggaaccctcg acgacgccct gctcgacaac ctcacccccg   67560
accgcgtcga caccgtcctc aaacccaagg ccgacgccgc ctggcacctg caccggctca   67620
cccgcgacac cgacctcgcc gcgttcgtcg tctactccgc ggtcgccggc ctcatgggca   67680
gcccggggca gggcaactac gtcgcggcga acgcgttcct cgacgcgctc gccgaacacc   67740
gccgtgcgca agggctgccc gcgcagtccc tcgcatgggg catgtgggcg gacgtcagcg   67800
cgctcaccgc gaaactcacc gacgcggacc gccagcgcat ccggcgcagc ggattcccgc   67860
cgttgagcgc cgcggacggc atgcggctgt tcgacgcggc gacgcgtacc ccggaaccgg   67920
tcgtcgtcgc gacgaccgtc gacctcaccc agctcgacgg cgccgtcgcg ccgttgctcc   67980
gcggtctggc cgcgcaccgg gccgggccgg cgcgcacggt cgcccgcaac gccggcgaag   68040
agcccctggc cgtgcgtctt gccgggcgta ccgccgccga gcagcggcgc atcatgcagg   68100
aggtcgtgct ccgccacgcg gccgcggtcc tcgcgtacgg gctgggcgac cgcgtggcgg   68160
cggaccgtcc gttccgcgag ctcggtttcg attcgctgac cgcggtcgac ctgcgcaatc   68220 ggctcgcgg cgagacgggg ctgcggctgc cgacgacgct ggtgttcagc cacccgacgg   68280
cggaggcgct caccgcccac ctgctcgacc tgatcgacgc tcccaccgcc cggatcgccg   68340
gggagtccct gcccgcggtg acggccgctc ccgtggcggc cgcgcgggac caggacgagc   68400
cgatcgccat cgtggcgatg gcgtgccggc tgcccggtgg tgtgacgtcg cccgaggacc   68460
tgtggcggct cgtcgagtcc ggcaccgacg cgatcaccac gcctcctgac gaccgcggct   68520
gggacgtcga cgcgctgtac gacgcggacc cggacgcggc cggcaaggcg tacaacctgc   68580
ggggcggtta cctggccggg gcggcggagt tcgacgcggc gttcttcgac atcagtccgc   68640
gcgaagcgct cggcatggac ccgcagcaac gcctgctgct cgaaacgcg tgggaggcga    68700 tcgagcgcgg ccggatcagt ccggcgtcgc tccgcggccg ggaggtcggc gtctatgtcg   68760
gtgcggccgc gcagggctac gggctgggcg ccgaggacac cgagggccac gcgatcaccg   68820
```

```
gtggttccac gagcctgctg tccggacggc tggcgtacgt gctcgggctg gagggcccgg   68880
cggtcaccgt ggacacggcg tgctcgtcgt ctctggtcgc gctgcatctg gcgtgccagg   68940
ggctgcgcct gggcgagtgc gaactcgctc tggccggagg ggtctccgta ctgagttcgc   69000
cggccgcgtt cgtggagttc tcccgccagc gcgggctcgc ggccgacggg cgctgcaagt   69060
cgttcggcgc gggcgcggac ggcacgacgt ggtccgaggg cgtgggcgtg ctcgtactgg   69120
aacggctctc cgacgccgag cggctcgggc acaccgtgct cgccgtcgtc cgcggcagcg   69180
ccgtcacgtc cgacgcgcc tccaacggcc tcaccgcgcc gaacgggctc tcgcagcagc   69240
gggtcatccg gaaggcgctc gccgcggccg ggctgaccgg cgccgacgtg gacgtcgtcg   69300
aggggcacgg caccggcacc cggctcggcg acccggtcga ggcggacgcg ctgctcgcga   69360
cgtacgggca ggaccgtccg gcaccggtct ggctgggctc gctgaagtcg aacatcggac   69420
atgccacggc cgcggccggt gtcgcgggcg tcatcaagat ggtgcaggcg atcggcgcgg   69480
gcacgatgcc gcgacgctg catgtggagg agccctcgcc cgccgtcgac tggagcaccg   69540
gacaggtgtc cctgctcggc tccaaccggc cctggccgga cgacgagcgt ccgcgccggg   69600
cggccgtctc cgcgttcggg ctcagcggga cgaacgcgca cgtcatcctg gaacagcacc   69660
gtccggcgcc cgtggcgtcc cagccgcccc ggccgccccg tgaggagtcc cagccgctgc   69720
cgtgggtgct ctccgcgcgg actccggccg cgctgcgggc ccaggcggcc cggctgcgcg   69780
accacctcgc ggcggcaccg gacgcggatc cgttggacat cgggtacgcg ctggccacca   69840
gccgcgccca gttcgcccac cgtgccgcgg tcgtcgccac caccccggac ggattccgtg   69900
ccgcgctcga cggcctcgcg gacggcgcgg aggcgcccgg agtcgtcacc gggaccgctc   69960
aggagcggcg cgtcgccttc ctcttcgacg gccaggcgc ccagcgcgcc ggaatggggc   70020
gcgagctcca ccgccggttc cccgtcttcg ccgccgcgtg ggacgaggtc tccgacgcgt   70080
tcggcaagca cctcaagcac tcccccacgg acgtctacca cggcgaacac ggcgctctcg   70140
cccatgacac cctgtacgcc caggccggcc tgttcacgct cgaagtggcg ctgctgcggc   70200
tgctggagca ctgggggtg cggccggacg tgctcgtcgg gcactccgtc ggcgaggtga   70260
ccgcggcgta cgcggcgggg gtgctcaccc tggcggacgc gacggagttg atcgtggccc   70320
ggggggcgggc gctgcgggcg ctgccgcccg ggcgatgct cgccgtcgac ggaagcccgg   70380
cggaggtcgg cgcccgcacg gatctggaca tcgccgcggt caacggcccg tccgccgtgg   70440
tgctcgccgg ttcgcggac gatgtggcg cgttcgaacg ggagtggtcg gcggccgggc   70500
ggcgcacgaa acgctcgac gtcgggcacg cgttccactc ccggcacgtc gacggtgcgc   70560
tcgacggctt ccgtacggtg ctggagtcgc tcgcgttcgg cgcggcgcgg ctgccggtgg   70620
tgtccacgac gacgggccgg gacgccgcgg acgacctcat aacgcccgcg cactggctgc   70680
gccatgcgcg tcggccggtg ctgttctcgg atgccgtccg ggagctggcc gaccgcggcg   70740
tcaccacgtt cgtggccgtc ggcccctccg gctccctggc gtcggccgcg gcggagagcg   70800
ccggggagga cgccgggacc taccacgcgg tgctgcgcgc ccggaccggt gaggagaccg   70860
cggcgctgac cgccctcgcc gagctgcacg cccacgcgt cccggtcgac ctggccgcgg   70920
tactggccgg tggccggcca gtggaccttc ccgtgtacgc gttccagcac cgttcctact   70980
ggctggcccc ggccgtggcg ggggcgccgg ccaccgtggc ggacaccggg ggtccggcgg   71040
agtccgagcc ggaggacctc accgtcgccg agatcgtccg tcgcgcacc gcggcgctgc   71100
tcggcgtcac ggaccccgcc gacgtcgatg cggaagcgac gttcttcgcg ctcggtttcg   71160
actcactggc ggtgcagcgg ctgcgcaacc agctcgcctc ggcaaccggg ctggacctgc   71220
```

```
cggcggccgt cctgttcgac cacgacaccc cggccgcgct caccgcgttc ctccaggacc    71280
ggatcgaggc cggccaggac cggatcgagg ccggcgagga cgacgacgcg cccaccgtgc    71340
tctcgctcct ggaggagatg gagtcgctcg acgccgcgga catcgcggcg acgccggccc    71400
cggagcgtgc ggccatcgcc gatctgctcg acaagctcgc ccatacctgg aaggactacc    71460
gatgagcacc gatacgcacg agggaacgcc gcccgccggc cgctgcccat tcgcgatcca    71520
ggacggtcac cgcgccatcc tggagagcgg cacggtgggt tcgttcgacc tgttcggcgt    71580
caagcactgg ctggtcgccg ccgccgagga cgtcaagctg gtcaccaacg atccgcggtt    71640
cagctcggcc gcgccgtccg agatgctgcc cgaccggcgg cccggctggt tctccgggat    71700
ggactcaccg gagcacaacc gctaccggca gaagatcgcg ggggacttca cactgcgcgc    71760
ggcgcgcaag cgggaggact tcgtcgccga ggccgccgac gcctgcctgg acgacatcga    71820
ggccgcggga cccggcaccg acctcatccc cgggtacgcc aagcggctgc cctccctcgt    71880
catcaacgcg ctgtacgggc tcacccctga ggagggggcc gtgctggagg cacggatgcg    71940
cgacatcacc ggctcggccg atctggacag cgtcaagacg ctgaccgacg acttcttcgg    72000
gcacgcgctg cggctggtcc gcgcgaagcg tgacgagcgg ggcgaggacc tgctgcaccg    72060
gctggcctcg gccgacgacg gcgagatctc gctcagcgac gacgaggcga cgggcgtgtt    72120
cgcgacgctg ctgttcgccg gccacgactc ggtgcagcag atggtcggct actgcctcta    72180
cgcactgctc agccaccccg agcagcaggc ggcgctgcgc gcgcgccgg agctggtcga    72240 caacgcggtc gaggagatgc tccgtttcct gcccgtcaac cagatgggcg taccgcgcgt    72300
ctgtgtcgag gacgtcgatg tgcggggcgt gcgcatccgt gcgggcgaca acgtgatccc    72360
gctctactcg acgccaacc gcgacccga ggtgttcccg cagcccgaca ccttcgatgt    72420
gacgcgcccg ctggagggca acttcgcgtt cggccacggc attcacaagt gtcccggcca    72480
gcacatcgcc cgggtgctca tcaaggtcgc ctgcctgcgg ttgttcgagc gtttcccgga    72540
cgtccggctg gccggcgacg tgccgatgaa cgaggggctc gggctgttca gcccggccga    72600
gctgcgggtc acctgggggg cggcatgagt caccccgtgg agacgttgcg gttgccgaac    72660
gggacgacgg tcgcgcacat caacgcgggc gaggcgcagt tcctctaccg ggagatcttc    72720
acccagcgct gctacctgcg ccacggtgtc gacctgcgcc cgggggacgt ggtgttcgac    72780
gtcggcgcga acatcggcat gttcacgctt ttcgcgcatc tggagtgtcc tggtgtgacc    72840
gtgcacgcct tcgagcccgc gcccgtgccg ttcgcggcgc tgcgggcgaa cgtgacgcgg    72900
cacggcatcc cgggccaggc ggaccagtgc gcggtctccg acagctccgg cacccggaag    72960
atgaccttct atcccgacgc cacgctgatg tccggtttcc acgcggatgc cgcggcccgg    73020
acggagctgt tgcgcacgct cggcctcaac ggcggctaca ccgccgagga cgtcgacacc    73080
atgctcgcgc aactgcccga cgtcagcgag gagatcgaaa cccctgtggt ccggctctcc    73140
gacgtcatcg cggagcgcgg tatcgaggcc atcggcctgc tgaaggtcga cgtggagaag    73200
agcgaacggc aggtcttcgc cggcctcgag gacaccgact ggccccgtat ccgccaggtc    73260
gtcgcggagg tccacgacat cgacggccgc ctcgaggagg tcgtcacgct gctccgcggc    73320
catggcttca ccgtggtcgc cgagcaggaa ccgctgttcg ccggcacggg catccaccag    73380
gtcgccgcgc ggcgggtggc cggctgagcg ccgtcggggc gcggccgtc cgcaccggcg    73440 gccgcggtgc ggacggcggc tcagccggcg tcggacagtt ccttgggcag ttgctgacgg    73500
cccttcaccc ccagcttgcg gaacacgttg gtgaggtgct gttccaccgt gctggaggtg    73560
```

```
acgaacagct ggctggcgat ctccttgttg gtgcgcccga ccgcggcgtg cgacgccacc    73620
cgccgctccg cctcggtcag cgatgtgatc cgctgcgccg gcgtcacgtc ctgggtgccg    73680
tccgcgtccg aggactcccc accgagccgc cggaggagcg gcacggctcc gcactgggtc    73740
gcgaggtgcc gtgcgcggcg gaacagtccc cgcgcacggc tgtgccgccg gagcatgccg    73800
cacgcttcgc ccatgtcggc gaggacgcgg gccagctcgt actggtcgcg gcacatgatg    73860
agcagatcgg cggcctcgtc gagcagttcg atccgcttgg ccggcggact gtaggccgcc    73920
tgcacccgca gcgtcatcac ccgcgcccgg gacccatcg gccgggacag ctgctcggag     73980
atgagcctca gccccctcgtc acggccgcgg ccgagcagca gaagcgcttc ggcggcgtcg    74040
acccgccaca gggccaggcc cggcacgtcg acggaccagc gtcgcatccg ctccccgcag    74100
tcccggaacg cgttgtacgc cgcccggtac cgcccggccg cgagatggtg ttgcccacgg    74160
gcccagacca tgtgcagtcc gaagaggctg tcggaggtct cctccggcaa cggctcggcg    74220
agccaccgct ccgccggtc caggtcgccc agtcggatcg cggcggccac ggtgctgctc      74280
agcggcaatg cggcggccat ccccaggag ggcacgaccc gggggggcgag cgcggcctcg     74340
ccgcattcga cggcggcggt caggtcgccg cggcgcagcg cggcctcggc gcggaaccc      74400
gcgtggaccg cctcgtcggc cggggtccgc atgttgtcgt caccggccag cttgtcgacc    74460
caggactgga cggcatcggt gtcctcggcg tagagcaggg ccagcaacgc catcatggtc    74520
gtggtccggt ccgtcgtgac ccgggagtgc tggagcacgt actcggcttt ggcctcggcc    74580
tgttcggacc agccgcgcag cgcgttgctc agggccttgt cggcgacggc gcggtgccgg    74640
acggctccgg aaaacgaggc gacctcgtcc tcggccggcg gatcggccgg acgcggcgga    74700
tcggccgcgc cgggatagat cagcgcgagg gacaggtccg cgacgcgcag gtgcgcccgg    74760
ccctgctcgc tcggggcggc ggagcgctgg gccgccagga cctcggcggc ctcgcccggc    74820
cgcccgtcca tcgccagcca gcaggcgagc gacacgcgcg gctcgctgga gaggagccgt    74880
tcccgcgacg cggtgagcag ctcgggcaca tgccggccgg atctggcggg atcgcagagc    74940
cgctcgatgg cggcggtgtc gacgcgcagt gcggcgtgga cggcggggtc gtcggaggcc    75000
cggtaggcga actccaggta ggtgacggcc tcgtcgagct cgccgcgcag gtggtgctcg    75060
cgcgcggcgt cggtgaacag cccggcgacc tcggcgccgt gcaccggcc ggtacccatc     75120
tggtggcggg cgagcacctt gctggccacg ccgcggtccc gcagcagttc cagcgccagc    75180
tcgtgcaggc cacgccgctc ggcggcggag aggtcgtcga gtacgacgga gcggccgcg     75240
gggtgcggga accgcccttc ccgcagcagc cgcccctcga ccagctgttc gtgggcctgc    75300
tcgaccgcct cggtgtcgag gccggtcatc cgctggacga gggtgagttc gacactctcg    75360
ccgagcacgg cggaagctcg ggcgacgctc agcgcggccg ggccgcaacg atagagcgac    75420
ccgaggtagg cgagccggta cgcccgcccc gcgaccactt ccaggcaccc tgaggtccgt    75480
gtccgtgcct cccggatgtc gtcgatcagg ccgtggccga ggagcaggtt gccgccggtc    75540
gcccggaacg cctgggccac cacgtcgtcg tgcgcgtcct ggccgaggtg ccggcgcacg    75600
agttcggtgg tctgcgcctc ggtgagcggg cgcagcgcga tctcctggta gtggcgcaga    75660
ctcagcagtg ccgcccggaa ttgggagtgg gcgggcgtcg gccggagcag ctcggtcagc    75720
acgatggcga cacgggcccg gctgatgcgg cgcgcgaggt ggagcaggca gcgcagcgac    75780
ggcgcgtcgg cgtggtgcac gtcgtcgatg ccgatcagta cgggccgctc cgcggcgagc    75840
gtcagcaccg tgcgggtgag ttcggtcccc aggcggttgt cgacgtcggc cggcaggttt    75900
tcgcacgatg ccgtcagccg gaccagctcc ggtgtccggg cggccagctc gggctggtcg    75960
```

-continued

```
aggagctggc cgagcatgcc gtacggcagg gcccgctcct ccatggagca caccgcgcga    76020
agggtgacga agccggcctt ggccgcggcg gcgtcgagga gttcggtctt gccgcaggcg    76080
atcggcccgg tgacggcggc gacgacgccc cgcccgcccc ccgctcgggt gagcgcccgg    76140
tggagggaac cgaactcgtc atcgcgggcg atcaggtctg ggggagataa gcgcgctatc    76200
acgaatggaa ctacctcgcg accgtcgtgg aaacccatag gcatcacatg gcttgttgat    76260
ctgtacggct gtgattcagc ctggcgggat gctgtgctac agatgggaag atgtgatcta    76320
gggccgtgcc gttccctcag gagccgaccg ccccgccgc cacccgccgt accccctggg    76380
ccaccagctc ggcgacccgc tcctggtggt cgacgaggta gaagtgcccg ccggggaaga    76440
cctccaccgt ggtcggcgcg gtcgtgtgcc cggcccaggc gtgggcctgc tccaccgtcg    76500
tcttcggatc gtcgtcaccg atgcacaccg tgatcggcgt ctccagcggc ggcgcgggct    76560
cccaccggta cgtctccgcc gcgtagtagt ccgcccgcaa cggcgccagg atcagcgcgc    76620
gcatttcgtc gtccgccatc acatcggcgc tcgtcccgcc gaggccgatg accgccgcca    76680
gcagctcgtc gtcggacgcg aggtggtcct ggtcggcgcg cggctgcgac ggcgcccgcc    76740
ggcccgagac gatcaggtgc gccaccggga gccgctgggc cagctcgaac gcgagtgtcg    76800
cgcccatgct gtggccgaac agcaccagcg gacggtccag ccccggcttc aacgcctcgg    76860
ccacgaggcc ggcgagaaca cgcaggtcgc gcaccgcctc ctcgtcgcgg cggtcctggc    76920
ggccggggta ctgcacggcg tacacgtccg ccaccggggc gagcgcacgg gccagcggaa    76980
ggtagaacgt cgccgatccg ccggcgtggg gcagcagcac cacccgtacc ggggcctcgg    77040
gcgtggggaa gaactgccgc agccagagtt ccgagctcac cgcacccct cggccgcgac    77100 ctggggagcc cggaaccggg tgatctcggc caagtgcttc tcccgcatct ccgggtcggt    77160
cacgccccat ccctcctccg gcgccagaca gaggacgccg actttgccgt tgtgcacatt    77220
gcgatgcaca tcgcgcaccg ccgacccgac gtcgtcgagc gggtaggtca ccgacagcgt    77280
cgggtgcacc atccccttgc agatcaggcg gttcgcctcc cacgcctcac gatagttcgc    77340
gaagtgggta ccgatgatcc gcttcacgga catccacagg taccgattgt caaaggcgtg    77400
ctcgtatccc gaggttgacg cgcaggtgac gatcgtgcca ccccgacgtg tcacgtagac    77460
actcgcgccg aacgtcgcgc gccccgggtg ctcgaacacg atgtcgggat cgtcaccgcc    77520
ggtcagctcc cggatc                                                   77536
```

<210> SEQ ID NO 2
<211> LENGTH: 360
<212> TYPE: PRT
<213> ORGANISM: Streptomyces sp.

<400> SEQUENCE: 2

```
Met Thr Ile Val Lys Cys Leu Val Trp Asp Leu Asp Asn Thr Leu Trp
1               5                   10                  15

Arg Gly Thr Val Leu Glu Asp Asp Glu Val Val Leu Thr Asp Glu Ile
            20                  25                  30

Arg Glu Val Ile Thr Thr Leu Asp Asp Arg Gly Ile Leu Gln Ala Val
        35                  40                  45

Ala Ser Lys Asn Asp His Asp Leu Ala Trp Glu Arg Leu Glu Arg Leu
    50                  55                  60

Gly Val Ala Glu Tyr Phe Val Leu Ala Arg Ile Gly Trp Gly Pro Lys
65                  70                  75                  80

Ser Gln Ser Val Arg Glu Ile Ala Thr Glu Leu Asn Phe Ala Pro Thr
```

```
                        85                  90                  95
Thr Ile Ala Phe Ile Asp Asp Gln Pro Ala Glu Arg Ala Glu Val Ala
            100                 105                 110

Phe His Leu Pro Glu Val Arg Cys Tyr Pro Ala Glu Gln Ala Ala Thr
            115                 120                 125

Leu Leu Ser Leu Pro Glu Phe Ser Pro Val Ser Thr Val Asp Ser
        130                 135                 140

Arg Arg Arg Arg Leu Met Tyr Gln Ala Gly Phe Ala Arg Asp Gln Ala
145                 150                 155                 160

Arg Glu Ala Tyr Ser Gly Pro Asp Glu Asp Phe Leu Arg Ser Leu Asp
                165                 170                 175

Leu Ser Met Thr Ile Ala Pro Ala Gly Glu Glu Leu Ser Arg Val
        180                 185                 190

Glu Glu Leu Thr Leu Arg Thr Ser Gln Met Asn Ala Thr Gly Val His
            195                 200                 205

Tyr Ser Asp Ala Asp Leu Arg Ala Leu Leu Thr Asp Pro Ala His Glu
        210                 215                 220

Val Leu Val Val Thr Met Gly Asp Arg Phe Gly Pro His Gly Ala Val
225                 230                 235                 240

Gly Ile Ile Leu Leu Glu Lys Lys Pro Ser Thr Trp His Leu Lys Leu
                245                 250                 255

Leu Ala Thr Ser Cys Arg Val Val Ser Phe Gly Ala Gly Ala Thr Ile
            260                 265                 270

Leu Asn Trp Leu Thr Asp Gln Gly Ala Arg Ala Gly Ala His Leu Val
        275                 280                 285

Ala Asp Phe Arg Arg Thr Asp Arg Asn Arg Met Met Glu Ile Ala Tyr
    290                 295                 300

Arg Phe Ala Gly Phe Ala Asp Ser Asp Cys Pro Cys Val Ser Glu Val
305                 310                 315                 320

Ala Gly Ala Ser Ala Ala Gly Val Glu Arg Leu His Leu Glu Pro Ser
                325                 330                 335

Ala Arg Pro Ala Pro Thr Thr Leu Thr Leu Thr Ala Ala Asp Ile Ala
            340                 345                 350

Pro Val Thr Val Ser Ala Ala Gly
        355                 360

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
ctagtgggca gatctggcag ct                                         22

<210> SEQ ID NO 4
<211> LENGTH: 14
<212> TYPE: DNA
<213> ORGANISM: Artificial Sequence
<220> FEATURE:
<223> OTHER INFORMATION: primer

<400> SEQUENCE: 4
gccagatctg ccca                                                  14

<210> SEQ ID NO 5
```

```
<211> LENGTH: 12
<212> TYPE: DNA
<213> ORGANISM: Artificial Sequence
<220> FEATURE:
<223> OTHER INFORMATION: primer

<400> SEQUENCE: 5
gggatgcatg gc                                                              12

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
ttaagccatg catccccatg                                                      20

<210> SEQ ID NO 7
<211> LENGTH: 24
<212> TYPE: DNA
<213> ORGANISM: Artificial Sequence
<220> FEATURE:
<223> OTHER INFORMATION: primer

<400> SEQUENCE: 7
cgactcacta gtgggcagat ctgg                                                 24

<210> SEQ ID NO 8
<211> LENGTH: 29
<212> TYPE: DNA
<213> ORGANISM: Artificial Sequence
<220> FEATURE:
<223> OTHER INFORMATION: primer

<400> SEQUENCE: 8
cacgcctagg ccggtcggtc tcgggccac                                            29

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
gcggctagct gctcgcccat cgcgggatgc                                           30

<210> SEQ ID NO 10
<211> LENGTH: 35
<212> TYPE: DNA
<213> ORGANISM: Artificial Sequence
<220> FEATURE:
<223> OTHER INFORMATION: primer

<400> SEQUENCE: 10
gatgtacagc tcgagtcggc acgcccggcc gcatc                                     35

<210> SEQ ID NO 11
<211> LENGTH: 23
<212> TYPE: DNA
<213> ORGANISM: Artificial Sequence
<220> FEATURE:
<223> OTHER INFORMATION: primer

<400> SEQUENCE: 11
```

```
cgactcactt aagccatgca tcc                                                 23

<210> SEQ ID NO 12
<211> LENGTH: 31
<212> TYPE: DNA
<213> ORGANISM: Artificial Sequence
<220> FEATURE:
<223> OTHER INFORMATION: primer

<400> SEQUENCE: 12
atcctaggcg ggcrggygtg tcgtccttcg g                                        31

<210> SEQ ID NO 13
<211> LENGTH: 32
<212> TYPE: DNA
<213> ORGANISM: Artificial Sequence
<220> FEATURE:
<223> OTHER INFORMATION: primer

<400> SEQUENCE: 13
atgctagccg ccgcgttccc cgtcttcgcg cg                                       32

<210> SEQ ID NO 14
<211> LENGTH: 32
<212> TYPE: DNA
<213> ORGANISM: Artificial Sequence
<220> FEATURE:
<223> OTHER INFORMATION: primer

<400> SEQUENCE: 14
atgctagcgg attcgtcggt ggtgttcgcc ga                                       32

<210> SEQ ID NO 15
<211> LENGTH: 31
<212> TYPE: DNA
<213> ORGANISM: Artificial Sequence
<220> FEATURE:
<223> OTHER INFORMATION: primer

<400> SEQUENCE: 15
atctcgagcc agtascgctg gtgytggaag g                                        31

<210> SEQ ID NO 16
<211> LENGTH: 4478
<212> TYPE: DNA
<213> ORGANISM: Artificial Sequence
<220> FEATURE:
<223> OTHER INFORMATION: primer

<400> SEQUENCE: 16
agatctggca gctcgccgaa gcgctgctga cgctcgtccg ggagagcacc gccgccgtgc         60
tcggccacgt gggtggcgag gacatccccg cgacggcggc gttcaaggac ctcggcatcg        120
actcgctcac cgcggtccag ctgcgcaacg ccctcaccga ggcgaccggt gtgcggctga        180
acgccacggc ggtcttcgac ttcccgaccc gcacgtgctc gccgggaag ctcggcgacg         240 aactgaccgg cacccgcgcg cccgtcgtgc cccggaccgc ggccacggcc ggtgcgcacg        300
acgagccgct ggcgatcgtg ggaatggcct gccggctgcc cggcggggtc gcgtcacccg        360
aggagctgtg gcacctcgtg gcatccggca ccgacgccat cacggagttc ccgacggacc        420
gcggctggga cgtcgacgcg atctacgacc cggaccccga cgcgatcggc aagaccttcg        480
tccggcacgg tggcttcctc accggcgcga caggcttcga cgcggcgttc ttcggcatca        540
```

```
gcccgcgcga ggccctcgcg atggacccgc agcagcgggt gctcctggag acgtcgtggg    600
aggcgttcga aagcgccggc atcaccccgg actcgacccg cggcagcgac accggcgtgt    660
tcgtcggcgc cttctcctac ggttacggca ccggtgcgga caccgacggc ttcggcgcga    720
ccggctcgca gaccagtgtg ctctccggcc ggctgtcgta cttctacggt ctggagggtc    780
cggcggtcac ggtcgacacg gcgtgttcgt cgtcgctggt ggcgctgcac caggccgggc    840
agtcgctgcg ctccggcgaa tgctcgctcg ccctggtcgg cggcgtcacg gtgatggcgt    900
ctcccggcgg cttcgtggag ttctcccggc agcgcggcct cgcgccggac ggccgggcga    960
aggcgttcgg cgcgggtgcg gacggcacga gcttcgccga gggtgccggt gtgctgatcg   1020
tcgagaggct ctccgacgcc gaacgcaacg gtcacaccgt cctggcggtc gtccgtggtt   1080
cggcggtcaa ccaggatggt gcctccaacg ggctgtcggc gccgaacggg ccgtcgcagg   1140
agcgggtgat ccggcaggcc ctggccaacg ccgggctcac ccggcggac gtggacgccg   1200 tcgaggccca cggcaccggc accaggctgg gcgaccccat cgaggcacag gcggtactgg   1260
ccacctacgg acaggagcgc gccacccccc tgctgctggg ctcgctgaag tccaacatcg   1320
gccacgccca ggccgcgtcc ggcgtcgccg gcatcatcaa gatggtgcag gccctccggc   1380
acggggagct gccgccgacg ctgcacgccg acgagccgtc gccgcacgtc gactggacgg   1440
ccggcgccgt cgaactgctg acgtcggccc ggccgtggcc cgagaccgac cggcctaggc   1500
gggcaggcgt gtcgtccttc gggatcagtg gcaccaacgc ccacgtcatc ctggaaagcg   1560 cacccccccac tcagcctgcg gacaacgcgg tgatcgagcg ggcaccggag tgggtgccgt   1620
tggtgatttc ggccaggacc cagtcggctt tgactgagca cgagggccgg ttgcgtgcgt   1680
atctggcggc gtcgcccggg gtggatatgc gggctgtggc atcgacgctg gcgatgacac   1740
ggtcggtgtt cgagcaccgt gccgtgctgc tgggagatga caccgtcacc ggcaccgctg   1800
tgtctgaccc tcgggcggtg ttcgtcttcc cgggacaggg gtcgcagcgt gctggcatgg   1860
gtgaggaact ggccgccgcg ttccccgtct tcgcgcggat ccatcagcag gtgtgggacc   1920
tgctcgatgt gcccgatctg gaggtgaacg agaccggtta cgcccagccg gccctgttcg   1980
caatgcaggt ggctctgttc gggctgctgg aatcgtgggg tgtacgaccg gacgcggtga   2040
tcggccattc ggtgggtgag cttgcggctg cgtatgtgtc cggggtgtgg tcgttggagg   2100
atgcctgcac tttggtgtcg gcgcgggctc gtctgatgca ggctctgccc gcgggtgggg   2160
tgatggtcgc tgtcccggtc tcggaggatg aggcccgggc cgtgctgggt gagggtgtgg   2220
agatcgccgc ggtcaacggc ccgtcgtcgg tggttctctc cggtgatgag gccgccgtgc   2280
tgcaggccgc ggaggggctg gggaagtgga cgcggctggc gaccagccac gcgttccatt   2340
ccgcccgtat ggaacccatg ctggaggagt tccggcggg cgccgaaggc ctgacctacc   2400
ggacgccgca ggtctccatg gccgttggtg atcaggtgac caccgctgag tactgggtgc   2460
ggcaggtccg ggacacggtc cggttcgcg agcaggtggc tcgtacgag acgccgtgt   2520 tcgtcgagct gggtgccgac cggtcactgg cccgcctggt cgacggtgtc gcgatgctgc   2580
acggcgacca cgaaatccag gccgcgatcg gcgccctggc ccacctgtat gtcaacggcg   2640
tcacggtcga ctggcccgcg ctcctgggcg atgctccggc aacacgggtg ctggaccttc   2700
cgacatacgc cttccagcac cagcgctact ggctcgagtc ggcacgcccg gccgcatccg   2760
acgggggcca cccgtgctg ggctccggta tcgccctcgc cgggtcgccg ggccgggtgt   2820
tcacgggttc cgtgccgacc ggtgcggacc gcgcggtgtt cgtcgccgag ctggcgctgg   2880
ccgccgcgga cgcggtcgac tgcgccacgg tcgagcggct cgacatcgcc tccgtgcccg   2940
```

-continued

```
gccggccggg ccatggccgg acgaccgtac agacctgggt cgacgagccg gcggacgacg    3000
gccggcgccg gttcaccgtg cacacccgca ccggcgacgc cccgtggacg ctgcacgccg    3060
aggggggtgct gcgccccccat ggcacggccc tgcccgatgc ggccgacgcc gagtggcccc  3120
caccgggcgc ggtgcccgcg gacgggctgc cgggtgtgtg gcgccggggg gaccaggtct   3180
tcgccgaggc cgaggtggac ggaccggacg gtttcgtggt gcaccccgac ctgctcgacg   3240
cggtcttctc cgcggtcggc gacggaagcc gccagccggc cggatggcgc gacctgacgg   3300
tgcacgcgtc ggacgccacc gtactgcgcg cctgcctcac ccggcgcacc gacggagcca   3360
tgggattcgc cgccttcgac ggcgccggcc tgccggtact caccgcggag gcggtgacgc   3420
tgcgggaggt ggcgtcaccg tccggctccg aggagtcgga cggcctgcac cggttggagt   3480
ggctcgcggt cgccgaggcg gtctacgacg gtgacctgcc cgagggacat gtcctgatca   3540
ccgccgccca ccccgacgac cccgaggaca tacccacccg cgcccacacc cgcgccaccc   3600
gcgtcctgac cgccctgcaa caccacctca ccaccaccga ccacaccctc atcgtccaca   3660
ccaccaccga ccccgccggc gccaccgtca ccggcctcac ccgcaccgcc cagaacgaac   3720
accccccaccg catccgcctc atcgaaaccg accaccccca caccccctc ccctggccc   3780
aactcgccac cctcgaccac ccccacctcc gcctcaccca ccaccctc caccaccc    3840
acctcacccc cctccacacc accaccccac ccaccaccac ccccctcaac cccgaacacg    3900
ccatcatcat caccggcggc tccggcaccc tcgccggcat cctcgcccgc cacctgaacc    3960
accccccacac ctacctcctc tcccgcaccc caccccccga cgccacccccc ggcacccacc   4020
tccccctgcga cgtcggcgac ccccaccaac tcgccaccac cctcacccac atcccccaac   4080
ccctcaccgc catcttccac accgccgcca ccctcgacga cggcatcctc cacgccctca   4140
ccccgaccg cctcaccacc gtcctccacc ccaaagccaa cgccgcctgg cacctgcacc    4200
acctcaccca aaaccaaccc ctcacccact tcgtcctcta ctccagcgcc gccgccgtcc   4260
tcggcagccc cggacaagga aactacgccg ccgccaacgc cttcctcgac gccctcgcca   4320
cccaccgcca cacccctcggc caacccgcca cctccatcgc ctggggcatg tggcacacca   4380
ccagcaccct caccggacaa ctcgacgacg ccgaccggga ccgcatccgc cgcggcggtt   4440
tcctcccgat cacggacgac gagggcatgg ggatgcat                            4478
```

<210> SEQ ID NO 17
<211> LENGTH: 1488
<212> TYPE: PRT
<213> ORGANISM: Artificial Sequence
<220> FEATURE:
<223> OTHER INFORMATION: primer

<400> SEQUENCE: 17

```
Ile Trp Gln Leu Ala Glu Ala Leu Leu Thr Leu Val Arg Glu Ser Thr
1               5                   10                  15

Ala Ala Val Leu Gly His Val Gly Gly Glu Asp Ile Pro Ala Thr Ala
            20                  25                  30

Ala Phe Lys Asp Leu Gly Ile Asp Ser Leu Thr Ala Val Gln Leu Arg
        35                  40                  45

Asn Ala Leu Thr Glu Ala Thr Gly Val Arg Leu Asn Ala Thr Ala Val
    50                  55                  60

Phe Asp Phe Pro Thr Pro His Val Leu Ala Gly Lys Leu Gly Asp Glu
65                  70                  75                  80

Leu Thr Gly Thr Arg Ala Pro Val Val Pro Arg Thr Ala Ala Thr Ala
```

-continued

```
                    85                  90                  95
Gly Ala His Asp Glu Pro Leu Ala Ile Val Gly Met Ala Cys Arg Leu
            100                 105                 110
Pro Gly Gly Val Ala Ser Pro Glu Glu Leu Trp His Leu Val Ala Ser
            115                 120                 125
Gly Thr Asp Ala Ile Thr Glu Phe Pro Thr Asp Arg Gly Trp Asp Val
            130                 135                 140
Asp Ala Ile Tyr Asp Pro Asp Pro Asp Ala Ile Gly Lys Thr Phe Val
145                 150                 155                 160
Arg His Gly Gly Phe Leu Thr Gly Ala Thr Gly Phe Asp Ala Ala Phe
                165                 170                 175
Phe Gly Ile Ser Pro Arg Glu Ala Leu Ala Met Asp Pro Gln Gln Arg
            180                 185                 190
Val Leu Leu Glu Thr Ser Trp Glu Ala Phe Glu Ser Ala Gly Ile Thr
            195                 200                 205
Pro Asp Ser Thr Arg Gly Ser Asp Thr Gly Val Phe Val Gly Ala Phe
            210                 215                 220
Ser Tyr Gly Tyr Gly Thr Gly Ala Asp Thr Asp Gly Phe Gly Ala Thr
225                 230                 235                 240
Gly Ser Gln Thr Ser Val Leu Ser Gly Arg Leu Ser Tyr Phe Tyr Gly
            245                 250                 255
Leu Glu Gly Pro Ala Val Thr Val Asp Thr Ala Cys Ser Ser Ser Leu
            260                 265                 270
Val Ala Leu His Gln Ala Gly Gln Ser Leu Arg Ser Gly Glu Cys Ser
            275                 280                 285
Leu Ala Leu Val Gly Gly Val Thr Val Met Ala Ser Pro Gly Gly Phe
            290                 295                 300
Val Glu Phe Ser Arg Gln Arg Gly Leu Ala Pro Asp Gly Arg Ala Lys
305                 310                 315                 320
Ala Phe Gly Ala Gly Ala Asp Gly Thr Ser Phe Ala Glu Gly Ala Gly
            325                 330                 335
Val Leu Ile Val Glu Arg Leu Ser Asp Ala Glu Arg Asn Gly His Thr
            340                 345                 350
Val Leu Ala Val Val Arg Gly Ser Ala Val Asn Gln Asp Gly Ala Ser
            355                 360                 365
Asn Gly Leu Ser Ala Pro Asn Gly Pro Ser Gln Glu Arg Val Ile Arg
            370                 375                 380
Gln Ala Leu Ala Asn Ala Gly Leu Thr Pro Ala Asp Val Asp Ala Val
385                 390                 395                 400
Glu Ala His Gly Thr Gly Thr Arg Leu Gly Asp Pro Ile Glu Ala Gln
            405                 410                 415
Ala Val Leu Ala Thr Tyr Gly Gln Glu Arg Ala Thr Pro Leu Leu Leu
            420                 425                 430
Gly Ser Leu Lys Ser Asn Ile Gly His Ala Gln Ala Ala Ser Gly Val
            435                 440                 445
Ala Gly Ile Ile Lys Met Val Gln Ala Leu Arg His Gly Glu Leu Pro
            450                 455                 460
Pro Thr Leu His Ala Asp Glu Pro Ser Pro His Val Asp Trp Thr Ala
465                 470                 475                 480
Gly Ala Val Glu Leu Leu Thr Ser Ala Arg Pro Trp Pro Glu Thr Asp
            485                 490                 495
Arg Pro Arg Arg Ala Gly Val Ser Ser Phe Gly Ile Ser Gly Thr Asn
            500                 505                 510
```

-continued

```
Ala His Val Ile Leu Glu Ser Ala Pro Pro Thr Gln Pro Ala Asp Asn
        515                 520                 525

Ala Val Ile Glu Arg Ala Pro Glu Trp Val Pro Leu Val Ile Ser Ala
        530                 535                 540

Arg Thr Gln Ser Ala Leu Thr Glu His Glu Gly Arg Leu Arg Ala Tyr
545                 550                 555                 560

Leu Ala Ala Ser Pro Gly Val Asp Met Arg Ala Val Ala Ser Thr Leu
                565                 570                 575

Ala Met Thr Arg Ser Val Phe Glu His Arg Ala Val Leu Leu Gly Asp
            580                 585                 590

Asp Thr Val Thr Gly Thr Ala Val Ser Asp Pro Arg Ala Val Phe Val
        595                 600                 605

Phe Pro Gly Gln Gly Ser Gln Arg Ala Gly Met Gly Glu Glu Leu Ala
        610                 615                 620

Ala Ala Phe Pro Val Phe Ala Arg Ile His Gln Gln Val Trp Asp Leu
625                 630                 635                 640

Leu Asp Val Pro Asp Leu Glu Val Asn Glu Thr Gly Tyr Ala Gln Pro
                645                 650                 655

Ala Leu Phe Ala Met Gln Val Ala Leu Phe Gly Leu Leu Glu Ser Trp
            660                 665                 670

Gly Val Arg Pro Asp Ala Val Ile Gly His Ser Val Gly Glu Leu Ala
        675                 680                 685

Ala Ala Tyr Val Ser Gly Val Trp Ser Leu Glu Asp Ala Cys Thr Leu
        690                 695                 700

Val Ser Ala Arg Ala Arg Leu Met Gln Ala Leu Pro Ala Gly Gly Val
705                 710                 715                 720

Met Val Ala Val Pro Val Ser Glu Asp Glu Ala Arg Ala Val Leu Gly
                725                 730                 735

Glu Gly Val Glu Ile Ala Ala Val Asn Gly Pro Ser Ser Val Val Leu
            740                 745                 750

Ser Gly Asp Glu Ala Ala Val Leu Gln Ala Ala Glu Gly Leu Gly Lys
        755                 760                 765

Trp Thr Arg Leu Ala Thr Ser His Ala Phe His Ser Ala Arg Met Glu
770                 775                 780

Pro Met Leu Glu Glu Phe Arg Ala Val Ala Glu Gly Leu Thr Tyr Arg
785                 790                 795                 800

Thr Pro Gln Val Ser Met Ala Val Gly Asp Gln Val Thr Thr Ala Glu
                805                 810                 815

Tyr Trp Val Arg Gln Val Arg Asp Thr Val Arg Phe Gly Glu Gln Val
            820                 825                 830

Ala Ser Tyr Glu Asp Ala Val Phe Val Glu Leu Gly Ala Asp Arg Ser
        835                 840                 845

Leu Ala Arg Leu Val Asp Gly Val Ala Met Leu His Gly Asp His Glu
        850                 855                 860

Ile Gln Ala Ala Ile Gly Ala Leu Ala His Leu Tyr Val Asn Gly Val
865                 870                 875                 880

Thr Val Asp Trp Pro Ala Leu Leu Gly Asp Ala Pro Ala Thr Arg Val
                885                 890                 895

Leu Asp Leu Pro Thr Tyr Ala Phe Gln His Gln Arg Tyr Trp Leu Glu
            900                 905                 910

Ser Ala Arg Pro Ala Ala Ser Asp Ala Gly His Pro Val Leu Gly Ser
        915                 920                 925
```

-continued

```
Gly Ile Ala Leu Ala Gly Ser Pro Gly Arg Val Phe Thr Gly Ser Val
    930                 935                 940

Pro Thr Gly Ala Asp Arg Ala Val Phe Val Ala Glu Leu Ala Leu Ala
945                 950                 955                 960

Ala Ala Asp Ala Val Asp Cys Ala Thr Val Glu Arg Leu Asp Ile Ala
                965                 970                 975

Ser Val Pro Gly Arg Pro Gly His Gly Arg Thr Thr Val Gln Thr Trp
            980                 985                 990

Val Asp Glu Pro Ala Asp Gly Arg Arg Arg Phe Thr Val His Thr
        995                 1000                1005

Arg Thr Gly Asp Ala Pro Trp Thr Leu His Ala Glu Gly Val Leu
    1010                1015                1020

Arg Pro His Gly Thr Ala Leu Pro Asp Ala Ala Asp Ala Glu Trp
    1025                1030                1035

Pro Pro Pro Gly Ala Val Pro Ala Asp Gly Leu Pro Gly Val Trp
    1040                1045                1050

Arg Arg Gly Asp Gln Val Phe Ala Glu Ala Glu Val Asp Gly Pro
    1055                1060                1065

Asp Gly Phe Val Val His Pro Asp Leu Leu Asp Ala Val Phe Ser
    1070                1075                1080

Ala Val Gly Asp Gly Ser Arg Gln Pro Ala Gly Trp Arg Asp Leu
    1085                1090                1095

Thr Val His Ala Ser Asp Ala Thr Val Leu Arg Ala Cys Leu Thr
    1100                1105                1110

Arg Arg Thr Asp Gly Ala Met Gly Phe Ala Ala Phe Asp Gly Ala
    1115                1120                1125

Gly Leu Pro Val Leu Thr Ala Glu Ala Val Thr Leu Arg Glu Val
    1130                1135                1140

Ala Ser Pro Ser Gly Ser Glu Glu Ser Asp Gly Leu His Arg Leu
    1145                1150                1155

Glu Trp Leu Ala Val Ala Glu Ala Val Tyr Asp Gly Asp Leu Pro
    1160                1165                1170

Glu Gly His Val Leu Ile Thr Ala Ala His Pro Asp Asp Pro Glu
    1175                1180                1185

Asp Ile Pro Thr Arg Ala His Thr Arg Ala Thr Arg Val Leu Thr
    1190                1195                1200

Ala Leu Gln His His Leu Thr Thr Asp His Thr Leu Ile Val
    1205                1210                1215

His Thr Thr Thr Asp Pro Ala Gly Ala Thr Val Thr Gly Leu Thr
    1220                1225                1230

Arg Thr Ala Gln Asn Glu His Pro His Arg Ile Arg Leu Ile Glu
    1235                1240                1245

Thr Asp His Pro His Thr Pro Leu Pro Leu Ala Gln Leu Ala Thr
    1250                1255                1260

Leu Asp His Pro His Leu Arg Leu Thr His His Thr Leu His His
    1265                1270                1275

Pro His Leu Thr Pro Leu His Thr Thr Thr Pro Pro Thr Thr Thr
    1280                1285                1290

Pro Leu Asn Pro Glu His Ala Ile Ile Ile Thr Gly Gly Ser Gly
    1295                1300                1305

Thr Leu Ala Gly Ile Leu Ala Arg His Leu Asn His Pro His Thr
    1310                1315                1320

Tyr Leu Leu Ser Arg Thr Pro Pro Pro Asp Ala Thr Pro Gly Thr
```

```
                1325              1330              1335

His Leu Pro Cys Asp Val Gly Asp Pro His Gln Leu Ala Thr Thr
    1340              1345              1350

Leu Thr His Ile Pro Gln Pro Leu Thr Ala Ile Phe His Thr Ala
    1355              1360              1365

Ala Thr Leu Asp Asp Gly Ile Leu His Ala Leu Thr Pro Asp Arg
    1370              1375              1380

Leu Thr Thr Val Leu His Pro Lys Ala Asn Ala Ala Trp His Leu
    1385              1390              1395

His His Leu Thr Gln Asn Gln Pro Leu Thr His Phe Val Leu Tyr
    1400              1405              1410

Ser Ser Ala Ala Ala Val Leu Gly Ser Pro Gly Gln Gly Asn Tyr
    1415              1420              1425

Ala Ala Ala Asn Ala Phe Leu Asp Ala Leu Ala Thr His Arg His
    1430              1435              1440

Thr Leu Gly Gln Pro Ala Thr Ser Ile Ala Trp Gly Met Trp His
    1445              1450              1455

Thr Thr Ser Thr Leu Thr Gly Gln Leu Asp Asp Ala Asp Arg Asp
    1460              1465              1470

Arg Ile Arg Arg Gly Gly Phe Leu Pro Ile Thr Asp Asp Glu Gly
    1475              1480              1485

<210> SEQ ID NO 18
<211> LENGTH: 4571
<212> TYPE: DNA
<213> ORGANISM: Artificial Sequence
<220> FEATURE:
<223> OTHER INFORMATION: primer

<400> SEQUENCE: 18
agatctggca gctcgccgaa gcgctgctga cgctcgtccg ggagagcacc gccgccgtgc    60
tcggccacgt gggtggcgag acatccccg cgacggcggc gttcaaggac ctcggcatcg   120
actcgctcac cgcggtccag ctgcgcaacg ccctcaccga ggcgaccggt gtgcggctga   180
acgccacggc ggtcttcgac ttcccgaccc cgcacgtgct cgccgggaag ctcggcgacg   240
aactgaccgg cacccgcgcg cccgtcgtgc cccggaccgc ggccacggcc ggtgcgcacg   300
acgagccgct ggcgatcgtg ggaatggcct gccggctgcc cggcggggtc gcgtcacccg   360
aggagctgtg gcacctcgtg gcatccggca ccgacgccat cacggagttc ccgacggacc   420
gcggctggga cgtcgacgcg atctacgacc cggaccccga cgcgatcggc aagaccttcg   480
tccggcacgg tggcttcctc accggcgcga caggcttcga cgcggcgttc ttcggcatca   540
gcccgcgcga ggccctcgcg atggaccgc agcagcgggt gctcctggag acgtcgtggg   600
aggcgttcga aagcgccggc atcacccccg actcgacccg cggcagcgac accggcgtgt   660
tcgtcggcgc cttctcctac ggttacggca ccggtgcgga caccgacggc ttcggcgcga   720
ccggctcgca gaccagtgtg ctctccggcc ggctgtcgta cttctacggt ctggagggtc   780
cggcggtcac ggtcgacacg gcgtgttcgt cgtcgctggt ggcgctgcac caggccgggc   840
agtcgctgcg ctccggcgaa tgctcgctcg cctggtcgg cggcgtcacg gtgatggcgt   900
ctcccggcgg cttcgtggag ttctcccggc agcgcggcct cgcgccggac ggccgggcga   960
aggcgttcgg cgcgggtgcg gacggcacga gcttcgccga gggtgccggt gtgctgatcg  1020
tcgagaggct ctccgacgcc gaacgcaacg gtcacaccgt cctggcggtc gtccgtggtt  1080
cggcggtcaa ccaggatggt gcctccaacg ggctgtcggc gccgaacggg ccgtcgcagg  1140
```

-continued

```
agcgggtgat ccggcaggcc ctggccaacg ccgggctcac cccggcggac gtggacgccg   1200
tcgaggccca cggcaccggc accaggctgg gcgaccccat cgaggcacag gcggtactgg   1260
ccacctacgg acaggagcgc gccaccccce tgctgctggg ctcgctgaag tccaacatcg   1320
gccacgccca ggccgcgtcc ggcgtcgccg gcatcatcaa gatggtgcag gccctccggc   1380
acggggagct gccgccgacg ctgcacgccg acgagccgtc gccgcacgtc gactggacgg   1440
ccggcgccgt cgaactgctg acgtcggccc ggccgtggcc cgagaccgac cggcctaggc   1500
gggcgggcgt gtcgtccttc ggagtcagcg gcaccaacgc ccacgtcatc ctggagagcg   1560
caccccccgc tcagcccgcg gaggaggcgc agcctgttga cgccggtg gtggcctcgg    1620 atgtgctgcc gctggtgata tcggccaaga cccagcccgc cctgaccgaa cacgaagacc   1680
ggctgcgcgc ctacctggcg gcgtcgcccg gggcggatat acgggctgtg gcatcgacgc   1740
tggcggtgac acgtcggtg ttcgagcacc gcgccgtact ccttggagat gacaccgtca    1800
ccggcaccgc ggtgaccgac cccaggatcg tgtttgtctt tcccgggcag gggtggcagt   1860
ggctggggat gggcagtgca ctgcgcgatt cgtcggtggt gttcgccgag cggatggccg   1920
agtgtgcggc ggcgttgcgc gagttcgtgg actgggatct gttcacggtt ctggatgatc   1980
cggcggtggt ggaccgggtt gatgtggtcc agcccgcttc ctgggcgatg atggtttccc   2040
tggccgcggt gtggcaggcg gccggtgtgc ggccggatgc ggtgatcggc cattcgcagg   2100
gtgagatcgc cgcagcttgt gtggcgggtg cggtgtcact acgcgatgcc gcccggatcg   2160
tgaccttgcg cagccaggcg atcgcccggg gcctggcggg ccggggcgcg atggcatccg   2220
tcgccctgcc cgcgcaggat gtcgagctgg tcgacgggc ctggatcgcc gcccacaacg    2280
ggcccgcctc caccgtgatc gcgggcaccc cggaagcggt cgaccatgtc ctcaccgctc   2340
atgaggcaca aggggtgcgg gtgcggcgga tcaccgtcga ctatgcctcg cacaccccgc   2400
acgtcgagct gatccgcgac gaactactcg acatcactag cgacagcagc tcgcagaccc   2460
cgctcgtgcc gtggctgtcg accgtggacg gcacctgggt cgacagcccg ctggacgggg   2520
agtactggta ccggaacctg cgtgaaccgg tcggtttcca ccccgccgtc agccagttgc   2580
aggcccaggg cgacaccgtg ttcgtcgagg tcagcgccag cccggtgttg ttgcaggcga   2640
tggacgacga tgtcgtcacg gttgccacgc tgcgtcgtga cgacggcgac gccaccegga   2700 tgctcaccgc cctggcacag gcctatgtcc acggcgtcac cgtcgactgg cccgccatcc   2760
tcggcaccac cacaacccgg gtactggacc ttccgaccta cgccttccaa caccagcggt   2820
actggctcga gtcggcacgc ccggccgcat ccgacgcggg ccaccccgtg ctgggctccg   2880
gtatcgccct cgccgggtcg ccgggccggg tgttcacggg ttccgtgccg accggtgcgg   2940
accgcgcggt gttcgtcgcc gagctggcgc tggccgccgc ggacgcggtc gactgcgcca   3000
cggtcgagcg gctcgacatc gcctccgtgc ccggccggcc gggccatggc cggacgaccg   3060
tacagacctg ggtcgacgag ccggcggacg acggccggcg ccggttcacc gtgcacaccc   3120
gcaccggcga cgccccgtgg acgctgcacg ccgaggggt gctgcgcccc catggcacgg   3180
ccctgcccga tgcggccgac gccgagtggc ccccaccggg cgcggtgccc gcggacgggc   3240
tgccgggtgt gtggcgccgg ggggaccagg tcttcgccga ggccgaggtg gacggaccgg   3300
acggtttcgt ggtgcacccc gacctgctcg acgcggtctt ctccgcggtc ggcgacggaa   3360
gccgccagcc ggccggatgg cgcgacctga cggtgcacgc gtcggacgcc accgtactgc   3420
gcgcctgcct cacccggcgc accgacggag ccatgggatt cgccgccttc gacggcgccg   3480
```

-continued

```
gcctgccggt actcaccgcg gaggcggtga cgctgcggga ggtggcgtca ccgtccggct   3540
ccgaggagtc ggacggcctg caccggttgg agtggctcgc ggtcgccgag gcggtctacg   3600
acggtgacct gcccgaggga catgtcctga tcaccgccgc ccaccccgac gaccccgagg   3660
acatacccac ccgcgcccac acccgcgcca cccgcgtcct gaccgccctg caacaccacc   3720
tcaccaccac cgaccacacc ctcatcgtcc acaccaccac cgaccccgcc ggcgccaccg   3780
tcaccggcct cacccgcacc gcccagaacg aacacccca ccgcatccgc ctcatcgaaa    3840
ccgaccaccc ccacaccccc ctcccctgg cccaactcgc caccctcgac cacccccacc    3900
tccgcctcac ccaccacacc ctccaccacc cccacctcac cccctccac accaccaccc    3960 cacccaccac cacccccctc aaccccgaac acgccatcat catcaccggc ggctccggca   4020
ccctcgccgg catcctcgcc cgccaccga accaccccca cacctacctc ctctcccgca    4080 ccccacccc cgacgccacc cccggcaccc acctcccctg cgacgtcggc gacccccacc    4140
aactcgccac caccctcacc cacatcccc aaccccctcac cgccatcttc cacaccgccg    4200
ccaccctcga cgacggcatc ctccacgccc tcacccccga ccgcctcacc accgtcctcc   4260
accccaaagc caacgccgcc tggcacctgc accacctcac ccaaaaccaa cccctcaccc   4320
acttcgtcct ctactccagc gccgccgccg tcctcggcag cccggacaa ggaaactacg    4380 ccgccgccaa cgccttcctc gacgccctcg ccacccaccg ccacaccctc ggccaacccg   4440
ccacctccat cgcctggggc atgtggcaca ccaccagcac cctcaccgga caactcgacg   4500
acgccgaccg ggaccgcatc cgccgcggcg gtttcctccc gatcacggac gacgagggca   4560
tggggatgca t                                                        4571
```

<210> SEQ ID NO 19
<211> LENGTH: 1517
<212> TYPE: PRT
<213> ORGANISM: Artificial Sequence
<220> FEATURE:
<223> OTHER INFORMATION: primer

<400> SEQUENCE: 19

```
Gln Leu Ala Glu Ala Leu Leu Thr Leu Val Arg Glu Ser Thr Ala Ala
1               5                   10                  15

Val Leu Gly His Val Gly Gly Glu Asp Ile Pro Ala Thr Ala Ala Phe
            20                  25                  30

Lys Asp Leu Gly Ile Asp Ser Leu Thr Ala Val Gln Leu Arg Asn Ala
        35                  40                  45

Leu Thr Glu Ala Thr Gly Val Arg Leu Asn Ala Thr Ala Val Phe Asp
    50                  55                  60

Phe Pro Thr Pro His Val Leu Ala Gly Lys Leu Gly Asp Glu Leu Thr
65                  70                  75                  80

Gly Thr Arg Ala Pro Val Val Pro Arg Thr Ala Thr Ala Gly Ala
                85                  90                  95

His Asp Glu Pro Leu Ala Ile Val Gly Met Ala Cys Arg Leu Pro Gly
            100                 105                 110

Gly Val Ala Ser Pro Glu Glu Leu Trp His Leu Val Ala Ser Gly Thr
        115                 120                 125

Asp Ala Ile Thr Glu Phe Pro Thr Asp Arg Gly Trp Asp Val Asp Ala
    130                 135                 140

Ile Tyr Asp Pro Asp Pro Asp Ala Ile Gly Lys Thr Phe Val Arg His
145                 150                 155                 160

Gly Gly Phe Leu Thr Gly Ala Thr Gly Phe Asp Ala Ala Phe Phe Gly
```

-continued

```
                165                 170                 175
Ile Ser Pro Arg Glu Ala Leu Ala Met Asp Pro Gln Gln Arg Val Leu
            180                 185                 190
Leu Glu Thr Ser Trp Glu Ala Phe Glu Ser Ala Gly Ile Thr Pro Asp
        195                 200                 205
Ser Thr Arg Gly Ser Asp Thr Gly Val Phe Val Gly Ala Phe Ser Tyr
    210                 215                 220
Gly Tyr Gly Thr Gly Ala Asp Thr Asp Gly Phe Gly Ala Thr Gly Ser
225                 230                 235                 240
Gln Thr Ser Val Leu Ser Gly Arg Leu Ser Tyr Phe Tyr Gly Leu Glu
            245                 250                 255
Gly Pro Ala Val Thr Val Asp Thr Ala Cys Ser Ser Ser Leu Val Ala
        260                 265                 270
Leu His Gln Ala Gly Gln Ser Leu Arg Ser Gly Glu Cys Ser Leu Ala
    275                 280                 285
Leu Val Gly Gly Val Thr Val Met Ala Ser Pro Gly Gly Phe Val Glu
290                 295                 300
Phe Ser Arg Gln Arg Gly Leu Ala Pro Asp Gly Arg Ala Lys Ala Phe
305                 310                 315                 320
Gly Ala Gly Ala Asp Gly Thr Ser Phe Ala Glu Gly Ala Gly Val Leu
            325                 330                 335
Ile Val Glu Arg Leu Ser Asp Ala Glu Arg Asn Gly His Thr Val Leu
        340                 345                 350
Ala Val Val Arg Gly Ser Ala Val Asn Gln Asp Gly Ala Ser Asn Gly
    355                 360                 365
Leu Ser Ala Pro Asn Gly Pro Ser Gln Glu Arg Val Ile Arg Gln Ala
370                 375                 380
Leu Ala Asn Ala Gly Leu Thr Pro Ala Asp Val Asp Ala Val Glu Ala
385                 390                 395                 400
His Gly Thr Gly Thr Arg Leu Gly Asp Pro Ile Glu Ala Gln Ala Val
            405                 410                 415
Leu Ala Thr Tyr Gly Gln Glu Arg Ala Thr Pro Leu Leu Leu Gly Ser
        420                 425                 430
Leu Lys Ser Asn Ile Gly His Ala Gln Ala Ala Ser Gly Val Ala Gly
    435                 440                 445
Ile Ile Lys Met Val Gln Ala Leu Arg His Gly Glu Leu Pro Pro Thr
450                 455                 460
Leu His Ala Asp Glu Pro Ser Pro His Val Asp Trp Thr Ala Gly Ala
465                 470                 475                 480
Val Glu Leu Leu Thr Ser Ala Arg Pro Trp Pro Glu Thr Asp Arg Pro
            485                 490                 495
Arg Arg Ala Gly Val Ser Ser Phe Gly Val Ser Gly Thr Asn Ala His
        500                 505                 510
Val Ile Leu Glu Ser Ala Pro Pro Ala Gln Pro Ala Glu Glu Ala Gln
    515                 520                 525
Pro Val Glu Thr Pro Val Val Ala Ser Asp Val Leu Pro Leu Val Ile
530                 535                 540
Ser Ala Lys Thr Gln Pro Ala Leu Thr Glu His Glu Asp Arg Leu Arg
545                 550                 555                 560
Ala Tyr Leu Ala Ala Ser Pro Gly Ala Asp Ile Arg Ala Val Ala Ser
            565                 570                 575
Thr Leu Ala Val Thr Arg Ser Val Phe Glu His Arg Ala Val Leu Leu
        580                 585                 590
```

-continued

```
Gly Asp Asp Thr Val Thr Gly Thr Ala Val Thr Asp Pro Arg Ile Val
            595                 600                 605
Phe Val Phe Pro Gly Gln Gly Trp Gln Trp Leu Gly Met Gly Ser Ala
610             615                 620
Leu Arg Asp Ser Ser Val Val Phe Ala Glu Arg Met Ala Glu Cys Ala
625             630                 635                 640
Ala Ala Leu Arg Glu Phe Val Asp Trp Asp Leu Phe Thr Val Leu Asp
            645                 650                 655
Asp Pro Ala Val Val Asp Arg Val Asp Val Gln Pro Ala Ser Trp
            660                 665                 670
Ala Met Met Val Ser Leu Ala Ala Val Trp Gln Ala Ala Gly Val Arg
            675                 680                 685
Pro Asp Ala Val Ile Gly His Ser Gln Gly Glu Ile Ala Ala Ala Cys
            690                 695                 700
Val Ala Gly Ala Val Ser Leu Arg Asp Ala Ala Arg Ile Val Thr Leu
705                 710                 715                 720
Arg Ser Gln Ala Ile Ala Arg Gly Leu Ala Gly Arg Gly Ala Met Ala
            725                 730                 735
Ser Val Ala Leu Pro Ala Gln Asp Val Glu Leu Val Asp Gly Ala Trp
            740                 745                 750
Ile Ala Ala His Asn Gly Pro Ala Ser Thr Val Ile Ala Gly Thr Pro
            755                 760                 765
Glu Ala Val Asp His Val Leu Thr Ala His Glu Ala Gln Gly Val Arg
            770                 775                 780
Val Arg Arg Ile Thr Val Asp Tyr Ala Ser His Thr Pro His Val Glu
785                 790                 795                 800
Leu Ile Arg Asp Glu Leu Leu Asp Ile Thr Ser Asp Ser Ser Ser Gln
            805                 810                 815
Thr Pro Leu Val Pro Trp Leu Ser Thr Val Asp Gly Thr Trp Val Asp
            820                 825                 830
Ser Pro Leu Asp Gly Glu Tyr Trp Tyr Arg Asn Leu Arg Glu Pro Val
            835                 840                 845
Gly Phe His Pro Ala Val Ser Gln Leu Gln Ala Gln Gly Asp Thr Val
            850                 855                 860
Phe Val Glu Val Ser Ala Ser Pro Val Leu Leu Gln Ala Met Asp Asp
865                 870                 875                 880
Asp Val Val Thr Val Ala Thr Leu Arg Arg Asp Asp Gly Asp Ala Thr
            885                 890                 895
Arg Met Leu Thr Ala Leu Ala Gln Ala Tyr Val His Gly Val Thr Val
            900                 905                 910
Asp Trp Pro Ala Ile Leu Gly Thr Thr Thr Arg Val Leu Asp Leu
            915                 920                 925
Pro Thr Tyr Ala Phe Gln His Gln Arg Tyr Trp Leu Glu Ser Ala Arg
            930                 935                 940
Pro Ala Ala Ser Asp Ala Gly His Pro Val Leu Gly Ser Gly Ile Ala
945                 950                 955                 960
Leu Ala Gly Ser Pro Gly Arg Val Phe Thr Gly Ser Val Pro Thr Gly
            965                 970                 975
Ala Asp Arg Ala Val Phe Val Ala Glu Leu Ala Leu Ala Ala Ala Asp
            980                 985                 990
Ala Val Asp Cys Ala Thr Val Glu  Arg Leu Asp Ile Ala  Ser Val Pro
            995                 1000                1005
```

-continued

Gly Arg Pro Gly His Gly Arg Thr Thr Val Gln Thr Trp Val Asp
    1010            1015                1020

Glu Pro Ala Asp Asp Gly Arg Arg Arg Phe Thr Val His Thr Arg
    1025            1030                1035

Thr Gly Asp Ala Pro Trp Thr Leu His Ala Glu Gly Val Leu Arg
    1040            1045                1050

Pro His Gly Thr Ala Leu Pro Asp Ala Ala Asp Ala Glu Trp Pro
    1055            1060                1065

Pro Pro Gly Ala Val Pro Ala Asp Gly Leu Pro Gly Val Trp Arg
    1070            1075                1080

Arg Gly Asp Gln Val Phe Ala Glu Ala Glu Val Asp Gly Pro Asp
    1085            1090                1095

Gly Phe Val Val His Pro Asp Leu Leu Asp Ala Val Phe Ser Ala
    1100            1105                1110

Val Gly Asp Gly Ser Arg Gln Pro Ala Gly Trp Arg Asp Leu Thr
    1115            1120                1125

Val His Ala Ser Asp Ala Thr Val Leu Arg Ala Cys Leu Thr Arg
    1130            1135                1140

Arg Thr Asp Gly Ala Met Gly Phe Ala Ala Phe Asp Gly Ala Gly
    1145            1150                1155

Leu Pro Val Leu Thr Ala Glu Ala Val Thr Leu Arg Glu Val Ala
    1160            1165                1170

Ser Pro Ser Gly Ser Glu Glu Ser Asp Gly Leu His Arg Leu Glu
    1175            1180                1185

Trp Leu Ala Val Ala Glu Ala Val Tyr Asp Gly Asp Leu Pro Glu
    1190            1195                1200

Gly His Val Leu Ile Thr Ala Ala His Pro Asp Asp Pro Glu Asp
    1205            1210                1215

Ile Pro Thr Arg Ala His Thr Arg Ala Thr Arg Val Leu Thr Ala
    1220            1225                1230

Leu Gln His His Leu Thr Thr Thr Asp His Thr Leu Ile Val His
    1235            1240                1245

Thr Thr Thr Asp Pro Ala Gly Ala Thr Val Thr Gly Leu Thr Arg
    1250            1255                1260

Thr Ala Gln Asn Glu His Pro His Arg Ile Arg Leu Ile Glu Thr
    1265            1270                1275

Asp His Pro His Thr Pro Leu Pro Leu Ala Gln Leu Ala Thr Leu
    1280            1285                1290

Asp His Pro His Leu Arg Leu Thr His Thr Leu His His Pro
    1295            1300                1305

His Leu Thr Pro Leu His Thr Thr Thr Pro Pro Thr Thr Thr Pro
    1310            1315                1320

Leu Asn Pro Glu His Ala Ile Ile Ile Thr Gly Gly Ser Gly Thr
    1325            1330                1335

Leu Ala Gly Ile Leu Ala Arg His Leu Asn His Pro His Thr Tyr
    1340            1345                1350

Leu Leu Ser Arg Thr Pro Pro Pro Asp Ala Thr Pro Gly Thr His
    1355            1360                1365

Leu Pro Cys Asp Val Gly Asp Pro His Gln Leu Ala Thr Thr Leu
    1370            1375                1380

Thr His Ile Pro Gln Pro Leu Thr Ala Ile Phe His Thr Ala Ala
    1385            1390                1395

Thr Leu Asp Asp Gly Ile Leu His Ala Leu Thr Pro Asp Arg Leu

```
                  1400            1405            1410
Thr Thr Val Leu His Pro Lys Ala Asn Ala Ala Trp His Leu His
    1415            1420            1425
His Leu Thr Gln Asn Gln Pro Leu Thr His Phe Val Leu Tyr Ser
    1430            1435            1440
Ser Ala Ala Ala Val Leu Gly Ser Pro Gly Gln Gly Asn Tyr Ala
    1445            1450            1455
Ala Ala Asn Ala Phe Leu Asp Ala Leu Ala Thr His Arg His Thr
    1460            1465            1470
Leu Gly Gln Pro Ala Thr Ser Ile Ala Trp Gly Met Trp His Thr
    1475            1480            1485
Thr Ser Thr Leu Thr Gly Gln Leu Asp Asp Ala Asp Arg Asp Arg
    1490            1495            1500
Ile Arg Arg Gly Gly Phe Leu Pro Ile Thr Asp Asp Glu Gly
    1505            1510            1515

<210> SEQ ID NO 20
<211> LENGTH: 4466
<212> TYPE: DNA
<213> ORGANISM: Artificial Sequence
<220> FEATURE:
<223> OTHER INFORMATION: primer

<400> SEQUENCE: 20
agatctggca gctcgccgaa gcgctgctga cgctcgtccg ggagagcacc gccgccgtgc    60
tcggccacgt gggtggcgag gacatccccg cgacggcggc gttcaaggac ctcggcatcg   120
actcgctcac cgcggtccag ctgcgcaacg ccctcaccga ggcgaccggt gtgcggctga   180
acgccacggc ggtcttcgac ttcccgaccc cgcacgtgct cgccgggaag ctcggcgacg   240
aactgaccgg cacccgcgcg cccgtcgtgc cccggaccgc ggccacggcc ggtgcgcacg   300
acgagccgct ggcgatcgtg gaatggcctg ccggctgcc ggcggggtc gcgtcacccg    360
aggagctgtg gcacctcgtg gcatccggca ccgacgccat cacggagttc ccgacggacc   420
gcggctggga cgtcgacgcg atctacgacc cggaccccga cgcgatcggc aagaccttcg   480
tccggcacgg tggcttcctc accggcgcga caggcttcga cgcggcgttc ttcggcatca   540
gcccgcgcga ggccctcgcg atggaccgc agcagcgggt gctcctggag acgtcgtggg   600
aggcgttcga aagcgccggc atcaccccgg actcgacccg cggcagcgac accggcgtgt   660
tcgtcggcgc cttctcctac ggttacggca ccggtgcgga caccgacggc ttcggcgcga   720
ccggctcgca gaccagtgtg ctctccggcc ggctgtcgta cttctacggt ctggagggtc   780
cggcggtcac ggtcgacacg gcgtgttcgt cgtcgctggt ggcgctgcac caggccgggc   840
agtcgctgcg ctccggcgaa tgctcgctcg ccctggtcgg cggcgtcacg gtgatggcgt   900
ctcccggcgg cttcgtggag ttctcccggc agcgcggcct cgcgccggac ggccgggcga   960
aggcgttcgg cgcgggtgcg gacggcacga gcttcgccga gggtgccggt gtgctgatcg  1020
tcgagaggct ctccgacgcc gaacgcaacg gtcacaccgt cctggcggtc gtccgtggtt  1080
cggcggtcaa ccaggatggt gcctccaacg ggctgtcggc gccgaacggg ccgtcgcagg  1140
agcgggtgat ccggcaggcc ctggccaacg ccgggctcac cccggcggac gtggacgccg  1200
tcgaggccca cggcaccggc accaggctgg gcgaccccat cgaggcacag gcggtactgg  1260
ccacctacgg acaggagcgc gccacccccc tgctgctggg ctcgctgaag tccaacatcg  1320
gccacgccca ggccgcgtcc ggcgtcgcgg gcatcatcaa gatggtgcag gccctccggc  1380
```

```
acggggagct gccgccgacg ctgcacgccg acgagccgtc gccgcacgtc gactggacgg    1440
ccggcgccgt cgaactgctg acgtcggccc ggccgtgggcc cgagaccgac cggccacggc    1500
gtgccgccgt ctcctcgttc ggggtgagcg gcaccaacgc ccacgtcatc ctggaggccg    1560
gaccggtaac ggagacgccc gcggcatcgc cttccggtga ccttcccctg ctggtgtcgg    1620
cacgctcacc ggaagcgctc gacgagcaga tccgccgact gcgcgcctac ctggacacca    1680
ccccggacgt cgaccgggtg gccgtggcac agacgctggc ccggcgcaca cacttcgccc    1740
accgcgccgt gctgctcggt gacaccgtca tcaccacacc cccgcggac cggcccgacg    1800
aactcgtctt cgtctactcc ggccagggca cccagcatcc cgcgatgggc gagcagctag    1860
ccgccgcgtt ccccgtcttc gcgcggatcc atcagcaggt gtgggacctg ctcgatgtgc    1920
ccgatctgga ggtgaacgag accggttacg cccagccggc cctgttcgca atgcaggtgg    1980
ctctgttcgg gctgctggaa tcgtgggggtg tacgaccgga cgcggtgatc ggccattcgg    2040
tgggtgagct tgcggctgcg tatgtgtccg gggtgtggtc gttggaggat gcctgcactt    2100
tggtgtcggc gcgggctcgt ctgatgcagg ctctgcccgc gggtgggggtg atggtcgctg    2160
tcccggtctc ggaggatgag gcccgggccg tgctgggtga gggtgtggag atcgccgcgg    2220
tcaacggccc gtcgtcggtg gttctctccg gtgatgaggc cgccgtgctg caggccgcgg    2280
aggggctggg gaagtggacg cggctggcga ccagccacgc gttccattcc gcccgtatgg    2340
aacccatgct ggaggagttc cgggcggtcg ccgaaggcct gacctaccgg acgccgcagg    2400
tctccatggc cgttggtgat caggtgacca ccgctgagta ctgggtgcgg caggtccggg    2460
acacggtccg gttcggcgag caggtggcct cgtacgagga cgccgtgttc gtcgagctgg    2520
gtgccgaccg gtcactggcc cgcctggtcg acggtgtcgc gatgctgcac ggcgaccacg    2580
aaatccaggc cgcgatcggc gccctggccc acctgtatgt caacggcgtc acggtcgact    2640
ggcccgcgct cctgggcgat gctccggcaa cacgggtgct ggaccttccg acatacgcct    2700
tccagcacca gcgctactgg ctcgagtcgg cacgcccggc cgcatccgac gcgggccacc    2760
ccgtgctggg ctccggtatc gccctcgccg ggtcgccggg ccgggtgttc acgggttccg    2820
tgccgaccgg tgcggaccgc gcggtgttcg tcgccgagct ggcgctggcc gccgcggacg    2880
cggtcgactg cgccacggtc gagcggctcg acatcgcctc cgtgcccggc cggccgggcc    2940
atggccggac gaccgtacag acctgggtcg acgagccggc ggacgacggc cggcgccggt    3000
tcaccgtgca cacccgcacc ggcgacgccc cgtggacgct gcacgccgag ggggtgctgc    3060
gccccatgg cacggccctg cccgatgcgg ccgacgccga gtggccccca ccgggcgcgg    3120
tgccgcgga cgggctgccg ggtgtgtggc gccggggga ccaggtcttc gccgaggccg    3180
aggtggacgg accggacggt ttcgtggtgc accccgacct gctcgacgcg gtcttctccg    3240
cggtcggcga cggaagccgc cagccggccg gatggcgcga cctgacggtg cacgcgtcgg    3300
acgccaccgt actgcgcgcc tgcctcaccc ggcgcaccga cggagccatg ggattcgccg    3360
ccttcgacgg cgccggcctg ccggtactca ccgcggaggc ggtgacgctg cgggaggtgg    3420
cgtcaccgtc cggctccgag gagtcggacg gcctgcaccg gttggagtgg ctcgcggtcg    3480
ccgaggcggt ctacgacggt gacctgcccg aggacatgt cctgatcacc gccgccacc    3540
ccgacgaccc cgaggacata cccacccgcg cccacacccg cgccaccgc gtcctgaccg    3600
ccctgcaaca ccacctcacc accaccgacc acaccctcat cgtccacacc accaccgacc    3660
ccgccggcgc caccgtcacc ggcctcaccc gcaccgccca gaacgaacac ccccaccgca    3720
tccgcctcat cgaaaccgac cacccccaca cccccctccc cctggcccaa ctcgccaccc    3780
```

-continued

```
tcgaccaccc ccacctccgc ctcacccacc acaccctcca ccaccccac ctcaccccc      3840 tccacaccac caccccaccc accaccaccc ccctcaaccc cgaacacgcc atcatcatca     3900
ccggcggctc cggcaccctc gccggcatcc tcgcccgcca cctgaaccac ccccacacct     3960
acctcctctc ccgcaccca ccccccgacg ccacccccgg cacccacctc cctgcgacg      4020 tcggcgaccc ccaccaactc gccaccaccc tcacccacat ccccaaccc ctcaccgcca     4080 tcttccacac cgccgccacc ctcgacgacg gcatcctcca cgccctcacc cccgaccgcc     4140
tcaccaccgt cctccacccc aaagccaacg ccgcctggca cctgcaccac ctcacccaaa     4200
accaacccct cacccacttc gtcctctact ccagcgccgc cgccgtcctc ggcagccccg     4260
gacaaggaaa ctacgccgcc gccaacgcct tcctcgacgc cctcgccacc caccgccaca     4320
ccctcggcca acccgccacc tccatcgcct ggggcatgtg gcacaccacc agcaccctca     4380
ccggacaact cgacgacgcc gaccgggacc gcatccgccg cggcggtttc ctcccgatca     4440
cggacgacga gggcatgggg atgcat                                         4466
```

<210> SEQ ID NO 21
<211> LENGTH: 1482
<212> TYPE: PRT
<213> ORGANISM: Artificial Sequence
<220> FEATURE:
<223> OTHER INFORMATION: primer

<400> SEQUENCE: 21

```
Gln Leu Ala Glu Ala Leu Leu Thr Leu Val Arg Glu Ser Thr Ala Ala
1               5                   10                  15

Val Leu Gly His Val Gly Gly Glu Asp Ile Pro Ala Thr Ala Ala Phe
            20                  25                  30

Lys Asp Leu Gly Ile Asp Ser Leu Thr Ala Val Gln Leu Arg Asn Ala
        35                  40                  45

Leu Thr Glu Ala Thr Gly Val Arg Leu Asn Ala Thr Ala Val Phe Asp
    50                  55                  60

Phe Pro Thr Pro His Val Leu Ala Gly Lys Leu Gly Asp Glu Leu Thr
65                  70                  75                  80

Gly Thr Arg Ala Pro Val Val Pro Arg Thr Ala Ala Thr Ala Gly Ala
                85                  90                  95

His Asp Glu Pro Leu Ala Ile Val Gly Met Ala Cys Arg Leu Pro Gly
            100                 105                 110

Gly Val Ala Ser Pro Glu Glu Leu Trp His Leu Val Ala Ser Gly Thr
        115                 120                 125

Asp Ala Ile Thr Glu Phe Pro Thr Asp Arg Gly Trp Asp Val Asp Ala
    130                 135                 140

Ile Tyr Asp Pro Asp Pro Asp Ala Ile Gly Lys Thr Phe Val Arg His
145                 150                 155                 160

Gly Gly Phe Leu Thr Gly Ala Thr Gly Phe Asp Ala Ala Phe Phe Gly
                165                 170                 175

Ile Ser Pro Arg Glu Ala Leu Ala Met Asp Pro Gln Gln Arg Val Leu
            180                 185                 190

Leu Glu Thr Ser Trp Glu Ala Phe Glu Ser Ala Gly Ile Thr Pro Asp
        195                 200                 205

Ser Thr Arg Gly Ser Asp Thr Gly Val Phe Val Gly Ala Phe Ser Tyr
    210                 215                 220

Gly Tyr Gly Thr Gly Ala Asp Asp Gly Phe Gly Ala Thr Gly Ser
225                 230                 235                 240
```

```
Gln Thr Ser Val Leu Ser Gly Arg Leu Ser Tyr Phe Tyr Gly Leu Glu
            245                 250                 255
Gly Pro Ala Val Thr Val Asp Thr Ala Cys Ser Ser Leu Val Ala
        260                 265                 270
Leu His Gln Ala Gly Gln Ser Leu Arg Ser Gly Glu Cys Ser Leu Ala
        275                 280                 285
Leu Val Gly Gly Val Thr Val Met Ala Ser Pro Gly Gly Phe Val Glu
        290                 295                 300
Phe Ser Arg Gln Arg Gly Leu Ala Pro Asp Gly Arg Ala Lys Ala Phe
305                 310                 315                 320
Gly Ala Gly Ala Asp Gly Thr Ser Phe Ala Glu Gly Ala Gly Val Leu
                325                 330                 335
Ile Val Glu Arg Leu Ser Asp Ala Glu Arg Asn Gly His Thr Val Leu
            340                 345                 350
Ala Val Val Arg Gly Ser Ala Val Asn Gln Asp Gly Ala Ser Asn Gly
            355                 360                 365
Leu Ser Ala Pro Asn Gly Pro Ser Gln Glu Arg Val Ile Arg Gln Ala
        370                 375                 380
Leu Ala Asn Ala Gly Leu Thr Pro Ala Asp Val Asp Ala Val Glu Ala
385                 390                 395                 400
His Gly Thr Gly Thr Arg Leu Gly Asp Pro Ile Glu Ala Gln Ala Val
                405                 410                 415
Leu Ala Thr Tyr Gly Gln Glu Arg Ala Thr Pro Leu Leu Leu Gly Ser
            420                 425                 430
Leu Lys Ser Asn Ile Gly His Ala Gln Ala Ala Ser Gly Val Ala Gly
        435                 440                 445
Ile Ile Lys Met Val Gln Ala Leu Arg His Gly Glu Leu Pro Pro Thr
        450                 455                 460
Leu His Ala Asp Glu Pro Ser Pro His Val Asp Trp Thr Ala Gly Ala
465                 470                 475                 480
Val Glu Leu Leu Thr Ser Ala Arg Pro Trp Pro Glu Thr Asp Arg Pro
                485                 490                 495
Arg Arg Ala Ala Val Ser Ser Phe Gly Val Ser Gly Thr Asn Ala His
            500                 505                 510
Val Ile Leu Glu Ala Gly Pro Val Thr Glu Thr Pro Ala Ala Ser Pro
        515                 520                 525
Ser Gly Asp Leu Pro Leu Leu Val Ser Ala Arg Ser Pro Glu Ala Leu
        530                 535                 540
Asp Glu Gln Ile Arg Arg Leu Arg Ala Tyr Leu Asp Thr Thr Pro Asp
545                 550                 555                 560
Val Asp Arg Val Ala Val Ala Gln Thr Leu Ala Arg Arg Thr His Phe
                565                 570                 575
Ala His Arg Ala Val Leu Leu Gly Asp Thr Val Ile Thr Thr Pro Pro
            580                 585                 590
Ala Asp Arg Pro Asp Glu Leu Val Phe Val Tyr Ser Gly Gln Gly Thr
        595                 600                 605
Gln His Pro Ala Met Gly Glu Gln Leu Ala Ala Phe Pro Val Phe
        610                 615                 620
Ala Arg Ile His Gln Val Trp Asp Leu Leu Asp Val Pro Asp Leu
625                 630                 635                 640
Glu Val Asn Glu Thr Gly Tyr Ala Gln Pro Ala Leu Phe Ala Met Gln
                645                 650                 655
```

-continued

```
Val Ala Leu Phe Gly Leu Leu Glu Ser Trp Gly Val Arg Pro Asp Ala
            660                 665                 670
Val Ile Gly His Ser Val Gly Glu Leu Ala Ala Ala Tyr Val Ser Gly
            675                 680                 685
Val Trp Ser Leu Glu Asp Ala Cys Thr Leu Val Ser Ala Arg Ala Arg
            690                 695                 700
Leu Met Gln Ala Leu Pro Ala Gly Val Met Val Ala Val Pro Val
705                 710                 715                 720
Ser Glu Asp Glu Ala Arg Ala Val Leu Gly Glu Gly Val Glu Ile Ala
                725                 730                 735
Ala Val Asn Gly Pro Ser Ser Val Val Leu Ser Gly Asp Glu Ala Ala
            740                 745                 750
Val Leu Gln Ala Ala Glu Gly Leu Gly Lys Trp Thr Arg Leu Ala Thr
            755                 760                 765
Ser His Ala Phe His Ser Ala Arg Met Glu Pro Met Leu Glu Glu Phe
            770                 775                 780
Arg Ala Val Ala Glu Gly Leu Thr Tyr Arg Thr Pro Gln Val Ser Met
785                 790                 795                 800
Ala Val Gly Asp Gln Val Thr Thr Ala Glu Tyr Trp Val Arg Gln Val
                805                 810                 815
Arg Asp Thr Val Arg Phe Gly Glu Gln Val Ala Ser Tyr Glu Asp Ala
                820                 825                 830
Val Phe Val Glu Leu Gly Ala Asp Arg Ser Leu Ala Arg Leu Val Asp
            835                 840                 845
Gly Val Ala Met Leu His Gly Asp His Glu Ile Gln Ala Ala Ile Gly
            850                 855                 860
Ala Leu Ala His Leu Tyr Val Asn Gly Val Thr Val Asp Trp Pro Ala
865                 870                 875                 880
Leu Leu Gly Asp Ala Pro Ala Thr Arg Val Leu Asp Leu Pro Thr Tyr
                885                 890                 895
Ala Phe Gln His Gln Arg Tyr Trp Leu Glu Ser Ala Arg Pro Ala Ala
                900                 905                 910
Ser Asp Ala Gly His Pro Val Leu Gly Ser Gly Ile Ala Leu Ala Gly
            915                 920                 925
Ser Pro Gly Arg Val Phe Thr Gly Ser Val Pro Thr Gly Ala Asp Arg
            930                 935                 940
Ala Val Phe Val Ala Glu Leu Ala Leu Ala Ala Asp Ala Val Asp
945                 950                 955                 960
Cys Ala Thr Val Glu Arg Leu Asp Ile Ala Ser Val Pro Gly Arg Pro
                965                 970                 975
Gly His Gly Arg Thr Thr Val Gln Thr Trp Val Asp Glu Pro Ala Asp
            980                 985                 990
Asp Gly Arg Arg Arg Phe Thr Val His Thr Arg Thr Gly Asp Ala Pro
            995                 1000                1005
Trp Thr Leu His Ala Glu Gly Val Leu Arg Pro His Gly Thr Ala
       1010                1015                1020
Leu Pro Asp Ala Ala Asp Ala Glu Trp Pro Pro Gly Ala Val
       1025                1030                1035
Pro Ala Asp Gly Leu Pro Gly Val Trp Arg Arg Gly Asp Gln Val
       1040                1045                1050
Phe Ala Glu Ala Glu Val Asp Gly Pro Asp Gly Phe Val Val His
       1055                1060                1065
Pro Asp Leu Leu Asp Ala Val Phe Ser Ala Val Gly Asp Gly Ser
```

-continued

```
                1070                1075                1080
Arg Gln Pro Ala Gly Trp Arg Asp Leu Thr Val His Ala Ser Asp
    1085                1090                1095
Ala Thr Val Leu Arg Ala Cys Leu Thr Arg Arg Thr Asp Gly Ala
    1100                1105                1110
Met Gly Phe Ala Ala Phe Asp Gly Ala Gly Leu Pro Val Leu Thr
    1115                1120                1125
Ala Glu Ala Val Thr Leu Arg Glu Val Ala Ser Pro Ser Gly Ser
    1130                1135                1140
Glu Glu Ser Asp Gly Leu His Arg Leu Glu Trp Leu Ala Val Ala
    1145                1150                1155
Glu Ala Val Tyr Asp Gly Asp Leu Pro Glu Gly His Val Leu Ile
    1160                1165                1170
Thr Ala Ala His Pro Asp Asp Pro Glu Asp Ile Pro Thr Arg Ala
    1175                1180                1185
His Thr Arg Ala Thr Arg Val Leu Thr Ala Leu Gln His His Leu
    1190                1195                1200
Thr Thr Thr Asp His Thr Leu Ile Val His Thr Thr Asp Pro
    1205                1210                1215
Ala Gly Ala Thr Val Thr Gly Leu Thr Arg Thr Ala Gln Asn Glu
    1220                1225                1230
His Pro His Arg Ile Arg Leu Ile Glu Thr Asp His Pro His Thr
    1235                1240                1245
Pro Leu Pro Leu Ala Gln Leu Ala Thr Leu Asp His Pro His Leu
    1250                1255                1260
Arg Leu Thr His His Thr Leu His His Pro His Leu Thr Pro Leu
    1265                1270                1275
His Thr Thr Thr Pro Pro Thr Thr Thr Pro Leu Asn Pro Glu His
    1280                1285                1290
Ala Ile Ile Ile Thr Gly Gly Ser Gly Thr Leu Ala Gly Ile Leu
    1295                1300                1305
Ala Arg His Leu Asn His Pro His Thr Tyr Leu Leu Ser Arg Thr
    1310                1315                1320
Pro Pro Pro Asp Ala Thr Pro Gly Thr His Leu Pro Cys Asp Val
    1325                1330                1335
Gly Asp Pro His Gln Leu Ala Thr Thr Leu Thr His Ile Pro Gln
    1340                1345                1350
Pro Leu Thr Ala Ile Phe His Thr Ala Ala Thr Leu Asp Asp Gly
    1355                1360                1365
Ile Leu His Ala Leu Thr Pro Asp Arg Leu Thr Thr Val Leu His
    1370                1375                1380
Pro Lys Ala Asn Ala Ala Trp His Leu His His Leu Thr Gln Asn
    1385                1390                1395
Gln Pro Leu Thr His Phe Val Leu Tyr Ser Ser Ala Ala Ala Val
    1400                1405                1410
Leu Gly Ser Pro Gly Gln Gly Asn Tyr Ala Ala Ala Asn Ala Phe
    1415                1420                1425
Leu Asp Ala Leu Ala Thr His Arg His Thr Leu Gly Gln Pro Ala
    1430                1435                1440
Thr Ser Ile Ala Trp Gly Met Trp His Thr Thr Ser Thr Leu Thr
    1445                1450                1455
Gly Gln Leu Asp Asp Ala Asp Arg Asp Arg Ile Arg Arg Gly Gly
    1460                1465                1470
```

Phe Leu  Pro Ile Thr Asp Asp  Glu Gly
    1475             1480

<210> SEQ ID NO 22
<211> LENGTH: 4547
<212> TYPE: DNA
<213> ORGANISM: Artificial Sequence
<220> FEATURE:
<223> OTHER INFORMATION: primer

<400> SEQUENCE: 22

| | | | | | |
|---|---|---|---|---|---|
| agatctggca | gctcgccgaa | gcgctgctga | cgctcgtccg | ggagagcacc | gccgccgtgc | 60 |
| tcggccacgt | gggtggcgag | gacatccccg | cgacggcggc | gttcaaggac | ctcggcatcg | 120 |
| actcgctcac | cgcggtccag | ctgcgcaacg | ccctcaccga | ggcgaccggt | gtgcggctga | 180 |
| acgccacggc | ggtcttcgac | ttcccgaccc | cgcacgtgct | cgccgggaag | ctcggcgacg | 240 |
| aactgaccgg | cacccgcgcg | cccgtcgtgc | cccggaccgc | ggccacggcc | ggtgcgcacg | 300 |
| acgagccgct | ggcgatcgtg | ggaatggcct | gccggctgcc | cggcggggtc | gcgtcacccg | 360 |
| aggagctgtg | gcacctcgtg | gcatccggca | ccgacgccat | cacggagttc | ccgacggacc | 420 |
| gcggctggga | cgtcgacgcg | atctacgacc | cggaccccga | cgcgatcggc | aagaccttcg | 480 |
| tccggcacgg | tggcttcctc | accggcgcga | caggcttcga | cgcggcgttc | ttcggcatca | 540 |
| gcccgcgcga | ggccctcgcg | atggacccgc | agcagcgggt | gctcctggag | acgtcgtggg | 600 |
| aggcgttcga | aagcgccggc | atcacccgg | actcgacccg | cggcagcgac | accggcgtgt | 660 |
| tcgtcggcgc | cttctcctac | ggttacggca | ccggtgcgga | caccgacggc | ttcggcgcga | 720 |
| ccggctcgca | gaccagtgtg | ctctccggcc | ggctgtcgta | cttctacggt | ctggagggtc | 780 |
| cggcggtcac | ggtcgacacg | gcgtgttcgt | cgtcgctggt | ggcgctgcac | caggccgggc | 840 |
| agtcgctgcg | ctccggcgaa | tgctcgctcg | ccctggtcgg | cggcgtcacg | gtgatggcgt | 900 |
| ctcccggcgg | cttcgtggag | ttctcccggc | agcgcggcct | cgcgccggac | ggccgggcga | 960 |
| aggcgttcgg | cgcgggtgcg | gacggcacga | gcttcgccga | gggtgccggt | gtgctgatcg | 1020 |
| tcgagaggct | ctccgacgcc | gaacgcaacg | gtcacaccgt | cctggcggtc | gtccgtggtt | 1080 |
| cggcggtcaa | ccaggatggt | gcctccaacg | ggctgtcggc | gccgaacggg | ccgtcgcagg | 1140 |
| agcgggtgat | ccggcaggcc | ctggccaacg | ccgggctcac | cccggcggac | gtggacgccg | 1200 |
| tcgaggccca | cggcaccggc | accaggctgg | gcgaccccat | cgaggcacag | gcggtactgg | 1260 |
| ccacctacgg | acaggagcgc | gccaccccc | tgctgctggg | ctcgctgaag | tccaacatcg | 1320 |
| gccacgccca | ggccgcgtcc | ggcgtcgccg | gcatcatcaa | gatggtgcag | gccctccggc | 1380 |
| acggggagct | gccgccgacg | ctgcacgccg | acgagccgtc | gccgcacgtc | gactggacgg | 1440 |
| ccggcgccgt | cgaactgctg | acgtcggccc | ggccgtggcc | cgagaccgac | cggccacggc | 1500 |
| gtgccgccgt | ctcctcgttc | ggggtgagcg | gcaccaacgc | ccacgtcatc | ctggaggccg | 1560 |
| gaccggtaac | ggagacgccc | gcggcatcgc | cttccggtga | ccttcccctg | ctggtgtcgg | 1620 |
| cacgctcacc | ggaagcgctc | gacgagcaga | tccgccgact | gcgcgcctac | ctggacacca | 1680 |
| ccccggacgt | cgaccgggtg | gccgtggcac | agacgctggc | ccggcgcaca | cacttcgccc | 1740 |
| accgcgccgt | gctgctcggt | gacaccgtca | tcaccacacc | ccccgcggac | cggcccgacg | 1800 |
| aactcgtctt | cgtctactcc | ggccagggca | cccagcatcc | cgcgatgggc | gagcagctag | 1860 |
| ccgattcgtc | ggtggtgttc | gccgagcgga | tggccgagtg | tgcggcggcg | ttgcgcgagt | 1920 |
| tcgtggactg | ggatctgttc | acggttctgg | atgatccggc | ggtggtggac | cgggttgatg | 1980 |

```
tggtccagcc cgcttcctgg gcgatgatgg tttccctggc cgcggtgtgg caggcggccg    2040
gtgtgcggcc ggatgcggtg atcggccatt cgcagggtga gatcgccgca gcttgtgtgg    2100
cgggtgcggt gtcactacgc gatgccgccc ggatcgtgac cttgcgcagc caggcgatcg    2160
cccggggcct ggcgggccgg ggcgcgatgg catccgtcgc cctgcccgcg caggatgtcg    2220
agctggtcga cggggcctgg atcgccgccc acaacgggcc cgcctccacc gtgatcgcgg    2280
gcaccccgga agcggtcgac catgtcctca ccgctcatga ggcacaaggg gtgcgggtgc    2340
ggcggatcac cgtcgactat gcctcgcaca ccccgcacgt cgagctgatc cgcgacgaac    2400
tactcgacat cactagcgac agcagctcgc agacccgct cgtgccgtgg ctgtcgaccg    2460
tggacgcac ctgggtcgac agcccgctgg acggggagta ctggtaccgg aacctgcgtg    2520
aaccggtcgg tttccacccc gccgtcagcc agttgcaggc ccagggcgac accgtgttcg    2580
tcgaggtcag cgccagcccg tgttgttgc aggcgatgga cgacgatgtc gtcacggttg    2640
ccacgctgcg tcgtgacgac ggcgacgcca cccggatgct caccgccctg gcacaggcct    2700
atgtccacgg cgtcaccgtc gactggcccg ccatcctcgg caccaccaca acccgggtac    2760
tggaccttcc gacctacgcc ttccaacacc agcggtactg gctcgagtcg gcacgcccgg    2820
ccgcatccga cgcgggccac cccgtgctgg gctccggtat cgccctcgcc gggtcgccgg    2880
gccgggtgtt cacgggttcc gtgccgaccg gtgcggaccg cgcggtgttc gtcgccgagc    2940
tggcgctggc cgccgcggac gcggtcgact gcgccacggt cgagcggctc gacatcgcct    3000
ccgtgcccgg ccgccgggc catggccgga cgaccgtaca gacctgggtc gacgagccgg    3060
cggacgacgg ccggcgccgg ttcaccgtgc acacccgcac cggcgacgcc ccgtggacgc    3120
tgcacgccga ggggtgctg cgcccccatg gcacggccct gcccgatgcg gccgacgccg    3180
agtggccccc accgggcgcg gtgcccgcgg acgggctgcc gggtgtgtgg cgccgggggg    3240
accaggtctt cgccgaggcc gaggtggacg gaccggacgg tttcgtggtg caccccgacc    3300
tgctcgacgc ggtcttctcc gcggtcggcg acggaagccg ccagccggcc ggatggcgcg    3360
acctgacggt gcacgcgtcg gacgccaccg tactgcgcgc ctgcctcacc cggcgcaccg    3420
acggagccat gggattcgcc gccttcgacg gcgccggcct gccggtactc accgcggagg    3480
cggtgacgct gcgggaggtg gcgtcaccgt ccggctccga ggagtcggac ggcctgcacc    3540
ggttggagtg gctcgcggtc gccgaggcgg tctacgacgg tgacctgccc gagggacatg    3600
tcctgatcac cgccgcccac cccgacgacc ccgaggacat acccaccgc gcccacaccc    3660
gcgccacccg cgtcctgacc gccctgcaac accacctcac caccaccgac cacaccctca    3720
tcgtccacac caccaccgac cccgccgcg ccaccgtcac cggcctcacc cgcaccgccc    3780
agaacgaaca ccccaccgc atccgcctca tcgaaaccga ccaccccac acccccctcc    3840
ccctggccca actcgccacc ctcgaccacc cccaccctccg cctcacccac cacacccctcc    3900
accacccca cctcaccccc ctccacacca ccaccccacc caccaccacc cccctcaacc    3960
ccgaacacgc catcatcatc accggcggct ccggcaccct cgccggcatc ctcgcccgcc    4020
acctgaacca ccccacacc tacctcctct cccgcacccc accccccgac gccaccccg    4080
gcacccacct ccccctgcgac gtcggcgacc ccaccaact cgccaccacc ctcacccaca    4140
tcccccaacc cctcaccgcc atcttccaca ccgccgccac cctcgacgac ggcatcctcc    4200
acgccctcac ccccgaccgc ctcaccaccg tcctccaccc caaagccaac gccgcctggc    4260
acctgcacca cctcacccaa aaccaacccc tcacccactt cgtcctctac tccagcgccg    4320
```

```
ccgccgtcct cggcagcccc ggacaaggaa actacgccgc cgccaacgcc ttcctcgacg    4380
ccctcgccac ccaccgccac accctcggcc aacccgccac ctccatcgcc tggggcatgt    4440
ggcacaccac cagcaccctc accggacaac tcgacgacgc cgaccgggac cgcatccgcc    4500
gcggcggttt cctcccgatc acggacgacg agggcatggg gatgcat                  4547
```

<210> SEQ ID NO 23
<211> LENGTH: 1509
<212> TYPE: PRT
<213> ORGANISM: Artificial Sequence
<220> FEATURE:
<223> OTHER INFORMATION: primer

<400> SEQUENCE: 23

```
Gln Leu Ala Glu Ala Leu Leu Thr Leu Val Arg Glu Ser Thr Ala Ala
1               5                   10                  15

Val Leu Gly His Val Gly Gly Glu Asp Ile Pro Ala Thr Ala Ala Phe
            20                  25                  30

Lys Asp Leu Gly Ile Asp Ser Leu Thr Ala Val Gln Leu Arg Asn Ala
        35                  40                  45

Leu Thr Glu Ala Thr Gly Val Arg Leu Asn Ala Thr Ala Val Phe Asp
    50                  55                  60

Phe Pro Thr Pro His Val Leu Ala Gly Lys Leu Gly Asp Glu Leu Thr
65                  70                  75                  80

Gly Thr Arg Ala Pro Val Val Pro Arg Thr Ala Ala Thr Ala Gly Ala
                85                  90                  95

His Asp Glu Pro Leu Ala Ile Val Gly Met Ala Cys Arg Leu Pro Gly
            100                 105                 110

Gly Val Ala Ser Pro Glu Glu Leu Trp His Leu Val Ala Ser Gly Thr
        115                 120                 125

Asp Ala Ile Thr Glu Phe Pro Thr Asp Arg Gly Trp Asp Val Asp Ala
    130                 135                 140

Ile Tyr Asp Pro Asp Pro Asp Ala Ile Gly Lys Thr Phe Val Arg His
145                 150                 155                 160

Gly Gly Phe Leu Thr Gly Ala Thr Gly Phe Asp Ala Ala Phe Phe Gly
                165                 170                 175

Ile Ser Pro Arg Glu Ala Leu Ala Met Asp Pro Gln Gln Arg Val Leu
            180                 185                 190

Leu Glu Thr Ser Trp Glu Ala Phe Glu Ser Ala Gly Ile Thr Pro Asp
        195                 200                 205

Ser Thr Arg Gly Ser Asp Thr Gly Val Phe Val Gly Ala Phe Ser Tyr
    210                 215                 220

Gly Tyr Gly Thr Gly Ala Asp Thr Asp Gly Phe Gly Ala Thr Gly Ser
225                 230                 235                 240

Gln Thr Ser Val Leu Ser Gly Arg Leu Ser Tyr Phe Tyr Gly Leu Glu
                245                 250                 255

Gly Pro Ala Val Thr Val Asp Thr Ala Cys Ser Ser Ser Leu Val Ala
            260                 265                 270

Leu His Gln Ala Gly Gln Ser Leu Arg Ser Gly Glu Cys Ser Leu Ala
        275                 280                 285

Leu Val Gly Gly Val Thr Val Met Ala Ser Pro Gly Gly Phe Val Glu
    290                 295                 300

Phe Ser Arg Gln Arg Gly Leu Ala Pro Asp Gly Arg Ala Lys Ala Phe
305                 310                 315                 320

Gly Ala Gly Ala Asp Gly Thr Ser Phe Ala Glu Gly Ala Gly Val Leu
```

-continued

```
                325                 330                 335
Ile Val Glu Arg Leu Ser Asp Ala Glu Arg Asn Gly His Thr Val Leu
            340                 345                 350
Ala Val Val Arg Gly Ser Ala Val Asn Gln Asp Gly Ala Ser Asn Gly
            355                 360                 365
Leu Ser Ala Pro Asn Gly Pro Ser Gln Glu Arg Val Ile Arg Gln Ala
            370                 375                 380
Leu Ala Asn Ala Gly Leu Thr Pro Ala Asp Val Asp Ala Val Glu Ala
385                 390                 395                 400
His Gly Thr Gly Thr Arg Leu Gly Asp Pro Ile Glu Ala Gln Ala Val
                405                 410                 415
Leu Ala Thr Tyr Gly Gln Glu Arg Ala Thr Pro Leu Leu Leu Gly Ser
            420                 425                 430
Leu Lys Ser Asn Ile Gly His Ala Gln Ala Ala Ser Gly Val Ala Gly
            435                 440                 445
Ile Ile Lys Met Val Gln Ala Leu Arg His Gly Glu Leu Pro Pro Thr
            450                 455                 460
Leu His Ala Asp Glu Pro Ser Pro His Val Asp Trp Thr Ala Gly Ala
465                 470                 475                 480
Val Glu Leu Leu Thr Ser Ala Arg Pro Trp Pro Glu Thr Asp Arg Pro
                485                 490                 495
Arg Arg Ala Ala Val Ser Ser Phe Gly Val Ser Gly Thr Asn Ala His
            500                 505                 510
Val Ile Leu Glu Ala Gly Pro Val Thr Glu Thr Pro Ala Ala Ser Pro
            515                 520                 525
Ser Gly Asp Leu Pro Leu Leu Val Ser Ala Arg Ser Pro Glu Ala Leu
            530                 535                 540
Asp Glu Gln Ile Arg Arg Leu Arg Ala Tyr Leu Asp Thr Thr Pro Asp
545                 550                 555                 560
Val Asp Arg Val Ala Val Ala Gln Thr Leu Ala Arg Arg Thr His Phe
                565                 570                 575
Ala His Arg Ala Val Leu Leu Gly Asp Thr Val Ile Thr Thr Pro Pro
            580                 585                 590
Ala Asp Arg Pro Asp Glu Leu Val Phe Val Tyr Ser Gly Gln Gly Thr
            595                 600                 605
Gln His Pro Ala Met Gly Glu Gln Leu Ala Asp Ser Ser Val Val Phe
            610                 615                 620
Ala Glu Arg Met Ala Glu Cys Ala Ala Ala Leu Arg Glu Phe Val Asp
625                 630                 635                 640
Trp Asp Leu Phe Thr Val Leu Asp Pro Ala Val Val Asp Arg Val
                645                 650                 655
Asp Val Val Gln Pro Ala Ser Trp Ala Met Met Val Ser Leu Ala Ala
            660                 665                 670
Val Trp Gln Ala Ala Gly Val Arg Pro Asp Ala Val Ile Gly His Ser
            675                 680                 685
Gln Gly Glu Ile Ala Ala Cys Val Ala Gly Ala Val Ser Leu Arg
            690                 695                 700
Asp Ala Ala Arg Ile Val Thr Leu Arg Ser Gln Ala Ile Ala Arg Gly
705                 710                 715                 720
Leu Ala Gly Arg Gly Ala Met Ala Ser Val Ala Leu Pro Ala Gln Asp
                725                 730                 735
Val Glu Leu Val Asp Gly Ala Trp Ile Ala Ala His Asn Gly Pro Ala
            740                 745                 750
```

```
Ser Thr Val Ile Ala Gly Thr Pro Glu Ala Val Asp His Val Leu Thr
            755                 760                 765

Ala His Glu Ala Gln Gly Val Arg Val Arg Ile Thr Val Asp Tyr
    770                 775                 780

Ala Ser His Thr Pro His Val Glu Leu Ile Arg Asp Glu Leu Leu Asp
785                 790                 795                 800

Ile Thr Ser Asp Ser Ser Gln Thr Pro Leu Val Pro Trp Leu Ser
                805                 810                 815

Thr Val Asp Gly Thr Trp Val Asp Ser Pro Leu Asp Gly Glu Tyr Trp
                820                 825                 830

Tyr Arg Asn Leu Arg Glu Pro Val Gly Phe His Pro Ala Val Ser Gln
            835                 840                 845

Leu Gln Ala Gln Gly Asp Thr Val Phe Val Glu Val Ser Ala Ser Pro
    850                 855                 860

Val Leu Leu Gln Ala Met Asp Asp Val Val Thr Val Ala Thr Leu
865                 870                 875                 880

Arg Arg Asp Asp Gly Asp Ala Thr Arg Met Leu Thr Ala Leu Ala Gln
                885                 890                 895

Ala Tyr Val His Gly Val Thr Val Asp Trp Pro Ala Ile Leu Gly Thr
                900                 905                 910

Thr Thr Thr Arg Val Leu Asp Leu Pro Thr Tyr Ala Phe Gln His Gln
            915                 920                 925

Arg Tyr Trp Leu Glu Ser Ala Arg Pro Ala Ala Ser Asp Ala Gly His
    930                 935                 940

Pro Val Leu Gly Ser Gly Ile Ala Leu Ala Gly Ser Pro Gly Arg Val
945                 950                 955                 960

Phe Thr Gly Ser Val Pro Thr Gly Ala Asp Arg Ala Val Phe Val Ala
                965                 970                 975

Glu Leu Ala Leu Ala Ala Asp Ala Val Asp Cys Ala Thr Val Glu
            980                 985                 990

Arg Leu Asp Ile Ala Ser Val Pro  Gly Arg Pro Gly His  Gly Arg Thr
            995                 1000                1005

Thr Val  Gln Thr Trp Val Asp  Glu Pro Ala Asp Asp  Gly Arg Arg
    1010                1015                1020

Arg Phe  Thr Val His Thr Arg  Thr Gly Asp Ala Pro  Trp Thr Leu
    1025                1030                1035

His Ala  Glu Gly Val Leu Arg  Pro His Gly Thr Ala  Leu Pro Asp
    1040                1045                1050

Ala Ala  Asp Ala Glu Trp Pro  Pro Pro Gly Ala Val  Pro Ala Asp
    1055                1060                1065

Gly Leu  Pro Gly Val Trp Arg  Arg Gly Asp Gln Val  Phe Ala Glu
    1070                1075                1080

Ala Glu  Val Asp Gly Pro Asp  Gly Phe Val Val His  Pro Asp Leu
    1085                1090                1095

Leu Asp  Ala Val Phe Ser Ala  Val Gly Asp Gly Ser  Arg Gln Pro
    1100                1105                1110

Ala Gly  Trp Arg Asp Leu Thr  Val His Ala Ser Asp  Ala Thr Val
    1115                1120                1125

Leu Arg  Ala Cys Leu Thr Arg  Arg Thr Asp Gly Ala  Met Gly Phe
    1130                1135                1140

Ala Ala  Phe Asp Gly Ala Gly  Leu Pro Val Leu Thr  Ala Glu Ala
    1145                1150                1155
```

-continued

Val Thr Leu Arg Glu Val Ala Ser Pro Ser Gly Ser Glu Glu Ser
       1160                1165                1170

Asp Gly Leu His Arg Leu Glu Trp Leu Ala Val Ala Glu Ala Val
       1175                1180                1185

Tyr Asp Gly Asp Leu Pro Glu Gly His Val Leu Ile Thr Ala Ala
       1190                1195                1200

His Pro Asp Asp Pro Glu Asp Ile Pro Thr Arg Ala His Thr Arg
       1205                1210                1215

Ala Thr Arg Val Leu Thr Ala Leu Gln His His Leu Thr Thr Thr
       1220                1225                1230

Asp His Thr Leu Ile Val His Thr Thr Thr Asp Pro Ala Gly Ala
       1235                1240                1245

Thr Val Thr Gly Leu Thr Arg Thr Ala Gln Asn Glu His Pro His
       1250                1255                1260

Arg Ile Arg Leu Ile Glu Thr Asp His Pro His Thr Pro Leu Pro
       1265                1270                1275

Leu Ala Gln Leu Ala Thr Leu Asp His Pro His Leu Arg Leu Thr
       1280                1285                1290

His His Thr Leu His His Pro His Leu Thr Pro Leu His Thr Thr
       1295                1300                1305

Thr Pro Pro Thr Thr Thr Pro Leu Asn Pro Glu His Ala Ile Ile
       1310                1315                1320

Ile Thr Gly Gly Ser Gly Thr Leu Ala Gly Ile Leu Ala Arg His
       1325                1330                1335

Leu Asn His Pro His Thr Tyr Leu Leu Ser Arg Thr Pro Pro Pro
       1340                1345                1350

Asp Ala Thr Pro Gly Thr His Leu Pro Cys Asp Val Gly Asp Pro
       1355                1360                1365

His Gln Leu Ala Thr Thr Leu Thr His Ile Pro Gln Pro Leu Thr
       1370                1375                1380

Ala Ile Phe His Thr Ala Ala Thr Leu Asp Asp Gly Ile Leu His
       1385                1390                1395

Ala Leu Thr Pro Asp Arg Leu Thr Thr Val Leu His Pro Lys Ala
       1400                1405                1410

Asn Ala Ala Trp His Leu His His Leu Thr Gln Asn Gln Pro Leu
       1415                1420                1425

Thr His Phe Val Leu Tyr Ser Ser Ala Ala Ala Val Leu Gly Ser
       1430                1435                1440

Pro Gly Gln Gly Asn Tyr Ala Ala Ala Asn Ala Phe Leu Asp Ala
       1445                1450                1455

Leu Ala Thr His Arg His Thr Leu Gly Gln Pro Ala Thr Ser Ile
       1460                1465                1470

Ala Trp Gly Met Trp His Thr Ser Thr Leu Thr Gly Gln Leu
       1475                1480                1485

Asp Asp Ala Asp Arg Asp Arg Ile Arg Arg Gly Gly Phe Leu Pro
       1490                1495                1500

Ile Thr Asp Asp Glu Gly
       1505

<210> SEQ ID NO 24
<211> LENGTH: 4725
<212> TYPE: DNA
<213> ORGANISM: Artificial Sequence
<220> FEATURE:
<223> OTHER INFORMATION: primer -continued

<400> SEQUENCE: 24

```
gcatgcggct gtacgaggcg gcacggcgca ccggaagtcc cgtggtggtg gcggccgcgc      60
tcgacgacgc gccggacgtg ccgctgctgc gcgggctgcg gcgtacgacc gtccggcgtg     120
ccgccgtccg ggaacgctct ctcgccgacc gctcgccgtg ctgcccgacg acgagcgcgc     180
cgacgcctcc ctcgcgttcg tcctggaaca gcaccgccac cgtgctcggc cacctgggcg     240
ccgaagacat cccggcgacg acgacgttca aggaactcgg catcgactcg ctcaccgcgg     300
tccagctgcg caacgcgctg accacggcga ccggcgtacg cctcaacgcc acagcggtct     360
tcgactttcc gacgccgcgc gcgctcgccg cgagactcgg cgacgagctg gccggtaccc     420
gcgcgcccgt cgcggcccgg accgcggcca ccgcggccgc gcacgacgaa ccgctggcga     480
tcgtgggcat ggcctgccgt ctgccgggcg gggtcgcgtc gccacaggag ctgtggcgtc     540
tcgtcgcgtc cggcaccgac gccatcacgg agttccccgc ggaccgcggc tgggacgtgg     600
acgcgctcta cgacccggac cccgacgcga tcggcaagac cttcgtccgg cacggcggct     660
tcctcgacgg tgcgaccggc ttcgacgcgg cgttcttcgg gatcagcccg cgcgaggccc     720
tggccatgga cccgcagcaa cgggtgctcc tggagacgtc ctgggaggcg ttcgaaagcg     780
cgggcatcac cccggacgcg gcgcggggca gcgacaccgg cgtgttcatc ggcgcgttct     840
cctacgggta cggcacgggt gcggatacca acggcttcgg cgcgacaggg tcgcagacca     900
gcgtgctctc cggccgcctc tcgtacttct acggtctgga gggcccttcg gtcacggtcg     960
acaccgcctg ctcgtcgtca ctggtcgccc tgcaccaggc agggcagtcc ctgcgctcgg    1020
gcgaatgctc gctcgccctg gtcggcggtg tcacggtgat ggcgtcgccc ggcggattcg    1080
tcgagttctc ccggcagcgc gggctcgcgc cggacgggcg ggcgaaggcg ttcggcgcgg    1140
gcgcggacgg tacgagcttc gccgagggcg ccggtgccct ggtggtcgag cggctctccg    1200
acgcggagcg ccacgccac accgtcctcg ccctcgtacg cggctccgcg ctaactccg    1260
acggcgcgtc gaacggtctg tcggcgccga acggcccctc ccaggaacgc gtcatccacc    1320
aggccctcgc gaacgcgaaa ctcacccccg ccgatgtcga cgcggtcgag gcgcacggca    1380
ccggcacccg cctcggcgac cccatcgagg cgcaggcgct gctcgcgacg tacgacagg    1440
accgggcgac gccctgctg ctcggctcgc tgaagtcgaa catcgggcac gcccaggccg    1500
cgtcagggt cgccgggatc atcaagatgg tgcaggccat ccggcacggg gaactgccgc    1560
cgacactgca cgcggacgag ccgtcgccgc acgtcgactg gacggccggt gccgtcgagc    1620
tcctgacgtc ggcccggccg tggccgggga ccggtcgccc gcgccgcgct gccgtctcgt    1680
cgttcggcgt gagcggcacg aacgcccaca tcatccttga ggcaggaccg gtcaaaacgg    1740
gaccggtcga ggcaggagcg atcgaggcag gaccggtcga agtaggaccg gtcgaggctg    1800
gaccgctccc cgcggcgccg ccgtcagcac cgggcgaaga ccttccgctg ctcgtgtcgg    1860
cgcgttcccc ggaggcactc gacgagcaga tcgggcgcct gcgcgcctat ctcgacaccg    1920
gcccgggcgt cgaccgggcg gccgtggcgc agacactggc ccggcgtacg cacttcaccc    1980
accgggccgt actgctcggg gacaccgtca tcggcgctcc ccccgcggac caggccgacg    2040
aactcgtctt cgtctactcc ggtcagggca cccagcatcc cgcgatgggc gagcaactcg    2100
cggccgcgtt ccccgtgttc gccgatgcct ggcacgacgc gctccgacgg ctcgacgacc    2160
ccgacccgca cgaccccaca cggagccagc acacgctctt cgcccaccag gcggcgttca    2220
ccgccctcct gaggtcctgg gacatcacgc cgcacgcgt catcggccac tcgctcggcg    2280
```

```
agatcaccgc cgcgtacgcc gccgggatcc tgtcgctcga cgacgcctgc accctgatca   2340
ccacgcgtgc ccgcctcatg cacacgcttc cgccgcccgg cgccatggtc accgtgctga   2400
ccagcgagga ggaggcccgt caggcgctgc ggccgggcgt ggagatcgcc gcggtcttcg   2460
gcccgcactc cgtcgtgctc tcgggcgacg aggacgccgt gctcgacgtc gcacagcggc   2520
tcggcatcca ccaccgtctg cccgcgccgc acgcgggcca ctccgcgcac atggaacccg   2580
tggccgccga gctgctcgcc accactcgcg agctccgtta cgaccggccc cacaccgcca   2640
tcccgaacga ccccaccacc gccgagtact gggccgagca ggtccgcaac cccgtgctgt   2700
tccacgccca cacccagcgg taccccgacg ccgtgttcgt cgagatcggc cccggccagg   2760
acctctcacc gctggtcgac ggcatcgccc tgcagaacgg cacggcggac gaggtgcacg   2820
cgctgcacac cgcgctcgcc cgcctcttca cacgcgcgc cacgctcgac tggtcccgca   2880
tcctcggcgg tgcttcgcgg cacgaccctg acgtcccctc gtacgcgttc agcggcgtc   2940
cctactggat cgagtcggct ccccggca cggccgactc gggccacccc gtcctcggca   3000
ccggagtcgc cgtcgccggg tcgccgggcc gggtgttcac gggtcccgtg cccgccggtg   3060
cggaccgcgc ggtgttcatc gccgaactgg cgctcgccgc cgccgacgcc accgactgcg   3120
ccacggtcga acagctcgac gtcacctccg tgcccggcgg atccgcccgc ggcagggcca   3180
ccgcgcagac ctgggtcgat gaacccgccg ccgacgggcg cgccgcttc accgtccaca   3240
cccgcgtcgg cgacgccccg tggacgctgc acgccgaggg ggttctccgc cccggccgcg   3300
tgccccagcc cgaagccgtc gacaccgcct ggccccccgcc gggcgcggtg cccgcggacg   3360
ggctgcccgg ggcgtggcga cgcgcggacc aggtcttcgt cgaagccgaa gtcgacagcc   3420
ctgacggctt cgtggcacac cccgacctgc tcgacgcggt cttctccgcg gtcggcgacg   3480
ggagccgcca gccgaccgga tggcgcgacc tcgcggtgca cgcgtcggac gccaccgtgc   3540
tgcgcgcctg cctcacccgc cgcgacagtg gtgtcgtgga gctcgccgcc ttcgacggtg   3600
ccggaatgcc ggtgctcacc gcggagtcgg tgacgctggg cgaggtcgcg tcggcaggcg   3660
gatccgacga gtcggacggt ctgcttcggc ttgagtggtt gccggtggcg gaggcccact   3720
acgacggtgc cgacgagctg cccgagggct acaccctcat caccgccaca caccccgacg   3780
accccgacga ccccaccaac ccccacaaca cacccacacg cacccacaca caaaccacac   3840
gcgtcctcac cgccctccaa caccacctca tcaccaccaa ccacaccctc atcgtccaca   3900
ccaccaccga ccccccaggc gccgccgtca ccggcctcac ccgcaccgca caaaacgaac   3960
accccggccg catccacctc atcgaaaccc accaccccca caccccactc cccctcaccc   4020
aactcaccac cctccaccaa ccccacctac gcctcaccaa caacccctc cacaccccc   4080
acctcacccc catcaccacc caccacaaca ccaccacaac caccccaac accccacccc   4140
tcaaccccaa ccacgccatc ctcatcaccg gcggctccgg caccctcgcc ggcatcctcg   4200
cccgccacct caaccacccc cacacctacc tcctctcccg cacaccacca cccccacca   4260
cacccggcac ccacatcccc tgcgacctca ccgaccccac ccaaatcacc caagccctca   4320
cccacatacc acaaccctc accggcatct tccacaccgc cgccacctc gacgacgcca   4380
ccctcaccaa cctcaccccc caacacctca ccaccaccct ccaacccaaa gccgacgccg   4440
cctggcacct ccaccaccac acccaaaacc aaccctcac ccacttcgtc ctctactcca   4500
gcgccgccgc caccctcggc agccccggcc aagccaacta cgccgccgcc aacgccttcc   4560
tcgacgccct cgccacccac cgccacaccc aaggacaacc cgccaccacc atcgcctggg   4620
gcatgtggca caccaccacc acactcacca gccaactcac cgacagcgac cgcgaccgca   4680
```

```
tccgccgcgg cggcttcctg ccgatctcgg acgacgaggg catgc                4725
```

<210> SEQ ID NO 25
<211> LENGTH: 1574
<212> TYPE: PRT
<213> ORGANISM: Artificial Sequence
<220> FEATURE:
<223> OTHER INFORMATION: primer

<400> SEQUENCE: 25

```
Met Arg Leu Tyr Glu Ala Ala Arg Arg Thr Gly Ser Pro Val Val
1               5                   10                  15

Ala Ala Ala Leu Asp Asp Ala Pro Asp Val Pro Leu Leu Arg Gly Leu
                20                  25                  30

Arg Arg Thr Thr Val Arg Arg Ala Val Arg Glu Arg Ser Leu Ala
            35                  40                  45

Asp Arg Ser Pro Cys Cys Pro Thr Thr Ser Ala Pro Thr Pro Pro Ser
50                  55                  60

Arg Ser Ser Trp Asn Ser Thr Ala Thr Val Leu Gly His Leu Gly Ala
65                  70                  75                  80

Glu Asp Ile Pro Ala Thr Thr Thr Phe Lys Glu Leu Gly Ile Asp Ser
                85                  90                  95

Leu Thr Ala Val Gln Leu Arg Asn Ala Leu Thr Thr Ala Thr Gly Val
                100                 105                 110

Arg Leu Asn Ala Thr Ala Val Phe Asp Phe Pro Thr Pro Arg Ala Leu
            115                 120                 125

Ala Ala Arg Leu Gly Asp Glu Leu Ala Gly Thr Arg Ala Pro Val Ala
130                 135                 140

Ala Arg Thr Ala Ala Thr Ala Ala Ala His Asp Glu Pro Leu Ala Ile
145                 150                 155                 160

Val Gly Met Ala Cys Arg Leu Pro Gly Gly Val Ala Ser Pro Gln Glu
                165                 170                 175

Leu Trp Arg Leu Val Ala Ser Gly Thr Asp Ala Ile Thr Glu Phe Pro
                180                 185                 190

Ala Asp Arg Gly Trp Asp Val Asp Ala Leu Tyr Asp Pro Asp Pro Asp
            195                 200                 205

Ala Ile Gly Lys Thr Phe Val Arg His Gly Gly Phe Leu Asp Gly Ala
210                 215                 220

Thr Gly Phe Asp Ala Ala Phe Phe Gly Ile Ser Pro Arg Glu Ala Leu
225                 230                 235                 240

Ala Met Asp Pro Gln Gln Arg Val Leu Leu Glu Thr Ser Trp Glu Ala
                245                 250                 255

Phe Glu Ser Ala Gly Ile Thr Pro Asp Ala Ala Arg Gly Ser Asp Thr
                260                 265                 270

Gly Val Phe Ile Gly Ala Phe Ser Tyr Gly Tyr Gly Thr Gly Ala Asp
            275                 280                 285

Thr Asn Gly Phe Gly Ala Thr Gly Ser Gln Thr Ser Val Leu Ser Gly
290                 295                 300

Arg Leu Ser Tyr Phe Tyr Gly Leu Glu Gly Pro Ser Val Thr Val Asp
305                 310                 315                 320

Thr Ala Cys Ser Ser Ser Leu Val Ala Leu His Gln Ala Gly Gln Ser
                325                 330                 335

Leu Arg Ser Gly Glu Cys Ser Leu Ala Leu Val Gly Gly Val Thr Val
                340                 345                 350
```

```
Met Ala Ser Pro Gly Gly Phe Val Glu Phe Ser Arg Gln Arg Gly Leu
        355                 360                 365
Ala Pro Asp Gly Arg Ala Lys Ala Phe Gly Ala Gly Ala Asp Gly Thr
    370                 375                 380
Ser Phe Ala Glu Gly Ala Gly Ala Leu Val Val Glu Arg Leu Ser Asp
385                 390                 395                 400
Ala Glu Arg His Gly His Thr Val Leu Ala Leu Val Arg Gly Ser Ala
                405                 410                 415
Ala Asn Ser Asp Gly Ala Ser Asn Gly Leu Ser Ala Pro Asn Gly Pro
            420                 425                 430
Ser Gln Glu Arg Val Ile His Gln Ala Leu Ala Asn Ala Lys Leu Thr
        435                 440                 445
Pro Ala Asp Val Asp Ala Val Glu Ala His Gly Thr Gly Thr Arg Leu
    450                 455                 460
Gly Asp Pro Ile Glu Ala Gln Ala Leu Leu Ala Thr Tyr Gly Gln Asp
465                 470                 475                 480
Arg Ala Thr Pro Leu Leu Leu Gly Ser Leu Lys Ser Asn Ile Gly His
                485                 490                 495
Ala Gln Ala Ala Ser Gly Val Ala Gly Ile Ile Lys Met Val Gln Ala
            500                 505                 510
Ile Arg His Gly Glu Leu Pro Pro Thr Leu His Ala Asp Glu Pro Ser
        515                 520                 525
Pro His Val Asp Trp Thr Ala Gly Ala Val Glu Leu Leu Thr Ser Ala
    530                 535                 540
Arg Pro Trp Pro Gly Thr Gly Arg Pro Arg Arg Ala Ala Val Ser Ser
545                 550                 555                 560
Phe Gly Val Ser Gly Thr Asn Ala His Ile Ile Leu Glu Ala Gly Pro
                565                 570                 575
Val Lys Thr Gly Pro Val Glu Ala Gly Ala Ile Glu Ala Gly Pro Val
            580                 585                 590
Glu Val Gly Pro Val Glu Ala Gly Pro Leu Pro Ala Ala Pro Pro Ser
        595                 600                 605
Ala Pro Gly Glu Asp Leu Pro Leu Leu Val Ser Ala Arg Ser Pro Glu
    610                 615                 620
Ala Leu Asp Glu Gln Ile Gly Arg Leu Arg Ala Tyr Leu Asp Thr Gly
625                 630                 635                 640
Pro Gly Val Asp Arg Ala Ala Val Ala Gln Thr Leu Ala Arg Arg Thr
                645                 650                 655
His Phe Thr His Arg Ala Val Leu Leu Gly Asp Thr Val Ile Gly Ala
            660                 665                 670
Pro Pro Ala Asp Gln Ala Asp Glu Leu Val Phe Val Tyr Ser Gly Gln
        675                 680                 685
Gly Thr Gln His Pro Ala Met Gly Glu Gln Leu Ala Ala Phe Pro
    690                 695                 700
Val Phe Ala Asp Ala Trp His Asp Ala Leu Arg Arg Leu Asp Pro
705                 710                 715                 720
Asp Pro His Asp Pro Thr Arg Ser Gln His Thr Leu Phe Ala His Gln
                725                 730                 735
Ala Ala Phe Thr Ala Leu Leu Arg Ser Trp Asp Ile Thr Pro His Ala
            740                 745                 750
Val Ile Gly His Ser Leu Gly Glu Ile Thr Ala Ala Tyr Ala Ala Gly
        755                 760                 765
Ile Leu Ser Leu Asp Asp Ala Cys Thr Leu Ile Thr Thr Arg Ala Arg
```

-continued

```
            770                 775                 780
Leu Met His Thr Leu Pro Pro Gly Ala Met Val Thr Val Leu Thr
785                 790                 795                 800

Ser Glu Glu Ala Arg Gln Ala Leu Arg Pro Gly Val Glu Ile Ala
                805                 810                 815

Ala Val Phe Gly Pro His Ser Val Val Leu Ser Gly Asp Glu Asp Ala
            820                 825                 830

Val Leu Asp Val Ala Gln Arg Leu Gly Ile His His Arg Leu Pro Ala
            835                 840                 845

Pro His Ala Gly His Ser Ala His Met Glu Pro Val Ala Ala Glu Leu
            850                 855                 860

Leu Ala Thr Thr Arg Glu Leu Arg Tyr Asp Arg Pro His Thr Ala Ile
865                 870                 875                 880

Pro Asn Asp Pro Thr Thr Ala Glu Tyr Trp Ala Glu Gln Val Arg Asn
                885                 890                 895

Pro Val Leu Phe His Ala His Thr Gln Arg Tyr Pro Asp Ala Val Phe
            900                 905                 910

Val Glu Ile Gly Pro Gly Gln Asp Leu Ser Pro Leu Val Asp Gly Ile
            915                 920                 925

Ala Leu Gln Asn Gly Thr Ala Asp Glu Val His Ala Leu His Thr Ala
            930                 935                 940

Leu Ala Arg Leu Phe Thr Arg Gly Ala Thr Leu Asp Trp Ser Arg Ile
945                 950                 955                 960

Leu Gly Gly Ala Ser Arg His Asp Pro Asp Val Pro Ser Tyr Ala Phe
                965                 970                 975

Gln Arg Arg Pro Tyr Trp Ile Glu Ser Ala Pro Pro Thr Ala Asp
                980                 985                 990

Ser Gly His Pro Val Leu Gly Thr  Gly Val Ala Val Ala  Gly Ser Pro
            995                 1000                1005

Gly Arg  Val Phe Thr Gly Pro  Val Pro Ala Gly Ala  Asp Arg Ala
            1010                1015                1020

Val Phe  Ile Ala Glu Leu Ala  Leu Ala Ala Ala Asp  Ala Thr Asp
            1025                1030                1035

Cys Ala  Thr Val Glu Gln Leu  Asp Val Thr Ser Val  Pro Gly Gly
            1040                1045                1050

Ser Ala  Arg Gly Arg Ala Thr  Ala Gln Thr Trp Val  Asp Glu Pro
            1055                1060                1065

Ala Ala  Asp Gly Arg Arg  Phe Thr Val His Thr  Arg Val Gly
            1070                1075                1080

Asp Ala  Pro Trp Thr Leu His  Ala Glu Gly Val Leu  Arg Pro Gly
            1085                1090                1095

Arg Val  Pro Gln Pro Glu Ala  Val Asp Thr Ala Trp  Pro Pro Pro
            1100                1105                1110

Gly Ala  Val Pro Ala Asp Gly  Leu Pro Gly Ala Trp  Arg Arg Ala
            1115                1120                1125

Asp Gln  Val Phe Val Glu Ala  Glu Val Asp Ser Pro  Asp Gly Phe
            1130                1135                1140

Val Ala  His Pro Asp Leu Leu  Asp Ala Val Phe Ser  Ala Val Gly
            1145                1150                1155

Asp Gly  Ser Arg Gln Pro Thr  Gly Trp Arg Asp Leu  Ala Val His
            1160                1165                1170

Ala Ser  Asp Ala Thr Val Leu  Arg Ala Cys Leu Thr  Arg Arg Asp
            1175                1180                1185
```

-continued

```
Ser Gly Val Val Glu Leu Ala Ala Phe Asp Gly Ala Gly Met Pro
    1190            1195                1200

Val Leu Thr Ala Glu Ser Val Thr Leu Gly Glu Val Ala Ser Ala
    1205            1210                1215

Gly Gly Ser Asp Glu Ser Asp Gly Leu Leu Arg Leu Glu Trp Leu
    1220            1225                1230

Pro Val Ala Glu Ala His Tyr Asp Gly Ala Asp Glu Leu Pro Glu
    1235            1240                1245

Gly Tyr Thr Leu Ile Thr Ala Thr His Pro Asp Pro Asp Asp
    1250            1255                1260

Pro Thr Asn Pro His Asn Thr Pro Thr Arg Thr His Thr Gln Thr
    1265            1270                1275

Thr Arg Val Leu Thr Ala Leu Gln His His Leu Ile Thr Thr Asn
    1280            1285                1290

His Thr Leu Ile Val His Thr Thr Asp Pro Pro Gly Ala Ala
    1295            1300                1305

Val Thr Gly Leu Thr Arg Thr Ala Gln Asn Glu His Pro Gly Arg
    1310            1315                1320

Ile His Leu Ile Glu Thr His His Pro His Thr Pro Leu Pro Leu
    1325            1330                1335

Thr Gln Leu Thr Thr Leu His Gln Pro His Leu Arg Leu Thr Asn
    1340            1345                1350

Asn Thr Leu His Thr Pro His Leu Thr Pro Ile Thr Thr His His
    1355            1360                1365

Asn Thr Thr Thr Thr Pro Asn Thr Pro Pro Leu Asn Pro Asn
    1370            1375                1380

His Ala Ile Leu Ile Thr Gly Gly Ser Gly Thr Leu Ala Gly Ile
    1385            1390                1395

Leu Ala Arg His Leu Asn His Pro His Thr Tyr Leu Leu Ser Arg
    1400            1405                1410

Thr Pro Pro Pro Pro Thr Thr Pro Gly Thr His Ile Pro Cys Asp
    1415            1420                1425

Leu Thr Asp Pro Thr Gln Ile Thr Gln Ala Leu Thr His Ile Pro
    1430            1435                1440

Gln Pro Leu Thr Gly Ile Phe His Thr Ala Ala Thr Leu Asp Asp
    1445            1450                1455

Ala Thr Leu Thr Asn Leu Thr Pro Gln His Leu Thr Thr Thr Leu
    1460            1465                1470

Gln Pro Lys Ala Asp Ala Ala Trp His Leu His His Thr Gln
    1475            1480                1485

Asn Gln Pro Leu Thr His Phe Val Leu Tyr Ser Ser Ala Ala Ala
    1490            1495                1500

Thr Leu Gly Ser Pro Gly Gln Ala Asn Tyr Ala Ala Ala Asn Ala
    1505            1510                1515

Phe Leu Asp Ala Leu Ala Thr His Arg His Thr Gln Gly Gln Pro
    1520            1525                1530

Ala Thr Thr Ile Ala Trp Gly Met Trp His Thr Thr Thr Thr Leu
    1535            1540                1545

Thr Ser Gln Leu Thr Asp Ser Asp Arg Asp Arg Ile Arg Arg Gly
    1550            1555                1560

Gly Phe Leu Pro Ile Ser Asp Asp Glu Gly Met
    1565            1570
```

<210> SEQ ID NO 26
<211> LENGTH: 4674
<212> TYPE: DNA
<213> ORGANISM: Artificial Sequence
<220> FEATURE:
<223> OTHER INFORMATION: primer

<400> SEQUENCE: 26

| | | | | | |
|---|---|---|---|---|---|
| gcatgcggct | gtacgaggcg | gcacggcgca | ccggaagtcc | cgtggtggtg | gcggccgcgc | 60 |
| tcgacgacgc | gccggacgtg | ccgctgctgc | gcgggctgcg | gcgtacgacc | gtccggcgtg | 120 |
| ccgccgtccg | ggaacgctct | ctcgccgacc | gctcgccgtg | ctgcccgacg | acgagcgcgc | 180 |
| cgacgcctcc | ctcgcgttcg | tcctggaaca | gcaccgccac | cgtgctcggc | cacctgggcg | 240 |
| ccgaagacat | cccggcgacg | acgacgttca | aggaactcgg | catcgactcg | ctcaccgcgg | 300 |
| tccagctgcg | caacgcgctg | accacggcga | ccggcgtacg | cctcaacgcc | acagcggtct | 360 |
| tcgactttcc | gacgccgcgc | gcgctcgccg | cgagactcgg | cgacgagctg | gccggtaccc | 420 |
| gcgcgcccgt | cgcggcccgg | accgcggcca | ccgcggccgc | gcacgacgaa | ccgctggcga | 480 |
| tcgtgggcat | ggcctgccgt | ctgccggcgc | gggtcgcgtc | gccacaggag | ctgtggcgtc | 540 |
| tcgtcgcgtc | cggcaccgac | gccatcacgg | agttccccgc | ggaccgcggc | tgggacgtgg | 600 |
| acgcgctcta | cgaccggac | cccgacgcga | tcggcaagac | cttcgtccgg | cacggcggct | 660 |
| tcctcgacgg | tgcgaccggc | ttcgacgcgg | cgttcttcgg | gatcagcccg | cgcgaggccc | 720 |
| tggccatgga | cccgcagcaa | cgggtgctcc | tggagacgtc | ctgggaggcg | ttcgaaagcg | 780 |
| cgggcatcac | cccggacgcg | gcgcggggca | gcgacaccgg | cgtgttcatc | ggcgcgttct | 840 |
| cctacgggta | cggcacgggt | gcggatacca | acggcttcgg | cgcgacaggg | tcgcagacca | 900 |
| gcgtgctctc | cggccgcctc | tcgtacttct | acggtctgga | gggcccttcg | gtcacggtcg | 960 |
| acaccgcctg | ctcgtcgtca | ctggtcgccc | tgcaccaggc | agggcagtcc | ctgcgctcgg | 1020 |
| gcgaatgctc | gctcgccctg | gtcggcggtg | tcacggtgat | ggcgtcgccc | ggcggattcg | 1080 |
| tcgagttctc | ccggcagcgc | gggctcgcgc | cggacgggcg | ggcgaaggcg | ttcgcgcgcg | 1140 |
| gcgcggacgg | tacgagcttc | gccgagggcg | ccggtgccct | ggtggtcgag | cggctctccg | 1200 |
| acgcggagcg | ccacgccac | accgtcctcg | ccctcgtacg | cggctccgcg | gctaactccg | 1260 |
| acggcgcgtc | gaacggtctg | tcggcgccga | acggcccctc | ccaggaacgc | gtcatccacc | 1320 |
| aggccctcgc | gaacgcgaaa | ctcaccccg | ccgatgtcga | cgcggtcgag | gcgcacggca | 1380 |
| ccggcacccg | cctcggcgac | cccatcgagg | cgcaggcgct | gctcgcgacg | tacgacagg | 1440 |
| accgggcgac | gccctgctg | ctcggctcgc | tgaagtcgaa | catcgggcac | gcccaggccg | 1500 |
| cgtcaggggt | cgccgggatc | atcaagatgg | tgcaggccat | ccggcacggg | gaactgccgc | 1560 |
| cgacactgca | cgcggacgag | ccgtcgccgc | acgtcgactg | gacggccggt | gccgtcgagc | 1620 |
| tcctgacgtc | ggcccggccg | tggcgggga | ccggtcgccc | taggcgggca | ggcgtgtcgt | 1680 |
| ccttcgggat | cagtggcacc | aacgcccacg | tcatcctgga | aagcgcaccc | cccactcagc | 1740 |
| ctgcggacaa | cgcggtgatc | gagcgggcac | cggagtgggt | gccgttggtg | atttcggcca | 1800 |
| ggacccagtc | ggctttgact | gagcacgagg | gccggttgcg | tgcgtatctg | gcggcgtcgc | 1860 |
| ccggggtgga | tatgcgggct | gtggcatcga | cgctggcgat | gacacggtcg | gtgttcgagc | 1920 |
| accgtgccgt | gctgctggga | gatgacaccg | tcaccggcac | cgctgtgtct | gaccctcggg | 1980 |
| cggtgttcgt | cttcccggga | caggggtcgc | agcgtgctgg | catgggtgag | gaactggccg | 2040 |
| ccgcgttccc | cgtcttcgcg | cggatccatc | agcaggtgtg | ggacctgctc | gatgtgcccg | 2100 |

```
atctggaggt gaacgagacc ggttacgccc agccggccct gttcgcaatg caggtggctc   2160
tgttcgggct gctggaatcg tggggtgtac gaccggacgc ggtgatcggc cattcggtgg   2220
gtgagcttgc ggctgcgtat gtgtccgggg tgtggtcgtt ggaggatgcc tgcactttgg   2280
tgtcggcgcg ggctcgtctg atgcaggctc tgcccgcggg tggggtgatg gtcgctgtcc   2340
cggtctcgga ggatgaggcc cgggccgtgc tgggtgaggg tgtggagatc gccgcggtca   2400
acggcccgtc gtcggtggtt ctctccggtg atgaggccgc cgtgctgcag gccgcggagg   2460
ggctggggaa gtggacgcgg ctggcgacca gccacgcgtt ccattccgcc cgtatggaac   2520
ccatgctgga ggagttccgg gcggtcgccg aaggcctgac ctaccggacg ccgcaggtct   2580
ccatggccgt tggtgatcag gtgaccaccg ctgagtactg ggtgcggcag gtccgggaca   2640
cggtccggtt cggcgagcag gtggcctcgt acgaggacgc cgtgttcgtc gagctgggtg   2700
ccgaccggtc actggcccgc ctggtcgacg gtgtcgcgat gctgcacggc gaccacgaaa   2760
tccaggccgc gatcggcgcc ctggcccacc tgtatgtcaa cggcgtcacg gtcgactggc   2820
ccgcgctcct gggcgatgct ccggcaacac gggtgctgga ccttccgaca tacgccttcc   2880
agcaccagcg ctactggctc gagtcggctc ccccggccac ggccgactcg ggccaccccg   2940
tcctcggcac cggagtcgcc gtcgccgggt cgccggggcg ggtgttcacg ggtcccgtgc   3000
ccgccggtgc ggaccgcgcg gtgttcatcg ccgaactggc gctcgccgcc gccgacgcca   3060
ccgactgcgc cacggtcgaa cagctcgacg tcacctccgt gcccggcgga tccgcccgcg   3120
gcagggccac cgcgcagacc tgggtcgatg aacccgccgc cgacgggcgg cgccgcttca   3180
ccgtccacac ccgcgtcggc gacgccccgt ggacgctgca cgccgagggg gttctccgcc   3240
ccggccgcgt gccccagccc gaagccgtcg acaccgcctg gcccccgccg ggcgcggtgc   3300
ccgcggacgg gctgcccggg gcgtggcgac gcgcggacca ggtcttcgtc gaagccgaag   3360
tcgacagccc tgacggcttc gtggcacacc ccgacctgct cgacgcggtc ttctccgcgg   3420
tcggcgacgg gagccgccag ccgaccggat ggcgcgacct cgcggtgcac cgtcggacg    3480 ccaccgtgct gcgcgcctgc ctcacccgcc gcgacagtgg tgtcgtggag ctcgccgcct   3540
tcgacggtgc cggaatgccg gtgctcaccg cggagtcggt gacgctgggc gaggtcgcgt   3600
cggcaggcgg atccgacgag tcggacggtc tgcttcggct tgagtggttg ccggtggcgg   3660
aggcccacta cgacggtgcc gacgagctgc ccgagggcta caccctcatc accgccacac   3720
accccgacga ccccgacgac cccaccaacc cccacaacac acccacacgc acccacacac   3780
aaaccacacg cgtcctcacc gccctccaac accacctcat caccaccaac cacaccctca   3840
tcgtccacac caccaccgac ccccaggcg ccgccgtcac cggcctcacc cgcaccgcac    3900
aaaacgaaca ccccggccgc atccacctca tcgaaaccca ccaccccac accccactcc    3960 ccctcaccca actcaccacc ctccaccaac cccacctacg cctcaccaac aacaccctcc   4020 acaccccca cctcaccccc atcaccaccc accacaacac caccacaacc cccccaaca    4080 ccccacccct caaccccaac cacgccatcc tcatcaccgg cggctccggc accctcgccg   4140
gcatcctcgc ccgccacctc aaccacccc acacctacct cctctcccgc acaccaccac   4200 ccccaccac acccggcacc cacatcccct gcgacctcac cgaccccacc caaatcaccc   4260
aagccctcac ccacatacca caaccctca ccggcatctt ccacaccgcc gccaccctcg   4320
acgacgccac cctcaccaac ctcacccccc aacacctcac caccacctc caacccaaag    4380 ccgacgccgc ctggcacctc caccaccaca cccaaaacca acccctcacc cacttcgtcc   4440
```

-continued

```
tctactccag cgccgccgcc accctcggca gccccggcca agccaactac gccgccgcca    4500
acgccttcct cgacgccctc gccacccacc gccacaccca aggacaaccc gccaccacca    4560
tcgcctgggg catgtggcac accaccacca cactcaccag ccaactcacc gacagcgacc    4620
gcgaccgcat ccgccgcggc ggcttcctgc cgatctcgga cgacgagggc atgc          4674
```

<210> SEQ ID NO 27
<211> LENGTH: 1557
<212> TYPE: PRT
<213> ORGANISM: Artificial Sequence
<220> FEATURE:
<223> OTHER INFORMATION: primer

<400> SEQUENCE: 27

```
Met Arg Leu Tyr Glu Ala Ala Arg Arg Thr Gly Ser Pro Val Val
1               5                   10                  15

Ala Ala Ala Leu Asp Asp Ala Pro Asp Val Pro Leu Leu Arg Gly Leu
            20                  25                  30

Arg Arg Thr Thr Val Arg Arg Ala Ala Val Arg Glu Arg Ser Leu Ala
        35                  40                  45

Asp Arg Ser Pro Cys Cys Pro Thr Thr Ser Ala Pro Thr Pro Pro Ser
50                  55                  60

Arg Ser Ser Trp Asn Ser Thr Ala Thr Val Leu Gly His Leu Gly Ala
65                  70                  75                  80

Glu Asp Ile Pro Ala Thr Thr Thr Phe Lys Glu Leu Gly Ile Asp Ser
                85                  90                  95

Leu Thr Ala Val Gln Leu Arg Asn Ala Leu Thr Thr Ala Thr Gly Val
            100                 105                 110

Arg Leu Asn Ala Thr Ala Val Phe Asp Phe Pro Thr Pro Arg Ala Leu
        115                 120                 125

Ala Ala Arg Leu Gly Asp Glu Leu Ala Gly Thr Arg Ala Pro Val Ala
    130                 135                 140

Ala Arg Thr Ala Ala Thr Ala Ala His Asp Glu Pro Leu Ala Ile
145                 150                 155                 160

Val Gly Met Ala Cys Arg Leu Pro Gly Gly Val Ala Ser Pro Gln Glu
                165                 170                 175

Leu Trp Arg Leu Val Ala Ser Gly Thr Asp Ala Ile Thr Glu Phe Pro
            180                 185                 190

Ala Asp Arg Gly Trp Asp Val Asp Ala Leu Tyr Asp Pro Asp Pro Asp
        195                 200                 205

Ala Ile Gly Lys Thr Phe Val Arg His Gly Gly Phe Leu Asp Gly Ala
    210                 215                 220

Thr Gly Phe Asp Ala Ala Phe Phe Gly Ile Ser Pro Arg Glu Ala Leu
225                 230                 235                 240

Ala Met Asp Pro Gln Gln Arg Val Leu Leu Glu Thr Ser Trp Glu Ala
                245                 250                 255

Phe Glu Ser Ala Gly Ile Thr Pro Asp Ala Ala Arg Gly Ser Asp Thr
            260                 265                 270

Gly Val Phe Ile Gly Ala Phe Ser Tyr Gly Tyr Gly Thr Gly Ala Asp
        275                 280                 285

Thr Asn Gly Phe Gly Ala Thr Gly Ser Gln Thr Ser Val Leu Ser Gly
    290                 295                 300

Arg Leu Ser Tyr Phe Tyr Gly Leu Glu Gly Pro Ser Val Thr Val Asp
305                 310                 315                 320

Thr Ala Cys Ser Ser Ser Leu Val Ala Leu His Gln Ala Gly Gln Ser
```

-continued

```
                325                 330                 335
Leu Arg Ser Gly Glu Cys Ser Leu Ala Leu Val Gly Gly Val Thr Val
                340                 345                 350
Met Ala Ser Pro Gly Gly Phe Val Glu Phe Ser Arg Gln Arg Gly Leu
                355                 360                 365
Ala Pro Asp Gly Arg Ala Lys Ala Phe Gly Ala Gly Ala Asp Gly Thr
            370                 375                 380
Ser Phe Ala Glu Gly Ala Gly Ala Leu Val Val Glu Arg Leu Ser Asp
385                 390                 395                 400
Ala Glu Arg His Gly His Thr Val Leu Ala Leu Val Arg Gly Ser Ala
                405                 410                 415
Ala Asn Ser Asp Gly Ala Ser Asn Gly Leu Ser Ala Pro Asn Gly Pro
                420                 425                 430
Ser Gln Glu Arg Val Ile His Gln Ala Leu Ala Asn Ala Lys Leu Thr
                435                 440                 445
Pro Ala Asp Val Asp Ala Val Glu Ala His Gly Thr Gly Thr Arg Leu
            450                 455                 460
Gly Asp Pro Ile Glu Ala Gln Ala Leu Leu Ala Thr Tyr Gly Gln Asp
465                 470                 475                 480
Arg Ala Thr Pro Leu Leu Leu Gly Ser Leu Lys Ser Asn Ile Gly His
                485                 490                 495
Ala Gln Ala Ala Ser Gly Val Ala Gly Ile Ile Lys Met Val Gln Ala
                500                 505                 510
Ile Arg His Gly Glu Leu Pro Pro Thr Leu His Ala Asp Glu Pro Ser
            515                 520                 525
Pro His Val Asp Trp Thr Ala Gly Ala Val Glu Leu Leu Thr Ser Ala
            530                 535                 540
Arg Pro Trp Pro Gly Thr Gly Arg Pro Arg Arg Ala Gly Val Ser Ser
545                 550                 555                 560
Phe Gly Ile Ser Gly Thr Asn Ala His Val Ile Leu Glu Ser Ala Pro
                565                 570                 575
Pro Thr Gln Pro Ala Asp Asn Ala Val Ile Glu Arg Ala Pro Glu Trp
                580                 585                 590
Val Pro Leu Val Ile Ser Ala Arg Thr Gln Ser Ala Leu Thr Glu His
                595                 600                 605
Glu Gly Arg Leu Arg Ala Tyr Leu Ala Ala Ser Pro Gly Val Asp Met
            610                 615                 620
Arg Ala Val Ala Ser Thr Leu Ala Met Thr Arg Ser Val Phe Glu His
625                 630                 635                 640
Arg Ala Val Leu Leu Gly Asp Asp Thr Val Thr Gly Thr Ala Val Ser
                645                 650                 655
Asp Pro Arg Ala Val Phe Val Phe Pro Gly Gln Gly Ser Gln Arg Ala
                660                 665                 670
Gly Met Gly Glu Glu Leu Ala Ala Ala Phe Pro Val Phe Ala Arg Ile
            675                 680                 685
His Gln Gln Val Trp Asp Leu Leu Asp Val Pro Asp Leu Glu Val Asn
            690                 695                 700
Glu Thr Gly Tyr Ala Gln Pro Ala Leu Phe Ala Met Gln Val Ala Leu
705                 710                 715                 720
Phe Gly Leu Leu Glu Ser Trp Gly Val Arg Pro Asp Ala Val Ile Gly
                725                 730                 735
His Ser Val Gly Glu Leu Ala Ala Ala Tyr Val Ser Gly Val Trp Ser
                740                 745                 750
```

-continued

```
Leu Glu Asp Ala Cys Thr Leu Val Ser Ala Arg Ala Arg Leu Met Gln
        755                 760                 765
Ala Leu Pro Ala Gly Gly Val Met Val Ala Val Pro Val Ser Glu Asp
        770                 775                 780
Glu Ala Arg Ala Val Leu Gly Glu Gly Val Glu Ile Ala Ala Val Asn
785                 790                 795                 800
Gly Pro Ser Ser Val Val Leu Ser Gly Asp Glu Ala Ala Val Leu Gln
                805                 810                 815
Ala Ala Glu Gly Leu Gly Lys Trp Thr Arg Leu Ala Thr Ser His Ala
                820                 825                 830
Phe His Ser Ala Arg Met Glu Pro Met Leu Glu Glu Phe Arg Ala Val
                835                 840                 845
Ala Glu Gly Leu Thr Tyr Arg Thr Pro Gln Val Ser Met Ala Val Gly
                850                 855                 860
Asp Gln Val Thr Thr Ala Glu Tyr Trp Val Arg Gln Val Arg Asp Thr
865                 870                 875                 880
Val Arg Phe Gly Glu Gln Val Ala Ser Tyr Glu Asp Ala Val Phe Val
                885                 890                 895
Glu Leu Gly Ala Asp Arg Ser Leu Ala Arg Leu Val Asp Gly Val Ala
                900                 905                 910
Met Leu His Gly Asp His Glu Ile Gln Ala Ala Ile Gly Ala Leu Ala
                915                 920                 925
His Leu Tyr Val Asn Gly Val Thr Val Asp Trp Pro Ala Leu Leu Gly
        930                 935                 940
Asp Ala Pro Ala Thr Arg Val Leu Asp Leu Pro Thr Tyr Ala Phe Gln
945                 950                 955                 960
His Gln Arg Tyr Trp Leu Glu Ser Ala Pro Pro Ala Thr Ala Asp Ser
                965                 970                 975
Gly His Pro Val Leu Gly Thr Gly Val Ala Val Ala Gly Ser Pro Gly
                980                 985                 990
Arg Val Phe Thr Gly Pro Val Pro Ala Gly Ala Asp Arg Ala Val Phe
        995                 1000                1005
Ile Ala Glu Leu Ala Leu Ala Ala Ala Asp Ala Thr Asp Cys Ala
        1010                1015                1020
Thr Val Glu Gln Leu Asp Val Thr Ser Val Pro Gly Gly Ser Ala
        1025                1030                1035
Arg Gly Arg Ala Thr Ala Gln Thr Trp Val Asp Glu Pro Ala Ala
        1040                1045                1050
Asp Gly Arg Arg Arg Phe Thr Val His Thr Arg Val Gly Asp Ala
        1055                1060                1065
Pro Trp Thr Leu His Ala Glu Gly Val Leu Arg Pro Gly Arg Val
        1070                1075                1080
Pro Gln Pro Glu Ala Val Asp Thr Ala Trp Pro Pro Gly Ala
        1085                1090                1095
Val Pro Ala Asp Gly Leu Pro Gly Ala Trp Arg Arg Ala Asp Gln
        1100                1105                1110
Val Phe Val Glu Ala Glu Val Asp Ser Pro Asp Gly Phe Val Ala
        1115                1120                1125
His Pro Asp Leu Leu Asp Ala Val Phe Ser Ala Val Gly Asp Gly
        1130                1135                1140
Ser Arg Gln Pro Thr Gly Trp Arg Asp Leu Ala Val His Ala Ser
        1145                1150                1155
```

```
Asp Ala Thr Val Leu Arg Ala Cys Leu Thr Arg Arg Asp Ser Gly
1160                1165                1170

Val Val Glu Leu Ala Ala Phe Asp Gly Ala Gly Met Pro Val Leu
1175                1180                1185

Thr Ala Glu Ser Val Thr Leu Gly Glu Val Ala Ser Ala Gly Gly
1190                1195                1200

Ser Asp Glu Ser Asp Gly Leu Leu Arg Leu Glu Trp Leu Pro Val
1205                1210                1215

Ala Glu Ala His Tyr Asp Gly Ala Asp Glu Leu Pro Glu Gly Tyr
1220                1225                1230

Thr Leu Ile Thr Ala Thr His Pro Asp Pro Asp Asp Pro Thr
1235                1240                1245

Asn Pro His Asn Thr Pro Thr Arg Thr His Thr Gln Thr Thr Arg
1250                1255                1260

Val Leu Thr Ala Leu Gln His His Leu Ile Thr Thr Asn His Thr
1265                1270                1275

Leu Ile Val His Thr Thr Thr Asp Pro Pro Gly Ala Ala Val Thr
1280                1285                1290

Gly Leu Thr Arg Thr Ala Gln Asn Glu His Pro Gly Arg Ile His
1295                1300                1305

Leu Ile Glu Thr His His Pro His Thr Pro Leu Pro Leu Thr Gln
1310                1315                1320

Leu Thr Thr Leu His Gln Pro His Leu Arg Leu Thr Asn Asn Thr
1325                1330                1335

Leu His Thr Pro His Leu Thr Pro Ile Thr Thr His His Asn Thr
1340                1345                1350

Thr Thr Thr Thr Pro Asn Thr Pro Pro Leu Asn Pro Asn His Ala
1355                1360                1365

Ile Leu Ile Thr Gly Gly Ser Gly Thr Leu Ala Gly Ile Leu Ala
1370                1375                1380

Arg His Leu Asn His Pro His Thr Tyr Leu Leu Ser Arg Thr Pro
1385                1390                1395

Pro Pro Pro Thr Thr Pro Gly Thr His Ile Pro Cys Asp Leu Thr
1400                1405                1410

Asp Pro Thr Gln Ile Thr Gln Ala Leu Thr His Ile Pro Gln Pro
1415                1420                1425

Leu Thr Gly Ile Phe His Thr Ala Ala Thr Leu Asp Asp Ala Thr
1430                1435                1440

Leu Thr Asn Leu Thr Pro Gln His Leu Thr Thr Thr Leu Gln Pro
1445                1450                1455

Lys Ala Asp Ala Ala Trp His Leu His His His Thr Gln Asn Gln
1460                1465                1470

Pro Leu Thr His Phe Val Leu Tyr Ser Ser Ala Ala Ala Thr Leu
1475                1480                1485

Gly Ser Pro Gly Gln Ala Asn Tyr Ala Ala Ala Asn Ala Phe Leu
1490                1495                1500

Asp Ala Leu Ala Thr His Arg His Thr Gln Gly Gln Pro Ala Thr
1505                1510                1515

Thr Ile Ala Trp Gly Met Trp His Thr Thr Thr Leu Thr Ser
1520                1525                1530

Gln Leu Thr Asp Ser Asp Arg Asp Arg Ile Arg Arg Gly Gly Phe
1535                1540                1545

Leu Pro Ile Ser Asp Asp Glu Gly Met
```

-continued 1550          1555

<210> SEQ ID NO 28
<211> LENGTH: 4767
<212> TYPE: DNA
<213> ORGANISM: Artificial Sequence
<220> FEATURE:
<223> OTHER INFORMATION: primer

<400> SEQUENCE: 28

| | |
|---|---|
| gcatgcggct gtacgaggcg gcacggcgca ccggaagtcc cgtggtggtg gcggccgcgc | 60 |
| tcgacgacgc gccggacgtg ccgctgctgc gcgggctgcg gcgtacgacc gtccggcgtg | 120 |
| ccgccgtccg ggaacgctct ctcgccgacc gctcgccgtg ctgcccgacg acgagcgcgc | 180 |
| cgacgcctcc ctcgcgttcg tcctggaaca gcaccgccac cgtgctcggc cacctgggcg | 240 |
| ccgaagacat cccggcgacg acgacgttca aggaactcgg catcgactcg ctcaccgcgg | 300 |
| tccagctgcg caacgcgctg accacggcga ccggcgtacg cctcaacgcc acagcggtct | 360 |
| tcgactttcc gacgccgcgc gcgctcgccg cgagactcgg cgacgagctg gccggtaccc | 420 |
| gcgcgcccgt cgcggcccgg accgcggcca cgcggccgc gcacgacgaa ccgctggcga | 480 |
| tcgtgggcat ggcctgccgt ctgccgggcg gggtcgcgtc gccacaggag ctgtggcgtc | 540 |
| tcgtcgcgtc cggcaccgac gccatcacgg agttccccgc ggaccgcggc tgggacgtgg | 600 |
| acgcgctcta cgacccggac cccgacgcga tcggcaagac cttcgtccgg cacggcggct | 660 |
| tcctcgacgg tgcgaccggc ttcgacgcgg cgttcttcgg gatcagcccg cgcgaggccc | 720 |
| tggccatgga cccgcagcaa cgggtgctcc tggagacgtc ctgggaggcg ttcgaaagcg | 780 |
| cgggcatcac cccggacgcg gcgcggggca gcgacaccgg cgtgttcatc ggcgcgttct | 840 |
| cctacgggta cggcacgggt gcggatacca acggcttcgg cgcgacaggg tcgcagacca | 900 |
| gcgtgctctc cggccgcctc tcgtacttct acggtctgga gggcccttcg gtcacggtcg | 960 |
| acaccgcctg ctcgtcgtca ctggtcgccc tgcaccaggc agggcagtcc ctgcgctcgg | 1020 |
| gcgaatgctc gctcgccctg gtcggcggtg tcacggtgat ggcgtcgccc ggcggattcg | 1080 |
| tcgagttctc ccggcagcgc gggctcgcgc cggacggggc ggcgaaggcg ttcggcgcgg | 1140 |
| gcgcggacgg tacgagcttc gccgagggcg ccggtgccct ggtggtcgag cggctctccg | 1200 |
| acgcggagcg ccacggccac accgtcctcg ccctcgtacg cggctccgcg ctaactccg | 1260 |
| acggcgcgtc gaacggtctg tcggcgccga cggcccctc ccaggaacgc gtcatccacc | 1320 |
| aggccctcgc gaacgcgaaa ctcaccccc cgatgtcga cgcggtcgag gcgcacggca | 1380 |
| ccggcacccg cctcggcgac cccatcgagg cgcaggcgct gctcgcgacg tacggacagg | 1440 |
| accgggcgac gccctgctg ctcggctcgc tgaagtcgaa catcgggcac gcccaggccg | 1500 |
| cgtcaggggt cgccgggatc atcaagatgg tgcaggccat ccggcacggg gaactgccgc | 1560 |
| cgacactgca cgcggacgag ccgtcgccgc acgtcgactg gacggccggt gccgtcgagc | 1620 |
| tcctgacgtc ggcccggccg tggccgggga ccggtcgccc taggcgggcg ggcgtgtcgt | 1680 |
| ccttcggagt cagcggcacc aacgcccacg tcatcctgga gagcgcaccc ccgctcagc | 1740 |
| ccgcggagga ggcgcagcct gttgagacgc cggtggtggc ctcggatgtg ctgccgctgg | 1800 |
| tgatatcggc caagacccag cccgccctga ccgaacacga agaccggctg cgcgcctacc | 1860 |
| tggcggcgtc gccggggcg gatatacggg ctgtggcatc gacgctggcg gtgacacggt | 1920 |
| cggtgttcga gcaccgcgcc gtactccttg gagatgacac cgtcaccggc accgcggtga | 1980 |
| ccgaccccag gatcgtgttt gtctttcccg ggcaggggtg gcagtggctg gggatgggca | 2040 |

-continued

```
gtgcactgcg cgattcgtcg gtggtgttcg ccgagcggat ggccgagtgt gcggcggcgt    2100
tgcgcgagtt cgtggactgg gatctgttca cggttctgga tgatccggcg gtggtggacc    2160
gggttgatgt ggtccagccc gcttcctggg cgatgatggt ttccctggcc gcggtgtggc    2220
aggcggccgg tgtgcggccg gatgcggtga tcggccattc gcagggtgag atcgccgcag    2280
cttgtgtggc gggtgcggtg tcactacgcg atgccgcccg gatcgtgacc ttgcgcagcc    2340
aggcgatcgc ccggggcctg cgggccgggg cgcgatggc atccgtcgcc ctgcccgcgc    2400
aggatgtcga gctggtcgac ggggcctgga tcgccgccca caacgggccc gcctccaccg    2460
tgatcgcggg caccccggaa gcggtcgacc atgtcctcac cgctcatgag gcacaagggg    2520
tgcgggtgcg gcggatcacc gtcgactatg cctcgcacac cccgcacgtc gagctgatcc    2580
gcgacgaact actcgacatc actagcgaca gcagctcgca gaccccgctc gtgccgtggc    2640
tgtcgaccgt ggacggcacc tgggtcgaca gcccgctgga cggggagtac tggtaccgga    2700
acctgcgtga accggtcggt ttccaccccg ccgtcagcca gttgcaggcc cagggcgaca    2760
ccgtgttcgt cgaggtcagc gccagcccgg tgttgttgca ggcgatggac gacgatgtcg    2820
tcacggttgc cacgctgcgt cgtgacgacg gcgacgccac ccggatgctc accgccctgg    2880
cacaggccta tgtccacggc gtcaccgtcg actggcccgc catcctcggc accaccacaa    2940
cccgggtact ggaccttccg acctacgcct tccaacacca gcggtactgg ctcgagtcgg    3000 ctccccggc cacggccgac tcgggccacc ccgtcctcgg caccggagtc gccgtcgccg    3060
ggtcgccggg ccgggtgttc acgggtcccg tgccgccgg tgcggaccgc gcggtgttca    3120
tcgccgaact ggcgctcgcc gccgccgacg ccaccgactg cgccacggtc gaacagctcg    3180
acgtcacctc cgtgcccggc ggatccgccc gcggcagggc caccgcgcag acctgggtcg    3240
atgaacccgc cgccgacggg cggcgccgct tcaccgtcca cacccgcgtc ggcgacgccc    3300
cgtggacgct gcacgccgag gggttctcc gccccgccg cgtgcccag cccgaagccg    3360 tcgacaccgc ctggccccg ccgggcgcgg tgcccgcgga cgggctgccc ggggcgtggc    3420
gacgcgcgga ccaggtcttc gtcgaagccg aagtcgacag ccctgacggc ttcgtggcac    3480
accccgacct gctcgacgcg gtcttctccg cggtcggcga cgggagccgc cagccgaccg    3540 gatgcgcga cctcgcggtg cacgcgtcgg acgccaccgt gctgcgcgcc tgcctcaccc    3600
gccgcgacag tggtgtcgtg gagctcgccg ccttcgacgg tgccggaatg ccggtgctca    3660
ccgcggagtc ggtgacgctg ggcgaggtcg cgtcggcagg cggatccgac gagtcggacg    3720
gtctgcttcg gcttgagtgg ttgccggtgg cggaggccca ctacgacggt gccgacgagc    3780
tgcccgaggg ctacaccctc atcaccgcca cacccccga cgaccccgac gaccccacca    3840 accccacaa cacacccaca cgcacccaca cacaaaccac acgcgtcctc accgccctcc    3900
aacaccacct catcaccacc aaccacaccc tcatcgtcca caccaccacc gaccccccag    3960
gcgccgccgt caccggcctc acccgcaccg cacaaaacga cacccggc cgcatccacc    4020 tcatcgaaac ccaccacccc cacaccccac tcccctcac ccaactcacc accctccacc    4080 aacccacct acgcctcacc aacaacaccc tccacacccc ccacctcacc cccatcacca    4140
cccaccacaa caccaccaca accaccccca cacccccacc cctcaacccc aaccacgcca    4200
tcctcatcac cggcggctcc ggcaccctcg ccggcatcct cgcccgccac ctcaaccacc    4260
cccacaccta cctcctctcc cgcacaccac cacccccac cacacccggc acccacatcc    4320
cctgcgacct caccgacccc acccaaatca cccaagccct cacccacata ccacaacccc    4380
```

-continued

```
tcaccggcat cttccacacc gccgccaccc tcgacgacgc caccctcacc aacctcaccc    4440
cccaacacct caccaccacc ctccaaccca agccgacgc cgcctggcac ctccaccacc    4500
acacccaaaa ccaacccctc acccacttcg tcctctactc cagcgccgcc gccaccctcg    4560
gcagccccgg ccaagccaac tacgccgccg ccaacgcctt cctcgacgcc ctcgccaccc    4620
accgccacac ccaaggacaa cccgccacca ccatcgcctg gggcatgtgg cacaccacca    4680
ccacactcac cagccaactc accgacgcg accgcgaccg catccgccgc ggcggcttcc    4740
tgccgatctc ggacgacgag ggcatgc                                       4767
```

<210> SEQ ID NO 29
<211> LENGTH: 1588
<212> TYPE: PRT
<213> ORGANISM: Artificial Sequence
<220> FEATURE:
<223> OTHER INFORMATION: primer

<400> SEQUENCE: 29

```
Met Arg Leu Tyr Glu Ala Ala Arg Arg Thr Gly Ser Pro Val Val Val
1               5                   10                  15

Ala Ala Ala Leu Asp Asp Ala Pro Asp Val Pro Leu Leu Arg Gly Leu
                20                  25                  30

Arg Arg Thr Thr Val Arg Arg Ala Ala Val Arg Glu Arg Ser Leu Ala
            35                  40                  45

Asp Arg Ser Pro Cys Cys Pro Thr Thr Ser Ala Pro Thr Pro Pro Ser
        50                  55                  60

Arg Ser Ser Trp Asn Ser Thr Ala Thr Val Leu Gly His Leu Gly Ala
65                  70                  75                  80

Glu Asp Ile Pro Ala Thr Thr Thr Phe Lys Glu Leu Gly Ile Asp Ser
                85                  90                  95

Leu Thr Ala Val Gln Leu Arg Asn Ala Leu Thr Thr Ala Thr Gly Val
                100                 105                 110

Arg Leu Asn Ala Thr Ala Val Phe Asp Phe Pro Thr Pro Arg Ala Leu
            115                 120                 125

Ala Ala Arg Leu Gly Asp Glu Leu Ala Gly Thr Arg Ala Pro Val Ala
        130                 135                 140

Ala Arg Thr Ala Ala Thr Ala Ala Ala His Asp Glu Pro Leu Ala Ile
145                 150                 155                 160

Val Gly Met Ala Cys Arg Leu Pro Gly Gly Val Ala Ser Pro Gln Glu
                165                 170                 175

Leu Trp Arg Leu Val Ala Ser Gly Thr Asp Ala Ile Thr Glu Phe Pro
                180                 185                 190

Ala Asp Arg Gly Trp Asp Val Asp Ala Leu Tyr Asp Pro Asp Pro Asp
            195                 200                 205

Ala Ile Gly Lys Thr Phe Val Arg His Gly Phe Leu Asp Gly Ala
        210                 215                 220

Thr Gly Phe Asp Ala Ala Phe Phe Gly Ile Ser Pro Arg Glu Ala Leu
225                 230                 235                 240

Ala Met Asp Pro Gln Gln Arg Val Leu Leu Glu Thr Ser Trp Glu Ala
                245                 250                 255

Phe Glu Ser Ala Gly Ile Thr Pro Asp Ala Ala Arg Gly Ser Asp Thr
                260                 265                 270

Gly Val Phe Ile Gly Ala Phe Ser Tyr Gly Tyr Gly Thr Gly Ala Asp
            275                 280                 285

Thr Asn Gly Phe Gly Ala Thr Gly Ser Gln Thr Ser Val Leu Ser Gly
```

-continued

```
            290                 295                 300
Arg Leu Ser Tyr Phe Tyr Gly Leu Glu Gly Pro Ser Val Thr Val Asp
305                 310                 315                 320

Thr Ala Cys Ser Ser Ser Leu Val Ala Leu His Gln Ala Gly Gln Ser
                325                 330                 335

Leu Arg Ser Gly Glu Cys Ser Leu Ala Leu Val Gly Gly Val Thr Val
                340                 345                 350

Met Ala Ser Pro Gly Gly Phe Val Glu Phe Ser Arg Gln Arg Gly Leu
                355                 360                 365

Ala Pro Asp Gly Arg Ala Lys Ala Phe Gly Ala Gly Ala Asp Gly Thr
370                 375                 380

Ser Phe Ala Glu Gly Ala Gly Ala Leu Val Val Glu Arg Leu Ser Asp
385                 390                 395                 400

Ala Glu Arg His Gly His Thr Val Leu Ala Leu Val Arg Gly Ser Ala
                405                 410                 415

Ala Asn Ser Asp Gly Ala Ser Asn Gly Leu Ser Ala Pro Asn Gly Pro
                420                 425                 430

Ser Gln Glu Arg Val Ile His Gln Ala Leu Ala Asn Ala Lys Leu Thr
                435                 440                 445

Pro Ala Asp Val Asp Ala Val Glu Ala His Gly Thr Gly Thr Arg Leu
450                 455                 460

Gly Asp Pro Ile Glu Ala Gln Ala Leu Leu Ala Thr Tyr Gly Gln Asp
465                 470                 475                 480

Arg Ala Thr Pro Leu Leu Leu Gly Ser Leu Lys Ser Asn Ile Gly His
                485                 490                 495

Ala Gln Ala Ala Ser Gly Val Ala Gly Ile Ile Lys Met Val Gln Ala
                500                 505                 510

Ile Arg His Gly Glu Leu Pro Pro Thr Leu His Ala Asp Glu Pro Ser
                515                 520                 525

Pro His Val Asp Trp Thr Ala Gly Ala Val Glu Leu Leu Thr Ser Ala
                530                 535                 540

Arg Pro Trp Pro Gly Thr Gly Arg Pro Arg Ala Gly Val Ser Ser
545                 550                 555                 560

Phe Gly Val Ser Gly Thr Asn Ala His Val Ile Leu Glu Ser Ala Pro
                565                 570                 575

Pro Ala Gln Pro Ala Glu Glu Ala Gln Pro Val Glu Thr Pro Val Val
                580                 585                 590

Ala Ser Asp Val Leu Pro Leu Val Ile Ser Ala Lys Thr Gln Pro Ala
                595                 600                 605

Leu Thr Glu His Glu Asp Arg Leu Arg Ala Tyr Leu Ala Ala Ser Pro
                610                 615                 620

Gly Ala Asp Ile Arg Ala Val Ala Ser Thr Leu Ala Val Thr Arg Ser
625                 630                 635                 640

Val Phe Glu His Arg Ala Val Leu Leu Gly Asp Asp Thr Val Thr Gly
                645                 650                 655

Thr Ala Val Thr Asp Pro Arg Ile Val Phe Val Phe Pro Gly Gln Gly
                660                 665                 670

Trp Gln Trp Leu Gly Met Gly Ser Ala Leu Arg Asp Ser Ser Val Val
                675                 680                 685

Phe Ala Glu Arg Met Ala Glu Cys Ala Ala Ala Leu Arg Glu Phe Val
                690                 695                 700

Asp Trp Asp Leu Phe Thr Val Leu Asp Pro Ala Val Val Asp Arg
705                 710                 715                 720
```

-continued

```
Val Asp Val Val Gln Pro Ser Trp Ala Met Met Val Ser Leu Ala
            725                 730                 735

Ala Val Trp Gln Ala Ala Gly Val Arg Pro Asp Ala Val Ile Gly His
            740                 745                 750

Ser Gln Gly Glu Ile Ala Ala Cys Val Ala Gly Ala Val Ser Leu
            755                 760                 765

Arg Asp Ala Ala Arg Ile Val Thr Leu Arg Ser Gln Ala Ile Ala Arg
            770                 775                 780

Gly Leu Ala Gly Arg Gly Ala Met Ala Ser Val Ala Leu Pro Ala Gln
785                 790                 795                 800

Asp Val Glu Leu Val Asp Gly Ala Trp Ile Ala Ala His Asn Gly Pro
            805                 810                 815

Ala Ser Thr Val Ile Ala Gly Thr Pro Glu Ala Val Asp His Val Leu
            820                 825                 830

Thr Ala His Glu Ala Gln Gly Val Arg Val Arg Arg Ile Thr Val Asp
            835                 840                 845

Tyr Ala Ser His Thr Pro His Val Glu Leu Ile Arg Asp Glu Leu Leu
            850                 855                 860

Asp Ile Thr Ser Asp Ser Ser Ser Gln Thr Pro Leu Val Pro Trp Leu
865                 870                 875                 880

Ser Thr Val Asp Gly Thr Trp Val Asp Ser Pro Leu Asp Gly Glu Tyr
            885                 890                 895

Trp Tyr Arg Asn Leu Arg Glu Pro Val Gly Phe His Pro Ala Val Ser
            900                 905                 910

Gln Leu Gln Ala Gln Gly Asp Thr Val Phe Val Glu Val Ser Ala Ser
            915                 920                 925

Pro Val Leu Leu Gln Ala Met Asp Asp Val Val Thr Val Ala Thr
            930                 935                 940

Leu Arg Arg Asp Asp Gly Asp Ala Thr Arg Met Leu Thr Ala Leu Ala
945                 950                 955                 960

Gln Ala Tyr Val His Gly Val Thr Val Asp Trp Pro Ala Ile Leu Gly
            965                 970                 975

Thr Thr Thr Thr Arg Val Leu Asp Leu Pro Thr Tyr Ala Phe Gln His
            980                 985                 990

Gln Arg Tyr Trp Leu Glu Ser Ala Pro Pro Ala Thr Ala Asp Ser Gly
            995                 1000                1005

His Pro Val Leu Gly Thr Gly Val Ala Val Ala Gly Ser Pro Gly
    1010                1015                1020

Arg Val Phe Thr Gly Pro Val Pro Ala Gly Ala Asp Arg Ala Val
    1025                1030                1035

Phe Ile Ala Glu Leu Ala Leu Ala Ala Ala Asp Ala Thr Asp Cys
    1040                1045                1050

Ala Thr Val Glu Gln Leu Asp Val Thr Ser Val Pro Gly Gly Ser
    1055                1060                1065

Ala Arg Gly Arg Ala Thr Ala Gln Thr Trp Val Asp Glu Pro Ala
    1070                1075                1080

Ala Asp Gly Arg Arg Arg Phe Thr Val His Thr Arg Val Gly Asp
    1085                1090                1095

Ala Pro Trp Thr Leu His Ala Glu Gly Val Leu Arg Pro Gly Arg
    1100                1105                1110

Val Pro Gln Pro Glu Ala Val Asp Thr Ala Trp Pro Pro Gly
    1115                1120                1125
```

-continued

```
Ala Val Pro Ala Asp Gly Leu Pro Gly Ala Trp Arg Arg Ala Asp
1130                1135                1140

Gln Val Phe Val Glu Ala Glu Val Asp Ser Pro Asp Gly Phe Val
1145                1150                1155

Ala His Pro Asp Leu Leu Asp Ala Val Phe Ser Ala Val Gly Asp
1160                1165                1170

Gly Ser Arg Gln Pro Thr Gly Trp Arg Asp Leu Ala Val His Ala
1175                1180                1185

Ser Asp Ala Thr Val Leu Arg Ala Cys Leu Thr Arg Arg Asp Ser
1190                1195                1200

Gly Val Val Glu Leu Ala Ala Phe Asp Gly Ala Gly Met Pro Val
1205                1210                1215

Leu Thr Ala Glu Ser Val Thr Leu Gly Glu Val Ala Ser Ala Gly
1220                1225                1230

Gly Ser Asp Glu Ser Asp Gly Leu Leu Arg Leu Glu Trp Leu Pro
1235                1240                1245

Val Ala Glu Ala His Tyr Asp Gly Ala Asp Glu Leu Pro Glu Gly
1250                1255                1260

Tyr Thr Leu Ile Thr Ala Thr His Pro Asp Pro Asp Asp Pro
1265                1270                1275

Thr Asn Pro His Asn Thr Pro Thr Arg Thr His Thr Gln Thr Thr
1280                1285                1290

Arg Val Leu Thr Ala Leu Gln His His Leu Ile Thr Thr Asn His
1295                1300                1305

Thr Leu Ile Val His Thr Thr Thr Asp Pro Pro Gly Ala Ala Val
1310                1315                1320

Thr Gly Leu Thr Arg Thr Ala Gln Asn Glu His Pro Gly Arg Ile
1325                1330                1335

His Leu Ile Glu Thr His His Pro His Thr Pro Leu Pro Leu Thr
1340                1345                1350

Gln Leu Thr Thr Leu His Gln Pro His Leu Arg Leu Thr Asn Asn
1355                1360                1365

Thr Leu His Thr Pro His Leu Thr Pro Ile Thr Thr His His Asn
1370                1375                1380

Thr Thr Thr Thr Thr Pro Asn Thr Pro Pro Leu Asn Pro Asn His
1385                1390                1395

Ala Ile Leu Ile Thr Gly Gly Ser Gly Thr Leu Ala Gly Ile Leu
1400                1405                1410

Ala Arg His Leu Asn His Pro His Thr Tyr Leu Leu Ser Arg Thr
1415                1420                1425

Pro Pro Pro Pro Thr Thr Pro Gly Thr His Ile Pro Cys Asp Leu
1430                1435                1440

Thr Asp Pro Thr Gln Ile Thr Gln Ala Leu Thr His Ile Pro Gln
1445                1450                1455

Pro Leu Thr Gly Ile Phe His Thr Ala Ala Thr Leu Asp Asp Ala
1460                1465                1470

Thr Leu Thr Asn Leu Thr Pro Gln His Leu Thr Thr Thr Leu Gln
1475                1480                1485

Pro Lys Ala Asp Ala Ala Trp His Leu His His Thr Gln Asn
1490                1495                1500

Gln Pro Leu Thr His Phe Val Leu Tyr Ser Ser Ala Ala Ala Thr
1505                1510                1515

Leu Gly Ser Pro Gly Gln Ala Asn Tyr Ala Ala Ala Asn Ala Phe
```

-continued

```
                1520                1525                1530
Leu Asp Ala Leu Ala Thr His Arg His Thr Gln Gly Gln Pro Ala
    1535                1540                1545

Thr Thr Ile Ala Trp Gly Met Trp His Thr Thr Thr Leu Thr
    1550                1555                1560

Ser Gln Leu Thr Asp Ser Asp Arg Asp Arg Ile Arg Arg Gly Gly
    1565                1570                1575

Phe Leu Pro Ile Ser Asp Asp Glu Gly Met
    1580                1585

<210> SEQ ID NO 30
<211> LENGTH: 4737
<212> TYPE: DNA
<213> ORGANISM: Artificial Sequence
<220> FEATURE:
<223> OTHER INFORMATION: primer

<400> SEQUENCE: 30
gcatgcggct gtacgagcg gcacggcgca ccggaagtcc cgtggtggtg gcggccgcgc     60
tcgacgacgc gccggacgtg ccgctgctgc gcgggctgcg cgtacgacc gtccggcgtg    120
ccgccgtccg ggaacgctct ctcgccgacc gctcgccgtg ctgcccgacg acgagcgcgc   180
cgacgcctcc ctcgcgttcg tcctggaaca gcaccgccac cgtgctcggc cacctgggcg   240
ccgaagacat cccggcgacg acgacgttca aggaactcgg catcgactcg ctcaccgcgg   300
tccagctgcg caacgcgctg accacggcga ccggcgtacg cctcaacgcc acagcggtct   360
tcgactttcc gacgccgcgc gcgctcgccg cgagactcgg cgacgagctg gccggtaccc   420
gcgcgcccgt cgcggcccgg accgcggcca ccgcggccgc gcacgacgaa ccgctggcga   480
tcgtgggcat ggcctgccgt ctgccgggcg gggtcgcgtc gccacaggag ctgtggcgtc   540
tcgtcgcgtc cggcaccgac gccatcacgg agttccccgc ggaccgcggc tgggacgtgg   600
acgcgctcta cgacccggac cccgacgcga tcggcaagac cttcgtccgg cacggcggct   660
tcctcgacgg tgcgaccggc ttcgacgcgg cgttcttcgg gatcagcccg cgcgaggccc   720
tggccatgga cccgcagcaa cgggtgctcc tggagacgtc ctgggaggcg ttcgaaagcg   780
cgggcatcac cccggacgcg gcgcggggca gcgacaccgg cgtgttcatc ggcgcgttct   840
cctacgggta cggcacgggt gcggatacca acggcttcgg cgcgacaggg tcgcagacca   900
gcgtgctctc cggccgcctc tcgtacttct acggtctgga gggcccttcg gtcacggtcg   960
acaccgcctg ctcgtcgtca ctggtcgccc tgcaccagga agggcagtcc ctgcgctcgg  1020
gcgaatgctc gctcgccctg gtcggcggtg tcacggtgat ggcgtcgccc ggcggattcg  1080
tcgagttctc ccggcagcgc gggctcgcgc cggacggcg ggcgaaggcg ttcggcgcgg  1140
gcgcggacgg tacgagcttc gccgagggcg ccggtgccct ggtggtcgag cggctctccg  1200
acgcggagcg ccacggccac accgtcctcg ccctcgtacg cggctccgcg ctaactccg   1260
acggcgcgtc gaacggtctg tcggcgccga cggcccctc ccaggaacgc gtcatccacc   1320
aggccctcgc gaacgcgaaa ctcaccccccg ccgatgtcga cgcggtcgag gcgcacggca   1380
ccggcacccg cctcggcgac cccatcgagg cgcaggcgct gctcgcgacg tacggacagg   1440
accgggcgac gcccctgctg ctcggctcgc tgaagtcgaa catcgggcac gcccaggccg   1500
cgtcaggggt cgccgggatc atcaagatgg tgcaggccat ccggcacggg gaactgccgc   1560
cgacactgca gcggacgag ccgtcgccgc acgtcgactg gacggccggt gccgtcgagc   1620
tcctgacgtc ggcccggccg tggccgggga ccggtcgccc gcgccgcgct gccgtctcgt   1680
```

```
cgttcggcgt gagcggcacg aacgcccaca tcatccttga ggcaggaccg gtcaaaacgg    1740
gaccggtcga ggcaggagcg atcgaggcag gaccggtcga agtaggaccg gtcgaggctg    1800
gaccgctccc cgcggcgccg ccgtcagcac cgggcgaaga ccttccgctg ctcgtgtcgg    1860
cgcgttcccc ggaggcactc gacgagcaga tcggcgcct gcgcgcctat ctcgacaccg    1920
gcccgggcgt cgaccgggcg gccgtggcgc agacactggc ccggcgtacg cacttcaccc    1980
accgggccgt actgctcggg gacaccgtca tcggcgctcc ccccgcggac caggccgacg    2040
aactcgtctt cgtctactcc ggtcagggca cccagcatcc cgcgatgggc gagcagctag    2100
ccgccgcgtt ccccgtcttc gcgcggatcc atcagcaggt gtgggacctg ctcgatgtgc    2160
ccgatctgga ggtgaacgag accggttacg cccagccggc cctgttcgca atgcaggtgg    2220
ctctgttcgg gctgctggaa tcgtggggtg tacgaccgga cgcggtgatc ggccattcgg    2280
tgggtgagct tgcggctgcg tatgtgtccg gggtgtggtc gttggaggat gcctgcactt    2340
tggtgtcggc gcgggctcgt ctgatgcagg ctctgcccgc gggtgggtg atggtcgctg    2400 tcccggtctc ggaggatgag gcccgggccg tgctgggtga gggtgtggag atcgccgcgg    2460
tcaacggccc gtcgtcggtg gttctctccg gtgatgaggc cgccgtgctg caggccgcgg    2520 agggggctggg gaagtggacg cggctggcga ccagccacgc gttccattcc gcccgtatgg    2580
aacccatgct ggaggagttc cgggcggtcg ccgaaggcct gacctaccgg acgccgcagg    2640
tctccatggc cgttggtgat caggtgacca ccgctgagta ctgggtgcgg caggtccggg    2700
acacggtccg gttcggcgag caggtggcct cgtacgagga cgccgtgttc gtcgagctgg    2760
gtgccgaccg gtcactggcc cgcctggtcg acggtgtcgc gatgctgcac ggcgaccacg    2820
aaatccaggc cgcgatcggc gccctggccc acctgtatgt caacggcgtc acggtcgact    2880
ggcccgcgct cctgggcgat gctccggcaa cacgggtgct ggaccttccg acatacgcct    2940
tccagcacca gcgctactgg ctcgagtcgg ctcccccggc cacggccgac tcgggccacc    3000
ccgtcctcgg caccggagtc gccgtcgccg gtcgccgggg ccgggtgttc acgggtcccg    3060
tgcccgccgt gcggaccgc gcggtgttca tcgccgaact ggcgctcgcc gccgccgacg    3120
ccaccgactg cgccacggtc gaacagctcg acgtcacctc cgtgcccggc ggatccgccc    3180
gcggcagggc caccgcgcag acctgggtcg atgaacccgc cgccgacggg cggcgccgct    3240
tcaccgtcca cacccgcgtc ggcgacgccc cgtggacgct gcacgccgag ggggttctcc    3300
gccccggccg cgtgccccag cccgaagccg tcgacaccgc ctggccccg ccgggcgcgg    3360 tgcccgcgga cgggctgccc ggggcgtggc gacgcgcgga ccaggtcttc gtcgaagccg    3420
aagtcgacag ccctgacggc ttcgtggcac accccgacct gctcgacgcg gtcttctccg    3480
cggtcggcga cgggagccgc cagccgaccg gatggcgcga cctcgcggtg cacgcgtcgg    3540
acgccaccgt gctgcgcgcc tgcctcaccc gccgcgacag tggtgtcgtg gagctcgccg    3600
ccttcgacgg tgccggaatg ccggtgctca ccgcggagtc ggtgacgctg ggcgaggtcg    3660
cgtcggcagg cggatccgac gagtcggacg gtctgcttcg gcttgagtgg ttgccggtgg    3720
cggaggccca ctacgacggt gccgacgagc tgcccgaggg ctacaccctc atcaccgcca    3780 cacccccga cgaccccgac gaccccacca accccacaa cacacccaca cgcacccaca    3840
cacaaaccac acgcgtcctc accgccctcc aacaccacct catcaccacc aaccacaccc    3900
tcatcgtcca caccaccacc gaccccccag gcgccgccgt caccggcctc acccgcaccg    3960
cacaaaacga acacccccggc cgcatccacc tcatcgaaac ccaccaccc cacacccccac    4020
```

-continued

```
tcccctcac ccaactcacc accctccacc aaccccacct acgcctcacc aacaacaccc    4080
tccacacccc ccacctcacc cccatcacca cccaccacaa caccaccaca accacccccca  4140 acacccacc cctcaacccc aaccacgcca tcctcatcac cggcggctcc ggcaccctcg    4200
ccggcatcct cgcccgccac ctcaaccacc cccacaccta cctcctctcc cgcacaccac   4260
caccccccac cacacccggc acccacatcc cctgcgacct caccgacccc acccaaatca   4320
cccaagccct cacccacata ccacaacccc tcaccggcat cttccacacc gccgccaccc   4380
tcgacgacgc caccctcacc aacctcaccc cccaacacct caccaccacc ctccaaccca   4440
aagccgacgc cgcctggcac ctccaccacc acacccaaaa ccaaccnctc acccacttcg   4500
tcctctactc cagcgccgcc gccacnctcg gcagccccgg ccaagccaac tacgccgccg   4560
ccaacgcctt cctcgacgcc ctcgccaccc accgccacac ccaaggacaa cccgccacca   4620
ccatcgcctg gggcatgtgg cacaccacca ccacactcac cagccaactc accgacagcg   4680
accgcgaccg catccgccgc ggcggcttcc tgccgatctc ggacgacgag ggcatgc      4737
```

<210> SEQ ID NO 31
<211> LENGTH: 1578
<212> TYPE: PRT
<213> ORGANISM: Artificial Sequence
<220> FEATURE:
<223> OTHER INFORMATION: primer

<400> SEQUENCE: 31

```
Met Arg Leu Tyr Glu Ala Ala Arg Arg Thr Gly Ser Pro Val Val Val
1               5                   10                  15

Ala Ala Ala Leu Asp Asp Ala Pro Asp Val Pro Leu Leu Arg Gly Leu
            20                  25                  30

Arg Arg Thr Thr Val Arg Arg Ala Val Arg Glu Arg Ser Leu Ala
        35                  40                  45

Asp Arg Ser Pro Cys Cys Pro Thr Thr Ser Ala Pro Thr Pro Pro Ser
    50                  55                  60

Arg Ser Ser Trp Asn Ser Thr Ala Thr Val Leu Gly His Leu Gly Ala
65                  70                  75                  80

Glu Asp Ile Pro Ala Thr Thr Thr Phe Lys Glu Leu Gly Ile Asp Ser
                85                  90                  95

Leu Thr Ala Val Gln Leu Arg Asn Ala Leu Thr Thr Ala Thr Gly Val
            100                 105                 110

Arg Leu Asn Ala Thr Ala Val Phe Asp Phe Pro Thr Pro Arg Ala Leu
        115                 120                 125

Ala Ala Arg Leu Gly Asp Glu Leu Ala Gly Thr Arg Ala Pro Val Ala
    130                 135                 140

Ala Arg Thr Ala Ala Thr Ala Ala Ala His Asp Glu Pro Leu Ala Ile
145                 150                 155                 160

Val Gly Met Ala Cys Arg Leu Pro Gly Gly Val Ala Ser Pro Gln Glu
                165                 170                 175

Leu Trp Arg Leu Val Ala Ser Gly Thr Asp Ala Ile Thr Glu Phe Pro
            180                 185                 190

Ala Asp Arg Gly Trp Asp Val Asp Ala Leu Tyr Asp Pro Asp Pro Asp
        195                 200                 205

Ala Ile Gly Lys Thr Phe Val Arg His Gly Gly Phe Leu Asp Gly Ala
    210                 215                 220

Thr Gly Phe Asp Ala Ala Phe Phe Gly Ile Ser Pro Arg Glu Ala Leu
225                 230                 235                 240
```

-continued

```
Ala Met Asp Pro Gln Gln Arg Val Leu Leu Glu Thr Ser Trp Glu Ala
            245                 250                 255

Phe Glu Ser Ala Gly Ile Thr Pro Asp Ala Ala Arg Gly Ser Asp Thr
        260                 265                 270

Gly Val Phe Ile Gly Ala Phe Ser Tyr Gly Tyr Gly Thr Gly Ala Asp
            275                 280                 285

Thr Asn Gly Phe Gly Ala Thr Gly Ser Gln Thr Ser Val Leu Ser Gly
    290                 295                 300

Arg Leu Ser Tyr Phe Tyr Gly Leu Glu Gly Pro Ser Val Thr Val Asp
305                 310                 315                 320

Thr Ala Cys Ser Ser Ser Leu Val Ala Leu His Gln Ala Gly Gln Ser
                325                 330                 335

Leu Arg Ser Gly Glu Cys Ser Leu Ala Leu Val Gly Gly Val Thr Val
            340                 345                 350

Met Ala Ser Pro Gly Gly Phe Val Glu Phe Ser Arg Gln Arg Gly Leu
        355                 360                 365

Ala Pro Asp Gly Arg Ala Lys Ala Phe Gly Ala Gly Ala Asp Gly Thr
    370                 375                 380

Ser Phe Ala Glu Gly Ala Gly Ala Leu Val Val Glu Arg Leu Ser Asp
385                 390                 395                 400

Ala Glu Arg His Gly His Thr Val Leu Ala Leu Val Arg Gly Ser Ala
                405                 410                 415

Ala Asn Ser Asp Gly Ala Ser Asn Gly Leu Ser Ala Pro Asn Gly Pro
            420                 425                 430

Ser Gln Glu Arg Val Ile His Gln Ala Leu Ala Asn Ala Lys Leu Thr
        435                 440                 445

Pro Ala Asp Val Asp Ala Val Glu Ala His Gly Thr Gly Thr Arg Leu
    450                 455                 460

Gly Asp Pro Ile Glu Ala Gln Ala Leu Leu Ala Thr Tyr Gly Gln Asp
465                 470                 475                 480

Arg Ala Thr Pro Leu Leu Leu Gly Ser Leu Lys Ser Asn Ile Gly His
                485                 490                 495

Ala Gln Ala Ala Ser Gly Val Ala Gly Ile Ile Lys Met Val Gln Ala
            500                 505                 510

Ile Arg His Gly Glu Leu Pro Pro Thr Leu His Ala Asp Glu Pro Ser
        515                 520                 525

Pro His Val Asp Trp Thr Ala Gly Ala Val Glu Leu Leu Thr Ser Ala
    530                 535                 540

Arg Pro Trp Pro Gly Thr Gly Arg Pro Arg Arg Ala Ala Val Ser Ser
545                 550                 555                 560

Phe Gly Val Ser Gly Thr Asn Ala His Ile Ile Leu Glu Ala Gly Pro
                565                 570                 575

Val Lys Thr Gly Pro Val Glu Ala Gly Ala Ile Glu Ala Gly Pro Val
            580                 585                 590

Glu Val Gly Pro Val Glu Ala Gly Pro Leu Pro Ala Ala Pro Pro Ser
        595                 600                 605

Ala Pro Gly Glu Asp Leu Pro Leu Leu Val Ser Ala Arg Ser Pro Glu
    610                 615                 620

Ala Leu Asp Glu Gln Ile Gly Arg Leu Arg Ala Tyr Leu Asp Thr Gly
625                 630                 635                 640

Pro Gly Val Asp Arg Ala Ala Val Ala Gln Thr Leu Ala Arg Arg Thr
                645                 650                 655

His Phe Thr His Arg Ala Val Leu Leu Gly Asp Thr Val Ile Gly Ala
```

-continued

```
                660                 665                 670
Pro Pro Ala Asp Gln Ala Asp Glu Leu Val Phe Val Tyr Ser Gly Gln
            675                 680                 685
Gly Thr Gln His Pro Ala Met Gly Glu Gln Leu Ala Ala Ala Phe Pro
            690                 695                 700
Val Phe Ala Arg Ile His Gln Gln Val Trp Asp Leu Leu Asp Val Pro
705                 710                 715                 720
Asp Leu Glu Val Asn Glu Thr Gly Tyr Ala Gln Pro Ala Leu Phe Ala
                725                 730                 735
Met Gln Val Ala Leu Phe Gly Leu Leu Glu Ser Trp Gly Val Arg Pro
            740                 745                 750
Asp Ala Val Ile Gly His Ser Val Gly Glu Leu Ala Ala Ala Tyr Val
            755                 760                 765
Ser Gly Val Trp Ser Leu Glu Asp Ala Cys Thr Leu Val Ser Ala Arg
            770                 775                 780
Ala Arg Leu Met Gln Ala Leu Pro Ala Gly Gly Val Met Val Ala Val
785                 790                 795                 800
Pro Val Ser Glu Asp Glu Ala Arg Ala Val Leu Gly Glu Gly Val Glu
                805                 810                 815
Ile Ala Ala Val Asn Gly Pro Ser Ser Val Val Leu Ser Gly Asp Glu
                820                 825                 830
Ala Ala Val Leu Gln Ala Ala Glu Gly Leu Gly Lys Trp Thr Arg Leu
            835                 840                 845
Ala Thr Ser His Ala Phe His Ser Ala Arg Met Glu Pro Met Leu Glu
            850                 855                 860
Glu Phe Arg Ala Val Ala Glu Gly Leu Thr Tyr Arg Thr Pro Gln Val
865                 870                 875                 880
Ser Met Ala Val Gly Asp Gln Val Thr Thr Ala Glu Tyr Trp Val Arg
                885                 890                 895
Gln Val Arg Asp Thr Val Arg Phe Gly Glu Gln Val Ala Ser Tyr Glu
                900                 905                 910
Asp Ala Val Phe Val Glu Leu Gly Ala Asp Arg Ser Leu Ala Arg Leu
            915                 920                 925
Val Asp Gly Val Ala Met Leu His Gly Asp His Glu Ile Gln Ala Ala
            930                 935                 940
Ile Gly Ala Leu Ala His Leu Tyr Val Asn Gly Val Thr Val Asp Trp
945                 950                 955                 960
Pro Ala Leu Leu Gly Asp Ala Pro Ala Thr Arg Val Leu Asp Leu Pro
                965                 970                 975
Thr Tyr Ala Phe Gln His Gln Arg Tyr Trp Leu Glu Ser Ala Pro Pro
                980                 985                 990
Ala Thr Ala Asp Ser Gly His Pro  Val Leu Gly Thr Gly  Val Ala Val
            995                 1000                1005
Ala Gly  Ser Pro Gly Arg Val  Phe Thr Gly Pro Val  Pro Ala Gly
            1010                1015                1020
Ala Asp  Arg Ala Val Phe Ile  Ala Glu Leu Ala Leu  Ala Ala Ala
            1025                1030                1035
Asp Ala  Thr Asp Cys Ala Thr  Val Glu Gln Leu Asp  Val Thr Ser
            1040                1045                1050
Val Pro  Gly Gly Ser Ala Arg  Gly Arg Ala Thr Ala  Gln Thr Trp
            1055                1060                1065
Val Asp  Glu Pro Ala Ala Asp  Gly Arg Arg Arg Phe  Thr Val His
            1070                1075                1080
```

-continued

```
Thr Arg Val Gly Asp Ala Pro Trp Thr Leu His Ala Glu Gly Val
1085                1090                1095
Leu Arg Pro Gly Arg Val Pro Gln Pro Glu Ala Val Asp Thr Ala
1100                1105                1110
Trp Pro Pro Gly Ala Val Pro Ala Asp Gly Leu Pro Gly Ala
1115                1120                1125
Trp Arg Arg Ala Asp Gln Val Phe Val Glu Ala Glu Val Asp Ser
1130                1135                1140
Pro Asp Gly Phe Val Ala His Pro Asp Leu Leu Asp Ala Val Phe
1145                1150                1155
Ser Ala Val Gly Asp Gly Ser Arg Gln Pro Thr Gly Trp Arg Asp
1160                1165                1170
Leu Ala Val His Ala Ser Asp Ala Thr Val Leu Arg Ala Cys Leu
1175                1180                1185
Thr Arg Arg Asp Ser Gly Val Val Glu Leu Ala Ala Phe Asp Gly
1190                1195                1200
Ala Gly Met Pro Val Leu Thr Ala Glu Ser Val Thr Leu Gly Glu
1205                1210                1215
Val Ala Ser Ala Gly Gly Ser Asp Glu Ser Asp Gly Leu Leu Arg
1220                1225                1230
Leu Glu Trp Leu Pro Val Ala Glu Ala His Tyr Asp Gly Ala Asp
1235                1240                1245
Glu Leu Pro Glu Gly Tyr Thr Leu Ile Thr Ala Thr His Pro Asp
1250                1255                1260
Asp Pro Asp Asp Pro Thr Asn Pro His Asn Thr Pro Thr Arg Thr
1265                1270                1275
His Thr Gln Thr Thr Arg Val Leu Thr Ala Leu Gln His His Leu
1280                1285                1290
Ile Thr Thr Asn His Thr Leu Ile Val His Thr Thr Asp Pro
1295                1300                1305
Pro Gly Ala Ala Val Thr Gly Leu Thr Arg Thr Ala Gln Asn Glu
1310                1315                1320
His Pro Gly Arg Ile His Leu Ile Glu Thr His His Pro His Thr
1325                1330                1335
Pro Leu Pro Leu Thr Gln Leu Thr Thr Leu His Gln Pro His Leu
1340                1345                1350
Arg Leu Thr Asn Asn Thr Leu His Thr Pro His Leu Thr Pro Ile
1355                1360                1365
Thr Thr His His Asn Thr Thr Thr Thr Pro Asn Thr Pro Pro
1370                1375                1380
Leu Asn Pro Asn His Ala Ile Leu Ile Thr Gly Gly Ser Gly Thr
1385                1390                1395
Leu Ala Gly Ile Leu Ala Arg His Leu Asn His Pro His Thr Tyr
1400                1405                1410
Leu Leu Ser Arg Thr Pro Pro Pro Thr Thr Pro Gly Thr His
1415                1420                1425
Ile Pro Cys Asp Leu Thr Asp Pro Thr Gln Ile Thr Gln Ala Leu
1430                1435                1440
Thr His Ile Pro Gln Pro Leu Thr Gly Ile Phe His Thr Ala Ala
1445                1450                1455
Thr Leu Asp Asp Ala Thr Leu Thr Asn Leu Thr Pro Gln His Leu
1460                1465                1470
```

| Thr | Thr | Thr | Leu | Gln | Pro | Lys | Ala | Asp | Ala | Ala | Trp | His | Leu | His |
|---|---|---|---|---|---|---|---|---|---|---|---|---|---|---|
| 1475 | | | | 1480 | | | | | 1485 | | | | | |

| His | His | Thr | Gln | Asn | Gln | Pro | Leu | Thr | His | Phe | Val | Leu | Tyr | Ser |
|---|---|---|---|---|---|---|---|---|---|---|---|---|---|---|
| | 1490 | | | | 1495 | | | | 1500 | | | | | |

| Ser | Ala | Ala | Ala | Thr | Leu | Gly | Ser | Pro | Gly | Gln | Ala | Asn | Tyr | Ala |
|---|---|---|---|---|---|---|---|---|---|---|---|---|---|---|
| 1505 | | | | | 1510 | | | | | 1515 | | | | |

| Ala | Ala | Asn | Ala | Phe | Leu | Asp | Ala | Leu | Ala | Thr | His | Arg | His | Thr |
|---|---|---|---|---|---|---|---|---|---|---|---|---|---|---|
| | 1520 | | | | 1525 | | | | 1530 | | | | | |

| Gln | Gly | Gln | Pro | Ala | Thr | Thr | Ile | Ala | Trp | Gly | Met | Trp | His | Thr |
|---|---|---|---|---|---|---|---|---|---|---|---|---|---|---|
| 1535 | | | | | 1540 | | | | | 1545 | | | | |

| Thr | Thr | Leu | Thr | Ser | Gln | Leu | Thr | Asp | Ser | Asp | Arg | Asp | Arg |
|---|---|---|---|---|---|---|---|---|---|---|---|---|---|
| 1550 | | | | 1555 | | | | | 1560 | | | | |

| Ile | Arg | Arg | Gly | Gly | Phe | Leu | Pro | Ile | Ser | Asp | Asp | Glu | Gly | Met |
|---|---|---|---|---|---|---|---|---|---|---|---|---|---|---|
| 1565 | | | | | 1570 | | | | | 1575 | | | | |

<210> SEQ ID NO 32
<211> LENGTH: 4818
<212> TYPE: DNA
<213> ORGANISM: Artificial Sequence
<220> FEATURE:
<223> OTHER INFORMATION: primer

<400> SEQUENCE: 32

```
gcatgcggct gtacgaggcg gcacggcgca ccggaagtcc cgtggtggtg gcggccgcgc      60
tcgacgacgc gccggacgtg ccgctgctgc gcgggctgcg gcgtacgacc gtccggcgtg     120
ccgccgtccg ggaacgctct ctcgccgacc gctcgccgtg ctgcccgacg acgagcgcgc     180
cgacgcctcc ctcgcgttcg tcctggaaca gcaccgccac cgtgctcggc cacctgggcg     240
ccgaagacat cccggcgacg acgacgttca aggaactcgg catcgactcg ctcaccgcgg     300
tccagctgcg caacgcgctg accacggcga ccggcgtacg cctcaacgcc acagcggtct     360
tcgactttcc gacgccgcgc gcgctcgccg cgagactcgg cgacgagctg gccggtaccc     420
gcgcgcccgt cgcggcccgg accgcggcca ccgcggccgc gcacgacgaa ccgctggcga     480
tcgtgggcat ggcctgccgt ctgccggcg gggtcgcgtc gccacaggag ctgtggcgtc     540
tcgtcgcgtc cggcaccgac gccatcacgg agttccccgc ggaccgcggc tgggacgtgg     600
acgcgctcta cgaccggac cccgacgcga tcggcaagac cttcgtccgg cacgcggct     660
tcctcgacgg tgcgaccggc ttcgacgcgg cgttcttcgg gatcagcccg cgcgaggccc     720
tggccatgga cccgcagcaa cgggtgctcc tggagacgtc ctgggaggcg ttcgaaagcg     780
cgggcatcac cccggacgcg gcgcggggca gcgacaccgg cgtgttcatc ggcgcgttct     840
cctacgggta cggcacgggt gcggatacca acggcttcgg cgcgacaggg tcgcagacca     900
gcgtgctctc cggccgcctc tcgtacttct acggtctgga gggcccttcg gtcacggtcg     960
acaccgcctg ctcgtcgtca ctggtcgccc tgcaccaggc agggcagtcc ctgcgctcgg    1020
gcgaatgctc gctcgccctg gtcggcggtg tcacggtgat ggcgtcgccc ggcggattcg    1080
tcgagttctc ccggcagcgc gggctcgcgc cggacgggcg ggcgaaggcg ttcggcgcgg    1140
gcgcggacgg tacgagcttc gccgagggcg ccggtgccct ggtggtcgag cggctctccg    1200
acgcggagcg ccacgccac accgtcctcg ccctcgtacg cggctccgcg ctaactccg    1260
acggcgcgtc gaacggtctg tcggcgccga acggcccctc ccaggaacgc gtcatccacc    1320
aggccctcgc gaacgcgaaa ctcacccccg ccgatgtcga cgcggtcgag gcgcacggca    1380
ccggcacccg cctcggcgac cccatcgagg cgcaggcgct gctcgcgacg tacgacagg    1440
```

-continued

```
accgggcgac gccsctgctg ctcggctcgc tgaagtcgaa catcgggcac gcccaggccg    1500
cgtcaggggt cgccgggatc atcaagatgg tgcaggccat ccggcacggg gaactgccgc    1560
cgacactgca cgcggacgag ccgtcgccgc acgtcgactg gacggccggt gccgtcgagc    1620
tcctgacgtc ggcccggccg tggccgggga ccggtcgccc gcgccgcgct gccgtctcgt    1680
cgttcggcgt gagcggcacg aacgcccaca tcatccttga ggcaggaccg gtcaaaacgg    1740
gaccggtcga ggcaggagcg atcgaggcag gaccggtcga agtaggaccg gtcgaggctg    1800
gaccgctccc cgcggcgccg ccgtcagcac cgggcgaaga ccttccgctg ctcgtgtcgg    1860
cgcgttcccc ggaggcactc gacgagcaga tcgggcgcct gcgcgcctat ctcgacaccg    1920
gcccgggcgt cgaccgggcg gccgtggcgc agacactggc ccggcgtacg cacttcaccc    1980
accgggccgt actgctcggg gacaccgtca tcggcgctcc ccccgcggac caggccgacg    2040
aactcgtctt cgtctactcc ggtcagggca cccagcatcc cgcgatgggc gagcagctag    2100
ccgattcgtc ggtggtgttc gccgagcgga tggccgagtg tgcggcggcg ttgcgcgagt    2160
tcgtggactg ggatctgttc acggttctgg atgatccggc ggtggtggac cgggttgatg    2220
tggtccagcc cgcttcctgg gcgatgatgg tttccctggc cgcggtgtgg caggcggccg    2280
gtgtgcggcc ggatgcggtg atcggccatt cgcagggtga gatcgccgca gcttgtgtgg    2340
cgggtgcggt gtcactacgc gatgccgccc ggatcgtgac cttgcgcagc caggcgatcg    2400 cccgggggcct ggcgggccgg ggcgcgatgg catccgtcgc cctgcccgcg caggatgtcg    2460
agctggtcga cggggcctgg atcgccgccc acaacgggcc cgcctccacc gtgatcgcgg    2520
gcaccccgga agcggtcgac catgtcctca ccgctcatga ggcacaaggg gtgcgggtgc    2580
ggcggatcac cgtcgactat gcctcgcaca ccccgcacgt cgagctgatc cgcgacgaac    2640
tactcgacat cactagcgac agcagctcgc agaccccgct cgtgccgtgg ctgtcgaccg    2700
tggacggcac ctgggtcgac agcccgctgg acggggagta ctggtaccgg aacctgcgtg    2760
aaccggtcgg tttccacccc gccgtcagcc agttgcaggc ccagggcgac accgtgttcg    2820
tcgaggtcag cgccagcccg gtgttgttgc aggcgatgga cgacgatgtc gtcacggttg    2880
ccacgctgcg tcgtgacgac ggcgacgcca cccggatgct caccgccctg gcacaggcct    2940
atgtccacgg cgtcaccgtc gactggcccc ccatcctcgg caccaccaca acccgggtac    3000
tggaccttcc gacctacgcc ttccaacacc agcggtactg gctcgagtcg gctcccccgg    3060
ccacggccga ctcgggccac cccgtcctcg gcaccggagt cgccgtcgcc gggtcgccgg    3120
gccgggtgtt cacgggtccc gtgcccgccg gtgcggaccg cgcggtgttc atcgccgaac    3180
tggcgctcgc cgccgccgac gccaccgact gcgccacggt cgaacagctc gacgtcacct    3240
ccgtgcccgg cggatccgcc cgcggcaggg ccaccgcgca gacctgggtc gatgaacccg    3300
ccgccgacgg gcggcgccgc ttcaccgtcc acacccgcgt cggcgacgcc ccgtggacgc    3360
tgcacgccga gggggttctc cgccccgcc gcgtgcccca gcccgaagcc gtcgacaccg    3420
cctggccccc gccgggcgcg gtgcccgcgg acgggctgcc cggggcgtgg cgacgcgcgg    3480
accaggtctt cgtcgaagcc gaagtcgaca gccctgacgg cttcgtggca cccccgaccc    3540
tgctcgacgc ggtcttctcc gcggtcggcg acgggagccg ccagccgacc ggatggcgcg    3600
acctcgcggt gcacgcgtcg gacgccaccg tgctgcgcgc ctgcctcacc cgccgcgaca    3660
gtggtgtcgt ggagctcgcc gccttcgacg gtgccggaat gccggtgctc accgcggagt    3720
cggtgacgct gggcgaggtc gcgtcggcag gcggatccga cgagtcggac ggtctgcttc    3780
ggcttgagtg gttgccggtg gcggaggccc actacgacgg tgccgacgag ctgcccgagg    3840
```

```
gctacaccct catcaccgcc acacaccccg acgaccccga cgaccccacc aaccccacac   3900
acacacccac acgcacccac acacaaacca cacgcgtcct caccgccctc aacaccacc    3960
tcatcaccac caaccacacc ctcatcgtcc acaccaccac cgaccccca ggcgccgccg    4020
tcaccggcct cacccgcacc gcacaaaacg aacaccccgg ccgcatccac ctcatcgaaa   4080
cccaccaccc ccacacccca ctccccctca cccaactcac caccctccac caaccccacc   4140
tacgcctcac caacaacacc ctccacaccc cccacctcac ccccatcacc acccaccaca   4200
acaccaccac aaccccccc aacacccac ccctcaaccc caaccacgcc atcctcatca    4260
ccggcggctc cggcacccctc gccggcatcc tcgcccgcca cctcaaccac cccacacct   4320
acctcctctc ccgcacacca ccaccccca ccacacccgg cacccacatc ccctgcgacc    4380
tcaccgaccc cacccaaatc acccaagccc tcacccacat accacaaccc ctcaccggca   4440
tcttccacac cgccgccacc ctcgacgacg ccaccctcac caacctcacc ccccaacacc   4500
tcaccaccac cctccaaccc aaagccgacg ccgcctggca cctccaccac cacacccaaa   4560
accaacccct caccccacttc gtcctctact ccagcgccgc cgccaccctc ggcagccccg   4620
gccaagccaa ctacgccgcc gccaacgcct tcctcgacgc cctcgccacc caccgccaca   4680
cccaaggaca acccgccacc accatcgcct ggggcatgtg gcacaccacc accacactca   4740
ccagccaact caccgacagc gaccgcgacc gcatccgccg cggcggcttc ctgccgatct   4800
cggacgacga gggcatgc                                                 4818
```

<210> SEQ ID NO 33
<211> LENGTH: 1605
<212> TYPE: PRT
<213> ORGANISM: Artificial Sequence
<220> FEATURE:
<223> OTHER INFORMATION: primer

<400> SEQUENCE: 33

```
Met Arg Leu Tyr Glu Ala Ala Arg Arg Thr Gly Ser Pro Val Val
1               5                   10                  15

Ala Ala Ala Leu Asp Asp Ala Pro Asp Val Pro Leu Leu Arg Gly Leu
            20                  25                  30

Arg Arg Thr Thr Val Arg Arg Ala Ala Val Arg Glu Arg Ser Leu Ala
        35                  40                  45

Asp Arg Ser Pro Cys Cys Pro Thr Thr Ser Ala Pro Thr Pro Pro Ser
    50                  55                  60

Arg Ser Ser Trp Asn Ser Thr Ala Thr Val Leu Gly His Leu Gly Ala
65                  70                  75                  80

Glu Asp Ile Pro Ala Thr Thr Thr Phe Lys Glu Leu Gly Ile Asp Ser
                85                  90                  95

Leu Thr Ala Val Gln Leu Arg Asn Ala Leu Thr Thr Ala Thr Gly Val
            100                 105                 110

Arg Leu Asn Ala Thr Ala Val Phe Asp Phe Pro Thr Pro Arg Ala Leu
        115                 120                 125

Ala Ala Arg Leu Gly Asp Glu Leu Ala Gly Thr Arg Ala Pro Val Ala
    130                 135                 140

Ala Arg Thr Ala Ala Thr Ala Ala His Asp Glu Pro Leu Ala Ile
145                 150                 155                 160

Val Gly Met Ala Cys Arg Leu Pro Gly Gly Val Ala Ser Pro Gln Glu
                165                 170                 175

Leu Trp Arg Leu Val Ala Ser Gly Thr Asp Ala Ile Thr Glu Phe Pro
```

-continued

```
                180                 185                 190
Ala Asp Arg Gly Trp Asp Val Asp Ala Leu Tyr Asp Pro Asp Pro Asp
            195                 200                 205

Ala Ile Gly Lys Thr Phe Val Arg His Gly Phe Leu Asp Gly Ala
    210                 215                 220

Thr Gly Phe Asp Ala Ala Phe Phe Gly Ile Ser Pro Arg Glu Ala Leu
225                 230                 235                 240

Ala Met Asp Pro Gln Gln Arg Val Leu Leu Glu Thr Ser Trp Glu Ala
                245                 250                 255

Phe Glu Ser Ala Gly Ile Thr Pro Asp Ala Ala Arg Gly Ser Asp Thr
            260                 265                 270

Gly Val Phe Ile Gly Ala Phe Ser Tyr Gly Tyr Gly Thr Gly Ala Asp
        275                 280                 285

Thr Asn Gly Phe Gly Ala Thr Gly Ser Gln Thr Ser Val Leu Ser Gly
    290                 295                 300

Arg Leu Ser Tyr Phe Tyr Gly Leu Glu Gly Pro Ser Val Thr Val Asp
305                 310                 315                 320

Thr Ala Cys Ser Ser Ser Leu Val Ala Leu His Gln Ala Gly Gln Ser
                325                 330                 335

Leu Arg Ser Gly Glu Cys Ser Leu Ala Leu Val Gly Gly Val Thr Val
            340                 345                 350

Met Ala Ser Pro Gly Gly Phe Val Glu Phe Ser Arg Gln Arg Gly Leu
        355                 360                 365

Ala Pro Asp Gly Arg Ala Lys Ala Phe Gly Ala Gly Ala Asp Gly Thr
    370                 375                 380

Ser Phe Ala Glu Gly Ala Gly Ala Leu Val Val Glu Arg Leu Ser Asp
385                 390                 395                 400

Ala Glu Arg His Gly His Thr Val Leu Ala Leu Val Arg Gly Ser Ala
                405                 410                 415

Ala Asn Ser Asp Gly Ala Ser Asn Gly Leu Ser Ala Pro Asn Gly Pro
            420                 425                 430

Ser Gln Glu Arg Val Ile His Gln Ala Leu Ala Asn Ala Lys Leu Thr
        435                 440                 445

Pro Ala Asp Val Asp Ala Val Glu Ala His Gly Thr Gly Thr Arg Leu
    450                 455                 460

Gly Asp Pro Ile Glu Ala Gln Ala Leu Leu Ala Thr Tyr Gly Gln Asp
465                 470                 475                 480

Arg Ala Thr Pro Leu Leu Leu Gly Ser Leu Lys Ser Asn Ile Gly His
                485                 490                 495

Ala Gln Ala Ala Ser Gly Val Ala Gly Ile Ile Lys Met Val Gln Ala
            500                 505                 510

Ile Arg His Gly Glu Leu Pro Pro Thr Leu His Ala Asp Glu Pro Ser
        515                 520                 525

Pro His Val Asp Trp Thr Ala Gly Ala Val Glu Leu Leu Thr Ser Ala
    530                 535                 540

Arg Pro Trp Pro Gly Thr Gly Arg Pro Arg Arg Ala Ala Val Ser Ser
545                 550                 555                 560

Phe Gly Val Ser Gly Thr Asn Ala His Ile Ile Leu Glu Ala Gly Pro
                565                 570                 575

Val Lys Thr Gly Pro Val Glu Ala Gly Ala Ile Glu Ala Gly Pro Val
            580                 585                 590

Glu Val Gly Pro Val Glu Ala Gly Pro Leu Pro Ala Ala Pro Pro Ser
        595                 600                 605
```

```
Ala Pro Gly Glu Asp Leu Pro Leu Leu Val Ser Ala Arg Ser Pro Glu
    610                 615                 620

Ala Leu Asp Glu Gln Ile Gly Arg Leu Arg Ala Tyr Leu Asp Thr Gly
625                 630                 635                 640

Pro Gly Val Asp Arg Ala Val Ala Gln Thr Leu Ala Arg Arg Thr
                645                 650                 655

His Phe Thr His Arg Ala Val Leu Leu Gly Asp Thr Val Ile Gly Ala
            660                 665                 670

Pro Pro Ala Asp Gln Ala Asp Glu Leu Val Phe Val Tyr Ser Gly Gln
        675                 680                 685

Gly Thr Gln His Pro Ala Met Gly Glu Gln Leu Ala Asp Ser Ser Val
    690                 695                 700

Val Phe Ala Glu Arg Met Ala Glu Cys Ala Ala Leu Arg Glu Phe
705                 710                 715                 720

Val Asp Trp Asp Leu Phe Thr Val Leu Asp Asp Pro Ala Val Val Asp
                725                 730                 735

Arg Val Asp Val Val Gln Pro Ala Ser Trp Ala Met Met Val Ser Leu
                740                 745                 750

Ala Ala Val Trp Gln Ala Ala Gly Val Arg Pro Asp Ala Val Ile Gly
            755                 760                 765

His Ser Gln Gly Glu Ile Ala Ala Ala Cys Val Ala Gly Ala Val Ser
770                 775                 780

Leu Arg Asp Ala Ala Arg Ile Val Thr Leu Arg Ser Gln Ala Ile Ala
785                 790                 795                 800

Arg Gly Leu Ala Gly Arg Gly Ala Met Ala Ser Val Ala Leu Pro Ala
                805                 810                 815

Gln Asp Val Glu Leu Val Asp Gly Ala Trp Ile Ala Ala His Asn Gly
            820                 825                 830

Pro Ala Ser Thr Val Ile Ala Gly Thr Pro Glu Ala Val Asp His Val
            835                 840                 845

Leu Thr Ala His Glu Ala Gln Gly Val Arg Val Arg Arg Ile Thr Val
850                 855                 860

Asp Tyr Ala Ser His Thr Pro His Val Glu Leu Ile Arg Asp Glu Leu
865                 870                 875                 880

Leu Asp Ile Thr Ser Asp Ser Ser Gln Thr Pro Leu Val Pro Trp
                885                 890                 895

Leu Ser Thr Val Asp Gly Thr Trp Val Asp Ser Pro Leu Asp Gly Glu
                900                 905                 910

Tyr Trp Tyr Arg Asn Leu Arg Glu Pro Val Gly Phe His Pro Ala Val
    915                 920                 925

Ser Gln Leu Gln Ala Gln Gly Asp Thr Val Phe Val Glu Val Ser Ala
    930                 935                 940

Ser Pro Val Leu Leu Gln Ala Met Asp Asp Val Val Thr Val Ala
945                 950                 955                 960

Thr Leu Arg Arg Asp Asp Gly Asp Ala Thr Arg Met Leu Thr Ala Leu
                965                 970                 975

Ala Gln Ala Tyr Val His Gly Val Thr Val Asp Trp Pro Ala Ile Leu
            980                 985                 990

Gly Thr Thr Thr Thr Arg Val Leu  Asp Leu Pro Thr Tyr  Ala Phe Gln
        995                 1000                 1005

His Gln  Arg Tyr Trp Leu Glu  Ser Ala Pro Pro Ala  Thr Ala Asp
    1010                 1015                 1020
```

-continued

```
Ser Gly His Pro Val Leu Gly Thr Gly Val Ala Val Ala Gly Ser
    1025                1030                1035

Pro Gly Arg Val Phe Thr Gly Pro Val Pro Ala Gly Ala Asp Arg
    1040                1045                1050

Ala Val Phe Ile Ala Glu Leu Ala Leu Ala Ala Ala Asp Ala Thr
    1055                1060                1065

Asp Cys Ala Thr Val Glu Gln Leu Asp Val Thr Ser Val Pro Gly
    1070                1075                1080

Gly Ser Ala Arg Gly Arg Ala Thr Ala Gln Thr Trp Val Asp Glu
    1085                1090                1095

Pro Ala Ala Asp Gly Arg Arg Phe Thr Val His Thr Arg Val
    1100                1105                1110

Gly Asp Ala Pro Trp Thr Leu His Ala Glu Gly Val Leu Arg Pro
    1115                1120                1125

Gly Arg Val Pro Gln Pro Glu Ala Val Asp Thr Ala Trp Pro Pro
    1130                1135                1140

Pro Gly Ala Val Pro Ala Asp Gly Leu Pro Gly Ala Trp Arg Arg
    1145                1150                1155

Ala Asp Gln Val Phe Val Glu Ala Glu Val Asp Ser Pro Asp Gly
    1160                1165                1170

Phe Val Ala His Pro Asp Leu Leu Asp Ala Val Phe Ser Ala Val
    1175                1180                1185

Gly Asp Gly Ser Arg Gln Pro Thr Gly Trp Arg Asp Leu Ala Val
    1190                1195                1200

His Ala Ser Asp Ala Thr Val Leu Arg Ala Cys Leu Thr Arg Arg
    1205                1210                1215

Asp Ser Gly Val Val Glu Leu Ala Ala Phe Asp Gly Ala Gly Met
    1220                1225                1230

Pro Val Leu Thr Ala Glu Ser Val Thr Leu Gly Glu Val Ala Ser
    1235                1240                1245

Ala Gly Gly Ser Asp Glu Ser Asp Gly Leu Leu Arg Leu Glu Trp
    1250                1255                1260

Leu Pro Val Ala Glu Ala His Tyr Asp Gly Ala Asp Glu Leu Pro
    1265                1270                1275

Glu Gly Tyr Thr Leu Ile Thr Ala Thr His Pro Asp Asp Pro Asp
    1280                1285                1290

Asp Pro Thr Asn Pro His Asn Thr Pro Thr Arg Thr His Thr Gln
    1295                1300                1305

Thr Thr Arg Val Leu Thr Ala Leu Gln His His Leu Ile Thr Thr
    1310                1315                1320

Asn His Thr Leu Ile Val His Thr Thr Thr Asp Pro Pro Gly Ala
    1325                1330                1335

Ala Val Thr Gly Leu Thr Arg Thr Ala Gln Asn Glu His Pro Gly
    1340                1345                1350

Arg Ile His Leu Ile Glu Thr His His Pro His Thr Pro Leu Pro
    1355                1360                1365

Leu Thr Gln Leu Thr Thr Leu His Gln Pro His Leu Arg Leu Thr
    1370                1375                1380

Asn Asn Thr Leu His Thr Pro His Leu Thr Pro Ile Thr Thr His
    1385                1390                1395

His Asn Thr Thr Thr Thr Pro Asn Thr Pro Pro Leu Asn Pro
    1400                1405                1410

Asn His Ala Ile Leu Ile Thr Gly Gly Ser Gly Thr Leu Ala Gly
```

-continued

```
                    1415                1420                1425

Ile Leu Ala Arg His Leu Asn His Pro His Thr Tyr Leu Leu Ser
        1430                1435                1440

Arg Thr Pro Pro Pro Pro Thr Pro Gly Thr His Ile Pro Cys
    1445                1450                1455

Asp Leu Thr Asp Pro Thr Gln Ile Thr Gln Ala Leu Thr His Ile
    1460                1465                1470

Pro Gln Pro Leu Thr Gly Ile Phe His Thr Ala Ala Thr Leu Asp
    1475                1480                1485

Asp Ala Thr Leu Thr Asn Leu Thr Pro Gln His Leu Thr Thr Thr
    1490                1495                1500

Leu Gln Pro Lys Ala Asp Ala Ala Trp His Leu His His His Thr
    1505                1510                1515

Gln Asn Gln Pro Leu Thr His Phe Val Leu Tyr Ser Ser Ala Ala
    1520                1525                1530

Ala Thr Leu Gly Ser Pro Gly Gln Ala Asn Tyr Ala Ala Ala Asn
    1535                1540                1545

Ala Phe Leu Asp Ala Leu Ala Thr His Arg His Thr Gln Gly Gln
    1550                1555                1560

Pro Ala Thr Thr Ile Ala Trp Gly Met Trp His Thr Thr Thr Thr
    1565                1570                1575

Leu Thr Ser Gln Leu Thr Asp Ser Asp Arg Asp Arg Ile Arg Arg
    1580                1585                1590

Gly Gly Phe Leu Pro Ile Ser Asp Asp Glu Gly Met
    1595                1600                1605

<210> SEQ ID NO 34
<211> LENGTH: 33
<212> TYPE: DNA
<213> ORGANISM: Artificial Sequence
<220> FEATURE:
<223> OTHER INFORMATION: primer

<400> SEQUENCE: 34
ggccgtccgc gccgtgcggc ggtctcgtcg ttc                                33

<210> SEQ ID NO 35
<211> LENGTH: 11
<212> TYPE: PRT
<213> ORGANISM: Artificial Sequence
<220> FEATURE:
<223> OTHER INFORMATION: primer

<400> SEQUENCE: 35

Gly Arg Pro Arg Arg Ala Ala Val Ser Ser Phe
1               5                   10

<210> SEQ ID NO 36
<211> LENGTH: 33
<212> TYPE: DNA
<213> ORGANISM: Artificial Sequence
<220> FEATURE:
<223> OTHER INFORMATION: primer

<400> SEQUENCE: 36
acccagcatc ccgcgatggg tgagcggctc gcc                                33

<210> SEQ ID NO 37
<211> LENGTH: 11
<212> TYPE: PRT
```

```
<213> ORGANISM: Artificial Sequence
<220> FEATURE:
<223> OTHER INFORMATION: primer

<400> SEQUENCE: 37

Thr Gln His Pro Ala Met Gly Glu Arg Leu Ala
1               5                   10

<210> SEQ ID NO 38
<211> LENGTH: 33
<212> TYPE: DNA
<213> ORGANISM: Artificial Sequence
<220> FEATURE:
<223> OTHER INFORMATION: primer

<400> SEQUENCE: 38
tacgccttcc agcggcggcc ctactggatc gag                                    33

<210> SEQ ID NO 39
<211> LENGTH: 11
<212> TYPE: PRT
<213> ORGANISM: Artificial Sequence
<220> FEATURE:
<223> OTHER INFORMATION: primer

<400> SEQUENCE: 39

Tyr Ala Phe Gln Arg Arg Pro Tyr Trp Ile Glu
1               5                   10

<210> SEQ ID NO 40
<211> LENGTH: 33
<212> TYPE: DNA
<213> ORGANISM: Artificial Sequence
<220> FEATURE:
<223> OTHER INFORMATION: primer

<400> SEQUENCE: 40
gaccggcccc gtcgggcggg cgtgtcgtcc ttc                                    33

<210> SEQ ID NO 41
<211> LENGTH: 11
<212> TYPE: PRT
<213> ORGANISM: Artificial Sequence
<220> FEATURE:
<223> OTHER INFORMATION: primer

<400> SEQUENCE: 41

Asp Arg Pro Arg Arg Ala Gly Val Ser Ser Phe
1               5                   10

<210> SEQ ID NO 42
<211> LENGTH: 33
<212> TYPE: DNA
<213> ORGANISM: Artificial Sequence
<220> FEATURE:
<223> OTHER INFORMATION: primer

<400> SEQUENCE: 42
tggcagtggc tggggatggg cagtgccctg cgg                                    33

<210> SEQ ID NO 43
<211> LENGTH: 11
<212> TYPE: PRT
<213> ORGANISM: Artificial Sequence
<220> FEATURE:
<223> OTHER INFORMATION: primer
```

-continued

```
<400> SEQUENCE: 43

Trp Gln Trp Leu Gly Met Gly Ser Ala Leu Arg
1               5                   10

<210> SEQ ID NO 44
<211> LENGTH: 33
<212> TYPE: DNA
<213> ORGANISM: Artificial Sequence
<220> FEATURE:
<223> OTHER INFORMATION: primer

<400> SEQUENCE: 44
tacgccttcc aacaccagcg gtactgggtc gag                                   33

<210> SEQ ID NO 45
<211> LENGTH: 11
<212> TYPE: PRT
<213> ORGANISM: Artificial Sequence
<220> FEATURE:
<223> OTHER INFORMATION: primer

<400> SEQUENCE: 45

Tyr Ala Phe Gln His Gln Arg Tyr Trp Val Glu
1               5                   10

<210> SEQ ID NO 46
<211> LENGTH: 33
<212> TYPE: DNA
<213> ORGANISM: Artificial Sequence
<220> FEATURE:
<223> OTHER INFORMATION: primer

<400> SEQUENCE: 46
ggccgagcgc gccgggcagg cgtgtcgtcc ttc                                   33

<210> SEQ ID NO 47
<211> LENGTH: 11
<212> TYPE: PRT
<213> ORGANISM: Artificial Sequence
<220> FEATURE:
<223> OTHER INFORMATION: primer

<400> SEQUENCE: 47

Gly Arg Ala Arg Arg Ala Gly Val Ser Ser Phe
1               5                   10

<210> SEQ ID NO 48
<211> LENGTH: 33
<212> TYPE: DNA
<213> ORGANISM: Artificial Sequence
<220> FEATURE:
<223> OTHER INFORMATION: primer

<400> SEQUENCE: 48
tcgcagcgtg ctggcatggg tgaggaactg gcc                                   33

<210> SEQ ID NO 49
<211> LENGTH: 11
<212> TYPE: PRT
<213> ORGANISM: Artificial Sequence
<220> FEATURE:
<223> OTHER INFORMATION: primer

<400> SEQUENCE: 49

Ser Gln Arg Ala Gly Met Gly Glu Glu Leu Ala
1               5                   10
```

<210> SEQ ID NO 50
<211> LENGTH: 33
<212> TYPE: DNA
<213> ORGANISM: Artificial Sequence
<220> FEATURE:
<223> OTHER INFORMATION: primer

<400> SEQUENCE: 50
tacgccttcc agcaccagcg ctactggctc gag                              33

<210> SEQ ID NO 51
<211> LENGTH: 11
<212> TYPE: PRT
<213> ORGANISM: Artificial Sequence
<220> FEATURE:
<223> OTHER INFORMATION: primer

<400> SEQUENCE: 51

Tyr Ala Phe Gln His Gln Arg Tyr Trp Leu Glu
1               5                   10

<210> SEQ ID NO 52
<211> LENGTH: 33
<212> TYPE: DNA
<213> ORGANISM: Artificial Sequence
<220> FEATURE:
<223> OTHER INFORMATION: primer

<400> SEQUENCE: 52
gcgcgaccgc gccgggcggg ggtctcgtcg ttc                              33

<210> SEQ ID NO 53
<211> LENGTH: 11
<212> TYPE: PRT
<213> ORGANISM: Artificial Sequence
<220> FEATURE:
<223> OTHER INFORMATION: primer

<400> SEQUENCE: 53

Ala Arg Pro Arg Arg Ala Gly Val Ser Ser Phe
1               5                   10

<210> SEQ ID NO 54
<211> LENGTH: 33
<212> TYPE: DNA
<213> ORGANISM: Artificial Sequence
<220> FEATURE:
<223> OTHER INFORMATION: primer

<400> SEQUENCE: 54
tggcagtggg cgggcatggc cgtcgacctg ctc                              33

<210> SEQ ID NO 55
<211> LENGTH: 11
<212> TYPE: PRT
<213> ORGANISM: Artificial Sequence
<220> FEATURE:
<223> OTHER INFORMATION: primer

<400> SEQUENCE: 55

Trp Gln Trp Ala Gly Met Ala Val Asp Leu Leu
1               5                   10

<210> SEQ ID NO 56
<211> LENGTH: 33

```
<212> TYPE: DNA
<213> ORGANISM: Artificial Sequence
<220> FEATURE:
<223> OTHER INFORMATION: primer

<400> SEQUENCE: 56
tacccgttcc agcgcgagcg cgtctggctc gaa                                    33

<210> SEQ ID NO 57
<211> LENGTH: 11
<212> TYPE: PRT
<213> ORGANISM: Artificial Sequence
<220> FEATURE:
<223> OTHER INFORMATION: primer

<400> SEQUENCE: 57

Tyr Pro Phe Gln Arg Glu Arg Val Trp Leu Glu
1               5                   10

<210> SEQ ID NO 58
<211> LENGTH: 33
<212> TYPE: DNA
<213> ORGANISM: Artificial Sequence
<220> FEATURE:
<223> OTHER INFORMATION: primer

<400> SEQUENCE: 58
gacggggtgc gccgggcagg tgtgtcggcg ttc                                    33

<210> SEQ ID NO 59
<211> LENGTH: 11
<212> TYPE: PRT
<213> ORGANISM: Artificial Sequence
<220> FEATURE:
<223> OTHER INFORMATION: primer

<400> SEQUENCE: 59

Asp Gly Val Arg Arg Ala Gly Val Ser Ala Phe
1               5                   10

<210> SEQ ID NO 60
<211> LENGTH: 33
<212> TYPE: DNA
<213> ORGANISM: Artificial Sequence
<220> FEATURE:
<223> OTHER INFORMATION: primer

<400> SEQUENCE: 60
gcccagtggg aaggcatggc gcgggagttg ttg                                    33

<210> SEQ ID NO 61
<211> LENGTH: 11
<212> TYPE: PRT
<213> ORGANISM: Artificial Sequence
<220> FEATURE:
<223> OTHER INFORMATION: primer

<400> SEQUENCE: 61

Ala Gln Trp Glu Gly Met Ala Arg Glu Leu Leu
1               5                   10

<210> SEQ ID NO 62
<211> LENGTH: 33
<212> TYPE: DNA
<213> ORGANISM: Artificial Sequence
<220> FEATURE:
<223> OTHER INFORMATION: primer
```

<400> SEQUENCE: 62
tatcctttcc agggcaagcg gttctggctg ctg                                    33

<210> SEQ ID NO 63
<211> LENGTH: 11
<212> TYPE: PRT
<213> ORGANISM: Artificial Sequence
<220> FEATURE:
<223> OTHER INFORMATION: primer

<400> SEQUENCE: 63

Tyr Pro Phe Gln Gly Lys Arg Phe Trp Leu Leu
1               5                   10

<210> SEQ ID NO 64
<211> LENGTH: 480
<212> TYPE: DNA
<213> ORGANISM: Artificial Sequence
<220> FEATURE:
<223> OTHER INFORMATION: primer

<400> SEQUENCE: 64
ccggcgccgt cgaactgctg acgtcggccc ggccgtggcc cgagaccgac cggccacggc     60
gtgccgccgc tcctcgttc ggggtgagcg caccaacgc ccacgtcatc ctggaggccg     120
gaccggtaac ggagacgccc gcggcatcgc cttccggtga ccttcccctg ctggtgtcgg    180
cacgctcacc ggaagcgctc gacgagcaga tccgccgact gcgcgcctac ctggacacca    240
ccccggacgt cgaccgggtg gccgtggcac agacgctggc ccggcgcaca cacttcgccc    300
accgcgccgt gctgctcggt gacaccgtca tcaccacacc cccgcggac cggcccgacg     360 aactcgtctt cgtctactcc ggccagggca cccagcatcc cgcgatgggc gagcagctcg    420
ccgccgccca tcccgtgttc gccgacgcct ggcatgaagc gctccgccgc cttgacaacc    480

<210> SEQ ID NO 65
<211> LENGTH: 159
<212> TYPE: PRT
<213> ORGANISM: Artificial Sequence
<220> FEATURE:
<223> OTHER INFORMATION: primer

<400> SEQUENCE: 65

Gly Ala Val Glu Leu Leu Thr Ser Ala Arg Pro Trp Pro Glu Thr Asp
1               5                   10                  15

Arg Pro Arg Arg Ala Ala Val Ser Ser Phe Gly Val Ser Gly Thr Asn
                20                  25                  30

Ala His Val Ile Leu Glu Ala Gly Pro Val Thr Glu Thr Pro Ala Ala
            35                  40                  45

Ser Pro Ser Gly Asp Leu Pro Leu Leu Val Ser Ala Arg Ser Pro Glu
        50                  55                  60

Ala Leu Asp Glu Gln Ile Arg Arg Leu Arg Ala Tyr Leu Asp Thr Thr
65                  70                  75                  80

Pro Asp Val Asp Arg Val Ala Val Ala Gln Thr Leu Ala Arg Arg Thr
                85                  90                  95

His Phe Ala His Arg Ala Val Leu Leu Gly Asp Thr Val Ile Thr Thr
            100                 105                 110

Pro Pro Ala Asp Arg Pro Asp Glu Leu Val Phe Val Tyr Ser Gly Gln
        115                 120                 125

Gly Thr Gln His Pro Ala Met Gly Glu Gln Leu Ala Ala Ala His Pro

```
                130              135              140
Val Phe Ala Asp Ala Trp His Glu Ala Leu Arg Arg Leu Asp Asn
145                 150                 155

<210> SEQ ID NO 66
<211> LENGTH: 120
<212> TYPE: DNA
<213> ORGANISM: Artificial Sequence
<220> FEATURE:
<223> OTHER INFORMATION: primer

<400> SEQUENCE: 66
tcctcggggc tgggtcacgg cacgacgcgg atgtgcccgc gtacgcgttc aacggcggc      60 actactggat cgagtcggca cgcccggccg catccgacgc gggccacccc gtgctgggct    120

<210> SEQ ID NO 67
<211> LENGTH: 39
<212> TYPE: PRT
<213> ORGANISM: Artificial Sequence
<220> FEATURE:
<223> OTHER INFORMATION: primer

<400> SEQUENCE: 67

Leu Gly Ala Gly Ser Arg His Asp Ala Asp Val Pro Ala Tyr Ala Phe
1               5                   10                  15

Gln Arg Arg His Tyr Trp Ile Glu Ser Ala Arg Pro Ala Ala Ser Asp
            20                  25                  30

Ala Gly His Pro Val Leu Gly
        35

<210> SEQ ID NO 68
<211> LENGTH: 480
<212> TYPE: DNA
<213> ORGANISM: Artificial Sequence
<220> FEATURE:
<223> OTHER INFORMATION: primer

<400> SEQUENCE: 68
tcggccaggc cgtggccgcg gaccggccgt ccgcgccgtg cggcggtctc gtcgttcggg      60
gtgagcggca ccaacgccca catcatcctg gaggccggac ccgaccagga ggagccgtcg    120
gcagaaccgg ccggtgacct cccgctgctc gtgtcggcac ggtccccgga ggcactggac    180
gagcagatcg ggcgcctgcg cgactatctc gacgccgccc ccggcgtgga cctggcggcc    240
gtggcgcgga cactggccac gcgtacgcac ttctcccacc gcgccgtact gctcggtgac    300
accgtcatca ccgctccccc cgtggaacag ccgggcgagc tcgtcttcgt ctactcggga    360
cagggcaccc agcatcccgc gatgggtgag cggctcgccg cagccttccc cgtgttcgcc    420
gacccggacg tacccgccta cgccttccag cggcggccct actggatcga gtccgcgccg    480

<210> SEQ ID NO 69
<211> LENGTH: 160
<212> TYPE: PRT
<213> ORGANISM: Artificial Sequence
<220> FEATURE:
<223> OTHER INFORMATION: primer

<400> SEQUENCE: 69

Ser Ala Arg Pro Trp Pro Arg Thr Gly Arg Pro Arg Arg Ala Ala Val
1               5                   10                  15

Ser Ser Phe Gly Val Ser Gly Thr Asn Ala His Ile Ile Leu Glu Ala
            20                  25                  30
```

```
Gly Pro Asp Gln Glu Pro Ser Ala Glu Pro Ala Gly Asp Leu Pro
            35                  40                  45

Leu Leu Val Ser Ala Arg Ser Pro Glu Ala Leu Asp Glu Gln Ile Gly
 50                  55                  60

Arg Leu Arg Asp Tyr Leu Asp Ala Ala Pro Gly Val Asp Leu Ala Ala
 65                  70                  75                  80

Val Ala Arg Thr Leu Ala Thr Arg Thr His Phe Ser His Arg Ala Val
                 85                  90                  95

Leu Leu Gly Asp Thr Val Ile Thr Ala Pro Val Glu Gln Pro Gly
            100                 105                 110

Glu Leu Val Phe Val Tyr Ser Gly Gln Gly Thr Gln His Pro Ala Met
            115                 120                 125

Gly Glu Arg Leu Ala Ala Ala Phe Pro Val Phe Ala Asp Pro Asp Val
            130                 135                 140

Pro Ala Tyr Ala Phe Gln Arg Arg Pro Tyr Trp Ile Glu Ser Ala Pro
145                 150                 155                 160
```

<210> SEQ ID NO 70
<211> LENGTH: 60
<212> TYPE: DNA
<213> ORGANISM: Artificial Sequence
<220> FEATURE:
<223> OTHER INFORMATION: primer

<400> SEQUENCE: 70
gacccggacg tacccgccta cgccttccag cggcggccct actggatcga gtccgcgccg   60

<210> SEQ ID NO 71
<211> LENGTH: 20
<212> TYPE: PRT
<213> ORGANISM: Artificial Sequence
<220> FEATURE:
<223> OTHER INFORMATION: primer

<400> SEQUENCE: 71

```
Asp Pro Asp Val Pro Ala Tyr Ala Phe Gln Arg Arg Pro Tyr Trp Ile
 1               5                  10                  15

Glu Ser Ala Pro
            20
```

<210> SEQ ID NO 72
<211> LENGTH: 6396
<212> TYPE: PRT
<213> ORGANISM: Streptomyces hygroscopicus

<400> SEQUENCE: 72

```
Met Pro Glu Gln Asp Lys Thr Val Glu Tyr Leu Arg Trp Ala Thr Ala
 1               5                  10                  15

Glu Leu Gln Lys Thr Arg Ala Glu Leu Ala Ala His Ser Glu Pro Leu
                20                  25                  30

Ala Ile Val Gly Met Ala Cys Arg Leu Pro Gly Gly Val Ala Ser Pro
            35                  40                  45

Glu Asp Leu Trp Gln Leu Leu Glu Ser Gly Gly Asp Gly Ile Thr Ala
 50                  55                  60

Phe Pro Thr Asp Arg Gly Trp Glu Thr Thr Ala Asp Gly Arg Gly Gly
 65                  70                  75                  80

Phe Leu Thr Gly Ala Ala Gly Phe Asp Ala Ala Phe Phe Gly Ile Ser
                 85                  90                  95
```

-continued

```
Pro Arg Glu Ala Leu Ala Met Asp Pro Gln Gln Arg Leu Ala Leu Glu
            100                 105                 110

Thr Ser Trp Glu Ala Phe Glu His Ala Gly Ile Asp Pro Gln Thr Leu
        115                 120                 125

Arg Gly Ser Asp Thr Gly Val Phe Leu Gly Ala Phe Phe Gln Gly Tyr
    130                 135                 140

Gly Ile Gly Ala Asp Phe Asp Gly Tyr Gly Thr Thr Ser Ile His Thr
145                 150                 155                 160

Ser Val Leu Ser Gly Arg Leu Ala Tyr Phe Tyr Gly Leu Glu Gly Pro
                165                 170                 175

Ala Val Thr Val Asp Thr Ala Cys Ser Ser Leu Val Ala Leu His
                180                 185                 190

Gln Ala Gly Gln Ser Leu Arg Ser Gly Glu Cys Ser Leu Ala Leu Val
            195                 200                 205

Gly Gly Val Thr Val Met Ala Ser Pro Ala Gly Phe Ala Asp Phe Ser
        210                 215                 220

Glu Gln Gly Gly Leu Ala Pro Asp Ala Arg Cys Lys Ala Phe Ala Glu
225                 230                 235                 240

Ala Ala Asp Gly Thr Gly Phe Ala Glu Gly Ser Gly Val Leu Ile Val
                245                 250                 255

Glu Lys Leu Ser Asp Ala Glu Arg Asn Gly His Arg Val Leu Ala Val
                260                 265                 270

Val Arg Gly Ser Ala Val Asn Gln Asp Gly Ala Ser Asn Gly Leu Ser
            275                 280                 285

Ala Pro Asn Gly Pro Ser Gln Glu Arg Val Ile Arg Gln Ala Leu Ala
        290                 295                 300

Asn Ala Gly Leu Thr Pro Ala Asp Val Asp Ala Val Glu Ala His Gly
305                 310                 315                 320

Thr Gly Thr Arg Leu Gly Asp Pro Ile Glu Ala Gln Ala Val Leu Ala
                325                 330                 335

Thr Tyr Gly Gln Gly Arg Asp Thr Pro Val Leu Leu Gly Ser Leu Lys
                340                 345                 350

Ser Asn Ile Gly His Thr Gln Ala Ala Ala Gly Val Ala Gly Val Ile
            355                 360                 365

Lys Met Val Leu Ala Met Arg His Gly Thr Leu Pro Arg Thr Leu His
        370                 375                 380

Val Asp Thr Pro Ser Ser His Val Asp Trp Thr Ala Gly Ala Val Glu
385                 390                 395                 400

Leu Leu Thr Asp Ala Arg Pro Trp Pro Glu Thr Asp Arg Pro Arg Arg
                405                 410                 415

Ala Gly Val Ser Ser Phe Gly Val Ser Gly Thr Asn Ala His Ile Ile
            420                 425                 430

Leu Glu Ser His Pro Arg Pro Ala Pro Glu Pro Ala Pro Ala Pro Asp
        435                 440                 445

Thr Gly Pro Leu Pro Leu Leu Leu Ser Ala Arg Thr Pro Gln Ala Leu
    450                 455                 460

Asp Ala Gln Val His Arg Leu Arg Ala Phe Leu Asp Asp Asn Pro Gly
465                 470                 475                 480

Ala Asp Arg Val Ala Val Ala Gln Thr Leu Ala Arg Arg Thr Gln Phe
                485                 490                 495

Glu His Arg Ala Val Leu Leu Gly Asp Thr Leu Ile Thr Val Ser Pro
            500                 505                 510

Asn Ala Gly Arg Gly Pro Val Val Phe Val Tyr Ser Gly Gln Ser Thr
```

-continued

```
             515                 520                 525
Leu His Pro His Thr Gly Arg Gln Leu Ala Ser Thr Tyr Pro Val Phe
        530                 535                 540
Ala Glu Ala Trp Arg Glu Ala Leu Asp His Leu Asp Pro Thr Gln Gly
545                 550                 555                 560
Pro Ala Thr His Phe Ala His Gln Thr Ala Leu Thr Ala Leu Leu Arg
                565                 570                 575
Ser Trp Gly Ile Thr Pro His Ala Val Ile Gly His Ser Leu Gly Glu
            580                 585                 590
Ile Thr Ala Ala His Ala Ala Gly Val Leu Ser Leu Arg Asp Ala Gly
                595                 600                 605
Ala Leu Leu Thr Thr Arg Thr Arg Leu Met Asp Gln Leu Pro Ser Gly
        610                 615                 620
Gly Ala Met Val Thr Val Leu Thr Ser Glu Glu Lys Ala Arg Gln Val
625                 630                 635                 640
Leu Arg Pro Gly Val Glu Ile Ala Ala Val Asn Gly Pro His Ser Leu
                645                 650                 655
Val Leu Ser Gly Asp Glu Glu Ala Val Leu Glu Ala Ala Arg Gln Leu
            660                 665                 670
Gly Ile His His Arg Leu Pro Thr Arg His Ala Gly His Ser Glu Arg
        675                 680                 685
Met Gln Pro Leu Val Ala Pro Leu Leu Asp Val Ala Arg Thr Leu Thr
    690                 695                 700
Tyr His Gln Pro His Thr Ala Ile Pro Gly Asp Pro Thr Thr Ala Glu
705                 710                 715                 720
Tyr Trp Ala His Gln Val Arg Asp Gln Val Arg Phe Gln Ala His Thr
                725                 730                 735
Glu Gln Tyr Pro Gly Ala Thr Phe Leu Glu Ile Gly Pro Asn Gln Asp
            740                 745                 750
Leu Ser Pro Leu Val Asp Gly Val Ala Ala Gln Thr Gly Thr Pro Asp
        755                 760                 765
Glu Val Arg Ala Leu His Thr Ala Leu Ala Gln Leu His Val Arg Gly
    770                 775                 780
Val Ala Ile Asp Trp Thr Leu Val Leu Gly Gly Asp Arg Ala Pro Val
785                 790                 795                 800
Thr Leu Pro Thr Tyr Pro Phe Gln His Lys Asp Tyr Trp Leu Arg Pro
                805                 810                 815
Thr Ser Arg Ala Asp Val Thr Gly Ala Gly Gln Glu Gln Val Ala His
            820                 825                 830
Pro Leu Leu Gly Ala Ala Val Ala Leu Pro Gly Thr Gly Gly Val Val
        835                 840                 845
Leu Thr Gly Arg Leu Ser Leu Ala Ser His Pro Trp Leu Gly Glu His
    850                 855                 860
Ala Val Asp Gly Thr Val Leu Leu Pro Gly Ala Ala Phe Leu Glu Leu
865                 870                 875                 880
Ala Ala Arg Ala Gly Asp Glu Val Gly Cys Asp Leu Leu His Glu Leu
                885                 890                 895
Val Ile Glu Thr Pro Leu Val Leu Pro Ala Thr Gly Gly Val Ala Val
            900                 905                 910
Ser Val Glu Ile Ala Glu Pro Asp Asp Thr Gly Arg Arg Ala Val Thr
        915                 920                 925
Val His Ala Arg Ala Asp Gly Ser Gly Leu Trp Thr Arg His Ala Gly
    930                 935                 940
```

-continued

```
Gly Phe Leu Gly Thr Ala Pro Ala Pro Ala Thr Ala Thr Asp Pro Ala
945                 950                 955                 960

Pro Trp Pro Pro Ala Glu Ala Gly Pro Val Asp Val Ala Asp Val Tyr
                965                 970                 975

Asp Arg Phe Glu Asp Ile Gly Tyr Ser Tyr Gly Pro Gly Phe Arg Gly
            980                 985                 990

Leu Arg Ala Ala Trp Arg Ala Gly Asp Thr Val Tyr Ala Glu Val Ala
        995                 1000                1005

Leu Pro Asp Glu Gln Ser Ala Asp Ala Ala Arg Phe Thr Leu His
    1010                1015                1020

Pro Ala Leu Leu Asp Ala Ala Phe Gln Ala Gly Ala Leu Ala Ala
    1025                1030                1035

Leu Asp Ala Pro Gly Gly Ala Ala Arg Leu Pro Phe Ser Phe Gln
    1040                1045                1050

Asp Val Arg Ile His Ala Ala Gly Ala Thr Arg Leu Arg Val Thr
    1055                1060                1065

Val Gly Arg Asp Gly Glu Arg Ser Thr Val Arg Met Thr Gly Pro
    1070                1075                1080

Asp Gly Gln Leu Val Ala Val Val Gly Ala Val Leu Ser Arg Pro
    1085                1090                1095

Tyr Ala Glu Gly Ser Gly Asp Gly Leu Leu Arg Pro Val Trp Thr
    1100                1105                1110

Glu Leu Pro Met Pro Val Pro Ser Ala Asp Asp Pro Arg Val Glu
    1115                1120                1125

Val Leu Gly Ala Asp Pro Gly Asp Gly Asp Val Pro Ala Ala Thr
    1130                1135                1140

Arg Glu Leu Thr Ala Arg Val Leu Gly Ala Leu Gln Arg His Leu
    1145                1150                1155

Ser Ala Ala Glu Asp Thr Thr Leu Val Val Arg Thr Gly Thr Gly
    1160                1165                1170

Pro Ala Ala Ala Ala Ala Gly Leu Val Arg Ser Ala Gln Ala
    1175                1180                1185

Glu Asn Pro Gly Arg Val Val Leu Val Glu Ala Ser Pro Asp Thr
    1190                1195                1200

Ser Val Glu Leu Leu Ala Ala Cys Ala Ala Leu Asp Glu Pro Gln
    1205                1210                1215

Leu Ala Val Arg Asp Gly Val Leu Phe Ala Pro Arg Leu Val Arg
    1220                1225                1230

Met Ser Asp Pro Ala His Gly Pro Leu Ser Leu Pro Asp Gly Asp
    1235                1240                1245

Trp Leu Leu Thr Arg Ser Ala Ser Gly Thr Leu His Asp Val Ala
    1250                1255                1260

Leu Ile Ala Asp Asp Thr Pro Arg Arg Ala Leu Glu Ala Gly Glu
    1265                1270                1275

Val Arg Ile Asp Val Arg Ala Ala Gly Leu Asn Phe Arg Asp Val
    1280                1285                1290

Leu Ile Ala Leu Gly Thr Tyr Thr Gly Ala Thr Ala Met Gly Gly
    1295                1300                1305

Glu Ala Ala Gly Val Val Val Glu Thr Gly Pro Gly Val Asp Asp
    1310                1315                1320

Leu Ser Pro Gly Asp Arg Val Phe Gly Leu Thr Arg Gly Gly Ile
    1325                1330                1335
```

-continued

```
Gly Pro Thr Ala Val Thr Asp Arg Arg Trp Leu Ala Arg Ile Pro
    1340                1345                1350

Asp Gly Trp Ser Phe Thr Thr Ala Ala Ser Val Pro Ile Val Phe
    1355                1360                1365

Ala Thr Ala Trp Tyr Gly Leu Val Asp Leu Gly Thr Leu Arg Ala
    1370                1375                1380

Gly Glu Lys Val Leu Val His Ala Ala Thr Gly Gly Val Gly Met
    1385                1390                1395

Ala Ala Ala Gln Ile Ala Arg His Leu Gly Ala Glu Leu Tyr Ala
    1400                1405                1410

Thr Ala Ser Thr Gly Lys Gln His Val Leu Arg Ala Ala Gly Leu
    1415                1420                1425

Pro Asp Thr His Ile Ala Asp Ser Arg Thr Thr Ala Phe Arg Thr
    1430                1435                1440

Ala Phe Pro Arg Met Asp Val Val Leu Asn Ala Leu Thr Gly Glu
    1445                1450                1455

Phe Ile Asp Ala Ser Leu Asp Leu Leu Asp Ala Asp Gly Arg Phe
    1460                1465                1470

Val Glu Met Gly Arg Thr Glu Leu Arg Asp Pro Ala Ala Ile Val
    1475                1480                1485

Pro Ala Tyr Leu Pro Phe Asp Leu Leu Asp Ala Gly Ala Asp Arg
    1490                1495                1500

Ile Gly Glu Ile Leu Gly Glu Leu Leu Arg Leu Phe Asp Ala Gly
    1505                1510                1515

Ala Leu Glu Pro Leu Pro Val Arg Ala Trp Asp Val Arg Gln Ala
    1520                1525                1530

Arg Asp Ala Leu Gly Trp Met Ser Arg Ala Arg His Ile Gly Lys
    1535                1540                1545

Asn Val Leu Thr Leu Pro Arg Pro Leu Asp Pro Glu Gly Ala Val
    1550                1555                1560

Val Leu Thr Gly Gly Ser Gly Thr Leu Ala Gly Ile Leu Ala Arg
    1565                1570                1575

His Leu Arg Glu Arg His Val Tyr Leu Leu Ser Arg Thr Ala Pro
    1580                1585                1590

Pro Glu Gly Thr Pro Gly Val His Leu Pro Cys Asp Val Gly Asp
    1595                1600                1605

Arg Asp Gln Leu Ala Ala Ala Leu Glu Arg Val Asp Arg Pro Ile
    1610                1615                1620

Thr Ala Val Val His Leu Ala Gly Ala Leu Asp Asp Gly Thr Val
    1625                1630                1635

Ala Ser Leu Thr Pro Glu Arg Phe Asp Thr Val Leu Arg Pro Lys
    1640                1645                1650

Ala Asp Gly Ala Trp Tyr Leu His Glu Leu Thr Lys Glu Gln Asp
    1655                1660                1665

Leu Ala Ala Phe Val Leu Tyr Ser Ser Ala Ala Gly Val Leu Gly
    1670                1675                1680

Asn Ala Gly Gln Gly Asn Tyr Val Ala Ala Asn Ala Phe Leu Asp
    1685                1690                1695

Ala Leu Ala Glu Leu Arg His Gly Ser Gly Leu Pro Ala Leu Ser
    1700                1705                1710

Ile Ala Trp Gly Leu Trp Glu Asp Val Ser Gly Leu Thr Ala Ala
    1715                1720                1725

Leu Gly Glu Ala Asp Arg Asp Arg Met Arg Arg Ser Gly Phe Arg
```

-continued

```
               1730                1735                1740
Ala Ile Thr Ala Gln Gln Gly Met His Leu Tyr Glu Ala Ala Gly
    1745                1750                1755
Arg Thr Gly Ser Pro Val Val Val Ala Ala Leu Asp Asp Ala
    1760                1765                1770
Pro Asp Val Pro Leu Leu Arg Gly Leu Arg Arg Thr Thr Val Arg
    1775                1780                1785
Arg Ala Ala Val Arg Glu Cys Ser Ser Ala Asp Arg Leu Ala Ala
    1790                1795                1800
Leu Thr Gly Asp Glu Leu Ala Glu Ala Leu Leu Thr Leu Val Arg
    1805                1810                1815
Glu Ser Thr Ala Ala Val Leu Gly His Val Gly Gly Glu Asp Ile
    1820                1825                1830
Pro Ala Thr Ala Ala Phe Lys Asp Leu Gly Ile Asp Ser Leu Thr
    1835                1840                1845
Ala Val Gln Leu Arg Asn Ala Leu Thr Glu Ala Thr Gly Val Arg
    1850                1855                1860
Leu Asn Ala Thr Ala Val Phe Asp Phe Pro Thr Pro His Val Leu
    1865                1870                1875
Ala Gly Lys Leu Gly Asp Glu Leu Thr Gly Thr Arg Ala Pro Val
    1880                1885                1890
Val Pro Arg Thr Ala Ala Thr Ala Gly Ala His Asp Glu Pro Leu
    1895                1900                1905
Ala Ile Val Gly Met Ala Cys Arg Leu Pro Gly Gly Val Ala Ser
    1910                1915                1920
Pro Glu Glu Leu Trp His Leu Val Ala Ser Gly Thr Asp Ala Ile
    1925                1930                1935
Thr Glu Phe Pro Thr Asp Arg Gly Trp Asp Val Asp Ala Ile Tyr
    1940                1945                1950
Asp Pro Asp Pro Asp Ala Ile Gly Lys Thr Phe Val Arg His Gly
    1955                1960                1965
Gly Phe Leu Thr Gly Ala Thr Gly Phe Asp Ala Ala Phe Phe Gly
    1970                1975                1980
Ile Ser Pro Arg Glu Ala Leu Ala Met Asp Pro Gln Gln Arg Val
    1985                1990                1995
Leu Leu Glu Thr Ser Trp Glu Ala Phe Glu Ser Ala Gly Ile Thr
    2000                2005                2010
Pro Asp Ser Thr Arg Gly Ser Asp Thr Gly Val Phe Val Gly Ala
    2015                2020                2025
Phe Ser Tyr Gly Tyr Gly Thr Gly Ala Asp Thr Asp Gly Phe Gly
    2030                2035                2040
Ala Thr Gly Ser Gln Thr Ser Val Leu Ser Gly Arg Leu Ser Tyr
    2045                2050                2055
Phe Tyr Gly Leu Glu Gly Pro Ala Val Thr Val Asp Thr Ala Cys
    2060                2065                2070
Ser Ser Ser Leu Val Ala Leu His Gln Ala Gly Gln Ser Leu Arg
    2075                2080                2085
Ser Gly Glu Cys Ser Leu Ala Leu Val Gly Gly Val Thr Val Met
    2090                2095                2100
Ala Ser Pro Gly Gly Phe Val Glu Phe Ser Arg Gln Arg Gly Leu
    2105                2110                2115
Ala Pro Asp Gly Arg Ala Lys Ala Phe Gly Ala Gly Ala Asp Gly
    2120                2125                2130
```

-continued

```
Thr Ser Phe Ala Glu Gly Ala Gly Val Leu Ile Val Glu Arg Leu
    2135            2140                2145

Ser Asp Ala Glu Arg Asn Gly His Thr Val Leu Ala Val Val Arg
    2150            2155                2160

Gly Ser Ala Val Asn Gln Asp Gly Ala Ser Asn Gly Leu Ser Ala
    2165            2170                2175

Pro Asn Gly Pro Ser Gln Glu Arg Val Ile Arg Gln Ala Leu Ala
    2180            2185                2190

Asn Ala Gly Leu Thr Pro Ala Asp Val Asp Ala Val Glu Ala His
    2195            2200                2205

Gly Thr Gly Thr Arg Leu Gly Asp Pro Ile Glu Ala Gln Ala Val
    2210            2215                2220

Leu Ala Thr Tyr Gly Gln Glu Arg Ala Thr Pro Leu Leu Leu Gly
    2225            2230                2235

Ser Leu Lys Ser Asn Ile Gly His Ala Gln Ala Ala Ser Gly Val
    2240            2245                2250

Ala Gly Ile Ile Lys Met Val Gln Ala Leu Arg His Gly Glu Leu
    2255            2260                2265

Pro Pro Thr Leu His Ala Asp Glu Pro Ser Pro His Val Asp Trp
    2270            2275                2280

Thr Ala Gly Ala Val Glu Leu Leu Thr Ser Ala Arg Pro Trp Pro
    2285            2290                2295

Glu Thr Asp Arg Pro Arg Arg Ala Ala Val Ser Ser Phe Gly Val
    2300            2305                2310

Ser Gly Thr Asn Ala His Val Ile Leu Glu Ala Gly Pro Val Thr
    2315            2320                2325

Glu Thr Pro Ala Ala Ser Pro Ser Gly Asp Leu Pro Leu Leu Val
    2330            2335                2340

Ser Ala Arg Ser Pro Glu Ala Leu Asp Glu Gln Ile Arg Arg Leu
    2345            2350                2355

Arg Ala Tyr Leu Asp Thr Thr Pro Asp Val Asp Arg Val Ala Val
    2360            2365                2370

Ala Gln Thr Leu Ala Arg Arg Thr His Phe Ala His Arg Ala Val
    2375            2380                2385

Leu Leu Gly Asp Thr Val Ile Thr Thr Pro Pro Ala Asp Arg Pro
    2390            2395                2400

Asp Glu Leu Val Phe Val Tyr Ser Gly Gln Gly Thr Gln His Pro
    2405            2410                2415

Ala Met Gly Glu Gln Leu Ala Ala Ala His Pro Val Phe Ala Asp
    2420            2425                2430

Ala Trp His Glu Ala Leu Arg Arg Leu Asp Asn Pro Asp Pro His
    2435            2440                2445

Asp Pro Thr His Ser Gln His Val Leu Phe Ala His Gln Ala Ala
    2450            2455                2460

Phe Thr Ala Leu Leu Arg Ser Trp Gly Ile Thr Pro His Ala Val
    2465            2470                2475

Ile Gly His Ser Leu Gly Glu Ile Thr Ala Ala His Ala Ala Gly
    2480            2485                2490

Ile Leu Ser Leu Asp Asp Ala Cys Thr Leu Ile Thr Thr Arg Ala
    2495            2500                2505

Arg Leu Met His Thr Leu Pro Pro Pro Gly Ala Met Val Thr Val
    2510            2515                2520
```

-continued

```
Leu Thr Ser Glu Glu Lys Ala Arg Gln Ala Leu Arg Pro Gly Val
2525                2530                2535

Glu Ile Ala Ala Val Asn Gly Pro His Ser Ile Val Leu Ser Gly
2540                2545                2550

Asp Glu Asp Ala Val Leu Thr Val Ala Gly Gln Leu Gly Ile His
2555                2560                2565

His Arg Leu Pro Ala Pro His Ala Gly His Ser Ala His Met Glu
2570                2575                2580

Pro Val Ala Ala Glu Leu Leu Ala Thr Thr Arg Gly Leu Arg Tyr
2585                2590                2595

His Pro Pro His Thr Ser Ile Pro Asn Asp Pro Thr Thr Ala Glu
2600                2605                2610

Tyr Trp Ala Glu Gln Val Arg Lys Pro Val Leu Phe His Ala His
2615                2620                2625

Ala Gln Gln Tyr Pro Asp Ala Val Phe Val Glu Ile Gly Pro Ala
2630                2635                2640

Gln Asp Leu Ser Pro Leu Val Asp Gly Ile Pro Leu Gln Asn Gly
2645                2650                2655

Thr Ala Asp Glu Val His Ala Leu His Thr Ala Leu Ala His Leu
2660                2665                2670

Tyr Ala Arg Gly Ala Thr Leu Asp Trp Pro Arg Ile Leu Gly Ala
2675                2680                2685

Gly Ser Arg His Asp Ala Asp Val Pro Ala Tyr Ala Phe Gln Arg
2690                2695                2700

Arg His Tyr Trp Ile Glu Ser Ala Arg Pro Ala Ala Ser Asp Ala
2705                2710                2715

Gly His Pro Val Leu Gly Ser Gly Ile Ala Leu Ala Gly Ser Pro
2720                2725                2730

Gly Arg Val Phe Thr Gly Ser Val Pro Thr Gly Ala Asp Arg Ala
2735                2740                2745

Val Phe Val Ala Glu Leu Ala Leu Ala Ala Ala Asp Ala Val Asp
2750                2755                2760

Cys Ala Thr Val Glu Arg Leu Asp Ile Ala Ser Val Pro Gly Arg
2765                2770                2775

Pro Gly His Gly Arg Thr Thr Val Gln Thr Trp Val Asp Glu Pro
2780                2785                2790

Ala Asp Asp Gly Arg Arg Arg Phe Thr Val His Thr Arg Thr Gly
2795                2800                2805

Asp Ala Pro Trp Thr Leu His Ala Glu Gly Val Leu Arg Pro His
2810                2815                2820

Gly Thr Ala Leu Pro Asp Ala Ala Asp Ala Glu Trp Pro Pro Pro
2825                2830                2835

Gly Ala Val Pro Ala Asp Gly Leu Pro Gly Val Trp Arg Arg Gly
2840                2845                2850

Asp Gln Val Phe Ala Glu Ala Glu Val Asp Gly Pro Asp Gly Phe
2855                2860                2865

Val Val His Pro Asp Leu Leu Asp Ala Val Phe Ser Ala Val Gly
2870                2875                2880

Asp Gly Ser Arg Gln Pro Ala Gly Trp Arg Asp Leu Thr Val His
2885                2890                2895

Ala Ser Asp Ala Thr Val Leu Arg Ala Cys Leu Thr Arg Arg Thr
2900                2905                2910

Asp Gly Ala Met Gly Phe Ala Ala Phe Asp Gly Ala Gly Leu Pro
```

-continued

```
              2915                2920                2925
     Val Leu Thr Ala Glu Ala Val Thr Leu Arg Glu Val Ala Ser Pro
              2930                2935                2940
     Ser Gly Ser Glu Glu Ser Asp Gly Leu His Arg Leu Glu Trp Leu
              2945                2950                2955
     Ala Val Ala Glu Ala Val Tyr Asp Gly Asp Leu Pro Glu Gly His
              2960                2965                2970
     Val Leu Ile Thr Ala Ala His Pro Asp Asp Pro Glu Asp Ile Pro
              2975                2980                2985
     Thr Arg Ala His Thr Arg Ala Thr Arg Val Leu Thr Ala Leu Gln
              2990                2995                3000
     His His Leu Thr Thr Thr Asp His Thr Leu Ile Val His Thr Thr
              3005                3010                3015
     Thr Asp Pro Ala Gly Ala Thr Val Thr Gly Leu Thr Arg Thr Ala
              3020                3025                3030
     Gln Asn Glu His Pro His Arg Ile Arg Leu Ile Glu Thr Asp His
              3035                3040                3045
     Pro His Thr Pro Leu Pro Leu Ala Gln Leu Ala Thr Leu Asp His
              3050                3055                3060
     Pro His Leu Arg Leu Thr His His Thr Leu His His Pro His Leu
              3065                3070                3075
     Thr Pro Leu His Thr Thr Thr Pro Pro Thr Thr Thr Pro Leu Asn
              3080                3085                3090
     Pro Glu His Ala Ile Ile Ile Thr Gly Gly Ser Gly Thr Leu Ala
              3095                3100                3105
     Gly Ile Leu Ala Arg His Leu Asn His Pro His Thr Tyr Leu Leu
              3110                3115                3120
     Ser Arg Thr Pro Pro Pro Asp Ala Thr Pro Gly Thr His Leu Pro
              3125                3130                3135
     Cys Asp Val Gly Asp Pro His Gln Leu Ala Thr Thr Leu Thr His
              3140                3145                3150
     Ile Pro Gln Pro Leu Thr Ala Ile Phe His Thr Ala Ala Thr Leu
              3155                3160                3165
     Asp Asp Gly Ile Leu His Ala Leu Thr Pro Asp Arg Leu Thr Thr
              3170                3175                3180
     Val Leu His Pro Lys Ala Asn Ala Ala Trp His Leu His His Leu
              3185                3190                3195
     Thr Gln Asn Gln Pro Leu Thr His Phe Val Leu Tyr Ser Ser Ala
              3200                3205                3210
     Ala Ala Val Leu Gly Ser Pro Gly Gln Gly Asn Tyr Ala Ala Ala
              3215                3220                3225
     Asn Ala Phe Leu Asp Ala Leu Ala Thr His Arg His Thr Leu Gly
              3230                3235                3240
     Gln Pro Ala Thr Ser Ile Ala Trp Gly Met Trp His Thr Thr Ser
              3245                3250                3255
     Thr Leu Thr Gly Gln Leu Asp Asp Ala Asp Arg Asp Arg Ile Arg
              3260                3265                3270
     Arg Gly Gly Phe Leu Pro Ile Thr Asp Asp Glu Gly Met Arg Leu
              3275                3280                3285
     Tyr Glu Ala Ala Val Gly Ser Gly Glu Asp Phe Val Met Ala Ala
              3290                3295                3300
     Ala Met Asp Pro Ala Gln Pro Met Thr Gly Ser Val Pro Pro Ile
              3305                3310                3315
```

```
Leu Ser Gly Leu Arg Arg Ser Ala Arg Arg Val Ala Arg Ala Gly
    3320            3325                3330

Gln Thr Phe Ala Gln Arg Leu Ala Glu Leu Pro Asp Ala Asp Arg
    3335            3340                3345

Gly Ala Ala Leu Thr Thr Leu Val Ser Asp Ala Thr Ala Ala Val
    3350            3355                3360

Leu Gly His Ala Asp Ala Ser Glu Ile Ala Pro Thr Thr Thr Phe
    3365            3370                3375

Lys Asp Leu Gly Ile Asp Ser Leu Thr Ala Ile Glu Leu Arg Asn
    3380            3385                3390

Arg Leu Ala Glu Ala Thr Gly Leu Arg Leu Ser Ala Thr Leu Val
    3395            3400                3405

Phe Asp His Pro Thr Pro Arg Val Leu Ala Ala Lys Leu Arg Thr
    3410            3415                3420

Asp Leu Phe Gly Thr Ala Val Pro Thr Pro Ala Arg Thr Ala Arg
    3425            3430                3435

Thr His His Asp Glu Pro Leu Ala Ile Val Gly Met Ala Cys Arg
    3440            3445                3450

Leu Pro Gly Gly Val Ala Ser Pro Glu Asp Leu Trp Gln Leu Val
    3455            3460                3465

Ala Ser Gly Thr Asp Ala Ile Thr Glu Phe Pro Thr Asp Arg Gly
    3470            3475                3480

Trp Asp Ile Asp Arg Leu Phe Asp Pro Asp Pro Asp Ala Pro Gly
    3485            3490                3495

Lys Thr Tyr Val Arg His Gly Gly Phe Leu Ala Glu Ala Ala Gly
    3500            3505                3510

Phe Asp Ala Ala Phe Phe Gly Ile Ser Pro Arg Glu Ala Arg Ala
    3515            3520                3525

Met Asp Pro Gln Gln Arg Val Ile Leu Glu Thr Ser Trp Glu Ala
    3530            3535                3540

Phe Glu Asn Ala Gly Ile Val Pro Asp Thr Leu Arg Gly Ser Asp
    3545            3550                3555

Thr Gly Val Phe Met Gly Ala Phe Ser His Gly Tyr Gly Ala Gly
    3560            3565                3570

Val Asp Leu Gly Gly Phe Gly Ala Thr Ala Thr Gln Asn Ser Val
    3575            3580                3585

Leu Ser Gly Arg Leu Ser Tyr Phe Phe Gly Met Glu Gly Pro Ala
    3590            3595                3600

Val Thr Val Asp Thr Ala Cys Ser Ser Ser Leu Val Ala Leu His
    3605            3610                3615

Gln Ala Ala Gln Ala Leu Arg Thr Gly Glu Cys Ser Leu Ala Leu
    3620            3625                3630

Ala Gly Gly Val Thr Val Met Pro Thr Pro Leu Gly Tyr Val Glu
    3635            3640                3645

Phe Cys Arg Gln Arg Gly Leu Ala Pro Asp Gly Arg Cys Gln Ala
    3650            3655                3660

Phe Ala Glu Gly Ala Asp Gly Thr Ser Phe Ser Glu Gly Ala Gly
    3665            3670                3675

Val Leu Val Leu Glu Arg Leu Ser Asp Ala Glu Arg Asn Gly His
    3680            3685                3690

Thr Val Leu Ala Val Val Arg Ser Ser Ala Val Asn Gln Asp Gly
    3695            3700                3705
```

-continued

```
Ala Ser Asn Gly Ile Ser Ala Pro Asn Gly Pro Ser Gln Gln Arg
    3710                3715                3720

Val Ile Arg Gln Ala Leu Asp Lys Ala Gly Leu Ala Pro Ala Asp
    3725                3730                3735

Val Asp Val Val Glu Ala His Gly Thr Gly Thr Pro Leu Gly Asp
    3740                3745                3750

Pro Ile Glu Ala Gln Ala Ile Ile Ala Thr Tyr Gly Gln Asp Arg
    3755                3760                3765

Asp Thr Pro Leu Tyr Leu Gly Ser Val Lys Ser Asn Ile Gly His
    3770                3775                3780

Thr Gln Thr Thr Ala Gly Val Ala Gly Val Ile Lys Met Val Met
    3785                3790                3795

Ala Met Arg His Gly Ile Ala Pro Lys Thr Leu His Val Asp Glu
    3800                3805                3810

Pro Ser Ser His Val Asp Trp Thr Glu Gly Ala Val Glu Leu Leu
    3815                3820                3825

Thr Glu Ala Arg Pro Trp Pro Asp Ala Gly Arg Pro Arg Arg Ala
    3830                3835                3840

Gly Val Ser Ser Leu Gly Ile Ser Gly Thr Asn Ala His Val Ile
    3845                3850                3855

Leu Glu Gly Val Pro Gly Pro Ser Arg Val Glu Pro Ser Val Asp
    3860                3865                3870

Gly Leu Val Pro Leu Pro Val Ser Ala Arg Ser Glu Ala Ser Leu
    3875                3880                3885

Arg Gly Gln Val Glu Arg Leu Glu Gly Tyr Leu Arg Gly Ser Val
    3890                3895                3900

Asp Val Ala Ala Val Ala Gln Gly Leu Val Arg Glu Arg Ala Val
    3905                3910                3915

Phe Gly His Arg Ala Val Leu Leu Gly Asp Ala Arg Val Met Gly
    3920                3925                3930

Val Ala Val Asp Gln Pro Arg Thr Val Phe Val Phe Pro Gly Gln
    3935                3940                3945

Gly Ala Gln Trp Val Gly Met Gly Val Glu Leu Met Asp Arg Ser
    3950                3955                3960

Ala Val Phe Ala Ala Arg Met Glu Glu Cys Ala Arg Ala Leu Leu
    3965                3970                3975

Pro His Thr Gly Trp Asp Val Arg Glu Met Leu Ala Arg Pro Asp
    3980                3985                3990

Val Ala Glu Arg Val Glu Val Val Gln Pro Ala Ser Trp Ala Val
    3995                4000                4005

Ala Val Ser Leu Ala Ala Leu Trp Gln Ala His Gly Val Val Pro
    4010                4015                4020

Asp Ala Val Ile Gly His Ser Gln Gly Glu Ile Ala Ala Ala Cys
    4025                4030                4035

Val Ala Gly Ala Leu Ser Leu Glu Asp Ala Ala Arg Val Val Ala
    4040                4045                4050

Leu Arg Ser Gln Val Ile Ala Ala Arg Leu Ala Gly Arg Gly Ala
    4055                4060                4065

Met Ala Ser Val Ala Leu Pro Ala Gly Glu Val Gly Leu Val Glu
    4070                4075                4080

Gly Val Trp Ile Ala Ala Arg Asn Gly Pro Ala Ser Thr Val Val
    4085                4090                4095

Ala Gly Glu Pro Ser Ala Val Glu Asp Val Val Thr Arg Tyr Glu
```

-continued

```
              4100                4105                4110
Thr Glu  Gly Val Arg Val  Arg Ile Ala Val  Asp Tyr Ala Ser
         4115                4120                4125
His Thr  Pro His Val Glu  Ala Ile Glu Asp  Leu Ala Glu Val
         4130                4135                4140
Leu Lys  Gly Val Ala Gly  Lys Ala Ala Ser  Val Ala Trp Trp Ser
         4145                4150                4155
Thr Val  Asp Ser Ala Trp  Val Thr Glu Pro  Val Asp Glu Ser Tyr
         4160                4165                4170
Trp Tyr  Arg Asn Leu Arg  Arg Pro Val Ala  Leu Asp Ala Ala Val
         4175                4180                4185
Ala Glu  Leu Asp Gly Ser  Val Phe Val Glu  Cys Ser Ala His Pro
         4190                4195                4200
Val Leu  Leu Pro Ala Met  Glu Gln Ala His  Thr Val Ala Ser Leu
         4205                4210                4215
Arg Thr  Gly Asp Gly Gly  Trp Glu Arg Trp  Leu Thr Ala Leu Ala
         4220                4225                4230
Gln Ala  Trp Thr Leu Gly  Ala Ala Val Asp  Trp Asp Thr Val Val
         4235                4240                4245
Glu Pro  Val Pro Gly Arg  Leu Leu Asp Leu  Pro Thr Tyr Ala Phe
         4250                4255                4260
Glu Arg  Arg Arg Tyr Trp  Leu Glu Ala Ala  Gly Ala Thr Asp Leu
         4265                4270                4275
Ser Ala  Ala Gly Leu Thr  Gly Ala Ala His  Pro Met Leu Ala Ala
         4280                4285                4290
Ile Thr  Ala Leu Pro Ala  Asp Asp Gly Gly  Val Val Leu Thr Gly
         4295                4300                4305
Arg Ile  Ser Leu Arg Thr  His Pro Trp Leu  Ala Asp His Ala Val
         4310                4315                4320
Arg Gly  Thr Val Leu Leu  Pro Gly Thr Ala  Phe Val Glu Leu Val
         4325                4330                4335
Ile Arg  Ala Gly Asp Glu  Thr Gly Cys Gly  Ile Val Asp Glu Leu
         4340                4345                4350
Val Ile  Glu Ser Pro Leu  Val Pro Ala Thr  Ala Ala Val Asp
         4355                4360                4365
Leu Ser  Val Thr Val Glu  Gly Ala Asp Glu  Ala Gly Arg Arg Arg
         4370                4375                4380
Val Thr  Val His Ala Arg  Thr Glu Gly Thr  Gly Ser Trp Thr Arg
         4385                4390                4395
His Ala  Ser Gly Thr Leu  Thr Pro Asp Thr  Pro Asp Thr Pro Asn
         4400                4405                4410
Ala Ser  Gly Val Val Gly  Ala Glu Pro Phe  Ser Gln Trp Pro Pro
         4415                4420                4425
Ala Thr  Ala Ala Ala Val  Asp Thr Ser Glu  Phe Tyr Leu Arg Leu
         4430                4435                4440
Asp Ala  Leu Gly Tyr Arg  Phe Gly Pro Met  Phe Arg Gly Met Arg
         4445                4450                4455
Ala Ala  Trp Arg Asp Gly  Asp Thr Val Tyr  Ala Glu Val Ala Leu
         4460                4465                4470
Pro Glu  Asp Arg Ala Ala  Asp Ala Asp Gly  Phe Gly Met His Pro
         4475                4480                4485
Ala Leu  Leu Asp Ala Ala  Leu Gln Ser Gly  Ser Leu Leu Met Leu
         4490                4495                4500
```

-continued

```
Glu Ser Asp Gly Glu Gln Ser Val Gln Leu Pro Phe Ser Trp His
    4505                4510                4515

Gly Val Arg Phe His Ala Thr Gly Ala Thr Met Leu Arg Val Ala
    4520                4525                4530

Val Val Pro Gly Pro Asp Gly Leu Arg Leu His Ala Ala Asp Ser
    4535                4540                4545

Gly Asn Arg Pro Val Ala Thr Ile Asp Ala Leu Val Thr Arg Ser
    4550                4555                4560

Pro Glu Ala Asp Leu Ala Pro Ala Asp Pro Met Leu Arg Val Gly
    4565                4570                4575

Trp Ala Pro Val Pro Val Pro Ala Gly Ala Gly Pro Ser Asp Ala
    4580                4585                4590

Asp Val Leu Thr Leu Arg Gly Asp Asp Ala Asp Pro Leu Gly Glu
    4595                4600                4605

Thr Arg Asp Leu Thr Thr Arg Val Leu Asp Ala Leu Leu Arg Ala
    4610                4615                4620

Asp Arg Pro Val Ile Phe Gln Val Thr Gly Gly Leu Ala Ala Lys
    4625                4630                4635

Ala Ala Ala Gly Leu Val Arg Thr Ala Gln Asn Glu Gln Pro Gly
    4640                4645                4650

Arg Phe Phe Leu Val Glu Thr Asp Pro Gly Glu Val Leu Asp Gly
    4655                4660                4665

Ala Lys Arg Asp Ala Ile Ala Ala Leu Gly Glu Pro His Val Arg
    4670                4675                4680

Leu Arg Asp Gly Leu Phe Glu Ala Ala Arg Leu Met Arg Ala Thr
    4685                4690                4695

Pro Ser Leu Thr Leu Pro Asp Thr Gly Ser Trp Gln Leu Arg Pro
    4700                4705                4710

Ser Ala Thr Gly Ser Leu Asp Asp Leu Ala Val Val Pro Thr Asp
    4715                4720                4725

Ala Pro Asp Arg Pro Leu Ala Ala Gly Glu Val Arg Ile Ala Val
    4730                4735                4740

Arg Ala Ala Gly Leu Asn Phe Arg Asp Val Thr Val Ala Leu Gly
    4745                4750                4755

Val Val Ala Asp Ala Arg Pro Leu Gly Ser Glu Ala Ala Gly Val
    4760                4765                4770

Val Leu Glu Thr Gly Pro Gly Val His Asp Leu Ala Pro Gly Asp
    4775                4780                4785

Arg Val Leu Gly Met Leu Ala Gly Ala Phe Gly Pro Val Ala Ile
    4790                4795                4800

Thr Asp Arg Arg Leu Leu Gly Arg Met Pro Asp Gly Trp Thr Phe
    4805                4810                4815

Pro Gln Ala Ala Ser Val Met Thr Ala Phe Ala Thr Ala Trp Tyr
    4820                4825                4830

Gly Leu Val Asp Leu Ala Gly Leu Arg Pro Gly Glu Lys Val Leu
    4835                4840                4845

Ile His Ala Ala Ala Thr Gly Val Gly Ala Ala Ala Val Gln Ile
    4850                4855                4860

Ala Arg His Leu Gly Ala Glu Val Tyr Ala Thr Thr Ser Ala Ala
    4865                4870                4875

Lys Arg His Leu Val Asp Leu Asp Gly Ala His Leu Ala Asp Ser
    4880                4885                4890
```

-continued

```
Arg Ser Thr Ala Phe Ala Asp Ala Phe Pro Val Asp Val Val
    4895              4900              4905

Leu Asn Ser Leu Thr Gly Glu Phe Leu Asp Ala Ser Val Gly Leu
    4910              4915              4920

Leu Ala Ala Gly Gly Arg Phe Ile Glu Met Gly Lys Thr Asp Ile
    4925              4930              4935

Arg His Ala Val Gln Gln Pro Phe Asp Leu Met Asp Ala Gly Pro
    4940              4945              4950

Asp Arg Met Gln Arg Ile Ile Val Glu Leu Leu Gly Leu Phe Ala
    4955              4960              4965

Arg Asp Val Leu His Pro Leu Pro Val His Ala Trp Asp Val Arg
    4970              4975              4980

Gln Ala Arg Glu Ala Phe Gly Trp Met Ser Ser Gly Arg His Thr
    4985              4990              4995

Gly Lys Leu Val Leu Thr Val Pro Arg Pro Leu Asp Pro Glu Gly
    5000              5005              5010

Ala Val Val Ile Thr Gly Gly Ser Gly Thr Leu Ala Gly Ile Leu
    5015              5020              5025

Ala Arg His Leu Gly His Pro His Thr Tyr Leu Leu Ser Arg Thr
    5030              5035              5040

Pro Pro Pro Asp Thr Thr Pro Gly Thr His Leu Pro Cys Asp Val
    5045              5050              5055

Gly Asp Pro His Gln Leu Ala Thr Thr Leu Ala Arg Ile Pro Gln
    5060              5065              5070

Pro Leu Thr Ala Val Phe His Thr Ala Gly Thr Leu Asp Asp Ala
    5075              5080              5085

Leu Leu Asp Asn Leu Thr Pro Asp Arg Val Asp Thr Val Leu Lys
    5090              5095              5100

Pro Lys Ala Asp Ala Ala Trp His Leu His Arg Leu Thr Arg Asp
    5105              5110              5115

Thr Asp Leu Ala Ala Phe Val Val Tyr Ser Ala Val Ala Gly Leu
    5120              5125              5130

Met Gly Ser Pro Gly Gln Gly Asn Tyr Val Ala Ala Asn Ala Phe
    5135              5140              5145

Leu Asp Ala Leu Ala Glu His Arg Arg Ala Gln Gly Leu Pro Ala
    5150              5155              5160

Gln Ser Leu Ala Trp Gly Met Trp Ala Asp Val Ser Ala Leu Thr
    5165              5170              5175

Ala Lys Leu Thr Asp Ala Asp Arg Gln Arg Ile Arg Arg Ser Gly
    5180              5185              5190

Phe Pro Pro Leu Ser Ala Ala Asp Gly Met Arg Leu Phe Asp Ala
    5195              5200              5205

Ala Thr Arg Thr Pro Glu Pro Val Val Val Ala Thr Thr Val Asp
    5210              5215              5220

Leu Thr Gln Leu Asp Gly Ala Val Ala Pro Leu Leu Arg Gly Leu
    5225              5230              5235

Ala Ala His Arg Ala Gly Pro Ala Arg Thr Val Ala Arg Asn Ala
    5240              5245              5250

Gly Glu Glu Pro Leu Ala Val Arg Leu Ala Gly Arg Thr Ala Ala
    5255              5260              5265

Glu Gln Arg Arg Ile Met Gln Glu Val Val Leu Arg His Ala Ala
    5270              5275              5280

Ala Val Leu Ala Tyr Gly Leu Gly Asp Arg Val Ala Ala Asp Arg
```

-continued

```
              5285                5290                5295

Pro Phe Arg Glu Leu Gly Phe Asp Ser Leu Thr Ala Val Asp Leu
    5300                5305                5310

Arg Asn Arg Leu Ala Ala Glu Thr Gly Leu Arg Leu Pro Thr Thr
    5315                5320                5325

Leu Val Phe Ser His Pro Thr Ala Glu Ala Leu Thr Ala His Leu
    5330                5335                5340

Leu Asp Leu Ile Asp Ala Pro Thr Ala Arg Ile Ala Gly Glu Ser
    5345                5350                5355

Leu Pro Ala Val Thr Ala Ala Pro Val Ala Ala Arg Asp Gln
    5360                5365                5370

Asp Glu Pro Ile Ala Ile Val Ala Met Ala Cys Arg Leu Pro Gly
    5375                5380                5385

Gly Val Thr Ser Pro Glu Asp Leu Trp Arg Leu Val Glu Ser Gly
    5390                5395                5400

Thr Asp Ala Ile Thr Thr Pro Pro Asp Asp Arg Gly Trp Asp Val
    5405                5410                5415

Asp Ala Leu Tyr Asp Ala Asp Pro Asp Ala Ala Gly Lys Ala Tyr
    5420                5425                5430

Asn Leu Arg Gly Gly Tyr Leu Ala Gly Ala Ala Glu Phe Asp Ala
    5435                5440                5445

Ala Phe Phe Asp Ile Ser Pro Arg Glu Ala Leu Gly Met Asp Pro
    5450                5455                5460

Gln Gln Arg Leu Leu Leu Glu Thr Ala Trp Glu Ala Ile Glu Arg
    5465                5470                5475

Gly Arg Ile Ser Pro Ala Ser Leu Arg Gly Arg Glu Val Gly Val
    5480                5485                5490

Tyr Val Gly Ala Ala Ala Gln Gly Tyr Gly Leu Gly Ala Glu Asp
    5495                5500                5505

Thr Glu Gly His Ala Ile Thr Gly Gly Ser Thr Ser Leu Leu Ser
    5510                5515                5520

Gly Arg Leu Ala Tyr Val Leu Gly Leu Glu Gly Pro Ala Val Thr
    5525                5530                5535

Val Asp Thr Ala Cys Ser Ser Ser Leu Val Ala Leu His Leu Ala
    5540                5545                5550

Cys Gln Gly Leu Arg Leu Gly Glu Cys Glu Leu Ala Leu Ala Gly
    5555                5560                5565

Gly Val Ser Val Leu Ser Ser Pro Ala Ala Phe Val Glu Phe Ser
    5570                5575                5580

Arg Gln Arg Gly Leu Ala Ala Asp Gly Arg Cys Lys Ser Phe Gly
    5585                5590                5595

Ala Gly Ala Asp Gly Thr Thr Trp Ser Glu Gly Val Gly Val Leu
    5600                5605                5610

Val Leu Glu Arg Leu Ser Asp Ala Glu Arg Leu Gly His Thr Val
    5615                5620                5625

Leu Ala Val Val Arg Gly Ser Ala Val Thr Ser Asp Gly Ala Ser
    5630                5635                5640

Asn Gly Leu Thr Ala Pro Asn Gly Leu Ser Gln Gln Arg Val Ile
    5645                5650                5655

Arg Lys Ala Leu Ala Ala Ala Gly Leu Thr Gly Ala Asp Val Asp
    5660                5665                5670

Val Val Glu Gly His Gly Thr Gly Thr Arg Leu Gly Asp Pro Val
    5675                5680                5685
```

-continued

```
Glu Ala Asp Ala Leu Leu Ala Thr Tyr Gly Gln Asp Arg Pro Ala
5690                5695                5700

Pro Val Trp Leu Gly Ser Leu Lys Ser Asn Ile Gly His Ala Thr
    5705                5710                5715

Ala Ala Ala Gly Val Ala Gly Val Ile Lys Met Val Gln Ala Ile
        5720                5725                5730

Gly Ala Gly Thr Met Pro Arg Thr Leu His Val Glu Glu Pro Ser
            5735                5740                5745

Pro Ala Val Asp Trp Ser Thr Gly Gln Val Ser Leu Leu Gly Ser
    5750                5755                5760

Asn Arg Pro Trp Pro Asp Asp Glu Arg Pro Arg Arg Ala Ala Val
    5765                5770                5775

Ser Ala Phe Gly Leu Ser Gly Thr Asn Ala His Val Ile Leu Glu
    5780                5785                5790

Gln His Arg Pro Ala Pro Val Ala Ser Gln Pro Pro Arg Pro Pro
    5795                5800                5805

Arg Glu Glu Ser Gln Pro Leu Pro Trp Val Leu Ser Ala Arg Thr
    5810                5815                5820

Pro Ala Ala Leu Arg Ala Gln Ala Ala Arg Leu Arg Asp His Leu
    5825                5830                5835

Ala Ala Ala Pro Asp Ala Asp Pro Leu Asp Ile Gly Tyr Ala Leu
    5840                5845                5850

Ala Thr Ser Arg Ala Gln Phe Ala His Arg Ala Ala Val Val Ala
    5855                5860                5865

Thr Thr Pro Asp Gly Phe Arg Ala Ala Leu Asp Gly Leu Ala Asp
    5870                5875                5880

Gly Ala Glu Ala Pro Gly Val Val Thr Gly Thr Ala Gln Glu Arg
    5885                5890                5895

Arg Val Ala Phe Leu Phe Asp Gly Gln Gly Ala Gln Arg Ala Gly
    5900                5905                5910

Met Gly Arg Glu Leu His Arg Arg Phe Pro Val Phe Ala Ala Ala
    5915                5920                5925

Trp Asp Glu Val Ser Asp Ala Phe Gly Lys His Leu Lys His Ser
    5930                5935                5940

Pro Thr Asp Val Tyr His Gly Glu His Gly Ala Leu Ala His Asp
    5945                5950                5955

Thr Leu Tyr Ala Gln Ala Gly Leu Phe Thr Leu Glu Val Ala Leu
    5960                5965                5970

Leu Arg Leu Leu Glu His Trp Gly Val Arg Pro Asp Val Leu Val
    5975                5980                5985

Gly His Ser Val Gly Glu Val Thr Ala Ala Tyr Ala Ala Gly Val
    5990                5995                6000

Leu Thr Leu Ala Asp Ala Thr Glu Leu Ile Val Ala Arg Gly Arg
    6005                6010                6015

Ala Leu Arg Ala Leu Pro Pro Gly Ala Met Leu Ala Val Asp Gly
    6020                6025                6030

Ser Pro Ala Glu Val Gly Ala Arg Thr Asp Leu Asp Ile Ala Ala
    6035                6040                6045

Val Asn Gly Pro Ser Ala Val Val Leu Ala Gly Ser Pro Asp Asp
    6050                6055                6060

Val Ala Ala Phe Glu Arg Glu Trp Ser Ala Ala Gly Arg Arg Thr
    6065                6070                6075
```

```
Lys Arg Leu Asp Val Gly His Ala Phe His Ser Arg His Val Asp
    6080            6085                6090
Gly Ala Leu Asp Gly Phe Arg Thr Val Leu Glu Ser Leu Ala Phe
    6095            6100                6105
Gly Ala Ala Arg Leu Pro Val Val Ser Thr Thr Thr Gly Arg Asp
    6110            6115                6120
Ala Ala Asp Asp Leu Ile Thr Pro Ala His Trp Leu Arg His Ala
    6125            6130                6135
Arg Arg Pro Val Leu Phe Ser Asp Ala Val Arg Glu Leu Ala Asp
    6140            6145                6150
Arg Gly Val Thr Thr Phe Val Ala Val Gly Pro Ser Gly Ser Leu
    6155            6160                6165
Ala Ser Ala Ala Ala Glu Ser Ala Gly Glu Asp Ala Gly Thr Tyr
    6170            6175                6180
His Ala Val Leu Arg Ala Arg Thr Gly Glu Glu Thr Ala Ala Leu
    6185            6190                6195
Thr Ala Leu Ala Glu Leu His Ala His Gly Val Pro Val Asp Leu
    6200            6205                6210
Ala Ala Val Leu Ala Gly Gly Arg Pro Val Asp Leu Pro Val Tyr
    6215            6220                6225
Ala Phe Gln His Arg Ser Tyr Trp Leu Ala Pro Ala Val Ala Gly
    6230            6235                6240
Ala Pro Ala Thr Val Ala Asp Thr Gly Gly Pro Ala Glu Ser Glu
    6245            6250                6255
Pro Glu Asp Leu Thr Val Ala Glu Ile Val Arg Arg Thr Ala
    6260            6265                6270
Ala Leu Leu Gly Val Thr Asp Pro Ala Asp Val Asp Ala Glu Ala
    6275            6280                6285
Thr Phe Phe Ala Leu Gly Phe Asp Ser Leu Ala Val Gln Arg Leu
    6290            6295                6300
Arg Asn Gln Leu Ala Ser Ala Thr Gly Leu Asp Leu Pro Ala Ala
    6305            6310                6315
Val Leu Phe Asp His Asp Thr Pro Ala Ala Leu Thr Ala Phe Leu
    6320            6325                6330
Gln Asp Arg Ile Glu Ala Gly Gln Asp Arg Ile Glu Ala Gly Glu
    6335            6340                6345
Asp Asp Asp Ala Pro Thr Val Leu Ser Leu Leu Glu Glu Met Glu
    6350            6355                6360
Ser Leu Asp Ala Ala Asp Ile Ala Ala Thr Pro Ala Pro Glu Arg
    6365            6370                6375
Ala Ala Ile Ala Asp Leu Leu Asp Lys Leu Ala His Thr Trp Lys
    6380            6385                6390
Asp Tyr Arg
    6395

<210> SEQ ID NO 73
<211> LENGTH: 7525
<212> TYPE: PRT
<213> ORGANISM: Streptomyces hygroscopicus

<400> SEQUENCE: 73

Met Ala Arg Val Glu Pro Ile Arg Pro Leu His Glu Leu Leu Arg Ile
1               5                   10                  15

His Ala Glu Arg Arg Gly Asp Arg Ile Ala Tyr Thr Asp Ser Gln Arg
            20                  25                  30
```

```
Ala Val Thr Tyr Thr Gln Leu Arg Leu Arg Ala Gly Arg Leu Ala Gly
             35                  40                  45

His Leu Ala Ala Ser Gly Val Asp Arg Gly Asp Arg Val Ala Met Leu
         50                  55                  60

Leu Gly Asn Arg Ile Glu Thr Ile Glu Val Tyr Leu Ala Ala Ala Arg
 65                  70                  75                  80

Ala Ala Ala Val Ala Val Pro Leu Asn Pro Asp Ala Ala Asp Ala Glu
                 85                  90                  95

Leu Ala His Phe Leu Thr Asp Ser Gly Ala Thr Val Leu Val Thr Asp
                100                 105                 110

Glu Thr His Leu Asp Gln Val Arg Arg Thr Gly Thr Asp Ala Thr Val
            115                 120                 125

Val Leu Val Gly Arg Arg Ala Pro Asp Cys Val Ser Tyr Glu Asp Leu
        130                 135                 140

Ala Gly Thr Glu Pro Pro Cys Pro Pro Arg Asp Asp Leu Gly Leu Asp
145                 150                 155                 160

Glu Pro Ala Trp Met Leu Tyr Thr Ser Gly Thr Thr Gly Arg Pro Lys
                165                 170                 175

Gly Val Val Ser Ala Gln Arg Ser Gly Leu Trp Ser Ala Met His Cys
                180                 185                 190

Asp Val Pro Ser Trp Arg Leu Thr Glu Asp Glu Leu Leu Trp Pro
            195                 200                 205

Ala Pro Leu Phe His Ser Leu Gly His His Leu Cys Leu Leu Ala Val
        210                 215                 220

Leu Thr Val Gly Ala Ser Ala Arg Ile Leu Gly Gly Phe Val Ala Arg
225                 230                 235                 240

Asp Val Leu Asp Ala Leu Ala Glu His Ser Ser Thr Val Leu Val Gly
                245                 250                 255

Val Pro Thr Met Tyr Arg Tyr Leu Leu Gly Ala Val Ser Gly Glu Pro
                260                 265                 270

Arg Ala Arg Ala Leu Arg Val Ala Leu Val Ala Gly Ser Thr Ser Pro
        275                 280                 285

Ala Ser Leu Thr Arg Asp Phe Glu Ala Thr Phe Gly Val Pro Leu Leu
        290                 295                 300

Asp Thr Tyr Gly Cys Thr Glu Thr Thr Gly Ser Leu Thr Ala Asn Thr
305                 310                 315                 320

Leu Glu Asp Ala Arg Val Pro Gly Ser Cys Gly Leu Pro Val Pro Gly
                325                 330                 335

Leu Ser Leu Arg Phe Val Asp Pro Val Ser Gly Ala Asp Val Ala Pro
                340                 345                 350

Gly Glu Glu Gly Glu Leu Trp Ala Ser Gly Pro Ser Leu Met Leu Gly
            355                 360                 365

Tyr His Ala Gln Pro Glu Ala Thr Ala Gln Val Leu Val Asp Gly Trp
        370                 375                 380

Tyr Arg Thr Gly Asp Leu Ala Arg Gln Ala Glu Thr Gly His Val Thr
385                 390                 395                 400

Ile Thr Gly Arg Val Lys Glu Leu Ile Ile Arg Gly Gly Glu Asn Ile
                405                 410                 415

His Pro Arg Glu Ile Glu Thr Val Ala Gln Glu Val Ala Gly Val Arg
            420                 425                 430

Asp Ala Ala Ala Ala Gly Arg Pro His Pro Val Leu Gly Asp Ile Pro
        435                 440                 445
```

-continued

```
Val Leu Tyr Val Val Ser Asp Gly Pro Arg Val Pro Ala Glu Ala Ile
    450                 455                 460
Leu Ala Glu Cys Arg Arg Arg Leu Ala Tyr Phe Lys Val Pro Asp Glu
465                 470                 475                 480
Ile Trp His Val Thr Thr Ile Pro Arg Thr Ala Ser Gly Lys Val Gln
                485                 490                 495
Arg Ala Arg Leu Ala Gly Leu Pro Ala His Leu Val Ala Thr Gly Ser
            500                 505                 510
Gly Glu Ala Thr Leu Cys Glu Leu Val Trp Glu Arg Arg Asp Leu Pro
        515                 520                 525
Gly Thr Pro Ser Pro Arg Arg Thr Val Val Thr Arg Ala Val Gly
    530                 535                 540
Val Gly Pro Ala Glu Ile Pro Asp Ala Asp Gln Ala Arg Leu Trp Asp
545                 550                 555                 560
Glu Ala Leu Arg Arg Gln Ala Ala Glu Pro Gly Ser Phe Val Leu Val
                565                 570                 575
Asp Thr Asp Gly Asp Asp Asp Leu Val Pro Ala Ala Ala Ser Leu Gly
            580                 585                 590
Glu Pro Gln Ile Ala Leu Arg Ala Gly Val Ala Tyr Val Pro Arg Leu
        595                 600                 605
Val Arg Ala Asp Thr Thr Pro Leu Pro Thr Ala Pro Val Gly Ala Ala
    610                 615                 620
Pro Ala Arg Leu Arg Asn Ala Pro Arg Pro Arg Arg Pro Ala Arg
625                 630                 635                 640
Arg Pro Ala Ala Pro Leu Ala Ala Gly Glu Val Arg Ile Asp Val Arg
                645                 650                 655
Ala Ala Gly Leu Asn Phe Arg Asp Val Leu Ile Ala Leu Gly Thr Tyr
            660                 665                 670
Pro Gly Glu Gly Glu Met Gly Gly Glu Ala Ala Gly Ile Val Thr Glu
        675                 680                 685
Val Gly Pro Gly Val Asp Asp Leu Ala Pro Gly Asp Arg Val Phe Gly
    690                 695                 700
Leu Val Gln Asp Ala Phe Arg Arg Ser Val Val Ala Asp Arg Arg Leu
705                 710                 715                 720
Val Ala Arg Ile Pro Arg Gly Trp Ser Phe Pro Ile Ala Ala Ser Val
                725                 730                 735
Pro Ile Val Phe Ala Thr Ala Trp Tyr Gly Leu Val Asp Ala Gly Glu
            740                 745                 750
Leu Arg Pro Gly Gln Lys Val Leu Val His Ala Ala Thr Gly Gly Val
        755                 760                 765
Gly Met Ala Ala Thr Arg Ile Ala Arg His Leu Gly Ala Glu Val Tyr
    770                 775                 780
Ala Thr Ala Ser Pro Ala Lys Gln His Leu Leu His Ala Asp Gly Phe
785                 790                 795                 800
Asp Thr Asp His Val Ala Asn Ser Arg Ser Ala Ala Phe Ala Asp Thr
                805                 810                 815
Phe Pro Pro Val Asp Val Leu Asn Ser Leu Thr Gly Glu Leu Leu
            820                 825                 830
Asp Ala Ser Ile Gly Leu Leu Ala Pro Gly Gly Arg Phe Val Glu Met
        835                 840                 845
Gly Lys Thr Asp Ile Arg His Ala Ala Gln Gln Pro Phe Asp Leu Ala
    850                 855                 860
Asp Val Asp Pro Ala Arg Leu Arg Glu Ile Leu Glu Leu Leu Leu Asp
```

-continued

```
              865                 870                 875                 880

Leu Phe Asp Arg Gly Glu Leu Cys Pro Leu Pro Val Gln Pro Trp Asp
                885                 890                 895

Ile Arg Arg Ala Arg Asp Ala Phe Ala Trp Met Ser His Ala Arg His
            900                 905                 910

Thr Gly Lys Met Val Leu Thr Val Pro Pro Ile Gly Pro Asp Ala
        915                 920                 925

Pro Val Leu Val Thr Gly Glu Asp Ala Asp Thr Val Ala Gly Leu Leu
    930                 935                 940

Arg Asp Glu Thr Gly Leu Thr His Val Thr Thr Ala Ala Glu Glu Ala
945                 950                 955                 960

Ala Asn Pro Gly Ala Leu Val His Val Leu Leu Asp Gly Pro Ala Gly
                965                 970                 975

Ala Asp Ala His Thr Arg Pro Arg Ala Ala Glu Gly Leu Pro Thr Val
                980                 985                 990

Thr Val Arg Ala Leu Pro Gly Ile Glu Arg Pro Ala Leu Thr Gly Asp
            995                 1000                1005

Leu Ile Glu Lys Ala Ile Ala Gly Gly Gly Ser Tyr Ile Val Ala
    1010                1015                1020

Arg Thr Gly Ser Ala Gly Ala Arg Ala Ala Thr Met Ala Gly Ala
    1025                1030                1035

Thr Pro Pro Ile Leu Thr Ala Leu Thr Gly Pro Ala Glu Pro Asp
    1040                1045                1050

Ala Thr Glu Gln Glu Trp Ala Asn Arg Leu Ala Ala Ala Arg Ala
    1055                1060                1065

Gly Arg Glu Asp Val Leu Leu Asp Leu Val Arg Asp Ser Val Ala
    1070                1075                1080

Thr Val Leu Gly Leu Pro Gly Ala Gly His Cys Ser Pro Asp Arg
    1085                1090                1095

Thr Phe Arg Glu Asn Gly Leu Asp Ser Leu Thr Thr Val Glu Phe
    1100                1105                1110

Thr Asn Thr Val Ala Ala Arg Thr Gly Leu Arg Val Pro Ala Ser
    1115                1120                1125

Thr Ala Phe Asp His Pro Thr Pro Arg Ala Phe Ala Ala His Leu
    1130                1135                1140

Ala Gly Ser Ala Thr Ala Ala Pro Ala Thr Ala Gln Thr Leu Gly
    1145                1150                1155

Ser Gly Asp Pro Val Ala Ile Val Gly Met Ala Cys Arg Leu Pro
    1160                1165                1170

Gly Gly Val Ala Ser Pro Glu Asp Leu Trp Arg Leu Val Ala Ala
    1175                1180                1185

Gly Thr Glu Ala Ile Thr Glu Phe Pro Thr Asp Arg Gly Trp Asp
    1190                1195                1200

Val Asp Ala Leu Tyr Asp Pro Asp Pro Asp Ala Ala Gly Arg Ser
    1205                1210                1215

Thr Thr Arg His Gly Gly Phe Leu Ala Gly Ala Gly Phe Asp Ala
    1220                1225                1230

Ala Phe Phe Gly Ile Ser Pro Asn Glu Ala Leu Ala Met Asp Pro
    1235                1240                1245

Gln Gln Arg Leu Ile Leu Glu Thr Ser Trp Glu Ala Phe Glu Asn
    1250                1255                1260

Ala Gly Ile Val Pro Asp Arg Leu Arg Glu Ser Asp Thr Gly Val
    1265                1270                1275
```

```
Phe Met Gly Ala Phe Asn Gln Gly Tyr Gly Val Gly Arg Asp Leu
    1280            1285            1290

Gly Gly Leu Gly Val Thr Ala Thr Gln Thr Ser Val Leu Ser Gly
    1295            1300            1305

Arg Leu Ser Tyr Val Tyr Gly Leu Gln Gly Pro Ala Val Thr Val
    1310            1315            1320

Asp Thr Ala Cys Ser Ser Ser Leu Val Ala Leu His Gln Ala Ala
    1325            1330            1335

Gln Ala Leu Arg Ala Gly Glu Cys Ser Leu Ala Leu Val Gly Gly
    1340            1345            1350

Val Thr Val Met Ala Asn Thr Ala Glu Leu Val Glu Phe Ser Arg
    1355            1360            1365

Gln Arg Gly Leu Ser Pro Asp Gly Arg Cys Lys Ala Phe Ala Asp
    1370            1375            1380

Ala Ala Asp Gly Thr Gly Phe Ala Glu Gly Val Gly Val Leu Val
    1385            1390            1395

Leu Glu Arg Leu Ser Asp Ala Glu Arg Asn Gly His Thr Val Leu
    1400            1405            1410

Ala Val Val Arg Gly Ser Ala Val Asn Gln Asp Gly Ala Ser Asn
    1415            1420            1425

Gly Leu Ser Ala Pro Asn Gly Val Ala Gln Gln Arg Val Ile Arg
    1430            1435            1440

Gln Ala Leu Val Asn Ala Gly Leu Arg Ala Ala Asp Val Asp Val
    1445            1450            1455

Val Glu Ala His Gly Thr Gly Thr Arg Leu Gly Asp Pro Ile Glu
    1460            1465            1470

Ala Gln Ala Val Leu Ala Ala Tyr Gly Gln Asp Arg Asp Thr Pro
    1475            1480            1485

Leu Tyr Leu Gly Ser Val Lys Ser Asn Ile Gly His Ala Gln Ala
    1490            1495            1500

Ala Ala Gly Val Ala Gly Val Ile Lys Met Val Met Ala Met Arg
    1505            1510            1515

His Gly Ile Ala Pro Lys Thr Leu His Val Asp Glu Pro Ser Ser
    1520            1525            1530

His Val Asp Trp Ser Ala Gly Ala Val Glu Leu Leu Thr Glu Ala
    1535            1540            1545

Arg Pro Trp Pro Glu Ser Asp Arg Ala Pro His Ala Gly Val Ser
    1550            1555            1560

Ser Phe Gly Val Ser Gly Thr Asn Ala His Val Ile Leu Glu Gly
    1565            1570            1575

Val Pro Gly Pro Ser Arg Val Glu Ser Gly Gly Asp Gly Leu Val
    1580            1585            1590

Pro Leu Pro Val Ser Ala Arg Gly Glu Val Ser Leu Arg Gly Gln
    1595            1600            1605

Val Glu Arg Leu Glu Gly Tyr Leu Arg Gly Gly Val Asp Val
    1610            1615            1620

Ala Ala Val Ala Gln Gly Leu Val Arg Glu Arg Ala Val Phe Gly
    1625            1630            1635

His Arg Ala Val Leu Leu Gly Asp Ala Arg Val Met Gly Val Ala
    1640            1645            1650

Val Asp Gln Pro Arg Thr Val Phe Val Phe Pro Gly Gln Gly Ala
    1655            1660            1665
```

-continued

```
Gln Trp Val Gly Met Gly Val Glu Leu Met Asp Arg Ser Ala Val
    1670            1675            1680

Phe Ala Ala Arg Met Glu Glu Cys Ala Arg Ala Leu Leu Pro His
    1685            1690            1695

Thr Gly Trp Asp Val Arg Glu Met Leu Ser Arg Ser Asp Val Ala
    1700            1705            1710

Glu Arg Val Glu Val Val Gln Pro Ala Ser Trp Ala Val Ala Val
    1715            1720            1725

Ser Leu Ala Ala Leu Trp Gln Ala His Gly Val Val Pro Asp Ala
    1730            1735            1740

Val Val Gly His Ser Gln Gly Glu Ile Ala Ala Ala Cys Val Ala
    1745            1750            1755

Gly Ala Leu Ser Leu Glu Asp Ala Ala Arg Val Val Ala Leu Arg
    1760            1765            1770

Ser Arg Val Ile Ala Ala Arg Leu Ala Gly Arg Gly Ala Met Ala
    1775            1780            1785

Ser Val Ala Leu Pro Ala Gly Glu Val Gly Leu Val Glu Gly Val
    1790            1795            1800

Trp Ile Ala Ala Arg Asn Gly Pro Ala Ser Thr Val Val Ala Gly
    1805            1810            1815

Asp Pro Ser Ala Val Glu Glu Val Val Ala Arg Tyr Glu Ala Asp
    1820            1825            1830

Gly Val Arg Val Arg Arg Ile Ala Val Asp Tyr Ala Ser His Thr
    1835            1840            1845

Pro His Val Glu Ala Ile Glu Asp Glu Leu Ala Glu Val Leu Lys
    1850            1855            1860

Gly Ile Ser Gly Gly Thr Gly Ser Val Ala Trp Trp Ser Thr Val
    1865            1870            1875

Asp Ser Ala Trp Val Thr Glu Pro Val Asp Glu Gly Tyr Trp Tyr
    1880            1885            1890

Arg Asn Leu Arg Arg Pro Val Ala Leu Asp Ala Ala Val Ala Glu
    1895            1900            1905

Leu Asp Gly Ser Val Phe Val Glu Cys Ser Ala His Pro Val Leu
    1910            1915            1920

Leu Pro Ala Met Glu Gln Ala Arg Thr Val Ala Ser Leu Arg Thr
    1925            1930            1935

Gly Asp Gly Gly Trp Glu Arg Trp Leu Gly Ala Leu Ala Gln Ala
    1940            1945            1950

Trp Thr Leu Gly Ala Gly Val Asp Trp Gly Thr Val Val Glu Pro
    1955            1960            1965

Val Pro Gly Arg Leu Leu Asp Leu Pro Thr Tyr Ala Phe Glu His
    1970            1975            1980

Arg Arg Tyr Trp Leu Glu Ala Ala Gly Ala Thr Asp Leu Ser Ala
    1985            1990            1995

Ala Gly Leu Thr Gly Ala Ala His Pro Met Leu Ala Ala Val Thr
    2000            2005            2010

Ala Leu Pro Ala Asp Asp Gly Gly Val Val Leu Thr Gly Arg
    2015            2020            2025

Ile Ser Leu Arg Thr His Pro Trp Leu Ala Asp His Ala Val Arg
    2030            2035            2040

Gly Thr Val Leu Leu Pro Gly Thr Ala Phe Val Glu Leu Val Ile
    2045            2050            2055

Arg Ala Gly Asp Glu Thr Gly Cys Gly Val Val Asp Glu Leu Val
```

-continued

```
                2060                2065                2070
    Ile Glu Ser Pro Leu Val Val Pro Val Thr Ala Ala Val Asp Val
        2075                2080                2085
    Ser Val Thr Val Glu Gly Ala Asp Glu Ala Gly Arg Arg Pro Val
        2090                2095                2100
    Thr Val His Ala Arg Thr Glu Gly Thr Gly Ser Trp Thr Arg His
        2105                2110                2115
    Ala Ser Gly Thr Leu Thr Pro Asp Thr Pro Asp Thr Ser Asn Ala
        2120                2125                2130
    Ser Gly Glu Pro Phe Ser Gln Trp Pro Pro Ala Thr Ala Ala Ala
        2135                2140                2145
    Val Asp Val Ser Gly Phe Tyr Asp Glu Leu Arg Asp Ala Gly Tyr
        2150                2155                2160
    Glu Tyr Gly Ser Ala Phe Gln Gly Leu Arg Ala Ala Trp Arg Asp
        2165                2170                2175
    Gly Asp Thr Val Tyr Ala Glu Val Ala Leu Pro Asp Glu Gln Ala
        2180                2185                2190
    Ala Glu Ala Asp Gly Phe Gly Val His Pro Ala Leu Leu Asp Ala
        2195                2200                2205
    Ala Leu His Ala Gly Arg Leu Asp Ala Gly Gly Gly Ile Glu Leu
        2210                2215                2220
    Pro Phe Ser Trp Thr Gly Val Arg Leu Asn Ala Thr Gly Ala Ala
        2225                2230                2235
    Ala Val Arg Val Ala Leu Thr Arg Gly Glu Ala Gly Val Ala Val
        2240                2245                2250
    Arg Val Ala Asp Pro Asp Gly Arg Pro Val Val Ser Val Asp Ser
        2255                2260                2265
    Leu Val Leu Arg Glu Arg Ala Asp Thr Pro Ser Gly Pro Asn Pro
        2270                2275                2280
    Leu Arg Leu Glu Trp Leu Ala Val Ala Glu Ala Val Tyr Asp Gly
        2285                2290                2295
    Asp Leu Pro Glu Gly His Val Leu Ile Thr Ala Ala His Pro Asp
        2300                2305                2310
    Asp Pro Glu Asp Ile Pro Thr Arg Ala His Thr Arg Ala Thr Arg
        2315                2320                2325
    Val Leu Thr Ala Leu Gln His His Leu Thr Thr Thr Asp His Thr
        2330                2335                2340
    Leu Ile Val His Thr Thr Thr Asp Pro Ala Gly Ala Thr Val Thr
        2345                2350                2355
    Gly Leu Thr Arg Thr Ala Gln Asn Glu His Pro His Arg Ile Arg
        2360                2365                2370
    Leu Ile Glu Thr Asp His Pro His Thr Pro Leu Pro Leu Ala Gln
        2375                2380                2385
    Leu Ala Thr Leu Asp His Pro His Leu Arg Leu Thr His His Thr
        2390                2395                2400
    Leu His Arg Pro His Leu Thr Pro Leu His Thr Thr Thr Pro Pro
        2405                2410                2415
    Thr Thr Thr Pro Leu Asn Pro Glu His Ala Ile Ile Ile Thr Gly
        2420                2425                2430
    Gly Ser Gly Thr Leu Ala Gly Ile Leu Ala Arg His Leu Asn His
        2435                2440                2445
    Pro His Thr Tyr Leu Leu Ser Arg Thr Pro Pro Asp Thr Thr
        2450                2455                2460
```

-continued

```
Pro Gly Thr His Leu Pro Cys Asp Val Gly Asp Pro His Gln Leu
2465                2470                2475
Ala Thr Thr Leu Ala His Ile Pro Gln Pro Leu Thr Ala Val Phe
2480                2485                2490
His Thr Ala Ala Thr Leu Asp Asp Gly Ile Leu Asp Ala Leu Thr
2495                2500                2505
Pro Asp Arg Leu Thr Thr Val Leu His Pro Lys Ala Asn Ala Ala
2510                2515                2520
Trp His Leu His His Leu Thr Gln Asn Gln Pro Leu Thr His Phe
2525                2530                2535
Val Leu Tyr Ser Ser Ala Ala Val Leu Gly Ser Pro Gly Gln
2540                2545                2550
Gly Asn Tyr Ala Ala Ala Asn Ala Phe Leu Asp Ala Leu Ala Thr
2555                2560                2565
His Arg His Thr Leu Gly Gln Pro Ala Thr Ser Ile Ala Trp Gly
2570                2575                2580
Met Trp His Thr Thr Ser Thr Leu Thr Gly Gln Leu Asp Asp Ala
2585                2590                2595
Asp Arg Gln Arg Val Arg Asp Gly Phe Arg Pro Leu Thr Glu Ala
2600                2605                2610
Glu Gly Thr His Phe Ile Asp Ala Ser Leu Ala Ala Asp Val Pro
2615                2620                2625
Phe Met Val Ala Ala Ile Pro Thr Glu Pro Val Arg Gln Arg Thr
2630                2635                2640
Glu Arg Arg Ile Ala Ala Arg Ala Glu Asp Asn Arg Asp Arg Asp
2645                2650                2655
Arg Asp Arg Asp Arg Asp Leu Leu Ala Ile Val Cys Ala Ala Thr
2660                2665                2670
Ala Ala Val Leu Gly His Ala Asp Ala Ser Glu Ile Thr Pro Thr
2675                2680                2685
Thr Ala Phe Lys Asp Leu Gly Ile Asp Ser Leu Ser Gly Val Arg
2690                2695                2700
Leu Arg Asn Ser Leu Ala Glu Thr Thr Gly Val Arg Leu Ser Ala
2705                2710                2715
Thr Ala Val Phe Asp His Pro Thr Pro Ala Ala Leu Ala Ala Arg
2720                2725                2730
Leu Asp Glu Glu Arg Arg Gly Glu Pro Ala Pro Ala Ala Pro Ala
2735                2740                2745
Ala Thr Val Pro Ala Pro Thr Val Ala Gly Asn Glu Pro Leu Ala
2750                2755                2760
Ile Val Ala Met Ala Cys Arg Met Pro Gly Gly Val Arg Ser Pro
2765                2770                2775
Glu Asp Leu Trp Arg Leu Val Asp Ser Gly Gly Asp Ala Ile Thr
2780                2785                2790
Glu Phe Pro Ala Asp Arg Gly Trp Asp Leu Ala Ala Leu Tyr Asp
2795                2800                2805
Pro Asn Pro Asp Ala Val Gly Lys Val Ser Val Arg His Gly Gly
2810                2815                2820
Phe Leu Thr Gly Ala Ala Asp Phe Asp Ala Ala Phe Phe Gly Ile
2825                2830                2835
Ser Pro Arg Glu Ala Leu Ala Met Asp Pro Gln Gln Arg Leu Val
2840                2845                2850
```

-continued

```
Leu Glu Ala Ser Trp Glu Ala Phe Glu Arg Ala Gly Ile Leu Pro
    2855                2860                2865
Glu Ser Val Arg Gly Ser Asp Thr Gly Val Phe Met Gly Ala Phe
    2870                2875                2880
Thr Gln Gly Tyr Gly Ala Gly Val Asp Leu Gly Gly Phe Gly Ala
    2885                2890                2895
Thr Gly Thr Pro Thr Ser Val Leu Ser Gly Arg Leu Ser Tyr Tyr
    2900                2905                2910
Phe Gly Leu Glu Gly Pro Ser Val Thr Val Asp Thr Ala Cys Ser
    2915                2920                2925
Ser Ser Leu Val Ala Leu His Gln Ala Ala Arg Ser Leu Arg Ser
    2930                2935                2940
Gly Glu Cys Ser Leu Ala Leu Val Gly Gly Val Thr Val Met Ala
    2945                2950                2955
Thr Thr Thr Gly Phe Val Glu Phe Ser Arg Gln Arg Gly Leu Ala
    2960                2965                2970
Pro Asp Gly Arg Ala Lys Ala Phe Ala Asp Thr Ala Asp Gly Thr
    2975                2980                2985
Ser Phe Ala Glu Gly Ala Gly Val Leu Val Leu Glu Arg Leu Ser
    2990                2995                3000
Asp Ala Thr Arg His Gly His Pro Val Leu Ala Leu Val Arg Gly
    3005                3010                3015
Ser Ala Val Asn Ser Asp Gly Ala Ser Asn Gly Leu Ser Ala Pro
    3020                3025                3030
Asn Gly Pro Ala Gln Gln Arg Val Ile Gln Arg Ala Leu Ala Asp
    3035                3040                3045
Ala Gly Leu Ala Pro Gly Asp Val Asp Ala Val Glu Ala His Gly
    3050                3055                3060
Thr Gly Thr Arg Leu Gly Asp Pro Val Glu Ala Gln Ala Leu Gln
    3065                3070                3075
Val Ala Tyr Gly Arg Glu Arg Val His Pro Leu Leu Ile Gly Ser
    3080                3085                3090
Leu Lys Ser Asn Ile Gly His Thr Gln Ala Ala Ala Gly Val Ala
    3095                3100                3105
Gly Val Ile Lys Met Val Met Ala Met Arg His Gly Val Leu Pro
    3110                3115                3120
Arg Thr Leu His Val Asp Glu Pro Ser Arg His Val Asp Trp Asp
    3125                3130                3135
Gly Asp Ile Arg Leu Leu His Arg Ser Glu Pro Trp Pro Val Thr
    3140                3145                3150
Gly Arg Ala Arg Arg Ala Gly Val Ser Ser Phe Gly Ile Ser Gly
    3155                3160                3165
Thr Asn Ala His Val Val Leu Glu Ala Gly Pro Pro Ala Ala Pro
    3170                3175                3180
Ala Pro Val Ser Ala Pro Glu Ala Glu Pro Val Pro Glu Asp Val
    3185                3190                3195
Val Trp Pro Met Ser Ala Arg Thr Pro Glu Gly Leu Arg Asp Val
    3200                3205                3210
Ala Gly Gln Leu Ala Pro Leu Thr Gly Ala Ala Ala Ala Val Gly
    3215                3220                3225
His Ser Leu Ala Thr Thr Arg Thr Ala Met Arg His Arg Ala Val
    3230                3235                3240
Val Pro Ala Arg Glu Ala Glu Ala Phe Ala Arg Gly Ala Glu Val
```

-continued

```
              3245                3250                3255
Pro Gly Ala Val Thr Gly Thr Ala Asp Val Thr Asp Thr Arg Val
    3260                3265                3270

Val Phe Ala Phe Pro Gly Gln Gly Ser Gln Trp Ala Gly Met Gly
    3275                3280                3285

Ala Glu Leu Leu Ala Thr Glu Pro Val Phe Ala Arg Arg Leu Arg
    3290                3295                3300

Glu Cys Ala Thr Ala Leu Ala Pro His Thr Gly Trp Asp Leu Leu
    3305                3310                3315

Asp Val Ile Ala Gln Arg Pro Gly Ala Pro Ala Phe Asp Arg Val
    3320                3325                3330

Asp Val Val Gln Pro Ala Ser Phe Ala Val Met Val Ala Leu Ala
    3335                3340                3345

Glu Leu Trp Arg Ala His Gly Val Ala Pro Ala Ala Val Val Gly
    3350                3355                3360

His Ser Gln Gly Glu Val Ala Ala Ala Cys Val Ala Gly Val Leu
    3365                3370                3375

Thr Leu Asp Asp Ala Ala Lys Val Val Ala Val Arg Ser Arg Leu
    3380                3385                3390

Val Ala Thr Glu Leu Ala Gly Gln Gly Gly Met Val Ser Val Pro
    3395                3400                3405

Pro Ala Asp Phe Asp Ala Ala Val Trp Ala Gly Arg Leu Glu Val
    3410                3415                3420

Ala Ala Val Asn Gly Pro Ala Ser Ile Val Val Ala Gly Ala Ala
    3425                3430                3435

Asp Ala Val Glu Glu Leu Leu Ala Ala Thr Pro Arg Ala Arg Arg
    3440                3445                3450

Ile Ala Val Asp Tyr Ala Ser His Thr Ala His Val Glu Thr Ile
    3455                3460                3465

Arg Gly Ala Leu Leu Asp Ala Leu Ala Gly Ile Thr Pro Arg Thr
    3470                3475                3480

Pro Asp Val Pro Phe Phe Ser Thr Val Asp Glu Ala Trp Leu Asp
    3485                3490                3495

Arg Pro Ala Asp Ala Ala Tyr Trp Tyr Asp Asn Leu Arg Arg Thr
    3500                3505                3510

Val Arg Phe Ala Ala Ala Thr Gly His Leu Ala Asp Arg Gly Tyr
    3515                3520                3525

Arg Ala Phe Val Glu Val Ser Ala His Pro Val Leu Thr Thr Ala
    3530                3535                3540

Leu Glu Asp Thr Leu Ala Gly His Ala His Thr Val Val Thr Gly
    3545                3550                3555

Thr Leu Arg Arg Gly Glu Gly Gly Leu Asp Arg Phe Thr Arg Ser
    3560                3565                3570

Leu Ala Ala Leu Trp Val Arg Gly Val Pro Val Thr Trp Ser Phe
    3575                3580                3585

Ala Thr Arg Arg Val Val Pro Leu Pro Thr Tyr Pro Phe Arg Arg
    3590                3595                3600

Asp Arg Tyr Trp Ile Asp Ala Glu Pro Ala Gly Thr Ser Gly His
    3605                3610                3615

Pro Leu Leu Gly Ser Trp Val Asp Leu Ala Arg Arg Arg Gly Arg
    3620                3625                3630

Ala Gly His Arg Gly Val Ser Val Arg Arg Gln Pro Trp Leu Ala
    3635                3640                3645
```

-continued

```
Asp His Glu Val Asp Gly Arg Val Ile Val Pro Gly Ser Ala Leu
    3650                3655                3660

Val Glu Leu Leu Ala Glu Ala Gly Ala Arg Leu Gly Thr Pro Glu
    3665                3670                3675

Ile Ala Glu Leu Thr Ile Val Ala Pro Val Val Asp Gly Asp
    3680                3685                3690

Gly Asp Thr Glu Ile Gln Ala Thr Val Gly Thr Glu Val Ser Gly
    3695                3700                3705

Arg Arg Ser Val Ser Leu His Ser Arg Thr Gly Thr Gly Pro Trp
    3710                3715                3720

Ala Leu Ser Ala Thr Gly Ala Leu Ser Val Asp Thr Gly Gly Pro
    3725                3730                3735

Ala Glu Pro Val Asp Trp Pro Ala Asp Ala Asp Pro Ala Asp
    3740                3745                3750

Leu Thr Gly Phe Tyr Asp Ala Leu Pro Leu Ser Tyr Gly Pro Ala
    3755                3760                3765

Phe Arg Ala Met Thr Ala Met Trp Thr Gly Glu Gly Arg Ala Tyr
    3770                3775                3780

Ala Ser Val Arg Leu Ala Glu Gln Leu Thr Asp Ala Arg Tyr Gly
    3785                3790                3795

Leu His Pro Val Leu Leu Asp Ala Ala Leu His Ala Leu Gly Thr
    3800                3805                3810

Val Phe Thr Asp Pro Glu Arg Arg Arg Leu Ala Phe Ser Trp Ser
    3815                3820                3825

Gly Val Arg Ile His Ala Arg Ala Ala Thr Ala Leu Arg Val Leu
    3830                3835                3840

Leu Glu Arg Val Gly Pro Asp Met Val Arg Ile Val Ala Thr Asp
    3845                3850                3855

Glu His Gly Ser Pro Val Leu Asp Val Asp Ser Leu Thr Val Arg
    3860                3865                3870

Ala Ala Asp Pro Asp Ala Glu Ala Leu Phe Glu Ile Ala Trp Val
    3875                3880                3885

Pro Val Pro Ala Ser Pro Val Pro Asp Trp Thr Tyr Leu Ala Asp
    3890                3895                3900

Val Pro Asp Gly Glu His Pro Pro Val Val Leu Ala Val Glu
    3905                3910                3915

Pro Gly Asp Pro Gly Thr Ser Pro Gly Ala Arg Thr Arg Glu Leu
    3920                3925                3930

Gly Arg Asp Leu Leu Thr Thr Val Gln Thr Trp Leu Ala Glu Pro
    3935                3940                3945

Arg Trp Ala Arg Ser Arg Leu Ile Val Ala Thr Arg Thr Gly Asp
    3950                3955                3960

Pro Ala Gln Glu Ala Leu Gly Gly Leu Val Arg Thr Ala Glu Thr
    3965                3970                3975

Glu His Pro Gly Arg Val Ala Leu Ile Glu Ala Asp Glu Ile Thr
    3980                3985                3990

Pro Ala Ala Ile Ala Ala Gly Leu Ala Ala Gly Asp Glu Pro His
    3995                4000                4005

Val Arg Val Ala Asp Gly Thr Ala Arg Ala Ala Arg Leu Arg Arg
    4010                4015                4020

Val Ala Ala Ala Thr Gly Thr Ser Pro Leu Thr Gly Gly Thr Val
    4025                4030                4035
```

-continued

| | | | | | | | | | | | |
|---|---|---|---|---|---|---|---|---|---|---|---|
|Leu|Val|Thr|Gly|Gly|Thr|Gly|Gly|Leu|Gly|Arg|Leu|Leu|Val|Asp|
| |4040| | | |4045| | | |4050| | | | | |
|His|Leu|Leu|Thr|Val|His|Glu|Ala|Ala|Glu|Val|Val|Val|Val|Ser|
| |4055| | | |4060| | | |4065| | | | | |
|Arg|Asn|Gly|Arg|Pro|Gly|Asp|Thr|Pro|Glu|Asp|Asp|Arg|Val|Arg|
| |4070| | | |4075| | | |4080| | | | | |
|Tyr|Val|Ala|Ala|Asp|Val|Val|Asp|Arg|Asp|Glu|Leu|Ala|Ala|Val|
| |4085| | | |4090| | | |4095| | | | | |
|Val|Ala|Asp|Val|Ala|Gln|Arg|Leu|Arg|Ala|Val|Val|His|Met|Ala|
| |4100| | | |4105| | | |4110| | | | | |
|Gly|Ile|Val|Asp|Asp|Ala|Ala|Val|Thr|Thr|Met|Arg|Pro|Glu|Gln|
| |4115| | | |4120| | | |4125| | | | | |
|Trp|Asp|Ala|Val|Leu|Arg|Val|Lys|Ala|Asp|Val|Ala|Trp|His|Leu|
| |4130| | | |4135| | | |4140| | | | | |
|His|Glu|Leu|Thr|Arg|Asp|Leu|Asp|Leu|Ala|Ala|Phe|Val|Leu|Tyr|
| |4145| | | |4150| | | |4155| | | | | |
|Ser|Ser|Ile|Ser|Ala|Thr|Phe|Gly|Gly|Ala|Gly|Gln|Ala|Asn|Tyr|
| |4160| | | |4165| | | |4170| | | | | |
|Ala|Thr|Gly|Asn|Ala|Phe|Leu|Asp|Ala|Leu|Ala|Arg|His|Arg|His|
| |4175| | | |4180| | | |4185| | | | | |
|His|Gln|Gly|Leu|Pro|Ala|Val|Ser|Leu|Ala|Trp|Gly|Leu|Trp|Asp|
| |4190| | | |4195| | | |4200| | | | | |
|Ala|Ala|Asp|Gly|Met|Gly|Gly|Arg|Leu|Thr|Ala|Thr|Asp|Leu|Ala|
| |4205| | | |4210| | | |4215| | | | | |
|Arg|Ile|Ala|Arg|Asn|Gly|Met|Thr|Pro|Met|Thr|Ala|Ala|Gln|Gly|
| |4220| | | |4225| | | |4230| | | | | |
|Leu|Ala|Leu|Phe|Asp|Ala|Ala|Leu|His|Thr|Asp|Arg|Pro|Ala|Leu|
| |4235| | | |4240| | | |4245| | | | | |
|Val|Pro|Ile|Arg|Leu|Asp|Leu|Ala|Ala|Val|Ala|Ala|Ser|Asp|Arg|
| |4250| | | |4255| | | |4260| | | | | |
|Val|Pro|Pro|Val|Leu|Arg|Thr|Leu|Val|Pro|Ala|Val|Arg|Arg|Thr|
| |4265| | | |4270| | | |4275| | | | | |
|Ser|Ala|Pro|Pro|Ala|Ala|Arg|Asp|Met|Leu|Asp|Leu|Val|Arg|Thr|
| |4280| | | |4285| | | |4290| | | | | |
|Ser|Ala|Ala|Ala|Val|Leu|Gly|His|Arg|Asp|Ala|His|Ala|Ile|Ala|
| |4295| | | |4300| | | |4305| | | | | |
|Pro|Ala|Arg|Ala|Phe|Arg|Glu|Val|Gly|Phe|Asp|Ser|Leu|Thr|Gly|
| |4310| | | |4315| | | |4320| | | | | |
|Val|Glu|Leu|Arg|Asn|Arg|Leu|Ala|Asp|Ala|Thr|Gly|Leu|Thr|Leu|
| |4325| | | |4330| | | |4335| | | | | |
|Pro|Ala|Thr|Leu|Val|Phe|Asp|His|Pro|Thr|Ala|Gln|Ala|Leu|Ala|
| |4340| | | |4345| | | |4350| | | | | |
|Ala|His|Leu|Asp|Glu|Leu|Ala|Gly|Ala|Arg|Ala|Thr|Thr|Arg|Arg|
| |4355| | | |4360| | | |4365| | | | | |
|Arg|Thr|Pro|Thr|Ala|Ala|Val|Arg|Gln|Asp|Glu|Pro|Leu|Ala|Ile|
| |4370| | | |4375| | | |4380| | | | | |
|Val|Gly|Met|Ala|Cys|Arg|Leu|Pro|Gly|Gly|Val|Ala|Ser|Pro|Glu|
| |4385| | | |4390| | | |4395| | | | | |
|Asp|Leu|Trp|Arg|Leu|Leu|Glu|Ser|Gly|Gly|Asp|Gly|Ile|Thr|Ala|
| |4400| | | |4405| | | |4410| | | | | |
|Phe|Pro|Thr|Asp|Arg|Gly|Trp|Asp|Val|Asp|Gly|Leu|Tyr|Asp|Pro|
| |4415| | | |4420| | | |4425| | | | | |
|Asp|Pro|Asp|His|Pro|Gly|Thr|Ser|Thr|Val|Arg|His|Gly|Gly|Phe|

-continued

```
              4430                4435                4440

Leu Ala Gly Val Ala Asp Phe Asp Ala Ala Phe Phe Gly Ile Ser
            4445                4450                4455

Pro Arg Glu Ala Leu Ala Met Asp Pro Gln Gln Arg Leu Val Leu
            4460                4465                4470

Glu Thr Ser Trp Glu Ala Leu Glu His Ala Gly Ile Leu Pro Glu
            4475                4480                4485

Ser Leu Arg Gly Ser Asp Thr Gly Val Phe Met Gly Gly Tyr Phe
            4490                4495                4500

Tyr Gly Tyr Gly Thr Gly Ala Asp Arg Gly Gly Phe Gly Ala Thr
            4505                4510                4515

Ser Thr Gln Thr Ser Val Leu Ser Gly Arg Leu Ser Tyr Phe Tyr
            4520                4525                4530

Gly Leu Glu Gly Pro Ala Val Thr Val Asp Thr Ala Cys Ser Ser
            4535                4540                4545

Ser Leu Val Ala Leu His Gln Ala Gly Gln Ser Leu Arg Ser Gly
            4550                4555                4560

Glu Cys Ser Leu Ala Val Val Gly Gly Val Thr Val Met Ala Ser
            4565                4570                4575

Pro Ser Gly Phe Val Asp Phe Ser Gln Gln Arg Gly Leu Ser Pro
            4580                4585                4590

Asp Gly Arg Cys Lys Ala Phe Ala Asp Ala Ala Asp Gly Thr Gly
            4595                4600                4605

Phe Ala Glu Gly Ser Gly Val Leu Ile Val Glu Arg Leu Ser Asp
            4610                4615                4620

Ala Glu Arg His Gly His Asn Val Leu Ala Val Val Arg Gly Ser
            4625                4630                4635

Ala Val Asn Gln Asp Gly Ala Ser Asn Gly Leu Ser Ala Pro Asn
            4640                4645                4650

Gly Pro Ser Gln Glu Arg Val Ile Arg Gln Ala Leu Ala Asn Ala
            4655                4660                4665

Gly Leu Thr Pro Ala Asp Val Asp Ala Val Glu Ala His Gly Thr
            4670                4675                4680

Gly Thr Arg Leu Gly Asp Pro Ile Glu Ala Gln Ala Val Leu Ala
            4685                4690                4695

Thr Tyr Gly Gln His Arg Asp Thr Pro Val Leu Leu Gly Ser Leu
            4700                4705                4710

Lys Ser Asn Ile Gly His Thr Gln Ala Ala Ala Gly Val Ala Gly
            4715                4720                4725

Val Ile Lys Met Val Leu Ala Met Arg His Gly Thr Leu Pro Arg
            4730                4735                4740

Thr Leu His Val Asp Thr Pro Ser Ser His Val Asp Trp Thr Ala
            4745                4750                4755

Gly Ala Val Glu Leu Leu Thr Asp Ala Arg Pro Trp Pro Glu Thr
            4760                4765                4770

Asp Arg Pro Arg Arg Ala Gly Val Ser Ser Phe Gly Val Ser Gly
            4775                4780                4785

Thr Asn Ala His Ile Ile Leu Glu Ser His Pro Arg Pro Ala Pro
            4790                4795                4800

Glu Pro Ala Pro Ala Pro Asp Thr Gly Pro Leu Pro Leu Leu Leu
            4805                4810                4815

Ser Ala Arg Thr Pro Gln Ala Leu Asp Ala Gln Val His Arg Leu
            4820                4825                4830
```

-continued

```
Arg Ala His Leu Ala Thr Gly Glu Glu Asp Glu Arg Ala Val Ala
    4835                4840                4845
Ala Ala Leu Leu Ala Arg Thr Ala Phe Pro His Arg Ala Ala Leu
    4850                4855                4860
Ile Gly Thr Asp Thr Val Thr Gly Ala Ala Glu Pro Asp Arg Arg
    4865                4870                4875
Leu Val Trp Leu Phe Ser Gly Gln Gly Ser Gln Arg Pro Gly Met
    4880                4885                4890
Gly Asp Gly Leu Ala Ala Ala Tyr Asp Val Phe Ala Arg Thr Arg
    4895                4900                4905
Arg Glu Val Leu Asp Ala Leu Asp Val Pro Ala Gly Leu Asp Leu
    4910                4915                4920
His Asp Thr Gly Tyr Ala Gln Pro Ala Val Phe Ala Leu Gln Val
    4925                4930                4935
Ala Leu Gly Ala Gln Leu Glu Ala Trp Gly Val Arg Pro Asp Ala
    4940                4945                4950
Phe Val Gly His Ser Ile Gly Glu Leu Ala Ala Ala Tyr Val Ala
    4955                4960                4965
Gly Val Trp Ser Leu Glu Asp Ala Cys Arg Leu Val Ser Ala Arg
    4970                4975                4980
Ala Arg Leu Met Gln Ala Leu Pro Ser Gly Gly Ala Met Ala Ala
    4985                4990                4995
Val Ile Ala Ser Glu Arg Asp Ala Leu Pro Leu Leu Arg Asp Gly
    5000                5005                5010
Val Glu Ile Ala Ala Val Asn Gly Pro Ala Ser Ile Val Leu Ser
    5015                5020                5025
Gly Asp Glu Glu Ala Val Leu Asp Val Ala Ala Arg Leu Gly Arg
    5030                5035                5040
Phe Thr Arg Leu Arg Thr Ser His Ala Phe His Ser Ala Arg Met
    5045                5050                5055
Glu Pro Met Leu Glu Glu Phe Arg Lys Val Ala Glu Ser Leu Thr
    5060                5065                5070
Tyr His Glu Pro Arg Ile Pro Met Ala Ala Gly Ala Ala Cys Thr
    5075                5080                5085
Thr Pro Glu Tyr Trp Val Arg Gln Val Arg Asp Thr Val Arg Phe
    5090                5095                5100
Gly Glu Gln Val Ala Ala His Asp Gly Ala Val Leu Leu Glu Ile
    5105                5110                5115
Gly Pro Asp Arg Ser Leu Thr Arg Leu Val Asp Gly Ile Pro Met
    5120                5125                5130
Leu His Ala Asp Asp Glu Pro Arg Ser Ala Leu Thr Ala Leu Ala
    5135                5140                5145
Arg Leu His Thr Asp Gly Val Thr Val Asp Trp Pro Lys Val Ile
    5150                5155                5160
Asp Pro Ala Pro Ala Arg Ala Ser His Pro Thr Tyr Pro Phe
    5165                5170                5175
Glu Arg Val Arg Tyr Trp Leu Gly Thr Gln Thr Ala Gly Asp Ala
    5180                5185                5190
Ala Pro Ala Gly Gln Thr Pro Val Ala His Pro Ala Leu Thr Ala
    5195                5200                5205
Ala Val Thr Leu Pro Gly Thr Gly Asp Leu Val Leu Thr Gly Arg
    5210                5215                5220
```

```
Val Asp Ala Ala Asp Pro Leu Ala His Ser Leu His Gly Leu Ala
5225                5230                5235

Val Leu Pro Ala Ala Ala Leu Leu Asp Leu Ala Ile Arg Ala Gly
5240                5245                5250

Asp Glu Ala Gly Cys Gly Ala Leu Asp Thr Phe Thr Val Asp Thr
5255                5260                5265

Pro Leu Thr Leu Pro Arg Ser Gly Ala Leu Ala Leu Ser Val Thr
5270                5275                5280

Val Ser Ala Pro Gly Ala Asp Gly Arg Arg Ala Val Thr Val His
5285                5290                5295

Thr Arg His Ala Ala Gly Glu Trp Thr Glu His Ala His Gly Ile
5300                5305                5310

Leu Ala Pro Asp Pro Arg Thr Ala Pro Ala Val Arg Glu Met Pro
5315                5320                5325

Ser Thr Trp Pro Pro Ala Thr Ala Arg Pro Val Asp Pro Asp Asp
5330                5335                5340

Ile Ala Asp Arg Leu Ala Arg Ala Gly Tyr Thr Asp Gly Pro Ala
5345                5350                5355

Leu Pro Arg Pro Arg Ala Val Trp Ala Asp Asp Ala Val Trp
5360                5365                5370

Ala Glu Val Ala Leu Ala Asp Gly Gln Leu Ala Asp Ala Gly Arg
5375                5380                5385

Tyr Gly Leu His Pro Ala Leu Leu Gly Ala Ala Leu Arg Leu Ala
5390                5395                5400

Ala Glu Gly Asp His Leu Pro Tyr Ala Phe Asp Asp Val Arg Val
5405                5410                5415

His Ala Thr Gly Ala Thr Ala Val Arg Val Ala Val Thr Ala Asp
5420                5425                5430

Gly Val His Leu Ala Asp Glu Thr Gly Gly Pro Val Ala Thr Ile
5435                5440                5445

Gly Ala Val Arg Arg Arg Pro Leu Thr Ile Thr Gly Ala Val Pro
5450                5455                5460

Gly Leu Leu Arg Pro Val Leu Ala Glu Leu Pro Glu Leu Pro Pro
5465                5470                5475

Thr Thr Ala Thr Thr Gly Arg Leu Asp Asp Pro Thr Val Pro Asp
5480                5485                5490

Val Val Ile Leu Pro Ala His Gly Gly Gly Ala Pro Leu Asp
5495                5500                5505

Asp Thr Arg Glu Leu Gly Ala Gly Val Leu Thr Ala Val Gln Arg
5510                5515                5520

Phe Leu Thr Asp Asp Arg Tyr Ala Asp Ala Val Leu Ala Val His
5525                5530                5535

Thr Gly Pro Gly Leu Ala Ser Ala Ala Ala Ala Gly Leu Val Arg
5540                5545                5550

Thr Ala Gln Ala Glu His Pro Gly Arg Ile Val Leu Val Asp Ala
5555                5560                5565

Ala Pro Asp Thr Ala Glu Pro Leu Leu Ala Ala Ala Thr Ala Leu
5570                5575                5580

Asp Glu Pro Gln Val Val Leu Arg Asp Gly Gln Val Tyr Ala Arg
5585                5590                5595

Arg Leu Ala Pro Ala Val Pro Ala Gly Asp Ala Pro Ala Leu Asp
5600                5605                5610

Pro Asp Gly Thr Val Leu Val Thr Gly Gly Ser Gly Thr Leu Ala
```

-continued

```
              5615                5620                5625
Gly Ile  Ile Ser Arg His  Leu Val Glu Arg  His Gly Val Arg Arg
        5630                5635                5640
Leu Leu Met Leu Ser Arg  Ser Gly Thr Ala Ser  Asp Val Pro Gly
        5645                5650                5655
Ala Glu Val Thr Ala Ile  Ala Cys Asp Val Ala  Asp Arg Asp Glu
        5660                5665                5670
Leu Ala Ser Val Leu Ala  Gly Ile Asp Pro Ala  His Pro Leu Thr
        5675                5680                5685
Ala Val Val His Thr Ala  Ala Val Leu Asp Asp  Gly Val Leu Thr
        5690                5695                5700
Ala Leu Thr Pro Asp Arg  Leu Glu Thr Val Leu  Arg Pro Lys Val
        5705                5710                5715
Asp Ala Ala Trp His Leu  His Glu Leu Thr Gln  Asp Thr Glu Leu
        5720                5725                5730
Ala Ala Phe Val Leu Tyr  Ser Ser Ala Ala Gly  Val Leu Gly Ser
        5735                5740                5745
Pro Gly Gln Gly Asn Tyr  Ala Ala Ala Asn Ala  Phe Leu Asp Ala
        5750                5755                5760
Leu Ala Glu Gln Arg Arg  Ala Ala Gly Leu Pro  Ala Leu Ser Val
        5765                5770                5775
Ala Trp Gly Leu Trp Glu  Pro Glu Ser Gly Leu  Thr Val Gly Thr
        5780                5785                5790
Gly Ala Arg Met Arg Arg  Asp Gly Val Thr Ala  Leu Thr Ala Glu
        5795                5800                5805
Gly Gly Leu Thr Leu Phe  Asp Ala Ala Leu Arg  Ser Ser Asp Pro
        5810                5815                5820
Ala Leu Val Ala Ala Asp  Pro Ala Gly Leu Gly  Ser Ser Pro Leu
        5825                5830                5835
Leu Arg Ala Pro Arg Arg  Glu Pro Arg Arg Arg  Ala Ala Gly Ala
        5840                5845                5850
Thr Thr Leu Ala Asp Arg  Ile Ala Arg Leu Ser  Ala Ala Asp Ala
        5855                5860                5865
Glu Lys Asp Val Leu Ala  Val Val Arg Gln Cys  Thr Ala Ala Val
        5870                5875                5880
Leu Gly His Asp Gly Ala  Ala Arg Val Glu Ala  Thr Ala Thr Phe
        5885                5890                5895
Lys Glu Leu Gly Val Asp  Ser Leu Met Ala Ile  Arg Leu Arg Asn
        5900                5905                5910
Ala Phe Thr Glu Ala Thr  Gly Val Arg Leu Pro  Ala Thr Ala Val
        5915                5920                5925
Phe Asp Phe Pro Thr Pro  Arg Ala Val Ala Ala  Lys Leu Thr Ala
        5930                5935                5940
Ala Leu Ser Gly Arg Thr  Ala Ser Pro Thr Arg  Thr Thr Thr Ala
        5945                5950                5955
Ala Val Arg Gln Asp Glu  Pro Leu Ala Ile Val  Gly Met Ala Cys
        5960                5965                5970
Arg Leu Pro Gly Gly Val  Ala Ser Pro Glu Asp  Leu Trp Arg Leu
        5975                5980                5985
Leu Glu Ser Gly Gly Asp  Gly Ile Thr Ala Phe  Pro Thr Asp Arg
        5990                5995                6000
Gly Trp Asp Val Asp Gly  Leu Tyr Asp Pro Asp  Pro Asp His Pro
        6005                6010                6015
```

-continued

```
Gly Thr Ser Thr Val Arg His Gly Gly Phe Leu Ala Gly Val Ala
6020            6025            6030

Asp Phe Asp Ala Ala Phe Phe Gly Ile Ser Pro Arg Glu Ala Leu
6035            6040            6045

Ala Met Asp Pro Gln Gln Arg Leu Val Leu Glu Thr Ser Trp Glu
6050            6055            6060

Ala Leu Glu His Ala Gly Ile Leu Pro Glu Ser Leu Arg Gly Ser
6065            6070            6075

Asp Thr Gly Val Phe Met Gly Ala Phe Ser Asp Gly Tyr Gly Leu
6080            6085            6090

Gly Thr Asp Leu Gly Gly Phe Gly Ala Thr Gly Thr Gln Thr Ser
6095            6100            6105

Val Leu Ser Gly Arg Leu Ser Tyr Phe Tyr Gly Leu Glu Gly Pro
6110            6115            6120

Ala Val Thr Val Asp Thr Ala Cys Ser Ser Ser Leu Val Ala Leu
6125            6130            6135

His Gln Ala Gly Gln Ser Leu Arg Ser Gly Glu Cys Ser Leu Ala
6140            6145            6150

Leu Val Gly Gly Val Thr Val Met Ala Ser Pro Ser Gly Phe Val
6155            6160            6165

Glu Phe Ser Gln Gln Arg Gly Leu Ala Pro Asp Ala Arg Cys Lys
6170            6175            6180

Ala Phe Ala Asp Ala Ala Asp Gly Thr Gly Phe Ala Glu Gly Ser
6185            6190            6195

Gly Val Leu Ile Val Glu Arg Leu Ser Asp Ala Glu Arg Asn Gly
6200            6205            6210

His Arg Val Leu Ala Val Val Arg Gly Ser Ala Val Asn Gln Asp
6215            6220            6225

Gly Ala Ser Asn Gly Leu Ser Ala Pro Asn Gly Pro Ser Gln Glu
6230            6235            6240

Arg Val Ile Arg Gln Ala Leu Ala Asn Ala Gly Leu Thr Pro Ala
6245            6250            6255

Asp Val Asp Ala Val Glu Ala His Gly Thr Gly Thr Arg Leu Gly
6260            6265            6270

Asp Pro Ile Glu Ala Gln Ala Val Leu Ala Thr Tyr Gly Gln Gly
6275            6280            6285

Arg Asp Thr Pro Val Leu Leu Gly Ser Leu Lys Ser Asn Ile Gly
6290            6295            6300

His Thr Gln Ala Ala Ala Gly Val Ala Gly Val Ile Lys Met Val
6305            6310            6315

Leu Ala Met Arg His Gly Thr Leu Pro Arg Thr Leu His Val Asp
6320            6325            6330

Thr Pro Ser Ser His Val Asp Trp Thr Ala Gly Ala Val Glu Leu
6335            6340            6345

Leu Thr Asp Ala Arg Pro Trp Pro Glu Thr Asp Arg Pro Arg Arg
6350            6355            6360

Ala Gly Val Ser Ser Phe Gly Val Ser Gly Thr Asn Ala His Val
6365            6370            6375

Leu Leu Glu Ala His Pro Ala Gly Glu Pro Pro Ala Glu Glu Pro
6380            6385            6390

Ser Ala Ser Lys Pro Gly Glu Pro Leu Ile Ala Thr Pro Leu Thr
6395            6400            6405
```

-continued

| | | | | | | | | | | | |
|---|---|---|---|---|---|---|---|---|---|---|---|
| Pro | Leu | Pro | Val | Ser | Ala | Arg | Thr | Ala | Thr | Ala | Leu | Asp | Gly | Gln |
| 6410 | | | | 6415 | | | | | 6420 | | |

Pro Leu Pro Val Ser Ala Arg Thr Ala Thr Ala Leu Asp Gly Gln
   6410                6415                6420

Val Arg Arg Leu Arg Glu His Leu Ala Ala Arg Pro Gly His Asp
   6425                6430                6435

Pro Arg Ala Ile Ala Ala Gly Leu Leu Ala Arg Arg Thr Thr Phe
   6440                6445                6450

Pro His Arg Ala Val Leu Leu Asp Asp Asp Val Val Thr Gly Thr
   6455                6460                6465

Ala Leu Thr Glu Pro Arg Thr Val Phe Val Phe Pro Gly Gln Gly
   6470                6475                6480

Pro Gln Trp Arg Gly Met Gly Val Glu Leu Met Ala Ala Ser Pro
   6485                6490                6495

Val Phe Ala Ala Arg Met Arg Gln Cys Ala Asp Ala Leu Ile Pro
   6500                6505                6510

His Thr Gly Trp Asp Pro Ile Ala Met Leu Asp Asp Pro Glu Val
   6515                6520                6525

Thr Arg Arg Val Asp Val Val His Pro Val Cys Trp Ala Val Met
   6530                6535                6540

Val Ser Leu Ala Ala Val Trp Glu Ala Ala Gly Val Arg Pro Asp
   6545                6550                6555

Ala Val Ile Gly His Ser Gln Gly Glu Ile Ala Ala Ala Cys Val
   6560                6565                6570

Ala Gly Ala Leu Thr Leu Glu Asp Gly Ala Arg Leu Val Ala Leu
   6575                6580                6585

Arg Ser Ala Leu Leu Leu Arg Glu Leu Ala Gly Arg Gly Ala Met
   6590                6595                6600

Gly Ser Val Ala Leu Pro Ala Ala Asp Val Glu Ala Asp Ala Ala
   6605                6610                6615

Arg Ile Asp Gly Val Trp Val Ala Gly Arg Asn Gly Ala Thr Thr
   6620                6625                6630

Thr Thr Val Ala Gly Arg Pro Asp Ala Val Glu Thr Leu Ile Ala
   6635                6640                6645

Asp Tyr Glu Ala Arg Gly Val Trp Val Arg Arg Ile Ala Val Asp
   6650                6655                6660

Cys Pro Thr His Thr Pro Phe Val Asp Pro Leu Tyr Asp Glu Leu
   6665                6670                6675

Gln Arg Ile Val Ala Asp Thr Thr Ser Arg Thr Pro Glu Ile Pro
   6680                6685                6690

Trp Phe Ser Thr Ala Asp Glu Arg Trp Ile Asp Ala Pro Leu Asp
   6695                6700                6705

Asp Glu Tyr Trp Phe Arg Asn Met Arg His Pro Val Gly Phe Ala
   6710                6715                6720

Thr Ala Val Thr Ala Ala Arg Glu Pro Gly Asp Thr Val Phe Val
   6725                6730                6735

Glu Val Ser Ala His Pro Val Leu Leu Pro Ala Ile Asp Gly Ala
   6740                6745                6750

Thr Val Ala Thr Leu Arg Arg Gly Gly Gly Val His Arg Leu Leu
   6755                6760                6765

Thr Ala Leu Ala Glu Ala His Thr Thr Gly Val Pro Val Asp Trp
   6770                6775                6780

Ala Ala Val Val Pro Ala Thr Ala Thr Ala His Asp Leu Pro Thr
   6785                6790                6795

Tyr Ala Phe His His Glu Arg Tyr Trp Ile Glu Thr Ala Ala Gly

-continued

```
                  6800             6805            6810
Thr Asp Ala Ser Gly Leu Gly Leu Asp Ala Val Asp His Pro Leu
    6815             6820            6825
Leu Ala Ala Ser Val Ala Leu Pro Asp Ser Asp Glu Val Leu Leu
    6830             6835            6840
Thr Gly Arg Phe Ser Leu Ala Thr His Pro Trp Leu Ala Gly His
    6845             6850            6855
Ser Val Asp Gly Ala Val Leu Leu Pro Gly Pro Ala Phe Leu Glu
    6860             6865            6870
Leu Ala Gly Arg Gly Ala Asp Glu Ala Gly Cys Asp Leu Leu Asp
    6875             6880            6885
Glu Leu Val Val Glu Thr Pro Leu Val Leu Pro Ala Thr Gly Ala
    6890             6895            6900
Val Gln Val Arg Val Thr Val Ala Ala Pro Asp Asp Thr Gly Arg
    6905             6910            6915
Arg Ala Val Arg Val His Ala Arg Thr Asp Gly Asp Arg Thr Trp
    6920             6925            6930
Thr Arg His Ala Ser Gly Phe Ala Gly Ile Ala Thr Thr Glu Pro
    6935             6940            6945
Ala Thr Thr Pro Gly Pro Trp Pro Pro Glu His Ala Glu Pro Val
    6950             6955            6960
Asp Val Ala Ala Phe Tyr Gln Arg Leu Asp Asp Ala Gly Tyr Glu
    6965             6970            6975
Phe Gly Pro Glu Phe Arg Gly Met Ser Ala Ala Trp Ser His Gly
    6980             6985            6990
Asp Thr Val Cys Ala Glu Val Ala Leu Asp Gly Ala Leu Ala Arg
    6995             7000            7005
Asp Ala Ala Arg Tyr Thr Leu His Pro Ala Leu Leu Val Thr Ala
    7010             7015            7020
Leu Gln Ala Gly Ser Ile Gly Ala Ala Ala Glu Asn Ala Gly Val
    7025             7030            7035
Arg Leu Pro Phe Ala Phe Thr Gly Val Arg Val His Thr Ser Gly
    7040             7045            7050
Ala Thr Lys Leu Arg Val Thr Phe Val His Gly Glu Gly Glu Gly
    7055             7060            7065
Gly Ala Arg Val His Leu Ala Asp Glu Leu Gly Arg Pro Val Ala
    7070             7075            7080
Gln Ile Gly Ser Leu Ile Thr Arg Pro Pro Ala Thr Thr Gly Pro
    7085             7090            7095
Asp Gly Asp Val Arg Leu Phe Arg Arg Thr Trp Thr Gly Val Arg
    7100             7105            7110
Ala Pro Ala Ala Pro Gly Thr Thr Ala Arg Arg Tyr Thr Asp Leu
    7115             7120            7125
Gly Asp Asp Ala Thr Pro Asp Val Ile Val Val Pro Val Ser Gly
    7130             7135            7140
Pro Asp Glu Val Arg Thr Ala Leu Asp Asp Pro Arg Thr Ala Gly
    7145             7150            7155
Ala Thr Leu Val Val Ser Ala Glu Ala Gly Pro Val Ala Gly Ala
    7160             7165            7170
Val Ala Ala Leu Leu Asp Thr Ala Glu Pro Gly Arg Leu Val Leu
    7175             7180            7185
Val Glu Thr Thr Asp Thr Val Thr Pro Arg Arg Ala Ala Ala Leu
    7190             7195            7200
```

```
Ser Arg Leu Asp Glu Pro His Leu Arg Leu Ala Asp Gly Arg Leu
    7205                7210                7215
Glu Ala Pro Arg Leu Val Pro Ala Ala Pro Thr Thr Ala Ala Ala
    7220                7225                7230
Ser Tyr Gly Asp Thr Val Leu Leu Ala Gly Gly Ser Glu Glu Leu
    7235                7240                7245
Ala Gly His Leu Gly Gly His Gly Ala Glu Val Ile Arg Tyr Glu
    7250                7255                7260
Pro Gly Thr Val Pro Glu Thr Pro Val Thr Ala Val Val His Ala
    7265                7270                7275
Asp Gly Thr Ala Glu Ser Ala Trp Glu Leu His Arg Leu Thr Arg
    7280                7285                7290
Asp Leu Asp Leu Thr Ala Phe Val Leu Ala Val Pro Ser Gly Glu
    7295                7300                7305
Ala Ala Gly Pro Leu Gln Ala Leu Ala Asp Leu Arg Arg Ala Gln
    7310                7315                7320
Gly Leu Pro Ala Val Ala Phe Thr Ala Ala Asp Arg Leu Thr
    7325                7330                7335
Asp Leu Leu Asp Ala Ala Cys Ala Thr Gly Glu Ala Val Val Val
    7340                7345                7350
Ala Thr Ala Pro Pro Gly Pro Gly Asp Pro Ser Pro Leu Trp Arg
    7355                7360                7365
Pro Ile Gln Arg Pro Thr Arg Arg Ser Ala Thr Asp Gly Gly Ser
    7370                7375                7380
Leu Leu Glu Arg Leu Pro Asp Leu Pro His Lys Glu Arg Glu Gln
    7385                7390                7395
Val Leu Leu Gly Val Val Arg Asp Thr Ala Ala Thr Leu Leu Gly
    7400                7405                7410
His Thr Asp Ala Ala Ala Val Thr Ala Thr Thr Ala Phe Lys Asp
    7415                7420                7425
Leu Gly Val Asp Ser Leu Thr Ala Leu Gly Leu Arg Asn Arg Leu
    7430                7435                7440
Ser Glu Ala Leu Gly Ile Pro Leu Pro Ala Thr Leu Val Phe Asp
    7445                7450                7455
Tyr Pro Ala Ala Gly Ala Leu Thr Arg His Leu Leu Thr Leu Leu
    7460                7465                7470
Ala Pro Asp Val Asn Gly Thr Pro Asp Asp Asn Gly Thr Pro Asp
    7475                7480                7485
Gly Gly Glu Pro Pro Ala Gln Ala Pro Ala Ser Thr Thr Thr Ala
    7490                7495                7500
Glu Pro Asp Asp Glu Leu Phe Asp Asp Met Asp Ala Asp Ala Leu
    7505                7510                7515
Ile Ala His Val Leu Lys Gly
    7520                7525

<210> SEQ ID NO 74
<211> LENGTH: 3591
<212> TYPE: PRT
<213> ORGANISM: Streptomyces hygroscopicus

<400> SEQUENCE: 74

Met Ala Glu Asn Asp Leu Ile Glu Ala Leu Arg Thr Ser Val Lys Asp
1               5                   10                  15

Asn Ala Gln Leu Arg Arg Glu Asn Thr Ala Leu Arg Ala Ala Ala Asn
```

-continued

```
                20                  25                  30
Glu Pro Leu Ala Val Gly Met Ala Cys Arg Leu Pro Gly Gly Val
            35                  40                  45
Thr Ser Pro Glu Glu Leu Trp Gln Leu Val Ala Asp Gly Arg Asp Ala
 50                  55                  60
Ile Gly Asp Phe Pro Thr Asp Arg Gly Trp Asp Val Ala Ala Leu His
 65                  70                  75                  80
Ala Ala Ala Glu Ser Ala Thr Gly Arg Ala Gly Leu Ala Gly Ala
                85                  90                  95
Ala Asp Phe Asp Ala Ala Phe Phe Gly Ile Ser Pro Arg Glu Ala Thr
                100                 105                 110
Ala Leu Asp Pro Gln Gln Arg Ile Leu Leu Glu Ile Ala Trp Glu Ala
            115                 120                 125
Leu Glu His Ala Gly Ile Val Pro Asp Thr Leu Arg Gly Ser Asp Thr
            130                 135                 140
Gly Val Phe Val Gly Gly Phe Tyr Tyr Gly Tyr Gly Thr Gly Ala Asp
145                 150                 155                 160
Leu Gly Gly Phe Gly Ala Tyr Ser Thr Gln Pro Ala Val Leu Ala Gly
                165                 170                 175
Arg Leu Ser Tyr Phe Phe Gly Met Glu Gly Pro Ala Val Thr Val Asp
            180                 185                 190
Thr Ala Cys Ser Ser Ser Leu Val Ala Leu His Gln Ala Gly Gln Ala
            195                 200                 205
Leu Arg Thr Gly Glu Cys Ser Leu Ala Leu Val Gly Gly Val Thr Val
210                 215                 220
Met Ala Ser Pro Gln Thr Phe Val Glu Phe Ser Arg Gln Gly Gly Val
225                 230                 235                 240
Ala Pro Asp Gly Arg Cys Lys Ala Phe Ala Asp Ala Ala Asp Gly Thr
                245                 250                 255
Gly Phe Ala Glu Gly Ala Gly Val Leu Val Val Glu Lys Leu Ser Asp
                260                 265                 270
Ala Glu Arg Asn Gly His Thr Val Leu Ala Val Val Arg Ser Ser Ala
            275                 280                 285
Val Asn Gln Asp Gly Ala Ser Asn Gly Ile Ser Ala Pro Asn Gly Pro
            290                 295                 300
Ser Gln Gln Arg Val Ile Arg Gln Ala Leu His Lys Ala Gly Leu Ala
305                 310                 315                 320
Pro Ala Asp Val Asp Val Val Glu Ala His Gly Thr Gly Thr Thr Leu
                325                 330                 335
Gly Asp Pro Ile Glu Ala His Ala Ile Leu Ala Thr Tyr Gly Gln Glu
                340                 345                 350
Arg Glu Val Pro Leu Leu Leu Gly Ser Leu Lys Ser Asn Ile Gly His
            355                 360                 365
Ala Gln Ala Ala Ala Gly Val Ala Gly Val Ile Lys Met Val Met Ala
            370                 375                 380
Met Arg Tyr Gly Ile Ala Pro Lys Thr Leu His Val Asp Glu Pro Ser
385                 390                 395                 400
Ser His Val Asp Trp Thr Glu Gly Ala Val Glu Leu Leu Thr Glu Ala
                405                 410                 415
Arg Ala Trp Pro Asp Ala Gly Arg Pro Arg Arg Ala Gly Val Ser Ala
            420                 425                 430
Phe Gly Val Ser Gly Thr Asn Ala His Val Ile Leu Glu Gly Val Pro
            435                 440                 445
```

-continued

```
Gly Pro Ser Arg Gly Glu Ser Ala Val Asp Gly Leu Val Pro Leu Pro
    450                 455                 460
Val Ser Ala Arg Ser Glu Val Ser Leu Arg Gly Gln Val Glu Arg Leu
465                 470                 475                 480
Glu Gly Tyr Leu Arg Gly Gly Val Asp Val Ala Ala Val Ala Gln
                485                 490                 495
Gly Leu Val Arg Glu Arg Ala Val Phe Gly His Arg Ala Val Leu Leu
                500                 505                 510
Gly Asp Ala Arg Val Met Gly Val Ala Val Asp Gln Pro Arg Thr Val
                515                 520                 525
Phe Val Phe Pro Gly Gln Gly Ala Gln Trp Val Gly Met Gly Val Glu
    530                 535                 540
Leu Met Ala Cys Ser Ala Val Phe Ala Ala Arg Met Glu Glu Cys Ala
545                 550                 555                 560
Arg Ala Leu Leu Pro His Thr Gly Trp Asp Val Arg Glu Met Leu Ala
                565                 570                 575
Arg Pro Asp Val Ala Glu Arg Val Glu Val Val Gln Pro Ala Ser Trp
                580                 585                 590
Ala Val Ala Val Ser Leu Ala Ala Leu Trp Gln Ala His Gly Val Val
            595                 600                 605
Pro Asp Ala Val Val Gly His Ser Gln Gly Glu Ile Ala Ala Ala Cys
    610                 615                 620
Val Ala Gly Ala Leu Ser Leu Glu Asp Ala Ala Arg Val Val Ala Leu
625                 630                 635                 640
Arg Ser Gln Val Ile Ala Gly Arg Leu Ala Gly Arg Gly Ala Met Ala
                645                 650                 655
Ser Val Ala Leu Pro Ala Gly Glu Val Asp Leu Val Glu Gly Val Trp
                660                 665                 670
Ile Ala Ala Arg Asn Gly Pro Ser Ser Thr Val Val Ala Gly Asp Pro
            675                 680                 685
Ser Ala Val Glu Glu Val Val Thr Arg Tyr Glu Ala Glu Gly Val Arg
    690                 695                 700
Val Arg Arg Ile Ala Val Asp Tyr Ala Ser His Thr Pro His Val Glu
705                 710                 715                 720
Ala Ile Glu Asp Glu Leu Ala Glu Val Leu Glu Gly Ile Ser Gly Gly
                725                 730                 735
Thr Gly Ser Val Ala Trp Trp Ser Thr Val Asp Ser Ala Trp Val Thr
                740                 745                 750
Glu Pro Val Asp Glu Gly Tyr Trp Tyr Arg Asn Leu Arg Arg Pro Val
            755                 760                 765
Ala Leu Asp Ala Ala Val Ala Glu Leu Asp Gly Ser Val Phe Val Glu
    770                 775                 780
Cys Ser Ala His Pro Val Leu Leu Pro Ala Met Glu Gln Ala His Thr
785                 790                 795                 800
Val Ala Ser Leu Arg Thr Gly Asp Gly Gly Trp Glu Arg Trp Leu Thr
                805                 810                 815
Ala Leu Ala Gln Ala Trp Thr Leu Gly Thr Ala Val Asp Trp Asp Thr
            820                 825                 830
Val Val Glu Pro Val Pro Gly Arg Leu Leu Asp Leu Pro Thr Tyr Ala
    835                 840                 845
Phe Glu His Arg Arg Tyr Trp Leu Glu Ala Ala Gly Ala Thr Asp Leu
850                 855                 860
```

-continued

```
Ser Ala Ala Gly Leu Thr Gly Ala Ala His Pro Met Leu Ala Ala Val
865                 870                 875                 880

Thr Ala Leu Pro Ala Asp Asp Gly Gly Val Val Leu Thr Gly Arg
            885                 890                 895

Ile Ser Leu Arg Thr His Pro Trp Leu Ala Asp His Ala Val Arg Gly
            900                 905                 910

Thr Val Leu Leu Pro Gly Thr Ala Phe Val Glu Leu Val Ile Arg Ala
            915                 920                 925

Gly Asp Glu Thr Gly Cys Gly Val Val Asp Glu Leu Val Ile Glu Thr
            930                 935                 940

Pro Leu Val Val Pro Val Thr Gly Ala Val Asp Val Ser Val Thr Val
945                 950                 955                 960

Glu Gly Ala Asp Glu Ala Gly Arg Arg Arg Val Thr Val His Ala Arg
                965                 970                 975

Thr Glu Gly Thr Asp Ser Trp Thr Arg His Ala Ser Gly Thr Leu Gly
            980                 985                 990

Arg Ala Gly Ser Val Ala Ala Val Pro Pro Pro Ala Trp Pro Pro Pro
        995                 1000                1005

Gly Ala Arg Arg Val Asp Val Ser Ala Phe Tyr Glu Arg Leu Ala
    1010                1015                1020

Glu Thr Gly Tyr Ser Tyr Gly Pro Ala Phe Gln Gly Leu Arg Thr
    1025                1030                1035

Ala Trp Arg Asp Gly Glu Thr Leu Tyr Ala Glu Val Glu Ile Ala
    1040                1045                1050

Gly Glu Gln Ala Asp Asp Thr Pro His Tyr Gly Val His Pro Ala
    1055                1060                1065

Leu Phe Asp Ala Ala Leu His Val Thr Cys Leu Pro Leu Leu Ala
    1070                1075                1080

Glu Gln Glu Ala Glu Val Arg Leu Pro Phe Ser Trp Ser Gly Val
    1085                1090                1095

Arg Phe His Thr Thr Gly Ala Thr Thr Leu Arg Val Thr Ile Thr
    1100                1105                1110

Gln Gly Pro Asp Gly Ala Ala Val His Ala Thr Asp Pro Val Gly
    1115                1120                1125

Gln Pro Val Val Thr Val Ala Ala Leu Thr Ala Arg Pro Val Asn
    1130                1135                1140

Val Asp Gly Asp Ala Ala Val Val Arg Asn Ser Leu Tyr Gly Leu
    1145                1150                1155

Ser Trp Thr Glu Leu Pro Thr Pro Gly Pro Gly Pro Ala Asp Ala
    1160                1165                1170

Val His Ile Val Ser Ala Leu Pro Glu Pro Gly Ala Asp Val Leu
    1175                1180                1185

Asp Glu Thr Tyr Arg Leu Thr Glu Phe Val Leu Gly Glu Leu His
    1190                1195                1200

Arg Val Ile Ala Glu Asp Gly Pro Ala Glu Thr Thr Leu Val Val
    1205                1210                1215

Arg Ile Asp Ala Gly Pro Val Gly Gly Ala Val Ala Gly Leu Val
    1220                1225                1230

Arg Ser Ala Gln Ala Glu His Pro Gly Arg Phe Val Leu Val Glu
    1235                1240                1245

Thr Gly Thr Asp Thr Pro Ile Glu Ala Leu Ala Ala Ala Thr Thr
    1250                1255                1260

Leu Ala Glu Pro Tyr Val Arg Val Thr Asp Gly Arg Tyr Glu Ala
```

-continued

```
            1265                    1270                    1275
Pro Arg Phe Thr Arg Thr Ala Ala Glu Thr Pro Glu Pro Leu
    1280                    1285                    1290

Leu Asp Pro Asp Gly Thr Val Val Ile Thr Gly Gly Ser Gly Val
    1295                    1300                    1305

Leu Ala Gly Leu Leu Ala Arg His Leu Val Ala Glu His Gly Ala
    1310                    1315                    1320

Arg His Leu Leu Leu Leu Ser Arg Ser Glu Pro Pro Ala Asp Thr
    1325                    1330                    1335

Pro Gly Val His Ile Arg Cys Asp Val Ala Asp Arg Asp Gln Leu
    1340                    1345                    1350

Ala Ala Ala Leu Ala Ala Ala Gly Arg Pro Leu Thr Ala Val Phe
    1355                    1360                    1365

His Thr Ala Ala Val Leu Asp Asp Gly Val Thr Thr Ala Leu Thr
    1370                    1375                    1380

Pro Glu Arg Leu Ala Thr Thr Leu Arg Pro Lys Ala Asp Gly Ala
    1385                    1390                    1395

Trp His Leu His Glu Leu Thr Arg Asp Ala Asp Leu Arg Ser Phe
    1400                    1405                    1410

Val Leu Tyr Ser Ser Val Ala Gly Ile Met Gly Gly Arg Gly Gln
    1415                    1420                    1425

Gly Asn Tyr Ser Ala Ala Asn Gly Phe Leu Asp Gly Leu Ala Thr
    1430                    1435                    1440

Leu Arg His Ala Glu Gly Leu Pro Ala Leu Ser Leu Ala Trp Gly
    1445                    1450                    1455

Leu Trp Ala Asp Asp Ser Gly Leu Thr Gly Ser Met Ser Gly Thr
    1460                    1465                    1470

Asn Arg Thr Arg Val Arg Arg Gly Gly Phe Arg Pro Met Ser Ala
    1475                    1480                    1485

Gly Val Gly Met Arg Leu Leu Glu Ala Ala Ala Gly Thr Gly Thr
    1490                    1495                    1500

Ala Phe Ala Val Ala Ala Thr Met Asp Leu Thr Ala His Thr Ser
    1505                    1510                    1515

Pro Leu Phe Ala Asp Leu Arg Arg Ala Val Ser Arg Pro Ala Ala
    1520                    1525                    1530

Ala Thr Ala Val Pro Leu Ala Asp Arg Leu Gly Thr Met Ser Gly
    1535                    1540                    1545

Ala Glu Arg Asp Thr Ala Leu Leu Ala Leu Val Arg Asp Asn Ala
    1550                    1555                    1560

Ala Ala Val Leu Gly His Ala Asp Ala Ala Asp Val Ser Ala Asp
    1565                    1570                    1575

Ala Ala Phe Lys Glu Leu Gly Ile Asp Ser Leu Thr Ala Val Glu
    1580                    1585                    1590

Leu Arg Asn Arg Leu Ala Ala Ala Thr Gly Val Arg Leu Pro Ala
    1595                    1600                    1605

Thr Leu Val Phe Asp Tyr Pro Thr Pro Arg Ala Ile Ala Ser Arg
    1610                    1615                    1620

Leu Asp Glu Ala Leu Val Gly Gly Ala Ala Pro Val Ala Val Pro
    1625                    1630                    1635

Thr Ala Ala Ala Thr Arg Asp Glu Pro Leu Ala Ile Val Gly Met
    1640                    1645                    1650

Ala Cys Arg Leu Pro Gly Gly Val Thr Ser Pro Asp Asp Leu Trp
    1655                    1660                    1665
```

-continued

```
Arg Met Val Asp Ser Gly Gly Asp Ala Val Thr Gly Phe Pro Ala
    1670                1675                1680

Asp Arg Gly Trp Asp Pro Ser Gly Leu Thr Gly Gly Ser Asp Thr
    1685                1690                1695

Asp Arg Gly Gly Phe Leu Ser Asp Ala Ala Gly Phe Asp Ala Ala
    1700                1705                1710

Phe Phe Gly Ile Ser Pro Arg Glu Ala Arg Ala Met Asp Pro Gln
    1715                1720                1725

Gln Arg Ile Leu Leu Glu Thr Thr Trp Glu Ala Phe Glu Ser Ala
    1730                1735                1740

Gly Ile Val Pro Gly Thr Leu Arg Gly Ser Asp Thr Gly Val Phe
    1745                1750                1755

Met Gly Ala Phe Ser Tyr Gly Tyr Gly Val Gly Ala Asp Leu Asp
    1760                1765                1770

Gly Phe Gly Ser Ile Gly Met Gln Pro Ser Val Leu Thr Gly Arg
    1775                1780                1785

Ile Ser Tyr Phe Tyr Gly Leu Gln Gly Pro Ala Phe Thr Val Asp
    1790                1795                1800

Thr Ala Cys Ser Ser Ser Leu Val Ala Leu His Gln Ala Gly His
    1805                1810                1815

Ala Leu Arg His Gly Glu Cys Ser Leu Ala Leu Val Gly Gly Val
    1820                1825                1830

Thr Val Met Ala Thr Pro Thr Gly Phe Val Glu Phe Gln Gln Gln
    1835                1840                1845

Gly Gly Leu Ser Pro Asp Gly Arg Cys Arg Ala Phe Ala Asp Ala
    1850                1855                1860

Ala Asn Gly Thr Gly Trp Ala Glu Gly Ala Gly Val Leu Val Leu
    1865                1870                1875

Glu Arg Leu Ser Asp Ala Glu Arg Asn Gly His Thr Val Leu Ala
    1880                1885                1890

Val Val Arg Gly Ser Ala Val Asn Gln Asp Gly Ala Ser Asn Gly
    1895                1900                1905

Leu Ser Ala Pro Asn Gly Pro Ser Gln Arg Val Ile Gln Gln
    1910                1915                1920

Ala Leu Val Asn Ala Gly Leu Arg Ala Ala Asp Val Asp Val Val
    1925                1930                1935

Glu Ala His Gly Thr Gly Thr Thr Leu Gly Asp Pro Ile Glu Ala
    1940                1945                1950

Gln Ala Ile Leu Ala Thr Tyr Gly Gln Glu Arg Glu Val Pro Leu
    1955                1960                1965

Leu Leu Gly Ser Leu Lys Ser Asn Ile Gly His Ala Gln Ala Ala
    1970                1975                1980

Ala Gly Val Ala Gly Val Ile Lys Met Val Met Ala Met Arg Tyr
    1985                1990                1995

Gly Ile Ala Pro Lys Thr Leu His Val Asp Glu Pro Ser Ser His
    2000                2005                2010

Val Asp Trp Ser Ala Gly Ala Val Glu Leu Leu Thr Glu Ala Arg
    2015                2020                2025

Pro Trp Pro Glu Ser Asp Arg Ala Pro His Ala Gly Val Ser Ser
    2030                2035                2040

Phe Gly Val Ser Gly Thr Asn Ala His Val Ile Leu Glu Gly Val
    2045                2050                2055
```

-continued

Pro Gly Pro Ser Arg Gly Glu Ser Val Val Asp Gly Leu Val Pro
2060                     2065             2070

Leu Pro Val Ser Ala Arg Gly Glu Val Ser Leu Arg Gly Gln Val
2075                     2080             2085

Glu Arg Leu Glu Gly Tyr Leu Arg Gly Gly Val Asp Val Ala
2090                     2095             2100

Ala Val Ala Gln Gly Leu Val Arg Glu Arg Ala Val Phe Gly His
2105                     2110             2115

Arg Ala Val Leu Leu Gly Asp Ala Arg Val Thr Gly Val Ala Val
2120                     2125             2130

Asp Gln Pro Arg Thr Val Phe Val Phe Pro Gly Gln Gly Ala Gln
2135                     2140             2145

Trp Val Gly Met Gly Val Glu Leu Met Ala His Ser Ala Val Phe
2150                     2155             2160

Ala Ala Arg Met Glu Glu Cys Ala Gln Ala Leu Leu Pro His Thr
2165                     2170             2175

Gly Trp Asp Val Arg Glu Met Leu Ala Arg Pro Asp Val Ala Glu
2180                     2185             2190

Arg Val Glu Val Val Gln Pro Ala Ser Trp Ala Val Ala Val Ser
2195                     2200             2205

Leu Ala Ala Leu Trp Gln Ala His Gly Val Val Pro Asp Ala Val
2210                     2215             2220

Ile Gly His Ser Gln Gly Glu Ile Ala Ala Ala Cys Val Ala Gly
2225                     2230             2235

Ala Leu Ser Leu Glu Asp Ala Ala Arg Val Val Ala Leu Arg Ser
2240                     2245             2250

Gln Val Ile Ala Ala Arg Leu Ala Gly Arg Gly Ala Met Ala Ser
2255                     2260             2265

Val Ala Leu Pro Ala Gly Glu Val Gly Leu Val Glu Gly Val Trp
2270                     2275             2280

Ile Ala Ala Arg Asn Gly Pro Ala Ser Thr Val Val Ala Gly Asp
2285                     2290             2295

Pro Ser Ala Val Glu Glu Val Val Ala Arg Tyr Glu Ala Glu Gly
2300                     2305             2310

Val Arg Val Arg Arg Ile Ala Val Asp Tyr Ala Ser His Thr Pro
2315                     2320             2325

His Val Glu Ala Ile Glu Asp Glu Leu Ala Lys Val Leu Glu Gly
2330                     2335             2340

Val Ala Gly Lys Ala Ala Ser Val Ala Trp Trp Ser Thr Val Asp
2345                     2350             2355

Ser Ala Trp Val Thr Glu Pro Val Asp Glu Gly Tyr Trp Tyr Arg
2360                     2365             2370

Asn Leu Arg Arg Pro Val Ala Leu Asp Ala Ala Val Ala Glu Leu
2375                     2380             2385

Asp Gly Ser Val Phe Val Glu Cys Ser Ala His Pro Val Leu Leu
2390                     2395             2400

Pro Ala Met Glu Gln Ala His Thr Val Ala Ser Leu Arg Thr Gly
2405                     2410             2415

Asp Gly Gly Trp Glu Arg Trp Leu Thr Ala Leu Ala Gln Ala Trp
2420                     2425             2430

Thr Leu Gly Thr Ala Val Asp Trp Asp Thr Val Val Glu Pro Val
2435                     2440             2445

Pro Gly Arg Leu Leu Asp Leu Pro Thr Tyr Ala Phe Glu His Arg

-continued

|     | 2450 |     |     | 2455 |     |     |     | 2460 |     |     |
|---|---|---|---|---|---|---|---|---|---|---|

Arg Tyr Trp Leu Glu Ala Ala Gly Ala Thr Asp Leu Ser Ala Ala
2465          2470              2475

Gly Leu Thr Gly Ala Ala His Pro Met Leu Ala Ala Val Thr Ala
2480          2485              2490

Leu Pro Ala Asp Asp Gly Gly Val Val Leu Thr Gly Arg Ile Ser
2495          2500              2505

Leu Arg Thr His Pro Trp Leu Ala Asp His Ala Val Arg Gly Thr
2510          2515              2520

Val Leu Leu Pro Gly Thr Ala Phe Val Glu Leu Val Ile Arg Ala
2525          2530              2535

Gly Asp Glu Thr Gly Cys Gly Ile Val Asp Glu Leu Val Ile Glu
2540          2545              2550

Ser Pro Leu Val Val Pro Val Thr Ala Ala Val Asp Val Ser Val
2555          2560              2565

Thr Val Glu Gly Ala Asp Glu Ala Gly Arg Arg Pro Val Thr Val
2570          2575              2580

His Ala Arg Thr Glu Gly Thr Gly Ser Trp Thr Arg His Ala Ser
2585          2590              2595

Gly Thr Leu Thr Pro Asp Thr Pro Asp Thr Pro Gly Val Val Gly
2600          2605              2610

Val Glu Pro Phe Ser Gln Trp Pro Pro Val Thr Ala Val Ala Val
2615          2620              2625

Asp Val Ser Gly Phe Tyr Asp Glu Leu Arg Asp Ala Gly Tyr Glu
2630          2635              2640

Tyr Gly Ser Ala Phe Gln Gly Leu Arg Ala Ala Trp Arg Asp Gly
2645          2650              2655

Asp Thr Val Tyr Ala Glu Val Ala Leu Pro Asp Glu Gln Ala Ala
2660          2665              2670

Glu Ala Asp Gly Phe Gly Val His Pro Ala Leu Leu Asp Ala Ala
2675          2680              2685

Leu His Ala Val Ala Leu Thr Thr Pro Asp Asp Ser Ala Ala Gly
2690          2695              2700

Leu Pro Phe Ala Trp Lys Gly Ala Arg Phe Val Ala Thr Gly Ser
2705          2710              2715

Ala Met Leu Arg Ala Val Ile Thr Arg Asp Gly Asp Glu Leu Ser
2720          2725              2730

Leu Arg Val Ala Asp Ser Ala Gly Gln Leu Val Ala Glu Ile Arg
2735          2740              2745

Thr Val Arg Thr Arg Pro Leu Ser Pro Pro Val Gly Thr Gly Leu
2750          2755              2760

Met Arg Leu Thr Trp Ile Glu Val Ala Ala Pro Thr Asp Val Pro
2765          2770              2775

Ala Thr Asp Val Asp Val Ile Thr Leu Pro Ala Ala Asp Gly Asp
2780          2785              2790

Asp Pro Val Ala Glu Thr Arg Ala Leu Thr Thr Arg Leu Leu Thr
2795          2800              2805

Ala Leu Thr Gly Ser Gly Gly Asp Leu Leu Val His Thr Thr Ala
2810          2815              2820

Gly Leu Ala Thr Gly Ala Ala Ala Gly Leu Leu Arg Ala Ala Gln
2825          2830              2835

Ala Glu Gln Pro Gly Arg Phe Val His Val Glu Thr Glu Ser Gly
2840          2845              2850

-continued

Val Thr Leu Ala Pro Glu Gln Gln Arg Ile Ala Val Ala Leu Gly
        2855                2860                2865

Glu Pro Arg Leu Arg Leu Arg Gly Gly Arg Phe Glu Ala Ala Arg
        2870                2875                2880

Leu Thr Arg Val Pro Glu Pro Leu Thr Val Pro Asp Ser Asp Thr
        2885                2890                2895

Trp Leu Ile Arg Pro Ala Arg Thr Gly Thr Leu Asp Gly Leu Thr
        2900                2905                2910

Ala Ala Asp Ser Ala Glu Pro Arg Arg Pro Leu Ala Pro Ala Glu
        2915                2920                2925

Val Arg Ile Gly Val Arg Ala Ala Gly Leu Asn Phe Arg Asp Val
        2930                2935                2940

Leu Ile Ala Leu Gly Thr Tyr Pro Gly Gln Gly Val Leu Gly Gly
        2945                2950                2955

Glu Ala Ala Gly Ile Val Leu Glu Thr Gly Ala Asp Val Ser Gly
        2960                2965                2970

Leu Ala Pro Gly Asp Arg Val Phe Gly Leu Val Gly Thr Gly Phe
        2975                2980                2985

Gly Pro Thr Val Ile Ala Asp His Arg Met Leu Gly Arg Met Pro
        2990                2995                3000

Asp Gly Trp Thr Phe Pro Gln Ala Ala Ser Val Met Thr Ala Phe
        3005                3010                3015

Ala Thr Ala Trp Tyr Gly Leu Val Asp Leu Ala Gly Leu Arg Pro
        3020                3025                3030

Gly Glu Lys Val Leu Ile His Ala Ala Thr Gly Gly Val Gly Ser
        3035                3040                3045

Ala Ala Arg Gln Ile Ala Arg His Leu Gly Ala Glu Val Tyr Ala
        3050                3055                3060

Thr Thr Ser Ala Ala Lys Arg His Leu Val Asp Leu Asp Gly Ala
        3065                3070                3075

His Leu Ala Asp Ser Arg Ser Thr Ala Phe Ala Asp Ala Phe Pro
        3080                3085                3090

Pro Val Asp Val Val Leu Asn Ser Leu Thr Gly Glu Leu Leu Asp
        3095                3100                3105

Ala Ser Val Gly Leu Leu Ala Pro Gly Gly Arg Phe Ile Glu Met
        3110                3115                3120

Gly Lys Thr Asp Ile Arg His Ala Val Gln Arg Pro Phe Asp Leu
        3125                3130                3135

Met Asp Ala Gly Pro Asp Arg Leu Lys Glu Ile Ile Ala Glu Leu
        3140                3145                3150

Leu Gly Leu Phe Ala Arg Gly Val Leu His Pro Leu Pro Val Thr
        3155                3160                3165

Val His Asp Met Arg Gln Val Arg Glu Ala Leu Ala Thr Met Ser
        3170                3175                3180

Arg Gly Glu His Thr Gly Lys Ile Val Leu Thr Val Pro Arg Pro
        3185                3190                3195

Leu Asp Pro Glu Gly Ala Val Val Ile Thr Gly Gly Ser Gly Thr
        3200                3205                3210

Leu Ala Gly Ile Leu Ala Arg His Leu Asn His Pro His Thr Tyr
        3215                3220                3225

Leu Leu Ser Arg Thr Pro Pro Pro Asp Thr Thr Pro Gly Thr His
        3230                3235                3240

```
Leu Pro Cys Asp Val Gly Asp Pro His Gln Leu Ala Thr Thr Leu
    3245                3250                3255

Ala His Ile Pro Gln Pro Leu Thr Ala Val Phe His Thr Ala Gly
    3260                3265                3270

Thr Leu Asp Asp Ala Leu Leu Asp Asn Leu Thr Pro Asp Arg Ile
    3275                3280                3285

Asp Thr Val Leu Lys Pro Lys Ala Asp Ala Ala Trp His Leu His
    3290                3295                3300

Arg Leu Thr Arg Asp Thr Asp Leu Ala Ala Phe Val Val Tyr Ser
    3305                3310                3315

Ser Ala Ala Gly Val Leu Gly Thr Pro Gly Gln Gly Asn Tyr Ala
    3320                3325                3330

Ala Ala Asn Ala Phe Leu Asp Ala Leu Ala Glu His Arg Arg Ala
    3335                3340                3345

Gln Gly Leu Pro Gly Leu Ser Ile Ala Trp Gly Leu Trp Asp Gln
    3350                3355                3360

Ala Ser Gly Leu Thr Ala Asp Leu Thr Asp Ala Asp Arg Arg Arg
    3365                3370                3375

Met Arg Lys Gly Gly Ala Ser Ala Leu Thr Ala Glu Gln Gly Met
    3380                3385                3390

Arg Met Tyr Asp Ala Ala Val His Thr Gly Thr Gly Ser Val Val
    3395                3400                3405

Ala Val Ala Gly Asp Leu Pro Pro Asp Leu Pro Leu Leu Arg Gly
    3410                3415                3420

Arg Pro Lys Pro Ser Ala Arg Arg Ser Ala Arg Asn Glu Gln Glu
    3425                3430                3435

Arg Pro Thr Asp Leu Leu Ala Leu Val Arg Gln Lys Ala Ala Ala
    3440                3445                3450

Val Leu Gly His Ala Asp Pro Glu Asp Ile Pro Glu Asp Ala Ala
    3455                3460                3465

Phe Arg Glu Leu Gly Val Asp Ser Leu Ile Ala Val Gln Leu Arg
    3470                3475                3480

Asn Gly Leu Asn Glu Ala Thr Gly Leu Arg Leu Ser Ala Thr Leu
    3485                3490                3495

Val Phe Asp Tyr Pro Ser Pro Arg Ala Leu Ala Asp Arg Ile Gly
    3500                3505                3510

Glu Leu Leu Ser Pro Asp Asp Pro Val Thr Val Leu Ala Gln
    3515                3520                3525

Leu Asp Arg Leu Glu Ala Leu Val Ala Gly Val Asp Pro Gly Ala
    3530                3535                3540

Arg Gln Ala Asp Ala Ile Gly Thr Arg Leu Asp Ala Leu Leu Asn
    3545                3550                3555

Arg Trp Arg Arg Glu Thr Arg Pro Thr Thr Pro Ala Gly Val Leu
    3560                3565                3570

Ser Ala Asp Ala Thr Ala Asp Glu Ile Phe Asp Leu Ile Asp Arg
    3575                3580                3585

Glu Leu Arg
    3590

<210> SEQ ID NO 75
<211> LENGTH: 1600
<212> TYPE: DNA
<213> ORGANISM: Streptomyces hygroscopicus

<400> SEQUENCE: 75
```

```
atggcgcgtg tggaaccaat ccggccgttg cacgaattgc tccgcatcca tgccgagcga        60
cgcggcgacc ggatcgccta cacggattcc caacgcgccg tgacgtacac gcaactccgg       120
ctccgggccg gccggctcgc cggacacctc gccgcgtccg cgtcgaccg cggcgaccgg        180
gtcgcgatgc tgctcggcaa ccggatcgag accatcgagg tctacctcgc cgccgcccgc      240
gccgccgccg tcgccgtccc gctcaacccg gacgccgccg acgccgaact cgcccacttc      300
ctgacggact ccggcgcgac cgtgctggtc accgacgaaa cccacctcga ccaggtgcgc      360
cgcaccggca ccgacgccac cgtcgtgctc gtcgggcgcc gggcaccgga ctgcgtctcc      420
tacgaggacc tcgccgggac cgagccgccg tgcccgcccc gcgacgacct cggcctggac      480
gaacccgcct ggatgctcta cacctccggc accaccggcc gtcccaaggg cgtggtttcc      540
gcacagcgca gcggcctgtg gtccgcgatg cactgcgacg tgccgtcctg gcggctgacc      600
gaggacgacg aactgctctg gcccgccccg ctgttccaca gcctcggcca ccacctctgc      660
ctgctcgccg tcctcacggt cggcgcgtcc gcccgtatcc tgggcggctt cgtcgcgcgt      720
gacgtcctcg acgccctggc cgaacactcc agcaccgtgc tcgtcggcgt gccgacgatg      780
taccgctacc tcctcggcgc cgtgtccggc gagccgcggg ctcgcgcgct cgcgcgtggcg     840
ctggtcgccg gatccacctc gccggcgtcg ctcaccaggg atttcgaggc gacgttcggc      900
gtgcccctgc tcgacacgta cggctgcacc gagacgaccg gctcgctcac cgccaacacc      960
ctggaggatg cgcggggttcc cggctcgtgc gggctgcccg tgccgggcct gtcgctgcgg    1020
ttcgtcgacc cggtgtccgg cgccgacgtg cacccggcg aggagggcga gctgtgggcg     1080
agcggggccga gcctcatgct cggctaccac gcccagccgg aggcgaccgc ccaggtgctc     1140
gtggacggct ggtaccgcac cggggacctc gcacgtcagg ccgagaccgg acacgtgacg    1200
atcaccggcc gggtcaagga gctgatcatc cgcggcgggg agaacatcca ccccgggag    1260
atcgagaccc tcgcccagga ggtggccggt gtccgggacg ccgccgcggc gggccgcccg     1320
caccccgtcc tcggcgacat acccgtgctc tacgtcgttt ccgacggccc ccgcgtcccc    1380
gccgaggcga tcctcgccga gtgccgccgc cggctcgcct acttcaaggt gcccgacgag    1440
atctggcacg tcaccacgat ccccgcacc gcgtcgggca aggtccagcg cgcgcggctc      1500
gcggggctgc cggcccatct ggtcgccacc ggcagtggcg aggccacgct gtgcgaactg    1560
gtctgggagc ggcgcgacct gcccggcacc ccgtcacccc                          1600
```

<210> SEQ ID NO 76
<211> LENGTH: 853
<212> TYPE: DNA
<213> ORGANISM: Streptomyces hygroscopicus

<400> SEQUENCE: 76

```
ggcgaggtcc gcatcgacgt ccgcgccgcg gggctgaact tccgcgacgt gctgatcgcg        60
ctcggcacct acccgggcga gggcgagatg ggcggggagg ccgcgggcat cgtgaccgaa      120
gtcggacccg cgtcgacga cctgccccc ggcgaccgcg tgttcggtct cgtgcaggac       180
gcgttccggc gcagcgtggt cgcggaccgg cggctggtcg cacggatccc acggggatgg    240
tcgttcccca tcgccgcgtc cgtgcccatc gtgttcgcca ccgcctggta cggcctcgtc     300
gacgcgggcg agctgcgacc cggccagaag gtcctggtca acgccgcgac gggcggtgtc    360
ggcatggcgg cgaccggat cgcccgccac ctcggcgccg aggtgtacgc caccgccagt    420
cccgccaaac aacacctgct gcacgccgac ggcttcgaca ccgaccatgt ggcgaactcc    480
```

| | |
|---|---:|
| cgcagcgccg cgttcgccga caccttcccg ccggtcgacg tcgtgctcaa ctcgctcacc | 540 |
| ggtgaactcc tcgacgcgtc catcggcctg ctcgcaccgg gcggccggtt cgtcgagatg | 600 |
| ggcaagaccg acatccgcca cgccgcccag cagccgttcg acctggccga cgtggatccc | 660 |
| gcgcgcctgc gggagatcct cgaactgctc ctcgacctgt tcgaccgcgg tgagctgtgc | 720 |
| ccgctgccgg tgcagccgtg ggacatccgc cgtgcgcggg acgcgttcgc gtggatgagc | 780 |
| cacgcccggc acaccggcaa gatggtcctc accgtgccgc ctccgatcgg cccggacgcg | 840 |
| ccggtcctgg tca | 853 |

<210> SEQ ID NO 77
<211> LENGTH: 517
<212> TYPE: DNA
<213> ORGANISM: Streptomyces hygroscopicus

<400> SEQUENCE: 77

| | |
|---|---:|
| gacggcccgg ccggcgccga cgcccacacc cggccacggg ccgcggaggg actccccacc | 60 |
| gtcaccgtcc gcgcgctgcc cggcatcgaa cggccggcgc tcaccggcga cctgatcgag | 120 |
| aaggccatcg cgggcggcgg ctcgtacatc gtgcccgga ccggttccgc cggggcgcgg | 180 |
| gccgcgacga tggcgggcgc cacgccgccg atcctcaccg cactgaccgg accggccgag | 240 |
| cccgacgcca cggaacagga gtgggcgaac cgcctcgccg cggcccgtgc gggccgggag | 300 |
| gacgtactgc tcgacctggt ccgcgacagc gtcgccaccg tcctgggcct gccgggcgcc | 360 |
| ggacactgct ccccggaccg cacgttccgc gagaacggcc tcgactgct caccaccgtc | 420 |
| gagttcacca acaccgtcgc cgcgcggacg ggtctgcggg tgcccgcgtc aaccgcgttc | 480 |
| gaccaccca ctccgcgtgc gttcgccgcc cacctcg | 517 |

<210> SEQ ID NO 78
<211> LENGTH: 1252
<212> TYPE: DNA
<213> ORGANISM: Streptomyces hygroscopicus

<400> SEQUENCE: 78

| | |
|---|---:|
| gaccccgtcg cgatcgtcgg catggcgtgc cgactgcccg gcggggtcgc ctcgccggag | 60 |
| gacctgtggc ggctcgtcgc cgccggtacc gaggcgatca ccgagttccc caccgaccgg | 120 |
| ggctgggacg tcgacgcgct gtacgacccg gacccggacg cggccggccg ctccacgaca | 180 |
| cgccacggcg gattcctggc cggcgccggg ttcgacgccg cgttcttcgg catcagtccg | 240 |
| aacgaggcgc tggcgatgga cccccagcag cgcctgatcc tggagacctc ctgggaggcg | 300 |
| ttcgagaacg ccggcatcgt gccggacagg ctccggagga cgacaccgg cgtgttcatg | 360 |
| ggcgcgttca accagggcta cggcgtcggc cgggacctgg gcgggctcgg tgtcacggcg | 420 |
| acgcagacga gcgtcctgtc cgggcgcctc tcgtacgtgt acggacttca gggcccggcg | 480 |
| gtcacggtcc acacggcgtg ctcgtcgtcg ctggtcgccc tgcaccaggc ggcacaggca | 540 |
| ctgcgggccg gggagtgctc cctggcgctg gtcggcggtg tcaccgtcat ggcgaacacc | 600 |
| gcagagctcg tggagttctc ccggcagcgc ggactctccc cggacggacg gtgcaaggcg | 660 |
| ttcgccgacg cggcggacgg gaccggcttc gccgagggcg tcggcgttct cgtgctggag | 720 |
| cggctctccg acgccgagcg caacgggcac accgttctcg cggtcgtccg cggctcggcg | 780 |
| gtgaaccagg acggtgcctc caacggactg tccgccccca acggcgtcgc ccagcagcgc | 840 |
| gtgatccggc aggcgttggt caacgccgga ctgcgcgccg ccgatgtgga cgtggtggag | 900 |
| gcgcacggca ccggcacgcg gctgggcgac ccgatcgagg cgcaggccgt cctcgcggcc | 960 |

| | |
|---|---|
| tacgggcagg accgcgacac gccgctctac ctcggttcgg tcaagtcgaa catcggtcat | 1020 |
| gcgcaggcgg ctgcgggtgt cgccggtgtc atcaagatgg tcatggcgat gcggcatggg | 1080 |
| atcgcgccga agacgctgca cgtggacgag ccgtcgtcgc atgtggactg gtcggccggt | 1140 |
| gcggtggagc tgctcaccga ggcgaggccg tggcccgagt cggatcgggc accgcatgcg | 1200 |
| ggtgtgtcgt cgttcggggt gagcggtacg aacgcgcacg tgatcctgga gg | 1252 |

<210> SEQ ID NO 79
<211> LENGTH: 1234
<212> TYPE: DNA
<213> ORGANISM: Streptomyces hygroscopicus

<400> SEQUENCE: 79

| | |
|---|---|
| ggtgttcctg ggccgtcgcg tgtggagtcg ggtggtgatg ggttggtgcc gttgccggtg | 60 |
| tcggctcgtg gtgaggtgag tctgcggggg caggtggagc ggctggaggg gtatctgcgc | 120 |
| gggggtgggg tggatgtggc cgcggtcgcg caggggttgg tgcgtgagcg tgctgtcttc | 180 |
| ggtcaccgtg cggtgctgct gggtgatgcc cgggtgatgg gtgtggcggt ggatcagccg | 240 |
| cgtacggtgt tcgtcttccc cgggcagggt gcccagtggg tgggcatggg cgtggaactc | 300 |
| atggaccgtt ccgcggtgtt cgcggctcgt atggaggagt gtgcgcgggc gttgttgccg | 360 |
| cacacgggct gggatgtgcg ggagatgttg tcgcggtcgg atgtggcgga gcgggtggag | 420 |
| gtggtccagc cggccagctg ggcggtcgcg gtgagcctgg ccgcgctgtg gcaggcgcat | 480 |
| ggggtcgtgc cggacgctgt ggtcggacac tcgcaggggg agatcgcggc ggcgtgtgtg | 540 |
| gccggagccc tcagcctgga ggacgccgcc cgcgtggtgg cgttgcgcag tcgggtgatc | 600 |
| gcggcgcggc tggccggccg gggggcgatg gcttcggtgg cgttgccggc cggtgaggtg | 660 |
| ggtctggtcg agggtgtgtg gatcgcggcg cgtaatggtc cggcttcgac ggtggtggcg | 720 |
| ggggacccgt cggcggtgga ggaggtggtg gcgcggtatg aggctgatgg ggtgcgggtg | 780 |
| cgtcgtatcg cggtcgacta cgcctcccac acgcctcacg tggaggccat cgaggacgaa | 840 |
| ctcgctgagg tactgaaggg aatttccggc gggaccgggt cggtggcgtg gtggtcgacc | 900 |
| gtggacagcg cctgggtgac cgagccggtg gatgaggggt actggtaccg gaacctgcgt | 960 |
| cgccctgtcg cgctggatgc ggcggtggcg gagctggacg ggtcggtgtt cgtggagtgc | 1020 |
| agtgcccatc cggtgctgct gccggcgatg gaacaggccc gcacggtggc gtcgttgcgg | 1080 |
| actggtgacg gtggctggga gcggtggctg ggggcgttgg cgcaggcgtg gactctgggt | 1140 |
| gcggggggtgg actggggcac ggtggtcgaa ccggtgccgg ggcggctgct ggatctgccc | 1200 |
| acctacgcgt tcgagcacag gcggtactgg ctgg | 1234 |

<210> SEQ ID NO 80
<211> LENGTH: 1168
<212> TYPE: DNA
<213> ORGANISM: Streptomyces hygroscopicus

<400> SEQUENCE: 80

| | |
|---|---|
| gaggcggccg gtgccaccga cctgtccgcg gccgggctga ccggggcggc gcatccgatg | 60 |
| ctggccgccg tcacagcact gcccgccgac gacggtggtg gtgttgttct caccggccgg | 120 |
| atctcattgc gtacgcatcc ctggctggct gatcacgcg tgcggggcac ggttctgctg | 180 |
| ccgggtacgg cgtttgtgga gctggtcatc cgggccggtg acgagaccgg ttgcggggtg | 240 |
| gtggatgaac tggtcatcga atccccgctc gtggtgccgg tgaccgcagc ggtggatgtg | 300 |

-continued

```
tcggtgaccg tggaaggggc cgatgaggcc ggacggcggc cggtgaccgt ccacgcgcgt      360
accgagggca cgggcagctg gacccggcac gccagcggca ccctgacccc cgacaccccg      420
gatacctcca acgcttccgg tgagccgttc tcgcagtggc cgccggccac ggccgcggcc      480
gtcgacgtct cggggttcta tgacgaactg cgggatgccg gttatgagta cgggtcggcg      540
ttccaggggt tgcgggctgc ctggcgtgat ggtgacaccg tgtatgccga ggtggcgctg      600
cccgacgagc aggccgccga gcggacggt ttcgtgtgc atccggcact gctcgacgcg       660
gccctgcacg ccgggcgcct cgacgcgggc ggcgggatcg agctgccgtt ctcctggacg      720
ggcgtgcgcc tgaacgccac cggggccgcc gcggtgcgcg tcgccctcac ccgggggggag     780 gccggcgtcg ccgtgcgcgt ggccgacccg gatggccgtc ctgtcgtgtc ggtggactcg      840
ctggtgctga gggagcgggc cgacaccccg tcggggccga accgctccg gttggagtgg       900 ctcgcggtcg ccgaggcggt ctacgacggt gacctgcccg agggacacgt cctgatcacc      960
gccgcccacc ccgacgaccc cgaggacata cccacccgcg cccacacccg cgccaccgc     1020 gtcctgaccg ccctgcaaca ccacctcacc accaccgacc acaccctcat cgtccacacc    1080
accaccgacc ccgccggcgc caccgtcacc ggcctcaccc gcaccgccca gaacgaacac    1140
ccccaccgca tccgcctcat cgaaaccg                                        1168
```

<210> SEQ ID NO 81
<211> LENGTH: 631
<212> TYPE: DNA
<213> ORGANISM: Streptomyces hygroscopicus

<400> SEQUENCE: 81

```
ctcaaccccg aacacgccat catcatcacc ggcggctccg gcaccctcgc cggcatcctc       60
gcccgccacc tgaaccaccc ccacacctac ctcctctccc gcaccccacc ccccgacacc      120 accccggca cccacctccc ctgcgacgtc ggcgaccccc accaactcgc caccaccctc       180
gcccacatcc cccaaccccct caccgccgtc ttccacaccg ccgccaccct cgacgacggc     240
atcctcgacg ccctcacccc cgaccgcctc accaccgtcc tccacccaa agccaacgcc     300 gcctggcacc tgcaccacct cacccaaaac caaccccctca cccacttcgt cctctactcc     360
agcgccgccg ccgtcctcgg cagccccgga caaggaaact acgccgccgc caacgccttc      420
ctcgacgccc tcgccaccca ccgccacacc ctcggccaac ccgccacctc catcgcctgg      480
ggcatgtggc acaccaccag cacccctcacc ggacaacttg acgacgccga ccggcagcgg     540
gtgcgcgacg ggttccggcc gctcaccgag gccgagggca cccacttcat cgacgcgagc     600
ctcgccgcgg acgtgccgtt catggtcgcg g                                    631
```

<210> SEQ ID NO 82
<211> LENGTH: 211
<212> TYPE: DNA
<213> ORGANISM: Streptomyces hygroscopicus

<400> SEQUENCE: 82

```
ctgctggcca tcgtgtgtgc ggccacggcc gccgtgctcg ccacgccga cgcctccgag        60 atcacgccca cgacggcgtt caaggacctc ggcatcgact cgctcagcgg tgtccggttg      120
cgcaacagcc tcgccgagac gacggggta cggctctccg cgacggccgt cttcgaccac      180
ccgacaccgg ccgcgctcgc cgcccgcctg g                                    211
```

<210> SEQ ID NO 83
<211> LENGTH: 1152

```
<212> TYPE: DNA
<213> ORGANISM: Streptomyces hygroscopicus

<400> SEQUENCE: 83
gagccgctgg cgatcgtggc catggcgtgc cggatgcccg gtggcgtgcg gtcaccggag    60
gacctgtggc ggctggtcga ctccggcggg gacgcgatca ccgagttccc cgccgaccgc   120
ggctgggacc tcgccgcgct ctacgacccg aaccccgacg cggtcggcaa ggtttccgtg   180
cgtcacggcg gcttcctcac cggcgccgcc gacttcgacg ccgcgttctt cgggatcagc   240
ccgcgtgagg cgctggcgat ggacccgcag cagcgtctgg tcctcgaagc gtcgtgggag   300
gcgttcgaac gagcgggcat cctgcccgaa agcgtccgcg gcagcgacac cggcgtattc   360
atgggcgcgt tcacccaggg ctacggcgcg gcgtggacc  tgggcggttt cggggcgacc   420
ggcacgccga ccagcgttct ctccggcgg  ctctcgtact acttcggtct ggagggcccg   480
tcggtcaccg tcgacacggc gtgttcgtcg tcgctggtgg cgctgcacca ggccgcgcgg   540
tcgctgcgct cggggagtg  ctcgctcgcc ctggtcggcg gtgtcacggt gatggcgacg   600
acgaccgggt tcgtcgagtt ctcccggcag cgcgggctcg cccccgacgg ccgtgccaag   660
gccttcgcgg acaccgcgga cggcacgagc ttcgccgagg gcgccggtgt cctggtgctg   720
gagcggctct ccgacgccac ccgccacggc caccccgtgc tggcgctggt gcgcggctcc   780
gcggtcaact ccgacggcgc gtcgaacggg ctgtccgccc cgaacgggcc tgcgcagcag   840
cgcgtcatcc agcgtgcgct cgccgacgcc ggcctggcgc cgggtgacgt cgacgccgtg   900
gaggcacacg gcaccggcac ccgtctcggc gaccccgtcg aggcccaggc cctgcaagtg   960
gcctacgggc gcgaacgcgt gcatccgctg ctgatcggct cgctcaagtc gaacatcggc  1020
cacacccagg ccgcggccgg cgtcgccggc gtcatcaaga tggtcatggc gatgcggcac  1080
ggcgtcctgc cgcgcacgct gcacgtcgac gagccgtccc ggcacgtcga ctgggacggc  1140
gacatccggc tg                                                       1152

<210> SEQ ID NO 84
<211> LENGTH: 1396
<212> TYPE: DNA
<213> ORGANISM: Streptomyces hygroscopicus

<400> SEQUENCE: 84
ctgcaccgca gtgagccgtg gccggtcacc gggcgcgccc ggcgtgcggg tgtctcgtcg    60
ttcggcatca gcggcaccaa cgcccatgtc gtcctggagg ccgggccccc cgccgcgccc   120
gcacccgtgt ccgcacccga agccgagccg gtgcccgagg acgtggtctg gccgatgtcg   180
gcccggaccc cggagggact gcgggacgtc gcgggacagc tggccccgct cactggcgcc   240
gcggccgcgg tcggccactc gctcgccacc acccggacgg ccatgcgcca ccgggcggtc   300
gtgcggcccc gagaggcgga ggcgttcgcc cgtggtgccg aagtgccggg ggccgtgacg   360
ggaaccgccg acgtcaccga cacgtgtc gtgttcgcgt tccccgggca gggctcccag   420
tgggccggca tgggtgccga actgctgccc accgagcccg tgttcgcccg gcggctccgc   480
gagtgcgcca cggcgctcgc cccgcacacc ggatgggacc tgctggacgt catcgcccag   540
cggcccggag cgcccgcgtt cgaccgggtc gatgtcgtgc agcccgcgtc gttcgcggtg   600
atggtggcgc tggcggagct gtggcgtgcg cacggggtcg cccccggccgc ggtcgtcggc   660
cactcccagg gcgaagtcgc cgcggcctgc gtcgccgggg tgctcaccct ggacgacgcc   720
gcgaaggtcg tcgcggtgcg cagccgactc gtcgccaccg aactggccgg gcagggcggc   780
```

| | |
|---|---|
| atggtctcgg tgccgcccgc cgacttcgac gccgccgtgt gggccgggcg cctggaggtc | 840 |
| gccgcggtca acggacccgc gtcgatcgtt gtcgccggtg cggccgacgc cgtggaggag | 900 |
| ctgctggccg ccacccccg cgcccgccgg atcgccgtcg actacgcgtc gcacaccgcg | 960 |
| catgtcgaaa cgatccgcgg cgcgctgctc gacgctctcg ccggcatcac tccgcgcacg | 1020 |
| ccggacgtcc cgttcttctc caccgtggac gaggcgtggc tggaccggcc gcggacgcc | 1080 |
| gcctactggt acgacaacct cgccgcacc gttcggttcg ccgccgcgac cggccacctg | 1140 |
| gcggaccgcg ataccgcgc gttcgtcgag gtcagcgcgc atcccgtgct caccaccgca | 1200 |
| ctggaggaca cgctcgccgg catgcgcat acgtcgtca ccggcacact gcggcgaggc | 1260 |
| gagggcggcc tggaccgctt cactcggtcg ctcgccgcgc tctgggtccg gggcgtgccc | 1320 |
| gtcacctggt cgttcgcgac gcgtcgggtg gtgccgctgc ccacgtaccc gttccgccgt | 1380 |
| gaccgctact ggatcg | 1396 |

<210> SEQ ID NO 85
<211> LENGTH: 1144
<212> TYPE: DNA
<213> ORGANISM: Streptomyces hygroscopicus

<400> SEQUENCE: 85

| | |
|---|---|
| gacgcggaac cggcgggaac gtccggccac ccgctgctcg gctcgtgggt cgacctcgcc | 60 |
| cgacggcgag ggcgcgctgg ccaccgcggt gtctcggtac gccgtcagcc ctggctcgcc | 120 |
| gaccacgagg tggacggccg ggtcatcgtg cccggctcgg cgctcgtgga actgctcgcc | 180 |
| gaagcgggag cccggctcgg cacgccggag atcgcggagc tgaccatcgt cgcgccggtg | 240 |
| gtggtcgacg gcgacggcga cacggagatc caggccaccg tcggaaccga ggtgtccgga | 300 |
| cggcggtcgg tgagtctgca cagccgtacc ggcacgggcc cctgggcgct cagtgcgacc | 360 |
| ggagcgctga gcgtggacac tggcggtccg gcggagcccg tggactggcc gcccgccgac | 420 |
| gccgacccgg ccgacctgac cggcttctac gacgcgctgc cgctctcgta cgggcccgcg | 480 |
| ttccgggcca tgaccgcgat gtggacgggg gagggccgcg cctacgcgtc ggtccgcctc | 540 |
| gccgaacagc tcaccgacgc ccggtacggg ctgcaccccg tgctgctcga cgcggccctg | 600 |
| cacgccctcg ggacggtctt cacggacccg gagcggcgcc ggctggcgtt ctcctggtcc | 660 |
| ggcgtgagga tccacgcgcg cgccgcgacc cgctgcgcg tgctgctgga acgcgtcggc | 720 |
| cccgacatgg tccgcatcgt cgccacggac gagcacggct caccggtcct tgacgtcgac | 780 |
| agcctgaccg tgcgggccgc cgaccccgat gccgaggcgc tgttcgagat cgcctgggtg | 840 |
| cccgtgcccg cgtcaccgt ccccgactgg acgtacctcg ccgacgtgcc cgacggcgag | 900 |
| caccccccgg tcgtggtcct ggccgtggaa cccggcgacc cgggcacctc gcccggcgcc | 960 |
| cggacccggg agctgggccg cgacctgctc accaccgtgc agacctggct cgccgagccg | 1020 |
| cgctgggcgc gatcccggct catcgtggcc acccgtaccg cgatcccgc gcaggaagcg | 1080 |
| ctcggcggcc tggtccggac ggcggagacg gagcatcccg gccgcgtcgc cctgatcgaa | 1140 |
| gcgg | 1144 |

<210> SEQ ID NO 86
<211> LENGTH: 658
<212> TYPE: DNA
<213> ORGANISM: Streptomyces hygroscopicus

<400> SEQUENCE: 86

| | |
|---|---|
| ccgctgaccg gcgggaccgt cctcgtcacc ggcggcaccg gcgggctcgg ccgcctcctc | 60 |

```
gtggaccacc tgctcaccgt gcacgaggcc gccgaggtcg tcgtggtgtc ccgcaacggc      120
cggcccggcg acacgccgga ggacgaccgc gtgcggtacg tggccgccga cgtcgtcgac      180
cgcgacgagc tggccgcagt cgtcgccgac gtcgcccagc ggctgcgcgc cgtcgtgcac      240
atggccggga tcgtcgacga cgcggccgtg acgaccatgc ggccggagca gtgggacgcc      300
gtgctgcggg tcaaggcgga cgtcgcctgg cacctgcacg agctgacgcg cgatctcgac      360
ctggccgcgt tcgtcctgta ctcgtccata tccgccacgt tcggcggcgc gggtcaggcc      420
aactacgcga ccggcaacgc gttcctcgac gcgctcgccc gccaccggca ccaccagggg      480
ctgcccgccg tctcgctcgc ctggggactg tgggacgcgg cggacgggat gggcgggcgg      540
ctgaccgcca ccgacctggc ccgcatcgcc cgcaacggca tgaccccgat gacggccgca      600
caggggctcg ccctgttcga cgcggccctg cacaccgacc ggcccgcgct cgtgccga       658

<210> SEQ ID NO 87
<211> LENGTH: 211
<212> TYPE: DNA
<213> ORGANISM: Streptomyces hygroscopicus

<400> SEQUENCE: 87
atgctcgacc tcgtccgtac cagcgctgcc gcggtgctcg gccaccgcga cgcccacgcc       60
atcgcacccg cgcgcgcgtt cagggaagtg ggcttcgact cgctgaccgg cgtcgaactg      120
cgcaaccggc tggccgacgc gacgggcctg acgctgcccg ctacgctcgt cttcgaccac      180
cccacggcgc aggcgctcgc cgcccacctg g                                    211

<210> SEQ ID NO 88
<211> LENGTH: 1255
<212> TYPE: DNA
<213> ORGANISM: Streptomyces hygroscopicus

<400> SEQUENCE: 88
gagccgttgg cgatcgtggg gatggcctgc cggctgccgg gtggggtcgc gtcgccggag       60
gacttgtggc ggctgctgga gtcgggtggt gacgggatca cggcgtttcc gacggaccgt      120
ggttgggacg tggacgggct gtacgatccc gatccggatc atccgggcac gtcgaccgtg      180
cgtcatggtg gcttcctcgc cggggtggcg gacttcgacg cggcgttctt cgggatcagt      240
ccgcgtgagg cgctggcgat ggacccgcag cagcgtctgg tcctggagac ctcgtgggag      300
gcgctggaac acgccgggat cctcccggag tcgctgcgcg aagcgacac cggcgtgttc       360 atgggcggct acttctacgg gtacggcact ggagccgacc gcggcggttt cggtgccacc      420
agcacccaga ccagtgtgct gtccggtcgg ctgtcgtact tctacggttt ggagggtccg      480
gcggtcacgg tggacacggc gtgttcgtcg tcgctggtgg cgctgcacca ggccgggcag      540
tcgctgcgct cggggagtg ctcgctcgcc gtggtcggcg cgtcacggt gatggcctcg        600 ccgtccggct tcgtggactt ctcccagcag cggggcctct ccccggacgg ccgctgcaag      660 gcgttcgcg atgcggctga tgcaccggt ttcgccgagg atccggtgt gctgatcgtc         720 gagaggctct ccgacgccga gcggcacggc cacaatgtcc tggcggtcgt gcgtggttcg      780
gcggtcaacc aggacggtgc ttccaacggg ttgtcggcgc gaacgggcc gtcgcaggag       840 cgggtgatcc ggcaggcgct ggccaacgcc gggctcaccc cggcggatgt ggacgctgtc      900
gaggcgcatg gcaccgggac caggctgggc gaccccatcg aggcgcaggc ggtactggcc      960
acctacgggc agcatcgcga caccccggtg ctgctgggct cgctgaagtc caacatcggc     1020
```

```
cacactcagg ccgccgcggg cgtcgccggt gtcatcaaga tggtcctcgc catgcggcac    1080
ggcaccctgc cgcgcaccct gcacgtggac acgccgtcct cgcacgtcga ctggacggcc    1140
ggcgccgtcg aactcctcac cgacgcccgc cctggcccg aaaccgaccg cccacggcgc    1200
gccggggtgt cctccttcgg cgttagcggc accaacgctc acatcatcct cgaaa         1255

<210> SEQ ID NO 89
<211> LENGTH: 1168
<212> TYPE: DNA
<213> ORGANISM: Streptomyces hygroscopicus

<400> SEQUENCE: 89
agccaccccc gaccggcccc cgaacccgcc ccggcacccg acaccggacc gctgcccctg     60
ctgctctcgg cacgcacccc gcaggcactc gacgcacagg tacaccgcct gcgcgcccac    120
ctcgccaccg gcgaggagga cgagcgcgcg gtggccgcgg ccctgctcgc ccgcacggcc    180
ttcccgcacc gggccgcgct gatcggcacc gacacggtca ccggcgccgc agaaccggac    240
cgccgcctcg tgtggctctt ctccggacag ggctcacaac gtcccggcat gggcgacgga    300
ctggccgccg cctacgacgt cttcgcccgc actcgccgcg aggtgctgga cgccctcgac    360
gtgcccgccg ggctcgacct ccacgacacc gggtacgccc agcccgcggt gttcgcgctc    420
caggtcgcac tcggcgcaca gctcgaggcg tggggcgtac gccgggacgc cttcgtgggc    480
cattcgatcg gcgagctggc cgccgcgtac gtcgccggcg tctggtccct ggaggacgcg    540
tgcaggctgg tgtccgcacg ggcccgcctg atgcaggcgc tgccgtccgg cggggcgatg    600
gccgccgtga tcgcgtcgga acgggacgcg ctgccgctgc tgcgggacgg cgtggagatc    660
gccgcggtca acgggcccgc gtcgatcgtg ctctccggtg acgaggaggc ggtgctcgac    720
gtcgcggccc ggctcggccg cttcacccgc ctgcggacca gccacgcgtt ccactcggcg    780
cggatggagc cgatgctcga ggagttccgc aaggtcgcgg agagcctgac gtaccacgag    840
ccgaggatcc cgatggccgc gggcgccgcc tgcaccacgc cggagtactg ggtacgacag    900
gtccgcgaca ccgtccggtt cggggaacag gtcgccgcgc acgacggggc ggtgctcctg    960
gagatcggcc cggaccggag cctgacccga ctcgtcgacg gcatcccgat gctgcacgcc   1020
gacgacgaac cgcgatccgc cctgaccgcg ctcgcccggc tgcacaccga cggcgtcacg   1080
gtcgactggc cgaaggtcat cgaccccgcg ccggcacgcg cctcgcaccc gccgacgtac   1140
ccgttcgagc gggtccgcta ctggctcg                                      1168

<210> SEQ ID NO 90
<211> LENGTH: 1150
<212> TYPE: DNA
<213> ORGANISM: Streptomyces hygroscopicus

<400> SEQUENCE: 90
ggcacccaga ccgcgggcga cgcggccccg gccggacaga cgccggtcgc gcacccggcg     60
ctgaccgcgg cggtcaccct gcccggcacc ggcgacctgg tgctcaccgg ccgggtcgac    120
gccgccgatc cgctggcgca ctccctgcac ggcctcgcgg tgctgcccgc gcggccctc     180 ctggatctgg cgatccgggc gggcgacgaa gccggctgcg gcgccctcga cacgttcacc    240
gtggacaccc cctcacgct gccgcggtcc ggtgcgctcg cgctctccgt cacggtgagc    300
gcgcccgggg cggacggccg ccgcgcggtc accgtgcaca cgcggcacgc ggcggggag    360 tggaccgagc acgcgcacgg aatcctcgcc cccgacccgc ggacggcccc ggccgtgcgg    420
gagatgccgt cgacgtggcc gccgccacg gcccggccgg tggaccccga cgacatcgcc    480
```

| | |
|---|---|
| gaccgtctgg cccgagccgg gtacacggac gggcccgcgc tgccccgccc gcgcgccgtc | 540 |
| tgggccgacg acgacgccgt ctgggcggaa gtggccctcg ccgacggaca gctcgccgac | 600 |
| gccggacggt acggcctgca cccggcgctg ctcggcgccg cactccgcct cgccgcggaa | 660 |
| ggggaccacc ttccgtacgc gttcgacgac gtccgcgtcc acgccaccgg cgccacggcg | 720 |
| gtacgcgtcg ccgtcaccgc tgacggcgta cacctcgcgg acgagaccgg cgggcccgtc | 780 |
| gccaccatcg gcgccgtgcg caggcgcccc ctgacgatca cgggagccgt tccgggcctg | 840 |
| ctgcgcccgt gctggccga gctcccggag ctgccgccca cgaccgcgac gaccggccgc | 900 |
| ctcgacgacc cgacggtccc ggacgtggtg atcctccccg cgcacggcgg cggcggtgcc | 960 |
| ccgctcgacg acaccgcga actgggcgcc ggcgtcctga ccgccgtgca gcgcttcctc | 1020 |
| accgacgacc ggtacgccga cgcggtcctg gccgtccaca ccgggcccgg tctcgcgtcg | 1080 |
| gccgcggccg ccggactggt gcggaccgcg caggccgaac accccggccg gatcgtcctc | 1140 |
| gtcgacgccg | 1150 |

<210> SEQ ID NO 91
<211> LENGTH: 649
<212> TYPE: DNA
<213> ORGANISM: Streptomyces hygroscopicus

<400> SEQUENCE: 91

| | |
|---|---|
| ctcgacccgg acggcaccgt gctcgtcacc ggtggctccg ggacgctggc cggcatcatc | 60 |
| agccgccacc tcgtcgaacg ccacggcgtg cgccggctgc tgatgctgtc gcgcagcggc | 120 |
| acggcgagcg acgtgcccgg cgccgaggtc acggcgatcg cctgcgacgt cgccgaccgg | 180 |
| gacgaactcg cctccgtact ggcggggatc gacccggcgc acccgctcac ggccgtcgtg | 240 |
| cacaccgcgg ccgtcctcga cgacggcgtc ctcaccgcgc tcacccccga ccggctcgag | 300 |
| acggtgctgc gcccgaaggt ggacgccgcg tggcacctgc acgaactcac ccaggacacg | 360 |
| gaactggccg cgttcgtcct ctactcgtcg gccgccggtg tgctcggcag ccccggacag | 420 |
| ggcaactacg cggccgcgaa cgcgttcctc gacgcgctgg ccgaacagcg ccgggcagcc | 480 |
| ggactgcccg cgttgtccgt ggcctggggc ctgtgggaac cggagagcgg gctgacggtc | 540 |
| ggcaccggcg cccgcatgcg ccgcgacggc gtgacggcgc tgaccgccga aggcggactg | 600 |
| acgctgttcg acgcggcgtt gcggtcctcg gacccggcgc tggtcgccg | 649 |

<210> SEQ ID NO 92
<211> LENGTH: 211
<212> TYPE: DNA
<213> ORGANISM: Streptomyces hygroscopicus

<400> SEQUENCE: 92

| | |
|---|---|
| gtgctcgccg tcgtccggca gtgcaccgcg gccgtactcg gccacgacgg tgccgcacgg | 60 |
| gtcgaggcga ccgccacgtt caaggaactc ggcgtcgact cgctcatggc gatccggctg | 120 |
| cgcaacgcct tcaccgaggc gacgggcgta cggctgcccg ccaccgcggt cttcgacttc | 180 |
| ccgacgccgc gcgccgtcgc ggcgaagctc a | 211 |

<210> SEQ ID NO 93
<211> LENGTH: 1255
<212> TYPE: DNA
<213> ORGANISM: Streptomyces hygroscopicus

<400> SEQUENCE: 93

```
gagccgttgg cgatcgtggg gatggcctgc cggctgccgg gtggggtcgc gtcgccggag    60
gacttgtggc ggctgctgga gtcgggtggt gacgggatca cggcgtttcc gacggaccgt   120
ggttgggacg tggacgggct gtacgatccc gatccggatc atccgggcac gtcgaccgtg   180
cgtcatggtg gcttcctcgc cggggtggcg gacttcgacg cggcgttctt cgggatcagt   240
ccgcgtgagg cgctggcgat ggacccgcag cagcgtctgg tcctggagac ctcgtgggag   300
gcgctggaac acgccgggat cctcccggag tcgctgcgcg gaagcgacac cggcgtgttc   360
atgggcgcct tctccgacgg gtacggactc ggcaccgacc tgggcggttt cggcgcgacc   420
ggcacccaga ccagtgtgct gtccggtcgg ctgtcgtact tctacggtct ggagggtccg   480
gcggtcacgg tcgacacggc gtgttcgtcg tcgctggtgg cgctgcacca ggccgggcag   540
tcactgcgct ccgcgaatg ctcgctcgcc ctggtcggcg cgtcacggt gatggcctcg   600
ccgtccggct tcgtcgagtt ctcccagcag cggggtctcg cgcccgacgc gcgctgcaag   660
gcgttcgcg atgcggctga cggcaccggt ttcgccgagg gtccggtgt gctgatcgtc   720
gagaggctct ccgatgccga gcgcaacggc caccgtgtgc tggcggttgt ccggggttcg   780
gcggtcaacc aggacggtgc ttccaacggg ttgtcggcgc cgaacgggcc ctcgcaggag   840
cgggtgatcc ggcaggccct ggccaacgcc gggctcaccc cggcggacgt ggacgccgtg   900
gaggcgcacg gcaccggcac caggctgggc gatcccatcg aggcacaggc ggtgctggcc   960
acctacgggc aggggcgcga caccccggtg ctgctgggct cgctgaagtc caacatcggc  1020
cacactcagg ccgccgcggg tgtcgccggt gtcatcaaga tggtcctcgc catgcggcac  1080
ggcaccctgc cgcgcaccct gcacgtggac acgccgtcct cgcacgtcga ctggacggcc  1140
ggcgccgtcg aactcctcac cgatgcccgg ccctggcccg agaccgaccg cccgcggcgc  1200
gccggtgtgt cctccttcgg cgtcagcggc accaacgccc acgtcctgct ggaag       1255

<210> SEQ ID NO 94
<211> LENGTH: 1285
<212> TYPE: DNA
<213> ORGANISM: Streptomyces hygroscopicus

<400> SEQUENCE: 94
gcccacccgg ccggggagcc gccggccgag gagccgtcgg cctcgaagcc cggtgagccg    60
ctgatcgcca cgccgctcac accactgccc gtctcggcgc ggaccgccac ggccctcgac   120
ggccaggtcc gccgactccg cgagcacctc gccgcccgtc ccggccacga cccgcgcgcc   180
atcgccgcgg gcctgctcgc caggcgtacg acgttcccgc accgccgcgt gctgctcgac   240
gacgacgtcg tcaccggcac ggcgctcacc gagccgcgca ccgtcttcgt cttccccgga   300
caaggaccgc agtggcgcgg catgggcgtc gaactgatgg cggcctcccc ggtgttcgcc   360
gccaggatgc gccaatgcgc cgacgcgctg atcccgcaca cgggctggga ccccatcgcc   420
atgctcgacg acccggaggt gacccgccgc gtcgacgtcg tgcaccccgt ctgctgggcc   480
gtcatggtgt cgctggccgc cgtgtgggag gccgcgggcg tacgcccgga cgccgtcatc   540
ggacactccc agggcgagat cgccgcgcc tgtgtcgccg gagcgctcac cctggaggac   600
ggtgcccgcc tcgtcgcgct gcgcagcgtt ctcctgctcc tgcgcgaact cgccggacgc   660
ggcgcgatgg gctcggtcgc gctcccgccc gcgacgtcag gcggatgc cgcccggatc   720
gacgcgtct gggtcgcggg ccgcaacggc gccaccacca cgaccgtcgc cgggcgcccg   780
gacgccgtcg aaacgctgat cgccgactac gaggcccgcg cgtctgggt cgccgcatc   840
gccgtcgact gcccgaccca caccccgttc gtcgacccgc tgtacgacga actccagcgg   900
```

```
atcgtcgcgg acaccacctc gcgcacgccc gagatcccgt ggttctccac cgccgacgaa    960
cgctggatcg acgcgccgct cgacgacgag tactggttcc gcaacatgcg ccaccccgta   1020
ggcttcgcca cggccgtgac cgctgcccgc gagccgggtg acaccgtgtt cgtcgaggtc   1080
agcgcgcacc ccgtgctgct gcccgcgatc gacggcgcga ccgtcgccac gctccgccgc   1140 ggcggggag  tccaccggct gctcaccgcg ctggccgagg cgcacacaac cggcgtgccc   1200
gtcgactggg cggcggtcgt ccccgcgacg gcgacggcac acgacctgcc cacatacgcc   1260
ttccaccatg agcgctactg gatcg                                         1285
```

<210> SEQ ID NO 95
<211> LENGTH: 1285
<212> TYPE: DNA
<213> ORGANISM: Streptomyces hygroscopicus

<400> SEQUENCE: 95

```
gcccacccgg ccggggagcc gccggccgag gagccgtcgg cctcgaagcc cggtgagccg     60
ctgatcgcca cgccgctcac accactgccc gtctcggcgc ggaccgccac ggccctcgac    120
ggccaggtcc gccgactccg cgagcacctc gccgcccgtc ccggccacga cccgcgcgcc    180
atcgccgcgg gcctgctcgc caggcgtacg acgttcccgc accgcgccgt gctgctcgac    240
gacgacgtcg tcaccggcac ggcgctcacc gagccgcgca ccgtcttcgt cttccccgga    300
caaggaccgc agtggcgcgg catgggcgtc gaactgatgg cggcctcccc ggtgttcgcc    360
gccaggatgc gccaatgcgc cgacgcgctg atcccgcaca cgggctggga ccccatcgcc    420
atgctcgacg acccggaggt gaccgccgc  gtcgacgtcg tgcaccccgt ctgctgggcc    480
gtcatggtgt cgctggccgc cgtgtgggag gccgcgggc  tacgcccgga cgccgtcatc    540
ggacactccc agggcgagat cgccgcggcc tgtgtcgccg gagcgctcac cctggaggac    600
ggtgcccgcc tcgtcgcgct gcgcagcgtt ctcctgctcc tgcgcgaact cgccggacgc    660
ggcgcgatgg gctcggtcgc gctcccggcc gccgacgtcg aggcggatgc cgcccggatc    720
gacggcgtct gggtcgcggg ccgcaacggc gccaccacca cgaccgtcgc cgggcgcccg    780
gacgccgtcg aaacgctgat cgccgactac gaggcccgcg gcgtctgggt cgccgcatc    840 gccgtcgact gcccgaccca caccccgttc gtcgacccgc tgtacgacga actccagcgg    900
atcgtcgcgg acaccacctc gcgcacgccc gagatcccgt ggttctccac cgccgacgaa    960
cgctggatcg acgcgccgct cgacgacgag tactggttcc gcaacatgcg ccaccccgta   1020
ggcttcgcca cggccgtgac cgctgcccgc gagccgggtg acaccgtgtt cgtcgaggtc   1080
agcgcgcacc ccgtgctgct gcccgcgatc gacggcgcga ccgtcgccac gctccgccgc   1140 ggcggggag  tccaccggct gctcaccgcg ctggccgagg cgcacacaac cggcgtgccc   1200
gtcgactggg cggcggtcgt ccccgcgacg gcgacggcac acgacctgcc cacatacgcc   1260
ttccaccatg agcgctactg gatcg                                         1285
```

<210> SEQ ID NO 96
<211> LENGTH: 211
<212> TYPE: DNA
<213> ORGANISM: Streptomyces hygroscopicus

<400> SEQUENCE: 96

```
ctgctcggcg tcgtccgcga caccgccgcc accctgctgg gccacaccga cgcggcggcg     60
gtcacggcca ccacggcgtt caaggacctc ggggtcgact cgctcaccgc gctcggcctg    120
```

-continued

```
cgcaaccggc tctccgaggc cctcggcatt ccgctgccgg ccacgctcgt cttcgactat    180
cccgccgccg gcgcgctcac ccgtcatctg c                                  211
```

POLYNUCLEOTIDES ENCODING THE FKBB GENE OF THE FK-520 POLYKETIDE SYNTHASE GENE CLUSTER

CROSS-REFERENCE TO RELATED APPLICATIONS

The present application is a divisional of U.S. patent application Ser. No. 09/940,316, filed 27 Aug. 2001, which is a divisional of U.S. patent application Ser. No. 09/410,551, filed 1 Oct. 1999, which claims the benefit of the filing date of U.S. provisional patent application Ser. Nos. 60/102,748, filed 2 Oct. 1998, 60/139,650, filed 17 Jun. 1999, and 60/123,810, filed 11 Mar. 1999, each of which is incorporated herein by reference.

Reference to Sequence Listing Submitted Via EFS-Web

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 300622002612seqlist.txt | Aug. 16, 2007 | 624,081 bytes |

FIELD OF THE INVENTION

The present invention relates to polyketides and the polyketide synthase (PKS) enzymes that produce them. The invention also relates generally to genes encoding PKS enzymes and to recombinant host cells containing such genes and in which expression of such genes leads to the production of polyketides. The present invention also relates to compounds useful as medicaments having immunosuppressive and/or neurotrophic activity. Thus, the invention relates to the fields of chemistry, molecular biology, and agricultural, medical, and veterinary technology.

BACKGROUND OF THE INVENTION

Polyketides are a class of compounds synthesized from 2-carbon units through a series of condensations and subsequent modifications. Polyketides occur in many types of organisms, including fungi and mycelial bacteria, in particular, the actinomycetes. Polyketides are biologically active molecules with a wide variety of structures, and the class encompasses numerous compounds with diverse activities. Tetracycline, erythromycin, epothilone, FK-506, FK-520, narbomycin, picromycin, rapamycin, spinocyn, and tylosin are examples of polyketides. Given the difficulty in producing polyketide compounds by traditional chemical methodology, and the typically low production of polyketides in wild-type cells, there has been considerable interest in finding improved or alternate means to produce polyketide compounds.

This interest has resulted in the cloning, analysis, and manipulation by recombinant DNA technology of genes that encode PKS enzymes. The resulting technology allows one to manipulate a known PKS gene cluster either to produce the polyketide synthesized by that PKS at higher levels than occur in nature or in hosts that otherwise do not produce the polyketide. The technology also allows one to produce molecules that are structurally related to, but distinct from, the polyketides produced from known PKS gene clusters. See, e.g., PCT publication Nos. WO 93/13663; 95/08548; 96/40968; 97/02358; 98/27203; and 98/49315; U.S. Pat. Nos. 4,874,748; 5,063,155; 5,098,837; 5,149,639; 5,672,491; 5,712,146; 5,830,750; and 5,843,718; and Fu et al., 1994, *Biochemistry* 33: 9321-9326; McDaniel et al., 1993, *Science* 262: 1546-1550; and Rohr, 1995, *Angew. Chem. Int. Ed. Engl.* 34(8): 881-888, each of which is incorporated herein by reference.

Polyketides are synthesized in nature by PKS enzymes. These enzymes, which are complexes of multiple large proteins, are similar to the synthases that catalyze condensation of 2-carbon units in the biosynthesis of fatty acids. PKSs catalyze the biosynthesis of polyketides through repeated, decarboxylative Claisen condensations between acylthioester building blocks. The building blocks used to form complex polyketides are typically acylthioesters, such as acetyl, butyryl, propionyl, malonyl, hydroxymalonyl, methylmalonyl, and ethylmalonyl CoA. Other building blocks include amino acid like acylthioesters. PKS enzymes that incorporate such building blocks include an activity that functions as an amino acid ligase (an AMP ligase) or as a non-ribosomal peptide synthetase (NRPS). Two major types of PKS enzymes are known; these differ in their composition and mode of synthesis of the polyketide synthesized. These two major types of PKS enzymes are commonly referred to as Type I or "modular" and Type II "iterative" PKS enzymes.

In the Type I or modular PKS enzyme group, a set of separate catalytic active sites (each active site is termed a "domain", and a set thereof is termed a "module") exists for each cycle of carbon chain elongation and modification in the polyketide synthesis pathway. The typical modular PKS is composed of several large polypeptides, which can be segregated from amino to carboxy termini into a loading module, multiple extender modules, and a releasing (or thioesterase) domain. The PKS enzyme known as 6-deoxyerythronolide B synthase (DEBS) is a Type I PKS. In DEBS, there is a loading module, six extender modules, and a thioesterase (TE) domain. The loading module, six extender modules, and TE of DEBS are present on three separate proteins (designated DEBS-1, DEBS-2, and DEBS-3, with two extender modules per protein). Each of the DEBS polypeptides is encoded by a separate open reading frame (ORF) or gene; these genes are known as eryAI, eryAII, and eryAIII. See Caffrey et al., 1992, *FEBS Letters* 304: 205, and U.S. Pat. No. 5,824,513, each of which is incorporated herein by reference.

Generally, the loading module is responsible for binding the first building block used to synthesize the polyketide and transferring it to the first extender module. The loading module of DEBS consists of an acyltransferase (AT) domain and an acyl carrier protein (ACP) domain. Another type of loading module utilizes an inactivated ketosynthase (KS) domain and AT and ACP domains. This inactivated KS is in some instances called $KS^Q$, where the superscript letter is the abbreviation for the amino acid, glutamine, that is present instead of the active site cysteine required for ketosynthase activity. In other PKS enzymes, including the FK-506 PKS, the loading module incorporates an unusual starter unit and is composed of a CoA ligase like activity domain. In any event, the loading module recognizes a particular acyl-CoA (usually acetyl or propionyl but sometimes butyryl or other acyl-CoA) and transfers it as a thiol ester to the ACP of the loading module.

The AT on each of the extender modules recognizes a particular extender-CoA (malonyl or alpha-substituted malonyl, i.e., methylmalonyl, ethylmalonyl, and 2-hydroxymalonyl) and transfers it to the ACP of that extender module to form a thioester. Each extender module is responsible for accepting a compound from a prior module, binding a building block, attaching the building block to the compound from the prior module, optionally performing one or more additional functions, and transferring the resulting compound to the next module.

Each extender module of a modular PKS contains a KS, AT, ACP, and zero, one, two, or three domains that modify the beta-carbon of the growing polyketide chain. A typical (non-loading) minimal Type I PKS extender module is exemplified by extender module three of DEBS, which contains a KS domain, an AT domain, and an ACP domain. These three domains are sufficient to activate a 2-carbon extender unit and attach it to the growing polyketide molecule. The next extender module, in turn, is responsible for attaching the next building block and transferring the growing compound to the next extender module until synthesis is complete.

Once the PKS is primed with acyl- and malonyl-ACPs, the acyl group of the loading module is transferred to form a thiol ester (trans-esterification) at the KS of the first extender module; at this stage, extender module one possesses an acyl-KS and a malonyl (or substituted malonyl) ACP. The acyl group derived from the loading module is then covalently attached to the alpha-carbon of the malonyl group to form a carbon-carbon bond, driven by concomitant decarboxylation, and generating a new acyl-ACP that has a backbone two carbons longer than the loading building block (elongation or extension).

The polyketide chain, growing by two carbons each extender module, is sequentially passed as covalently bound thiol esters from extender module to extender module, in an assembly line-like process. The carbon chain produced by this process alone would possess a ketone at every other carbon atom, producing a polyketone, from which the name polyketide arises. Most commonly, however, additional enzymatic activities modify the beta keto group of each two carbon unit just after it has been added to the growing polyketide chain but before it is transferred to the next module.

Thus, in addition to the minimal module containing KS, AT, and ACP domains necessary to form the carbon-carbon bond, and as noted above, other domains that modify the beta-carbonyl moiety can be present. Thus, modules may contain a ketoreductase (KR) domain that reduces the keto group to an alcohol. Modules may also contain a KR domain plus a dehydratase (DH) domain that dehydrates the alcohol to a double bond. Modules may also contain a KR domain, a DH domain, and an enoylreductase (ER) domain that converts the double bond product to a saturated single bond using the beta carbon as a methylene function. An extender module can also contain other enzymatic activities, such as, for example, a methylase or dimethylase activity.

After traversing the final extender module, the polyketide encounters a releasing domain that cleaves the polyketide from the PKS and typically cyclizes the polyketide. For example, final synthesis of 6-dEB is regulated by a TE domain located at the end of extender module six. In the synthesis of 6-dEB, the TE domain catalyzes cyclization of the macrolide ring by formation of an ester linkage. In FK-506, FK-520, rapamycin, and similar polyketides, the TE activity is replaced by a RapP (for rapamycin) or RapP like activity that makes a linkage incorporating a pipecolate acid residue. The enzymatic activity that catalyzes this incorporation for the rapamycin enzyme is known as RapP, encoded by the rapP gene. The polyketide can be modified further by tailoring enzymes; these enzymes add carbohydrate groups or methyl groups, or make other modifications, i.e., oxidation or reduction, on the polyketide core molecule. For example, 6-dEB is hydroxylated at C-6 and C-12 and glycosylated at C-3 and C-5 in the synthesis of erythromycin A.

In Type I PKS polypeptides, the order of catalytic domains is conserved. When all beta-keto processing domains are present in a module, the order of domains in that module from N-to-C-terminus is always KS, AT, DH, ER, KR, and ACP. Some or all of the beta-keto processing domains may be missing in particular modules, but the order of the domains present in a module remains the same. The order of domains within modules is believed to be important for proper folding of the PKS polypeptides into an active complex. Importantly, there is considerable flexibility in PKS enzymes, which allows for the genetic engineering of novel catalytic complexes. The engineering of these enzymes is achieved by modifying, adding, or deleting domains, or replacing them with those taken from other Type I PKS enzymes. It is also achieved by deleting, replacing, or adding entire modules with those taken from other sources. A genetically engineered PKS complex should of course have the ability to catalyze the synthesis of the product predicted from the genetic alterations made.

Alignments of the many available amino acid sequences for Type I PKS enzymes has approximately defined the boundaries of the various catalytic domains. Sequence alignments also have revealed linker regions between the catalytic domains and at the N- and C-termini of individual polypeptides. The sequences of these linker regions are less well conserved than are those for the catalytic domains, which is in part how linker regions are identified. Linker regions can be important for proper association between domains and between the individual polypeptides that comprise the PKS complex. One can thus view the linkers and domains together as creating a scaffold on which the domains and modules are positioned in the correct orientation to be active. This organization and positioning, if retained, permits PKS domains of different or identical substrate specificities to be substituted (usually at the DNA level) between PKS enzymes by various available methodologies. In selecting the boundaries of, for example, an AT replacement, one can thus make the replacement so as to retain the linkers of the recipient PKS or to replace them with the linkers of the donor PKS AT domain, or, preferably, make both constructs to ensure that the correct linker regions between the KS and AT domains have been included in at least one of the engineered enzymes. Thus, there is considerable flexibility in the design of new PKS enzymes with the result that known polyketides can be produced more effectively, and novel polyketides useful as pharmaceuticals or for other purposes can be made.

By appropriate application of recombinant DNA technology, a wide variety of polyketides can be prepared in a variety of different host cells provided one has access to nucleic acid compounds that encode PKS proteins and polyketide modification enzymes. The present invention helps meet the need for such nucleic acid compounds by providing recombinant vectors that encode the FK-520 PKS enzyme and various FK-520 modification enzymes. Moreover, while the FK-506 and FK-520 polyketides have many useful activities, there remains a need for compounds with similar useful activities but with better pharmacokinetic profile and metabolism and fewer side-effects. The present invention helps meet the need for such compounds as well.

SUMMARY OF THE INVENTION

In one embodiment, the present invention provides recombinant DNA vectors that encode all or part of the FK-520 PKS enzyme. Illustrative vectors of the invention include cosmid pKOS034-120, pKOS034-124, pKOS065-C31, pKOS065-C3, pKOS065-M27, and pKOS165-M21. The invention also provides nucleic acid compounds that encode the various domains of the FK-520 PKS, i.e., the KS, AT, ACP, KR, DH, and ER domains. These compounds can be readily used, alone or in combination with nucleic acids encoding other FK-520 or non-FK-520 PKS domains, as intermediates in the construction of recombinant vectors that encode all or part of PKS enzymes that make novel polyketides.

The invention also provides isolated nucleic acids that encode all or part of one or more modules of the FK-520 PKS, each module comprising a ketosynthase activity, an acyl transferase activity, and an acyl carrier protein activity. The invention provides an isolated nucleic acid that encodes one or more open reading frames of FK-520 PKS genes, said open reading frames comprising coding sequences for a CoA ligase activity, an NRPS activity, or two or more extender modules. The invention also provides recombinant expression vectors containing these nucleic acids.

In another embodiment, the invention provides isolated nucleic acids that encode all or a part of a PKS that contains at least one module in which at least one of the domains in the module is a domain from a non-FK-520 PKS and at least one domain is from the FK-520 PKS. The non-FK-520 PKS domain or module originates from the rapamycin PKS, the FK-506 PKS, DEBS, or another PKS. The invention also provides recombinant expression vectors containing these nucleic acids.

In another embodiment, the invention provides a method of preparing a polyketide, said method comprising transforming a host cell with a recombinant DNA vector that encodes at least one module of a PKS, said module comprising at least one FK-520 PKS domain, and culturing said host cell under conditions such that said PKS is produced and catalyzes synthesis of said polyketide. In one aspect, the method is practiced with a *Streptomyces* host cell. In another aspect, the polyketide produced is FK-520. In another aspect, the polyketide produced is a polyketide related in structure to FK-520. In another aspect, the polyketide produced is a polyketide related in structure to FK-506 or rapamycin.

In another embodiment, the invention provides a set of genes in recombinant form sufficient for the synthesis of ethylmalonyl CoA in a heterologous host cell. These genes and the methods of the invention enable one to create recombinant host cells with the ability to produce polyketides or other compounds that require ethylmalonyl CoA for biosynthesis. The invention also provides recombinant nucleic acids that encode AT domains specific for ethylmalonyl CoA. Thus, the compounds of the invention can be used to produce polyketides requiring ethylmalonyl CoA in host cells that otherwise are unable to produce such polyketides.

In another embodiment, the invention provides a set of genes in recombinant form sufficient for the synthesis of 2-hydroxymalonyl CoA and 2-methoxymalonyl CoA in a heterologous host cell. These genes and the methods of the invention enable one to create recombinant host cells with the ability to produce polyketides or other compounds that require 2-hydroxymalonyl CoA for biosynthesis. The invention also provides recombinant nucleic acids that encode AT domains specific for 2-hydroxymalonyl CoA and 2-methoxymalonyl CoA. Thus, the compounds of the invention can be used to produce polyketides requiring 2-hydroxymalonyl CoA or 2-methoxymalonyl CoA in host cells that are otherwise unable to produce such polyketides.

In another embodiment, the invention provides a compound related in structure to FK-520 or FK-506 that is useful in the treatment of a medical condition. These compounds include compounds in which the C-13 methoxy group is replaced by a moiety selected from the group consisting of hydrogen, methyl, and ethyl moieties. Such compounds are less susceptible to the main in vivo pathway of degradation for FK-520 and FK-506 and related compounds and thus exhibit an improved pharmacokinetic profile. The compounds of the invention also include compounds in which the C-15 methoxy group is replaced by a moiety selected from the group consisting of hydrogen, methyl, and ethyl moieties. The compounds of the invention also include the above compounds further modified by chemical methodology to produce derivatives such as, but not limited to, the C-18 hydroxyl derivatives, which have potent neurotrophin but not immunosuppresion activities.

Thus, the invention provides polyketides having the structure:

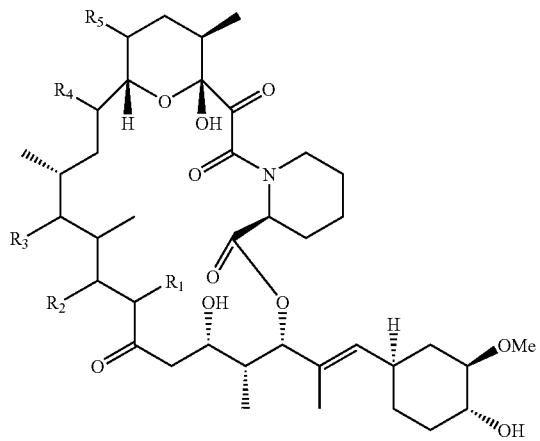

wherein, $R_1$ is hydrogen, methyl, ethyl, or allyl; $R_2$ is hydrogen or hydroxyl, provided that when $R_2$ is hydrogen, there is a double bond between C-20 and C-19; $R_3$ is hydrogen or hydroxyl; $R_4$ is methoxyl, hydrogen, methyl, or ethyl; and $R_5$ is methoxyl, hydrogen, methyl, or ethyl; but not including FK-506, FK-520, 18-hydroxy-FK-520, and 18-hydroxy-FK-506. The invention provides these compounds in purified form and in pharmaceutical compositions.

In another embodiment, the invention provides a method for treating a medical condition by administering a pharmaceutically efficacious dose of a compound of the invention. The compounds of the invention may be administered to achieve immunosuppression or to stimulate nerve growth and regeneration.

These and other embodiments and aspects of the invention will be more fully understood after consideration of the attached Drawings and their brief description below, together with the detailed description, examples, and claims that follow.

DETAILED DESCRIPTION OF THE INVENTION

Figure 1:
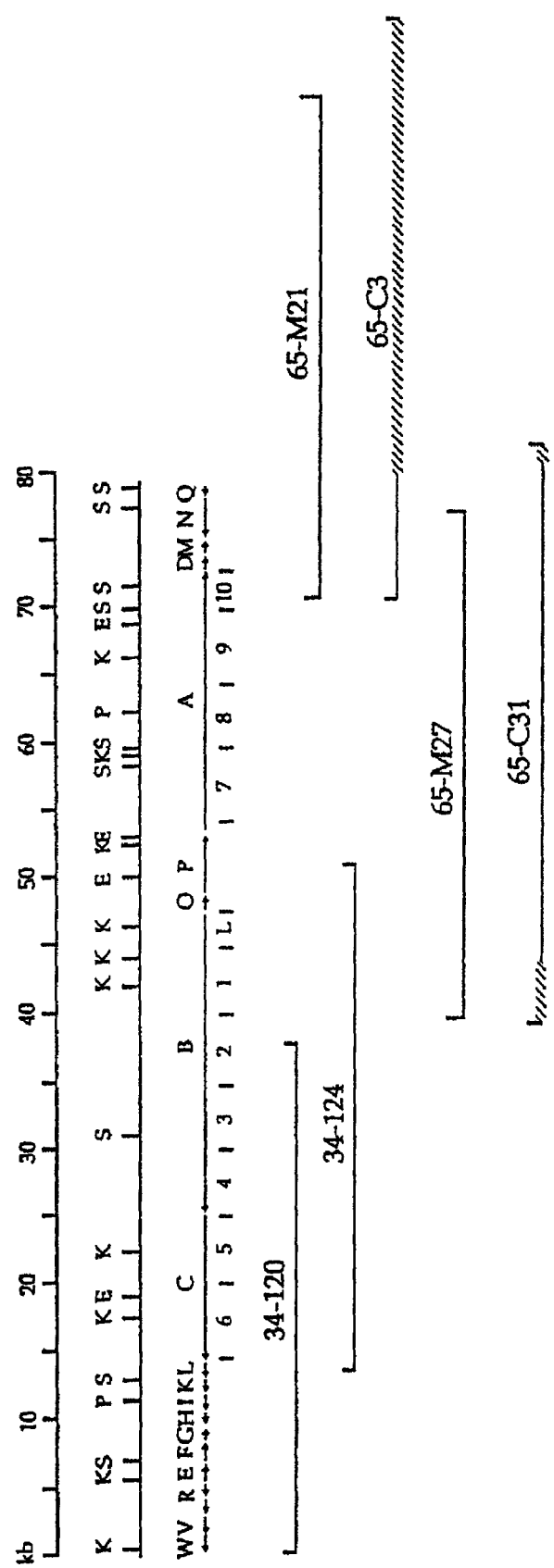
FIG. 1 shows a diagram of the FK-520 biosynthetic gene cluster. The top line provides a scale in kilobase pairs (kb). The second line shows a restriction map with selected restriction enzyme recognition sequences indicated. K is KpnI; X is XhoI, S is SacI; P is PstI; and E is EcoRI. The third line indicates the position of FK-520 PKS and related genes. Genes are abbreviated with a one letter designation, i.e., C is fkbC. Immediately under the third line are numbered segments showing where the loading module (L) and ten different extender modules (numbered 1-10) are encoded on the various genes shown. At the bottom of the Figure, the DNA inserts of various cosmids of the invention (i.e., 34-124 is cosmid pKOS034-124) are shown in alignment with the FK-520 biosynthetic gene cluster.

Given the valuable pharmaceutical properties of polyketides, there is a need for methods and reagents for producing large quantities of polyketides, as well as for producing related compounds not found in nature. The present invention provides such methods and reagents, with particular application to methods and reagents for producing the polyketides known as FK-520, also known as ascomycin or L-683,590 (see Holt et al., 1993, *JACS* 115:9925), and FK-506, also known as tacrolimus. Tacrolimus is a macrolide immunosuppressant used to prevent or treat rejection of transplanted heart, kidney, liver, lung, pancreas, and small bowel allografts. The drug is also useful for the prevention and treatment of graft-versus-host disease in patients receiving bone marrow transplants, and for the treatment of severe, refractory uveitis. There have been additional reports of the unapproved use of tacrolimus for other conditions, including alopecia universalis, autoimmune chronic active hepatitis, inflammatory bowel disease, multiple sclerosis, primary biliary cirrhosis, and scleroderma. The invention provides methods and reagents for making novel polyketides related in structure to FK-520 and FK-506, and structurally related polyketides such as rapamycin.

The FK-506 and rapamycin polyketides are potent immunosuppressants, with chemical structures shown below.

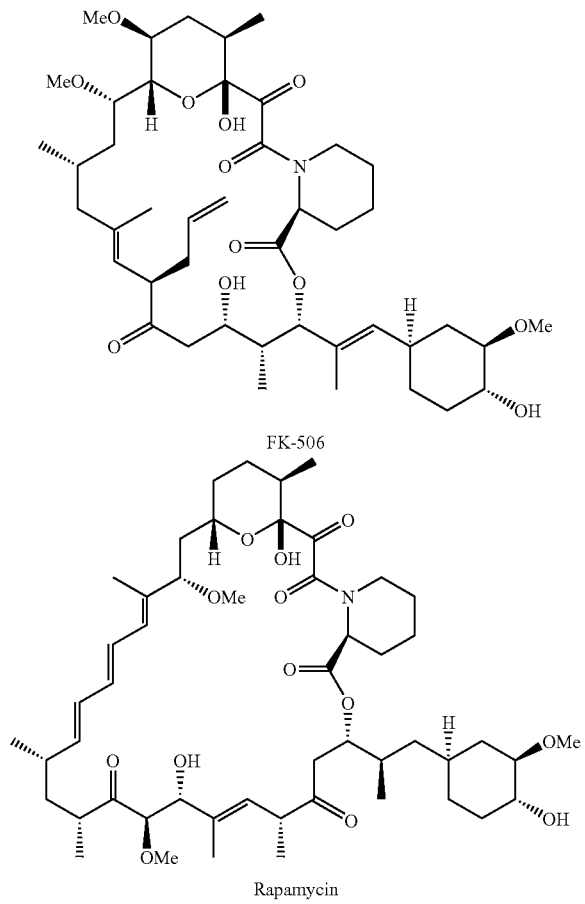

FK-520 differs from FK-506 in that it lacks the allyl group at C-21 of FK-506, having instead an ethyl group at that position, and has similar activity to FK-506, albeit reduced immunosuppressive activity.

These compounds act through initial formation of an intermediate complex with protein "immunophilins" known as FKBPs (FK-506 binding proteins), including FKBP-12. Immunophilins are a class of cytosolic proteins that form complexes with molecules such as FK-506, FK-520, and rapamycin that in turn serve as ligands for other cellular targets involved in signal transduction. Binding of FK-506, FK-520, and rapamycin to FKBP occurs through the structurally similar segments of the polyketide molecules, known as the "FKBP-binding domain" (as generally but not precisely indicated by the stippled regions in the structures above). The FK-506-FKBP complex then binds calcineurin, while the rapamycin-FKBP complex binds to a protein known as RAFT-1. Binding of the FKBP-polyketide complex to these second proteins occurs through the dissimilar regions of the drugs known as the "effector" domains.

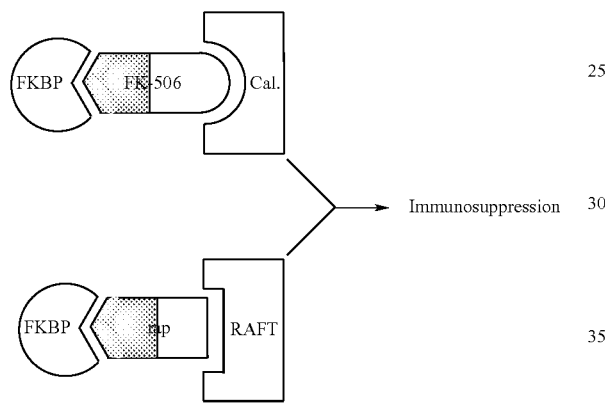

The three component FKBP-polyketide-effector complex is required for signal transduction and subsequent immunosuppressive activity of FK-506, FK-520, and rapamycin. Modifications in the effector domains of FK-506, FK-520, and rapamycin that destroy binding to the effector proteins (calcineurin or RAFT) lead to loss of immunosuppressive activity, even though FKBP binding is unaffected. Further, such analogs antagonize the immunosuppressive effects of the parent polyketides, because they compete for FKBP. Such non-immunosuppressive analogs also show reduced toxicity (see Dumont et al., 1992, *Journal of Experimental Medicine* 176, 751-760), indicating that much of the toxicity of these drugs is not linked to FKBP binding.

In addition to immunosuppressive activity, FK-520, FK-506, and rapamycin have neurotrophic activity. In the central nervous system and in peripheral nerves, immunophilins are referred to as "neuroimmunophilins". The neuroimmunophilin FKBP is markedly enriched in the central nervous system and in peripheral nerves. Molecules that bind to the neuroimmunophilin FKBP, such as FK-506 and FK-520, have the remarkable effect of stimulating nerve growth. In vitro, they act as neurotrophins, i.e., they promote neurite outgrowth in NGF-treated PC12 cells and in sensory neuronal cultures, and in intact animals, they promote regrowth of damaged facial and sciatic nerves, and repair lesioned serotonin and dopamine neurons in the brain. See Gold et al., June 1999, *J. Pharm. Exp. Ther.* 289(3): 1202-1210; Lyons et al., 1994, *Proc. National Academy of Science* 91: 3191-3195; Gold et al., 1995, *Journal of Neuroscience* 15: 7509-7516; and Steiner et al., 1997, *Proc. National Academy of Science* 94: 2019-2024. Further, the restored central and peripheral neurons appear to be functional.

Compared to protein neurotrophic molecules (BNDF, NGF, etc.), the small-molecule neurotrophins such as FK-506, FK-520, and rapamycin have different, and often advantageous, properties. First, whereas protein neurotrophins are difficult to deliver to their intended site of action and may require intra-cranial injection, the small-molecule neurotrophins display excellent bioavailability; they are active when administered subcutaneously and orally. Second, whereas protein neurotrophins show quite specific effects, the small-molecule neurotrophins show rather broad effects. Finally, whereas protein neurotrophins often show effects on normal sensory nerves, the small-molecule neurotrophins do not induce aberrant sprouting of normal neuronal processes and seem to affect damaged nerves specifically. Neuroimmunophilin ligands have potential therapeutic utility in a variety of disorders involving nerve degeneration (e.g. multiple sclerosis, Parkinson's disease, Alzheimer's disease, stroke, traumatic spinal cord and brain injury, peripheral neuropathies).

Recent studies have shown that the immunosuppressive and neurite outgrowth activity of FK-506, FK-520, and rapamycin can be separated; the neuroregenerative activity in the absence of immunosuppressive activity is retained by agents which bind to FKBP but not to the effector proteins calcineurin or RAFT. See Steiner et al., 1997, *Nature Medicine* 3: 421-428.

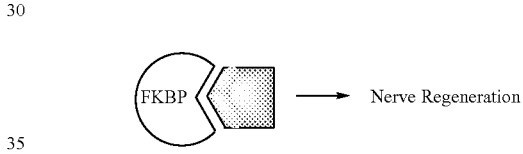

Available structure-activity data show that the important features for neurotrophic activity of rapamycin, FK-520, and FK-506 lie within the common, contiguous segments of the macrolide ring that bind to FKBP. This portion of the molecule is termed the "FKBP binding domain" (see VanDuyne et al., 1993, *Journal of Molecular Biology* 229: 105-124.). Nevertheless, the effector domains of the parent macrolides contribute to conformational rigidity of the binding domain and thus indirectly contribute to FKBP binding.

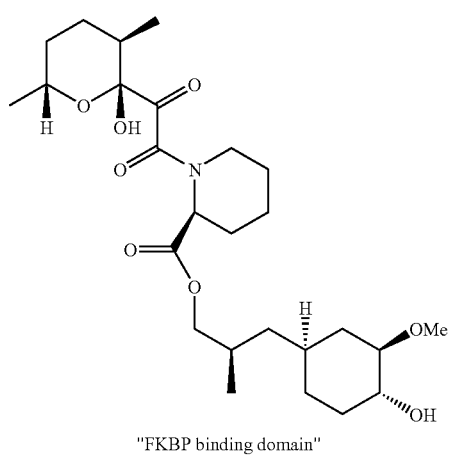

"FKBP binding domain"

There are a number of other reported analogs of FK-506, FK-520, and rapamycin that bind to FKBP but not the effector protein calcineurin or RAFT. These analogs show effects on nerve regeneration without immunosuppressive effects.

Naturally occurring FK-520 and FK-506 analogs include the antascomycins, which are FK-506-like macrolides that lack the functional groups of FK-506 that bind to calcineurin (see Fehr et al., 1996, *The Journal of Antibiotics* 49: 230-233). These molecules bind FKBP as effectively as does FK-506; they antagonize the effects of both FK-506 and rapamycin, yet lack immunosuppressive activity.

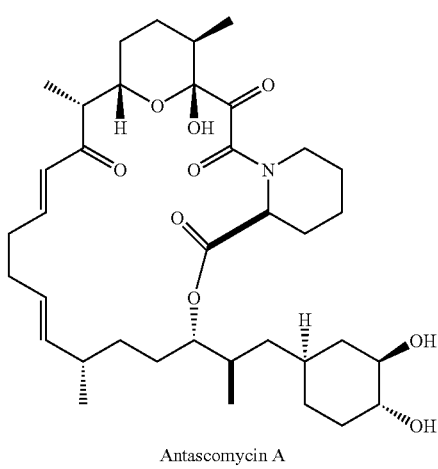

Antascomycin A

Other analogs can be produced by chemically modifying FK-506, FK-520, or rapamycin. One approach to obtaining neuroimmunophilin ligands is to destroy the effector binding region of FK-506, FK-520, or rapamycin by chemical modification. While the chemical modifications permitted on the parent compounds are quite limited, some useful chemically modified analogs exist. The FK-520 analog L-685,818 ($ED_{50}$=0.7 nM for FKBP binding; see Dumont et al., 1992), and the rapamycin analog WAY-124,466 ($IC_{50}$=12.5 nM; see Ocain et al., 1993, *Biochemistry Biophysical Research Communications* 192: 1340-134693) are about as effective as FK-506, FK-520, and rapamycin at promoting neurite outgrowth in sensory neurons (see Steiner et al., 1997).

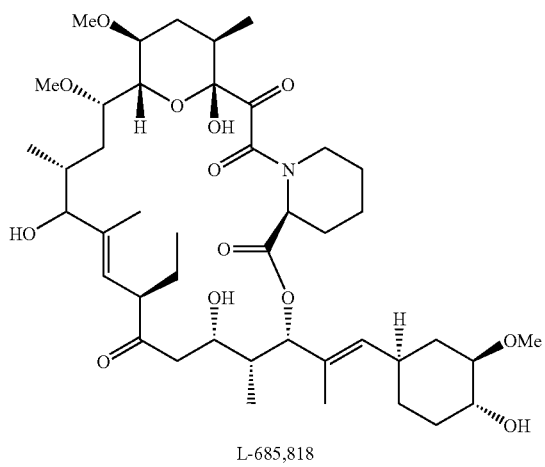

L-685,818

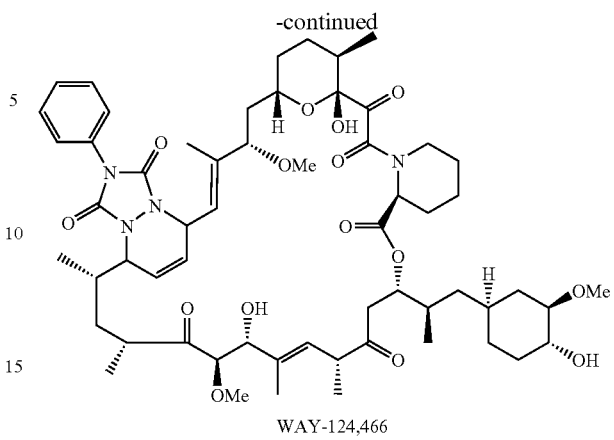

WAY-124,466

One of the few positions of rapamycin that is readily amenable to chemical modification is the allylic 16-methoxy group; this reactive group is readily exchanged by acid-catalyzed nucleophilic substitution. Replacement of the 16-methoxy group of rapamycin with a variety of bulky groups has produced analogs showing selective loss of immunosuppressive activity while retaining FKBP-binding (see Luengo et al., 1995, *Chemistry & Biology* 2: 471-481). One of the best compounds, 1, below, shows complete loss of activity in the splenocyte proliferation assay with only a 10-fold reduction in binding to FKBP.

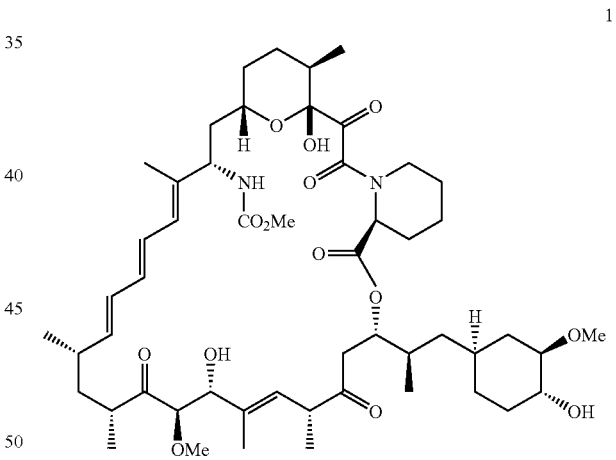

1

There are also synthetic analogs of FKBP binding domains. These compounds reflect an approach to obtaining neuroimmunophilin ligands based on "rationally designed" molecules that retain the FKBP-binding region in an appropriate conformation for binding to FKBP, but do not possess the effector binding regions. In one example, the ends of the FKBP binding domain were tethered by hydrocarbon chains (see Holt et al., 1993, *Journal of the American Chemical Society* 115: 9925-9938); the best analog, 2, below, binds to FKBP about as well as FK-506. In a similar approach, the ends of the FKBP binding domain were tethered by a tripeptide to give analog 3, below, which binds to FKBP about 20-fold poorer than FK-506. These compounds are anticipated to have neuroimmunophilin binding activity.

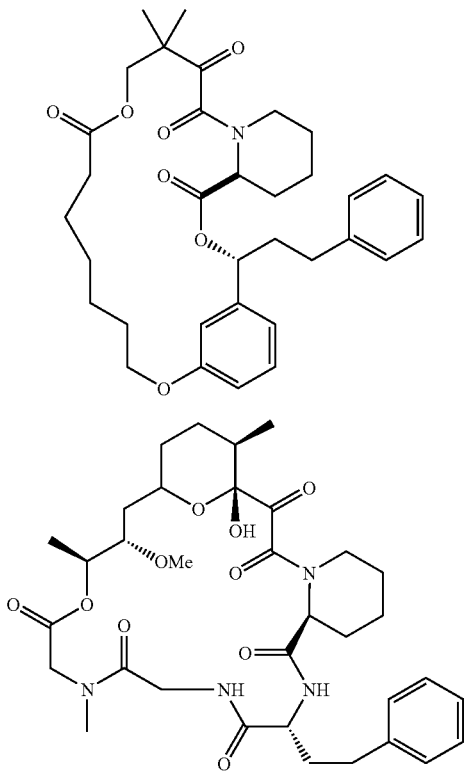

In a primate MPTP model of Parkinson's disease, administration of FKBP ligand GPI-1046 caused brain cells to regenerate and behavioral measures to improve. MPTP is a neurotoxin, which, when administered to animals, selectively damages nigral-striatal dopamine neurons in the brain, mimicking the damage caused by Parkinson's disease. Whereas, before treatment, animals were unable to use affected limbs, the FKBP ligand restored the ability of animals to feed themselves and gave improvements in measures of locomotor activity, neurological outcome, and fine motor control. There were also corresponding increases in regrowth of damaged nerve terminals. These results demonstrate the utility of FKBP ligands for treatment of diseases of the CNS.

From the above description, two general approaches towards the design of non-immunosuppressant, neuroimmunophilin ligands can be seen. The first involves the construction of constrained cyclic analogs of FK-506 in which the FKBP binding domain is fixed in a conformation optimal for binding to FKBP. The advantages of this approach are that the conformation of the analogs can be accurately modeled and predicted by computational methods, and the analogs closely resemble parent molecules that have proven pharmacological properties. A disadvantage is that the difficult chemistry limits the numbers and types of compounds that can be prepared. The second approach involves the trial and error construction of acyclic analogs of the FKBP binding domain by conventional medicinal chemistry. The advantages to this approach are that the chemistry is suitable for production of the numerous compounds needed for such interactive chemistry-bioassay approaches. The disadvantages are that the molecular types of compounds that have emerged have no known history of appropriate pharmacological properties, have rather labile ester functional groups, and are too conformationally mobile to allow accurate prediction of conformational properties.

The present invention provides useful methods and reagents related to the first approach, but with significant advantages. The invention provides recombinant PKS genes that produce a wide variety of polyketides that cannot otherwise be readily synthesized by chemical methodology alone. Moreover, the present invention provides polyketides that have either or both of the desired immunosuppressive and neurotrophic activities, some of which are produced only by fermentation and others of which are produced by fermentation and chemical modification. Thus, in one aspect, the invention provides compounds that optimally bind to FKBP but do not bind to the effector proteins. The methods and reagents of the invention can be used to prepare numerous constrained cyclic analogs of FK-520 in which the FKBP binding domain is fixed in a conformation optimal for binding to FKBP. Such compounds will show neuroimmunophilin binding (neurotrophic) but not immunosuppressive effects. The invention also allows direct manipulation of FK-520 and related chemical structures via genetic engineering of the enzymes involved in the biosynthesis of FK-520 (as well as related compounds, such as FK-506 and rapamycin); similar chemical modifications are simply not possible because of the complexity of the structures. The invention can also be used to introduce "chemical handles" into normally inert positions that permit subsequent chemical modifications.

Several general approaches to achieve the development of novel neuroimmunophilin ligands are facilitated by the methods and reagents of the present invention. One approach is to make "point mutations" of the functional groups of the parent FK-520 structure that bind to the effector molecules to eliminate their binding potential. These types of structural modifications are difficult to perform by chemical modification, but can be readily accomplished with the methods and reagents of the invention.

A second, more extensive approach facilitated by the present invention is to utilize molecular modeling to predict optimal structures ab initio that bind to FKBP but not effector molecules. Using the available X-ray crystal structure of FK-520 (or FK-506) bound to FKBP, molecular modeling can be used to predict polyketides that should optimally bind to FKBP but not calcineurin. Various macrolide structures can be generated by linking the ends of the FKBP-binding domain with "all possible" polyketide chains of variable length and substitution patterns that can be prepared by genetic manipulation of the FK-520 or FK-506 PKS gene cluster in accordance with the methods of the invention. The ground state conformations of the virtual library can be determined, and compounds that possess binding domains most likely to bind well to FKBP can be prepared and tested.

Once a compound is identified in accordance with the above approaches, the invention can be used to generate a focused library of analogs around the lead candidate, to "fine tune" the compound for optimal properties. Finally, the genetic engineering methods of the invention can be directed towards producing "chemical handles" that enable medicinal chemists to modify positions of the molecule previously inert to chemical modification. This opens the path to previously prohibited chemical optimization of lead compounds by time-proven approaches.

Moreover, the present invention provides polyketide compounds and the recombinant genes for the PKS enzymes that produce the compounds that have significant advantages over FK-506 and FK-520 and their analogs. The metabolism and pharmacokinetics of tacrolimus has been extensively studied, and FK-520 is believed to be similar in these respects.

Absorption of tacrolimus is rapid, variable, and incomplete from the gastrointestinal tract (Harrison's Principles of Internal Medicine, 14th edition, 1998, McGraw Hill, 14, 20, 21, 64-67). The mean bioavailability of the oral dosage form is 27%, (range 5 to 65%). The volume of distribution (VolD) based on plasma is 5 to 65 L per kg of body weight (L/kg), and is much higher than the VolD based on whole blood concentrations, the difference reflecting the binding of tacrolimus to red blood cells. Whole blood concentrations may be 12 to 67 times the plasma concentrations. Protein binding is high (75 to 99%), primarily to albumin and alpha-acid glycoprotein. The half-life for distribution is 0.9 hour; elimination is biphasic and variable: terminal-11.3 hr (range, 3.5 to 40.5 hours). The time to peak concentration is 0.5 to 4 hours after oral administration.

Tacrolimus is metabolized primarily by cytochrome P450 3A enzymes in the liver and small intestine. The drug is extensively metabolized with less than 1% excreted unchanged in urine. Because hepatic dysfunction decreases clearance of tacrolimus, doses have to be reduced substantially in primary graft non-function, especially in children. In addition, drugs that induce the cytochrome P450 3A enzymes reduce tacrolimus levels, while drugs that inhibit these P450s increase tacrolimus levels. Tacrolimus bioavailability doubles with co-administration of ketoconazole, a drug that inhibits P450 3A. See, Vincent et al., 1992, In vitro metabolism of FK-506 in rat, rabbit, and human liver microsomes: Identification of a major metabolite and of cytochrome P450 3A as the major enzymes responsible for its metabolism, *Arch. Biochem. Biophys.* 294: 454-460; Iwasaki et al., 1993, Isolation, identification, and biological activities of oxidative metabolites of FK-506, a potent immunosuppressive macrolide lactone, *Drug Metabolism & Disposition* 21: 971-977; Shiraga et al., 1994, Metabolism of FK-506, a potent immunosuppressive agent, by cytochrome P450 3A enzymes in rat, dog, and human liver microsomes, *Biochem. Pharmacol.* 47: 727-735; and Iwasaki et al., 1995, Further metabolism of FK-506 (Tacrolimus); Identification and biological activities of the metabolites oxidized at multiple sites of FK-506, *Drug Metabolism & Disposition* 23: 28-34. The cytochrome P450 3A subfamily of isozymes has been implicated as important in this degradative process.

Figure 6:
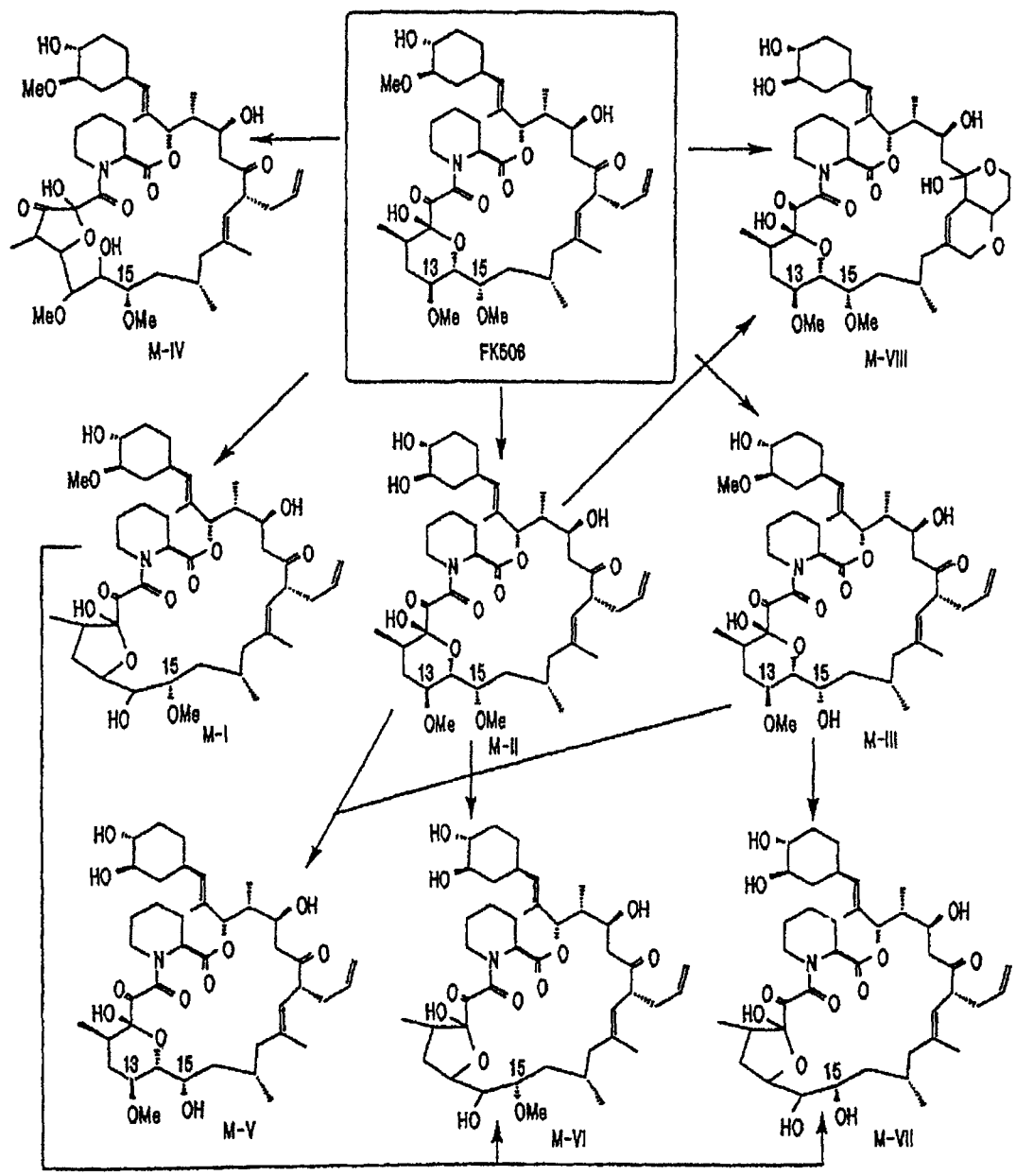
FIG. 6 shows the proposed degradative pathway for tacrolimus (FK-506) metabolism.
Figure 7A:
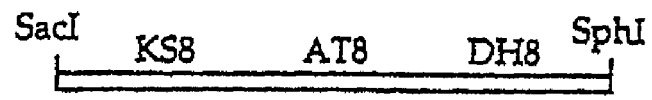
FIG. 7 shows a schematic process for the construction of recombinant PKS genes of the invention that encode PKS enzymes that produce 13-desmethoxy FK-506 and FK-520 polyketides of the invention, as described in Example 4, below.
Figure 7B:
Figure 7C:
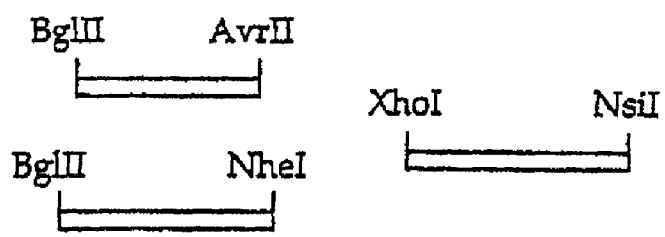
Figure 7D:
Figure 7E:
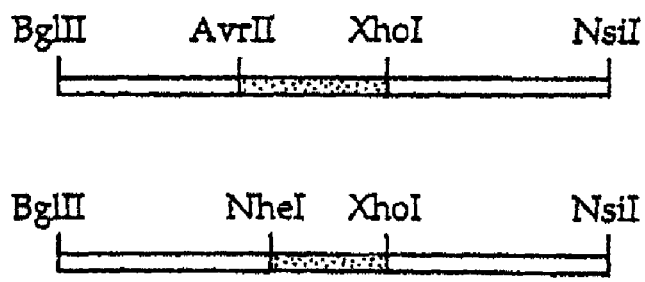

Structures of the eight isolated metabolites formed by liver microsomes are shown in FIG. 6. Four metabolites of FK-506 involve demethylation of the oxygens on carbons 13, 15, and 31, and hydroxylation of carbon 12. The 13-demethylated (hydroxy) compounds undergo cyclizations of the 13-hydroxy at C-10 to give MI, MVI and MVII, and the 12-hydroxy metabolite at C-10 to give I. Another four metabolites formed by oxidation of the four metabolites mentioned above were isolated by liver microsomes from dexamethasone treated rats. Three of these are metabolites doubly demethylated at the methoxy groups on carbons 15 and 31 (M-V), 13 and 31 (M-VI), and 13 and 15 (M-VII). The fourth, M-VIII, was the metabolite produced after demethylation of the 31-methoxy group, followed by formation of a fused ring system by further oxidation. Among the eight metabolites, M-II has immuno-suppressive activity comparable to that of FK-506, whereas the other metabolites exhibit weak or negligible activities. Importantly, the major metabolite of human, dog, and rat liver microsomes is the 13-demethylated and cyclized FK-506 (M-I).

Thus, the major metabolism of FK-506 proceeds via 13-demethylation followed by cyclization to the inactive M-I, this representing about 90% of the metabolic products after a 10 minute incubation with liver microsomes. Analogs of tacrolimus that do not possess a C-13 methoxy group would not be susceptible to the first and most important biotransformation in the destructive metabolism of tacrolimus (i.e. cyclization of 13-hydroxy to C-10). Thus, a 13-desmethoxy analog of FK-506 should have a longer half-life in the body than does FK-506. The C-13 methoxy group is believed not to be required for binding to FKBP or calcineurin. The C-13 methoxy is not present on the identical position of rapamycin, which binds to FKBP with equipotent affinity as tacrolimus. Also, analysis of the 3-dimensional structure of the FKBP-tacrolimus-calcineurin complex shows that the C-13 methoxy has no interaction with FKBP and only a minor interaction with calcineurin. The present invention provides C-13-desmethoxy analogs of FK-506 and FK-520, as well as the recombinant genes that encode the PKS enzymes that catalyze their synthesis and host cells that produce the compounds.

These compounds exhibit, relative to their naturally occurring counterparts, prolonged immunosuppressive action in vivo, thereby allowing a lower dosage and/or reduced frequency of administration. Dosing is more predictable, because the variability in FK-506 dosage is largely due to variation of metabolism rate. FK-506 levels in blood can vary widely depending on interactions with drugs that induce or inhibit cytochrome P450 3A (summarized in USP Drug Information for the Health Care Professional). Of particular importance are the numerous drugs that inhibit or compete for CYP 3A, because they increase FK-506 blood levels and lead to toxicity (Prograf package insert, Fujisawa☐US, Rev 4/97, Rec 6/97). Also important are the drugs that induce P450 3A (e.g. Dexamethasone), because they decrease FK-506 blood levels and reduce efficacy. Because the major site of CYP 3A action on FK-506 is removed in the analogs provided by the present invention, those analogs are not as susceptible to drug interactions as the naturally occurring compounds.

Hyperglycemia, nephrotoxicity, and neurotoxicity are the most significant adverse effects resulting from the use of FK-506 and are believed to be similar for FK-520. Because these effects appear to occur primarily by the same mechanism as the immunosuppressive action (i.e. FKBP-calcineurin interaction), the intrinsic toxicity of the desmethoxy analogs may be similar to FK-506. However, toxicity of FK-506 is dose related and correlates with high blood levels of the drug (Prograf package insert, Fujisawa☐US, Rev 4/97, Rec 6/97). Because the levels of the compounds provided by the present invention should be more controllable, the incidence of toxicity should be significantly decreased with the 13-desmethoxy analogs. Some reports show that certain FK-506 metabolites are more toxic than FK-506 itself, and this provides an additional reason to expect that a CYP 3A resistant analog can have lower toxicity and a higher therapeutic index.

Thus, the present invention provides novel compounds related in structure to FK-506 and FK-520 but with improved properties. The invention also provides methods for making these compounds by fermentation of recombinant host cells, as well as the recombinant host cells, the recombinant vectors in those host cells, and the recombinant proteins encoded by those vectors. The present invention also provides other valuable materials useful in the construction of these recombinant vectors that have many other important applications as well. In particular, the present invention provides the FK-520 PKS genes, as well as certain genes involved in the biosynthesis of FK-520 in recombinant form.

FK-520 is produced at relatively low levels in the naturally occurring cells, *Streptomyces hygroscopicus* var. *ascomyceticus*, in which it was first identified. Thus, another benefit provided by the recombinant FK-520 PKS and related genes of the present invention is the ability to produce FK-520 in greater quantities in the recombinant host cells provided by the invention. The invention also provides methods for making novel FK-520 analogs, in addition to the desmethoxy analogs described above, and derivatives in recombinant host cells of any origin.

The biosynthesis of FK-520 involves the action of several enzymes. The FK-520 PKS enzyme, which is composed of the fkbA, fkbB, fkbC, and fkbP gene products, synthesizes the core structure of the molecule. There is also a hydroxylation at C-9 mediated by the P450 hydroxylase that is the fkbD gene product and that is oxidized by the fkbO gene product to result in the formation of a keto group at C-9. There is also a methylation at C-31 that is mediated by an O-methyltransferase that is the fkbM gene product. There are also methylations at the C-13 and C-15 positions by a methyltransferase believed to be encoded by the fkbG gene; this methyltransferase may act on the hydroxymalonyl CoA substrates prior to binding of the substrate to the AT domains of the PKS during polyketide synthesis. The present invention provides the genes encoding these enzymes in recombinant form. The invention also provides the genes encoding the enzymes involved in ethylmalonyl CoA and 2-hydroxymalonyl CoA biosynthesis in recombinant form. Moreover, the invention provides Streptomyces hygroscopicus var. ascomyceticus recombinant host cells lacking one or more of these genes that are useful in the production of useful compounds.

The cells are useful in production in a variety of ways. First, certain cells make a useful FK-520-related compound merely as a result of inactivation of one or more of the FK-520 biosynthesis genes. Thus, by inactivating the C-31 O-methyltransferase gene in Streptomyces hygroscopicus var. ascomyceticus, one creates a host cell that makes a desmethyl (at C-31) derivative of FK-520. Second, other cells of the invention are unable to make FK-520 or FK-520 related compounds due to an inactivation of one or more of the PKS genes. These cells are useful in the production of other polyketides produced by PKS enzymes that are encoded on recombinant expression vectors and introduced into the host cell.

Moreover, if only one PKS gene is inactivated, the ability to produce FK-520 or an FK-520 derivative compound is restored by introduction of a recombinant expression vector that contains the functional gene in a modified or unmodified form. The introduced gene produces a gene product that, together with the other endogenous and functional gene products, produces the desired compound. This methodology enables one to produce FK-520 derivative compounds without requiring that all of the genes for the PKS enzyme be present on one or more expression vectors. Additional applications and benefits of such cells and methodology will be readily apparent to those of skill in the art after consideration of how the recombinant genes were isolated and employed in the construction of the compounds of the invention.

The FK-520 biosynthetic genes were isolated by the following procedure. Genomic DNA was isolated from Streptomyces hygroscopicus var. ascomyceticus (ATCC 14891) using the lysozyme/proteinase K protocol described in Genetic Manipulation of Streptomyces-A Laboratory Manual (Hopwood et al., 1986). The average size of the DNA was estimated to be between 80-120 kb by electrophoresis on 0.3% agarose gels. A library was constructed in the Super-COS™ vector according to the manufacturer's instructions and with the reagents provided in the commercially available kit (Stratagene). Briefly, 100 µg of genomic DNA was partially digested with 4 units of Sau3A I for 20 min. in a reaction volume of 1 mL, and the fragments were dephosphorylated and ligated to SuperCos vector arms. The ligated DNA was packaged and used to infect log-stage XL1-BlueMR cells. A library of about 10,000 independent cosmid clones was obtained.

Based on recently published sequence from the FK-506 cluster (Motamedi and Shafiee, 1998, Eur. J. Biochem. 256: 528), a probe for the fkbO gene was isolated from ATCC 14891 using PCR with degenerate primers. With this probe, a cosmid designated pKOS034-124 was isolated from the library. With probes made from the ends of cosmid pKOS034-124, an additional cosmid designated pKOS034-120 was isolated. These cosmids (pKOS034-124 and pKOS034-120) were shown to contain DNA inserts that overlap with one another. Initial sequence data from these two cosmids generated sequences similar to sequences from the FK-506 and rapamycin clusters, indicating that the inserts were from the FK-520 PKS gene cluster. Two EcoRI fragments were subcloned from cosmids pKOS034-124 and pKOS034-120. These subclones were used to prepare shotgun libraries by partial digestion with Sau3AI, gel purification of fragments between 1.5 kb and 3 kb in size, and ligation into the pLitmus28 vector (New England Biolabs). These libraries were sequenced using dye terminators on a Beckmann CEQ2000 capillary electrophoresis sequencer, according to the manufacturer's protocols.

To obtain cosmids containing sequence on the left and right sides of the sequenced region described above, a new cosmid library of ATCC 14891 DNA was prepared essentially as described above. This new library was screened with a new JkbM probe isolated using DNA from ATCC 14891. A probe representing the JkbP gene at the end of cosmid pKOS034-124 was also used. Several additional cosmids to the right of the previously sequenced region were identified. Cosmids pKOS065-C3 1 and pKOS065-C3 were identified and then mapped with restriction enzymes. Initial sequences from these cosmids were consistent with the expected organization of the cluster in this region. More extensive sequencing showed that both cosmids contained in addition to the desired sequences, other sequences not contiguous to the desired sequences on the host cell chromosomal DNA. Probing of additional cosmid libraries identified two additional cosmids, pKOS065-M27 and pKOS065-M2 1, that contained the desired sequences in a contiguous segment of chromosomal DNA. Cosmids p1105034-124 (PTA-729), pKOS034- 120 (PTA-728), pKOS065-M27 (PTA-726), and pKOS065-M21 (PTA-727) have been deposited with the American Type Culture Collection, located at 10801 University Boulevard, Manassas. Virginia 20110-2209, USA, on Sep. 20, 1999. The complete nucleotide sequence of the coding sequences of the genes that encode the proteins of the FK-520 PKS are shown below but can also be determined from the cosmids of the invention deposited with the ATCC using standard methodology.

Figure 3:
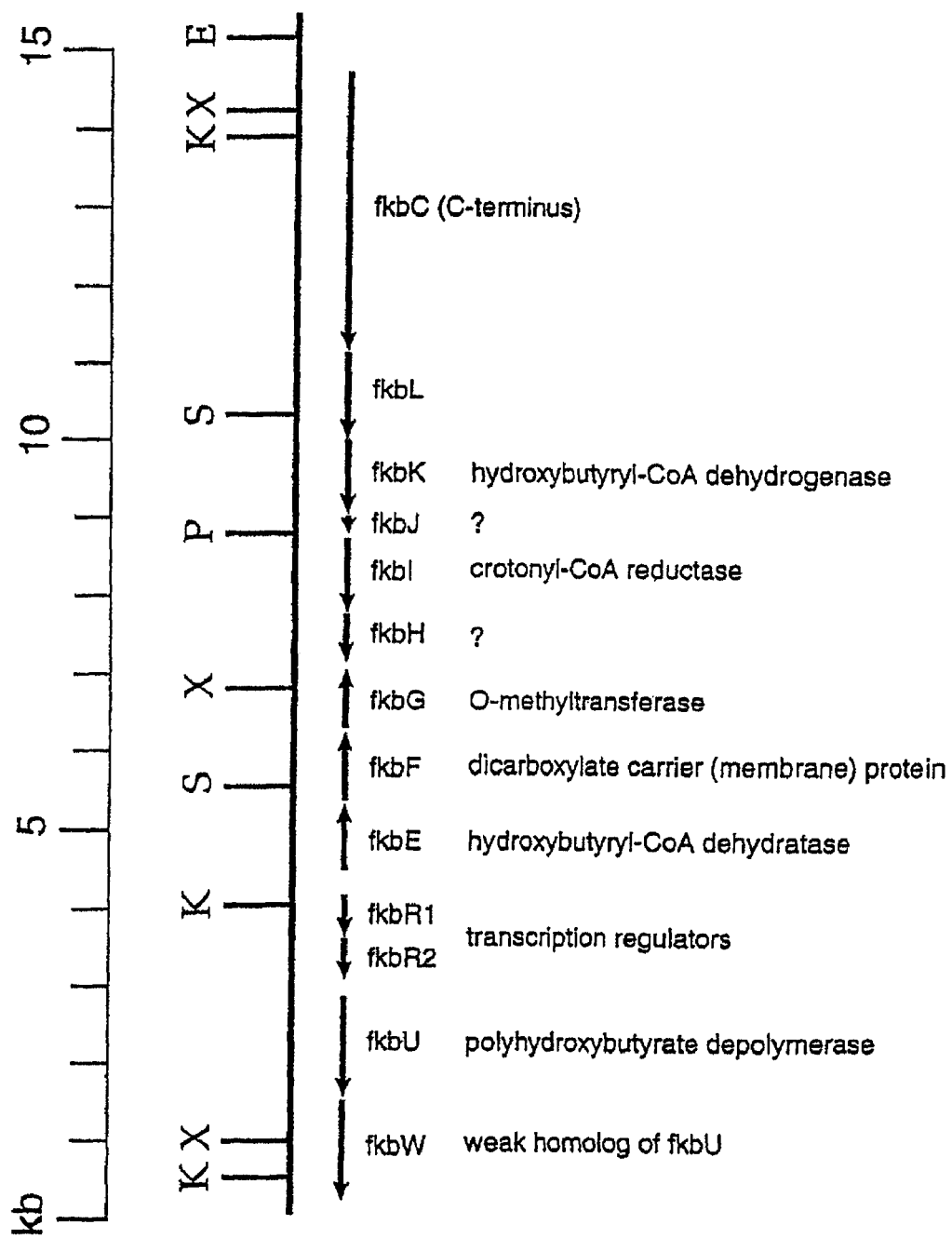
FIG. 3 shows a close-up view of the left end of the FK-520 gene cluster, which contains at least ten additional genes. The ethyl side chain on carbon 21 of FK-520 (FIG. 2) is derived from an ethylmalonyl CoA extender unit that is incorporated by an ethylmalonyl specific AT domain in extender module 4 of the PKS. At least four of the genes in this region code for enzymes involved in ethylmalonyl biosynthesis. The polyhydroxybutyrate depolymerase is involved in maintaining hydroxybutyryl-CoA pools during FK-520 production. Polyhydroxybutyrate accumulates during vegetative growth and disappears during stationary phase in other *Streptomyces* (Ranade and Vining, 1993, *Can. J. Microbiol.* 39:377). Open reading frames with unknown function are indicated with a question mark.

Referring to FIGS. 1 and 3, the FK-520 PKS gene cluster is composed of four open reading frames designated fkbB, fkbC, fkbA, and fkbP. The fkbB open reading frame encodes the loading module and the first four extender modules of the PKS. The fkbC open reading frame encodes extender modules five and six of the PKS. The fkbA open reading frame encodes extender modules seven, eight, nine, and ten of the PKS. The fkbP open reading frame encodes the NRPS of the PKS. Each of these genes can be isolated from the cosmids of the invention described above. The DNA sequences of these genes are provided below (SEQ ID NO:1) preceded by the following table identifying the start and stop codons of the open reading frames of each gene and the modules and domains contained therein.

| Nucleotides | Gene or Domain |
|---|---|
| complement (412-1836) | fkbW |
| complement (2020-3579) | fkbV |
| complement (3969-4496) | fkbR2 |
| complement (4595-5488) | fkbR1 |
| 5601-6818 | fkbE |
| 6808-8052 | fkbF |
| 8156-8824 | fkbG |
| complement (9122-9883) | fkbH |
| complement (9894-10994) | fkbI |
| complement (10987-11247) | fkbJ |
| complement (11244-12092) | fkbK |
| complement (12113-13150) | fkbL |
| complement (13212-23988) | fkbC (SEQ ID NO:74) |
| complement (23992-46573) | fkbB (SEQ ID NO:73) |
| 46754-47788 | fkbO |
| 47785-52272 | fkbP |
| 52275-71465 | fkbA (SEQ ID NO:72) |
| 71462-72628 | fkbD |
| 72625-73407 | fkbM |
| complement (73460-76202) | fkbN |
| complement (76336-77080) | JkbQ |
| complement (77076-77535) | JkbS |
| complement (44974-46573) | CoA ligase of loading domain |
| complement (43777-44629) | ER of loading domain |
| complement (43144-43660) | ACP of loading domain |
| complement (41842-43093) | KS of extender module 1 (KS1) |
| complement (40609-41842) | AT1 |
| complement (39442-40609) | DH1 |
| complement (38677-39307) | KR1 |
| complement (38371-38581) | ACP1 |
| complement (37145-38296) | KS2 |
| complement (35749-37144) | AT2 |
| complement (34606-35749) | DH2 (inactive) |
| complement (33823-34480) | KR2 |
| complement (33505-33715) | ACP2 |
| complement (32185-33439) | KS3 |
| complement (31018-32185) | AT3 |
| complement (29869-31018) | DH3 (inactive) |
| complement (29092-29740) | KR3 |
| complement (28750-28960) | ACP3 |
| complement (27430-28684) | KS4 |
| complement (26146-27430) | AT4 |
| complement (24997-26146) | DH4 (inactive) |
| complement (24163-24373) | ACP4 |
| complement (22653-23892) | KS5 |
| complement (21420-22653) | AT5 |
| complement (20241-21420) | DH5 |
| complement (19464-20097) | KR5 |
| complement (19116-19326) | ACP5 |
| complement (17820-19053) | KS6 |
| complement (16587-17820) | AT6 |
| complement (15438-16587) | DH6 |
| complement (14517-15294) | ER6 |
| complement (13761-14394) | KR6 |
| complement (13452-13662) | ACP6 |
| 52362-53576 | KS7 |
| 53577-54716 | AT7 |
| 54717-55871 | DH7 |
| 56019-56819 | ER7 |
| 56943-57575 | KR7 |
| 57711-57920 | ACP7 |
| 57990-59243 | KS8 |
| 59244-60398 | AT8 |
| 60399-61412 | DH8 (inactive) |
| 61548-62180 | KR8 |
| 62328-62537 | ACP8 |
| 62598-63854 | KS9 |
| 63855-65084 | AT9 |
| 65085-66254 | DH9 |
| 66399-67175 | ER9 |
| 67299-67931 | KR9 |
| 68094-68303 | ACP9 |
| 68397-69653 | KS10 |

-continued

| 69654-70985 | AT10 |
| 71064-71273 | ACP10 |

```
   1 GATCTCAGGC ATGAAGTCCT CCAGGCGAGG CGCCGAGGTG GTGAACACCT CGCCGCTGCT
  61 TGTACGGACC ACTTCAGTCA GCGGCGATTG CGGAACCAAG TCATCCGGAA TAAAGGGCGG
 121 TTACAAGATC CTCACATTGC GCGACCGCCA GCATACGCTG AGTTGCCTCA GAGGCAAACC
 181 GAAAGGGCGC GGGCGGTCCG CACCAGGGCG GAGTACGCGA CGAGAGTGGC GCACCCGCGC
 241 ACCGTCACCT CTCTCCCCCG CCGGCGGGAT GCCCGGCGTG ACACGGTTGG GCTCTCCTCG
 301 ACGCTGAACA CCCGCGCGGT GTGGCGTCGG GGACACCGCC TGGCATCGGC CGGGTGACGG
 361 TACGGGGAGG GCGTACGGCG GCCGTGGCTC GTGCTCACGG CCGCCGGGCG GTCATCCGTC
 421 GAGACGGCAC TCGGCGAGCA GGGACGCCTG GTCGGCACCT GCGGGCCGGA CGACCGTGTG
 481 GTTCGCGGGC GGGCGGTGGC CGGTGGTGAG CCAGCTCTCC AGGGCGGTGA AGGCTGAGCG
 541 GTGACACGGC AGCAAAGGCC GGAGTCGGTC GGGGAAGGTG TCGACGAGGG CGTCGGTGTG
 601 CGTGCCGTCC TCGATGCGGT AGTAGCGGTA CCGGCCGCCA GGCCGCTGCC GGACATACGC
 661 GCGTACACGT CGGAGCCCGG GCGGCAGGCA GCAGCACGTC GAGAGTGCCT GGATGGTGAT
 721 CAGCGGCTTG CCGATACGAC CGGTCAACGC GATGCGTTCC ACGGCCGCGT GGACGCCGGA
 781 GGAGCGGGTG GCGTAGTCGT AGTCGGCATC GCAGCCCGGG ACCGTCCCCG GGCGCAATA
 841 CGGTGTGCCG GCTTCCTTCT CCCCATCGAA GCCGGGGTCG AACTCCTCGC GGTAGACGCG
 901 CTGCGTCAGA TCCCAGTAGA CCTCGTGGTG GTACGGCCAC AAGAACTCGG AGTCGGCCGG
 961 GAACCCGGCG CGGAGCAGCG CCTCGCGCGC CTGGCCGGCT GCGGGGCCGC CTGCCGCGTA
1021 GGTGGGGTAG TCGCGCAGGG CGGCCGGCAG GAAGGTGAAG AGGTTGGGAC CCTCCGCGCG
1081 CCACAGGGTG CCTTCCCAGT CGACTCCTCC GTCGTACAGC TCGGGATGGT TCTCCAGCTG
1141 CCAGCGCACG AGGTAGCCGC CGTTGGACAT CCCGGTGACC AGGGTGCGCT CGAGCGGCCG
1201 GTGGTAGCGC TGGGCGACCG ACGCGCGGGC GGCCCGGGTC AGCTGGGTGA GGCGGGTGTT
1261 CCACTCGGCG ACGCGTCGC CCGGCCGGGA GCCATCACGG TAGAACGCGG GGCCGGTGTT
1321 GCCCTTGTCG GTGGCGGCGT AGGCGTAACC GCGGGCGAGC ACCCAGTCGG CGATGGCCCG
1381 GTCGTTGGCG TACTGCTCGC GGTTACCGGG GGTGCCGGCC ACGACCAGGC CACCGTTCCA
1441 GCGGTCGGGC AGCCGGATGA CGAACTGGGC GTCGTGGTTC CACCCGTGGT TGGTGTTGGT
1501 GGTGGAGGTG TCGGGGAAGT AGCCGTCGAT CTGGATCCCG GGCACTCCGG TGGGAGTGGC
1561 CAGGTTCTTG GGCGTCAGCC CTGCCCAGTC CGCCGGGTCG GTGTGGCCGG TGGCCGCCGT
1621 TCCCGCCGTG GTCAGCTCGT CCAGGCAGTC GGCCTGCTGA CGTGCCGCCG CCCGGGACACG
1681 CAGCTGGGAC AGACGGGCGC AGTGACCGTC CGGGGCATCG GGAGCAGGCC GGGCCGTGGC
1741 CGGTGAGGGG AGCAGGACGG CGACTGCGGC CAGGGTGAGA GCGCCGAGGC CGGTGCGTCT
1801 TCTCGGGGCC CGTCCGACAC CGAGGGGCAG AACCATGGAG AGCCTCCAGA CGTGCGGATG
1861 GATGACGGAC TGGAGGCTAG GTCGCGCACG GTGGAGACGA ACATGGGTGC GCCCGCCATG
1921 ACTGAGGCCC CTCAGAGGTG GGCCGCCGCC ATGACGGGCG CGGGACCGCG GGCGCTCCGG
1981 GGCGGTGCCC GCGGCCGCCA CCGGTTCCGG GTCCCCGGGT CAGGGACAGG TGTCGTTCGC
2041 GACGGTGAAG TAGCCGGTCG GCGACTCTTT CAAGGTGGTC GTGACGAAGG TGTTGTACAG
2101 GCCCATGTTC TGGCCGGAGC CCTTGGCGTA GGTGTAACCG GCGCTCGTCG TGGCGCGGCC
2161 CGCCTGGACG TGAGCGTAGT TGCCGGCGGT CCAGCAGACG GCCGTGGCAC CGGTCGTCTG
2221 CGCGGTGACC GCGCCCGAGA GCGGTCCGGC CTTGCCGTCC GCGTCCCGGG CGGCGACCGC
2281 GTAGGTGTGC GATGTGCCCG CCCTCAGGCC GGTGTCCGTG TACGACGTCG TGGCGGACGT
2341 GGTGATCTGG GCACCGTCGC GGTGGACGGC GTAGTCGGTG GCGCCGTCGA CGGGTTTCCA
2401 GGTCAGGCTG ATGGTGGTGT CGGTGGCGCC GGTGGCGGCC AGGCCGGACG GAGCGGGCAG
2461 CGAACCGGGG TCGGAGGCGA ATCCGCTCAG GCCGAAGAAC TGCGTGATCC AGTAGCTGGA
2521 ACAGATCGAG TCCAGGAAGT AGGCGGCGCC GGTGCTGCCG CACTGCTGTG CTCCGGTGCC
2581 GGGATCGACC GGGGTGCCGT GCCCGATGCC CGGCACCCGG TTCACCTTCCA CGGCCACCGA
2641 TCCGTCCGCG GCCAGGTACT CCTCGTGCCG GGTGGAGTTC GGGCCGATCA CCGAGGTACG
2701 GTCCGGCGTC TGGGACACGC CGTGCACAGC GGTCCACTGG TCGCGCAACT CGTCGGCGTT
2761 GCGCGGCGCG ACGGTGGTGT CCTTGTCGCC GTGCCAGATG GCCACGCGCG GCCACGGGCC
2821 CGACCACGAG GGTAGCCGT CACGGACCCG CCGCGCCCAC TGGTCCGCGG TCAGGTCGGT
2881 CCCGGGGTTC ATGCACAGGT ACGCGCTGCT GACGTCGGTG CACAGCCGA AGGGCAGGCC
2941 GGCGACGACC GCGCCGGCCT GGAAGACGTC CGGATAGGTG GCGAGCATCA CCGACGTCAT
3001 GGCACCGCCG GCGGACAGCC CGGTGATGTA GGTGCGTGG GGGTCCGCGC CGTAGGCGGA
3061 GACGGTGTGA GCGGCCATCT GCCGGATCGA CGCGGCTTCG CCCTGGCCCC TGCGGTTGTC
3121 GCTGCTCTGG AACCAGTTGA AGCACCTGTT CGCGTTGTTC GACGACGTGG TCTCGGCGAA
3181 CACGAGCAGG AAGCCATAGC GGTCCGCGAA TGAGAGCAGG CCGGAGTTGT CGGCGTAGCC
3241 CTGGGCGTCC TGGGTGCAAC CGTGCAGGGC GAACACCACC GCCGGCTCCG CCCGGCCGGA
3301 CGCGGGCCGG TAGACGTACA TGTTCAGCCG GCCCGGGTTC GTGCCGAAGT CCGCGACCTC
3361 GGTCAGGTCC GCCTTGGTCA GACCGGGCTT GGCCAGGCCC GCCGCGGCGT GGGCCGTCGG
3421 CGCCGGGCCG AGCAGGGCCG CTCCGAGTAC GAGGGCCACG ACGGCCACGA GACGGGTGAG
3481 CACCCCCGC CGTCCCGGAC GCGACAACGA CCCGACCGGC GGCGAGGAGG AGAGGGGGAA
3541 CAGCGGGGTG AGGATTCCCC GGAACGGCGG CGGCTGCATG GCGGCTCCCT CGATGTCGTG
3601 GGGGGGACAC GGAGGGCTCC CTGACGTCGA TCAGTGGGAG CGCCCCGGTG CCCGGCACCG
3661 TAGGGGTGGT TCAACCCGCA ACGGTATGGC CCGGAGCACC ACACCCCGCA CCGCGCGATG
3721 TGCGCCCGGA CGGATTGTGT CGCCTTGCGG AATCTGATAC CCGGACGCGA CGAACGCCCG
3781 ACCCGACACG GGTAGGGCGT CATGGTGTCC GACTCGGCCG GTGGGCCTTG CCTGCCCTGG
3841 ACGGACCGGG CGTCGGCGGA CCGGGCGTCG GCGGGCTGGG CGGTATGGCG GCCGAGGACG
3901 CCAGCCGCGT GGGGCGGCCG CGCCCAAGTG CAGTACGCCG ACCGTGGCCG GCGGGAGGGC
3961 CGGACCGGTC AGTGCAGTCC CGCGGCCCTG CGGGACCGCT CGTCCCAGAC GGTGTTCACC
4021 GCGGCGAACC GGGGTCCGTG TCCGCGGCGG TAGACCATCA GTGTCCGCTC GAAGGTGATG
4081 ACGATGCACAC CGTCCTGGTT GTAGCCGATG GTGCGCACGC TGATGATGCC TACGTCAGGT
4141 CGGCTGGCGG ACTCCCGGGT GTTCAGGACC TCGGACTGCG AGTAGATGGT GTCGCCCTCG
4201 AAGACGGGGT TCGGCAGCCT GACCCGGTCC CAGCCGAGGT TGGCCATCAC ATGCTGGGAG
4261 ATGTCGGTGA CGCTCTGCCC GGTGACCAGG GCGAGGGTGA AGGTGGAGTC CACCAGCGGG
4321 TTGCCCCAGG TGGTGCCCGC CGAGTAGTGG CGGTCGAAGT GCAGCGGCGC GGTGTTCTGC
4381 GTCAGGAGCG TGAGCCAGGA GTTGTCGGTC TCCAGGACCG TGCGGCCCAG GGGGTGGCGG
4441 TACACGTCGC CGGTGGTGAA GTCCTCGAAG TAGCGGCCCT GCCAGCCCTC GACCACAGCG
4501 GTGCGGGTGG CGTCCTGGTC CGGGTTCTCA GTCGTCATGG CGCTCATTCT GGGAAGTCCC
```

-continued

```
4561 CGGTCCGCTG TGAAATGCCG AACCTTCACC GGGCTCATAC GTGCGGCGCA TGAGCCCTGG
4621 ACCGTACGTA GTCGTAGAAC CTCGCCACCA CTGGCGCGCG TGGTCCTCCG GCGAGTGTGA
4681 CCACGCCGAC CGTGCGCCGC GCCTGCGGGT CGTCGAGCGG CACGGCGACG GCGTGGTCAC
4741 CGGGCCCGGA CGGGCTGCCG GTGAGGGGGG CGACGGCCAC ACCGAGGCCG GCGGCGACCA
4801 GGGCCCGCAG CGTGCTCAGC TCGGTGCTCT CCAGGACGAC CCGCGGCACG AATCCGGCCG
4861 CGGCGCACAG CCGGTCGGTG ATCTGGCGCA GTCCGAAGAC CGGCTCCAGT GCCACGAACG
4921 CCTCATCGGC CAGCTCCGCG GTCCGCACCC GGCGGCGTCT GGCCAGCCGG TGTCGGGGTG
4981 GGACGAGCAG GCACAGTGCC TCGTCCCGCA GTGGTGTCCA CTCCACATCG TCCCGGGCGG
5041 GTCGTGGGCT GGTCAGCCCC AGGTCCAGCC TGCTGTTGCG GACGTCGTCG ACCACGGCGT
5101 CGGCGGCGTC GCCGCGCAGT TCGAAGGTGG TGCCGGGAGC CAGCCGGCGG TACCCGGCGA
5161 GGAGGTCGGG CACCAGCCAG GTGCCGTAGG AGTGCAGGAA ACCCAGTGCC ACGGTGCCGG
5221 TGTCGGGGTC GATCAGGGCG GTGATGCGCT GCTCGGCGCC GGAGACCTCA CTGATCGCGC
5281 GCAGGGCGTG GGCGCGGAAG ACCTCGCCGT ACTTGTTGAG CCGGAGCCGG TTCTGGTGCC
5341 GGTCGAACAG CGGCACGCCC ACTCGTCGCT CCAGCCGCCG GATGGCCCTG GACAGGGTCG
5401 GCTGGGAGAT GTTGAGCCGT TCCGCGGTGA TCGTCACGTG CTCGTGCTCG GCCAAGGCCG
5461 TGAACCACTG CAACTCCCGT ATCTCCATGC AGGGACTATA CGTACCGGGC ATGGTCCTGG
5521 CGAGGTTTCG TCATTTCACA GCGGCCGGGC GGCGGCCCAC AGTGAGTCCT CACCAACCAG
5581 GACCCCATGG GAGGGACCCC ATGTCCGAGC CGCATCCTCG CCCTGAACAG GAACGCCCCG
5641 CCGGGCCCCT GTCCGGTCTG CTCGTGGTTT CTTTGGAGCA GGCCGTCGCC GCTCCGTTCG
5701 CCACCCGCCA CCTGGCGGAC CTGGGCGCCC GTGTCATCAA GATCGAACGC CCCGGCAGCG
5761 GCGACCTCGC CCGCGGCTAC GACCGCACGG TGCGTGGCAT GTCCAGCCAC TTCGTCTGGC
5821 TGAACCGGGG GAAGGAGAGC GTCCAGCTCG ATGTGCGCTC GCCGGAGGGC AACCGGCACC
5881 TGCACGCCTT GGTGGACCGG GCCGATGTCC TGGTGCAGAA TCTGGCACCC GGCGCCGCGG
5941 GCCGCCTGGC ATCGGCCACC AGGTCCTCGC GCGGAGCCAC CGAGGCTGAT CACCTGCGGA
6001 CATATCCGGC TACGGCAGTA CCGGCTGCTA CCGCGGACCG CAAGGCGTAC GACCTCCTGG
6061 TCCAGTGCGA AGCGGGGCTG GTCTCCATCA CCGGCACCCC CGAGACCCCG TCCAAGGTGG
6121 GCCTGTCCAT CGCGGACATC TGTGCGGGGA TGTACGCGTA CTCCGGCATC CTCACGGCCC
6181 TGCTGAAGCG GGCCCGCACC GGCCGGGGCT CGCAGTTGGA GGTCTCGATG CTCGAAGCCC
6241 TCGGTGAATG GATGGGATAC GCCGAGTACT ACACGCGCTA CGGCGGCACC GCTCCGGCCC
6301 GCGCCGGCGC CAGCCACGCG ACGATCGCCC CCTACGCCC GTTCACCACG CGCGACGGGC
6361 AGACGATCAA TCTCGGGCTC CAGAACGAGC GGGAGTGGGC TTCCTTCTGC GGTGTCGTGC
6421 TACAACGCCC CGGTCTCTGC GACGACCCGC GCTTTTCCGG CAACGCCGAC CGGGTGGCGC
6481 ACCGCACCGA GCTCGACGCC CTGGTGAGCG AGGTGACGGG CACGCTCACC GGCGAGGAAC
6541 TGGTGGCGCG GCTGGAGGAG GCGTCGATCG CCTACGCACG CCAGCGCACC GTGCGGGAGT
6601 TCAGCGAACA CCCCCAACTG CGTGACCGTG GACGCTGGGC TCCGTTCGAC AGCCCGGTCG
6661 GTGCGCTGGA GGGCCTGATC CCCCCGGTCA CCTTCCACGG CGAGCACCCG CGGCGGCTGG
6721 GCCGGGTCCC GGAGCTGGGC GAGOATACOG AGTCCGTCCT GGCGTGGCTG GCCGCGCCCC
6781 ACAGCGCCGA CCGCGAAGAG GCCGGCCATG CCGAATGAAC TCACCGGAGT CCTGATCCTG
6841 GCCGCCGTGT TCCTGCTCGC CGGCGTACGG GGGCTGAACA TGGGCCTGCT CGCGCTGGTC
6901 GCCACCTTTC TGCTCGGGGT GGTCGCACTC GACCGAACGC CGGACGAGGT GCTGGCGGGT
6961 TTCCCCGCGA GCATGTTCCT GGTGCTGGTC GCCGTCACGT TCCTCTTCGG GATCGCCCGC
7021 GTCAACGGCA CGGTGGACTG GCTGGTACGT GTCGCGGTGC GGGCGGTGGG GGCCCGGGTG
7081 GGAGCCGTCC CCTGGGTGCT CTTCGGCCTG GCGGCACTGC TCTGCGCGAC AGGCGCGGCC
7141 TCGCCCGCGG CGGTGGCGAT CGTGGCGCCG ATCAGCGTCG CGTTCGCCGT CAGGCACCGC
7201 ATCGATCGC TGTACGCCGG ACTGATGGCG GTGAACGGCC CCGCAGCCGG CAGTTTCGCC
7261 CCCTCCGGGA TCCTGGGCGG CATCGTCCAC TCGGCGCTGG AGAAGAACCA TCTGCCCGTC
7321 AGCGGCGGGC TGCTCTTCGC AGGCACCTTC GCCTTCAACC TGGCGGTCGC CGCGGTGTCA
7381 TGGCTCGTCC TCGGGCGCAG GCGCCTCGAA CCACATGACC TGGACGAGGA CACCGATCCC
7441 ACGGAAGGGG ACCCGGCTTC CCGCCCCGGC GCGGAACACG TGATGACGCT GACCGCGATG
7501 GCCGCGCTGG TGCTGGGAAC CACGGTCCTC TCCCTGGACA CCGGCTTCCT GGCCCTCACC
7561 TTGGCGGCGT TGCTGGCGCT GCTCTTCCCG CGCACCTCCC AGCAGGCCAC CAAGGAGATC
7621 GCCTGGCCCG TGGTGCTGCT GGTATGCGGG ATCGTGACCT ACGTCGCCCT GCTCCAGGAG
7681 CTGGGCATCG TGGACTCCCT GGGGAAGATG ATCGCGGCGA TCGGCACCCC GCTGCTGGCC
7741 GCCCTGGTGA TCTGCTACGT GGGCGGTGTC GTCTCGGCCT TCGCCTGCAC CACCGGGATC
7801 CTCGGTGCCC TGATGCCGCT GTCCGAGCCG TTCCTGAAGT CCGGTGCCAT CGGGACGACC
7861 GGCATGGTGA TGGCCCTGGC GGCCGCGGCG ACCGTGGTGG ACGCGAGTCC CTTCTCCACC
7921 AATGGTGCTC TGGTGGTGGC CAACGCTCCC GAGCGGCTGC GGCCCGGCGT GTACCAGGGG
7981 TTGCTGTGGT GGGGCGCCGG GGTGTGCGCA GGGCCCGGCC CGGCCGCCTG GGCGGCCTTC
8041 GTGGTGGCGT GAGCGCAGCG GAGCGGGAAT CCCCTGGAGC CCGTTTCCCG TGCTGTGTCG
8101 CTGACGTAGC GTCAAGTCCA CGTGCCGGGC GGGCAGTACG CCTAGCATGT CGGGCATGGC
8161 TAATCAGATA ACCCTGTCCG ACACGCTGCT CGCTTACGTA CGGAAGGTGT CCCTGCGCGA
8221 TGACGAGGTG CTGAGCCGGC TGCGCGCGCA GACGGCCGAG CTGCGGGCG GTGGCGTACT
8281 GCCGGTGCAG GCCGAGGAGG GACAGTTCCT CGAGTTCCTG GTGCGGTTGA CCGGCGGCGC
8341 TCAGGTGCTG GAGATCGGGA CGTACACCGG CTACAGCACG CTCTGCCTGG CCCGCGGATT
8401 GGCGCCCGGG GGCCGTGTGG TGACGTGCGA TGTCATGCCG AAGTGGCCCG AGGTGGGCGA
8461 GCGGTACTGG GAGGAGGCCG GGGTTGCCGA CCGGATCGAC GTCCGGATCG GCGACGCCCG
8521 GACCGTCCTC ACCGGGCTGC TCGACGAGGC GGGCGCGGGG CCGGAGTCGT TCGACATGGT
8581 GTTCATCGAC GCCGACAAGG CCGGCTACCC CGCCTACTAC GAGGCGGCGC TGCCGCTGGT
8641 ACGCCGCGGC GGGCTGATCG TCGTCGACAA CACGCTGTTC TTCGGCCGGG TGGCCGACGA
8701 AGCGGTGCAG GACCCGGACA CGGTCGCGGT ACGCGAACTC AACGCGGCAC TGCGCGACGA
8761 CGACCGGGTG GACCTGGCGA TGCTGACGAC GGCCGACGGC GTCACCCTGC TGCGGAAACG
8821 GTGACCGGGG CGATGTCGGC GGCGGTCAGC GTCAGCGTCG TCGCGCGGG CCTCGCGGAG
8881 GGCTCCAGAT GCAGGCGTTC GACGCCGGCG GCGGAAGCGC CGCCACCTC GGACACGCAG
8941 GGGCAGTCGG AGTCCGCGAA GCCCGCGAAC CGGTAGGCGA TCTCCATCAT GCGGTTGCGG
9001 TCCGTACGCC GGAAGTCCGC CACCAGGTGC GCCCCGCGC GGGCGCCCTG GTCCGTGAGC
9061 CAGTTCAGGA TCGTCGCACC GGCACCGAAC GACACGACCC GGCAGGACGT GGCGAGCAGT
9121 TTCAGGTGCC ACGTCGACGG CTTCTTCTCC AGCAGGATGA TGCCGACGGC GCCGTGCGGG
9181 CCGAAGCGGT CGCCCATGGT GACGACGAGG ACCTCATGGG CGGGATCGGT GAGCACGCGC
9241 GCAGGTCGGC GTCGGAGTAG TGCACGCCGG TCGCGTTCAT CTGGCTGGTC CGCAGCGTCA
```

```
      -continued
 9301 GTTCCTCGAC GCGGCTGAGT TCCTCCTCCC CCGCGGGTGC GATCGTCATG GAGAGGTCGA
 9361 GCGAGCGCAG GAAGTCCTCG TCGGGACCGG AGTACGCCTC CCGGGCCTGG TCGCGCGCGA
 9421 AACCCGCCTG GTACATCAGG CGGCGCCGAC GCGAGTCGAC CGTGGACACC GGCGGGCTGA
 9481 ACTCCGGCAG CGACAGGAGC GTGGCCGCCT GCTCGGCCGG GTAGCACCGC ACCTCGGGCA
 9541 GGTGGAACGC CACCTCGGCA CGCTCGGCGG GCTGGTCGTC GATGAACGCG ATCGTGGTCG
 9601 GTGCGAAGTT CAGCTCCGTG GCGATCTCGC GGACGGACTG CGACTTCGGC CCCCATCCGA
 9661 TGCGGGCCAG CACGAAGTAC TCCGCCACAC CGAGGCGTTC CAGACGCTCC CACGCGAGGT
 9721 CGTGGTCGTT CTTGCTCGCC ACCGCCTGGA GGATGCCGCG GTCGTCGAGC GTGGTGATCA
 9781 CCTCGCGGAT CTCGTCGGTG AGGACCACCT CGTCGTCCTC CAGCACGGTG CCCCGCCACA
 9841 AGGTGTTGTC CAGGTCCCAG ACCAGACACT TGACAATGGT CATGGCTGTC CTCTCAAGCC
 9901 GGGAGCGCCA GCGCGTGCTG GGCCAGCATC ACCCGGCACA TCTCGCTGCT GCCCTCGATG
 9961 ATCTCCATGA GCTTGGCGTC GCGGTACGCC CGTTCGACGA CGTGTCCCTC TCTCGCGCCT
10021 GCCGACGCGA GCACCTGTGC GGCGGTCGCG GCCCCGGCGG CGGCTCGTTC GGCGGCGACG
10081 TGCTTGGCCA GGATCGTCGC GGGCACCATC TCGGGCGAGC CCTCGTCCCA GTGGTCGCTG
10141 GCGTACTCGC ACACGCGGGC CGCGATCTGC TCCGCGGTCC ACAGGTCGGC GATGTGCCCG
10201 GCGACGAGTT GGTGGTCGCG GAGCGGCCGG CCGAACTGCT CCCGGGTCCG GGCGTGGGCC
10261 ACCGCGGCGG TGCGGCAGGC CCGCAGGATC CCGACGCAGC CCCAGGCGAC CGACTTGCGC
10321 CCGTAGGCGA GTGACGCCGC GACCAGCATC GGCAGTGACG CGCCGGAGCC GGCCAGGACC
10381 GCGCCGGCCG GCACACGCAC CTGGTCCAGG TGCAGATCGG CGTGGCCGGC GGCGCGGCAG
10441 CCGGACGGCT TCGGGACGCG CTCGACGCGT ACGCCGGGGG TGTCGGCGGG CACGACCACC
10501 ACCGCACCGG AACCATCCTC CTGGAGACCG AAGACGACCA GGTGGTCCGC GTAGGCGGCG
10561 GCAGTCGTCC AGACCTTGTG GCCGTCGACG ACAGCGGTGT CCCCGTCGAG CCGAACCCGC
10621 GTCCGCATCG CCGACAGATC GCTGCCCGCC TGCCGCTCAC TGAAGCCGAC GGCCGCGAGT
10681 TTCCCGCTGG TCAGCTCCTT CAGGAAGGTC GCCCGCTGAC CGGCGTCGCC GAGCCGCTGC
10741 ACGGTCCACG CGGCCATGCC CTGCGACGTC ATGACACTGC GCAGCGAACT GCAGAGGCTG
10801 CCGACGTGTG CGGTGAACTC GCCGTTCTCC CGGCTGCCGA GTCCCAGACC GCCGTGCTCG
10861 GCCGCCACTT CCGCGCAGAG CAGGCCGTCG GCGCCGAGCC GGACGAGCAG GTCGCGCGGC
10921 AGTTCGCCGG ACGTGTCCCA CTCGGCGGCC CGGTCACCGA CAAGGTCGGT CAGCAGCGCG
10981 TCACGCTCAG GCATCGACGG CCCGCAGCCG GTGGACGAGT GCGACCATGG ACTCGACGGT
11041 ACGGAAGTTC GCGAGCTGGA GGTCCGGGCC GGCGATCGTG ACGTCGAACG TCTTCTCCAG
11101 GTACACGACC AGTTCCATCG CGAACAGCGA CGTGAGGCCG CCCTCCGCGA ACAGGTCGCG
11161 GTCCACGGGC CAGTCCGACC TGGTCTTCGT CTTGAGGAAC GCGACCAACG CGTGCGCGAC
11221 GGGGTCGTCC TTGACGGGTG CGGTCATGAG AACACCTTCT CGTATTCGTA GAAGCCCCGG
11281 CCGGTCTTCC GGCCGTGGTG TCCCTCGCGG ACCTTGCCCA GCAGCAGGTC ACAGGGGCGG
11341 CTGCGCTCGT CGCCGGTGCG TTTGTGCAGC ACCCACAGCG CGTCGACGAG GTTGTCGATG
11401 CCGATCAGGT CCGCGGTGCG CAGCGGCCCG GTCGGATGGC CGAGGCACCC CGTCATGAGC
11461 GCGTCGACGT CCTCGACGGA CGCGGTGCCC TCCTGCACGA TCCGCGCCGC GTCGTTGATC
11521 ATCGGGTGGA GCAGCCGGCT CGTGACGAAG CCGGGCGCGT CCCGGACGAC GATCGGCTTG
11581 CGCCGCAGCG CCGCGAGCAG GTCCCCGGCG GCGGCCATGG CCTTCTCACC GGTCCGGGGT
11641 CCGCGGATCA CCTCGACCGT CGGGATCAGG TACGACGGGT TCATGAAGTG CGTGCCGAGC
11701 AGGTCCTCGG GCCGGGCCAG GGAGTCGGCC AGTTCGTCAA CCGGGATCGA CGACGTGTTC
11761 GTGATGACCG GGATACCGGG CGCCGCTGCC GAGACCGTGG CGAGTACCTC CGCCTTGACC
11821 TCGGCGTCCT CGACGACGGC CTCGATCACC GCGGTGGCCG TACCGATCGC GGGCAGCGCG
11881 GACGTGGCCG TCCGCAGCAC ACCGGGGTCG GCCTCGGCGG GCCCGGCCAC GAGTTGTGCC
11941 GTCCGCAGTT CGGTGGCGAT CCGCGCCCGC GCCGCGTAA GGATCTCCTC GGACGTGTCA
12001 ACGAGTGTCA CCGGGACGCC GTGGCGCAGC GCGAGCGTGG TGATGCCGGT GCCCATCACT
12061 CCCGCGCCGA GCACGATCAG CTGGTGGTCC ACGCTGTTTC CTCCCTCCGG GGTCACCATG
12121 GCAGCGAGTA CGGGTCGAGG ACGTCTTCCG GGGTCGACCC GATCGCGTCC TTGCGGCCGA
12181 GGCCGAGTTC GTCGGCGAAG CCGAGCAGCA CGTCGAACGC GATGTGGTCG GCGAACGCGC
12241 TGCCCGTCGA GTCGAGGACG CTCAGGCTGT CCCGGTGGTC CGCCGCGGTG TCCGGTGCCG
12301 CGCACAGGGC CGCCAGCGAC GGGCCGAGCT CGCCGGTCCG CAGTTGCTGG TACTCGCCCT
12361 CGGCGCGGGC CTGCCCCGGA TGGTCGACGC AGATGAACGC GTCGTCGAGC AGGGTCTTCG
12421 GCAGTTCGGT CTTGCCCGGC TCGTCGGCGC CGATGGCGTT CACATGCAGG TGCGGCAGCC
12481 GCGGCTCGGC GGGCAGCACC GGCCCTTTGC CCGAGGGCAC CGAGGTGACG GTGGACAGGA
12541 CATCCGCGGC GGCGGCGGCC TCCGCCGGAT CGGTCACCTT GACCGGCAGT CCGAGGAACG
12601 CGATGCGGTC CGCGAACGAC GCCGCGTGGC CGGGGTCGGT GTCGCTGACC AGGATCCGCT
12661 CGATGGGCAG GACCCTGCTG AGCGCGTGCG CCTGGGTCAC CGCCTGTGCG CCCGCGCCGA
12721 TCAGCGTGAG CGTGGCGCTG TCGGACCGGG CCAGCAGCCG GCTCGCGACG GCGGCGACCG
12781 CGCCGGTCCG CATCGCGGTG ATCACGCCTG CGTCGGCGAG GGCGGTCAGA CTGCCGCTGT
12841 CGTCGTCGAG GCGCGACATC GTGCCGACGA TCGTCGGCAG CCGGAAGCGC GGATAGTTGT
12901 GCGGACTGTA CGAAACCGTC TTCATGGTCA CGCCGACACC GGGGACCCGG TACGGCATGA
12961 ACTCGATGAC GCCGGGAATG TCGCCGCCGC GGTACGCGGC GGCGCCTCGG
13021 CGAACTCGCC GCGGCCGAGC GCGGCGAACC CGTCGTCAG CTCGCTGATC AGCCGGTCCA
13081 TCATCACGTC GCGGCCGATC ACGGAGAGAA TCCGCTTGAT GTCACGTTGG CGCAGGACCC
13141 TGGTCTGCAT GTGTCACCTC CCTTTCGTGG CCGGAGCTGT CTTGGTGGTG CCGCTCGGGG
13201 CGGCTTCCGT TCTCATCGCA GCTCCCTGTC GATGAGGTCG AAAATCTGT CCGCGGTCGC
13261 GTCCGCGGAC AGCACGCCGG CCGGCGTGGT CGGGCGGGTC TCCCGCCGCC AGCGGTTGAG
13321 CAGGGCGTCC AGCCGGGTTC CGATCGCGTC CGCCTGGCGG GCGCCCGGGT CGACACCGGC
13381 AACGAGTGCT TCCAGCCGGT CGAGCTGCGC GAGCACCACG GTCACCGGGT CGTCCGGGGA
13441 CAGCAGTTCA CCGATGCGGT CGGCGAGTGC GCGCGGCGAC GGGTAGTCGA AGACGAGCGT
13501 GGCGGACAGT CGCAGACCGG TCGCCTCGTT GAGGCCGTTG CGCAGCTGCA CCGCGATGAG
13561 CGAGTCCACA CCGAGTTCCC GGAACGCCGC GTCCTCCGGG ATGTCCTCCG GGTCGGCGTG
13621 GCCCAGGACG GCCGCTGCCT TCTGCCGGAC GAGGGCGAGC AGGTCGGTGG GGCGTTCCTG
13681 CTCGTTGCGG GCGCTCCGGC GGGCCGACGG CTTGGGCCGG CCACGCAGCA GCGGGAGGTC
13741 CGGCGGCAGG TCGCCCGCCA CGGCGACGAC ACTGCCCGTT CCGGTGTGGA CGGCGGCGTC
13801 GTACATGCGC ATGCCCTGTT CGGCGGTGAG CGCGCTCGCC CCACCCTTGC GCATACGGCG
13861 CCGGTCGGCG TCGGTCAGGT CCGCGGTCAG GCCACTCGCC TGGTCCCACA GCCCCACGC
13921 GATCGACAGC CCTGGCAGCC CTTGTGCACG CCGGTGTTCG GCGAGCGCGT CGAGGAACGC
13981 GTTCGCCGCC GCGTAGTTGC CCTGACCGGG GGTGCCCAGC ACACCGGCCG CCGACGAGTA
```

-continued

```
14041 GACGACGAAT GCGGCGAGGT CGGTGTCGCG GGTGAGCCGG TGCAGGTGCC AGGCGGCGTC
14101 GGCCTTGGGT TTGAGGACGG TGTCGATGCG GTCGGGGGTG AGGTTGTCGA GCAGGGCGTC
14161 GTCGAGGGTT CCGGCGGTGT GGAAGACGGC GGTGAGGGGT TGAGGGATGT GGGCGAGGGT
14221 GGTGGCGAGT TGGTGGGGGT CGCCGACGTC GGCGGGGAGG TGGGTGCCGG GGGTGGTGTC
14281 GGGGGGTGGG GTGCGGGAGA GGAGGTAGGT GTGGGGGTGG TTCAGGTGGC GGGCGAGGAT
14341 GCCGGCGAGG GTGCCGGAGC CGCCGGTGAT GACGACGGCC CCCTCGGGGT CCAGCGGCCG
14401 CGGGACCGTG AGGACGATCT TGCCGGTGTG CTCGCCGCGG CTCATGGTCG CCAGCGCCTC
14461 GCGGACCTGC CGCATGTCGT GCACCGTCAC CGGCAGCGGG TGCACACAC CGCGCGCGAA
14521 CAGGCCGAGC AGCTCCGCGA TGATCTCCTT GAGCCGGTCG GGCCCCGCGT CCATCAGGTC
14581 GAACGGTCGC TGGACGGCGT GCCGGATGTC CGTCTTCCCC ATCTCGATGA ACCGGCCACC
14641 CGGCGCGAGC AGGCCGACGG ACGCGTCGAG GAGTTCACCG GTGAGCGAGT TGAGCACGAC
14701 GTCGACCGGC GGGAACGCGT CGGCGAACGC GGTGCTGCGG GAATCGGCCA GATGCGCTCC
14761 GTCCAGGTCC ACCAGATGGC GCTTCGCGGC GCTGGTGGTC GCGTACACCT CCGCGCCCAG
14821 GTGCCGCGCG ATCTGCCGGG CGGCGGAACC GACACCGCCG GTGGCCGCGT GGATCAGGAC
14881 CTTCTCGCCG GGGCGCAGCC CGGCGAGGTC GACCAGGCCG TACCACGCGG TCGCGAACGC
14941 GGTCATCACG GACGCCGCCT GCGGGAACGT CCAGCATCCGGC CGAGCATCCG
15001 GTGGTCGGCG ATGACCGTGG GGCCGAAGCC GGTGCCGACG AGGCCGAAGA CGCGGTCGCC
15061 CGGTGCCAGA CCGGAGACGT CGGCGCCGGT CTCCAGGACG ATGCCCGCGG CCTCGCCGCC
15121 GAGCACGCCC TGACCGGGGT AGGTGCCGAG CGCGATCAGC ACATCGCGGA AGTTGAGGCC
15181 CGCCGCACGC ACACCGATCC GGACCTCGGC CGGGGCGAGG GGGCGCCGGG GCTCCGCCGA
15241 GTCGCCGCGC GTGAGGCCGT CGAGGGTGCC CGTCCGCGCC GGCCGGATCA GCCACGTGTC
15301 GCTGTCCGGC ACGGTGAGCG GCTCCGGCAC CCGGGTGAGG CGGGCCGCCT CGAACCGGCC
15361 GCCGCGCAGC CGCAGACGCG GCTCGCCGAG TGCGACGGCG ATGCGCTGCT GCTCGGGGGC
15421 GAGCGTGACG CCGGACTCGG TGTCGACGTG GACGAACCGG CCGGGCTGCT CGGCCTGGGG
15481 GGCGCGCAGC AGTCCGGCCG CCGCGCCGGT GGCGAGGCCC GCGGTGGTGT GCACGAGCAG
15541 ATCCCCGCCG GAGCCGGTCA GGGCGGTCAG CAGCCGGGTG GTGAGCGCAC GCGTCTCGGC
15601 CACCGGGTCG TCGCCATCAG CGGCAGGCAA CGTGATGACG TCCACGTCGG TCGCGGGGAC
15661 ATCCGTGGGT GCGGCGACCT CGATCCAGGT GAGACGCATC AGGCCGGTGC CGACGGGTGG
15721 GGACAGCGGG CGGGTGCGGA CCGTCCGGAT CTCGGCGACG AGTTGGCCGG CGGAGTCGGC
15781 GACGCGCAGA CTCAGCTCGT CGCCGTCACG AGTGATCACG GCTCGGAGCA TGGCCGAGCC
15841 CGTGGCGACG AACCGGGCCC CCTTCCAGGC GAACGGCAGA CCCGCAGCGC TGTCGTCCGG
15901 CGTGGTGAGG GCGACGGCGT GCAGGGCCGC GTCGAGCAGC GCCGGATGCA CACCGAAACC
15961 GTCCGCCTCG GCGGCCTGCT GTCGGGCAG GGCCACCTCG GCATACACGG TGTCACCATC
16021 ACGCCAGGCA GCCCGCAACC CCTGGAACGC CGACCCGTAC TCATAACCGG CATCCCGCAG
16081 TTCGTCATAG AACCCCGAGA CGTCGACGGC CACGGCCGTG ACCGGCGGCC ACTGCGAGAA
16141 CGGCTCCACA CCGACAACAC CGGGGGTGTC GGGGGTGTCG GGGGTCAGGG TGCCGCTGGC
16201 GTGCCGGGTC CAGCTGCCCG TGCCCTCGGT ACGCGCGTGG ACGGTCACCG GCCGCCGTTC
16261 GGCCTCATCA GCCCCTTCCA CGGTCACCGA CACATCCACC GCTGCGGTCA CCGGCACCAC
16321 AAGGGGGGAT TCGATGACCA GCTCGTCCAC TATCCCGCAA CCGGTCTCGT CACCGGCCCG
16381 GATGACCAGC TCCACAAACG CCGTACCCGG CAGCAGGACC GTGCCCCGCA CCGCGTGATC
16441 AGCCAGCCAG GGGTGAGTGC GCAATGAGAT CCGGCCAGTG AGAACAACAC CACCATCGTC
16501 GGCGGGCAGC GCTGTGACAG CGGCCAGCAT CGGATGCGCC GCACCCGTCA ACCCCGCCGC
16561 CGACAGATCG GTGGCACCGG CCGCCTCCAG CCAGTACCGC CTGTGCTCGA ACGCGTACGT
16621 GGGCAGATCC AGCAGCCGTC CCGGCACCGG TTCGACCACC GTGTCCCAGT CCACTGCCGT
16681 GCCCAGGGTC CACGCCTGCG CCAACGCCGT CAGCCACCGC TCCCAGCCGC CACCGCCGGT
16741 CCGCAACGAC GCCACCGTGT GAGCCTGCTC CATCGCCGGC AGCAGCACCG GATGGGCACT
16801 GCACTCCACG AACACCGACC CATCCAGCTC CGCCACCGCC GCGTCCAACG CCACCGGACG
16861 ACGCAGATTC CGGTACCAGT ACCCCTCATC CACCGGCTCC GTCACCCAGG CGCTGTCCAC
16921 GGTCGACCAC CACGCCACCG ACGCGGCCTT CCCTGCCACC CCCTCCAGTA CCTTGGCCAG
16981 TTCATCCTCG ATGGCTTCCA CGTGGGCGT GTGGGAGGCG TAGTCGACCG CGATACGACG
17041 CACCCGCACG CCTTCGGCCT CATACCGCGC CACCACCTCC TCCACCGCCG ACGGGTCCCC
17101 CGCCACCACC GTCGAAGCCG GGCCGTTACG CGCCGCGATC CACACACCT CGACCAGACC
17161 GACCTCACCG GCCGGCAACG CCACCGAAGC CATCGCTCCC CGCCCGGCCA GTCGCGCCGC
17221 GATGACCTGA CTGCGCAATG CCACCACGCG GGCGGCGTCC TCGAGGCTGA GGGCTCCGGC
17281 CACGCACGCC GCCGCGATCT CGCCCTGGGA GTGTCCGATC ACCGCGTCCG GCACGACCCC
17341 ATGCGCCTGC CACAGCGCGG CCAGGCTCAC CGCGACCGCC CAGCTGGCCG GCTGGACCAC
17401 CTCCACCCGC TCCGCCACAT CCGGCCGCGC CAACATCTCC CGCACATCCC AGCCCGTGTG
17461 CGGCAGCAAC GCCTGAGCGC ACTCCTCCAT ACGCGCGGCG AACACCGCGG AGTGGGCCAT
17521 GAGTTCCACG CCCATGCCGA CCCACTGGGC GCCCTGGCCG GGGAAGACGA ACACCGTACG
17581 CGGCTGGTCC ACCGCCACAC CCGTCACCCG GCATCGCCC AGCAGCACCG CACGGTGACC
17641 GAAGACAGCA CGCTCCCGCA CCAACCCCTG CGCGACCGCG GCCACATCCA CACCACCCCC
17701 GCGCAGATAC CCCTCCAGCC GCTCCACCTG CCCCCGCAGA CTCACCTCAC CACGAGCCGA
17761 CACCGGCAAC GGCACCAACC CGTCAACAAC CGACTCCCCA CGCGACGGCC CAGGAACACC
17821 CTCAAGGATC ACGTGCGCGT TCGTACCGCT CACCCCGAAC GACGACACAC CCGCATGCGG
17881 TGCCCGATCC GACTCGGGCC ACGGCCTCGC CTCGGTGAGC AGCTCCACCG CACCGGCCGA
17941 CCAGTCCACA TGCGACGACG GCTCGTCCAC ATGCAGCGCT TTCGGCGGA TCCCGTACCG
18001 CATCGCCATG ACCATCTTGA TCACACCGGC GACACCCGCC GCCGCCTGCG CATGACCGAT
18061 GTTCGACTTC AACGAACCCA GCAGCAGCGG AACCTCACGC TCCTGCCCGT ACGTCGCCAG
18121 AATGGCCTGC GCCTCGATGG GATCGCCCAG CGTCGTCCCC GTCCCGTGCG CCTCCACCAC
18181 GTCCACATCG GCGGCGCGCA GTCCGGCGTT CACCAACGCC TGCTGGATGA CACGCTGCTG
18241 GGACGGGCCG TTGGGGGCGG ACAGCCCGTT GGAGGCACCG TCCTGGTTCA CCGCCGACCC
18301 GCGGACGACC GCGAGAACGG TGTGTCCGTT GCGCTCGGCG TCGAGAGCC GCTCCAGCAC
18361 AAGAACGCCG GCGCCCTCCG CCCAGCCGGT GCCGTTGGCG GCGTCCGCGA ACGCGCGGCA
18421 GCGCCGTCG GGGGAGAGTC CGCCCTGCTG CTGGAATTCC ACGAACCCGG TCGGGGTCGC
18481 CATGACGGTG ACACCGCCGA CCAGCGCCAG CGAGCACTCC CCGTGGCGCA GTGCGTGCCC
18541 GGCCTGGTGC AGCGCGACCA GCGACGACGA GCACGCCGTG TCCACCGTGA ACGCCGGTCC
18601 CTGGAGCCCA TAGAAGTACG AGATCCGGCC GGTGAGCACG CTGGGCTGCA TGCCGATCGA
18661 GCCGAACCCG TCCAGGTCCG CGCCGACGCC GTACCCGTAC GAGAAGGCGC CCATGAACAC
18721 GCCGGTGTCG CTGCCGCGCA GTGTGCCCGG CACGATGCCC GCGCTCTCGA ACGCCTCCCA
```

```
18781 TGTCGTTTCC AGCAGGATCC GCTGCTGGGG GTCCATGGCC CGTGCCTCAC GGGGGCTGAT
18841 GCCGAAGAAC GCGGCATCGA AGCCGGCGGC GTCGGAGAGG AAGCCGCCGC GGTCCGTGTC
18901 CGATCCGCCG GTGAGGCCGG ACGGGTCCCA GCCACGGTCG GCCGGGAAGC CGGTGACCGC
18961 GTCGCCGCCA CTGTCCACCA TGCCGCACAG GTCGTCGGGC GAGGTGACGC CGCCCGGCAG
19021 TCGGCAGGCC ATGCCCACGA TGGCCAGCGG TTCGTGCACG GTCGCGGCGG CTGTGGGAAC
19081 AGCGACCGGT GCGGCACCAC CGACCAGAGC CTCGTCCAAC CGCGACGCGA TGGCCCGCGG
19141 CGTCGGGTAG TCGAAGACAA GCGTGGCGGG CAGTCGGACA CCGGTCGCCG CGGCGAGTCG
19201 GTTCCGCAGT TCGACGGCGG TCAGCGAGTC GATACCCAGT TCCTTGAAGG CCGCGTCCGC
19261 GGACACGTCC GCGGCGTCCG CGTGGCCGAG CACCGCCGCC GCGTTGTCGC GGACCAGTGC
19321 CAGCAGCGCG GTGTCCCGCT CAGCGCCGGA CATGGTGCCG AGCCGGTCGG CGAGCGGAAC
19381 GGCGGTGGCC GCCGCCGGGC GCGATACGGC GCGGCGCAGA TCGGCGAAAA GCGGCGATGT
19441 GTGCGCGGTG AGGTCCATCG TGGCCGCCAC GGCGAACGCG GTGCCGGTTC CGGCCGCGGC
19501 TTCCAGCAGG CGCATGCCCA CACCGGCCGA CATGGGGCGG AAACCGCCGC GGCGGACACG
19561 GGTGCGGTTG GTGCCGCTCA TGCTGCCGGT GAGTCCGCTG TCATCGGCCC AGAGGCCCCA
19621 GGCCAGCGAC AGCGCGGGCA GTCCTTCGGC ATGGCGCAGC GTCGCGAGTC CGTCGAGGAA
19681 CCCGTTCGCC GCCGAGTAGT TGCCCTGGCC GCGGCGCCCC ATGATGCCCG CGACGGACGA
19741 GTAGAGGACG AACGAGCGCA GGTCCGCGTC CCGGGTCAGC TCGTGCAGGT GCCAGGCGCC
19801 GTCGGCTTTG GGGCGCAGTG TGGTGGCGAG CCGCTCCGGG GTGAGTGCCG TGGTCACGCC
19861 GTCGTCGAGC ACGGCTGCCG TGTGGAAGAC CGCCGTGAGC GGCCTGCCGG CGGCGGCGAG
19921 CGCGGCGGCG AGCTGGTCCC GGTCGGCGAC GTCACAGCGG ATGTGGACAC CGGGAGTGTC
19981 CGCCGGCGGT TCGCTGCGCG ACAGCAACAG GAGGTGGCGG GCGCCATGCT CGGCGACGAG
20041 ATGCCGGGCG AGGAGACCTG CCAGCACACC CGAGCCGCCG GTGATGACCA CCGTGCCGTC
20101 CGGGTCGAGC AGCGGTTCGG GCGTTTCCGC GGCGGCCGTG CGGGTGAACC GCGGCGCTTC
20161 GTACCGGCCG TCGGTGACGC GGACGTACGG CTCGGCCAGT GTCGTGGCGG CGGCCAGCGC
20221 CTCGATGGGG GTGTCGGTGC CGGTCTCCAC CAGCACGAAC CGGCCCGGGT GCTCGGCCTG
20281 GGCGGACCGG ACGAGGCCGG CGACCGCTCC TCCGACCGGT CCCGCGTCGA TCCGGACGAC
20341 GAGGGTGGTC TCCGCAGGGC CGTCCTCGGC GATCACCCGG TGCAGCTCGC CGAGCACGAA
20401 CTCGGTGAGC CGGTACGTCT CGTCGAGGAC ATCCGCGCCC GGTTCCGGGA GCGCGGAGAC
20461 GATGTGGACC GCGTCCGCAG GACCGGGCCC GGGAGTGGGC AGCTCGGTCC AGGAGAGGCC
20521 GTACAAGGAG TTCCGTACGA CGGCGGCGTC GCCGTCGACG TTCACCGGTC GCGCGGTCAG
20581 CGCGGCGACG GTCACCACCG GTTGGCCGAC CGGGTCCGTC GCATGCACGG CAGCGCCGTC
20641 CGGGCCCTGA GTGATCGTGA CGCGCAGCGT GGTGGCCCCG GTCGTGTGGA ACCGCACGCC
20701 GCTCCACGAG AACGGCAGCC GCACCTCCGC TTCCTGTTCC GCGAGCAGCG GCAGGCAGGT
20761 GACGTGCAAG GCCGCGTCGA ACAGCGCCGG GTGGACGCCA TAGTGCGGCG TGTCGTCCGC
20821 CTGTTCCCCG GCGATCTCCA CCTCGGCGTA CAGGGTTTCG CCGTCGCGCC AGGCGGTGCG
20881 CAGTCCCTGG AACGCTGGGC CGTAGCTGTA GCCGGTCTCG GCCAGCCGCT CGTAGAACGC
20941 GCTCACGTCG ACGCGTCGCG CGCCCGGCGG CGGCGGCGGA CCGCCGCGAC
21001 GCTTCCGGCC CGGCCGAGGG TGCCGCTGGC GTGCCGGGTC CAGCTGTCCG TGCCCTCGGT
21061 ACGCGCGTGG ACGGTCACTC GCCGCCGTCC GGCCTCATCG GCCCCTTCGA CGGTCACCGA
21121 CACATCCACC GCGCCGGTCA CCGGCACCAC GAGCGGGGTC TCGATGACCA GTTCATCCAC
21181 CACCCCGCAA CCGGTCTCGT CACCGGCCCG GATGACCAGG TCCACAAACG CCGTACCCGG
21241 CAGCAGAACC GTGCCCCGCA CCGCGTGATC AGCCAGCCAG GGATGCGTAC GCAACGAGAT
21301 CCGGCCAGTG AGAACAACAC CACCACCGTC GTCGGCGGGC AGTGCTGTGA CGGCGGCCAG
21361 CATCGGATGC GCCGCCCCGG TCAGCCCGGC CGCGGACAGA TCGGTGGCAC CGGCCGCCTC
21421 CAGCCAGTAC CGCCTGTGCT CGAACGCGTA GGTGGGCAGA TCGAGCAGCC GTCCCGGCAC
21481 CGGTTCGACC ACCGTGTCCC AGTCCACTGC CGTGCCCAGG GTCCACGCCT GCGCCAACGC
21541 CGTCAGCCAC CGCTCCCAGC CGCCGTCACC GGTCCGCAAC GACGCCACCG TGTGAGCCTG
21601 TTCCATCGCC GGCAGCAGCA CCGGATGGGC GCTGCACTCC ACGAACACGG ACCCGTCCAG
21661 CTCCGCCACC GCCGCGTCCA GCGCGACGGG GCGACGCAGG TTCCGGTACC AGTAGCCCTC
21721 ATCCACCGGC TCGGTCACCC AGGCGCTGTC CACCGTGGAC CACCAGGCA CCGACCCGGT
21781 CCCGCCGGAA ATCCCTCCA GTACCTCGGC CAACTCGTCC TCGATGGCTT CCACGTGGGG
21841 CGTGTGGGAG GCGTAGTCGA CCGCGATACG GCGCACTCGC ACGCCTTCGG CCTCGTACCG
21901 CGTCACCACT TCTTCCACCG CGGACGGGTC CCCCGCCACC ACAGTGAAG ACGGGCCGTT
21961 ACGCGCCGCG ATCCACACGC CCTCGACCAG GTCCACCTCA CCGGCCGGCA ACGCCACCGA
22021 AGCCATCGCC CCCCGCCCGG CCAGCCGCCC GGCGATCACC TGGCTGCGCA AGGCCACCAC
22081 GCGGGCGGCG TCCTCAAGGC TGAGGGCTCC GGCCACACAC GCCGCCGCGA TCTCGCCCTG
22141 GGAGTGTCCG ACCACCGCGT CCGGCACGAC CCCATGCGCC TGCCACAGCG CGGCCAGGCT
22201 CACCGCGACC GCCCAGCTGG CCGGCTGGAC CACCTCCACC CGCTCCGCCA CATCCGGCCG
22261 CGCCAACATC TCCCGCACAT CCCAGCCCGT GTGCGGCAAC AACGCCCGCG CACACTCCTC
22321 CATACGAGCC GCGAACACCG CAGAACACGC CATCAACTCC ACACCCATGC CCACCCACTG
22381 AGCACCCTGC CCGGGAAAGA CGAACACCGT ACGCGGCTGA TCCACCGCCA CACCCATCAC
22441 CCGGGCATCG CCCAACAACA CCGCACGGTG ACCGAAGACA GCACGCTCAC GCACCAACCC
22501 CTGCGCGACC GCGGCCACAT CCACACCACC CCGCGCAGA TACCCCTCCA GCCGCTCCAC
22561 CTGCCCCCGC AGACTCACCT CACTCCGAGC CGACACCGGC AACGGCACCA ACCCATCGAC
22621 AGCCGACTCC CCACGCGACG GCCCGGGAAC ACCCTCAAGG ATCACGTGCG CGTTCGTACC
22681 GCTCACCCCG AAAGCGGAGA CACCGGCCCG GCGCACGCCG GCCACGCCCG
22741 CGCCTCGGTG AGCAGTTCCA CCGCGCCCTC GGTCCAGTCC ACATGCGACG ACGGCTCGTC
22801 CACATGCAGC GTCTTCGGCG CGATGCCATA CCGCATCGCC ATGACCATCT TGATGACACC
22861 GGCGACACCC GCAGCCGCCT GCGCATGACC GATGTTCGAC TTCAACGAAC CAGCAGCAG
22921 CGGAACCTCA CGCTCCTGCC CGTACGTCGC CAGAATCGCA TGCGCCTCGA TGGGATCGCC
22981 CAGCGTCGTC CCCGTCCCGT GCGCCTCCAC CACGTCCACG TCGCGGGGG CGAGCCCCGC
23041 CTTGTGGAGG GCCTGGCGGA TGACGCGCTG CTGGGAGGGG CCGTTGGGTG CGGAGATGCC
23101 GTTGGAGGCG CCGTCCTGGT TGACGGCGGA GGAGCGGACG ACCGCGAGGA CGGTGTGTCC
23161 GTTGCGCTCG GCGTCGGAGA GCTTTTCGAC GACGAGGACG CCGGCCCCT CGGCGAAACC
23221 GGTGCCGTCC GCCGCGTCAG CGAACGCCTT GCACCGTCCG TCCGCGTCGA CGCCGCCCTG
23281 CCGGGAGAAC TCCACGAAGG TCTGTGGTGA TGCCATCACT GTGACACCAC CGACCAGCGC
23341 CAGCGAGCAC TCCCCGGTCC GCAGCGCCTG CCCGGCCTGG TGCAGCGCGA CCAGCGACGA
23401 CGAACACGCC GTGTCGACCG TGACCGCCGG ACCCTCCATG CCGAAGAAGT ACGACAGCCG
23461 TCCGGCGAGC ACCGCGGGCT GTGTGCTGTA GGCGCCGAAT CCGCCCAGGT CCGCGCCCGT
```

```
23521 GCCGTAGCCG TAGTAGAAGC CGCCGACGAA GACGCCGGTG TCGCTGCCGC GCAGGGTGTC
23581 CGGCACGATG CCGGCGTGTT CGAGCGCCTC CCAGGCGATT TCGAGGAGGA TCCGCTGCTG
23641 CGGGTCGAGT GCGGTGGCCT CGCGCGGACT GATGCCGAAG AACGCGGCAT CGAAGTCGGC
23701 GGCGCCCGCG AGTGCGCCGG CCCGCCCGGT GGCGGACTCG GCGGCGGCGT GCAGCGCGGG
23761 CACGTCCCAG CCGCGGTCGG TGGGGAAGTC GCCGATCGCG TCGCGGCCGT CCGCGACGAG
23821 CTGCCACAGC TCTTCCGGTG AGGTGACGCC GCCCGGCAGT CGGCAGGCCA TGCCGACGAC
23881 GGCGAGCGGC TCGTTCGCCG CGGCGCGCAG CGCGGTGTTC TCCCGGCGGA GCTGCGCGTT
23941 GTCCTTGACC GACGTCCGCA GCGCCTCGAT CAGGTCGTTC TCGGCCATCG CCTCATCCCT
24001 TCAGCACGTG CGCGATGAGC GCGTCTGCGT CCATGTCGTC GAACAGTTCG TCGTCCGGCT
24061 CCGCGGTCGT GGTGCTCGCG GGTGCCTGTG CCGGTGGTTC ACCGCCGTCC GGGGTCCCGT
24121 TGTCGTCCGG GGTCCCGTTG ACGTCCGGGG CCAGGAGGGT CAGCAGATGA CGGGTGAGCG
24181 CGCCGGCGGC GGGATAGTCG AAGACGAGCG TGGCCGGCAG CGGACTGCCG AGGGCCTCGG
24241 AGAGCCGGTT GCGCAGGCCA AGCGCGGTGA GCGAGTCGAC CCCGAGGTCC TTGAACGCCG
24301 TGGTGGCCGT GACCGCCGCC GCGTCGGTGT GGCCCAGCAG GGTGGCGGCG GTGTCGCGGA
24361 CGACGCCGAG CAGCACCTGT TCCCGTTCCT TGTGGGGCAG GTCCGGCAGG CGTTCCAGCA
24421 GGGAGCCGCC GTCGGTCGCG GAGCGCCGGG TGGGGCGCTG GATCGGTCGC CACAGCGGTG
24481 ACGGGTCGCC GGGCCCGGGT GGGGCGGTCG CCACGACCAC GGCTTCCCCG GTGGCGCACG
24541 CGGCGTCGAG GAGGTCGGTC AGCCGGTCCG CCGCGGCGGT GAACGCCACG GCCGGCAGGC
24601 CTTGTGCCCG GCGCAGGTCG GCCAGGGCCT GGAGCGGTCC GGCCGCCTCG CCGGACGGAA
24661 CGGCGAGAAC GAACGCGGCT AGGTCGAGGT CGCGGGTCAG GCGGTGCAGT TCCCAGGCCG
24721 ACTCGGCGGT GCCGTCCGCG TGGACGACCG CGGTCACCGG GGTTTCCGGC ACTGTGCCCG
24781 GCTCGTACCG GATCACTTCG GCGCCGTGTC CGCCGAGGTG TCCGGCGAGT TCCTCCGAAC
24841 CGCCCGCGAG GAGGACGGTG TCGCCGTACG AGGCCGCGGC CGTGGTGGGC GCGGCGGGGA
24901 CGAGGCGGGG CGCTTCGAGG CGCCCGTCGG CCAGGCGCAG GTGCGGTTCG TCGAGGCGGG
24961 AGAGGGCGGC GGCGCGGCGG GGGGTGACCG TGTCGGTGGT CTCCACGAGC ACGAGCGGGC
25021 CCGGTTCCGC GGTGTCGAGC AGTGCGGCGA CGGCACCGGC GACGGGCCCG GCCTCGGCGG
25081 ACACCACCAG CGTGGCGCCG GCGGTCCTCG GGTCGTCCAG TGCGGTACGG ACCTCGTCGG
25141 GACCGGATAC CGGGACGACG ATGACGTCGG GCGTGGCGTC GTCGCCGAGG TCGGTGTACC
25201 GGCGGGCCGT GGTGCCGGGT GCCGCCGGGG CCCGGACGCG GGTCCAGGTG CGCCGGAACA
25261 GCCGCACGTC CCCGTCCGGG CCCGTCGTGG CGGGGGGCCG GGTGATGAGC GAGCCGATCT
25321 GAGCCACCGG CCGTCCCAGT TCGTCGGCGA GGTGCACGCG GGCGCCGCCC TCGCCCTCGC
25381 CGTGGACGAA GGTGACGCGC AGTTTCGTGG CGCCGCTGGT GTGGACACGG ACGCCGGTGA
25441 ACGCGAACGG CAACCGTACC CCCGCGTTCT CGGCGGCCGC GCCGATGCTG CCCGCTTGCA
25501 GCGCGGTGAC GAGCAGCGCC GGGTGCAGTG TGTAGCGGGC GGCGTCCCTG GCGAGGGCGC
25561 CGTCGAGGGC GACTTCGGCG CAGACGGTGT CTCCGTGGCT CCACGCGGCG GACATGCCGC
25621 GGAACTCGGG GCCGAACTCG TATCCCGCGT CGTCGAGTCG CTGGTAGAAG GCCGCGACGT
25681 CGACCGGTTC CGCGTGCTCG GGCGGCCAGG GCCCCGGCGT GGTGGCCGGT TCGGTGGTGG
25741 CGATGCCGGC GAAGCCGGAG GCGTGGCGGG TCCATGTCCG GTCGCCGTCC GTCCGGGCGT
25801 GGACGCGCAC GGCACGGCGT CCGGTGTCGT CGGGCGCGGC GACGGTCACG CGCACCTGGA
25861 CGGCGCCGGT GGCGGGCAGG ACCAGCGGTG TCTCGACGAC CAGTTCGTCG AGCAGGTCGC
25921 AGCCTGCCTC GTCGGCGCCG CGTCCGGCCA ATTCAGGAA GGCGGGTCCG GGCAGCAGTA
25981 CGGCGCCGTC GACGGAGTGA CCGGCCAGCC ATGGGTGGGT GGCCAGCGAG AACCGGCCGG
26041 TGAGCAGCAC CTCGTCGGAG TCGGGGAGCG CCACCGACGG GGCGAGCAGC GGGTGGTCGA
26101 CGGCGTCGAG TCCGAGGCCG GAAGCGTCCG TGCCGGCCGC GGTCTCGATC CAGTAGCGCT
26161 CATGGTGGAA GGCGTATGTG GGCAGGTCGT GTGCCGTCGC CGTCGCGGGG ACGCCGCCG
26221 CCCAGTCGAC GGGCACGCCG GTTGTGTGCG CCTCGGCCAG CGCGGTGAGC AGCCGGTGGA
26281 CTCCCCCGCC GCGGCGGAGC GTGGCGACGG TCGCGCCGTC GATCGCGGGC AGCAGCACGG
26341 GGTGCGCGCT GACCTCGACG AACACGGTGT CACCCGGCTC GCGGGCAGCG GTCACGGCCG
26401 TGGCGAAGCC TACGGGGTGG CGCATGTTGC GGAACCAGTA CTCGTCGTCG AGCGGCGCGT
26461 CGATCCAGCG TTCGTCGGCG GTGGAGAACC ACGGGATCTC GGGCGTGCGC GAGGTGGTGT
26521 CCGCGACGAT CCGCTGGAGT TCGTCGTACA GCGGGTCGAC GAACGGGGTG TGGGTCGGGC
26581 AGTCGACGGC GATGCGGCGC ACCCAGACGC GCGGGCCTC GTAGTCGGCG ATCAGCGTTT
26641 CGACGGCGTC CGGGCGCCCG GCGACGGTCG TGGTGGTGGC GCCGTTGCGG CCCGCGACCC
26701 AGACGCCGTC GATCCGGGCG GCATCCGCCT CGACGTCGAC GCCGGGAGC GCGACCGAGC
26761 CCATCGCGCC GCGTCCGGCG AGTTCGCGCA GGAGCAGGAG AACGCTGCGC AGCGCGACGA
26821 GGCGGGCACC GTCCTCCAGG GTGAGCGCTC CGGCGACACA GGCCGCGGCG ATCTGGCCCT
26881 GGGAGTGTCC GATGACGGCG TCCGGGCGTA CGCCCGCGGC CTCCCACACG GCGGCCAGCG
26941 ACACCATGAC GGCCCAGCAG ACGGGGTGCA GCGACGTCGAC GCGGCGGGTC ACCTCCGGGT
27001 CGTCGAGCAT GGCGATGGGG TCCCAGCCCG TGTGCGGGAT CAGCGCGTCG GCGCATTGGC
27061 GCATCCTGGC GGCGAACACC GGGGAGGCCG CCATCAGTTC GACGCCCATG CCGCGCCACT
27121 GCGGTCCTTG TCCGGGGAAG ACGAAGACGG TGCGCGGCTC GGTGAGCGCC GTGCCGGTGA
27181 CGACGTCGTC GTCGAGCAGC ACGGCGCGGT GCGGGAACGT CGTACGCCTG GCGAGCAGGC
27241 CCGCGGCGAT GGCGCGCGGG TCGTGGCCGG GACGGGCGGC GAGGTGCTCG CGGAGTCGGC
27301 GGACCTGCC GTCGAGGGCC GTGGCGGTCC GCGCCAGAC GGGCAGTGGT GTGAGCGGCG
27361 TGGCGATCAG CGGCTCACCG GGCTTCGAGG CCGACGGCTC CTCGGCCGGC GGCTCCCCGG
27421 CCGGGTGGGC TTCCAGCAGG ACGTGGGCGT TGGTGCCGCT GACGCCGAAG GAGGACACAC
27481 CGGCGCGCCG CGGGCGGTCG GTCTCGGGCC AGGGCCGGGC ATCGGTGAGG AGTTCGACGG
27541 CGCCGGCCGT CCAGTCGACG TGCGAGGACG GCGTGTCCAC GTGCAGGGTG CGCGGCAGGG
27601 TGCCGTGCCG CATGGCGAGG ACCATCTTGA TGACACCGGC GACACCCGCG GCGGCCTGAG
27661 TGTGGCCGAT GTTGGACTTC AGCGAGCCCA GCGCACCGGG GGTGTCGCGC CCCTGCCCGT
27721 AGGTGGCCAG CACCGCCTGT GCCTCGATGG GATCGCCCAG CCTGGTGCCG GTGCCGTGCG
27781 CCTCCACGGC GTCCACGTCC GCCGGGGTGA GCCCGGCGTT GGCCAGGGCC TGCCGGATCA
27841 CCCGCTCCTG CGAGGGCCCG TTCGGCGCCG ACAACCCGTT GGAAGCACCG TCCTGGTTGA
27901 CCGCGAACC CCGGACAACC GCCAGCACAC GGTGGCCGTT GCGCTGGCCA TCGGAGAGCC
27961 TCTCGACGAT CAGCACACCG GACCCCTCGG CGAAACCGGT GCCGTCAGCC GCATCCGACG
28021 ACGCCTTGCA GCGCGCGTCG GGCGCGAGAC CCCGCTGCTG GGAGAACTCG ACGAAGCCGG
28081 ACGGCGAGGC CATCACCGTG ACGCCGCCGA CCAGGGCGAG CGAGCATTCG CCGGAGCGCA
28141 GTGACTGCCC GGCCTGGTGC AGCGCCACCA GCGACGACGA ACACGCCGTG TCGACCGTGA
28201 CCGCCGGACC CTCCAGACCG TAGAAGTACG ACAGCCGACC GGACAGCACA CTGGTCTGGG
```

```
28261 TGCCGGTCGC GCCGAAACCG CCCAGGTCGG TGCCGAGTCC GTACCCGTCG GAGAAGGCGC
28321 CCATGAACAC GCCGGTGTCG CTTCCGCGCA GCGACTCCGG GAGGATCCCG GCGTGTTCCA
28381 GCGCCTCCCA CGAGGTCTCC AGGACCAGAC GCTGCTGCGG GTCCATCGCC AGCGCCTCAC
28441 GCGGACTGAT CCCGAAGAAC GCCGCGTCGA AGTCCGCCAC CCCGGCGAGG AAGCCACCAT
28501 GACGCACGGT CGACGTGCCC GGATGATCCG GATCGGGATC GTACAGCCCG TCCACGTCCC
28561 AACCACGGTC CGTCGGAAAC GCCGTGATCC CGTCACCACC CGACTCCAGC AGCCGCCACA
28621 AGTCCTCCGG CGACGCGACC CCACCCGGCA GCCGGCAGGC CATCCCCACG ATCGCCAACG
28681 GCTCGTCCTG CCGGACGGCC GCGGTCGTGG TGCGGGTCGG CGATGCCGTC CGGCCGGACA
28741 GCGCCGCGGT GAGCTTCGCC GCGACGGCGC GCGGCGTCGG GAAGTCGAAG ACCGCGGTGG
28801 CGGGCAGCCG TACGCCCGTC GCCTCGGTGA AGGCGTTGCG CAGCCGGATC GCCATGAGCG
28861 AGTCGACGCC GAGTTCCTTG AACGTGGCGG TCGCCTCGAC CCGTGCGGCA CCGTCGTGGC
28921 CGAGTACGGC CGCGGTGCAC TGCCGGACGA CGGCGAGCAC GTCCTTTTCG GCGTCCGCGG
28981 CGGAGAGCCG CGCGATCCGG TCGGCGAGGG TGGTGGCGCC GGCCGCCCGG CGCCGCGGCT
29041 CCCGGCGCGG TGCGCGCAGC AGGGGCGAGC TGCCGAGGCC GGCCGGGTCG GCGGCGACCA
29101 GCGCCGGGTC CGAGGACCGG AACGCCGCGT CGAACAGCGT CAGTCCGCCT TCGGCGGTCA
29161 GCGCCGTCAC GCCGTCGCGG CGCATGCGGG CGCCGGTGCC GACCGTCAGC CCGCTCTCCG
29221 GTTCCCACAG GCCCCAGGCC ACGGACAACG CGGGCAGTCC GGCTGCCCGG CGCTGTTCGG
29281 CCAGCGCGTC GAGGAACGCG TTCGCGGCCG CGTAGTTGCC CTGTCCGGGG CTGCCGAGCA
29341 CACCGGCGGC CGACGAGTAG AGGACGAACG CGGCCAGTTC CGTGTCCTGG GTGAGTTCGT
29401 GCAGGTGCCA CGCGGCGTCC ACCTTCGGGC GCAGCACCGT CTCGAGCCGG TCGGGGGTGA
29461 GCGCGGTGAG GACGCCGTCG TCGAGGACGG CCGGTGTG CACGACGGCC GTGAGCGGGT
29521 GCGCCGGGTC GATCCCCGCC AGTACGGAGG CGAGTTCGTC CCGGTCGGCG ACGTCGCAGG
29581 CGATCGCCGT GACCTCGGCG CCGGGCACGT CGCTCGCCGT GCCGCTGCGC GACAGCATCA
29641 GCAGCCGGCG CACGCCGTGG CGTTCGACGA GGTGGCGGCT GATGATGCCG GCCAGCGTCC
29701 CGGAGCCACC GGTGACGAGC ACGGTGCCGT CCGGGTCGAG CGCCGGAGCG TCACCCGCCG
29761 GGACCGCCGG GGCCAGACGG CGGGCGTACA CCTGCCGTC ACGCAGCACC ACCTGGGGCT
29821 CATCGAGCGC GGTGGCCGCT GCGAGCAGCG GCTCGGCGGT GTCCGGGGCG GCGTCGACGA
29881 GGACGATCCG GCCGGGGTGT TCGCCTGCG CGGTCCGCAC CAGTCCGGCG GCCGCGGCCG
29941 ACGCGAGACC GGGCCCGGTG TGGACGGCCA GGACCGCGTC GGCGTACCGG TCGTCGGTGA
30001 GGAAGCGCTG CACGGCGGTC AGGACGCCGG CGCCCAGTTC GCGGGTGTCG TCGAGCGGGG
30061 CACCGCCGCC GCCGTGCGCG GGGAGGATCA CCACGTCCGG GACCGTCGGG TCGTCGAGGC
30121 GGCCGGTCGT CGCGGTCGTG GGCGGCAGCT CCGGGAGCTC GGCCAGCACC GGGCGCAGCA
30181 GGCCCGGAAC GGCTCCCGTG ATCGTCAGGG GGCGCCTGCG CACGGCGCCG ATGGTGGCGA
30241 CGGGCCCGCC GGTCTCGTCC GCGAGGTGTA GCCCGTCAGC GGTGACGGCG ACGCGTACCG
30301 CCGTGGCGCC GGTGGCGTGG ACGCGGACGT CGTCGAACGC GTACGGAAGG TGGTCCCCTT
30361 CCGCGGCGAG GCGGAGTGCG GCGCCGAGCA GCGCCGGGTG CAGGCCGTAC CGTCCGGCGT
30421 CGGCGAGCTG TCCGTCGGCG AGGGCCACTT CCGCCCAGAC GGCGTCGTCG TCGGCCCAGA
30481 CGGCGCGCGG GCGGGGCAGC GCGGGCCCGT CCGTGTACCC GGCTCGGGCC AGACGGTCGG
30541 CGATGTCGTC GGGGTCCACC GGCCGGGCCG TGGCGGGCGG CCACGTCGAC GGCATCTCCC
30601 GCACGGCCGG GGCCGTCCGC GGGTCGGGGG CGAGGATTCC GTGCGCGTGC TCGGTCCACT
30661 CCCCCGCCGC GTGCCGCGTG TGCACGGTGA CCGCGGCGGG GCCGTCCGCC CCGGGCGGGG
30721 TCACCGTGAC GGAGAGCGCG AGCGCACCGG ACCGCGGCAG CGTGAGGGGG GTGTCCACGG
30781 TGAACGTGTC GAGGGCGCCG CAGCCGGCTT CGTCGCCCGC CCGGATCGCC AGATCCAGGA
30841 GGGCCGCGGC GGGCAGCACC GCGAGGCCGT GCAGGGAGTG CGCCAGCGGA TCGGCGGCGT
30901 CGACCCGGCC GGTGAGCACC AGGTCGCCGG TGCCGGGCAG GGTGACCGCC GCGGTCAGCG
30961 CCGGGTGCGC GACCGGCGTC TGTCCGGCCG GGGCGCGTC GCCCGCGGTC TGGGTGCCGA
31021 GCCAGTAGCG GACCCGCTCG AACGGGTACG TCGGCGGGTG CGAGGCGCGT GCCGGCGCGG
31081 GGTCGATGAC CTTCGGCCAG TCGACCGTGA CGCCGTCGGT GTGCAGCCGG GCGAGCGCGG
31141 TCAGGGCGGA TCGCGGTTCG TCGTCGGCGT CAGCATCGG GATGCCGTCG ACGAGTCGGG
31201 TCAGGCTCCG GTCCGGGCCG ATCTCCAGGA GCACCGCCCC GTCGTGCGCG GCGACCTGTT
31261 CCCCGAACCG GACGGTGTCG CGGACCTGTC GTACCCAGTA CTCCGGCGTG GTGCAGGCGG
31321 CGCCCGCGGC CATCGGGATC TCCGGCTCGT GGTACGTCAG GCTCTCCGCG ACCTTGCGGA
31381 ACTCCTCGAG CATCGGCTCC ATCCGCGCCG AGTGGAACGC GTGGCTGGTC CGCACGGGAG
31441 TGAAGCGGCC GAGCCGGGCC GCGACGTCGA GCACCGCCTC CTCGTCACCG GAGAGGAGGA
31501 TCGACGCGGG CCCGTTGACC GCGGCGATCT CCACGCCGTC CCGCAGCAGC GGCAGCGCGT
31561 CCCGTTCCGA CGCGATCACG GCGGCCATCG CCCCGCCGGA CGGCAGCGCC TGCATCAGGC
31621 GGGCCCGTGC GGACACCAGC CTGCACGCGT CCTCCAGGGA CCAGACGCCG GCGACGTACG
31681 CGGCGGCCAG CTCGCCGATC GAATGGCCCA GCAAGGCGTC CGGGCGTACG CCCCACGCCT
31741 CGAGCTGTGC GCCGAGTGCG ACCTGGACGG CGAACACCGC GGGCTGGGCG TACCCGGTGT
31801 CGTGGAGGTC GAGCCCGGCG GGCACGTCGA GGGCGTCCAG CACCTCGCGG CGAGTGCGGG
31861 CGAAGACGTC GTAGGCGGCG GCCAGTCCGT CGCCCATGCC GGGACGTTGT GAGCCCTGTC
31921 CGGAGAAGAG CCACACGAGG CGGCGGTTCG GTTCTGCGGC GCCGGTGACC GTGTCGGTGC
31981 CGATCAGCGC GGCCCGGTGC GGGAAGGCCG TGCGGGCGAG CAGGGCCGCG GCCACCGCGC
32041 GCTCGTCCTC CTCGCCGGTG GCGAGGTGGG CGCGCAGGCG GTGTACCTGT GCGTCGAGTG
32101 CCTGCGGGGT GCGTGCCGAG AGCAGCAGGG GCAGCGGTCC GGTGTCGGGT GCCGGGGCGG
32161 GTTCGGGGGC CGGTCGGGGG TGGCTTTCGA GGATGATGTG AGCGTTGGTG CCGCTAACGC
32221 CGAAGGAGGA CACCCCGGCC GCCGTGGGC GGTCGGTTTC GGGCCAGGGG CGGGCGTCGG
32281 TGAGGAGTTC GACGGCGCCG GCCGTCCAGT CGACGTGCGA GGACGGCGTG TCCACGTGCA
32341 GGGTGCGCGG CAGGGTGCCG TGCCGCATGG CGAGGACCAT CTTGATGACA CCGGCGACGC
32401 CCGCGGCGGC CTGAGTGTGG CCGATGTTGG ACTTCAGCGA GCCCAGCAGC ACCGGGGTGT
32461 CGCGATGCTG CCCGTAGGTG GCCAGTACCG CCTGCGCCTC GATGGGGTCG CCCAGCCTGG
32521 TCCCGGTGCC ATGCGCCTCG ACAGCGTCCA CATCCGCCGG GGTGAGCCCG GCGTTGGCCA
32581 GCGCCTGCCG GATCACCCGC TCCTGCGACG GCCCGTTCGG CGCCGACAAC CCGTTGGAAG
32641 CACCGTCCTG GTTGACCGCC GAACCACGCA CGACCGCGAG GACATTGTGG CCGTGCCGCT
32701 CGGCGTCGGA GAGCCTCTCG ACGATCAGCA CACCGGATCC CTCGGCGAAA CCGGTGCCAT
32761 CAGCCGCATC CGCGAACGCC TTGCAGCGGC CGTCCGGGGA GAGGCCCCGC TGCTGGGAGA
32821 AGTCCACGAA GCCGGACGGC GAGGCCATCA CCGTGACGCC GCCGACCACG GCGAGCGAGC
32881 ACTCCCCCGA GCGCAGCGAC TGCCCGGCCT GGTGCAGCGC CACCAGCGAC GACGAACACG
32941 CCGTGTCCAC CGTGACCGCC GGACCCTCCA AACCGTAGAA GTACGACAGC CGACCGGACA
```

-continued

```
33001 GCACACTGGT CTGGGTGCTG GTGGCACCGA AACCGCCGCG GTCGGCTCCA GTGCCGTACC
33061 CGTAGAAGTA GCCGCCCATG AACACGCCGG TGTCGCTTCC GCGCAGCGAC TCCGGGAGGA
33121 TCCCGGCGTG TTCCAGCGCC TCCCACGAGG TCTCCAGGAC CAGACGCTGC TGCCGGGTCCA
33181 TCGCCAGCGC CTCACGCGGA CTGATCCCGA AGAACGCCGC GTCGAAGTCC GCCACCCCGG
33241 CGAGGAAGCC ACCATGACGC ACGGTCGACG TGCCCGGATG ATCCGGATCG GGATCGTACA
33301 GCCCGTCCAC GTCCCAACCA CGGTCCGTCG GAAACGCCGT GATCCCGTCA CCACCCGACT
33361 CCAGCAGCCG CCACAAGTCC TCCGGCGACG CGACCCCACC CGGCAGCCGG CAGGCCATCC
33421 CCACGATCGC CAACGGCTCG TCCTGCCGGA CGGCCGCGGT CGGGGTACGC CGCCGGGTGG
33481 TGGCCCGCGC GCCGGCCAGT TCGTCCAGGT GGGCGGCGAG CGCCTGCGCC GTGGGGTGGT
33541 CGAAGACGAG CGTAGCGGGC AGCGTCAGGC CCGTCGCGTC GGCCAGCCGG TTGCGCAGTT
33601 CGACGCCGGT CAGCGAGTCG AAGCCCACTT CCCTGAACGC GCGCGCGGGT GCGATGGCGT
33661 GGGCGTCGCG GTGGCCGAGC ACCGCGGCAG CGCTGGTACG GACGAGGTCG AGCATGTCGC
33721 GCGCGGCCGG AGGTGCGGAC GTGCGCCGGA CGGCCGGCAC GAGGGTGCGT AGGACCGGCG
33781 GGACCCGGTC GGACGCGGCG ACGGCGGCGA GGTCGAGCCG GATCGGCACG AGCGCGGGCC
33841 GGTCGGTGTG CAGGGCCGCG TCGAACAGGG CGAGCCCCTG TGCGGCCGTC ATCGGGGTCA
33901 TGCCGTTGCG GGCGATGCGG GCCAGGTCGG TGGCGGTCAG CCGCCCGCCC ATCCCGTCCG
33961 CCGCGTCCCA CAGTCCCCAG GCGAGCGAGA CGGCGGGCAG CCCCTGGTGG TGCCGGTGGC
34021 GGGCGAGCGC GTCGAGGAAC GCGTTGCCGG TCGCGTAGTT GGCCTGACCC GCGCCGCCGA
34081 ACGTGGCGGA TATGGACGAG TACAGGACGA ACGCGGCCAG GTCGAGATCG CGCGTCAGCT
34141 CGTGCAGGTG CCAGGCGACG TCCGCCTTGA CCCGCAGCAC GGCGTCCCAC TGCTCCGGCC
34201 GCATGGTCGT CACGGCCGCG TCGTCGACGA TCCCGGCCAT GTGCACGACG GCGCGCAGCC
34261 GCTGGGCGAC GTCGGCGACG ACTGCGGCCA GCTCGTCGCG GTCGACGACG TCGGCGGCCA
34321 CGTACCGCAC GCGGTCGTCC TCCGGCGTGT CGCCGGGCCG GCCGTTGCGG GACACCACGA
34381 CGACCTCGGC GGCCTCGTGC ACGGTGAGCA GGTGGTCCAC GAGGAGGCGG CCGAGCCCGC
34441 CGGTGCCGCC GGTGACGAGG ACGGTCCCGC CGGTCAGCGG GGAGGTTCCG GTGGCCGCGG
34501 CGACACGGCG CAGACGGGCC GCACGCGCTG TGCCGTCGGC GACCCGGACG TGCGGCTCGT
34561 CGCCGGCGGC GAGCCCGGCC GCTATGGCGG CGGGCGTGAT CTCGTCCGCT TCGATCAGGG
34621 CGACGCGGCC GGGATGCTCC GTCTCCGCCG TCCGGACCAG GCCGCCGAGC GCTTCCTGCG
34681 CGGGATCGCC GGTACGGGTG GCCACGATGA GCCGGGATCG CGCCCAGCGC GGCTCGGCGA
34741 GCCAGGTCTG CACGGTGGTG AGCAGGTCGC GGCCCAGCTC CCGGGTCCGG GCGCCGGGCG
34801 AGGTGCCCGG GTCGCCGGGT TCCACGGCCA GGACCACGAC CGGGGGGTGC TCGCCGTCGG
34861 GCACGTCGGC GAGGTACGTC CAGTCGGGGA CGGGTGACGC GGGCACGGGC ACCCAGGCGA
34921 TCTCGAACAG CGCCTCGGCA TCGGGGTCGG CGGCCCGCAC GGTCAGGCTG TCGACGTCAA
34981 GGACCGGTGA GCCGTGCTCG TGCGTGGCGA CGATGCGGAC CATGTCGGGG CCGACGCGTT
35041 CCAGCAGCAC GCGCAGCGCG GTCGCGGCGC GCGCGTGGAT CCTCACGCCG GACCAGGAGA
35101 ACGCCAGCCG GCGCCGCTCG GGTCCGTGA AGACCGTCCC GAGGGCGTGC AGGGCCGCGT
35161 CGAGCAGCAC GGGGTGCAGC CCGTACCGGG CGTCGGTGAG CTGTTCGGCG AGGCGGACCG
35221 ACGCGTAGGC GCGGCCCTCC CCCGTCCACA TCGCGGTCAT GGCCCGGAAC GCGGGCCCGT
35281 ACGAGAGCGG CAGCGCGTCG TAGAAGCCGG TCAGGTCGGC CGGGTCGGCG TCGGCGGGCG
35341 GCCAGTCCAC GGGCTCCGCC GGACCGCCAG TGTCCACGCT CAGCGCTCCG GTCGCACTGA
35401 GCGCCCAGGG GCCCGTGCCG GTACGGCTGT GCAGACTCAC CGACCGCCGT CCGGACACCT
35461 CGGTTCCGAC GGTGGCCTGG ATCTCCGTGT CGCCGTCGCC GTCGACCACC ACCGGCGCGA
35521 CGATGGTCAG CTCCGCGATC TCCGGCGTGC CGAGCCGGGC TCCCGCTTCG GCGAGCAGTT
35581 CCACGAGCGC CGAGCCGGGC ACGATGACCC GGCCGTCCAC CTCGTGGTCG GCGAGCCAGG
35641 GCTGACGGCG TACCGAGACA CCCGCGGTGGC CAGCGCCGCC TCGCCGTCGG GCGAGGTCGA
35701 CCCACGAGCC GAGCAGCGGG TGGCCGGACG TTCCCGCCGG TTCCGCGTCG ATCCAGTAGC
35761 GGTCACGCGG GAACGGGTAC GTGGGCAGCG GCACCACCCG ACGCGTCGCG AACGACCAGG
35821 TGACGGGCAC GCCCCGGACC CAGAGCGCGG CGAGCGACCG AGTGAAGCGG TCCAGGCCGC
35881 CCTCGCCTCG CCGCAGTGTG CCGGTGACGA CCGTATGCGC ATGCCCGGCG AGCGTGTCCT
35941 CCAGTGCGGT GGTGAGCACG GGATGCGCGC TGACCTCGAC GAACGCGCGG TATCCGCGGT
36001 CCGCCAGGTG GCCGGTCGCG GCGGCGAACC GAACGGTGCG GCGCAGGTTG TCGTACCAGT
36061 AGGCGGCGTC CGCGGGCCGG TCCAGCCACG CCTCGTCCAC GGTGGAGAAG AACGGGACGT
36121 CCGGCGTGCG CGGAGTGATG CCGGCGAGAG CGTCGAGCAG CGCGCCGCGG ATCGTTTCGA
36181 CATGCGCGGT GTGCGACGCG TAGTCGACGG CGATCCGGCG GGCGCGGGGG GTGGCGGCCA
36241 GCAGCTCCTC CACGGCGTCG GCCGCACCGG CGACAACGAT CGACGCGGGT CCGTTGACCG
36301 CGGCGACCTC CAGGCGCCCG GCCCACACGG CGGCGTCGAA GTCGGCGGGC GGCACCGAGA
36361 CCATGCCGCC CTGCCCGGCC AGTTCGGTGG CGACGAGTCG GCTGCGCACC GCGACGACCT
36421 TCGCGGCGTC GTCCAGGGTG AGCACCCCGG CGCGGCACT TCGCCCTGGG
36481 AGTGCCGAC GACCGCGGCC GGGGCGACCC CGTGCGCACG CCACAGCTCC GCCAGCGCCA
36541 CCATCACCGC GAACGACGCG GGCTGCACGA CATCGACCCG GTCGAACGCG GGCGCTCCGG
36601 GCCGCTGGGC GATGACGTCC AGCAGGTCCC ATCCGGTGTG CGGGGCGAGC GCCGTGGCGC
36661 ACTCGCGGAG CCGCCGGGCG AACACGGGCT CGGTGGCGAG CAGTTCGGCA CCCATGCCGG
36721 CCCACTGGGA GCCCTGCCCG GGGAACGCGA ACACGACACG TGTGTCGGTG ACGTCGGCGG
36781 TTCCCGTCAC GGCCCCCGGC ACTTCGGCAC CACGGGCGAA CGCCTCCGCC TCTCGGGCCG
36841 GCACGACCGC CCGGTGGCGC ATGGCCGTCC GGGTGGTGGC GAGCGAGTGG CCGACCGCGG
36901 CCGCGGCGCC AGTGAGCGGG GCCAGCTGTC CCGCGACGTC CCGCAGTCCC TCGGGGTCC
36961 GGGCCGACAT CGGCCAGACC ACGTCCTCGG GCACCGGCTC GGCTTCGGGT GCGGACACGG
37021 GTGCGGGCGC GGCGGGGGGC CCGGCCTCCA GGACGACATG GGCGTTGGTG CCGCTGATGC
37081 CGAACGACGA GACACCCGCA CGCCGGGCGC GCCCGGTGAC CGGCCACGGC TCACTGCGGT
37141 GCAGCAGCCG GATGTCGCGG TCCCAGTCGA CGTGCCGGGA CGGCTCGTCG ACGTGCAGCG
37201 TGCGCGGCAG GACGCCGTGC CGCATCGCCA TGACCATCTT GATGACGCCG GCGACGCCGG
37261 CCGCGGCCTG GGTGTGCCG ATGTTCGACT TGAGCGAGCC GATCAGCAGC GGATGCACGC
37321 GTTCGCGCCC GTAGGCCACT TGCAGGGCCT GGGCCTCGAC GGGGTCGCCG AGACGGGTGC
37381 CGGTGCCGTG TGCCTCCACG GCGTCGACGT CACCCGGCGC CAGGCCGGCG TCGGCGAGCG
37441 CACGCTGGAT GACGCGCTGC TGCGCAGGCC CGTTCGGGGC GGACAGCCCG TTCGACGCGC
37501 CGTCGGAGTT GACCGCGGAG CCGCGCACCA GCGCCAGCAC GGGGTGGCCG TGGCGGGTGG
37561 CGTCGGAGAG CCGCTCCAGC ACCAGGACAC CGGCGCCCTC GGCGAAGCTC GTGCCGTCCG
37621 CGGTGTCCGC GAAGGCCTTG GCACGGCCGT CGGGGGCGAG CCCGCGCTGC CGGGAGAACT
37681 CGACGAACCC GGTCGTCGTC GCCATCACCG TGACACCGCC GACCAGGGCG AGCGAGCACT
```

-continued

```
37741 CCCCCGAGCG CAGCGACCGC GCGGCCTGGT GCAGCGCCAC CAGCGACGAC GAACACGCCG
37801 TGTCGACGGT GACCGACGGG CCCTCCAGAC CGAAGTAGTA CGAGAGCCGC CCGGAGAGAA
37861 CGCTGGTCGG CGTGCCGGTC GCCCCGAAAC CGCCCAGGTC CACGCCCGCG CCGTAGCCCT
37921 GGGTGAACGC GCCCATGAAT ACGCCGGTGT CGCTGCCGCG GACGCTTTCG GGCAGGATGC
37981 CCGCTCGTTC GAACGCCTCC CACGACGCTT CGAGGACCAG ACGCTGCTGC GGGTCCATCG
38041 CCAGCGCCTC ACGCGGGCTG ATCCCGAAGA ACGCGGCGTC GAAGTCGGCG GCGCCGGTGA
38101 GGAAGCCGCC GTGACGCACG GAAACCTTGC CGACCGCGTC GGGGTTCGGG TCGTAGAGCG
38161 CGGCGAGGTC CCAGCCGCGG TCGGCGGGGA ACTCGGTGAT CGCGTCCCCG CCGGAGTCGA
38221 CCAGCCGCCA CAGGTCCTCC GGTGACCGCA CGCCACCGGG CATCCGGCAC GCCATGGCCA
38281 CGATCGCCAG CGGCTCGTTC CCCGCCACCG TCGGTGCGGG CACTGTCGCC GCCGGAGCGG
38341 CAGGGGCCGG CTCACCCCGC CGTTCCTCAT CCAGGCGGGC GGCGAGCGCG GCCGGTGTCG
38401 GGTGGTCGAA GACGGCCGTC GCGGAGAGCC GTACCCCCGT CGTCTCGGCG AGGCTGTTGC
38461 GCAACCGGAC ACCGCTGAGC GAGTCGATGC CGAGGTCCTT GAACGCCGTC GTGGGCGTGA
38521 TCTCGGAGGC GTCGGCGTGG CCGAGCACGG CGGCCGTGGC CGCACACACG ATGGCCAGCA
38581 GGTCACGATC GCGGTCGCGG TCGCGGTCGC GGTTGTCCTC CGCACGGGCG GCGATGCGGC
38641 GCTCGGTCCG CTGCCGGACG GGCTCGGTGG GAATCGCCGC GACCATGAAC GGCACGTCCG
38701 CGGCGAGGCT CGCCGTCGATG AAGTGGGTGC CCTCGGCCTC GGTGAGCGGC CGGAACCCGT
38761 CGCGCACCCG GTGCCGGTCG GCGTCGTCAA GTTGTCCGGT GAGGGTGCTG GTGGTGTGCC
38821 ACATGCCCCA GGCGATGGAG GTGGCGGGTT GGCCGAGGGT GTGGCGGTGG GTGGCGAGGG
38881 CGTCGAGGAA GGCGTTGGCG GCGGCGTAGT TTCCTTGTCC GGGGCTGCCG AGGACGGCGG
38941 CGGCGCTGGA GTAGAGGACG AAGTGGGTGA GGGGTTGGTT TTGGGTGAGG TGGTGCAGGT
39001 GCCAGGCGGC GTTGGCTTTG GGGTGGAGGA CGGTGGTGAG GCGCTGGGG GTGAGGGCGT
39061 CGAGGATGCC GTGGTCGAGG GTGGCGGCGG TGTGGAAGAC GGCGGTGAGG GGTTGGGGGA
39121 TGTGGGCGAG GGTGGTGGCG AGTTGGTGGG GGTCGCCGAC GTCGCAGGGG AGGTGGGTGC
39181 CGGGGGTTGGT GTCGGGGGGT GGGGTGCGGG AGAGGAGGTA GGTGTGGGGG TGGTTCAGGT
39241 GGCGGGCGAG GATGCCGGCG AGGGTGCCGG AGCCGCCGGT GATGATGATG GCGTGTTCGG
39301 GGTTGAGGGG GGTGGTGGTG GGTGGGGTGG TGGTGTGGAG GGGGGTGAGG TGGGGTCGGT
39361 GGAGGGTGTG GTGGGTGAGG CGGAGGTGGG GGGTGGTCGAG GGTGGCGAGT TGGGCCAGGG
39421 GGAGGGGAGT GTGGGGGTGG TCGGTTTCGA TGAGGCGGAT GCGGTGGGGG TGTTCGTTCT
39481 GGGCGGTGCG GGTGAGGCCG GTGACGGTGG CGCCGGCGGG GTCGGTGGTG GTGTGGACGA
39541 TGAGGGTGTG GTCGGTGGTG GTGAGGTGGT GTTGCAGGGC GGTCAGGACG CGGGTGGCGC
39601 GGGTGTGGGC GCGGGTGGGT ATGTCCTCGG GGTCGTCGGG GTGGGCGGCG GTGATCAGGA
39661 CGTGTCCCTC GGGCAGGTCA CCGTCGTAGA CCGCCTCCGG GACCGCGAGC CACTCCAACC
39721 GGAGCGGGTT CGGCCCCGAC GGGGTGTCGG CCCGCTCCCT CAGCACCAGC GAGTCCACCG
39781 ACACGACAGG ACGGCCATCC GGGTCGGCCA CGCGCACGGC GACGCCGGCC TCCCCCCGGG
39841 TGAGGGCGAC GCGCACCGCG GCGGCCCCGG TGGCGTTCAG GCGCACGCCC GTCCAGGAGA
39901 ACGGCAGCTC GATCCCGCCG CCCGCGTCGA GGCGCCCGGC GTGCAGGGCC GCGTCGAGCA
39961 GTGCCGGATG CACACCGAAA CCGTCCGCCT GGCCGGCCTG CTCGTCGGGC AGCGCCACCT
40021 CGGCATACAC GGTGTCACCA TCACGCCAGG CAGCCCGCAA CCCCTGGAAC GCCGACCCGT
40081 ACTCATAACC GGCATCCCGC AGTTCGTCAT AGAACCCCGA CGACGTCGACG GCCGCGGCCG
40141 TGGCCGGCGG CCACTGCGAG AACGGCTCAC CGGAAGCGTT GGAGGTATCC GGGGTGTCGG
40201 GGGTCAGGGT GCCGCTGGCG TGCCGGGTCC AGCTGCCCGT GCCCTCGGTA CGCGCGTGGA
40261 CGGTCACCGG CCGCCGTCCG GCCTCATCGG CCCCTTCCAC GGTCACCGAC ACATCCACCG
40321 CTGCGGTCAC CGGCACCACG AGCGGGGATT CGATGACCAG TTCATCCACC ACCCCGCAAC
40381 CGGTCTCGTC ACCGGCCCGG ATGACCAGCT CCACAAACGC CGTACCCGGC AGCAGAACCG
40441 TGCCCCGCAC CGCGTGATCA GCCAGCCAGG GATGCGTACG CAATGAGATC CGGCCGGTGA
40501 GAACAACACC ACCACCGTCG TCGGCGGGCA GTGCTGTGAC GGCGGCCAGC ATCGGATGCG
40561 CCGCCCCGGT CAGCCCGGCC GCGGACAGGT CGGTGGCACC GGCCGCCTCC AGCCAGTACC
40621 GCCTGTGCTC GAACGCGTAG GTGGGCAGAT CCAGCAGCCG CCCCGGCACG GGTTCGACCA
40681 CCGTGCCCCA GTCCACCCCC GCACCCGAGG TCCACGCCTG CGCCAACGCC CCCAGCCACC
40741 GCTCCCAGCC ACCGTCACCA GTCCGCAACG ACGCCACCGT GCGGGCCTGT TCCATCGCCG
40801 GCAGCAGCAC CGGATGGGCA CTGCACTCCA CGAACACCGA CCCGTCCAGC TCCGCCACCG
40861 CGGATCAG CGCGACAGGG CGACGCAGGT TCCGGTACCA GTACCCCTCA TCCACCGGCT
40921 CGGTCACCCA GGCGCTGTCC ACGGTCGACC ACCACGCCAC CGACCCGGTC CCGCCGGAAA
40981 TTCCCTTCAG TACCTCAGCG AGTTCGTCCT CGATGGCCTC CACGTGAGGC GTGTGGGAGG
41041 CGTAGTCGAC CGCGATACGA CGCACCCGCA CCCCATCAGC CTCATACCGC GCCACCACCT
41101 CCTCCACCGC CGACGGGTCC CCCGCCACCA CCGTCGAAGC CGGACCATTA CGCGCCGCGA
41161 TCCACACACC CTCGACCAGA CCCACCTCAC CGGCCGGCAA CGCCACCGAA GCCATCGCCC
41221 CCCGCCGGCC CAGCCGCGCC GCGATCACCC GACTGCGCAA CGCCACCACG CGGGCGGCGT
41281 CCTCCAGGCT GAGGGCTCCG GCCACACACG CCGCCGCGAT CTCCCCCTGC GAGTGTCCGA
41341 CCACAGCGTC CGGCACGACC CCATGCGCCT GCCACAGCGC GGCCAGGCTC ACCGCGACCG
41401 CCCAGCTGGC CGGCTGACC ACCTCCACCC GCTCCGCCAC ATCCGACCGC GACAACATCT
41461 CCCGCACATC CCAGCCCGTG TGCGGCAACA ACGCCCGCGC ACACTCCTCC ATACGAGCCG
41521 CGAACACCGC GGAACGGTCC ATGAGTTCCA CGCCCATGCC CACCCACTGG GCACCCTGCC
41581 CGGGGAAGAC GAACACCGTA CGCGGCTGAT CCACCGCCAC ACCCATCACC CGGGCATCAC
41641 CCAGCAGCAC CGCACGGTGA CCGAAGACAG CACGCTCACG CACCAACCCC TGCGCGACCG
41701 CGGCCACATC CACCCCACCC CCGCGCAGAT ACCCCTCCAG CCGCTCCACC TGCCCCGCA
41761 GACTCACCTC ACCACGAGCC GACACCGGCA ACGGCACCAA CCCATCACCA CCCGACTCCA
41821 CACGCGACGG CCCAGGAACA CCCTCCAGGA TCACGTGCGC GTTCGTACCG CTCACCCCGA
41881 ACGACGACAC ACCCGCATGC GGTGCCCGAT CCGACTCGGG CCACGGCCTC GCCTCGGTGA
41941 GCAGCTCCAC CGCACCGGCC GACCAGTCCA CATGCGACGA CGGCTCGTCC ACGTGCAGCG
42001 TCTTCGGCGC GATCCCATGC CGCATCGCCA TGACCATCTT GATGACACCG GCGACACCCG
42061 CAGCCGCCTG CGCATGACCC ATGTTCGACT TGACCGAACC GAGGTAGAGC GGCGTGTCGC
42121 GGTCCTGCCC GTAGGCCGCG AGGACGGCCT GCGCTCGAT CGGGTCGCCG AGCCGCGTGC
42181 CGGTGCCGTG CGCCTCCACC ACGTCCACAT CGGCGGCGCG CAGTCGGCG TTGACCAACG
42241 CCTGCCGGAT CACGCGCTGC TGGGCGACGC CGTTGGGGGC GGACAGTCCG TTGGAGGCAC
42301 CGTCCTGGTT CACCGCCGAG CCGCGGACGA CCGCGAGAAC GGTGTGCCCG TTGCGCTCGG
42361 CGTCGGAGAG CCGCTCCAGC ACGAGAACGC CGACGCCCTC GGCGAAGCCG GTCCCGTCCG
42421 CCGCGTCGGC GAACGCCTTG CACCGTCCGT CCGGGGAGAG TCCGCGCTGC CGGGAGAACT
```

-continued

```
42481 CCACGAGCTC TGCGGTGTTC GCCATGACGG TGACACCGCC GACCAGCGCC AGGGAGCACT
42541 CCCCGGCCCG CAGTGCCTGT GCCGCCTGGT GCAGGGCGAC CAGCGACGAC GAGCACGCCG
42601 TGTCGACCGT GACCGCCGGG CCCTGAAGTC CGTACACGTA CGAGAGGCGC CCGGACAGGA
42661 CGCTCGTCTG CGTCGCCGTG ACACCGAGCC CGCCCAGGTC CCGGCCGACG CCGTAGCCCT
42721 GGTTGAACGC GCCCATGAAC ACGCCGGTGT CGCTCTCCCG GAGCCTGTCC GGCACGATGC
42781 CGGCGTTCTC GAACGCCTCC CAGGAGGTCT CCAGGATCAG GCGCGCTGGG GGGTCCATCG
42841 CCAGCGCCTC GTTCGGACTG ATGCCGAAGA ACGCGGCGTC GAACCCGGCG CCGGCCAGGA
42901 ATCCGCCGTG GCGTGTCGTG GAGCGGCCGG CCGCGTCCGG GTCCGGGTCG TACAGCGCGT
42961 CGACGTCCCA GCCCCGGTCG GTGGGGAACT CGGTGATCGC CTCGGTACCG GCGGCGACGA
43021 GCCGCCACAG GTCCTCCGGC GAGGCGACCC CGCCGGGCAG TCGGCACGCC ATGCCGACGA
43081 TCGCGACGGG GTCGCCGGAG CCGAGGGTCT GGGCGGTCGC GGGTGCCGCT GTCGCGGAGC
43141 CGGCGAGGTG GGCGGCGAAC GCACGGGGAG TGGGGTGGTC GAACGCGGTT GACGCGGGCA
43201 CCCGCAGACC CGTCCGCGCG GCGACGGTGT TGGTGAACTC GACGGTGGTG AGCGAGTCGA
43261 GGCCGTTCTC GCGGAACGTG CGGTCCGGGG AGCAGTGTCC GGCGCCCGGC AGGCCCAGGA
43321 CGGTGGCGAC GCTGTCGCGG ACCAGGTCGA GCAGTACGTC CTCCCGGCCC GCACGGGCCG
43381 CGGCGAGGCG GTTCGCCCAC TCCTGTTCCG TGGCGTCGGG CTCGGCCGTC CCGGTCAGTG
43441 CGGTGAGGAT CGGCGGCGTG GCGCCCGCCA TCGTCGCGGC CCGCGCCCCG GCGGAACCGG
43501 TCCGGGCCAC GATGTACGAG CCGCCGCCCG CGATGGCCTT CTCGATCAGG TCGCCGGTGA
43561 GCGCCGGCCG TTCGATGCCG GGCAGCGCGC GGACGGTGAC GGTGGGGAGT CCCTCCGCGG
43621 CCCGTGGCCG GGTGTGGGCG TCGGCGCCGG CCGGGCCGTC GAGCAGGACG TGCACGAGCG
43681 CGCCGGGGTT CGCGGCTTCC TCGGCTGCGG TGGTCACGTG GGTGAGGCCG GTCTCGTCGC
43741 GGAGCAGGCC GGCGACGGTG TCGGCGTCCT CCCCGGTGAC CAGGACCGGC GCGTCCGGGC
43801 CGATCGGAGG CGGCACGGTG AGGACCATCT TGCCGGTGTG CCGGGCGTGG CTCATCCACG
43861 CGAACGCGTC CCGCGCACGG CGGATGTCCC ACGGCTGCAC CGGCAGCGGG CACAGCTCAC
43921 CGCGGTCGAA CAGGTCGAGG AGCAGTTCGA GGATCTCCCG CAGGCGCGCG GGATCCACGT
43981 CGGCCAGGTC GAACGGCTGC TGGGCGGCGT GGCGGATGTC GGTCTTGCCC ATCTCGACGA
44041 ACCGGCCGCC CGGTGCGAGC AGGCCGATGG ACGCGTCGAG GAGTTCACCG GTGAGCGAGT
44101 TGAGCACGAC GTCGACCGGC GGGAAGGTGT CGGCGAACGC GGCGCTGCGG GAGTTCGCCA
44161 CATGGTCGGT GTCGAAGCCG TCGGCGTGCA GCAGGTGTTG TTTGGCGGGA CTGGCGGTGG
44221 CGTACACCTC GGCGCCGAGG TGGCGGGCGA TCCGGGTCGC CGCCATGCCG ACACCGGCCCG
44281 TCGCGGCGTG GACCAGGACC TTCTGGCCGG GTCGCAGCTC GCCCGCGTCG ACGAGGCCGT
44341 ACCAGGCGGT GGCGAACACG ATGGGCACGG ACGCGGCGAT GGGGAACGAC CATCCCCGTG
44401 GGATCCGTGC GACCAGCCGC CGGTCCGCGA CCGAACGCG TCCTGCACGA
44461 GACCGAACAC GCGGTCGCCG GGGGCCAGGT CGTCGACGCC GGGTCCGACT TCGGTCACGA
44521 TGCCCGCGGC CTCCCCGCCC ATCTCGCCCT CGCCCGGGTA GGTGCCGAGC GCGATCAGCA
44581 CGTCGCGGAA GTTCAGCCCC GCGGCGCGGA CGTCGATGCG GACCTCGCCG GCGGCCAGGG
44641 GCGCGGCGGG ACGTCGAGCG GGGCGACGAC GAGGTCGCGA AGCGTTCCGG AGGCGGGCGG
44701 GCGCAGCGCC CACTGGCGCG GTCGGCAGGG GGTGGTGTC CGCGCGTACC AGCCGGGGCA
44761 CGTAGGCCAC GCCGGCCCGC AGCGCGATCT GGGGTTCGCC GAGCGAGGCC GCGGCGGGGA
44821 CGAGGTCGTC ATCGCCGTCC GTGTCCACCA GCACGAACGA TCCGGGTTCG GCGGCCTGGC
44881 GGCGCAGCGC CTCGTCCCAG AGCCGGGCCT GGTCGGCCTC CGGGATCTCC GCCGGGCCGA
44941 CGCCCACCGC GCGGCGGGTG ACGACCGTCC GGCGGGGTGA CGGGGTGCCG GGCAGGTCGC
45001 GCCGCTCCCA GACCAGTTCG CACAGCGTGG CCTCGCCACT GCCGGTGGCG ACCAGATGGG
45061 CCGGCAGCCC CGCGAGCCGC GCGCGCTGGA CCTTGCCCGA CGCGGTGCGG GGGATCGTGG
45121 TGACGTGCCA GATCTCGTCG GCACCTTGA AGTAGGCGAG CCGGCGCCGG CACTCGGCGA
45181 GGATCGCCTC GGCGGGGACG CGGGGGCCGT CGGAAACGAC GTAGAGCACG GGTATGTCGC
45241 CGAGGACGGG GTGCGGGCGG CCCGCCGCGG CGGCGTCCCG GACACCGGCC ACCTCCTGGG
45301 CGACGGTCTC GATCTCCCGG GGGTGGATGT TCTCCCCGCC GCGGATGATC AGCTCCTTGA
45361 CCCGGCCGGT GATCGTCACG TGTCCGGTCT CGGCCTGACG TGCGAGGTCC CCGGTGCGGT
45421 ACCAGCCGTC CACGAGCACC TGGGGGGGTCG CCTCCGGCTG GGCGTGGTAG CCGAGCATGA
45481 GGCTCGGCCC GCTCGCCCAC AGCTCGCCCT CCTCGCCGGG TGCCACGTCG GCGCCGGACA
45541 CCGGGTCGAC GAACCGCAGC GACAGGCCCG GCACGGGCAG CCCGCACGAG CCGGGAACCC
45601 GCGCATCCTC CAGGGTGTTG GCGGTGAGCG AGCCGGTCGT CTCGGTGCAG CCGTACGTGT
45661 CGAGCAGGGG CACGCCGAAC GTCGCCTCGA AATCCCTGGT GAGCGACGCC GGCGAGGTGG
45721 ATCCGGCGAC CAGCGCCACG CGCAGCGCGC GAGCCCGCGG CTCGCCGGAC ACGGCGCCGA
45781 GGAGGTAGCG GTACATCGTC GGCACGCCGA CGAGCACGGT GCTGGAGTGT TCGGCCAGGG
45841 CGTCGAGGAC GTCACGCGCG ACGAAGCCGC CAGGATACG GCGGACGCG CCGACCGTGA
45901 GGACGGCGAG CAGGCAGAGG TGGTGGCCGA GCGTGTGGAA CAGCGGGGCG GCCAGAGCA
45961 GTTCGTCGTC CTCGGTCAGC CGCCAGGACG GCACGTCGCA GTGCATCGCG GACCACAGGC
46021 CGCTGCGCTG TGCGGAAACC ACGCCCTTGG GACGCCGGT GGTGCCGGAG GTGTAGAGCA
46081 TCCAGGCGGG TTCGTCCAGG CCGAGGTCGT CGCGGGGCGG GCACGGCGGC TCGGTCCCGG
46141 CGAGGTCCTC GTAGGAGACG CAGTCCGGTG CCCGGCGCGC GACGAGCACG GGCGGTGGCGT
46201 CGGTGCCGGT GCGGCGCACC TGGTCGAGGT GGGTTTCGTC GGTGACCAGC ACGGTCGCGC
46261 CGGAGTCCGT CAGGAAGTGG GCGAGTTCGG CGTCGGCGGC GTCCGGGTTG AGCGGGACGG
46321 CGACGGCGGC GGCGCGGGCG GCGGCGAGGT AGACCTCGAT GGTCTCGATC CGGTTGCCGA
46381 GCAGCATCGC GACCCGGTCG CCGCGGTTCGA CGCCGGACGC GGCGAGGTGT CCGGCGAGCC
46441 GGCCGGCCCG GAGCCGGAGT TGCGTGTACG TCACGGCGCG TTGGGAATCC GTGTAGGCGA
46501 TCCGGTCGCC GCGTCGCTCG GCATGGATGC GGAGCAATTC GTGCAACGGC CGGATTGGTT
46561 CCACACGCGC CATGGAAACA CCTTTCTCTC GACCAACCGC ACAACAGCAC GGAACCGGCC
46621 ACGAGTAGAC GCCGGCGGTC CTAGCAGCGT TTTCCGGACG GCCACCCCCT GAAGATCCCC
46681 CTACCGTGGC CGGCCTCCCC GGACGCTCAT CTAGGGGGTT GCACGCATAC CGCCGTGCGT
46741 AATTGCCTTC CTGATGACCG ATGCCGGACG CCAGGGAAGG GTGGAGGCGT TGTCCATATC
46801 TGTCACGGCG CCGTATTGCC GCTTCGAGAA GACCGGATCA CCGGACCTCG AGGGTGACGA
46861 GACGGTGCTC GGCCTGATCG AGCACGGCAC CGGCCACACC GACGTGTCGC TGGTGGACGG
46921 TGCTCCCCGG ACCGCCGTGC ACACCACGAC CCGTGACGAC GAGGCGTTCA CCGAGGTCTG
46981 GCACGCACAG CGCCCTGTCG AGTCCGGCAT GGACAACGGC ATCGCCTGGG GCCGCACCGA
47041 CGCGTACCTG TTCGGTGTCG TGCGCACCGG CGAGAGCGGC AGGTACGCCG ATGCCACCGC
47101 GGCCCTCTAC ACGAACGTCT TCCAGCTCAC CCGGTCGCTG GGGTATCCCC TGCTCGCCCG
47161 GACCTGGAAC TACGTCAGCG GTATCAACAC GACGAACGCG GACGGGCTGG AGGTGTACCG
```

```
47221 GGACTTCTGC GTGGGCCGCG CCCAGGCGCT CGACGAGGGC GGGATCGACC CGGCCACCAT
47281 GCCCGCGGCC ACCGGTATCG GCGCCCACGG GGGCGGCATC ACCTGCGTGT TCCTCGCCGC
47341 CCGGGGCGGA GTGCGGATCA ACATCGAGAA CCCCGCCGTC CTCACGGCCC ACCACTACCC
47401 GACGACGTAC GGTCCGCGGC CCCCGGTCTT CGCACGGGCC ACCTGGCTGG GCCCGCCGGA
47461 GGGGGGCCGG CTGTTCATCT CCGCGACGGC CGGCATCCTC GGACACCGAA CGGTGCACCA
47521 CGGTGATGTG ACCGGCCAGT GCGAGGTCGC CCTCGACAAC ATGGCCCGGG TCATCGGCGC
47581 GGAGAACCTG CGGCGCCACG GCGTCCAGCG GGGGCACGTC CTCGCCGACG TGGACCACCT
47641 CAAGGTCTAC GTCCGCCGCC GCGAGGATCT CGATACGGTC CGCCGGGTCT GCGCCGCACG
47701 CCTGTCGAGC ACCGCGGCCG TCGCCCTTTT GCACACCGAC ATAGCCCGCG AGGATCTGCT
47761 CGTCGAAATC GAAGGCATGG TGGCGTGACA ATACCCGGTA AAAGGCCCGC GACGCTGCGC
47821 CTCGGCGGAT CCGCGAAGAG AAAGAAGAGC GTCACCGCAC AGCGCGGCAG CCCGGTCCTT
47881 TCGTCCTTCG CACAGCGGCG GATCTGGTTT CTCCAGCAAT TGGACCCGGA GAGCAACGCC
47941 TATAATCTCC CGCTCGTGCA ACGCCTGCGC GGTCTATTGG ACGCGCCGGC CCTGGAGCGT
48001 GCGCTGGCGC TCGTCGTCGC GCGCCACGAG GCGTTGCGGA CGGTGTTCGA CACCGCCGAC
48061 GGCGAGCCCC TCCAGCGGGT GCTTCCCGCC CCGGAACACC TCCTGCGCCA CGCGCGGGCG
48121 GGCAGCGAGG AGGACGCCGC CCGGCTCGTC CGCGACGAGA TCGCCGCGCC GTTCGACCTC
48181 GCCACCGGGC CGTTGATCAG GGCCCTGCTG ATCCGCCTCG GTGACGACGA CCACGTTCTC
48241 GCGGTGACCG TGCACCATGT CGCCGGCGAC GGCTGGTCGT TCGGGCTCCT CCAACATGAA
48301 CTCGCAGCCC ACTACACGGC GCTGCGCGAC ACTGCCCGCC CTGCCGAACT GCCGCCGTTG
48361 CCGGTGCAGT ACGCCGACTT CGCCGCCTGG GAGCGGCGCG AACTCACCGG CGCCGGACTG
48421 GACAGGCGTC TGGCCTACTG GCGCGAGCAA CTCCGGGGCG CCCCGGCGCG GCTCGCCCTC
48481 CCCACCGACC GTCCCCGCCC GCCGGTCGCC GACGCGGACG CGGGCATGGC CGAGTGGCGG
48541 CCGCCGGCCG CGCTGGCCAC CGCGGTCCTC ACGCTCGCGC GCGACTCCGG TGCGTCCGTG
48601 TTCATGACCC TGCTGGCGGC CTTCCAAGCG GTCCTGCCC GGCAGGCGGG CACGCGGGAC
48661 GTGCTGGTCG GCACGCCCGT GGCGAACCGT ACGCGGGCGG CGTACGAGGG CCTGATCGGA
48721 ATGTTCGTCA CACGCTCGC GCTGCGCGGC GACCTCTCGG GCGATCCGTC GTTCCGGGAA
48781 CTCCTCGACC GdTGCCGGGC CACGACCACG GACGCGTTCG CCCACGCCGA CCTGCCGTTC
48841 GAGAACGTCA TCGAACTCGT CGCACCGGAA CGCGACCTGT CGGTCAACCC GGTCGTCCAG
48901 GTGCTGTTGC AGGTGCTGCG GCGCGACGCG GCGCAGGCCG CGCTGCCCGG CATCGCGGCC
48961 GAACCGTTCC GCACCGGACG CTGGTTCACC CGCTTCGACC TCGAATTCCA TGTGTACGAG
49021 GAGCCGGGTG GCGCGCTGAC CGGCGAACTG CTCTACAGCC GTGCGCTGTT CGACGAGCCA
49081 CGGATCACGG GGTTGCTGGA GGAGTTCACG GCGGTGCTTC AGGCGGTCAC CGCCGACCCG
49141 GACGTACGGC TGTCGCGGCT GCCGGCCGGC GACGCGACGG CGGCAGCGCC CGTGGTGCCC
49201 TCGAACGACA CGGCGCGGGA CCTGCCCGTC GACACGCTGC CGGGCCTGCT GGCCCGGTAC
49261 GCCGCACGCA CCCCCGGCGC CGTGGCCGTC ACCGACCCGC ACATOTOOCT CACCTACGCG
49321 CAGCTGGACC GGCGGGCGAA CCGCCTCGCG CACCTGCTCC GCGCGCGCGG CACCGCCACC
49381 GGCGACCTGG TCGGGATCTG CGCCGATCGC GGCGCCGGAC CTGACCCGG CATCGTGGGG
49441 ATCCTCAAGG CGGGCGCCGC TTATGTGCCG CTGGACCCCG AACATCCTCC GGAGCGCACG
49501 GCGTTCGTGC TGGCCGACGC GCAGCTGACC ACGGTGGTGG CGCACGAGGT CTACCGTTCC
49561 CGGTTCCCCG ATGTGCCGCA CGTGGTGGCG TTGGACGACC CGGAGCTGGA CCGGCAGCCG
49621 GACGACACGG CGCCGGACGT CGAGCTGGAC CGGGACGCCG TCGCCTACGC GATCTACACG
49681 TCCGGGTCGA CCGGCAGGCC GAAGGCCGTG CTCATGCCGG GTGTCAGCGC CGTCAACCTG
49741 CTGCTCTGGC AGGAGCGCAC GATGGGCCGC GAGCCGGCCA GCCGCACCGT CCAGTTCGTG
49801 ACGCCCACGT TCGACTACTC GGTGCAGGAG ATCTTTTCCG CGCTGCTGGG CGGCACGCTC
49861 GTCATCCCGC CGGACGAGGT GCGGTTCGAC TCGCCCGGGAC TCGCCCGGTG GATGGACGAA
49921 CAGGCGATTA CCCGGATCTA CGCGCCGACG GCCGTACTGC GCGCGCTGAT CGAGCACGTC
49981 GATCCGCACA GCGACCAGCT CGCCGCCCTG CGGCACCTGT GCCAGGGCGG CGAGGCGCTG
50041 ATCCTCGACG CGCGGTTGCG CGAGCTGTGC CGGCACCGGC CCCACCTGCG CGTGCACAAT
50101 CACTACGGTC CGGCCGAAAG CCAGCTCATC ACCGGGTACA CGCTGCCCGC CGACCCCGAC
50161 GCGTGGCCCG CCACCGCACC GATCGGCCCG CCGATCGACA ACACCCGCAT CCATCTGCTC
50221 GACGAGGCGA TGCGGCCGGT TCCGGACGGT ATGCCGGGGC AGCTCTGCGT CGCCGGCGTC
50281 GGCCTCGCCC GTGGGTACCT GGCCCGTCCC GAGCTGACCC CGAGCGCTG GGTGCCGGGA
50341 GATGCGGTCG GCGAGGAGCG CATGTACCTC ACCGGCGACC TGGCCGCCG CGCGCCCGAC
50401 GGCGACCTGG AATTCCTCGG CCGGATCGAC GACCAGGTCA AGATCCGCGG CATCCGCGTC
50461 GAACCGGGTG AGATCGAGAG CCTGCTCGCC GAGGACGCCC GCGTCACGCA GGCGCGGGTG
50521 TCCGTGCGCG AGGACCGGCG GGGCGAGAAG TTCCTGGCCG CGTACGTCGT ACCGGTGGCC
50581 GGCCGGCACG GCGACGACTT CGCCGCGTCG CTGCGCGCGG GACTGGCCGC CCGGCTGCCC
50641 GCCGCGCTCG TGCCCTCCGC CGTCGTCCTG GTGGAGCGAC TGCCGAGGAC CACGAGCGGC
50701 AAGGTGGACC GGCGCGCGCT GCCCGACCCG GAGCCGGGCC CGGCGTCGAC CGGGGCGGTT
50761 ACGCCCCGCA CCGATGCCGA GCGGACGGTG TGCCGGATCT TCCAGGAGGT GCTCGACGTC
50821 CCGCGGGTCG GTGCCGACGA CGACTTCTTC ACGCTCGGCG GGCACTCCCT GCTCGCCACC
50881 CGGGTCGTCT CCCGCATCCG CCCGAGCTG GGTGCGATG TCCCGCTGCG TACGCTCTTC
50941 GACGGGCGGA CGCCCGCCGC GCTCGCCCGT GCGGCGGACG AGGCCGGCCC GGCGCCCTG
51001 CCCCCGATCG CGCCCTCCGC GGAGAACGGG CCGGCCCCC TCACCGCGGC ACAGGAACAG
51061 ATGCTGCACT CGCACGGCTC GCTGCTCGCC GCGCCCTCCT ACACGGTCGC CCCGTACGGG
51121 TTCCGGCTGC GCGGGCCACT CGACCGCGAA CGGCACGGCA CGGCACTGAC CCGGATCGCG
51181 GCGCGCCACG AGCCGCTGCG GACCGGGTTC GCGATCGGG AACAGGTCGT CCGGCCGCCC
51241 GCTCCGGTGC GCGCCGAGGT GGTTCCGGTG CCGGTCGGCC ACGTCGACGC CGCGGTCCGG
51301 GTCGCCCACC GGGAGCTGAC CCGGCCGTTC GACCTCGTGA ACGGGTCGTT GCTGCGTGCC
51361 GTGCTGCTGC CGCTGGGCGC CGAGGATCAC GTGCTGCTGC TGATGCTGCA CCACCTCGCC
51421 GGTGACGGAT GGTCCTTCGA CCTCCTGGTC CGGGAGTTGT CGGGGACGCA ACCGGACCTT
51481 CCGGTGTCCT ACACGGACGT GGCCCGGTGG GAACGGAGTC CGGCCGTGAT CGCGGCCAGG
51541 GAGAACGACC GGGCCTACTG GCGCCGGCGG CTGGGGGGCG CCACCGCGCC GGAGCTGCCC
51601 GCGCGTCCGG CCGGCGGGGC ACCGACCGGG CGGCGTTCC TGTGGACGCT CAAGGACACC
51661 GCCGTCCTGG CGGCACGCCG GGTCGCGGAC GCCCACGACG CGACGTTGCA CGAAACCGTG
51721 CTCGGCGCCT TCGCCCTGGT CGTGGCGGAG ACCGCCGACA CCGACGACGT GCTCGTCGCG
51781 ACGCCGTTCG CGGACCGGGG GTACGCCGGG ACCGACCACC TCATCGGCTT CTTCGCGAAG
51841 GTCCTCGCGC TGCGCCTCGA CCTCGGCGGC ACGCCGTCGT TCCCCGAGGT GCTGCGCCGG
51901 GTGCACACCG CGATGGTGGG CGCGCACGCC CACCAGGCGG TGCCCTACTC CGCGCTGCGC
```

-continued

```
51961 GCCGAGGACC CCGCGCTGCC GCCGGCCCCC GTGTCGTTCC AGCTCATCAG CGCGCTCAGC
52021 GCGGAACTGC GGCTGCCCGG CATGCACACC GAGCCGTTCC CCGTCGTCGC CGAGACCGTC
52081 GACGAGATGA CCGGCGAACT GTCGATCAAC CTCTTCGACG ACGGTCGCAC CGTCTCCGGC
52141 GCGGTGGTCC ACGATGCCGC GCTGCTCGAC CGTGCCACGG TCGACGATTT GCTCACCCGG
52201 GTGGAGGCGA CGCTGCGTGC CGCCGCGGGC GACCTCACCG TACGCGTCAC CGGTTACGTG
52261 GAAAGCGAGT AGCCATGCCC GAGCAGGACA AGACAGTCGA GTACCTTCGC TGGCGACCG
52321 CGGAACTCCA GAAGACCCGT GCGGAACTCG CCGCGCACAG CGAGCCGTTG GCGATCGTGG
52381 GGATGGCCTG CCGGCTGCCC GGCGGGGTCG CGTCGCCGGA GGACCTGTGG CAGTTGCTGG
52441 AGTCCGGTGG CGACGGCATC ACCGCGTTCC CCACGGACCG GGGCTGGGAG ACCACCGCCG
52501 ACGGTCGCGG CGGCTTCCTC ACCGGGGCGG CCGGCTTCGA CGCGGCGTTC TTCGGCATCA
52561 GCCCGCGCGA GGCGCTGGCG ATGGACCCGC AGCAGCGCCT GGCCCTGGAG ACCTCGTGGG
52621 AGGCGTTCGA GCACGCGGGC ATCGATCCGC AGACGCTGCG GGGCAGTGAC ACGGGGGTGT
52681 TCCTCGGCGC GTTCTTCCAG GGGTACGGCA TCGGCGCCGA CTTCGACGGT TACGGCACCA
52741 CGAGCATTCA CACGAGCGTG CTCTCCGGCC GCCTCGCGTA CTTCTAGGGT CTGGAGGGTC
52801 CGGCGGTCAC GGTCGACACG GCGTGTTCGT CGTCGCTGGT GGCGCTGCAC CAGGCCGGGC
52861 AGTCGCTGCG CTCCGGCGAA TGCTCGCTCG CCCTGGTCGG CGGCGTCACG GTGATGGCCT
52921 CGCCGGCGGG GTTCGCGGAC TTCTCCGAGC AGGGCGGCCT GGCCCCCGAC GCGCGCTGCA
52981 AGGCCTTCGC GGAAGCGGCT GACGGCACCG GTTTCGCCGA GGGGTCCGGC GTCCTGATCG
53041 TCGAGAAGCT GTCCGACGCC GAGCGCAACG GCCACCGCGT GCTGGCGGTC GTCCGGGGTT
53101 CCGCCGTCAA CCAGGACGGT GCCTCCAACG GGCTGTCCGC GCCGAACGGG CCGTCGCAGG
53161 AGCGGGTGAT CCGGCAGGCC CTGGCCAACG CCGGACTCAC CCCGGCGGAC GTGGACGCCG
53221 TCGAGGCCCA CGGCACCGGC ACCAGGCTGG GCGACCCCAT CGAGGCACAG GCCGTGCTGG
53281 CCACCTACGG GCAGGGGCGC GACACCCCTG TGCTGCTGGG CTCGCTGAAG TCCAACATCG
53341 GCCACACCCA GGCCGCCGCG GGCGTCGCCG GGGTGTCATCAA GATGGTCCTC GCCATGCGGC
53401 ACGGCACCCT GCCCCGCACC CTGCACGTGG ACACGCCGTC CTCGCACGTC GACTGGACGG
53461 CCGGCGCCGT CGAACTCCTC ACCGACGCCC GGCCCTGGCC CGAAACCGAC CGCCCACGGC
53521 GCGCCGGTGT CTCCTCCTTC GGCGTCAGCG GCACCAACGC CCACATCATC CTCGAAAGCC
53581 ACCCCCGACC GGCCCCCGAA CCCGCCCCGG CACCCGACAC CGGACCGCTG CCGCTGCTGC
53641 TCTCGCCCG CACCCCGCAG GCACTCGACG CACAGGTACA CCGCCTGCGC GCGTTCCTCG
53701 ACGACAACCC CGGCGCGGAC CGGGTCGCCG TCGCGCAGAC ACTCGCCCGG CGCACCCAGT
53761 TCGAGCACCG CGCCGTGCTG CTCGGCGACA CGCTCATCAC CGTGAGCCCG AACGCCGGCC
53821 GCGGACCGGT GGTCTTCGTC TACTCGGGGC AAAGCACGCT GCACCCGCAC ACCGGGCGGC
53881 AACTCGCGTC CACCTACCCC GTGTTCGCCG AAGCGTGGCG CGAGGCCCTC GACCACCTCG
53941 ACCCCACCCA GGGCCCGGCC ACGCACTTCG COCACCAGAC CGCGCTCACC GCGCTCCTGC
54001 GGTCCTGGGG CATCACCCCG CACGCGGTCA TCGGCCACTC CCTCGGTGAG ATCACCGCCG
54061 CGCACGCCGC CGGTGTCCTG TCCCTGAGGG ACGCGGGCGC GCTCCTCACC ACCCGCACCC
54121 GCCTGATGGA CCAACTGCCG TCGGGCGGCG CGATGGTCAC CGTCCTGACC AGCGAGGAAA
54181 AGGCACGCCA GGTGCTGCGG CCGGGCGTGG AGATCGCCGC CGTCAACGGC CCCCACTCCC
54241 TCGTGCTGTC CGGGGACGAG GAAGCCGTAC TCGAAGCGCC CCGGCAGCTC GGCATCCACC
54301 ACCGCCTGCC GACCCGCCAC GCCGGCCACT CCGAGCGCAT GCAGCCACTC GTCGCCCCCC
54361 TCCTCGACGT CGCCCGGACC CTGACGTACC ACCAGCCCCA CACCGCCATC CCCGGCGACC
54421 CCACCACCGC CGAATACTGG GCGCACCAGG TCCGCGACCA AGTACGTTTC CAGGCGCACA
54481 CCGAGCAGTA CCCGGGCGCG ACGTTCCTCG AGATCGGCCC CAACCAGGAC CTCTCGCCGC
54541 TCGTCGACGG CGTTGCCGCC CAGACCGGTA CGCCCGACGA GGTGCGGGCG CTGCACACCG
54601 CGCTCGCGCA GCTCCACGTC CGCGGCGTCG CGATCGACTG GACGCTCGTC CTCGGCCGAG
54661 ACCGCGCGCC CGTCACGCTG CCCACGTATC CGTTCCAGCA CAAGGACTAC TGGCTGCGGC
54721 CCACCTCCCG GGCCGATGTG ACCGGCGCGG GGCAGGAGCA GGTGGCGCAC CCGCTGCTCG
54781 GCGCCGCGGT CGCGCTGCCC GGCACGGGCG GAGTCGTCCT GACCGGCCGC CTGTCGCTGG
54841 CCTCCCATCC GTGGCTCGGC GAGCACGCGG TCGACGACGC CGTGCTCGTG CTCGGCCGGG
54901 CCTTCCTCGA ACTCGCGGCG CGCGCCGGCG ACGAGGTCGG CTGCGACCTG CTGCACGAAC
54961 TCGTCATCGA GACGCCGCTC GTGCTGCCCG CGACCGGCGG TGTGGCGGTC TCCGTCGAGA
55021 TCGCCGAACC CGACGACACG GGGCGGCGGG CGGTCACCGT CCACGCGCGG GCCGACGGCT
55081 CGGGGCCTGTG GACCCGACAC GCCGGCGGAT TCCTCGGCAC GGCACCGGCA CCGGCCACGG
55141 CCACGGACCC GGCACCCTGG CCGCCCGCGG AAGCCGGACC GGTCGACGTC GCCGACGTCT
55201 ACGACCGGTT CGAGGACATC GGGTACTCCT ACGGACCGGG CTTCCGGGGG CTGCGGGCCG
55261 CCTGGCGCGC CGGCGACACC GTGTACGCCG AGGTCGCGCT CCCCGACGAG CAGAGCGCCG
55321 ACGCCGCCCG TTTCACGCTG CACCCCGCGC TGCTCGACGC CGCGTTCCAG GCCGGCGCGC
55381 TGGCCGCGCT CGACGCACCC GGCGGGGCGG CCCGACTGCC GTTCTCGTTC CAGGACGTCC
55441 GCATCCACGC GGCCGGGGCG ACGCGGCTGC GGGTCACGGT CGGCCGCGAC GGCGAGCGCA
55501 GCACCGTCCG CATGACCGGC CCGGACGGGC AGCTGGTGGC CGTGGTCGGT GCCGTGCTGT
55561 CGCGCCCGTA CGCGGAAGGC TCCGGTGACG GCCTGCTGCG CCCGGTCTGG ACCGAGCTGC
55621 CGATGCCCGT CCCGTCCGCG GACGATCCGC GGTGGAGGT CCTCGGCGCC GACCCGGGCG
55681 ACGGCGACGT TCCGGCGGCC ACCCGGGAGC TGACCGCCCG CGTCCTCGGC GCGCTCCAGC
55741 GCCACCTGTC CGCCGCCGAG GACACCACCT GGTGGTACGG ACCGGCACC GGCCCGGCCG
55801 CTGCCGCCGC CGCGGGTCTG GTCCGCTCGG CGCAGGCGGA GAACCCCGGC CGCGTCGTGC
55861 TCGTCGAGGC GTCCCCGGAC ACCTCGGTGG AGCTGCTCGC CGCGTGCGCC GGCTGGACCG
55921 AACCGCAGCT GGCCGTCCGG GACGGCGTGC TCTTCGCGCC GCGGCTGGTC CGGATGTCCG
55981 ACCCCGCGCA CGGCCCGCTG TCCCTGCCGG ACGGCGACTG GCTGCTCACC CGGTCCGCCT
56041 CCGGCACGTT GCACGACGTC GCGCTCATAG CCGACGACAC GCCCCGGCGG GCGCTCGAAG
56101 CCGGCGAGGT CCGCATCGAC GTCCGCGCGG CCGGACTGAA CTTCCGCGAT GTGCTGATCG
56161 CGCTCGGGAC GTACACCGGG GCCACGGCCA TGGGCGGCGA GGCCGCGGGC GTCGTGGTGG
56221 AGACCGGGCC CGGCGTGGAC GACCTGTCCC CCGGCGACCG GGTGTTCGGC CTGACCCGGG
56281 GCGGCATCGG CCCGACGGCC GTCACCGACC GGCGCTGGCC GGCCCGGATC CCCGACGGCT
56341 GGAGCTTCAC CACGGCGGCG TCCGTCCCGA TCGTGTTCGC GACCGGCTGG TACGGCCTGG
56401 TCGACCTCGG CACACTGCGC GCCGGCGAGA AGGTCCTCGT CCACGCGGCC ACCGGCGGTG
56461 TCGGCATGGC CGCCGCACAG ATCGCCCGCC ACCTGGGCGC CGAGCTCTAC GCCACCGCCA
56521 GTACCGGCAA GCAGCACGTC CTGCGCGCCG CCGGGCTGCC CGACACGCAC ATCGCCGACT
56581 CTCGGACGAC CGCGTTCCGG ACCGCTTTCC CGCGCATGGA CGTCGTCCTG AACGCGCTGA
56641 CCGGCGAGTT CATCGACGCG TCGCTCGACC TGCTGGACGC CGACGGCCGG TTCGTCGAGA
```

-continued

```
56701 TGGGCCGCAC CGAGCTGCGC GACCCGGCCG CGATCGTCCC CGCCTACCTG CCGTTCGACC
56761 TGCTGGACGC GGGCGCCGAC CGCATCGGCG AGATCCTGGG CGAACTGCTC CGGCTGTTCG
56821 ACGCGGGCGC GCTGGAGCCG CTGCCGGTCC GTGCCTGGGA CGTCCGGCAG GCACGCGACG
56881 CGCTCGGCTG GATGAGCCGC GCCCGCCACA TCGGCAAGAA CGTCCTGACG CTGCCCCGGC
56941 CGCTCGACCC GGAGGGCGCC GTCGTCCTCA CCGGCGGCTC CGGCACGCTC GCCGGCATCC
57001 TCGCCCGCCA CCTGCGCGAA CGGCATGTCT ACCTGCTGTC CCGGACGGCA CCGCCCGAGG
57061 GGACGCCCGG CGTCCACCTG CGCTGCGACG TCGGTGACCG GGACCAGCTG GCGGCGGCCC
57121 TGGAGCGGGT GGACCGGCCG ATCACCGCCG TGGTGCACCT CGCCGGTGCG CTGGACGACG
57181 GCACCGTCGC GTCGCTCACC CCCGAGCGTT TCGACACGGT GCTGCGCCCG AAGGCCGACG
57241 GCGCCTGGTA CCTGCACGAG CTGACGAAGG AGCAGGACCT CGCCGCGTTC GTGCTCTACT
57301 CGTCGGCCGC CGGCGTGCTC GGCAACGCCG GCCAGGGCAA CTACGTCGCC GCGAACGCGT
57361 TCCTCGACGC GCTCGCCGAG CTGCGCCACG GTTCCGGGCT GCCGGCCCTC TCCATCGCCT
57421 GGGGGCTCTG GGAGGACGTG AGCGGGGTCA CCGGCGGCGCT CGGCGAAGCG GACCGGGACC
57481 GGATGCGGCC CAGCGGTTTC CGGGCCATCA CCGCGCAACA GGGCATGCAC CTGTACGAGG
57541 CGGCCGGCCG CACCGGAAGT CCCGTGGTGG TCGCGGCGGC GCTCGACGAC GCGCCGGACG
57601 TGCCGCTGCT GCGCGGCCTG CGGCGGACGA CCGTCCGGCG GGCCGCCGTC CGGGAGTGTT
57661 CGTCCGCCGA CCCGCTCGCC GCGCTGACCG GCGACGAGCT CGCCGAAGCG CTGCTGACGC
57721 TCGTCCGGGA GAGCACCGCC GCCGTGCTCG GCCACGTGGG TGGCGAGGAC ATCCCCGCGA
57781 CGGCGGCGTT CAAGGACCTC GGCATCGACT CGCTCACCGC GGTCCAGCTG CGCAACGCCC
57841 TCACCGAGGC GACCGGTGTG CGGCTGAACG CCACGGCGGT CTTCGACTTC CCGACCCCGC
57901 ACGTGCTCGC CGGGAAGCTC GGCGACGAAC TGACCGGCAC CGGCGCGCCC GTCGTGCCCC
57961 GGACCGCGGC CACGGCCGGT GCGCACGACG AGCCGCTGGC GATCGTGGGA ATGGCCTGCC
58021 GGCTGCCCGG CGGGGTCGCG TCACCCGAGG AGCTGTGGCA CCTCGTGGCA TCCGGCACCG
58081 ACGCCATCAC GGAGTTCCCG ACGGACCGCG GCTGGGACGT CGACGCGATC TACGACCCGG
58141 ACCCCGACGC GATCGGCAAG ACCTTCGTCC GGCACGGTGG CTTCCTCACC GGCGCGACAG
58201 GCTTCGACGC GGCGTTCTTC GGCATCAGCC CGCGCGAGGC CCTCGCGATG GACCCGCAGC
58261 AGCGGGTGCT CCTGGAGACG TCGTGGGAGG CGTTCGAAAG CGCCGGCATC ACCCCGGACT
58321 CGACCCGCGG CCAGCGACACC GGCGTGTTCG TCGGCGCCTT CTCCTACGGT TACGGCACCG
58381 GTGCGGACAC CGACGGCTTC GGCGCGACCG GCTCGCAGAC CAGTGTGCTC TCCGGCCGGC
58441 TGTCGTACTT CTACGGTCTG GAGGGTCCGG CGGTCACGGT CGACACGGCG TGTTCGTCGT
58501 CGCTGGTGGC GCTGCACCAG GCCGGGCAGT CGCTGCGCTC CGGCGAATGC TCGCTCGCCC
58561 TGGTCGGCGG CGTCACGGTG ATGGCGTCTC CCGGCGGCTT CGTGGAGTTC TCCCGGCAGC
58621 GCGGCCTCGC GCCGGACGGC CGGGCGAAGG CGTTCGGCGC GGGTGCGGAC GGCACGAGCT
58681 TCGCCGAGGG TGCCGGTGTG CTGATCGTCG AGAGGCTCTC CGACGCCGAA CGCAACGGTC
58741 ACACCGTCCT GGCGGTCGTC CGTGGTTCGG CGGTCAACCA GGATGGTGCC TCCAACGGGC
58801 TGTCGGCGCC GAACGGGCCG TCGCAGGAGC GGGTGATCCG GCAGGCCCTG GCCAACGCCG
58861 GGCTCACCCC GGCGGACGTG GACGCCGTCG AGGCCCACGG CACCGGCACC AGGCTGGGCG
58921 ACCCCATCGA GGCACAGGCG GTACTGGCCA CCTACGGACA GGAGCGCGCC ACCCCCCTGC
58981 TGCTGGGCTC GCTGAAGTCC AACATCGGCC ACGCCCAGGC CGCGTCCGGC GTCGCCGGCA
59041 TCATCAAGAT GGTGCAGGCC CTCCGGCACG GGGAGCTGCC GCCGACGCTG CACGCCGACG
59101 AGCCGTCGCC GCACGTCGAC TGGACGGCCG GCGCCGTCGA ACTGCTGACG TCGGCCCGGC
59161 CGTGCCCCGA GACCGACCGG CCACGGCGTG CCGCCGTCTC CTCGTTCGGG GTGAGCGGCA
59221 CCAACGCCCA CGTCATCCTG GAGGCCGGAC CGGTAACGGA GACGCCCGCG GCATCGCCTT
59281 CCGGTGACCT TCCCCTGCTG GTGTCGGCAC GCTCACCGGA AGCGCTCGAC GAGCAGATCC
59341 GCCGACTGCG CGCCTACCTG GACACCACCC GGCGCGTCGA CCGGGTGGCC GTGGCACAGA
59401 CGCTGGCCCG GCGCACACAC TTCGCCCACC GCGCCGTGCT GCTCGGTGAC ACCGTCATCA
59461 CCACACCCCC CGCGGACCGG CCCGACGAAC TCGTCTTCGT CTACTCCGGC CAGGGCACCC
59521 AGCATCCCGC GATGGGCGAG CAGCTCGCCG CCGCCCATCC CGTGTTCGCC GACGCCTGGC
59581 ATGAAGCGCT CCGCCGCCTT GACAACCCCG ACCCCCACGA CCCCACGCAC AGCCAGCATG
59641 TGCTCTTCGC CCACCAGGCG GCGTTCACCG CCCTCCTGCG GTCCTGGGGC ATCACCCCGC
59701 ACGCGGTCAT CGGCCAGTCG CTGGGCGAGA TCACCGCGGC GCACGCCGCC GGCATCCTGT
59761 CGCTGGACGA CGCGTGCACC CTGATCACCA CGCGCGCCCG CCTCATGCAC ACGCTCCCGC
59821 GACCCGGTGC CATGGTCACC GTACTGACCA GCGAAGAGAA GGCACGCCAG GCGTTGCGGC
59881 CGGGCGTGGA GATCGCCGCC GTCAACGGGC CCCACTCCAT CGTGCTGTCC GGGGACGAGG
59941 ACGCCGTGCT CACCGTCGCC GGGCAGCTCG GCATCCACCA CCGCCTGCCC GCCCCGCACG
60001 CCGGGCACTC CGCGCACATG GAGCCCGTGG CCGCCGAGCT GCTCGCCACC ACCCGCGGGC
60061 TCCGCTACCA CCCTCCCCAC ACCTCCATTC CGAACGACCC CACCACCGCT GAGTACTGGG
60121 CCGAGCAGGT CCGCAAGCCG GTGCTGTTCC ACGCCCACGC GCAGCAGTAC CCGGACGCCG
60181 TGTTCGTGGA GATCGGCCCC GGCCAGGACC TCTCCCCGCT CGTCGACGGG ATCCCGCTGC
60241 AGAACGGCAC CGCGGACGAG GTGCACGCGC TGCACACCGC GCTCGCGCAC CTCTACGCGC
60301 GCGGTGCCAC GCTCGACTGG CCCCGCATCC TCGGGGCTGG GTCACGGCAC GACGCGGATG
60361 TGCCCGCGTA CGCGTTCCAA CGGCGGCACT ACTGGATCGA GTCGGCACGC CCGGCCGCAT
60421 CCGACGCGGG CCACCCCGTG CTGGGCTCCG GTATCGCCCT CGCCGGGTCG CCGGGCCGGG
60481 TGTTCACGGG TTCCGTGCCG ACCGGTGCGG ACCGCGCGGT GTTCGTCGCC GAGCTGGCGC
60541 TGGCCGCCGC GGACGCGGTC GACTGCGCCA CGGTCGAGCG GCTCGACATC GCCTCCGTGC
60601 CCGGCCGCCC GGGCCATGGC CGGACGACCG TACAGACCTG GGTCGACGAG CCGGCGGAGG
60661 ACGGCCGGCG CCGGTTCACC GTGCACACCC GCACCGGCGA CGCCCCGTGG ACGCTGCACG
60721 CCGAGGGGGT GCTGCGCCCC CATGGCACGG CCCTGCCCGA TGCGGCCGAC GCCGAGTGGC
60781 CCCCACCGGG CGCGGTGCCC GCGGACGGGC TGCCGGGTGT GTGGCGCCGG GGGGACCAGG
60841 TCTTCGCCGA GGCCGAGGTG GACGGACCGG ACGGTTTCGT GGTGCACCCC GACCTGCTCG
60901 ACGCGGTCTT CTCCGCGGTC GGCGACGGAA GCCGCCAGCC GGCCGGATGG CGCGACCTGA
60961 CGGTGCACGG GTCGGACGCC ACCGTACTGC GCGCCTGCCT CACCCGGCGC ACCGACGGAG
61021 CCATGGGATT CGCCGCCTTC GACGGCGCCG GCCTGCCGGT ACTCACCGCG GAGGCGGTGA
61081 CGCTGCGGGA GGTGGCGTCA CCGTCCGGCT CCGAGGAGTG GGACGGCTG CACCGGTTGG
61141 AGTGGCTCGC GGTCGCCGAG GCGGTCTACG ACGGTGACCT GCCGAGGGA CATGTCCTGA
61201 TCACCGCCGC CCACCCCGAC GACCCCGAGG ACATACCCAC CCGCGCCCAC ACCCGCGCCA
61261 CCGGCGTCCT GACCGCCCTG CAACACCACC TCACCACCAC CGACCACACC CTCATCGTCC
61321 ACACCACCAC CGACCCCGCC GGCGCCACCG TCACCGGCCT CACCCGCACC GCCCAGAACG
61381 AACACCCCCA CCGCATCCGC CTCATCGAAA CCGACCACCC CCACACCCCC CTCCCCCTGG
```

-continued

```
61441 CCCAACTCGC CACCCTCGAC CACCCCCACC TCCGCCTCAC CCACCACACC CTCCACCACC
61501 CCCACCTCAC CCCCCTCCAC ACCACCACCC CACCCACCAC CACCCCCCTC AACCCCGAAC
61561 ACGCCATCAT CATCACCGGC GGCTCCGGCA CCCTCGCCGG CATCCTCGCC CGCCACCTGA
61621 ACCACCCCCA CACCTACCTC CTCTCCCGCA CCCCACCCCC CGACGCCACC CCCGGCACCC
61681 ACCTCCCCTG CGACGTCGGC GACCCCCACC AACTCCGCAC CACCCTCACC CACATCCCCC
61741 AACCCCTCAC CGCCATCTTC CACACCGCCG CCACCCTCGA CGACGGCATC CTCCACGCCC
61801 TCACCCCCGA CCGCCTCACC ACCGTCCTCC ACCCCAAAGC CAACGCCGCC TGGCACCTGC
61861 ACCACCTCAC CCAAAACCAA CCCCTCACCC ACTTCGTCCT CTACTCCAGC GCCGCCGCCG
61921 TCCTCGGCAG CCCCGGACAA GGAAACTACG CCGCCGCCAA CGCCTTCCTC GACGCCCTCG
61981 CCACGCACCG CCACACCCTC GGCCAACCCG CCACCTCCAT CGCCTGGGGC ATGTGGCACA
62041 OCACCAGGAC CCTCACCGGA CAACTCGACG ACGCCGACCG GGACCGCATC CGCCGCGGCG
62101 GTTTCCTCCC GATCACGGAC GACGAGGGCA TGCGCCTCTA CGAGGCGGCC GTCGGCTCCG
62161 GCGAGGACTT CGTCATGGCC GCCGCGATGG ACCCGGCACA GCCGATGACC GGCTCCGTAC
62221 CGCCCATCCT GAGCGGCCTG CGCAGGAGCG CGCGGCGCGT CGCCCGTGCC GGGCAGACGT
62281 TCGCCCAGCG GCTCGCCGAG CTGCCCGACG CCGACCGCGG CGCGGCGCTG ACCACCCTCG
62341 TCTCGGACGC CACGGCCGCC GTGCTCGGCC ACGCCGACGC CTCCGAGATC GCGCCGACCA
62401 CGACGTTCAA GGACCTCGGC ATCGACTCGC TCACCGCGAT CGAGCTGCGC AACCGGCTCG
62461 CGGAGGCGAC CGGGCTGCGG CTGAGTGCCA CGCTGGTGTT CGACCACCCG ACACCTCGGG
62521 TCCTCGCCGC CAAGCTCCGC ACCGATCTGT TCGGCACGGC CGTGCCCACG CCCGCGCGGA
62581 CGGCACGGAC CCACCACGAC GAGCCACTCG CGATCGTCGG CATGGCGTGC CGACTGCCCG
62641 GCGGGGTCGC CTCGCCGGAG GACCTGTGGC AGCTCGTGGC GTCCGGCACC GACGCGATCA
62701 CCGAGTTCCC CACCGACCGC GGCTGGGACA TCGACCGGCT GTTCGACCCG GACCCGGACG
62761 CCCCCGGCAA GACCTACGTC CGGCACGGCG GCTTCCTCGC CGAGGCCGCC GGCTTCGATG
62821 CCGCGTTCTT CGGCATCAGC CCGCGCGAGG CACGGCCACT GGACCCGGCAC AGCGCGTCA
62881 TCCTCGAAAC CTCCTGGGAG GCGTTCGAGA ACGCGGGCAT CGTGCCGGAC ACGCTGCGCG
62941 GCAGCGACAC CGGCGTGTTC ATGGGCGCGT TCTCCCATGG GTACGGCGCC GGCGTCGACC
63001 TGGGCGGGTT CGGCGCCACC GCCACGCAGA ACAGCGTGCT CTCCGGCCGG TTGTCGTACT
63061 TCTTCGGCAT GGAGGGCCCG GCCGTCACCG TCGACACCGC CTGCTCGTCG TCGCTGGTCG
63121 CCCTGCACCA CGGGCACGAG CGCGCTGCGGA CTGGAGAATG CTCGCTGGCC CTCGCCGGCG
63181 GTGTCACGGT GATGCCCACC CCGCTGGGCT ACGTCGAGTT CTGCCGCCAG CGGGGACTCG
63241 CCCCCGACGG CCGTTGCCAG GCCTTCGCGG AAGGCGCCGA CGGCACGAGC TTCTCGGAGG
63301 GCGCCGGCGT TCTTGTGCTG GAGCGGCTCT CCGACGCCGA GCGCAACGGA CACACCGTCC
63361 TCGCGGTCGT CCGCTCCTCG GCCGTCAACC AGGACGGCGC CTCCAACGGC ATCTCCGCAC
63421 CCAACGGCCC CTCCCAGCAG CGCGTCATCC GCCAGGCCCT CGACAAGGCC GGGCTCGCCC
63481 CCGCCGACGT GGACGTGGTG GAGGCCCACG GCACCGGAAC CCCGCTGGGC GACCCGATCG
63541 AGGCACAGGC CATCATCGCG ACCTACGGCC AGGACCGCGA CACACCGCTC TACCTCGGTT
63601 CGGTCAAGTC GAACATCGGA CACCCAGA CCACCGCCGG TGTCGCCGGC GTCATCAAGA
63661 TGGTCATGGC GATGCGCCAC GGCATCGCGC CGAAGCACT GCACGTGGAC GAGCCGTCGT
63721 CGCATGTGGA CTGGACCGAG GGTGCGGTGG AACTGCTCAC CGAGGCGAGG CCGTGGCCCG
63781 ACGCGGGACG CCCGCGCCGC GCGGGCGTGT CGTCGCTCGG TATCAGCGGT ACGAACGCCC
63841 ACGTGATCCT TGAGGGTGTT CCCGGGCCGT CGCGTGTGGA GCCGTCTGTT GACGGGTTGG
63901 TGCCGTTGCC GGTGTCGGCT CGGAGTGAGG CGAGTCTGCG GGGGCAGGTG GAGCGGCTGG
63961 AGGGGTATCT GCGCGGGAGT GTGGATGTGG CCGCGGTCGC GCAGGGGTTG GTGCGTGAGC
64021 GTGCTGTCTT CGGTCACCGT GCGGTACTGC TGGGTGATGC CCGGGTGATG GGTGTGGCGG
64081 TGGATCAGCC GCGTACGGTG TTCGTCTTTC CCGGGCAGGG TGCTCAGTGG GTGCATCATGG
64141 GTGTGGAGTT GATGGACCGT TCTGCGGTGT TCGCGGCTCG TATGGAGGAG TGTGCGCGGG
64201 CGTTGTTGCC GCACACGGGC TGGGATGTGC GGGAGATGTT GGCGCGGCCG GATGTGGCGG
64261 AGCGGGTGGA GGTGGTCCAG CCGGCCAGCT GGGCGGTCGC GGTCAGCCTG GCCGCACTGT
64321 GGCAGGCCCA CGGGGTCGTA CCCGACGCGG TGATCGGACA CTCCCAGGGC GAGATCGCGG
64381 CGGCGTGCGT GGCCGGGGCC CTCAGCCTTG AGGACGCCGC CCGCGTGGTG GCCTTGCGCA
64441 GCCAGGTCAT CGCGGCGCGA CTGGCCGGGC GGGGAGCGAT GGCTTCGGTG GCATTGCCGG
64501 CCGGTGAGGT CGGTCTGGTC GAGGGCGTGT GGATCGCGGC GCGTAACGGC CCCGCCTCGA
64561 CAGTCGTGGC CGGCGAGCCG TCGGCGGTGG AGGACGTGGT GACGCGGTAT GAGACCGAAG
64621 GCGTGCGAGT GCGTCGTATC GCCGTCGACT ACGCCTCCCA CACGCCCCAC GTGGAAGCCA
64681 TCGAGGACGA ACTGCTGAGG GTACTGAAGG GAGTTGCAGG GAAGGCCGCG TCGGTGGCGT
64741 GGTGGTCGAC CGTGGACAGC GCCTGGGTGA CCGAGCCGGT GGATGAGAGT TACTGGTACC
64801 GGAACCTGCG TCGCCCCGTC GCGCTGGACG CGGCGGTGGC GGAGCTGGAC GGGTCCGTGT
64861 TCGTGGAGTG CAGCGCCCAT CCGGTGCTGC TGCCGGTGAT GGAACAGGCC CACACGGTGG
64921 CGTCGTTGCG CACCGGTGAC GGCGGCTGGG AGCGATGGCT GACGGCGTTG GCGCAGGCGT
64981 GGACCCTGGG CGCGGCAGTG GACTGGGACA CGGTGGTCGA ACCGGTGCCA GGGCGGCTGC
65041 TCGATCTGCC CACCTACGCG TTCGAGCGCC GGCGCTACTG GCTGGAAGCG GCCGGTGCCA
65101 CCGACCTGTC CGCGGCCGGG CTGACAGGGG CAGCACATCC CATGCTGGCC GCCATCACGG
65161 CACTACCCGC CGACGACGGT GGTGTTGTTC TCACCGGCCG GATCTCGTTG CGCACGCATC
65221 CCTGGCTGGC TGATCACGCG GTGCGGGGCA CGGTCCTGCT GCCGGGCACG GCCTTTGTGG
65281 AGCTGGTCAT CCGGGCCGGT GACGAGACCG GTTGCGGGAT AGTGGATGAA CTGGTCATCG
65341 AATCCCCCCT CGTGGTGCCG GCGACCGCAG CCGTGGATCT GTCGGTGACC GTGGAAGGAG
65401 CTGACGAGGC CGGACGGCGG CGAGTGACCG TCCACGCCCG CACCGAAGGC ACCGGCAGCT
65461 GGACCCGGCA CGCCAGCGGC ACCCTGACCC CCGACACCCC CGACACCCCC AACGCTTCCG
65521 GTGTTGTCGG TGCGGAGCCG TTCTCGCAGT GGCCACCTGC CACTGCCGCG GCCGTCGACA
65581 CCTCGGAGTT CTACTTGCGC CTGGACGCGC TGGGCTACCG GTTCGGACCC ATGTTCCGCG
65641 GAATGCGGGC TGCCTGGCGT GATGGTGACA CCGTGTACGC CGAGGTCGCG CTCCCCGAGG
65701 ACCGTGCCGC CGACGCGGAC GGTTTCGGCA TGCACCCGGC GCTGCTCGAC GCGGCCTTGC
65761 AGAGCGGCAG CCTGCTCATG CTGGAATCGG ACGGCAGCA GAGCGTGCAA CTGCCGTTCT
65821 CCTGGACACG CGTCCGGTTC CACGCGACGG GCGCGACCAT GCTGGGGTG CCGGTCGTAC
65881 CGGGCCCGGA CGGCCTCCGG CTGCATGCCG CGGACAGCGG GAACCGTCCC GTCGCGACGA
65941 TCGACGCGCT CGTGACCCGG TCCCCGGAAG CGGACCTCGC GCCCGCCGAT CCGATGCTGC
66001 GGGTCGGGTG GCCCCGGTG CCCGTACCTG CCGGGGCCGG TCCGTCCGAC GCGGACGTGC
66061 TGACGCTGCG CGGCGACGAC GCCGACCCGC TCGGGGAGAC CCGGGACCTG ACCACCCGTG
66121 TTCTCGACGC GCTGCTCCGG GCCGACCGGC CGGTGATCTT CCAGGTGACC GGTGGCCTCG
```

```
66181 CCGCCAAGGC GGCCGCAGGC CTGGTCCGCA CCGCTCAGAA CGAGCAGCCC GGCCGCTTCT
66241 TCCTCGTCGA AACGGACCCG GGAGAGGTCC TGGACGGCGC GAAGCGCGAC GCGATCGCGG
66301 CACTCGGCGA GCCCCATGTG CGGCTGCGCG ACGGCCTCTT CGAGGCAGCC CGGCTGATGC
66361 GGGCCACGCC GTCCCTGACG CTCCCGGACA CCGGGTGTCG GCAGCTGCGG CCGTCCGCCA
66421 CCGGTTCCCT CGACGACCTT GCCGTCGTCC CCACCGACGC CCCGGACCGG CCGCTCGCGG
66481 CCGGCGAGGT GCGGATCGCG GTACGCGCGG CGGGCCTGAA CTTCCGGGAT GTCACGGTCG
66541 CGCTCGGTGT GGTCGCCGAT GCGCGTCCGC TCGGCAGCGA GGCCGCGGGT GTCGTCCTGG
66601 AGACCGGCCC CGGTGTGCAC GACCTGGCGC CCGGCGACCG GGTCCTGGGG ATGCTCGCGG
66661 GCGCCTTCGG ACCGGTCGCG ATCACCGACC GGCGGCTGCT CGGCCGGATG CCGGACGGCT
66721 GGACGTTCCC GCAGGCGGCG TCCGTGATGA CCGCGTTCGC GACCGCGTGG TACGGCCTGG
66781 TCGACCTGGC CGGGCTGCGC CCCGGCGAGA AGGTCCTGAT CCACGCGGCG GCGACCGGTG
66841 TCGGCGCGGC GGCCGTCCAG ATCGCGCGGC ATCTGGGCGC GGAGGTGTAC GCGACCACCA
66901 GCGCCGCGAA GCGCCATCTG GTGGACCTGG ACGGAGCGCA TCTGGCCGAT TCCCGCAGCA
66961 CCGCGTTCGC CGACGCGTTC CCGCCGGTCG ATGTCGTGCT CAACTCGCTC ACCGGTGAAT
67021 TCCTCGACGC GTCCGTCGGC CTGCTCGCGG CGGGTGGCCG GTTCATCGAG ATGGGGAAGA
67081 CGGACATCCG GCACGCCGTC CAGCAGCCGT TCGACCTGAT GGACGCCGGC CCCGACCGGA
67141 TGCAGCGGAT CATCGTCGAG CTGCTCGGCC TGTTCGCGCG CGACGTGCTG CACCCGCTGC
67201 CGGTCCACGC CTGGGACGTG CGGCAGGCGC GGGAGGCGTT CGGCTGGATG AGCAGCGGGC
67261 GTCACACCGG CAAGCTGGTG CTGACGGTCC CGCGGCCGCT GGATCCCGAG GGGGCCGTCG
67321 TCATCACCGG CGGCTCCGGC ACCCTCGCCG GCATCCTCGC CCGCCACCTG GGCCACCCCC
67381 ACACCTACCT GCTCTCCCGC ACCCCACCCC CCGACACCAC CCCCGGCACC CACCTCCCCT
67441 GCGACGTCGG CGACCCCCAC CAACTCGCCA CCACCCTCGC CCGCATCCCC CAACCCCTCA
67501 CCGCCGTCTT CCACACCGCC GGAACCCTCG ACGACGCCCT GCTCGACAAC CTCACCCCCG
67561 ACCGCGTCGA CACCGTCCTC AAACCCAAGG CCGACCCCGC CTGGCACCTG CACCGGCTCA
67621 CCCGCGACAC CGACCTCGCC GCGTTCGTCG TCTACTCCGC GGTCGCCGGC CTCATGGGCA
67681 GCCCGGGGCA GGGCAACTAC GTCGCGGCGA ACGCGTTCCT CGACGCGCTC GCCGAACACC
67741 GCCGTGCGCA AGGGCTGCCC GCGCAGTCCC TCGCATGGGG CATGTGGGCG GACGTCAGCG
67801 CGCTCACCGC GAAACTCACC GACGCGGACC GCCAGCGCAT CCGGCGCAGC GGATTCCCGC
67861 CGTTGAGCGC CGCGGACGGC ATGCGGCTGT TCGACGCGGC GACGCGTACC CCGGAACCGG
67921 TCGTCGTCGC GACGACCGTC GACCTCACCC AGCTCGACGG CGCCGTCGCG CCGTTGCTCC
67981 GCGGTCTGGC CGCGCACCGG GCCGGGCCGG CGCGCACGGT CGCCCGCAAC GCCGGCGAAG
68041 AGCCCCTGGC CGTGCGTCTT GCCGGGCGTA CCGCCGCCGA GCAGCGGCGC ATCATGCAGG
68101 AGGTCGTGCT CCGCCACGCG GCCGCGGTCC TCGCGTACGG GCTGGGCGAC CGCGTGGCGG
68161 CGGACCGTCC GTTCCGCGAG CTCGGTTTCG ATTCGCTGAC CGCGGTCGAC CTGCGCAATC
68221 GGCTCGCGGC CGAGACGGGG CTGCGGCTGC CGACGACGCT GGTGTTCAGC CACCCGACGG
68281 CGGAGGCGCT CACCGCCCAC CTGCTCGACC TGATCGACGC TCCCACCGCC CGGATCGCCG
68341 GGGAGTCCT GCCCGCGGTG ACGGCCGCTC CCGTGGCGGC CGCGCGGGAC CAGGACGAGC
68401 CGATCGCCAT CGTGGCGATG GCGTGCCGGC TGCCCGGTGG TGTGACGTCG CCCGAGGACC
68461 TGTGGCGGCT CGTCGAGTCC GGCACCGACG CGATCACCAC GCCTCCTGAC GACCGCGGCT
68521 GGGACGTCGA CGCGCTGTAC GACGCGGACC CGGACGCGGC CGGCAAGGCG TACAACCTGC
68581 GGGGCGGTTA CCTGGCCGGG GCGGCGGAGT TCGACGCGGC GTTCTTCGAC ATCAGTCCGC
68641 GCGAAGCGCT CGGCATGGAC CCGCAGCAAC GCCTGCTGCT CGAAACGGCG TGGGAGGCGA
68701 TCGAGCGCGG CCCGGATCAGT CCGGCGTCGC TCCGCGGCCG GGAGGTCGGC GTCTATGTCG
68761 GTGCGGCCGC GCAGGGCTAC GGGCTGGGCG CCGAGGACAC CGAGGGCCAC GCGATCACCG
68821 GTGGTTCCAC GAGCCTGCTG TCCGGACGGC TGGCGTACGT GCTCGGGCTG GAGGGCCCGG
68881 CGGTCACCGT GGACACGGCG TGCTCGTCGT CTCTGGTCGC GCTGCATCTG GCGTGCCAGG
68941 GGCTGCGCCT GGGCGAGTGC GAACTCGCTC TGGCCGGAGG GGTCTCCGTA CTGAGTTCGC
69001 CGGCCGCGTT CGTGGAGTTC TCCCGCCAGC GCGGGCTCGC GGCCGACGGG CGCTGCAAGT
69061 CGTTCGGCGC GGGCGCGGAC GGCACGACGT GGTCCGAGGG CGTGGGCGTG CTCGTACTGG
69121 AACGGCTCTC CGACGCCGAG CGGCTCGGGC ACACCGTGCT CGCCGTCGTC CGCGGCAGCG
69181 CCGTCACGTC CGACGGCGCC TCCAACGGCC TCACCGCGCC GAACGGGCTC TCGCAGCAGC
69241 GGGTCATCCG GAAGGCGCTC GCCGCGGCCG GGCTGACCGG CGCCGACGTG GACGTCGTCG
69301 AGGGGCACGG CACCGGCACC CGGCTCGGCG ACCCGGTCGA GGCGGACGCG CTGCTCGCGA
69361 CGTACGGGCA GGACCGTCCG GCACCGGTCT GGCTGGGCTC GCTGAAGTCG AACATCGGAC
69421 ATGCCACGGC CGCGGCCGGT GTCGCGGGCG TCATCAAGAT GGTGCAGGCG ATCGGCGCGG
69481 GCACGATGCC GCGGACGCTG CATGTGGAGG AGCCCTCGCC CGCCGTCGAC TGGAGCACCG
69541 GACAGGTGTC CCTGCTCGGC TCCAACCGGC CCTGGCCGGA CGACGAGCGT CCGCGCCGGG
69601 CGGCCGTCTC CGCGTTCGGG CTCAGCGGGA CGAACGCGCA CGTCATCCTG GAACAGCACC
69661 GTCCGGCGCC CGTGGCGTCC CAGCCGCCCC GGCCGCCCCG TGAGGAGTCC CAGCCGCTGC
69721 CGTGGGTGCT CTCCGCGCGG ACTCCGGCCG CGCTGCGGGC CAGGCGGCC CGGCTGCGCG
69781 ACCACCTCGC GGCGGCACCG GACGCGGATC CGTTGGACAT CGGGTACGCG CTGGCCACCA
69841 GCCGCGCCCA GTTCGCCGAC CGTGCCGCGG TCGTCGCCAC CACCCCGGAC GGATTCCGTG
69901 CCGCGCTCGA CGGCCTCGCG GACGGCGCGG AGGCGCCCGG AGTCGTCACC GGGACCGCTC
69961 AGGAGCGGCG CGTCGCCTTC CTCTTCGACG GCCAGGGCGC CCAGCGCGCC GGAATGGGGC
70021 GCGAGCTCCA CCGCCGGTTC CCCGTCTTCG CCGCCGCGTG GACGAGGTC TCCGACGCGT
70081 TCGGCAAGCA CCTCAAGCAC TCCCCCACGG ACGTCTACCA CGGCGAACAC GCGCTCTCG
70141 CCCATGACAC CCTGTACGCC CAGGCCGGCC TGTTCACGCT CGAAGTGGCG CTGCTGCGGC
70201 TGCTGGAGCA CTGGGGGGTG CGGCCGGACG TGCTCGTCGG CACTCCGTC GGCGAGGTGA
70261 CCGCGGCGTA CGCGGCGGGG GTGCTCACCC TGGCGGACGC GACGGAGTTG ATCGTGGCCC
70321 GGGGGCGGGC GCTGCGGGCG CTGCCGCCCG GGGCGATGCT CGCCGTCGAC GGAAGCCGG
70381 CGGAGGTCGG CGCCCGCACG GATCTGGACA TCGCGCGGT CAACGCCCG TCCGCCGTGG
70441 TGCTCGGCGG TTCGCCGGAC GATGTGGCGG CGTTCGAACG GGAGTGGTCG GCGGCCGGGC
70501 GGCGCACGAA ACGGCTCGAC GTCGGGCACG CGTTCCACTC CCGGCACGTC GACGGTGCGC
70561 TCGACGGCTT CCGTACGGTG CTGGAGTCGC TCGCGTTCGG CGCGGCGGG CTGCCGGTGA
70621 TGTCCACGAC GACGGGCCGG GACGCCGCGG ACGACCTCAT AACGCGCGCG CACTGGCTGC
70681 GCCATGCGCG TCGGCCGGTG CTGTTCTCGG ATGCCGTCCG GGAGCTGGCC GACCGCGGCG
70741 TCACCACGTT CGTGGCCGTC GGCCCCTCCG GCTCCCTGGC GTCGGCCGCG GCGGAGAGCG
70801 CCGGGGAGGA CGCCGGGACC TACCACGCGG TGCTGCGCGC CCGGACCGGT GAGGAGACCG
70861 CGGCGCTGAC CGCCCTCGCC GAGCTGCACG CCCACGGCGT CCCGGTCGAC CTGGCCGCGG
```

-continued

```
70921 TACTGGCCGG TGGCCGGCCA GTGGACCTTC CCGTGTACGC GTTCCAGCAC CGTTCCTACT
70981 GGCTGGCCCC GGCCGTGGCG GGGGCGCCGG CCACCGTGGC GGACACCGGG GGTCCGGCGG
71041 AGTCCGAGCC GGAGGACCTC ACCGTCGCCG AGATCGTCCG TCGGCGCACC GCGGCGCTGC
71101 TCGGCGTCAC GGACCCCGCC GACGTCGATG CGGAAGCGAC GTTCTTCGCG CTCGGTTTCG
71161 ACTCACTGGC GGTGCAGCGG CTGCGCAACC AGCTCGCCTC GGCAACCGGG CTGGACCTGC
71221 CGGCGGCCGT CCTGTTCGAC CACGACACCC CGGCCGCGCT CACCGCGTTC CTCCAGGACC
71281 GGATCGAGGC CGGCCAGGAC CGGATCGAGG CCGGCGAGGA CGACGACGCG CCCACCGTGC
71341 TCTCGCTCCT GGAGGAGATG GAGTCGCTCG ACGCCGCGGA CATCGCGGCG ACGCCGGCCC
71401 CGGAGCGTGC GGCCATCGCC GATCTGCTCG ACAAGCTCGC CCATACCTGG AAGGACTACC
71461 GATGAGCACC GATACGCACG AGGGAACGCC GCCCGCCGGC CGCTGCCCAT TCGCGATCCA
71521 GGACGGTCAC CGCGCCATCC TGGAGAGCGG CACGGTGGGT TCGTTCGACC TGTTCGGCGT
71581 CAAGCACTGG CTGGTCGCCG CCGCCGAGGA CGTCAAGCTG GTCACCAACG ATCCGCGGTT
71641 CAGCTCGGCC GCGCCGTCCG AGATGCTGCC CGACCGGCGG CCCGGCTGGT TCTCCGGGAT
71701 GGACTCACCG GAGCACAACC GCTACCGGCA GAAGATCGCG GGGGACTTCA CACTGCGCGC
71761 GGCGCGCAAG CGGGAGGACT TCGTCGCCGA GGCCGCCGAC GCCTGCCTGG ACGACATCGA
71821 GGCCGCGGGA CCCGGCACCG ACCTCATCCC CGGGTACGCC AAGCGGCTGC CCTCCCTCGT
71881 CATCAACGCG CTGTACGGGC TCACCCCTGA GGAGGGGGCC GTGCTGGAGG CACGGATGCG
71941 CGACATCACC GGCTCGGCCG ATCTGGACAG CGTCAAGACG CTGACCGACG ACTTCTTCGG
72001 GCACGCGCTG CGGCTGGTCC GCGCGAAGCG TGACGAGCGG GGCGAGGACC TGCTGCACCG
72061 GCTGGCCTCG GCCGACGACG GCGAGATCTC GCTCAGCGAC GACGAGGCGA CGGGCGTGTT
72121 CGCGACGCTG CTGTTCGCCG GCCACGACTC GGTGCAGCAG ATGGTCGGCT ACTGCCTCTA
72181 CGCACTGCTC AGCCACCCCG AGCAGCAGGC GGCGCTGCGC GCGCGCCCGG AGCTGGTCGA
72241 CAACGCGGTC GAGGAGATGC TCCGTTTCCT GCCCGTCAAC CAGATGGGCG TACCGCGCGT
72301 CTGTGTCGAG GACGTCGATG TGCGGGGCGT GCGCATCCGT GCGGGCGAA ACGTGATCCC
72361 GCTCTACTCG ACGGCCAACC GCGACCCCGA GGTGTTCCCG CAGCCCGACA CCTTCGATGT
72421 GACGCGCCCG CTGGAGGGCA ACTTCGCGTT CGGCCACGGC ATTCACAAGT GTCCCGGCCA
72481 GCACATCGCC CGGGTGCTCA TCAAGGTCGC CTGCCTGCGG TTGTTCGAGC GTTTCCCGGA
72541 CGTCCGGCTG GCGGGCGACG TGCCGATGAA CGAGGGGCTC GGGCTGTTCA GCCCGGCCGA
72601 GCTGCGGGTC ACCTGGGGGG CGGCATGAGT CACCCGGTGG AGAGTTGCG GTTGCCGAAC
72661 GGGACGACGG TCGCGCACAT CAACGCGGGC GAGGCGCAGT TCCTCTACCG GGAGATCTTC
72721 ACCCAGCGCT GCTACCTGCG CCACGGTGTC GACCTGCGCC CGGGGGACGT GGTGTTCGAC
72781 GTCGGCGCGA ACATCGGCAT GTTCACGCTT TTCGCGCATC TGGAGTGTCC TGGTGTGACC
72841 GTGCACGCCT TCGAGCCCGC GCCCGTGCCG TTCGCGGCGC TGCGGGCGAA CGTGACGCGG
72901 CACGGCATCC CGGGCCAGGC GGACCAGTGC GCGGTCTCCG ACAGCTCCGG CAGCCGGAAG
72961 ATGACCTTCT ATCCCGACGC CACGCTGATG TCCGGTTTCC ACGCGGATGC CGCGGCCCGG
73021 ACGGAGCTGT TGCGCACGCT CGGCCTCAAC GGCGGCTACA CCGCCGAGGA CGTCGACACC
73081 ATGCTCGCGC AACTGCCCGA CGTCAGCGAG GAGATCGACA CCCCTGTGGT CGACGCTCC
73141 GACGTCATCG CGGAGCGCGG TATCGAGGCC ATCGGCCTGC TGAAGGTCGA CGTGGAGAAG
73201 AGCGAACGGC AGGTCTTCGC CGGCCTCGAG GACACCGACT GGCCCCGTAT CCGCCAGGTC
73261 GTCGCGGAGG TCCACGACAT CGACGCGCG CTCGAGGAGG TCGTCACGCT GCTCCGCGGC
73321 CATGGCTTCA CCGTGGTCGC CGAGCAGGAA CCGCTGTTCG CCGGCACGGG CATCCACCAG
73381 GTCGCCGCGC GGCGGGTGGC CGGCTGAGCG CCGTCGGGGC CGCGGCCGTC CGCACCGGCG
73441 GCCGCGGTGC GGACGGCGGC TCAGCCGGCG TCGGACAGTT CCTTGGGCAG TTGCTGACGG
73501 CCCTTCACCC CCAGCTTGCG GAACACGTTG GTGAGGTGCT GTTCCACCGT GCTGGAGGTG
73561 ACGAACAGCT GGCTGGCGAT CTCCTTGTTG GTGCGCCCGA CCGCGGCGTG CGACGCCACC
73621 GGCCGCTCCG CCTCGGTCAG CGATGTGATC CGCTGCGCCG GCGTCACGTG CTGGGTGCCG
73681 TCCGCGTCCG AGGACTCCCC ACCGAGCCGC CGGAGGAGCG CACGGCTCC GCACTGGGTC
73741 GCGAGGTGCC GTGCGCGGCG GAACAGTCCC CGCGCACGGC TGTGCCGCCG GAGCATGCCG
73801 CACGCTTCGC CCATGTCGGC GAGGACGCGG GCCAGCTGCT ACTGGTCGCG GCACATGATG
73861 AGCAGATCGG CGGCCTCGTC GAGCAGTTCG ATCCGCTTGG CCGGCGGACT GTAGGCCGCC
73921 TGCACCCGCA GCGTCATCAC CCGCGCCCGG GACCCCATCG GCCGGGACAG CTGCTCGGAG
73981 ATGAGCCTCA GCCCCTCGTC ACGGCCGCGG CCGAGCAGCA GAAGCGCTTC GGCGGCGTCG
74041 ACCCGCCACA GGGCCAGGCC CGGCACGTCG ACGGACCAGC GTCGATCCG CTCCCCGCAG
74101 TCCCGGAACG CGTTGTACGC CGCCCGGTAC CGCCCGGCG CGAGATGGTG TTGCCCACGG
74161 GCCCAGACCA TGTGCAGTCC GAAGAGGCTG TCGGAGGTCT CCTCCGGCAA CGGCTCGGCG
74221 AGCCACCGCT CCGCCCGGTC CAGGTCGCCC AGTCGGATCG CGGCGGCCAC GGTGCTGCTC
74281 AGCGGCAATG CGGCGGCCAT CCCCCAGGAG GGCACGACCC GGGGGGCGAG CGCGGCCTCG
74341 CCGCATTCGA CGGCGGCGGT CAGGTCGCCG CGGCCTCGGC CGGCCTTCGG GCGGAACCCC
74401 GCGTGGACCG CCTCGTCGGC CGGGGTCCGC ATGTTGTCGT CACCGGCCAG CTTGTCGACC
74461 CAGGACTGGA CGGCATCGGT GTCCTCGGCG TAGAGCAGGG CCAGCAACGC CATCATGGTC
74521 GTGGTCCGGT CCGTCGTGAC CCGGGAGTGC TGGAGCACGT ACTCGGCTTT GGCCTCGGCC
74581 TGTTCGGACC AGCCGCGCAG CGCGTTGCTC AGGGCCTTGT CGGCGACGGC GCGGTGCCGG
74641 ACGGCTCCGG AAAACGAGGC GACCTCGTCC TCGGCCGGCG GATCGGCCGG ACGGGCGGA
74701 TCGGCCGCGC CGGGATAGAT CAGCGCGAGG GACAGGTCCG CGACGCGCAG GTGCGCCCGG
74761 CCCTGCTCGC TCGGGCGCGG GGAGCGCTGG GCCGCCAGGA CCTCGGCGGC CTCGCCCGGC
74821 CGCCCGTCCA TCGCCAGCCA GCAGGCGAGC GACACGGCGT GCTCGCTGGA GAGGAGCCGT
74881 TCCCGCGACG CGGTGAGCAG CTCGGGCACA TGCCGGCCGG ATCTGGCGGG ATCGCAGAGC
74941 CGCTCGATGG CGGCGGTGTC GACGCGCAGT GCGGCGTGGA CGGCGGGGTC GTCGGAGGCC
75001 CGGTAGGCGA ACTCCAGGTA GGTGACGGCC TCGTCGAGCT CGCCGCGCAG GTGGTGCTCG
75061 CGCGCGGCGT CGGTGAACAG CCCGGCGACC TCGGCGCCGT GCACCCGGCG GGTACCCATC
75121 TGGTGGCGGG CGAGCACCTT GCTGGCCACG CCGCGGTCCC GCAGCAGTTC CAGCGCCAGC
75181 TCGTGCAGGC CACGCCGCTC GGCGGCGGAG AGGTCGTCGA GTACGACGGA GCGGGCCGCG
75241 GGGTGCGGGA ACCGCCCTTC CCGCAGCAGC CGCCCCTCGA CCAGCTGTTC GTGGGCCTGC
75301 TCGACCGCCT CCGTGTCGAG CGGCGGTCATC CGCTGGACGA GGGTGAGTTC GACACTCTCG
75361 CCGAGCACGG CGGAAGCTCG GGCGACGCTC AGCGCGGCCG GGCGCAACG ATAGAGCGAC
75421 CCGAGGTAGG CGAGCCGGTA CGCCCGCCCC GCGACCACTT CCAGGCACCC TGAGGTCCGT
75481 GTCCGTGCCT CCCGGATGTC GTCGATCAGG CCGTGGCCGA GGAGCAGGTT GCCGCCGGTC
75541 GCCCGGAACG CCTGGGCCAC CACGTCGTCG TGCGCGTCCT GGCCGAGGTG CCGGCGCACG
75601 AGTTCGGTGG TCTGCGCCTC GGTGAGCGGG CGCAGCGCGA TCTCCTGGTA GTGGCGCAGA
```

```
-continued
75661 CTCAGCAGTG CCGCCCGGAA TTGGGAGTGG GCGGGCGTCG GCCGGAGCAG CTCGGTCAGC
75721 ACGATGGCGA CACGGGCCCG GCTGATGCGG CGCGCGAGGT GGAGCAGGCA GCGCAGCGAC
75781 GGCGCGTCGG CGTGGTGCAC GTCGTCGATG CCGATCAGTA CGGGCCGCTC CGCGGCGAGC
75841 GTCAGCACCG TGCGGGTGAG TTCGGTCCCC AGGCGGTTGT CGACGTCGGC CGGCAGGTTT
75901 TCGCACGATG CCGTCAGCCG GACCAGCTCC GGTGTCCGGG CGGCCAGCTC GGGCTGGTCG
75961 AGGAGCTGGC CGAGCATGCC GTACGGCAGG GCCCGCTCCT CCATGGAGCA CACCGCGCGA
76021 AGGGTGACGA AGCCGGCCTT GGCCGCGGCG GCGTCGAGGA GTTCGGTCTT GCCGCAGGCG
76081 ATCGGCCCGG TGACGGCGGC GACGACGCCC CGCCCGCCCG CCGCTCGGGT GAGCGCCCGG
76141 TGGAGGGAAC CGAACTCGTC ATCGCGGGCG ATCAGGTCTG GGGGAGATAA GCGCGCTATC
76201 ACGAATGGAA CTACCTCGCG ACCGTCGTGG AAACCCATAG GCATCACATG GCTTGTTGAT
76261 CTGTACGGCT GTGATTCAGC CTGGCGGGAT GCTGTGCTAC AGATGGGAAG ATGTGATCTA
76321 GGGCCGTGCC GTTCCCTCAG GAGCCGACCG CCCCCGGCGC CACCCGCCGT ACCCCCTGGG
76381 CCACCAGCTC GGCGACCCGC TCCTGGTGGT CGACGAGGTA GAAGTGCCCG CCGGGGAAGA
76441 CCTCCACCGT GGTCGGCGCG GTCGTGTGCC OGGOCCAGGO GTGGGCCTGC TCCACCGTCG
76501 TCTTCGGATC GTCGTCACCG ATGCACACCG TGATCGGCGT CTCCAGCGGC GGCGCGGGCT
76561 CCCACCGGTA CGTCTCCGCC GCGTAGTAGT CCGCCCGCAA CGGCGCCAGG ATCAGCGCGC
76621 GCATTTCGTC GTCCGCCATC ACATCGGCGC TCGTCCCGCC GAGGCCGATG ACCGCCGCCA
76681 GCAGCTCGTC GTCGGACGCG AGGTGGTCCT GGTCGGCGCG CGGCTGCGAC GGCGCCCGCC
76741 GGCCCGAGAC GATCAGGTGC GCCACCGGGA GCCGCTGGGC CAGCTCGAAC GCGAGTGTCG
76801 CGCCCATGCT GTGGCCGAAC AGCACCAGCG GACGGTCCAG CCCCGGCTTC AACGCCTCGG
76861 CCACGAGGCC GGCGAGAACA CGCAGGTCGC GCACCGCCTC CTCGTCGCGG CGGTCCTGGC
76921 GGCCGGGGTA CTGCACGGCG TACACGTCCG CCACCGGGGC GAGCGCACGG GCCAGCGGAA
76981 GGTAGAACGT CGCCGATCCG CCGGCGTGGG GCAGCAGCAC CACCCGTACC GGGGCCTCGG
77041 GCGTGGGGAA GAACTGCCGC AGCCAGAGTT CCGAGCTCAC CGCACCCCCT CGGCCGCGAC
77101 CTGGGGAGCC CGGAACCGGG TGATCTCGGC CAAGTGCTTC TCCCGCATCT CCGGGTCGGT
77161 CACGCCCCAT CCCTCCTCCG GCGCCAGACA GAGGACGCCG ACTTTGCCGT TGTGCACATT
77221 GCGATGCACA TCGCGCACCG CCGACCCGAC GTCGTCGAGC GGGTAGGTCA CCGACAGCGT
77281 CGGGTGCACC ATCCCCTTGC AGATCAGGCG GTTCGCCTCC CACGCCTCAC GATAGTTCGC
77341 GAAGTGGGTA CCGATGATCC GCTTCACGGA CATCCACAGG TACCGATTGT CAAAGGCGTG
77401 CTCGTATCCC GAGGTTGACG CGCAGGTGAC GATCGTGCCA CCCCGACGTG TCACGTAGAC
77461 ACTCGCGCCG AACGTCGCGC GCCCCGGGTG CTCGAACACG ATGTCGGGAT CGTCACCGCC
77521 GGTCAGCTCC CGGATC
```

Those of skill in the art will recognize that, due to the degenerate nature of the genetic code, a variety of DNA compounds differing in their nucleotide sequences can be used to encode a given amino acid sequence of the invention. The native DNA sequence encoding the FK-520 PKS of *Streptomyces hygroscopicus* is shown herein merely to illustrate a preferred embodiment of the invention, and the present invention includes DNA compounds of any sequence that encode the amino acid sequences of the polypeptides and proteins of the invention. In similar fashion, a polypeptide can typically tolerate one or more amino acid substitutions, deletions, and insertions in its amino acid sequence without loss or significant loss of a desired activity. The present invention includes such polypeptides with alternate amino acid sequences, and the amino acid sequences shown merely illustrate preferred embodiments of the invention.

The recombinant nucleic acids, proteins, and peptides of the invention are many and diverse. To facilitate an understanding of the invention and the diverse compounds and methods provided thereby, the following general description of the FK-520 PKS genes and modules of the PKS proteins encoded thereby is provided. This general description is followed by a more detailed description of the various domains and modules of the FK-520 PKS contained in and encoded by the compounds of the invention. In this description, reference to a heterologous PKS refers to any PKS other than the FK-520 PKS. Unless otherwise indicated, reference to a PKS includes reference to a portion of a PKS. Moreover, reference to a domain, module, or PKS includes reference to the nucleic acids encoding the same and vice-versa, because the methods and reagents of the invention provide or enable one to prepare proteins and the nucleic acids that encode them.

The FK-520 PKS is composed of three proteins encoded by three genes designated fkbA, fkbB, and fkbC. The fkbA ORF encodes extender modules 7-10 of the PKS. The fkbB ORF encodes the loading module (the CoA ligase) and extender modules 1-4 of the PKS. The fkbC ORF encodes extender modules 5'-6 of the PKS. The fkbP ORF encodes the NRPS that attaches the pipecolic acid and cyclizes the FK-520 polyketide.

The loading module of the FK-520 PKS includes a CoA ligase, an ER domain, and an ACP domain. The starter building block or unit for FK-520 is believed to be a dihydroxy-cyclohexene carboxylic acid, which is derived from shikimate. The recombinant DNA compounds of the invention that encode the loading module of the FK-520 PKS and the corresponding polypeptides encoded thereby are useful for a variety of methods and in a variety of compounds. In one embodiment, a DNA compound comprising a sequence that encodes the FK-520 loading module is inserted into a DNA compound that comprises the coding sequence for a heterologous PKS. The resulting construct, in which the coding sequence for the loading module of the heterologous PKS is replaced by the coding sequence for the FK-520 loading module, provides a novel PKS coding sequence. Examples of heterologous PKS coding sequences include the rapamycin, FK-506, rifamycin, and avermectin PKS coding sequences. In another embodiment, a DNA compound comprising a sequence that encodes the FK-520 loading module is inserted into a DNA compound that comprises the coding sequence for the FK-520 PKS or a recombinant FK-520 PKS that produces an FK-520 derivative.

In another embodiment, a portion of the loading module coding sequence is utilized in conjunction with a heterologous coding sequence. In this embodiment, the invention provides, for example, either replacing the CoA ligase with a different CoA ligase, deleting the ER, or replacing the ER with a different ER. In addition, or alternatively, the ACP can be replaced by another ACP. In similar fashion, the corresponding domains in another loading or extender module can be replaced by one or more domains of the FK-520 PKS. The resulting heterologous loading module coding sequence can be utilized in conjunction with a coding sequence for a PKS that synthesizes FK-520, an FK-520 derivative, or another polyketide.

The first extender module of the FK-520 PKS includes a KS domain, an AT domain specific for methylmalonyl CoA, a DH domain, a KR domain, and an ACP domain. The recombinant DNA compounds of the invention that encode the first extender module of the FK-520 PKS and the corresponding polypeptides encoded thereby are useful for a variety of applications. In one embodiment, a DNA compound comprising a sequence that encodes the FK-520 first extender module is inserted into a DNA compound that comprises the coding sequence for a heterologous PKS. The resulting construct, in which the coding sequence for a module of the heterologous PKS is either replaced by that for the first extender module of the FK-520 PKS or the latter is merely added to coding sequences for modules of the heterologous PKS, provides a novel PKS coding sequence. In another embodiment, a DNA compound comprising a sequence that encodes the first extender module of the FK-520 PKS is inserted into a DNA compound that comprises the remainder of the coding sequence for the FK-520 PKS or a recombinant FK-520 PKS that produces an FK-520 derivative.

In another embodiment, all or only a portion of the first extender module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting either the DH or KR or both; replacing the DH or KR or both with another DH or KR; and/or inserting an ER. In replacing or inserting KR, DH, and ER domains, it is often beneficial to replace the existing KR, DH, and ER domains with the complete set of domains desired from another module. Thus, if one desires to insert an ER domain, one may simply replace the existing KR and DH domains with a KR, DH, and ER set of domains from a module containing such domains. In addition, the KS and/or ACP can be replaced with another KS and/or ACP. In each of these replacements or insertions, the heterologous KS, AT, DH, KR, ER, or ACP coding sequence can originate from a coding sequence for another module of the FK-520 PKS, from a gene for a PKS that produces a polyketide other than FK-520, or from chemical synthesis. The resulting heterologous first extender module coding sequence can be utilized in conjunction with a coding sequence for a PKS that synthesizes FK-520, an FK-520 derivative, or another polyketide. In similar fashion, the corresponding domains in a module of a heterologous PKS can be replaced by one or more domains of the first extender module of the FK-520 PKS.

In an illustrative embodiment of this aspect of the invention, the invention provides recombinant PKSs and recombinant DNA compounds and vectors that encode such PKSs in which the KS domain of the first extender module has been inactivated. Such constructs are especially useful when placed in translational reading frame with the remaining modules and domains of an FK-520 or FK-520 derivative PKS. The utility of these constructs is that host cells expressing, or cell free extracts containing, the PKS encoded thereby can be fed or supplied with N-acylcysteamine thioesters of novel precursor molecules to prepare FK-520 derivatives. See U.S. patent application Ser. No. 60/117,384, filed 27 Jan. 1999, and PCT patent publication Nos. US97/02358 and US99/03986, each of which is incorporated herein by reference.

The second extender module of the FK-520 PKS includes a KS, an AT specific for methylmalonyl CoA, a KR, an inactive DH, and an ACP. The recombinant DNA compounds of the invention that encode the second extender module of the FK-520 PKS and the corresponding polypeptides encoded thereby are useful for a variety of applications. In one embodiment, a DNA compound comprising a sequence that encodes the FK-520 second extender module is inserted into a DNA compound that comprises the coding sequence for a heterologous PKS. The resulting construct, in which the coding sequence for a module of the heterologous PKS is either replaced by that for the second extender module of the FK-520 PKS or the latter is merely added to coding sequences for the modules of the heterologous PKS, provides a novel PKS coding sequence. In another embodiment, a DNA compound comprising a sequence that encodes the second extender module of the FK-520 PKS is inserted into a DNA compound that comprises the coding sequence for the remainder of the FK-520 PKS or a recombinant FK-520 PKS that produces an FK-520 derivative.

In another embodiment, all or a portion of the second extender module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting the KR and/or the inactive DH; replacing the KR with another KR; and/or inserting an active DH or an active DH and an ER. In addition, the KS and/or ACP can be replaced with another KS and/or ACP. In each of these replacements or insertions, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous second extender module coding sequence can be utilized in conjunction with a coding sequence from a PKS that synthesizes FK-520, an FK-520 derivative, or another polyketide. In similar fashion, the corresponding domains in a module of a heterologous PKS can be replaced by one or more domains of the second extender module of the FK-520 PKS.

The third extender module of the FK-520 PKS includes a KS, an AT specific for malonyl CoA, a KR, an inactive DH, and an ACP. The recombinant DNA compounds of the invention that encode the third extender module of the FK-520 PKS and the corresponding polypeptides encoded thereby are useful for a variety of applications. In one embodiment, a DNA compound comprising a sequence that encodes the FK-520 third extender module is inserted into a DNA compound that comprises the coding sequence for a heterologous PKS. The resulting construct, in which the coding sequence for a module of the heterologous PKS is either replaced by that for the third extender module of the FK-520 PKS or the latter is merely added to coding sequences for the modules of the heterologous PKS, provides a novel PKS coding sequence. In another embodiment, a DNA compound comprising a sequence that encodes the third extender module of the FK-520 PKS is inserted into a DNA compound that comprises the coding sequence for the remainder of the FK-520 PKS or a recombinant FK-520 PKS that produces an FK-520 derivative.

In another embodiment, all or a portion of the third extender module coding sequence is utilized in conjunction with other PKS coding sequences to create a hybrid module. In this embodiment, the invention provides, for example, either replacing the malonyl CoA specific AT with a methylmalonyl CoA, ethylmalonyl CoA, or 2-hydroxymalonyl CoA specific AT; deleting the KR and/or the inactive DH; replacing the KR with another KR; and/or inserting an active DH or an active DH and an ER. In addition, the KS and/or ACP can be replaced with another KS and/or ACP. In each of these replacements or insertions, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous third extender module coding sequence can be utilized in conjunction with a coding sequence from a PKS that synthesizes FK-520, an FK-520 derivative, or another polyketide. In similar fashion, the corresponding domains in a module of a heterologous PKS can be replaced by one or more domains of the third extender module of the FK-520 PKS.

The fourth extender module of the FK-520 PKS includes a KS, an AT that binds ethylmalonyl CoA, an inactive DH, and an ACP. The recombinant DNA compounds of the invention that encode the fourth extender module of the FK-520 PKS and the corresponding polypeptides encoded thereby are useful for a variety of applications. In one embodiment, a DNA compound comprising a sequence that encodes the FK-520 fourth extender module is inserted into a DNA compound that comprises the coding sequence for a heterologous PKS. The resulting construct, in which the coding sequence for a module of the heterologous PKS is either replaced by that for the fourth extender module of the FK-520 PKS or the latter is merely added to coding sequences for the modules of the heterologous PKS, provides a novel PKS coding sequence. In another embodiment, a DNA compound comprising a sequence that encodes the fourth extender module of the FK-520 PKS is inserted into a DNA compound that comprises the remainder of the coding sequence for the FK-520 PKS or a recombinant FK-520 PKS that produces an FK-520 derivative.

In another embodiment, a portion of the fourth extender module coding sequence is utilized in conjunction with other PKS coding sequences to create a hybrid module. In this embodiment, the invention provides, for example, either replacing the ethylmalonyl CoA specific AT with a malonyl CoA, methylmalonyl CoA, or 2-hydroxymalonyl CoA specific AT; and/or deleting the inactive DH, inserting a KR, a KR and an active DH, or a KR, an active DH, and an ER. In addition, the KS and/or ACP can be replaced with another KS and/or ACP. In each of these replacements or insertions, the heterologous KS, AT, DH, KR, ER, or ACP coding sequence can originate from a coding sequence for another module of the FK-520 PKS, a PKS for a polyketide other than FK-520, or from chemical synthesis. The resulting heterologous fourth extender module coding sequence can be utilized in conjunction with a coding sequence for a PKS that synthesizes FK-520, an FK-520 derivative, or another polyketide. In similar fashion, the corresponding domains in a module of a heterologous PKS can be replaced by one or more domains of the fourth extender module of the FK-520 PKS.

As illustrative examples, the present invention provides recombinant genes, vectors, and host cells that result from the conversion of the FK-506 PKS to an FK-520 PKS and vice-versa. In one embodiment, the invention provides a recombinant set of FK-506 PKS genes but in which the coding sequences for the fourth extender module or at least those for the AT domain in the fourth extender module have been replaced by those for the AT domain of the fourth extender module of the FK-520 PKS. This recombinant PKS can be used to produce FK-520 in recombinant host cells. In another embodiment, the invention provides a recombinant set of FK-520 PKS genes but in which the coding sequences for the fourth extender module or at least those for the AT domain in the fourth extender module have been replaced by those for the AT domain of the fourth extender module of the FK-506 PKS. This recombinant PKS can be used to produce FK-506 in recombinant host cells.

Other examples of hybrid PKS enzymes of the invention include those in which the AT domain of module 4 has been replaced with a malonyl specific AT domain to provide a PKS that produces 21-desethyl-FK520 or with a methylmalonyl specific AT domain to provide a PKS that produces 21-desethyl-21-methyl-FK520. Another hybrid PKS of the invention is prepared by replacing the AT and inactive KR domain of FK-520 extender module 4 with a methylmalonyl specific AT and an active KR domain, such as, for example, from module 2 of the DEBS or oleandolide PKS enzymes, to produce 21-desethyl-21-methyl-22-desoxo-22-hydroxy-FK520. The compounds produced by these hybrid PKS enzymes are neurotrophins.

The fifth extender module of the FK-520 PKS includes a KS, an AT that binds methylmalonyl CoA, a DH, a KR, and an ACP. The recombinant DNA compounds of the invention that encode the fifth extender module of the FK-520 PKS and the corresponding polypeptides encoded thereby are useful for a variety of applications. In one embodiment, a DNA compound comprising a sequence that encodes the FK-520 fifth extender module is inserted into a DNA compound that comprises the coding sequence for a heterologous PKS. The resulting construct, in which the coding sequence for a module of the heterologous PKS is either replaced by that for the fifth extender module of the FK-520 PKS or the latter is merely added to coding sequences for the modules of the heterologous PKS, provides a novel PKS. In another embodiment, a DNA compound comprising a sequence that encodes the fifth extender module of the FK-520 PKS is inserted into a DNA compound that comprises the coding sequence for the FK-520 PKS or a recombinant FK-520 PKS that produces an FK-520 derivative.

In another embodiment, a portion of the fifth extender module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting any one or both of the DH and KR; replacing any one or both of the DH and KR with either a KR and/or DH; and/or inserting an ER. In addition, the KS and/or ACP can be replaced with another KS and/or ACP. In each of these replacements or insertions, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous fifth extender module coding sequence can be utilized in conjunction with a coding sequence for a PKS that synthesizes FK-520, an FK-520 derivative, or another polyketide. In similar fashion, the corresponding domains in a module of a heterologous PKS can be replaced by one or more domains of the fifth extender module of the FK-520 PKS.

In an illustrative embodiment, the present invention provides a set of recombinant FK-520 PKS genes in which the coding sequences for the DH domain of the fifth extender module have been deleted or mutated to render the DH non-functional. In one such mutated gene, the KR and DH coding sequences are replaced with those encoding only a KR domain from another PKS gene. The resulting PKS genes code for the expression of an FK-520 PKS that produces an FK-520 analog that lacks the C-19 to C-20 double bond of FK-520 and has a C-20 hydroxyl group. Such analogs are preferred neurotrophins, because they have little or no immunosuppressant activity. This recombinant fifth extender module coding sequence can be combined with other coding sequences to make additional compounds of the invention. In an illustrative embodiment, the present invention provides a recombinant FK-520 PKS that contains both this fifth extender module and the recombinant fourth extender module described above that comprises the coding sequence for the fourth extender module AT domain of the FK-506 PKS. The invention also provides recombinant host cells derived from FK-506 producing host cells that have been mutated to prevent production of FK-506 but that express this recombinant PKS and so synthesize the corresponding (lacking the C-19 to C-20 double bond of FK-506 and having a C-20 hydroxyl group) FK-506 derivative. In another embodiment, the present invention provides a recombinant FK-506 PKS in which the DH domain of module 5 has been deleted or otherwise rendered inactive and thus produces this novel polyketide.

The sixth extender module of the FK-520 PKS includes a KS, an AT specific for methylmalonyl CoA, a KR, a DH, an ER, and an ACP. The recombinant DNA compounds of the invention that encode the sixth extender module of the FK-520 PKS and the corresponding polypeptides encoded thereby are useful for a variety of applications. In one embodiment, a DNA compound comprising a sequence that encodes the FK-520 sixth extender module is inserted into a DNA compound that comprises the coding sequence for a heterologous PKS. The resulting construct, in which the coding sequence for a module of the heterologous PKS is either replaced by that for the sixth extender module of the FK-520 PKS or the latter is merely added to coding sequences for the modules of the heterologous PKS, provides a novel PKS coding sequence. In another embodiment, a DNA compound comprising a sequence that encodes the sixth extender module of the FK-520 PKS is inserted into a DNA compound that comprises the coding sequence for the remainder of the FK-520 PKS or a recombinant FK-520 PKS that produces an FK-520 derivative.

In another embodiment, a portion of the sixth extender module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting any one, two, or all three of the KR, DH, and ER; and/or replacing any one, two, or all three of the KR, DH, and ER with another KR, DH, and ER. In addition, the KS and/or ACP can be replaced with another KS and/or ACP. In each of these replacements, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous sixth extender module coding sequence can be utilized in conjunction with a coding sequence for a PKS that synthesizes FK-520, an FK-520 derivative, or another polyketide. In similar fashion, the corresponding domains in a module of a heterologous PKS can be replaced by one or more domains of the sixth extender module of the FK-520 PKS.

In an illustrative embodiment, the present invention provides a set of recombinant FK-520 PKS genes in which the coding sequences for the DH and ER domains of the sixth extender module have been deleted or mutated to render them non-functional. In one such mutated gene, the KR, ER, and DH coding sequences are replaced with those encoding only a KR domain from another PKS gene. This can also be accomplished by simply replacing the coding sequences for extender module six with those for an extender module having a methylmalonyl specific AT and only a KR domain from a heterologous PKS gene, such as, for example, the coding sequences for extender module two encoded by the eryAI gene. The resulting PKS genes code for the expression of an FK-520 PKS that produces an FK-520 analog that has a C-18 hydroxyl group. Such analogs are preferred neurotrophins, because they have little or no immunosuppressant activity. This recombinant sixth extender module coding sequence can be combined with other coding sequences to make additional compounds of the invention. In an illustrative embodiment, the present invention provides a recombinant FK-520 PKS that contains both this sixth extender module and the recombinant fourth extender module described above that comprises the coding sequence for the fourth extender module AT domain of the FK-506 PKS. The invention also provides recombinant host cells derived from FK-506 producing host cells that have been mutated to prevent production of FK-506 but that express this recombinant PKS and so synthesize the corresponding (having a C-18 hydroxyl group) FK-506 derivative. In another embodiment, the present invention provides a recombinant FK-506 PKS in which the DH and ER domains of module 6 have been deleted or otherwise rendered inactive and thus produces this novel polyketide.

The seventh extender module of the FK-520 PKS includes a KS, an AT specific for 2-hydroxymalonyl CoA, a KR, a DH, an ER, and an ACP. The recombinant DNA compounds of the invention that encode the seventh extender module of the FK-520 PKS and the corresponding polypeptides encoded thereby are useful for a variety of applications. In one embodiment, a DNA compound comprising a sequence that encodes the FK-520 seventh extender module is inserted into a DNA compound that comprises the coding sequence for a heterologous PKS. The resulting construct, in which the coding sequence for a module of the heterologous PKS is either replaced by that for the seventh extender module of the FK-520 PKS or the latter is merely added to coding sequences for the modules of the heterologous PKS, provides a novel PKS coding sequence. In another embodiment, a DNA compound comprising a sequence that encodes the seventh extender module of the FK-520 PKS is inserted into a DNA compound that comprises the coding sequence for the remainder of the FK-520 PKS or a recombinant FK-520 PKS that produces an FK-520 derivative.

In another embodiment, a portion or all of the seventh extender module coding sequence is utilized in conjunction with other PKS coding sequences to create a hybrid module. In this embodiment, the invention provides, for example, either replacing the 2-hydroxymalonyl CoA specific AT with a methylmalonyl CoA, ethylmalonyl CoA, or malonyl CoA specific AT; deleting the KR, the DH, and/or the ER; and/or replacing the KR, DH, and/or ER. In addition, the KS and/or ACP can be replaced with another KS and/or ACP. In each of these replacements or insertions, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous seventh extender module coding sequence can be utilized in conjunction with a coding sequence for a PKS that synthesizes FK-520, an FK-520 derivative, or another polyketide. In similar fashion, the corresponding domains in a module of a heterologous PKS can be replaced by one or more domains of the seventh extender module of the FK-520 PKS.

In an illustrative embodiment, the present invention provides a set of recombinant FK-520 PKS genes in which the coding sequences for the AT domain of the seventh extender module has been replaced with those encoding an AT domain for malonyl, methylmalonyl, or ethylmalonyl CoA from another PKS gene. The resulting PKS genes code for the expression of an FK-520 PKS that produces an FK-520 analog that lacks the C-15 methoxy group, having instead a hydrogen, methyl, or ethyl group at that position, respectively. Such analogs are preferred, because they are more slowly metabolized than FK-520. This recombinant seventh extender module coding sequence can be combined with other coding sequences to make additional compounds of the invention. In an illustrative embodiment, the present invention provides a recombinant FK-520 PKS that contains both this seventh extender module and the recombinant fourth extender module described above that comprises the coding sequence for the fourth extender module AT domain of the FK-506 PKS. The invention also provides recombinant host cells derived from FK-506 producing host cells that have been mutated to prevent production of FK-506 but that express this recombinant PKS and so synthesize the corresponding (C-15-desmethoxy) FK-506 derivative. In another embodiment, the present invention provides a recombinant FK-506 PKS in which the AT domain of module 7 has been replaced and thus produces this novel polyketide.

In another illustrative embodiment, the present invention provides a hybrid PKS in which the AT and KR domains of module 7 of the FK-520 PKS are replaced by a methylmalonyl specific AT domain and an inactive KR domain, such as, for example, the AT and KR domains of extender module 6 of the rapamycin PKS. The resulting hybrid PKS produces 15-desmethoxy-15-methyl-16-oxo-FK-520, a neurotrophin compound.

The eighth extender module of the FK-520 PKS includes a KS, an AT specific for 2-hydroxymalonyl CoA, a KR, and an ACP. The recombinant DNA compounds of the invention that encode the eighth extender module of the FK-520 PKS and the corresponding polypeptides encoded thereby are useful for a variety of applications. In one embodiment, a DNA compound comprising a sequence that encodes the FK-520 eighth extender module is inserted into a DNA compound that comprises the coding sequence for a heterologous PKS. The resulting construct, in which the coding sequence for a module of the heterologous PKS is either replaced by that for the eighth extender module of the FK-520 PKS or the latter is merely added to coding sequences for the modules of the heterologous PKS, provides a novel PKS coding sequence. In another embodiment, a DNA compound comprising a sequence that encodes the eighth extender module of the FK-520 PKS is inserted into a DNA compound that comprises the coding sequence for the remainder of the FK-520 PKS or a recombinant FK-520 PKS that produces an FK-520 derivative.

In another embodiment, a portion of the eighth extender module coding sequence is utilized in conjunction with other PKS coding sequences to create a hybrid module. In this embodiment, the invention provides, for example, either replacing the 2-hydroxymalonyl CoA specific AT with a methylmalonyl CoA, ethylmalonyl CoA, or malonyl CoA specific AT; deleting or replacing the KR; and/or inserting a DH or a DH and an ER. In addition, the KS and/or ACP can be replaced with another KS and/or ACP. In each of these replacements, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous eighth extender module coding sequence can be utilized in conjunction with a PKS that synthesizes FK-520, an FK-520 derivative, or another polyketide. In similar fashion, the corresponding domains in a module of a heterologous PKS can be replaced by one or more domains of the eighth extender module of the FK-520 PKS.

In an illustrative embodiment, the present invention provides a set of recombinant FK-520 PKS genes in which the coding sequences for the AT domain of the eighth extender module has been replaced with those encoding an AT domain for malonyl, methylmalonyl, or ethylmalonyl CoA from another PKS gene. The resulting PKS genes code for the expression of an FK-520 PKS that produces an FK-520 analog that lacks the C-13 methoxy group, having instead a hydrogen, methyl, or ethyl group at that position, respectively. Such analogs are preferred, because they are more slowly metabolized than FK-520. This recombinant eighth extender module coding sequence can be combined with other coding sequences to make additional compounds of the invention. In an illustrative embodiment, the present invention provides a recombinant FK-520 PKS that contains both this eighth extender module and the recombinant fourth extender module described above that comprises the coding sequence for the fourth extender module AT domain of the FK-506 PKS. The invention also provides recombinant host cells derived from FK-506 producing host cells that have been mutated to prevent production of FK-506 but that express this recombinant PKS and so synthesize the corresponding (C-13-desmethoxy) FK-506 derivative. In another embodiment, the present invention provides a recombinant FK-506 PKS in which the AT domain of module 8 has been replaced and thus produces this novel polyketide.

The ninth extender module of the FK-520 PKS includes a KS, an AT specific for methylmalonyl CoA, a KR, a DH, an ER, and an ACP. The recombinant DNA compounds of the invention that encode the ninth extender module of the FK-520 PKS and the corresponding polypeptides encoded thereby are useful for a variety of applications. In one embodiment, a DNA compound comprising a sequence that encodes the FK-520 ninth extender module is inserted into a DNA compound that comprises the coding sequence for a heterologous PKS. The resulting construct, in which the coding sequence for a module of the heterologous PKS is either replaced by that for the ninth extender module of the FK-520 PKS or the latter is merely added to coding sequences for the modules of the heterologous PKS, provides a novel PKS coding sequence. In another embodiment, a DNA compound comprising a sequence that encodes the ninth extender module of the FK-520 PKS is inserted into a DNA compound that comprises the coding sequence for the remainder of the FK-520 PKS or a recombinant FK-520 PKS that produces an FK-520 derivative.

In another embodiment, a portion of the ninth extender module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting any one, two, or all three of the KR, DH, and ER; and/or replacing any one, two, or all three of the KR, DH, and ER with another KR, DH, and/or ER. In addition, the KS and/or ACP can be replaced with another KS and/or ACP. In each of these replacements, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous ninth extender module coding sequence can be utilized in conjunction with a PKS that synthesizes FK-520, an FK-520 derivative, or another polyketide. In similar fashion, the corresponding domains in a module of a heterologous PKS can be replaced by one or more domains of the ninth extender module of the FK-520 PKS.

The tenth extender module of the FK-520 PKS includes a KS, an AT specific for malonyl CoA, and an ACP. The recombinant DNA compounds of the invention that encode the tenth extender module of the FK-520 PKS and the corresponding polypeptides encoded thereby are useful for a variety of applications. In one embodiment, a DNA compound comprising a sequence that encodes the FK-520 tenth extender module is inserted into a DNA compound that comprises the coding sequence for a heterologous PKS. The resulting construct, in which the coding sequence for a module of the heterologous PKS is either replaced by that for the tenth extender module of the FK-520 PKS or the latter is merely added to coding sequences for the modules of the heterologous PKS, provides a novel PKS coding sequence. In another embodiment, a DNA compound comprising a sequence that encodes the tenth extender module of the FK-520 PKS is inserted into a DNA compound that comprises the coding sequence for the remainder of the FK-520 PKS or a recombinant FK-520 PKS that produces an FK-520 derivative.

In another embodiment, a portion or all of the tenth extender module coding sequence is utilized in conjunction with other PKS coding sequences to create a hybrid module. In this embodiment, the invention provides, for example, either replacing the malonyl CoA specific AT with a methylmalonyl CoA, ethylmalonyl CoA, or 2-hydroxymalonyl CoA specific AT; and/or inserting a KR, a KR and DH, or a KR, DH, and an ER. In addition, the KS and/or ACP can be replaced with another KS and/or ACP. In each of these replacements or insertions, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous tenth extender module coding sequence can be utilized in conjunction with a coding sequence for a PKS that synthesizes FK-520, an FK-520 derivative, or another polyketide. In similar fashion, the corresponding domains in a module of a heterologous PKS can be replaced by one or more domains of the tenth extender module of the FK-520 PKS.

The FK-520 polyketide precursor produced by the action of the tenth extender module of the PKS is then attached to pipecolic acid and cyclized to form FK-520. The enzyme FkbP is the NRPS like enzyme that catalyzes these reactions. FkbP also includes a thioesterase activity that cleaves the nascent FK-520 polyketide from the NRPS. The present invention provides recombinant DNA compounds that encode the fkbP gene and so provides recombinant methods for expressing the fkbP gene product in recombinant host cells. The recombinant fkbP genes of the invention include those in which the coding sequence for the adenylation domain has been mutated or replaced with coding sequences from other NRPS like enzymes so that the resulting recombinant FkbP incorporates a moiety other than pipecolic acid. For the construction of host cells that do not naturally produce pipecolic acid, the present invention provides recombinant DNA compounds that express the enzymes that catalyze at least some of the biosynthesis of pipecolic acid (see Nielsen et al., 1991, Biochem. 30: 5789-96). The fkbL gene encodes a homolog of RapL, a lysine cyclodeaminase responsible in part for producing the pipecolate unit added to the end of the polyketide chain. The fkbB and fkbL recombinant genes of the invention can be used in heterologous hosts to produce compounds such as FK-520 or, in conjunction with other PKS or NRPS genes, to produce known or novel polyketides and non-ribosmal peptides.

Figure 2:
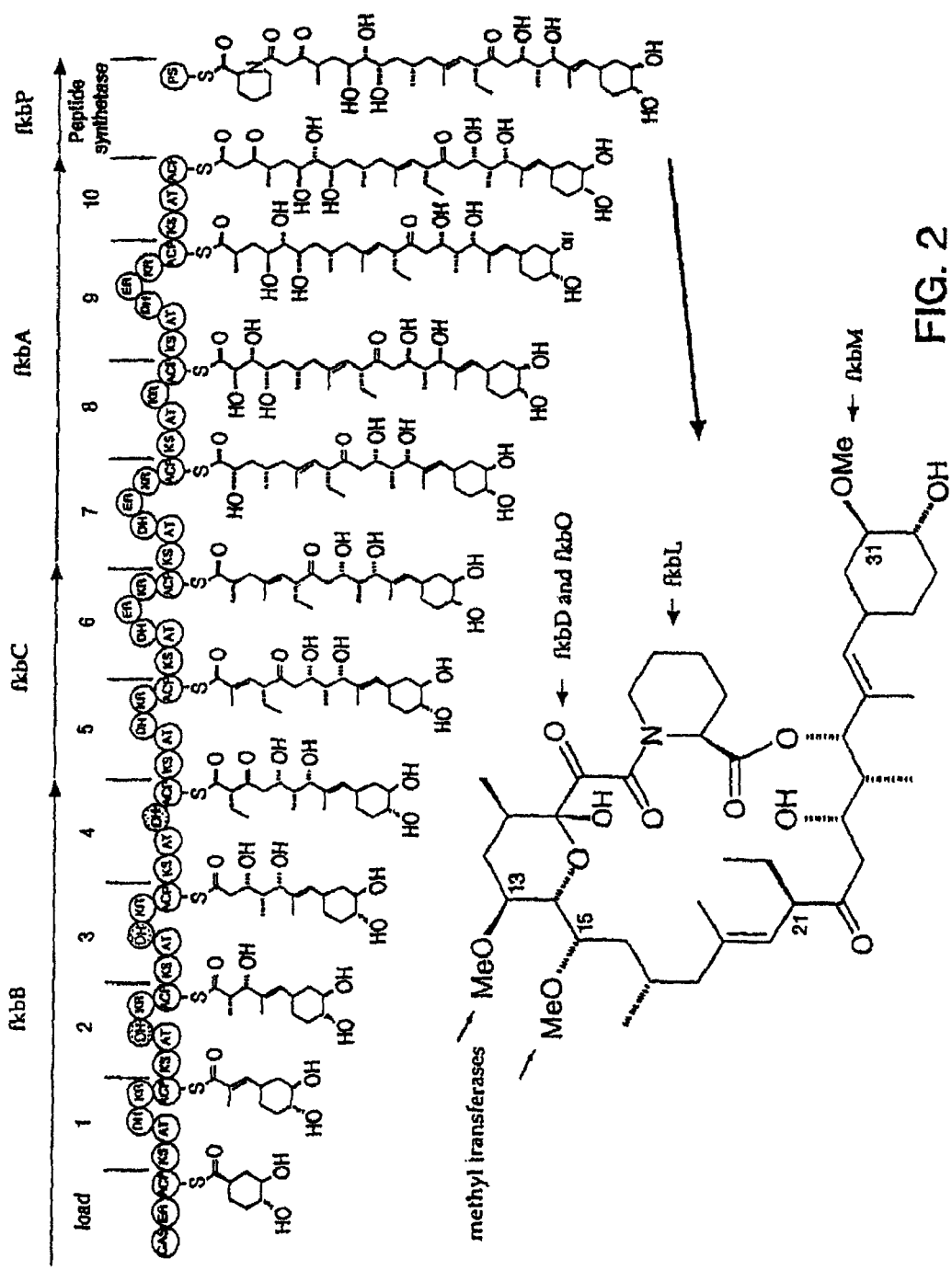
FIG. 2 shows the loading module (load), the ten extender modules, and the peptide synthetase domain of the FK-520 PKS, together with, on the top line, the genes that encode the various domains and modules. Also shown are the various intermediates in FK-520 biosynthesis, as well as the structure of FK-520, with carbons 13, 15, 21, and 31 numbered. The various domains of each module and subdomains of the loading module are also shown. The darkened circles showing the DH domains in modules 2, 3, and 4 indicate that the dehydratase domain is not functional as a dehydratase; this domain may affect the stereochemistry at the corresponding position in the polyketide. The substituents on the FK-520 structure that result from the action of non-PKS enzymes are also indicated by arrows, together with the types of enzymes or the genes that code for the enzymes that mediate the action. Although the methyltransferase is shown acting at the C-13 and C-15 hydroxyl groups after release of the polyketide from the PKS, the methyltransferase may act on the 2-hydroxymalonyl substrate prior to or contemporaneously with its incorporation during polyketide synthesis.

The present invention also provides recombinant DNA compounds that encode the P450 oxidase and methyltransferase genes involved in the biosynthesis of FK-520. FIG. 2 shows the various sites on the FK-520 polyketide core structure at which these enzymes act. By providing these genes in recombinant form, the present invention provides recombinant host cells that can produce FK-520. This is accomplished by introducing the recombinant PKS, P450 oxidase, and methyltransferase genes into a heterologous host cell. In a preferred embodiment, the heterologous host cell is Streptomyces coelicolor CH999 or Streptomyces lividans K4-114, as described in U.S. Pat. No. 5,830,750 and U.S. patent application Ser. No. 08/828,898, filed 31 Mar. 1997, and 09/181,833, filed 28 Oct. 1998, each of which is incorporated herein by reference. In addition, by providing recombinant host cells that express only a subset of these genes, the present invention provides methods for making FK-520 precursor compounds not readily obtainable by other means.

In a related aspect, the present invention provides recombinant DNA compounds and vectors that are useful in generating, by homologous recombination, recombinant host cells that produce FK-520 precursor compounds. In this aspect of the invention, a native host cell that produces FK-520 is transformed with a vector (such as an SCP2* derived vector for Streptomyces host cells) that encodes one or more disrupted genes (i.e., a hydroxylase, a methyltransferase, or both) or merely flanking regions from those genes. When the vector integrates by homologous recombination, the native, functional gene is deleted or replaced by the non-functional recombinant gene, and the resulting host cell thus produces an FK-520 precursor. Such host cells can also be complemented by introduction of a modified form of the deleted or mutated non-functional gene to produce a novel compound.

In one important embodiment, the present invention provides a hybrid PKS and the corresponding recombinant DNA compounds that encode those hybrid PKS enzymes. For purposes of the present invention a hybrid PKS is a recombinant PKS that comprises all or part of one or more modules and thioesterase/cyclase domain of a first PKS and all or part of one or more modules, loading module, and thioesterase/cyclase domain of a second PKS. In one preferred embodiment, the first PKS is all or part of the FK-520 PKS, and the second PKS is only a portion or all of a non-FK-520 PKS.

One example of the preferred embodiment is an FK-520 PKS in which the AT domain of module 8, which specifies a hydroxymalonyl CoA and from which the C-13 methoxy group of FK-520 is derived, is replaced by an AT domain that specifies a malonyl, methylmalonyl, or ethylmalonyl CoA. Examples of such replacement AT domains include the AT domains from modules 3, 12, and 13 of the rapaymycin PKS and from modules 1 and 2 of the erythromycin PKS. Such replacements, conducted at the level of the gene for the PKS, are illustrated in the examples below. Another illustrative example of such a hybrid PKS includes an FK-520 PKS in which the natural loading module has been replaced with a loading module of another PKS. Another example of such a hybrid PKS is an FK-520 PKS in which the AT domain of module three is replaced with an AT domain that binds methylmalonyl CoA.

In another preferred embodiment, the first PKS is most but not all of a non-FK-520 PKS, and the second PKS is only a portion or all of the FK-520 PKS. An illustrative example of such a hybrid PKS includes an erythromycin PKS in which an AT specific for methylmalonyl CoA is replaced with an AT from the FK-520 PKS specific for malonyl CoA.

Those of skill in the art will recognize that all or part of either the first or second PKS in a hybrid PKS of the invention need not be isolated from a naturally occurring source. For example, only a small portion of an AT domain determines its specificity. See U.S. provisional patent application Ser. No. 60/091,526, incorporated herein by reference. The state of the art in DNA synthesis allows the artisan to construct de novo DNA compounds of size sufficient to construct a useful portion of a PKS module or domain. For purposes of the present invention, such synthetic DNA compounds are deemed to be a portion of a PKS.

Thus, the hybrid modules of the invention are incorporated into a PKS to provide a hybrid PKS of the invention. A hybrid PKS of the invention can result not only:

(i) from fusions of heterologous domain (where heterologous means the domains in that module are from at least two different naturally occurring modules) coding sequences to produce a hybrid module coding sequence contained in a PKS gene whose product is incorporated into a PKS, but also:

(ii) from fusions of heterologous module (where heterologous module means two modules are adjacent to one another that are not adjacent to one another in naturally occurring PKS enzymes) coding sequences to produce a hybrid coding sequence contained in a PKS gene whose product is incorporated into a PKS, (iii) from expression of one or more FK-520 PKS genes with one or more non-FK-520 PKS genes, including both naturally occurring and recombinant non-FK-520 PKS genes, and (iv) from combinations of the foregoing.

Various hybrid PKSs of the invention illustrating these various alternatives are described herein.

Examples of the production of a hybrid PKS by co-expression of PKS genes from the FK-520 PKS and another non-FK-520 PKS include hybrid PKS enzymes produced by coexpression of FK-520 and rapamycin PKS genes. Preferably, such hybrid PKS enzymes are produced in recombinant *Streptomyces* host cells that produce FK-520 or FK-506 but have been mutated to inactivate the gene whose function is to be replaced by the rapamycin PKS gene introduced to produce the hybrid PKS. Particular examples include (i) replacement of the fkbC gene with the rapB gene; and (ii) replacement of the fkbA gene with the rapC gene. The latter hybrid PKS produces 13,15-didesmethoxy-FK-520, if the host cell is an FK-520 producing host cell, and 13,15-didesmethoxy-FK-506, if the host cell is an FK-506 producing host cell. The compounds produced by these hybrid PKS enzymes are immunosuppressants and neurotrophins but can be readily modified to act only as neurotrophins, as described in Example 6, below.

Other illustrative hybrid PKS enzymes of the invention are prepared by replacing the fkbA gene of an FK-520 or FK-506 producing host cell with a hybrid fkbA gene in which: (a) the extender module 8 through 10, inclusive, coding sequences have been replaced by the coding sequences for extender modules 12 to 14, inclusive, of the rapamycin PKS; and (b) the module 8 coding sequences have been replaced by the module 8 coding sequence of the rifamycin PKS. When expressed with the other, naturally occurring FK-520 or FK-506 PKS genes and the genes of the modification enzymes, the resulting hybrid PKS enzymes produce, respectively, (a) 13-desmethoxy-FK-520 or 13-desmethoxy-FK-506; and (b) 13-desmethoxy-13-methyl-FK-520 or 13-desmethoxy-13-methyl-FK-506. In a preferred embodiment, these recombinant PKS genes of the invention are introduced into the producing host cell by a vector such as pHU204, which is a plasmid pRM5 derivative that has the well-characterized SCP2* replicon, the colE1 replicon, the tsr and bla resistance genes, and a cos site. This vector can be used to introduce the recombinant fkbA replacement gene in an FK-520 or FK-506 producing host cell (or a host cell derived therefrom in which the endogenous fkbA gene has either been rendered inactive by mutation, deletion or homologous recombination with the gene that replaces it) to produce the desired hybrid PKS.

In constructing hybrid PKSs of the invention, certain general methods may be helpful. For example, it is often beneficial to retain the framework of the module to be altered to make the hybrid PKS. Thus, if one desires to add DH and ER functionalities to a module, it is often preferred to replace the KR domain of the original module with a KR, DH, and ER domain-containing segment from another module, instead of merely inserting DH and ER domains. One can alter the stereochemical specificity of a module by replacement of the KS domain with a KS domain from a module that specifies a different stereochemistry. See Lau et al., 1999, "Dissecting the role of acyltransferase domains of modular polyketide synthases in the choice and stereochemical fate of extender units," *Biochemistry* 38(5):1643-1651, incorporated herein by reference. Stereochemistry can also be changed by changing the KR domain. Also, one can alter the specificity of an AT domain by changing only a small segment of the domain. See Lau et al., supra. One can also take advantage of known linker regions in PKS proteins to link modules from two different PKSs to create a hybrid PKS. See Gokhale et al., 16 Apr. 1999, "Dissecting and Exploiting Intermodular Communication in Polyketide Synthases," *Science* 284: 482-485, incorporated herein by reference.

The following Table lists references describing illustrative PKS genes and corresponding enzymes that can be utilized in the construction of the recombinant PKSs and the corresponding DNA compounds that encode them of the invention. Also presented are various references describing tailoring enzymes and corresponding genes that can be employed in accordance with the methods of the present invention.

Avermectin

U.S. Pat. No. 5,252,474 to Merck.

MacNeil et al., 1993, *Industrial Microorganisms: Basic and Applied Molecular Genetics*, Baltz, Hegeman, & Skatrud, eds. (ASM), pp. 245-256, A Comparison of the Genes Encoding the Polyketide Synthases for Avermectin, Erythromycin, and Nemadectin.

MacNeil et al., 1992, *Gene* 115: 119-125, Complex Organization of the *Streptomyces avermitilis* genes encoding the avermectin polyketide synthase.

Ikeda et al., August 1999, Organization of the biosynthetic gene cluster for the polyketide anthelmintic macrolide avermectin in *Streptomyces avermitilis*, *Proc. Natl. Acad. Sci. USA* 96: 9509-9514.

Candicidin (FR008)
Hu et al., 1994, *Mol. Microbiol.* 14:163-172.

Epothilone
U.S. Pat. App. Ser. No. 60/130,560, filed 22 Apr. 1999.

Erythromycin
PCT Pub. No. 93/13663 to Abbott.
U.S. Pat. No. 5,824,513 to Abbott.
Donadio et al., 1991, *Science* 252:675-9.
Cortes et al., 8 Nov. 1990, *Nature* 348:176-8, An unusually large multifunctional polypeptide in the erythromycin producing polyketide synthase of *Saccharopolyspora erythraea*.
Glycosylation Enzymes
PCT Pat. App. Pub. No. 97/23630 to Abbott.

FK-506
Motamedi et al., 1998, The biosynthetic gene cluster for the macrolactone ring of the immunosuppressant FK-506, *Eur. J. biochem.* 256: 528-534.
Motamedi et al., 1997, Structural organization of a multifunctional polyketide synthase involved in the biosynthesis of the macrolide immunosuppressant FK-506, *Eur. J. Biochem.* 244: 74-80.
Methyltransferase
U.S. Pat. No. 5,264,355, issued 23 Nov. 1993, Methylating enzyme from *Streptomyces* MA6858. 31-O-desmethyl-FK-506 methyltransferase.
Motamedi et al., 1996, Characterization of methyltransferase and hydroxylase genes involved in the biosynthesis of the immunosuppressants FK-506 and FK-520, *J. Bacteriol.* 178: 5243-5248.

*Streptomyces hygroscopicus*
U.S. patent application Ser. No. 09/154,083, filed 16 Sep. 1998.

Lovastatin
U.S. Pat. No. 5,744,350 to Merck.

Narbomycin
U.S. patent application Ser. No. 60/107,093, filed 5 Nov. 1998, and Ser. No. 60/120,254, filed 16 Feb. 1999.

Nemadectin
MacNeil et al, 1993, supra.

Niddamycin
Kakavas et al., 1997, Identification and characterization of the niddamycin polyketide synthase genes from *Streptomyces caelestis*, *J. Bacteriol.* 179: 7515-7522.

Oleandomycin
Swan et al., 1994, Characterisation of a *Streptomyces antibioticus* gene encoding a type I polyketide synthase which has an unusual coding sequence, *Mol. Gen. Genet.* 242: 358-362.
U.S. patent application Ser. No. 60/120,254, filed 16 Feb. 1999.
Olano et al., 1998, Analysis of a *Streptomyces antibioticus* chromosomal region involved in oleandomycin biosynthesis, which encodes two glycosyltransferases responsible for glycosylation of the macrolactone ring, *Mol. Gen. Genet.* 259(3): 299-308.

Picromycin
PCT patent application US99/15047, filed 2 Jul. 1999.
Xue et al., 1998, Hydroxylation of macrolactones YC-17 and narbomycin is mediated by the pikC-encoded cytochrome P450 in *Streptomyces venezuelae*, *Chemistry & Biology* 5(11): 661-667.
Xue et al., October 1998, A gene cluster for macrolide antibiotic biosynthesis in *Streptomyces venezuelae*: Architecture of metabolic diversity, *Proc. Natl. Acad. Sci. USA* 95: 12111 12116.

Platenolide
EP Pat. App. Pub. No. 791,656 to Lilly.

Rapamycin
Schwecke et al., August 1995, The biosynthetic gene cluster for the polyketide rapamycin, *Proc. Natl. Acad. Sci. USA* 92:7839-7843.
Aparicio et al., 1996, Organization of the biosynthetic gene cluster for rapamycin in *Streptomyces hygroscopicus*: analysis of the enzymatic domains in the modular polyketide synthase, *Gene* 169: 9-16.

Rifamycin
August et al., 13 Feb. 1998, Biosynthesis of the ansamycin antibiotic rifamycin: deductions from the molecular analysis of the rifbiosynthetic gene cluster of *Amycolatopsis mediterranei* S669, *Chemistry & Biology*, 5(2): 69-79.

Sorangium PKS
U.S. patent application Ser. No. 09/144,085, filed 31 Aug. 1998.

Soraphen
U.S. Pat. No. 5,716,849 to Novartis.
Schupp et al., 1995, *J Bacteriology* 177: 3673-3679. A *Sorangium cellulosum* (Myxobacterium) Gene Cluster for the Biosynthesis of the Macrolide Antibiotic Soraphen A: Cloning, Characterization, and Homology to Polyketide Synthase Genes from Actinomycetes.

Spiramycin
U.S. Pat. No. 5,098,837 to Lilly.
Activator Gene
U.S. Pat. No. 5,514,544 to Lilly.

Tylosin
EP Pub. No. 791,655 to Lilly.
U.S. Pat. No. 5,876,991 to Lilly.
Kuhstoss et al., 1996, *Gene* 183:231-6., Production of a novel polyketide through the construction of a hybrid polyketide synthase.
Tailoring Enzymes
Merson-Davies and Cundliffe, 1994, *Mol. Microbiol.* 13: 349-355. Analysis of five tylosin biosynthetic genes from the tylBA region of the *Streptomyces fradiae* genome.

As the above Table illustrates, there are a wide variety of polyketide synthase genes that serve as readily available sources of DNA and sequence information for use in constructing the hybrid PKS-encoding DNA compounds of the invention. Methods for constructing hybrid PKS-encoding DNA compounds are described without reference to the FK-520 PKS in PCT patent publication No. 98/51695; U.S. Pat. Nos. 5,672,491 and 5,712,146 and U.S. patent application Ser. No. 09/073,538, filed 6 May 1998, and 09/141,908, filed 28 Aug. 1998, each of which is incorporated herein by reference.

The hybrid PKS-encoding DNA compounds of the invention can be and often are hybrids of more than two PKS genes. Moreover, there are often two or more modules in the hybrid PKS in which all or part of the module is derived from a second (or third) PKS. Thus, as one illustrative example, the present invention provides a hybrid FK-520 PKS that contains the naturally occurring loading module and FkbP as well as modules one, two, four, six, seven, and eight, nine, and ten of the FK-520 PKS and further contains hybrid or heterologous modules three and five. Hybrid or heterologous module three contains an AT domain that is specific of methylmalonyl CoA and can be derived for example, from the erythromycin or rapamycin PKS genes. Hybrid or heterologous module five contains an AT domain that is specific for malonyl CoA and can be derived for example, from the picromycin or rapamycin PKS genes.

While an important embodiment of the present invention relates to hybrid PKS enzymes and corresponding genes, the present invention also provides recombinant FK-520 PKS genes in which there is no second PKS gene sequence present but which differ from the FK-520 PKS gene by one or more deletions. The deletions can encompass one or more modules and/or can be limited to a partial deletion within one or more modules. When a deletion encompasses an entire module, the resulting FK-520 derivative is at least two carbons shorter than the gene from which it was derived. When a deletion is within a module, the deletion typically encompasses a KR, DH, or ER domain, or both DH and ER domains, or both KR and DH domains, or all three KR, DH, and ER domains.

To construct a hybrid PKS or FK-520 derivative PKS gene of the invention, one can employ a technique, described in PCT Pub. No. 98/27203 and U.S. patent application Ser. No. 08/989,332, filed 11 Dec. 1997, now U.S. Pat. No. 6,033,883, each of which is incorporated herein by reference, in which the large PKS gene is divided into two or more, typically three, segments, and each segment is placed on a separate expression vector. In this manner, each of the segments of the gene can be altered, and various altered segments can be combined in a single host cell to provide a recombinant PKS gene of the invention. This technique makes more efficient the construction of large libraries of recombinant PKS genes, vectors for expressing those genes, and host cells comprising those vectors.

Thus, in one important embodiment, the recombinant DNA compounds of the invention are expression vectors. As used herein, the term expression vector refers to any nucleic acid that can be introduced into a host cell or cell-free transcription and translation medium. An expression vector can be maintained stably or transiently in a cell, whether as part of the chromosomal or other DNA in the cell or in any cellular compartment, such as a replicating vector in the cytoplasm. An expression vector also comprises a gene that serves to produce RNA that is translated into a polypeptide in the cell or cell extract. Furthermore, expression vectors typically contain additional functional elements, such as resistance-conferring genes to act as selectable markers.

The various components of an expression vector can vary widely, depending on the intended use of the vector. In particular, the components depend on the host cell(s) in which the vector will be used or is intended to function. Vector components for expression and maintenance of vectors in $E.$ $coli$ are widely known and commercially available, as are vector components for other commonly used organisms, such as yeast cells and $Streptomyces$ cells.

In a preferred embodiment, the expression vectors of the invention are used to construct recombinant $Streptomyces$ host cells that express a recombinant PKS of the invention. Preferred $Streptomyces$ host cell/vector combinations of the invention include $S.$ $coelicolor$ CH999 and $S.$ $lividans$ K4-114 host cells, which do not produce actinorhodin, and expression vectors derived from the pRM1 and pRM5 vectors, as described in U.S. Pat. No. 5,830,750 and U.S. patent application Ser. No. 08/828,898, filed 31 Mar. 1997, and 09/181, 833, filed 28 Oct. 1998, each of which is incorporated herein by reference.

The present invention provides a wide variety of expression vectors for use in $Streptomyces$. For replicating vectors, the origin of replication can be, for example and without limitation, a low copy number vector, such as SCP2* (see Hopwood et al., $Genetic$ $Manipulation$ $of$ $Streptomyces:$ $A$ $Laboratory$ $manual$ (The John Innes Foundation, Norwich, U.K., 1985); Lydiate et al., 1985, $Gene$ 35: 223-235; and Kieser and Melton, 1988, $Gene$ 65: 83-91, each of which is incorporated herein by reference), SLP1.2 (Thompson et al., 1982, $Gene$ 20: 51-62, incorporated herein by reference), and SG5(ts) (Muth et al., 1989, $Mol.$ $Gen.$ $Genet.$ 219: 341-348, and Bierman et al., 1992, $Gene$ 116: 43-49, each of which is incorporated herein by reference), or a high copy number vector, such as pIJ101 and pJV1 (see Katz et al., 1983, $J.$ $Gen.$ $Microbiol.$ 129: 2703-2714; Vara et al., 1989, $J.$ $Bacteriol.$ 171: 5782-5781; and Servin-Gonzalez, 1993, $Plasmid$ 30: 131-140, each of which is incorporated herein by reference). Generally, however, high copy number vectors are not preferred for expression of genes contained on large segments of DNA. For non-replicating and integrating vectors, it is useful to include at least an $E.$ $coli$ origin of replication, such as from pUC, p1P, p1I, and pBR. For phage based vectors, the phages phiC31 and KC515 can be employed (see Hopwood et al., supra).

Typically, the expression vector will comprise one or more marker genes by which host cells containing the vector can be identified and/or selected. Useful antibiotic resistance conferring genes for use in $Streptomyces$ host cells include the ermE (confers resistance to erythromycin and other macrolides and lincomycin), tsr (confers resistance to thiostrepton), aadA (confers resistance to spectinomycin and streptomycin), aacC4 (confers resistance to apramycin, kanamycin, gentamicin, geneticin (G418), and neomycin), hyg (confers resistance to hygromycin), and vph (confers resistance to viomycin) resistance conferring genes.

The recombinant PKS gene on the vector will be under the control of a promoter, typically with an attendant ribosome binding site sequence. The present invention provides the endogenous promoters of the FK-520 PKS and related biosynthetic genes in recombinant form, and these promoters are preferred for use in the native hosts and in heterologous hosts in which the promoters function. A preferred promoter of the invention is the fkbO gene promoter, comprised in a sequence of about 270 bp between the start of the open reading frames of the fkbO and fkbB genes. The fkbO promoter is believed to be bi-directional in that it promotes transcription of the genes fkbO, fkbP, and fkbA in one direction and fkbB, fkbC, and fkbL in the other. Thus, in one aspect, the present invention provides a recombinant expression vector comprising the promoter of the fkbO gene of an FK-520 producing organism positioned to transcribe a gene other than fkbO. In a preferred embodiment the transcribed gene is an FK-520 PKS gene. In another preferred embodiment, the transcribed gene is a gene that encodes a protein comprised in a hybrid PKS.

Heterologous promoters can also be employed and are preferred for use in host cells in which the endogenous FK-520 PKS gene promoters do not function or function poorly. A preferred heterologous promoter is the actI promoter and its attendant activator gene actII-ORF4, which is provided in the pRM1 and pRM5 expression vectors, supra. This promoter is activated in the stationary phase of growth when secondary metabolites are normally synthesized. Other useful $Streptomyces$ promoters include without limitation those from the ermE gene and the melC1 gene, which act constitutively, and the tipA gene and the merA gene, which can be induced at any growth stage. In addition, the T7 RNA polymerase system has been transferred to $Streptomyces$ and can be employed in the vectors and host cells of the invention.

In this system, the coding sequence for the T7 RNA polymerase is inserted into a neutral site of the chromosome or in a vector under the control of the inducible merA promoter, and the gene of interest is placed under the control of the T7 promoter. As noted above, one or more activator genes can also be employed to enhance the activity of a promoter. Activator genes in addition to the actII-ORF4 gene discussed above include dnrI, redD, and ptpA genes (see U.S. patent application Ser. No. 09/181,833, supra) to activate promoters under their control.

Figure 4:
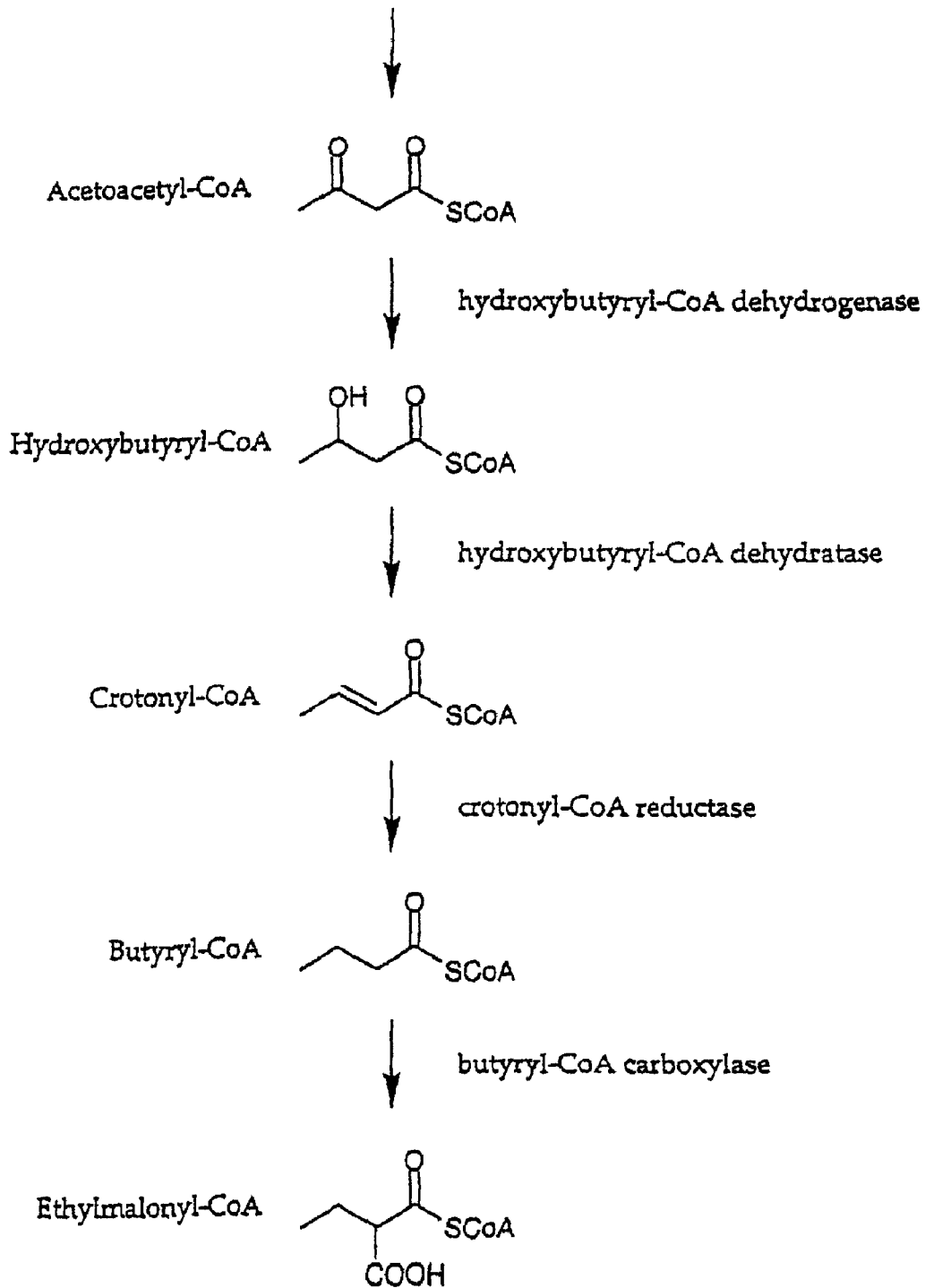
FIG. 4 shows a biosynthetic pathway for the biosynthesis of ethylmalonyl CoA from acetoacetyl CoA consistent with the function assigned to four of the genes in the FK-520 gene cluster shown in FIG. 3.
Figure 5:
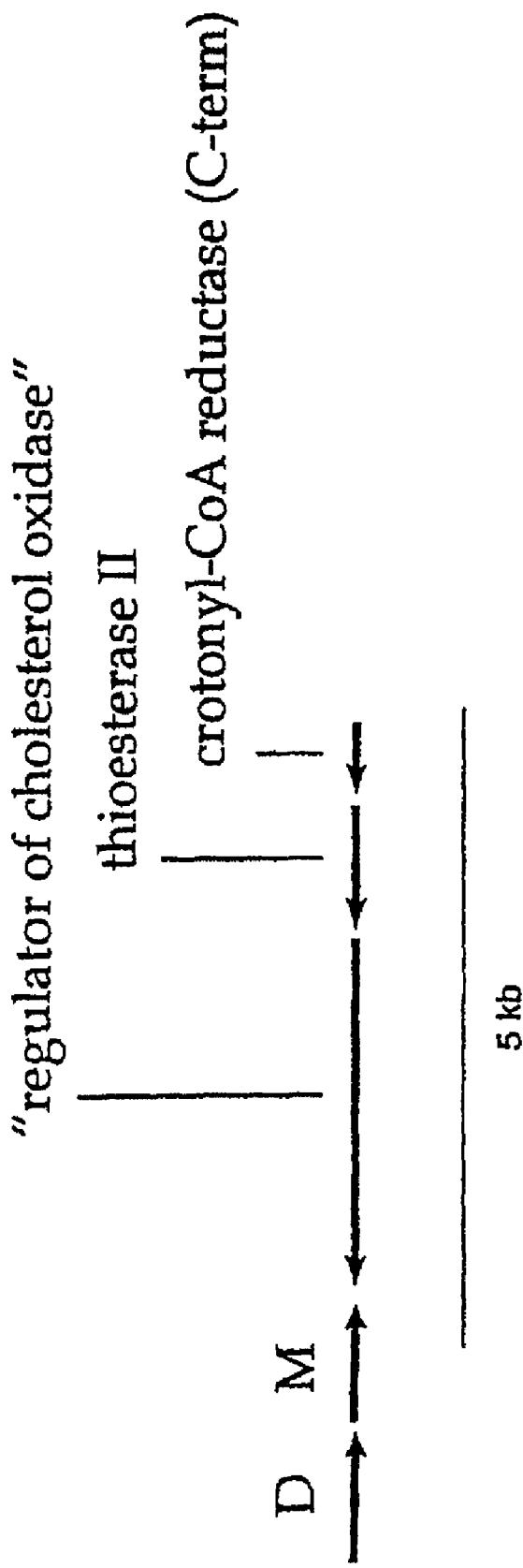
FIG. 5 shows a close-up view of the right-end of the FK-520 PKS gene cluster (and of the sequences on cosmid pKOS065-C31). The genes shown include fkbD, fkbM (a methyl transferase that methylates the hydroxyl group on C-31 of FK-520) fkbN (a homolog of a gene described as a regulator of cholesterol oxidase and that is believed to be a transcriptional activator), fkbQ (a type II thioesterase, which can increase polyketide production levels), and fkbS (a crotonyl-CoA reductase involved in the biosynthesis of ethylmalonyl CoA).

In addition to providing recombinant DNA compounds that encode the FK-520 PKS, the present invention also provides DNA compounds that encode the ethylmalonyl CoA and 2-hydroxymalonyl CoA utilized in the synthesis of FK-520. Thus, the present invention also provides recombinant host cells that express the genes required for the biosynthesis of ethylmalonyl CoA and 2-hydroxymalonyl CoA. FIGS. 3 and 4 show the location of these genes on the cosmids of the invention and the biosynthetic pathway that produces ethylmalonyl CoA.

For 2-hydroxymalonyl CoA biosynthesis, the fkbH, fkbI, fkbJ, and fkbK genes are sufficient to confer this ability on *Streptomyces* host cells. For conversion of 2-hydroxymalonyl to 2-methoxymalonyl, the fkbG gene is also employed. While the complete coding sequence for fkbH is provided on the cosmids of the invention, the sequence for this gene provided herein may be missing a T residue, based on a comparison made with a similar gene cloned from the ansamitocin gene cluster by Dr. H. Floss. Where the sequence herein shows one T, there may be two, resulting in an extension of the fkbH reading frame to encode the amino acid sequence (SEQ ID NO:2):

MTIVKCLVWDLDNTLWRGTVLEDDEVVLTDEIREVITTLDDRGILQAVAS

KNDHDLAWERLERLGVAEYFVLARIGWGPKSQSVREIATELNFAPTTIAF

IDDQPAERAEVAFHLPEVRCYPAEQAATLLSLPEFSPPVSTVDSRRRRLM

YQAGFARDQAREAYSGPDEDFLRSLDLSMTIAPAGEEELSRVEELTLRTS

QMNATGVHYSDADLRALLTDPAHEVLVVTMGDRFGPHGAVGIILLEKKPS

TWHLKLLATSCRVVSFGAGATILNWLTDQGARAGAHLVADFRRTDRNRMM

EIAYRFAGFADSDCPCVSEVAGASAAGVERLHLEPSARPAPTFJTLTLTA

ADIAPVTVSAAG.

For ethylmalonyl CoA biosynthesis, one requires only a crotonyl CoA reductase, which can be supplied by the host cell but can also be supplied by recombinant expression of the fkbS gene of the present invention. To increase yield of ethylmalonyl CoA, one can also express the fkbE and fkbU genes as well. While such production can be achieved using only the recombinant genes above, one can also achieve such production by placing into the recombinant host cell a large segment of the DNA provided by the cosmids of the invention. Thus, for 2-hydroxymalonyl and 2-methoxymalonyl CoA biosynthesis, one can simply provide the cells with the segment of DNA located on the left side of the FK-520 PKS genes shown in FIG. 1. For ethylmalonyl CoA biosynthesis, one can simply provide the cells with the segment of DNA located on the right side of the FK-520 PKS genes shown in FIG. 1 or, alternatively, both the right and left segments of DNA.

The recombinant DNA expression vectors that encode these genes can be used to construct recombinant host cells that can make these important polyketide building blocks from cells that otherwise are unable to produce them. For example, *Streptomyces coelicolor* and *Streptomyces lividans* do not synthesize ethylmalonyl CoA or 2-hydroxymalonyl CoA. The invention provides methods and vectors for constructing recombinant *Streptomyces coelicolor* and *Streptomyces lividans* that are able to synthesize either or both ethylmalonyl CoA and 2-hydroxymalonyl CoA. These host cells are thus able to make polyketides, those requiring these substrates, that cannot otherwise be made in such cells.

In a preferred embodiment, the present invention provides recombinant *Streptomyces* host cells, such as *S. coelicolor* and *S. lividans*, that have been transformed with a recombinant vector of the invention that codes for the expression of the ethylmalonyl CoA biosynthetic genes. The resulting host cells produce ethylmalonyl CoA and so are preferred host cells for the production of polyketides produced by PKS enzymes that comprise one or more AT domains specific for ethylmalonyl CoA. Illustrative PKS enzymes of this type include the FK-520 PKS and a recombinant PKS in which one or more AT domains is specific for ethylmalonyl CoA.

In a related embodiment, the present invention provides *Streptomyces* host cells in which one or more of the ethylmalonyl or 2-hydroxymalonyl biosynthetic genes have been deleted by homologous recombination or rendered inactive by mutation. For example, deletion or inactivation of the fkbG gene can prevent formation of the methoxyl groups at C-13 and C-15 of FK-520 (or, in the corresponding FK-506 producing cell, FK-506), leading to the production of 13,15-didesmethoxy-13,15-dihydroxy-FK-520 (or, in the corresponding FK-506 producing cell, 13,15-didesmethoxy-13, 15-dihydroxy-FK-506). If the fkbG gene product acts on 2-hydroxymalonyl and the resulting 2-methoxymalonyl substrate is required for incorporation by the PKS, the AT domains of modules 7 and 8 may bind malonyl CoA and methylmalonyl CoA. Such incorporation results in the production of a mixture of polyketides in which the methoxy groups at C-13 and C-15 of FK-520 (or FK-506) are replaced by either hydrogen or methyl.

This possibility of non-specific binding results from the construction of a hybrid PKS of the invention in which the AT domain of module 8 of the FK-520 PKS replaced the AT domain of module 6 of DEBS. The resulting PKS produced, in *Streptomyces lividans*, 6-dEB and 2-desmethyl-6-dEB, indicating that the AT domain of module 8 of the FK-520 PKS could bind malonyl CoA and methylmalonyl CoA substrates. Thus, one could possibly also prepare the 13,15-desmethoxy-FK-520 and corresponding FK-506 compounds of the invention by deleting or otherwise inactivating one or more or all of the genes required for 2-hydroxymalonyl CoA biosynthesis, i.e., the fkbH, fkbI, fkbJ, and fkbK genes. In any event, the deletion or inactivation of one or more biosynthetic genes required for ethylmalonyl and/or 2-hydroxymalonyl production prevents the formation of polyketides requiring ethylmalonyl and/or 2-hydroxymalonyl for biosynthesis, and the resulting host cells are thus preferred for production of polyketides that do not require the same.

The host cells of the invention can be grown and fermented under conditions known in the art for other purposes to produce the compounds of the invention. See, e.g., U.S. Pat. Nos. 5,194,378; 5,116,756; and 5,494,820, incorporated herein by reference, for suitable fermentation processes. The compounds of the invention can be isolated from the fermentation broths of these cultured cells and purified by standard procedures. Preferred compounds of the invention include the following compounds: 13-desmethoxy-FK-506; 13-desmethoxy-FK-520; 13,15-didesmethoxy-FK-506; 13,15- didesmethoxy-FK-520; 13-desmethoxy-18-hydroxy-FK-506; 13-desmethoxy-18-hydroxy-FK-520; 13,15-didesmethoxy-18-hydroxy-FK-506; and 13,15-didesmethoxy-18-hydroxy-FK-520. These compounds can be further modified as described for tacrolimus and FK-520 in U.S. Pat. Nos. 5,225,403; 5,189,042; 5,164,495; 5,068,323; 4,980,466; and 4,920,218, incorporated herein by reference.

Figure 8A:
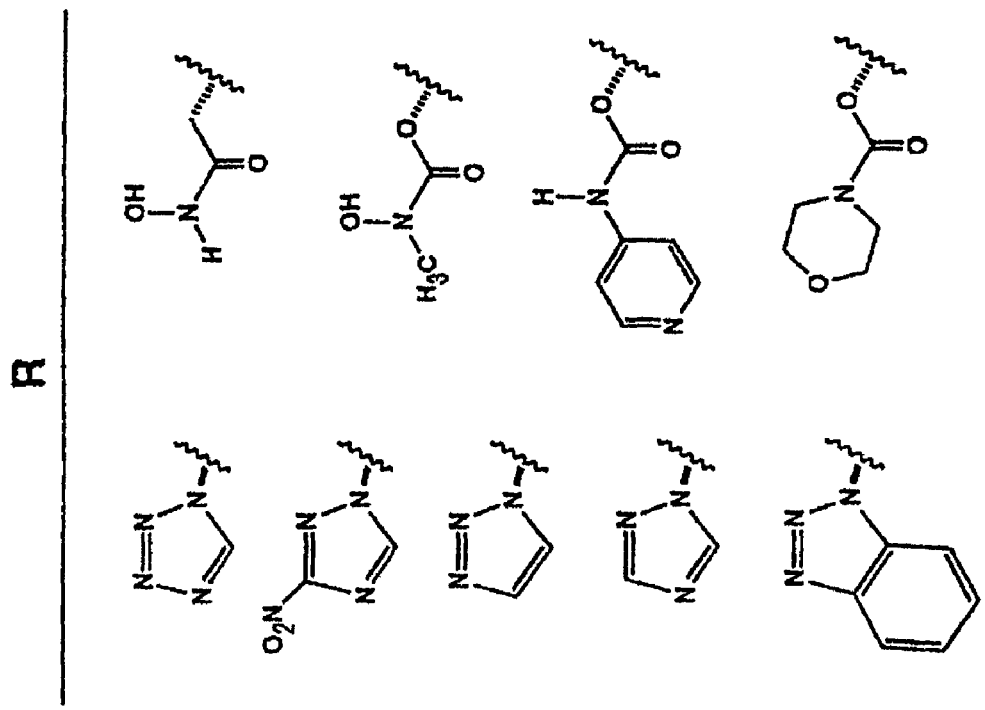
FIG. 8, in Parts A and B, shows certain compounds of the invention preferred for dermal application in Part A and a synthetic route for making those compounds in Part B.
Figure 8A:
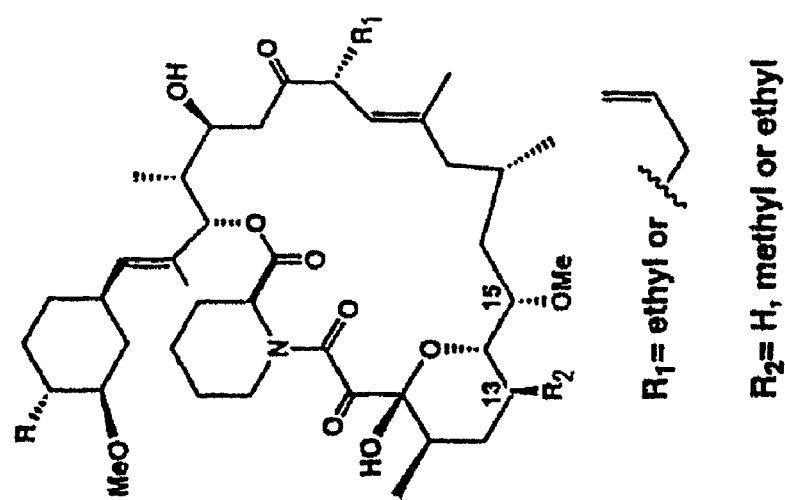
Figure 8B:
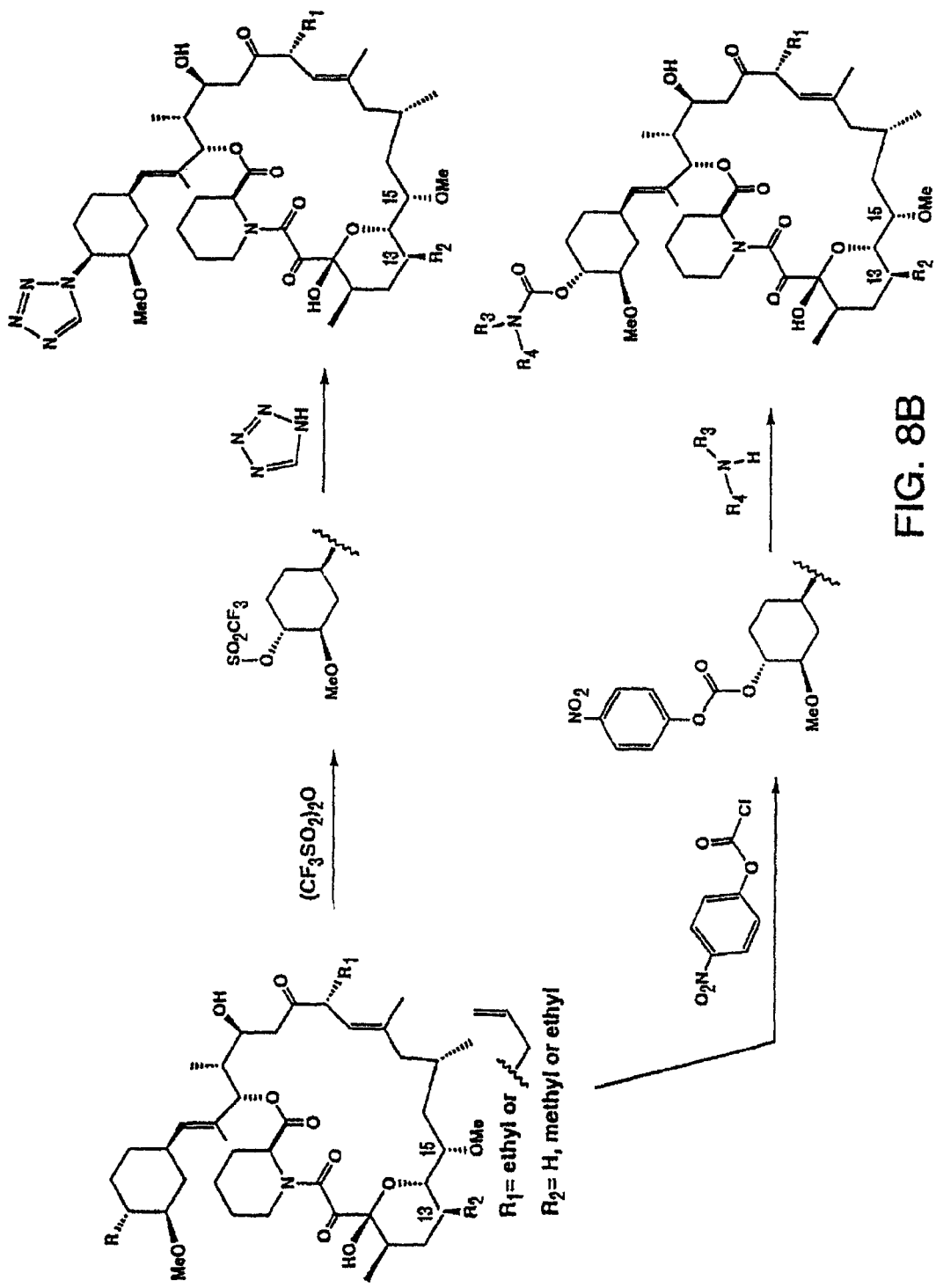

Other compounds of the invention are shown in FIG. 8, Parts A and B. In FIG. 8, Part A, illustrative C-32-substituted compounds of the invention are shown in two columns under the heading R. The substituted compounds are preferred for topical administration and are applied to the dermis for treatment of conditions such as psoriasis. In FIG. 8, Part B, illustrative reaction schemes for making the compounds shown in FIG. 8, Part A, are provided. In the upper scheme in FIG. 8, Part B, the C-32 substitution is a tetrazole moiety, illustrative of the groups shown in the left column under R in FIG. 8, Part A. In the lower scheme in FIG. 8, Part B, the C-32 substitution is a disubstituted amino group, where $R_3$ and $R_4$ can be any group similar to the illustrative groups shown attached to the amine in the right column under R in FIG. 8, Part A. While FIG. 8 shows the C-32-substituted compounds in which the C-15-methoxy is present, the invention includes these C-32-substituted compounds in which C-15 is ethyl, methyl, or hydrogen. Also, while C-21 is shown as substituted with ethyl or allyl, the compounds of the invention includes the C-32-substituted compounds in which C-21 is substituted with hydrogen or methyl.

To make these C-32-substituted compounds, FIG. 8, Part B, provides illustrative reaction schemes. Thus, a selective reaction of the starting compound (see FIG. 8, Part B, for an illustrative starting compound) with trifluoromethanesulfonic anhydride in the presence of a base yields the C-32O-triflate derivative, as shown in the upper scheme of FIG. 8, Part B. Displacement of the triflate with 1H-tetrazole or triazole derivatives provides the C-32 tetrazole or teiazole derivative. As shown in the lower scheme of FIG. 8, Part B, reacting the starting compound with p-nitrophenylchloroformate yields the corresponding carbonate, which, upon displacement with an amino compound, provides the corresponding carbamate derivative.

The compounds can be readily formulated to provide the pharmaceutical compositions of the invention. The pharmaceutical compositions of the invention can be used in the form of a pharmaceutical preparation, for example, in solid, semi-solid, or liquid form. This preparation contains one or more of the compounds of the invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, solutions, emulsions, suspensions, and any other form suitable for use. Suitable formulation processes and compositions for the compounds of the present invention are described with respect to tacrolimus in U.S. Pat. Nos. 5,939,427; 5,922,729; 5,385,907; 5,338,684; and 5,260,301, incorporated herein by reference. Many of the compounds of the invention contain one or more chiral centers, and all of the stereoisomers are included within the scope of the invention, as pure compounds as well as mixtures of stereoisomers. Thus the compounds of the invention may be supplied as a mixture of stereoisomers in any proportion.

The carriers which can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid, or liquified form. In addition, auxiliary stabilizing, thickening, and coloring agents and perfumes may be used. For example, the compounds of the invention may be utilized with hydroxypropyl methylcellulose essentially as described in U.S. Pat. No. 4,916,138, incorporated herein by reference, or with a surfactant essentially as described in EPO patent publication No. 428,169, incorporated herein by reference.

Oral dosage forms may be prepared essentially as described by Hondo et al., 1987, *Transplantation Proceedings XIX*, Supp. 6: 17-22, incorporated herein by reference. Dosage forms for external application may be prepared essentially as described in EPO patent publication No. 423,714, incorporated herein by reference. The active compound is included in the pharmaceutical composition in an amount sufficient to produce the desired effect upon the disease process or condition.

For the treatment of conditions and diseases relating to immunosuppression or neuronal damage, a compound of the invention may be administered orally, topically, parenterally, by inhalation spray, or rectally in dosage unit formulations containing conventional non-toxic pharmaceutically acceptable carriers, adjuvant, and vehicles. The term parenteral, as used herein, includes subcutaneous injections, and intravenous, intramuscular, and intrasternal injection or infusion techniques.

Dosage levels of the compounds of the present invention are of the order from about 0.01 mg to about 50 mg per kilogram of body weight per day, preferably from about 0.1 mg to about 10 mg per kilogram of body weight per day. The dosage levels are useful in the treatment of the above-indicated conditions (from about 0.7 mg to about 3.5 mg per patient per day, assuming a 70 kg patient). In addition, the compounds of the present invention may be administered on an intermittent basis, i.e., at semi-weekly, weekly, semi-monthly, or monthly intervals.

The amount of active ingredient that may be combined with the carrier materials to produce a single dosage form will vary depending upon the host treated and the particular mode of administration. For example, a formulation intended for oral administration to humans may contain from 0.5 mg to 5 g of active agent compounded with an appropriate and convenient amount of carrier material, which may vary from about 5 percent to about 95 percent of the total composition. Dosage unit forms will generally contain from about 0.5 mg to about 500 mg of active ingredient. For external administration, the compounds of the invention can be formulated within the range of, for example, 0.00001% to 60% by weight, preferably from 0.001% to 10% by weight, and most preferably from about 0.005% to 0.8% by weight. The compounds and compositions of the invention are useful in treating disease conditions using doses and administration schedules as described for tacrolimus in U.S. Pat. Nos. 5,542,436; 5,365,948; 5,348,966; and 5,196,437, incorporated herein by reference. The compounds of the invention can be used as single therapeutic agents or in combination with other therapeutic agents. Drugs that can be usefully combined with compounds of the invention include one or more immunosuppressant agents such as rapamycin, cyclosporin A, FK-506, or one or more neurotrophic agents.

It will be understood, however, that the specific dosage level for any particular patient will depend on a variety of factors. These factors include the activity of the specific compound employed; the age, body weight, general health, sex, and diet of the subject; the time and route of administration and the rate of excretion of the drug; whether a drug combination is employed in the treatment; and the severity of the particular disease or condition for which therapy is sought.

A detailed description of the invention having been provided above, the following examples are given for the purpose of illustrating the present invention and shall not be construed as being a limitation on the scope of the invention or claims.

Complementary Sequences of fkbB Coding Regions

Complementary Sequence of Nucleotides 44974-46573 of SID: 1:
```
atggcgcgtgtggaaccaatccggccgttgcacgaattgctccgcatccatgccgagcgacgcggcgaccggatcgcctacacggattcccaacgcgccgt
gacgtacacgcaactccggctccgggccggccggctcgccggacacctcgccgcgtccggcgtcgaccgcggcgaccgggtcgcgatgctgctggcaaccg
gatcgagaccatcgaggtctacctcgccgccgccgcgccgcgccgcgtcgccgtcccgctcaacccggacgccgccgacgccgaactcgcccacttcctga
cggactccggcgcgaccgtgctggtcaccgacgaaacccacctcgaccaggtgcgccgcaccggcaccgacgccaccgtcgtgctcgtcgggcgccgggca
ccggactgcgtctcctacgaggacctcgccgggaccgagccgccgtgcccgcccgcgacgacctcggcctggacgaacccgcctggatgctctacacctc
cggcaccaccggccgtcccaagggcgtggtttccgcacagcgcagcggcctggtgcgacgtgccgtcctggcggctgaccgaggacg
acgaactgctctggcccgcccgctgttccacagcctcggccaccacctctgcctgctcgccgtcctcacggtcggcgcgtccgcccgtatcctgggcggc
ttcgtcgcgcgtgacgtcctcgacgccctggccgaacactccagcaccgtgctcgtcggcgtgccgacgatgtaccgctacctcctcggcgccgtgtccgg
cgagccgcggctcgcgcgctgcgcgtggcgctggtcgccggatccacctcgccggcgtcgctcaccagggatttcgaggcgacgttcggcgtgccctgc
tcgacacgtacggctgcaccgagacgaccggctcgctcaccgccaacaccctggaggatgcgcgggttcccggctcgtgcgggctgcccgtgccgggcctg
tcgctgcggttcgtcgaccggtgtccggcgccgacgtggcaccggcgaggagggcgagctgtgggcgagcgggccgagcctcatgctcggctaccacgc
ccagccggaggcgaccgcccaggtgctcgtggacggctggtaccgcaccgggacctcgcacgtcaggccgagaccggacacgtgacgatcaccggccggg
tcaaggagctgatcatccgcggcggggagaacatccaccccgggagatcgagaccgtcgcccaggaggtggccggtgtccgggacgccgccgcgtacgtc
gcgggccgcccgcacccccgtcctcggcgacataccccgtgctcgtttccgacggccccccgcgtccccgccgaggcgatcctcgccgagtgccgccgccggt
cgcctacttcaaggtgcccgacgagatctggcacgtcaccacgatccccccgcaccgcgtcgggcaaggtccagcgccgcggctcgcggggctgccggccc
atctggtcgccaccggcagtggcgaggccacgctgtgcgaactggtctgggagcggcgcgacctgcccggcacccgtcacccc (SEQ ID NO: 75)
```

Complementary Sequence of Nucleotides 43777-44629 of SID: 1:
```
ggcgaggtccgcatcgacgtccgcgccgcggggctgaacttccgcgacgtgctgatcgcgctcggcacctacccgggcgagggcgagatgggcgggagc
cgcgggcatcgtgaccgaagtcggaccggcgtcgacgacctggccccggcgaccgcgtgttcggtctcgtgcaggacgcgttccggcgcagcgtggtcg
cggaccggcggctggtcgcacggatcccacgggatggtcgttccccatcgccgcgtccgtgcccatcgtgttcgccaccgcctggtacggcctcgtcgac
gcgggcgagctgcgaccggccagaaggtcctggtccacgccgcgacgggcggtgtcggcatggcggcgaccggatcgcccgccacctcggcgccgaggt
gtacgccaccgccagtcccgccaaacaacacctgctgcacgccgacggcttcgacaccgaccatgtggcgaactcccgcagcgccgcgttcgccgacacct
tcccgccggtcgacgtcgtgctcaactcgctcaccggtgaactcctcgacgcgtccatcggcctgctcgcaccgggcggccggttcgtcgagatgggcaag
accgacatccgccacgccgcccagcagccgttcgacctggccgacgtggatcccgcgcgcctgcgggagatcctcgaactgctcctcgacctgttcgaccg
cggtgagctgtgcccgctgccggtgcagccgtgggacatccgccgtgcgcgggacgcgttcgcgtggatgagccacgcccggcacaccggcaagatggtcc
tcaccgtgccgcctccgatcggcccggacgcgccggtcctggtca (SEQ ID NO: 76)
```

Complementary Sequence of Nucleotides 43144-43660 of SID: 1:
```
gacggcccggccggcgccgacgcccacacccggccacgggccgcggagggactccccaccgtcaccgtccgcgcgctgcccggcatcgaacggccggcgct
caccggcgacctgatcgagaaggccatcgcggggcggcggctcgtacatcgtggcccggaccggttccgccggggcgcgggccgcgacgatggcgggcgcca
cgccgccgatcctcaccgcactgaccggaccggccgagcccgacgccacggaacaggagtgggcgaaccgcctcgccgcggcccgtgcgggccgggaggac
gtactgctcgacctggtccgcgacagcgtcgccaccgtcctgggcctgccgggcgccggacactgtcccggaccgcacgttccgcgagaacggcctcgac
tcgctcaccaccgtcgagttcaccaacaccgtcgccgcgcggacgggtctgcgggtgcccgcgtcaaccgcgttcgaccaccccactccgcgtgcgttcgc
cgcccacctcg (SEQ ID NO: 77)
```

Complementary Sequence of Nucleotides 41842-43093 of SID: 1:
```
gacccgtcgcgatcgtcggcatggcgtgccgactgcccggcggggtcgcctcgccggaggacctgtggcggctcgtcgccgccggtaccgaggcgatcac
cgagttccccaccgaccggggctgggacgtcgacgcgctgtacgaccccggaccgggccggcgcctccacgacacgccacgcgggattcctggccg
gcgccgggttcgacgccgcgttcttcggcatcagtccgaacgaggcgctggcgatggaccccagcagcgcctgatcctggagacctcctggaggcgttc
gagaacgccggcatcgtgccggacaggctccgggagagcgacaccggcgtgttcatgggcgcgttcaaccagggctacggcgtcggccgggacctgggcgg
gctcggtgtcacggcgacgcagacgagcgtcctgtccgggcgcctctcgtacgtgtacggacttcagggccggcggtcacggtcgacacggcgtgctcgt
cgtcgctggtcgccctgcaccaggcggcacaggcactgcgggccggggagtgctccctggcgctggtcggcggtgtcaccgtcatggcgaacaccgcagag
ctcgtggagttctcccggcagcgcggactctcccgcggagcggtgcaaggcgttcgccgacgcgcggaccggagccggcttcgccgagggcgtcggcgt
tctcgtgctggagcggctctccgacgccgagcgcaacgggcacaccgttctcgccggtcgtccgcggctcggcggtgaaccaggacggtgcctccaacggac
tgtccgcccaacggcgtcgcccagcagcgcgtgatccggcaggcgttggtcaacgccggactgcgcgccgccgatgtggacgtggtggaggcgcacggc
accggcacgcggctgggcgaccgatcgaggcgcaggccgtcctcgcggcctacgggcaggaccgcgacacgccgctctacctcggttcggtcaagtcgaa
catcggtcatgcgcaggcggctgcgggtgtcgccggtgtcatcaagatggtcatggcgatgcggcatgggatcgcgccgaagacgctgcacgtggacgagc
cgtcgtcgcatgtggactggtcggccggtgcggtggagctgctcaccgaggcgaggccgtggcccgagtcggatcgggcaccgcatgcgggtgtgtcgtcg
ttcgggggtgagcggtacgaacgcgcacgtgatcctggagg (SEQ ID NO: 78)
```

Complementary Sequence of Nucleotides 40609-41842 of SID: 1:
```
ggtgttcctgggccgtcgcgtgtggagtcgggtggtgatgggttggtgccgttgccggtgtcggctcgtggtgaggtgagtctgcgggggcaggtggagcg
gctggaggggtatctgcgcggggtggggtggatgtggccgcggtcgcgcaggggttggtgcgtgagcgtgctgtcttcggtcaccgtgcggtgctgctgg
gtgatgcccgggtgatgggtgtggcggtggatcagccgcgtacggtgttcgtcttccccgggcagggtgcccagtgggtgggcatgggcgtggaactcatg
gaccgttccgcggtgttcgcggctcgtatggaggagtgtgcgcgggcgttgttgccgcacacgggctgggatgtgcgggagatgtgtcgcggtcggatgt
ggcggagcggtggaggtggtccagccggccagctgggcggtcgcggtgagcctggccgcgctgtggcaggcgcatggggtcgtgccgacgctgtggtcg
gacactcgcaggggagatcgcggcggcgtgtgtggccggagccctcagcctggaggacgccgcccgcgtggtggcgttgcgcagtcgggtgatcgcggcg
cggctggccggccgggggcgatggcttcggtggcgttgccggccggtgaggtgggtctggtcgagggtgtgtggatcgcggcgcgtaatggtccggcttc
gacggtggtgcggggaccccgtcggcggtggaggagggtgcgggtgatggggtcgatgtgatggggtgcgggtgcgtcgtatccggtcgactacgcctccc
acacgcctcacgtggaggccatcgaggacgaactcgctgaggtactgaaggggaatttccggcgggacccgggtcggtggcgtggtggtcgaccggtggacagc
gcctgggtgaccgagccggtggatgaggggtactggtaccggaacctgcgtcgccctgtcgcgctggatgcggcggtggcggagctggacgggtcggtgtt
cgtggagtgcagtgcccatccggtgctgctgccggcgatggaacaggcccgcacggtggcgtcgttgcggactggtgacggtggctgggagcggtggctgg
gggcgttggcgcaggcgtggactctggtgcggggtggactggggcacggtggtcgaaccggtgccggggcggctgctggatctgcccacctacgcgttc
gagcacaggcggtactggctgg (SEQ ID NO: 79)
```

-continued

Complementary Sequences of fkbB Coding Regions

Complementary Sequence of Nucleotides 39442-40609 of SID: 1:
gaggcggccggtgccaccgacctgtccgcggccgggctgaccggggcggcgcatccgatgctggccgccgtcacagcactgcccgccgacgacggtggtgg
tgttgttctcaccggccggatctcattgcgtacgcatccctggctggctgatcacgcggtgcggggcacggttctgctgccgggtacggcgtttgtggagc
tggtcatccgggccggtgacgagaccggttgcggggtggtggatgaactggtcatcgaatccccgctcgtggtgccggtgaccgcagcggtggatgtgtcg
gtgaccgtggaagggccgatgaggccggacggccggccggtgacgtccacgcgcgtaccgagggcacgggcagctggaccccggcacgccagcggcaccct
gaccccgacacccggataccctccaacgcttccggtgagccgttctcgcagtggccgccggccacggccgcggccgtcgacgtctcgggggttctatgacg
aactgcgggatgccggttatgagtacgggtcggcgttccagggggttgcgggctgcctggcgtgatggtgacaccgtgtatgccgaggtggcgctgcccgac
gagcaggccgccgaggcggacggtttcggtgtgcatccggcactgctcgacgcggccctgcacgccgggcgcctcgacgcgggcggcgggatcgagctgcc
gttctcctggacgggcgtgcgcctgaacgccaccgggggccgccgcggtgcgtcgccctcaccgggggggaggccggcgtcgccgtgcgcgtggccgacc
cggatggccgtcctgtcgtgtcggtggactcgctggtgctgagggagcgggccgacacccgtcggggcgaaccgctccggttggagtggctcgcggtc
gccgaggcggtctacgacggtgacctgcccgagggacacgtcctgatcaccgccgcccacccgacgaccccgaggacataccaccgcgcccacacccg
cgccacccgcgtcctgaccgccctgcaacaccacctcaccaccaccgaccacaccctcatcgtccacaccaccaccgaccccgccggcgccaccgtcaccg
gcctcacccgcaccgcccagaacgaacaccccaccgcatccgcctcatcgaaaccg (SEQ ID NO: 80)

Complementary Sequence of Nucleotides 38677-39307 of SID: 1:
ctcaaccccgaacacgccatcatcatcaccggcggctccggcaccctcgccggcatcctcgcccgccacctgaaccaccccacacctacctcctctcccg
caccccaccccccgacaccaccccccggcaccccacctccccctgcgacgtcggcgaccccccaccaactcgccaccaccctcgcccacatccccaaccctca
ccgccgtcttccacaccgccgccacctcgacgacggcatcctcgacgccctcacccccgaccgcctcaccaccgtcctccaccccaaagccaacgccgcc
tggcacctgcaccacctcacccaaaaccaaccccctcacccacttcgtcctctactccagcgccgccgccgtcctcggcagcccggacaaggaaactacgc
cgccgccaacgccttcctcgacgccctcgccaccaccgccacaccctcggccaacccgccacctccatcgcctggggcatgtggcacaccaccagcaccc
tcaccggacaacttgacgacgccgaccggcagcgggtgcgcgacgggttccggccgctcaccgaggccgagggcacccacttcatcgacgcgagcctcgcc
gcggacgtgccgttcatggtcgcgg (SEQ ID NO: 81)

Complementary Sequence of Nucleotides 38371-38581 of SID: 1:
ctgctggccatcgtgtgtgcggccacggccgccgtgctcggccacgccgacgcctccgagatcacgcccacgacggcgttcaaggacctcggcatcgactc
gctcagcggtgtccggttgcgcaacagcctcgccgagacgacgggggtacggctctccgcgacggccgtcttcgaccacccgacaccggccgcgctcgccg
cccgcctgg (SEQ ID NO: 82)

Complementary Sequence of Nucleotides 37141-38296 of SID: 1:
gagccgctggcgatcgtggccatggcgtgccggatgccggtggcgtgccgtcacggaggacctgtgcggctggtcgactccggcggggacgcgatcac
cgagttccccgccgaccgcggctgggacctcgccgcgcgctctacgaccgaacccgacgcggtcggcaaggtttccgtgcgtcacggcggcttcctcaccg
gcgccgccgacttcgacgccgcgttcttcgggatcagcccgcgtgaggcgctggcgatggaccgcagcagcgtctggtcctcgaagcgtcgtgggaggcg
ttcgaacgagcgggcatcctgcccgaaagcgtccgcggcagcgacaccggcgtattcatgggcgcgttcacccagggctacggcgcgggcgtggacctggg
cggtttcggggcgaccggcacgccgaccagcgttctctccgggcggctctcgtactacttcggtctggaggggcccgtcggtcaccgtcgacacggcgtgtt
cgtcgtcgctggtggcgctgcaccaggccgcgcggtcgctgcgctcggggagtgctcgctcgccctggtcggcggtgtcacggtgatggcgacgacgacc
gggttcgtcgagttctcccggcagcgcgggctcgccccccgacggccgtgccaaggccttcgcggacaccggacggcacgagcttcgccgagggcgccgg
tgtcctggtgctggagcggctctccgacgccaccgccacggccaccccgtgctggcgctggtgcgcggctccgcggtcaactccgacggcgcgtcgaacg
ggctgtccgccccgaacgggcctgcgcagcagcgcgtcatccagcgtgcgctcgccgacgccggctggcgccgggtgacgtcgacgccgtggaggcacac
ggcaccggcacccgtctcggcgacccgtcgaggcccaggccctgcaagtggcctacgggcgcgaacgcgtgcatccgctgctgatcggctcgctcaagtc
gaacatcggccacaccaggccggccggcgtcgccggcgtcatcaagatggtcatggcgatgcggcacggcgtcctgccgcgcacgctgcacgtcgacg
agccgtcccggcacgtcgactgggacggcgacatccggctg (SEQ ID NO: 83)

Complementary Sequence of Nucleotides 35749-37144 of SID: 1:
ctgcaccgcagtgagccgtggccggtcaccgggcgcgcccggcgtgcgggtgtctcgtcgttcggcatcagcggcaccaacgccatgtcgtcctggaggc
cgggcccccgccgcgcccgcaccgtgtccgcaccgaagccgagccggtgcccgaggacgtggtctggccgatgtcggccggaccccggagggactgc
gggacgtcgcgggacagctggccccgctcactggcgccgcggccgcggtcggccactcgctcgccaccaccggacggccatgcgccaccgggcggtcgtg
ccggcccgagaggcggaggcgttcgccgtgcgtcgccgaagtgccggggccgtgacggggccgtcaccgacacacgtgtgtcgcgttccc
cgggcagggctcccagtgggccggcatggtgccgaactgctcgccaccgagccgtgttcgcccggcggctccgcgagtgcgccacggcgctcgcccccgc
acaccggatgggacctgctggacgtcatcgcccagcggcccggagcgcccgcgttcgacgggtcgatgtcgtcagcccgcgtcgttcgcggtgatggtg
gcgctggcggagctgtggcgtgcgcacggggtcgcccgcgccgcggtcgtcggccactcccagggcgaagtcgccgcggcctgcgtcgccggggtgctcac
cctggacgacgccgcgaaggtcgtcgcggtgcgcagccgactcgtcgccaccgaactggccgggcaggggcggcatggtctcggtgccgcccgccgacttcg
acgccgccgtgtgggccgggcgcctggaggtcgccggtcaacggaccccgtcgatcgttgtcgccggtgcggccgacgccgtggaggagctgctggcc
gccacccccgcgcccgccggatcgccgtcgactacgcgtcgcacaccgcgcatgtcgaaacgatccgcggcgcgctgctcgacgctctcgccggcatcac
tccgcgcacgccggacgtcccgttcttctccaccgtggacgaggcgtggctggaccggcccgcggacgccgcctactggtacgacaacctgcgccgcaccg
ttcggttcgccgccgcgaccggccaccacctgccggaccgcggataccgcgcgtcgtcgaggtcagccgcatccgtgctcaccaccgcactggaggacacg
ctcgccgggcatcgcgcatacgtcgtcaccggcacactgcggcgaggcgagggcggcctggaccgcttcactcggtcgctcgccgcgctctgggtccgggg
cgtgcccgtcacctggtcgttcgcgacgcgtcgggtggtgccgctgcccacgtaccgttccgccgtgaccgctactggatcg (SEQ ID NO: 84)

Complementary Sequence of Nucleotides 34606-35749 of SID: 1:
gacgcggaaccggcgggaacgtccggccaccgctgctcggctcgtgggtcgacctcgcccgacggcgagggcgcgctggccaccgcggtgtctcggtacg
ccgtcagccctggctcgccgaccacgaggtggacggccgggtcatcgtgcccggctcggcgctcgtggaactgctcgccgaagcgggagccggctcggca
cgccggagatcgcggagctgaccatcgtcgcgccggtggtggtcgacggcgacggcgacacggagatccaggccaccgtcggaaccgaggtgtccggacgg
cggtcggtgagtctgcacagccgtaccggcacgggccctgggcgctcagtgcgaccggagcgctgagcgtggacactggcggtccggcggagccgtgga
ctggccgcccgcgacgccgaccgccgaccgaccgacgccgacggcttctacgacgcgtccgctctcgtacgggccccgcgttccgggccatgaccgcgatgtgga
cggggagggccgcgcctacgcgtcggtccgcctcgccgaacagctcaccgacgccggtacgggctgcacccccgtgctgctcgacgcggccctgcacgcc
ctcgggacggtcttcacggaccccgagcggcgccggctggcgttctcctggtccggcgtgaggatccacgcgcgcgccgcgaccgcgctgcgcgtgctgct
ggaacgcgtcggccccgacatggtccgcatcgtcgccacggacgagcacggctcaccggtccttgacgtcgacagcctgaccgtgcgggcgcgccacccg
atgccgaggcgctgttcgagatcgcctgggtgcccgtcgccccgcctcaccgtccccgactggacgtacctcgccgacgtgcccgacggcgagcacccccg
gtcgtggtcctggccgtggaaccggcgacccgggcacctcgccggcgcccggcccggagctgggccgacctgctcaccaccgtcagacctggct
cgccgagccgcgctgggcgcgatcccggctcatcgtggccaccgtaccggcgatccgcgcaggaagcgctcggcggcctggtccggacggcggagacgg
agcatccggccgcgtcgccctgatcgaagcgg (SEQ ID NO: 85)

Complementary Sequence of Nucleotides 33823-34480 of SID: 1:
ccgctgaccggcgggaccgtcctcgtcaccggcggcaccggcgggctcggcgcctcctcgtggaccacctgctcaccgtgcacgaggccgccgaggtcgt
cgtggtgtcccgcaacggccggcccggcgacacgccggaggacgaccgcgtgcggtacgtggccgccgacgtcgtcgaccgcgacgagctggccgcagtcg
tcgccgacgtcgcccagcggctgcgcgccgtcgtgcacatggccgggatcgtcgacgacgcggccgtgacgaccatgcggccggagcagtgggacgccgtg

Complementary Sequences of fkbB Coding Regions ctgcgggtcaaggcggacgtcgcctggcacctgcacgagctgacgcgcgatctcgacctggccgcgttcgtcctgtactcgtccatatccgccacgttcgg
cggcgcgggtcaggccaactacgcgaccggcaacgcgttcctcgacgcgctcgcccgccaccgaccaccagggcgtgcccgccgtctcgctcgcctggg
gactgtgggacgcggcggacgggatgggcgggcggctgaccgccaccgacctggcccgcatcgcccgcaacggcatgaccccgatgacggccgcacaggg
ctcgccctgttcgacgcggccctgcacaccgaccggcccgcgctcgtgccga (SEQ ID NO: 86)

Complementary Sequence of Nucleotides 33505-33715 of SID: 1:
atgctcgacctcgtccgtaccagcgctgccgcggtgctcggccaccgcgacgcccacgccatcgcacccgcgcgcgcgttcagggaagtgggcttcgactc
gctgaccggcgtcgaactgcgcaaccggctggccgacgcgacgggcctgacgctgcccgctacgctcgtcttcgaccaccccacggcgcaggcgctcgccg
cccacctgg (SEQ ID NO: 87)

Complementary Sequence of Nucleotides 32185-33439 of SID: 1:
gagccgttggcgatcgtggggatggcctgccggctgccgggtggggtcgcgtcgccggaggacttgtggcggctgctggagtcgggtggtgacgggatcac
ggcgtttccgacggaccgtggttgggacgtggacgggctgtacgatcccgatccggatcatccgggcacgtcgaccgtgcgtcatggtggcttcctcgccg
gggtggcggacttcgacgcggcgttcttcgggatcagtccgcgtgaggcgctggcgatggacccgcagcagcgtctggtcctggagacctcgtgggaggcg
ctggaacacgccgggatcctcccggagtcgctgcgcggaagcgacaccggcgtgttcatgggcggctacttctacggtttggagggtccggcggtcacggtggacacggcgtgtt
cgtcgtcgctggtggcgctgcaccaggccgggcagtcgctgcgctcggggagtgctcgctcgccgtggtcggcggcgtcacggtgatggcctcgccgtcc
ggcttcgtggacttctcccagcagcggggcctctcccgacggccgctgcaaggcgttcgcggatgcggctgatggcaccggtttcgccgagggatccgg
tgtgctgatcgtcgagaggctctccgacgccgagcggcacgaccacaatgtcctggcggtcgtgcgtggttcggcggtcaaccaggacggtgcttccaacg
ggttgtcggcgccgaacgggccgtcgcaggagcgggtgatccggcaggcgctggccaacgccgggctcacccccggggatgtggacgctgtcgaggcgcat
ggcaccgggaccaggctgggcgaccccatcgaggcgcaggcggtactggccacctacgggcagcatcgcgacaccccggtgctgctgggctcgctgaagtc
caacatcggccacactcaggccgccgcgggcgtcgccggtgtcatcaagatggtcctcgccatgcggcacggcaccctgccgcgcaccctgcacgtggaca
cgccgtcctcgcacgtcgactggacggccggccgcgtcgaactcctcaccgacgccgccctggcccgaaaccgaccgccacggcgcgccggggtgtcc
tccttcggcgttagcggcaccaacgctcacatcatcctcgaaa (SEQ ID NO: 88)

Complementary Sequence of Nucleotides 31018-32185 of SID: 1:
agccaccccgaccggccccgaaccgccccggcaccgacaccggaccgctgccctgctgctctcggcacgcaccccgcaggcactcgacgcacaggt
acaccgcctgcgcgcccacctcgccaccggcgaggaggacgagcgcgcggtggccgcggcccctgctcgcccgcacggccttccccgcaccgggccgcgctga
tcggcaccgacacggtcaccggcgccgcagaaccggaccgccgcctcgtgtggctcttctccggacagggctcacaaacgtcccggcatgggcgacggactg
gccgccgcctacgacgtcttcgcccgcactcgccgcgaggtgctggacgccctcgacgtgccgccgggctcgacctccacgacaccgggtacgcccagcc
cgcggtgttcgcgctccaggtcgcactcggcgcacagctcgaggcgtggggcgtacgcccggacgccttcgtgggccattcgatcggcgagctggccgccg
cgtacgtcgccggcgtctggtccctggaggacgcgtgcaggctggtgtccgcacggcccgcctgatgcaggcgctgccgtccggcggggcgatgccgcc
gtgatcgcgtcggaacgggacgcgctgccgctgctgcgggacggcgtggagatcgccgcggtcaacgggcccgcgtcgatcgtgctctccggtgacgagga
ggcggtgctcgacgtcgcggcccggctcggccgcttcacccgcctgcggaccagccacgcgttccactcggcgcggatggagccgatgctcgaggagttcc
gcaaggtcgcggagagcctgacgtaccacgagccgaggatcccgatggccgcgccgctgcaccacgccggagtactgggtacgacaggtccgcgac
accgtccggttcggggaacaggtcgccgcgcacgacgggcggtgctcctggagatcggcccggaccggagcctgaccgactcgtcgacggcatcccgat
gctgcacgccgacgacgaaccgcgatccgcctgaccgcgctcgcccggctgcacaccgacggcgtcacggtcgactggccgaaggtcatcgaccccgcgc
cggcacgcgcctcgcacccgccgacgtacccgttcgagcgggtccgctactggctcg (SEQ ID NO: 89)

Complementary Sequence of Nucleotides 29869-31018 of SID: 1:
ggcacccagaccgcggggcgacgcggccccggccggacagacgccggtcgcgcacccggcgctgaccgcggcggtcaccctgcccggcaccggcgacctggt
gctcaccggccgggtcgacgccgccgatccgctggcgcactccctgcacggcctcgcggtgctgcccgccgcggccctcctggatctggcgatccgggcgg
gcgacgaagccggctgcggcgccctcgacacgttcaccgtggacacccccctcacgctgccgcggtccggtgcgctcgcgctctccgtccacggtgagcgcg
cccggggcggacggccgccgccgcgtcaccgtgcacacgcggcacgcggcggggagtggacgagcacgcacggaatcctcgcccccgaccgcggac
ggccccggccgtgcgggagatgccgtcgacgtggccgcccgccacgccccggcggtggaccccgacacatccgccgaccgtctgcccgagccgggtaca
cggacggcccgcgctgccccgcccgcgccgtctgggccgacgacgacgccgtctgggcggaagtggccctcgccgacggacagctcgccgacgccgga
cggtacggcctgcaccggcgctgctcggcgccgcactccgcctcgccgggaagggaccaccttccgtacgcgttcgacgacgtccgcgtccacgccac
cggcgccacggcggtacgcgtcaccgctcgccgtcaccgctgaccgcggtacacctcgcgacgaccggcgggcccgctgccaccatcggcgccgtgcgcaggcgcc
ccctgacgatcacgggagccgttccgggcctgctgcgcccggtgctggccgagctcccggagctgccgcccacgaccgcgacgaccggcgcctcgacgac
ccgacggtcccggacgtggtgatcctccccgcgcacggcggcggcggtgcccgctcgacgacacccgcgaactgggcgccggcgtcctgaccgccgtgca
gcgcttcctcaccgacgaccggtacgccgacgcggtcctggccgtccacaccgggccggtctcgcgtcggccgcggccgccggactggtgcggaccgcgc
aggccgaacaccccggccggatcgtcctcgtcgacgccg (SEQ ID NO: 90)

Complementary Sequence of Nucleotides 29092-29740 of SID: 1:
ctcgacccggacggcaccgtgctcgtcaccggtggctccgggacgctggccggcatcatcagccgccacctcgtcgaacgccacggcgtgcgccggctgct
gatgctgtcgcgcagcggcacggcgagcgacgtgccggcgccgaggtcacggcgatcgcctgcgacgtcgccgaccgggacgaactcgcctccgtactgg
cggggatcgaccggcgcaccgctcacggccgctcgtgcacaccggccgtcctcgacgacggcgtcctcaccgcgtcacccccgaccggctcgagacg
gtgctcgcgcccgaaggtggacgccgcgtgcacctgcacgaactcacccaggacacggaactggccgcgttcgtcctctactcgtcggccgccggtgtgct
cggcagccccggacagggcaactacgcggccgcgaacgcgttcctcgacgcgctggccgaacagccgcccgggcagccggactgcccgcgttgtccgtggcct
ggggcctgtgggaaccggagagcgggctgacggtcggcaccggcgcccgcatgcgccgcgacggcgtgacggcgctgaccgcgaaggcggactgacgctg
ttcgacgcggcgttgcggtcctcggacccggcgctggtcgccg (SEQ ID NO: 91)

Complementary Sequence of Nucleotides 28750-28960 of SID: 1:
gtgctcgccgtcgtccggcagtgcaccgcggccgtactcggccacgacggtgccgcacgggtcgaggcgaccgccacgttcaaggaactcggcgtcgactc
gctcatggcgatccggctgcgcaacgccttcaccgaggcgacgggcgtacggctgcccgccaccgcggtcttcgacttcccgacgccgcgcgccgtcgcgg
cgaagctca (SEQ ID NO: 92)

Complementary Sequence of Nucleotides 27430-28684 of SID: 1:
gagccgttggcgatcgtggggatggcctgccggctgccgggtggggtcgcgtcgccggaggacttgtggcggctgctggagtcgggtggtgacgggatcac
ggcgtttccgacggaccgtggttgggacgtggacgggctgtacgatcccgatccggatcatccgggcacgtcgaccgtgcgtcatggtggcttcctcgccg
gggtggcggacttcgacgcggcgttcttcgggatcagtccgcgtgaggcgctggcgatggacccgcagcagcgtctggtcctggagacctcgtgggaggcg
ctggaacacgccgggatcctcccggagtcgctgcgcggaagcgacaccggcgtgttcatgggcgcttctccgacgggtacggactcggcaccgacctggg
cggtttcggcgccaccagcacccagaccagtgtgctgtccggtcggctgtcgtacttctacggtttggagggtccggcggtcacggtggacacggcgtgtt
cgtcgtcgctggtggcgctgcaccaggccgggcagtcactcgcgctccggcgaatgctcgctcgccctggtcggcggcgtcacggtgatggcctcgccgtcc
ggcttcgtcgagttctcccagcagcggggtctcgcgcccgacgcgcgctgcaaggcgttcgcggatgcggctgacggcaccggtttcgccgaggggtccgg
tgtgctgatcgtcgagaggctctccgatgccgagcgcaacgccaccgtgtgctggcggttgtccggggttcggcggtcaaccaggacggtgcttccaacg
ggttgtcggcgccgaacgggccctcgcaggagcgggtgatccggcaggccctggccaacgccgggctcacccccgcggacgtggacgccgtggaggcgcac -continued Complementary Sequences of fkbB Coding Regions

```
ggcaccggcaccaggctgggcgatcccatcgaggcacaggcggtgctggccacctacgggcaggggcgcgacaccccggtgctgctgggctcgctgaagtc
caacatcggccacactcaggccgccgcgggtgtcgccggtgtcatcaagatggtcctcgccatgcggcacggcaccctgccgcgcaccctgcacgtggaca
cgccgtcctcgcacgtcgactggacggccggcgccgtcgaactcctcaccgatgcccggccctggcccgagaccgaccgcccgcggcgcgccggtgtgtcc
tccttcggcgtcagcggcaccaacgcccacgtcctgctggaag (SEQ ID NO: 93)
```

Complementary Sequence of Nucleotides 26146-27430 of SID: 1:
```
gcccacccggccggggagccgccggccgaggagccgtcggcctcgaagcccggtgagccgctgatcgccacgccgctcacaccactgcccgtctcggcgcg
gaccgccacggccctcgacggccaggtccgccgactccgcgagcacctcgccgcccgtcccggccacgacccgcgcgccatcgccgcgggcctgctcgcca
ggcgtacgacgttcccgcaccgcgccgtgctgctcgacgacgacgtcgtcaccggcacggcgctcaccgagccgcgcaccgtcttcgtcttcccccggacaa
ggaccgcagtggcgcggcatgggcgtcgaactgatggcggcctccccggtgttcgccgccaggatgcgccaatgcgccgacgcgctgatcccgcacacggg
ctgggaccccatcgccatgctcgacgaccggaggtgacccgccgcgtcgacgtcgtgcaccccgtctgctgggccgtcatggtgtcgctggccgccgtgt
gggaggccgcgggcgtacgcccggacgccgtcatcggacactcccagggcgagatcgccgcggcctgtgtcgccggagcgctcaccctggaggacggtgcc
cgcctcgtcgcgctgcgcagcgttctcctgctcctgcgcgaactcgccggacgcggcgcgatgggctcggtcgcgctcccggccgccgacgtcgaggcgga
tgccgcccggatcgacggcgtctgggtcgcgggccgcaacggcgccaccaccacgaccgtcgccgggcgcccggacgccgtcgaaacgctgatcgccgact
acgaggcccgcggcgtctgggtgcgccgcatcgccgtcgactgcccgacccacacccccgttcgtcgaccgctgtacgacgaactccagcggatcgtcgcg
gacaccacctcgcgcacgcccgagatcccgtggttctccaccgccgacgaacgctggatcgacgcgccgctcgacgacgagtactggttccgcaacatgcg
ccaccccgtaggcttcgccacggccgtgaccgctgcccgcgagccgggtgacaccgtgttcgtcgaggtcagcgcgcacccccgtgctgctgcccgcgatcg
acggcgcgaccgtcgccacgctccgccgcggcgggggagtccaccggctgctcaccgcgctggccgaggcgcacacaaccggcgtgcccgtcgactgggcg
gcggtcgtccccgcgacggcgacggcacacgacctgcccacatacgccttccaccatgagcgctactggatcg (SEQ ID NO: 94)
```

Complementary Sequence of Nucleotides 24997-26146 of SID: 1:
```
gcccacccggccggggagccgccggccgaggagccgtcggcctcgaagcccggtgagccgctgatcgccacgccgctcacaccactgcccgtctcggcgcg
gaccgccacggccctcgacggccaggtccgccgactccgcgagcacctcgccgcccgtcccggccacgacccgcgcgccatcgccgcgggcctgctcgcca
ggcgtacgacgttcccgcaccgcgccgtgctgctcgacgacgacgtcgtcaccggcacggcgctcaccgagccgcgcaccgtcttcgtcttcccccggacaa
ggaccgcagtggcgcggcatgggcgtcgaactgatggcggcctccccggtgttcgccgccaggatgcgccaatgcgccgacgcgctgatcccgcacacggg
ctgggaccccatcgccatgctcgacgaccggaggtgacccgccgcgtcgacgtcgtgcaccccgtctgctgggccgtcatggtgtcgctggccgccgtgt
gggaggccgcgggcgtacgcccggacgccgtcatcggacactcccagggcgagatcgccgcggcctgtgtcgccggagcgctcaccctggaggacggtgcc
cgcctcgtcgcgctgcgcagcgttctcctgctcctgcgcgaactcgccggacgcggcgcgatgggctcggtcgcgctcccggccgccgacgtcgaggcgga
tgccgcccggatcgacggcgtctgggtcgcgggccgcaacggcgccaccaccacgaccgtcgccgggcgcccggacgccgtcgaaacgctgatcgccgact
acgaggcccgcggcgtctgggtgcgccgcatcgccgtcgactgcccgacccacacccccgttcgtcgaccgctgtacgacgaactccagcggatcgtcgcg
gacaccacctcgcgcacgcccgagatcccgtggttctccaccgccgacgaacgctggatcgacgcgccgctcgacgacgagtactggttccgcaacatgcg
ccaccccgtaggcttcgccacggccgtgaccgctgcccgcgagccgggtgacaccgtgttcgtcgaggtcagcgcgcacccccgtgctgctgcccgcgatcg
acggcgcgaccgtcgccacgctccgccgcggcgggggagtccaccggctgctcaccgcgctggccgaggcgcacacaaccggcgtgcccgtcgactgggcg
gcggtcgtccccgcgacggcgacggcacacgacctgcccacatacgccttccaccatgagcgctactggatcg (SEQ ID NO: 95)
```

Complementary Sequence of Nucleotides 24163-24373 of SID: 1:
```
ctgctcggcgtcgtccgcgacaccgccgccacccctgctgggccacaccgacgcggcggcggtcacggccaccacggcgttcaaggacctcggggtcgactc
gctcaccgcgctcggcctgcgcaaccggctctccgaggccctcggcattccgctgccggccacgctcgtcttcgactatcccgccgccggcgcgctcaccc
gtcatctgc (SEQ ID NO: 96)
```

EXAMPLE 1

Replacement of Methoxyl with Hydrogen or Methyl at C-13 of FK-520

The C-13 methoxyl group is introduced into FK-520 via an AT domain in extender module 8 of the PKS that is specific for hydroxymalonyl and by methylation of the hydroxyl group by an S-adenosyl methionine (SAM) dependent methyltransferase. Metabolism of FK-506 and FK-520 primarily involves oxidation at the C-13 position into an inactive derivative that is further degraded by host P450 and other enzymes. The present invention provides compounds related in structure to FK-506 and FK-520 that do not contain the C-13 methoxy group and exhibit greater stability and a longer half-life in vivo. These compounds are useful medicaments due to their immunosuppressive and neurotrophic activities, and the invention provides the compounds in purified form and as pharmaceutical compositions.

The present invention also provides the novel PKS enzymes that produce these novel compounds as well as the expression vectors and host cells that produce the novel PKS enzymes. The novel PKS enzymes include, among others, those that contain an AT domain specific for either malonyl CoA or methylmalonyl CoA in module 8 of the FK-506 and FK-520 PKS. This example describes the construction of recombinant DNA compounds that encode the novel FK-520 PKS enzymes and the transformation of host cells with those recombinant DNA compounds to produce the novel PKS enzymes and the polyketides produced thereby.

To construct an expression cassette for performing module 8 AT domain replacements in the FK-520 PKS, a 4.6 kb SphI fragment from the FK-520 gene cluster was cloned into plasmid pLitmus 38 (a cloning vector available from New England Biolabs). The 4.6 kb SphI fragment, which encodes the ACP domain of module 7 followed by module 8 through the KR domain, was isolated from an agarose gel after digesting the cosmid pKOS65-C31 with Sph I. The clone having the insert oriented so the single SacI site was nearest to the SpeI end of the polylinker was identified and designated as plasmid pKOS60-21-67. To generate appropriate cloning sites, two linkers were ligated sequentially as follows. First, a linker was ligated between the SpeI and SacI sites to introduce a BglII site at the 5' end of the cassette, to eliminate interfering polylinker sites, and to reduce the total insert size to 4.5 kb (the limit of the phage KC515). The ligation reactions contained 5 picomolar unphosphorylated linker DNA and 0.1 picomolar vector DNA, i.e., a 50-fold molar excess of linker to vector. The linker had the following sequence (SEQ ID NOS:3-4):

5'-CTAGTGGGCAGATCTGGCAGCT-3'

3'-ACCCGTCTAGACCG-5'

The resulting plasmid was designated pKOS60-27-1.

Next, a linker of the following sequence was ligated between the unique SphI and AflII sites of plasmid pKOS60-27-1 to introduce an NsiI site at the 3' end of the module 8 cassette. The linker employed was (SEQ ID NOS:5-6):

```
5'-GGGATGCATGGC-3'

3'-GTACCCCTACGTACCGAATT-5'
```

The resulting plasmid was designated pKOS60-29-55.

To allow in-frame insertions of alternative AT domains, sites were engineered at the 5' end (Avr II or Nhe I) and 3' end (Xho I) of the AT domain using the polymerase chain reaction (PCR) as follows. Plasmid pKOS60-29-55 was used as a template for the PCR and sequence 5' to the AT domain was amplified with the primers SpeBgl-fwd and either Avr-rev or Nhe-rev: (SEQ ID NOS:7-9)

```
SpeBgl-fwd    5'-CGACTCACTAGTGGGCAGATCTGG-3'

Avr-rev       5'-CACGCCTAGGCCGGTCGGTCTCGGGGCAC-3'

Nhe-rev       5'-GCGGCTAGCTGCTCGCCCATCGCGGGATGC-3'
```

The PCR included, in a 50 µl reaction, 5 µl of 10×Pfu polymerase buffer (Stratagene), 5 µl 10×z-dNTP mixture (2 mM dATP, 2 mM dCTP, 2 mM dTTP, 1 mM dGTP, 1 mM 7-deaza-GTP), 5 µl DMSO, 2 µl of each primer (10 µM), 1 µl of template DNA (0.1 µg/µl), and 1 µl of cloned Pfu polymerase (Stratagene). The PCR conditions were 95° C. for 2 min., 25 cycles at 95° C. for 30 sec., 60° C. for 30 sec., and 72° C. for 4 min., followed by 4 min. at 72° C. and a hold at 0° C. The amplified DNA products and the Litmus vectors were cut with the appropriate restriction enzymes (BglII and AvrII or SpeI and NheI), and cloned into either pLitmus 28 or pLitmus38 (New England Biolabs), respectively, to generate the constructs designated pKOS60-37-4 and pKOS60-37-2, respectively.

Plasmid pKOS60-29-55 was again used as a template for PCR to amplify sequence 3' to the AT domain using the primers BsrXho-fwd and NsiAfl-rev (SEQ ID NOS:10-11):

```
BsrXho-fwd
5'-GATGTACAGCTCGAGTCGGCACGCCCGGCCGCATC-3'

NsiAfl-rev
5'-CGACTCACTTAAGCCATGCATCC-3'
```

PCR conditions were as described above. The PCR fragment was cut with BsrGI and AflII, gel isolated, and ligated into pKOS60-37-4 cut with Asp718 and AflII and inserted into pKOS60-37-2 cut with BsrGI and AflII, to give the plasmids pKOS60-39-1 and pKOS60-39-13, respectively. These two plasmids can be digested with AvrII and XhoI or NheI and XhoI, respectively, to insert heterologous AT domains specific for malonyl, methylmalonyl, ethylmalonyl, or other extender units.

Malonyl and methylmalonyl-specific AT domains were cloned from the rapamycin cluster using PCR amplification with a pair of primers that introduce an AvrII or NheI site at the 5' end and an XhoI site at the 3' end. The PCR conditions were as given above and the primer sequences were as follows (SEQ ID NOS:12-15):

RATN1 5'-ATCCTAGGCGGGCRGGYGTGTCGTCCTTCGG-3'
(3' end of Rap KS sequence and universal for malonyl and methylmalonyl CoA),
RATMN2 5'-ATGCTAGCCGCCGCGTTCCCCGTCTTCGCGCG-3'
(Rap AT shorter version 5'-sequence and specific for malonyl CoA),
RATMMN2 5'-ATGCTAGCGGATTCGTCGGTGGTGTTCGCCGA-3'
(Rap AT shorter version 5'-sequence and specific for methylmalonyl CoA), and
RATC 5'-ATCTCGAGCCAGTASCGCTGGTGYTGGAAGG-3'
(Rap DH 5'-sequence and universal for malonyl and methylmalonyl CoA).

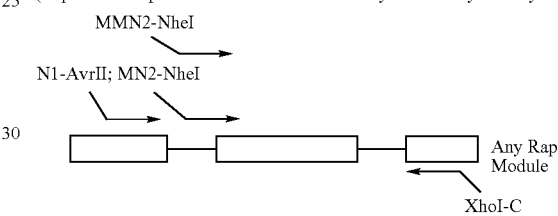

Because of the high sequence similarity in each module of the rapamycin cluster, each primer was expected to prime any of the AT domains. PCR products representing ATs specific for malonyl or methylmalonyl extenders were identified by sequencing individual cloned PCR products. Sequencing also confirmed that the chosen clones contained no cloning artifacts. Examples of hybrid modules with the rapamycin AT12 and AT13 domains are shown in a separate figure.

The AvrII-XhoI restriction fragment that encodes module 8 of the FK-520 PKS with the endogenous AT domain replaced by the AT domain of module 12 of the rapamycin PKS has the DNA sequence and encodes the amino acid sequence shown below. The AT of rap module 12 is specific for incorporation of malonyl units (SEQ ID NOS:16-17).

```
AGATCTGGCAGCTCGCCGAAGCGCTGCTGACGCTCGTCCGGGAGAGCACC          50
  I   W   Q   L   A   E   A   L   L   T   L   V   R   E   S   T

GCCGCCGTGCTCGGCCACGTGGGTGGCGAGGACATCCCCGCGACGGCGGC         100
  A   A   V   L   G   H   V   G   G   E   D   I   P   A   T   A   A

GTTCAAGGACCTCGGCATCGACTCGCTCACCGCGGTCCAGCTGCGCAACG         150
  F   K   D   L   G   I   D   S   L   T   A   V   W   L   R   N

CCCTCACCGAGGCGACCGGTGTGCGGCTGAACGCCACGGCGGTCTTCGAC         200
  A   L   T   E   A   T   G   V   R   L   N   A   T   A   V   F   D

TTCCCGACCCCGCACGTGCTCGCCGGGAAGCTCGGCGACGAACTGACCGG         250
  F   P   T   P   H   V   L   A   G   K   L   G   D   E   L   T   G

CACCCGCGCGCCCGTCGTGCCCCGGACCGCGGCCACGGCCGGTGCGCACG         300
  T   R   A   P   V   V   P   R   T   A   A   T   A   G   A   H
```

```
                            -continued
ACGAGCCGCTGGCGATCGTGGGAATGGCCTGCCGGCTGCCCGGCGGGGTC        350
 D   E   P   L   A   I   V   G   M   A   C   R   L   P   G   G   V GCGTCACCCGAGGAGCTGTGGCACCTCGTGGCATCCGGCACCGACGCCAT        400
 A   S   P   E   E   L   W   H   L   V   A   S   G   T   D   A   I CACGGAGTTCCCGACGGACCGCGGCTGGGACGTCGACGCGATCTACGACC        450
  T   E   F   P   T   D   R   G   W   D   V   D   A   I   Y   D CGGACCCCGACGCGATCGGCAAGACCTTCGTCCGGCACGGTGGCTTCCTC        500
 P   D   P   D   A   I   G   K   T   F   V   R   H   G   G   F   L ACCGGCGCGACAGGCTTCGACGCGGCGTTCTTCGGCATCAGCCCGCGCGA        550
  T   G   A   T   G   F   D   A   A   F   F   G   I   S   P   R   E GGCCCTCGCGATGGACCCGCAGCAGCGGGTGCTCCTGGAGACGTCGTGGG        600
   A   L   A   M   D   P   Q   Q   R   V   L   L   E   T   S   W AGGCGTTCGAAAGCGCCGGCATCACCCCGGACTCGACCCGCGGCAGCGAC        650
 E   A   F   E   S   A   G   I   T   P   D   S   T   R   G   S   D ACCGGCGTGTTCGTCGGCGCCTTCTCCTACGGTTACGGCACCGGTGCGGA        700
  T   G   V   F   V   G   A   F   S   Y   G   Y   G   T   G   A   D CACCGACGGCTTCGGCGCGACCGGCTCGCAGACCAGTGTGCTCTCCGGCC        750
   T   D   G   F   G   A   T   G   S   Q   T   S   V   L   S   G GGCTGTCGTACTTCTACGGTCTGGAGGGTCCGGCGGTCACGGTCGACACG        800
 R   L   S   Y   F   Y   G   L   E   G   P   A   V   T   V   D   T GCGTGTTCGTCGTCGCTGGTGGCGCTGCACCAGGCCGGGCAGTCGCTGCG        850
 A   C   S   S   S   L   V   A   L   H   Q   A   G   Q   S   L   R CTCCGGCGAATGCTCGCTCGCCCTGGTCGGCGGCGTCACGGTGATGGCGT        900
  S   G   E   C   S   L   A   L   V   G   G   V   T   V   M   A CTCCCGGCGGCTTCGTGGAGTTCTCCCGGCAGCGCGGCCTCGCGCCGGAC        950
 S   P   G   G   F   V   E   F   S   R   Q   R   G   L   A   P   D GGCCGGGCGAAGGCGTTCGGCGCGGGTGCGGACGGCACGAGCTTCGCCGA       1000
  G   R   A   K   A   F   G   A   G   A   D   G   T   S   F   A   E GGGTGCCGGTGTGCTGATCGTCGAGAGGCTCTCCGACGCCAACGCAACG       1050
   G   A   G   V   L   I   V   E   R   L   S   D   A   E   R   N GTCACACCGTCCTGGCGGTCGTCCGTGGTTCGGCGGTCAACCAGGATGGT       1100
 G   H   T   V   L   A   V   V   R   G   S   A   V   N   Q   D   G GCCTCCAACGGGCTGTCGGCGCCGAACGGGCCGTCGCAGGAGCGGGTGAT       1150
  A   S   N   G   L   S   A   P   N   G   P   S   Q   E   R   V   I CCGGCAGGCCCTGGCCAACGCCGGGCTCACCCCGGCGGACGTGGACGCCG       1200
   R   Q   A   L   A   N   A   G   L   T   P   A   D   V   D   A TCGAGGCCCACGGCACCGGCACCAGGCTGGGCGACCCCATCGAGGCACAG       1250
 V   E   A   H   G   T   G   T   R   L   G   D   P   I   E   A   Q GCGGTACTGGCCACCTACGGACAGGAGCGCGCCACCCCCCTGCTGCTGGG       1300
  A   V   L   A   T   Y   G   Q   E   R   A   T   P   L   L   L   G CTCGCTGAAGTCCAACATCGGCCACGCCCAGGCCGCGTCCGGCGTCGCCG       1350
   S   L   K   S   N   I   G   H   A   Q   A   A   S   G   V   A GCATCATCAAGATGGTGCAGGCCCTCCGGCACGGGGAGCTGCCGCCGACG       1400
 G   I   I   K   M   V   Q   A   L   R   H   G   E   L   P   P   T CTGCACGCCGACGAGCCGTCGCCGCACGTCGACTGGACGGCCGGCGCCGT       1450
  L   H   A   D   E   P   S   P   H   V   D   W   T   A   G   A   V CGAACTGCTGACGTCGGCCCGGCCGTGGCCCGAGACCGACCGGCCTAGGC       1500
   E   L   L   T   S   A   R   P   W   P   E   T   D   R   P   R GGGCAGGCGTGTCGTCCTTCGGGATCAGTGGCACCAACGCCCACGTCATC       1550
 R   A   G   V   S   S   F   G   I   S   G   T   N   A   H   V   I CTGGAAAGCGCACCCCCCACTCAGCCTGCGGACAACGCGGTGATCGAGCG       1600
  L   E   S   A   P   P   T   Q   P   A   D   N   A   V   I   E   R GGCACCGGAGTGGGTGCCGTTGGTGATTTCGGCCAGGACCCAGTCGGCTT       1650
   A   P   E   W   V   P   L   V   I   S   A   R   T   Q   S   A
```

```
TGACTGAGCACGAGGGCCGGTTGCGTGCGTATCTGGCGGCGTCGCCCGGG      1700
 L  T  E  H  E  G  R  L  R  A  Y  L  A  A  S  P  G

GTGGATATGCGGGCTGTGGCATCGACGCTGGCGATGACACGGTCGGTGTT      1750
 V  D  M  R  A  V  A  S  T  L  A  M  T  R  S  V  F

CGAGCACCGTGCCGTGCTGCTGGGAGATGACACCGTCACCGGCACCGCTG      1800
 E  H  R  A  V  L  L  G  D  D  T  V  T  G  T  A

TGTCTGACCCTCGGGCGGTGTTCGTCTTCCCGGGACAGGGGTCGCAGCGT      1850
 V  S  D  P  R  A  V  F  V  F  P  G  Q  G  S  Q  R

GCTGGCATGGGTGAGGAACTGGCCGCCGCGTTCCCCGTCTTCGCGCGGAT      1900
 A  G  M  G  E  E  L  A  A  A  F  P  V  F  A  R  I

CCATCAGCAGGTGTGGGACCTGCTCGATGTGCCCGATCTGGAGGTGAACG      1950
 H  Q  Q  V  W  D  L  L  D  V  P  D  L  E  V  N

AGACCGGTTACGCCCAGCCGGCCCTGTTCGCAATGCAGGTGGCTCTGTTC      2000
 E  T  G  Y  A  Q  P  A  L  F  A  M  Q  V  A  L  F

GGGCTGCTGGAATCGTGGGGTGTACGACCGGACGCGGTGATCGGCCATTC      2050
 G  L  L  E  S  W  G  V  R  P  D  A  V  I  G  H  S

GGTGGGTGAGCTTGCGGCTGCGTATGTGTCCGGGGTGTGGTCGTTGGAGG      2100
 B  G  E  L  A  A  A  Y  V  S  G  V  W  S  L  E

ATGCCTGCACTTTGGTGTCGGCGCGGGCTCGTCTGATGCAGGCTCTGCCC      2150
 D  A  C  T  L  V  S  A  R  A  R  L  M  Q  A  L  P

GCGGGTGGGGTGATGGTCGCTGTCCCGGTCTCGGAGGATGAGGCCCGGGC      2200
 A  G  G  V  M  V  A  V  P  V  S  E  D  E  A  R  A

CGTGCTGGGTGAGGGTGTGGAGATCGCCGCGGTCAACGGCCCGTCGTCGG      2250
 V  L  G  E  G  V  E  I  A  A  V  N  G  P  S  S

TGGTTCTCTCCGGTGATGAGGCCGCCGTGCTGCAGGCCGCGGAGGGGCTG      2300
 V  V  L  S  G  D  E  A  A  V  L  Q  A  A  E  G  L

GGGAAGTGGACGCGGCTGGCGACCAGCCACGCGTTCCATTCCGCCCGTAT      2350
 G  K  W  T  R  L  A  T  S  H  A  F  H  S  A  R  M

GGAACCCATGCTGGAGGAGTTCCGGGCGGTGGCCGAAGGCCTGACCTACC      2400
 E  P  M  L  E  E  F  R  A  V  A  E  G  L  T  Y

GGACGCCGCAGGTCTCCATGGCCGTTGGTGATCAGGTGACCACCGCTGAG      2450
 R  T  P  Q  V  S  M  A  V  G  D  Q  V  T  T  A  E

TACTGGGTGCGGCAGGTCCGGGACACGGTCCGGTTCGGCGAGCAGGTGGC      2500
 Y  W  V  R  Q  V  R  D  T  V  R  F  G  E  Q  V  A

CTCGTACGAGGACGCCGTGTTCGTCGAGCTGGGTGCCGACCGGTCACTGG      2550
 S  Y  E  D  A  V  F  V  E  L  G  A  D  R  S  L

CCCGCCTGGTCGACGGTGTCGCGATGCTGCACGGCGACCACGAAATCCAG      2600
 A  R  L  V  D  G  V  A  M  L  H  G  D  H  E  I  Q

GCCGCGATCGGCGCCCTGGCCCACCTGTATGTCAACGGCGTCACGGTCGA      2650
 A  A  I  G  A  L  A  H  L  Y  V  N  G  V  T  V  D

CTGGCCCGCGCTCCTGGGCGATGCTCCGGCAACACGGGTGCTGGACCTTC      2700
 W  P  A  L  L  G  D  A  P  A  T  R  V  L  D  L

CGACATACGCCTTCAGCACCAGCGCTACTGGCTCGAGTCGGCACGCCCG      2750
 P  T  Y  A  F  Q  H  Q  R  Y  W  L  E  S  A  R  P

GCCGCATCCGACGCGGGCCACCCCGTGCTGGGCTCCGGTATCGCCCTCGC      2800
 A  A  S  D  A  G  H  P  V  L  G  S  G  I  A  L  A

CGGGTCGCCGGGCCGGGTGTTCACGGGTTCCGTGCCGACCGGTGCGGACC      2850
 G  S  P  G  R  V  F  T  G  S  V  P  T  G  A  D

GCGCGGTGTTCGTCGCCGAGCTGGCGCTGGCCGCCGCGGACGCGGTCGAC      2900
 R  A  V  F  V  A  E  L  A  L  A  A  A  D  A  V  D

TGCGCCACGGTCGAGCGGCTCGACATCGCCTCCGTGCCCGGCCGGCCGGG      2950
 C  A  T  V  E  R  L  D  I  A  S  V  P  G  R  P  G
```

```
CCATGGCCGGACGACCGTACAGACCTGGGTCGACGAGCCGGCGGACGACG        3000
  H  G  R  T  T  V  Q  T  W  V  D  E  P  A  D  D

GCCGGCGCCGGTTCACCGTGCACACCCGCACCGGCGACGCCCCGTGGACG        3050
 G  R  R  R  F  T  V  H  T  R  T  G  D  A  P  W  T

CTGCACGCCGAGGGGGTGCTGCGCCCCCATGGCACGGCCCTGCCCGATGC        3100
  L  H  A  E  G  V  L  R  P  H  G  T  A  L  P  D  A

GGCCGACGCCGAGTGGCCCCCACCGGGCGCGGTGCCCGCGGACGGGCTGC        3150
  A  D  A  E  W  P  P  P  G  A  V  P  A  D  G  L

CGGGTGTGTGGCGCCGGGGGGACCAGGTCTTCGCCGAGGCCGAGGTGGAC        3200
 P  G  V  W  R  R  G  D  Q  V  F  A  E  A  E  V  D

GGACCGGACGGTTTCGTGGTGCACCCCGACCTGCTCGACGCGGTCTTCTC        3250
 G  P  D  G  F  V  V  H  P  D  L  L  D  A  V  F  S

CGCGGTCGGCGACGGAAGCCGCCAGCCGGCCGGATGGCGCGACCTGACGG        3300
  A  V  G  D  G  S  R  Q  P  A  G  W  R  D  L  T

TGCACGCGTCGGACGCCACCGTACTGCGCGCCTGCCTCACCCGGCGCACC        3350
 V  H  A  S  D  A  T  V  L  R  A  C  L  T  R  R  T

GACGGAGCCATGGGATTCGCCGCCTTCGACGGCGCCGGCCTGCCGGTACT        3400
 D  G  A  M  G  F  A  A  F  D  G  A  G  L  P  V  L

CACCGCGGAGGCGGTGACGCTGCGGGAGGTGGCGTCACCGTCCGGCTCCG        3450
  T  A  E  A  V  T  L  R  E  V  A  S  P  S  G  S

AGGAGTCGGACGGCCTGCACCGGTTGGAGTGGCTCGCGGTCGCCGAGGCG        3500
 E  E  S  D  G  L  H  R  L  E  W  L  A  V  A  E  A

GTCTACGACGGTGACCTGCCCGAGGGACATGTCCTGATCACCGCCGCCCA        3550
 V  Y  D  G  D  L  P  E  G  H  V  L  I  T  A  A  H

CCCCGACGACCCCGAGGACATACCCACCCGCGCCCACACCCGCGCCACCC        3600
  P  D  D  P  E  D  I  P  T  R  A  H  T  R  A  T

GCGTCCTGACCGCCCTGCAACACCACCTCACCACCACCGACCACACCCTC        3650
 R  V  L  T  A  L  Q  H  H  L  T  T  T  D  H  T  L

ATCGTCCACACCACCACCGACCCCGCCGGCGCCACCGTCACCGGCCTCAC        3700
  I  V  H  T  T  T  D  P  A  G  A  T  V  T  G  L  T

CCGCACCGCCCAGAACGAACACCCCCACCGCATCCGCCTCATCGAAACCG        3750
  R  T  A  Q  N  E  H  P  H  R  I  R  L  I  E  T

ACCACCCCCACACCCCCTCCCCCTGGCCCAACTCGCCACCCTCGACCAC        3800
 D  H  P  H  T  P  L  P  L  A  Q  L  A  T  L  D  H

CCCCACCTCCGCCTCACCCACCACACCCTCCACCACCCCACCTCACCCC        3850
 P  H  L  R  L  T  H  H  T  L  H  H  P  H  L  T  P

CCTCCACACCACCACCCCACCCACCACCACCCCCTCAACCCCGAACACG        3900
  L  H  T  T  T  P  P  T  T  T  P  L  N  P  E  H

CCATCATCATCACCGGCGGCTCCGGCACCCTCGCCGGCATCCTCGCCCGC        3950
  A  I  I  I  T  G  G  S  G  T  L  A  G  I  L  A  R

CACCTGAACCACCCCACACCTACCTCCTCTCCCGCACCCCACCCCCCGA        4000
  H  L  N  H  P  H  T  Y  L  L  S  R  T  P  P  P  D

CGCCACCCCCGGCACCCACCTCCCCTGCGACGTCGGCGACCCCCACCAAC        4050
  A  T  P  G  T  H  L  P  C  D  V  G  D  P  H  Q

TCGCCACCACCCTCACCCACATCCCCCAACCCCTCACCGCCATCTTCCAC        4100
  L  A  T  T  L  T  H  I  P  Q  P  L  T  A  I  F  H

ACCGCCGCCACCCTCGACGACGGCATCCTCCACGCCCTCACCCCCGACCG        4150
  T  A  A  T  L  D  D  G  I  L  H  A  L  T  P  D  R

CCTCACCACCGTCCTCCACCCCAAAGCCAACGCCGCCTGGCACCTGCACC        4200
  L  T  T  V  L  H  P  K  A  N  A  A  W  H  L  H

ACCTCACCCAAAACCAACCCCTCACCCACTTCGTCCTCTACTCCAGCGCC        4250
 H  L  T  Q  N  Q  P  L  T  H  F  V  L  Y  S  S  A
```

-continued

```
GCCGCCGTCCTCGGCAGCCCCGGACAAGGAAACTACGCCGCCGCCAACGC      4300
 A  A  V  L  G  S  P  G  Q  G  N  Y  A  A  A  N  A

CTTCCTCGACGCCCTCGCCACCCACCGCCACACCCTCGGCCAACCCGCCA      4350
  F  L  D  A  L  A  T  H  R  H  T  L  G  Q  P  A

CCTCCATCGCCTGGGGCATGTGGCACACCACCAGCACCCTCACCGGACAA      4400
 T  S  I  A  W  G  M  W  H  T  T  S  L  T  G  Q

CTCGACGACGCCGACCGGGACCGCATCCGCCGCGGCGGTTTCCTCCCGAT      4450
  L  D  D  A  D  R  D  R  I  R  R  G  G  F  L  P  I

CACGGACGACGAGGGCATGGGGATGCAT
   T  D  D  E  G
```
                                       15

The AvrII-XhoI restriction fragment that encodes module 8 of the FK-520 PKS with the endogenous AT domain replaced by the AT domain of module 13 (specific for methylmalonyl CoA) of the rapamycin PKS has the DNA sequence and encodes the amino acid sequence shown below (SEQ ID NOS:18-19).

```
AGATCTGGCAGCTCGCCGAAGCGCTGCTGACGCTCGTCCGGGAGAGCACC      50
  Q  L  A  E  A  L  L  T  L  V  R  E  S  T

GCCGCCGTGCTCGGCCACGTGGGTGGCGAGGACATCCCCGCGACGGCGGC      100
 A  A  V  L  G  H  V  G  G  E  D  I  P  A  T  A  A

GTTCAAGGACCTCGGCATCGACTCGCTCACCGCGGTCCAGCTGCGCAACG      150
  F  K  D  L  G  I  D  S  L  T  A  V  Q  L  R  N

CCCTCACCGAGGCGACCGGTGTGCGGCTGAACGCCACGGCGGTCTTCGAC      200
 A  L  T  E  A  T  G  V  R  L  N  A  T  A  V  F  D

TTCCCGACCCCGCACGTGCTCGCCGGGAAGCTCGGCGACGAACTGACCGG      250
  F  P  T  P  H  V  L  A  G  K  L  G  D  E  L  T  G

CACCCGCGCGCCCGTCGTGCCCCGGACCGCGGCCACGGCCGGTGCGCACG      300
   T  R  A  P  V  V  P  R  T  A  A  T  A  G  A  J

ACGAGCCGCTGGCGATCGTGGGAATGGCCTGCCGGCTGCCCGGCGGGGTC      350
  D  E  P  L  A  I  V  G  M  A  C  R  L  P  G  G  V

GCGTCACCCGAGGAGCTGTGGCACCTCGTGGCATCCGGCACCGACGCCAT      400
 A  S  P  E  E  L  W  H  L  V  A  S  G  T  D  A  I

CACGGAGTTCCCGACGGACCGCGGCTGGGACGTCGACGCGATCTACGACC      450
  T  E  F  P  T  D  R  G  W  D  V  D  A  I  Y  D

CGGACCCCGACGCGATCGGCAAGACCTTCGTCCGGCACGGTGGCTTCCTC      500
 P  D  P  D  A  I  G  K  T  F  V  R  H  G  G  F  L

ACCGGCGCGACAGGCTTCGACGCGGCGTTCTTCGGCATCAGCCCGCGCGA      550
  T  G  A  T  G  F  D  A  A  F  F  G  I  S  P  R  E

GGCCCTCGCGATGGACCCGCAGCAGCGGGTGCTCCTGGAGACGTCGTGGG      600
  A  L  A  M  D  P  Q  Q  R  V  L  L  E  T  S  W

AGGCGTTCGAAAGCGCCGGCATCACCCCGGACTCGACCCGCGGCAGCGAC      650
 E  A  F  E  S  A  G  I  T  P  D  S  T  R  G  S  D

ACCGGCGTGTTCGTCGGCGCCTTCTCCTACGGTTACGGCACCGGTGCGGA      700
  T  G  V  F  V  G  A  F  S  Y  G  Y  G  T  G  A  D

CACCGACGGCTTCGGCGCGACCGGCTCGCAGACCAGTGTGCTCTCCGGCC      750
   T  D  G  F  G  A  T  G  S  Q  T  S  V  L  S  G

GGCTGTCGTACTTCTACGGTCTGGAGGGTCCGGCGGTCACGGTCGACACG      800
 R  L  S  Y  F  Y  G  L  E  G  P  A  V  T  V  D  T

GCGTGTTCGTCGTCGCTGGTGGCGCTGCACCAGGCCGGGCAGTCGCTGCG      850
 A  C  S  S  S  L  V  A  L  H  Q  A  G  Q  S  L  R

CTCCGGCGAATGCTCGCTCGCCCTGGTCGGCGGCGTCACGGTGATGGCGT      900
  S  G  E  C  S  L  A  L  V  G  G  V  T  V  M  A

CTCCCGGCGGCTTCGTGGAGTTCTCCCGGCAGCGCGGCCTCGCGCCGGAC      950
 S  P  G  G  F  V  E  F  S  R  Q  R  G  L  A  P  D
```

-continued

```
GGCCGGGCGAAGGCGTTCGGCGCGGGTGCGGACGGCACGAGCTTCGCCGA    1000
 G  R  A  K  A  F  G  A  G  A  D  G  T  S  F  A  E

GGGTGCCGGTGTGCTGATCGTCGAGAGGCTCTCCGACGCCAACGCAACG     1050
  G  A  G  V  L  I  V  E  R  L  S  D  A  E  R  N

GTCACACCGTCCTGGCGGTCGTCCGTGGTTCGGCGGTCAACCAGGATGGT    1100
 G  H  T  V  L  A  V  V  R  G  S  A  V  N  Q  D  G

GCCTCCAACGGGCTGTCGGCGCCAACGGGCCGTCGCAGGAGCGGGTGAT     1150
  A  S  N  G  L  S  A  P  N  G  P  S  Q  E  R  V  I

CCGGCAGGCCCTGGCCAACGCCGGGCTCACCCCGGCGGACGTGGACGCCG    1200
 R  Q  A  L  A  N  A  G  L  T  P  A  D  V  D  A

TCGAGGCCCACGGCACCGGCACCAGGCTGGGCGACCCCATCGAGGCACAG    1250
 V  E  A  H  G  T  G  T  R  L  G  D  P  I  E  A  Q

GCGGTACTGGCCACCTACGGACAGGAGCGCGCCACCCCCCTGCTGCTGGG    1300
  A  V  L  A  T  Y  G  Q  E  R  A  T  P  L  L  L  G

CTCGCTGAAGTCCAACATCGGCCACGCCCAGGCCGCGTCCGGCGTCGCCG    1350
  S  L  K  S  N  I  G  H  A  Q  A  A  S  G  V  A

GCATCATCAAGATGGTGCAGGCCCTCCGGCACGGGGAGCTGCCGCCGACG    1400
 G  I  I  K  M  V  Q  A  L  R  H  G  E  L  P  P  T

CTGCACGCCGACGAGCCGTCGCCGCACGTCGACTGGACGGCCGGCGCCGT    1450
 L  H  A  D  E  P  S  P  H  V  D  W  T  A  G  A  V

CGAACTGCTGACGTCGGCCCGGCCGTGGCCCGAGACCGACCGGCCTAGGC    1500
  E  L  L  T  S  A  R  P  W  P  E  T  D  R  P  R

GGGCGGGCGTGTCGTCCTTCGGAGTCAGCGGCACCAACGCCCACGTCATC    1550
 R  A  G  V  S  S  F  G  V  S  G  T  N  A  H  V  I

CTGGAGAGCGCACCCCCCGCTCAGCCCGCGGAGGAGGCGCAGCCTGTTGA    1600
 L  E  S  A  P  P  A  Q  P  A  E  E  A  Q  P  V  E

GACGCCGGTGGTGGCCTCGGATGTGCTGCCGCTGGTGATATCGGCCAAGA    1650
  T  P  V  V  A  S  D  V  L  P  L  V  I  S  A  K

CCCAGCCCGCCCTGACCGAACACGAAGACCGGCTGCGCGCCTACCTGGCG    1700
 T  Q  P  A  L  T  E  H  E  D  R  L  R  A  Y  L  A

GCGTCGCCCGGGGCGGATATACGGGCTGTGGCATCGACGCTGGCGGTGAC    1750
 A  S  P  G  A  D  I  R  A  V  A  S  T  L  A  V  T

ACGGTCGGTGTTCGAGCACCGCGCCGTACTCCTTGGAGATGACACCGTCA    1800
  R  S  V  F  E  H  R  A  V  L  L  G  D  D  T  V

CCGGCACCGCGGTGACCGACCCCAGGATCGTGTTTGTCTTTCCCGGGCAG    1850
 T  G  T  A  V  T  D  P  R  I  V  F  V  F  P  G  Q

GGGTGGCAGTGGCTGGGGATGGGCAGTGCACTGCGCGATTCGTCGGTGGT    1900
 G  W  Q  W  L  G  M  G  S  A  L  R  D  S  S  V  V

GTTCGCCGAGCGGATGGCCGAGTGTGCGGCGGCGTTGCGCGAGTTCGTGG    1950
  F  A  E  R  M  A  E  C  A  A  A  L  R  E  F  V

ACTGGGATCTGTTCACGGTTCTGGATGATCCGGCGGTGGTGGACCGGGTT    2000
 D  W  D  L  F  T  V  L  D  D  P  A  V  V  D  R  V

GATGTGGTCCAGCCCGCTTCCTGGGCGATGATGGTTTCCCTGGCCGCGGT    2050
  D  V  V  Q  P  A  S  W  A  M  M  V  S  L  A  A  V

GTGGCAGGCGGCCGGTGTGCGGCCGGATGCGGTGATCGGCCATTCGCAGG    2100
  W  Q  A  A  G  V  R  P  D  A  V  I  G  H  S  Q

GTGAGATCGCCGCAGCTTGTGTGGCGGGTGCGGTGTCACTACGCGATGCC    2150
 G  E  I  A  A  A  C  V  A  G  A  V  S  L  R  D  A

GCCCGGATCGTGACCTTGCGCAGCCAGGCGATCGCCCGGGGCCTGGCGGG    2200
  A  R  I  V  T  L  R  S  Q  A  I  A  R  G  L  A  G

CCGGGGCGCGATGGCATCCGTCGCCCTGCCCGCGCAGGATGTCGAGCTGG    2250
  R  G  A  M  A  S  V  A  L  P  A  Q  D  V  E  L
```

-continued

```
TCGACGGGGCCTGGATCGCCGCCCACAACGGGCCCGCCTCCACCGTGATC         2300
 V  D  G  A  W  I  A  A  H  N  G  P  A  S  T  V  I

GCGGGCACCCCGGAAGCGGTCGACCATGTCCTCACCGCTCATGAGGCACA         2350
 A  G  T  P  E  A  V  D  H  V  L  T  A  H  E  A  Q

AGGGGTGCGGGTGCGGCGGATCACCGTCGACTATGCCTCGCACACCCCGC         2400
  G  V  R  V  R  R  I  T  V  D  Y  A  S  H  T  P

ACGTCGAGCTGATCCGCGACGAACTACTCGACATCACTAGCGACAGCAGC         2450
 H  V  E  L  I  R  D  E  L  L  D  I  T  S  D  S  S

TCGCAGACCCCGCTCGTGCCGTGGCTGTCGACCGTGGACGGCACCTGGGT         2500
 S  Q  T  P  L  V  P  W  L  S  T  V  D  G  T  W  V

CGACAGCCCGCTGGACGGGGAGTACTGGTACCGGAACCTGCGTGAACCGG         2550
  D  S  P  L  D  G  E  Y  W  Y  R  N  L  R  E  P

TCGGTTTCCACCCCGCCGTCAGCCAGTTGCAGGCCCAGGGCGACACCGTG         2600
 V  G  F  H  P  A  V  S  Q  L  Q  A  Q  G  D  T  V

TTCGTCGAGGTCAGCGCCAGCCCGGTGTTGTTGCAGGCGATGGACGACGA         2650
  F  V  E  V  S  A  S  P  V  L  L  Q  A  M  D  D  D

TGTCGTCACGGTTGCCACGCTGCGTCGTGACGACGGCGACGCCACCCGGA         2700
  V  V  T  V  A  T  L  R  R  D  D  G  D  A  T  R

TGCTCACCGCCCTGGCACAGGCCTATGTCCACGGCGTCACCGTCGACTGG         2750
 M  L  T  A  L  A  Q  A  Y  V  H  G  V  T  V  D  W

CCCGCCATCCTCGGCACCACCACAACCCGGGTACTGGACCTTCCGACCTA         2800
 P  A  I  L  G  T  T  T  T  R  V  L  D  L  P  T  Y

CGCCTTCCAACACCAGCGGTACTGGCTCGAGTCGGCACGCCCGGCCGCAT         2850
  A  F  Q  H  Q  R  Y  W  L  E  S  A  R  P  A  A

CCGACGCGGGCCACCCCGTGCTGGGCTCCGGTATCGCCCTCGCCGGGTCG         2900
 S  D  A  G  H  P  V  L  G  S  G  I  A  L  A  G  S

CCGGGCCGGGTGTTCACGGGTTCCGTGCCGACCGGTGCGGACCGCGCGGT         2950
  P  G  R  V  F  T  G  S  V  P  T  G  A  D  R  A  V

GTTCGTCGCCGAGCTGGCGCTGGCCGCCGCGGACGCGGTCGACTGCGCCA         3000
  F  V  A  E  L  A  L  A  A  A  D  A  V  D  C  A

CGGTCGAGCGGCTCGACATCGCCTCCGTGCCCGGCCGGCCGGGCCATGGC         3050
 T  V  E  R  L  D  I  A  S  V  P  G  R  P  G  H  G

CGGACGACCGTACAGACCTGGGTCGACGAGCCGGCGGACGACGGCCGGCG         3100
  R  T  T  V  Q  T  W  V  D  E  P  A  D  D  G  R  R

CCGGTTCACCGTGCACACCCGCACCGGCGACGCCCCGTGGACGCTGCACG         3150
  R  F  T  V  H  T  R  T  G  D  A  P  W  T  L  H

CCGAGGGGGTGCTGCGCCCCCATGGCACGGCCCTGCCCGATGCGGCCGAC         3200
 A  E  G  V  L  R  P  H  G  T  A  L  P  D  A  A  D

GCCGAGTGGCCCCCACCGGGCGCGGTGCCCGCGGACGGGCTGCCGGGTGT         3250
  A  E  W  P  P  P  G  A  V  P  A  D  G  L  P  G  V

GTGGCGCCGGGGGGACCAGGTCTTCGCCGAGGCCGAGGTGGACGGACCGG         3300
  W  R  R  G  D  Q  V  F  A  E  A  E  V  D  G  P

ACGGTTTCGTGGTGCACCCCGACCTGCTCGACGCGGTCTTCTCCGCGGTC         3350
 D  G  F  V  V  H  P  D  L  L  D  A  V  F  S  A  V

GGCGACGGAAGCCGCCAGCCGGCCGGATGGCGCGACCTGACGGTGCACGC         3400
 G  D  G  S  R  Q  P  A  G  W  R  D  L  T  V  H  A

GTCGGACGCCACCGTACTGCGCGCCTGCCTCACCCGGCGCACCGACGGAG         3450
  S  D  A  T  V  L  R  A  C  L  T  R  R  T  D  G

CCATGGGATTCGCCGCCTTCGACGGCGCCGGCCTGCCGGTACTCACCGCG         3500
 A  M  G  F  A  A  F  D  G  A  G  L  P  V  L  T  A

GAGGCGGTGACGCTGCGGGAGGTGGCGTCACCGTCCGGCTCCGAGGAGTC         3550
  E  A  V  T  L  R  E  V  A  S  P  S  G  S  E  E  S
```

```
GGACGGCCTGCACCGGTTGGAGTGGCTCGCGGTCGCCGAGGCGGTCTACG        3600
 D  G  L  H  R  L  E  W  L  A  V  A  E  A  V  Y

ACGGTGACdTGCCCGAGGGACATGTCCTGATCACCGCCGCCCACCCCGAC        3650
 D  G  D  L  P  E  G  H  V  L  I  T  A  A  H  P  D

GACCCCGAGGACATACCCACCCGCGCCCACACCCGCGCCACCCGCGTCCT        3700
 D  P  E  D  I  P  T  R  A  H  T  R  A  T  R  V  L

GACCGCCCTGCAACACCACCTCACCACCACCGACCACACCCTCATCGTCC        3750
   T  A  L  Q  H  H  L  T  T  T  D  H  T  L  I  V

ACACCACCACCGACCCCGCCGGCGCCACCGTCACCGGCCTCACCCGCACC        3800
 H  T  T  T  D  P  A  G  A  T  V  T  G  L  T  R  T

GCCCAGAACGAACACCCCCACCGCATCCGCCTCATCGAAACCGACCACCC        3850
 A  Q  N  E  H  P  H  R  I  R  L  I  E  T  D  H  P

CCACACCCCCCTCCCCCTGGCCCAACTCGCCACCCTCGACCACCCCCACC        3900
   H  T  P  L  P  L  A  Q  L  A  T  L  D  H  P  H

TCCGCCTCACCCACCACACCCTCCACCACCCCCACCTCACCCCCCTCCAC        3950
 L  R  L  T  H  H  T  L  H  H  P  H  L  T  P  L  H

ACCACCACCCCCACCCACCACCACCCCCCTCAACCCCGAACACGCCATCAT        4000
 T  T  T  P  P  T  T  T  P  L  N  P  E  H  A  I  I

CATCACCGGCGGCTCCGGCACCCTCGCCGGCATCCTCGCCCGCCACCTGA        4050
   I  T  G  G  S  G  T  L  A  G  I  L  A  R  H  L

ACCACCCCCACACCTACCTCCTCTCCCGCACCCCACCCCCCGACGCCACC        4100
 N  H  P  H  T  Y  L  L  S  R  T  P  P  P  D  A  T

CCCGGCACCCACCTCCCCTGCGACGTCGGCGACCCCCACCAACTCGCCAC        4150
 P  G  T  H  L  P  C  D  V  G  D  P  H  Q  L  A  T

CACCCTCACCCACATCCCCCAACCCCTCACCGCCATCTTCCACACCGCCG        4200
   T  L  T  H  I  P  Q  P  L  T  A  I  F  H  T  A

CCACCCTCGACGACGGCATCCTCCACGCCCTCACCCCCGACCGCCTCACC        4250
 A  T  L  D  D  G  I  L  H  A  L  T  P  D  R  L  T

ACCGTCCTCCACCCCAAAGCCAACGCCGCCTGGCACCTGCACCACCTCAC        4300
   T  V  L  H  P  K  A  N  A  A  W  H  L  H  H  L  T

CCAAAACCAACCCCTCACCCACTTCGTCCTCTACTCCAGCGCCGCCGCCG        4350
 Q  N  Q  P  L  T  H  F  V  L  Y  S  S  A  A  A

TCCTCGGCAGCCCCGGACAAGGAAACTACGCCGCCGCCAACGCCTTCCTC        4400
 V  L  G  S  P  G  Q  G  N  Y  A  A  A  N  A  F  L

GACGCCCTCGCCACCCACCGCCACACCCTCGGCCAACCCGCCACCTCCAT        4450
   D  A  L  A  T  H  R  H  T  L  G  Q  P  A  T  S  I

CGCCTGGGGCATGTGGCACACCACCAGCACCCTCACCGGACAACTCGACG        4500
 A  W  G  M  W  H  T  T  S  T  L  T  G  Q  L  D

ACGCCGACCGGGACCGCATCCGCCGCGGCGGTTTCCTCCCGATCACGGAC        4550
 D  A  D  R  D  R  I  R  R  G  G  F  L  P  I  T  D

GACGAGGGCATGGGGATGCAT
 D  E  G
```

The NheII-XhoI restriction fragment that encodes module 8 of the FK-520 PKS with the endogenous AT domain replaced by the AT domain of module 12 (specific for malonyl CoA) of the rapamycin PKS has the DNA sequence and encodes the amino acid sequence shown below (SEQ ID NOS:20-21).

```
AGATCTGGCAGCTCGCCGAAGCGCTGCTGACGCTCGTCCGGGAGAGCACC            50
   Q  L  A  E  A  L  L  T  L  V  R  E  S  T

GCCGCCGTGCTCGGCCACGTGGGTGGCGAGGACATCCCCGCGACGGCGGC           100
 A  A  V  L  G  H  V  G  G  E  D  I  P  A  T  A  A

GTTCAAGGACCTCGGCATCGACTCGCTCACCGCGGTCCAGCTGCGCAACG           150
 F  K  D  L  G  I  D  S  L  T  A  V  Q  L  R  N
```

```
CCCTCACCGAGGCGACCGGTGTGCGGCTGAACGCCACGGCGGTCTTCGAC          200
 A  L  T  E  A  T  G  V  R  L  N  A  T  A  V  F  D

TTCCCGACCCCGCACGTGCTCGCCGGGAAGCTCGGCGACGAACTGACCGG          250
 F  P  T  P  H  V  L  A  G  K  L  G  D  E  L  T  G

CACCCGCGCGCCCGTCGTGCCCCGGACCGCGGCCACGGCCGGTGCGCACG          300
   T  R  A  P  V  V  P  R  T  A  A  T  A  G  A  H

ACGAGCCGCTGGCGATCGTGGGAATGGCCTGCCGGCTGCCCGGCGGGGTC          350
 D  E  P  L  A  I  V  G  M  A  C  R  L  P  G  G  V

GCGTCACCCGAGGAGCTGTGGCACCTCGTGGCATCCGGCACCGACGCCAT          400
 A  S  P  E  E  L  W  H  L  V  A  S  G  T  D  A  I

CACGGAGTTCCCGACGGACCGCGGCTGGGACGTCGACGCGATCTACGACC          450
   T  E  F  P  T  D  R  G  W  D  V  D  A  I  Y  D

CGGACCCCGACGCGATCGGCAAGACCTTCGTCCGGCACGGTGGCTTCCTC          500
 P  D  P  D  A  I  G  K  T  F  V  R  H  G  G  F  L

ACCGGCGCGACAGGCTTCGACGCGGCGTTCTTCGGCATCAGCCCGCGCGA          550
   T  G  A  T  G  F  D  A  A  F  F  G  I  S  P  R  E

GGCCCTCGCGATGGACCCGCAGCAGCGGGTGCTCCTGGAGACGTCGTGGG          600
   A  L  A  M  D  P  Q  Q  R  V  L  L  E  T  S  W

AGGCGTTCGAAAGCGCCGGCATCACCCCGGACTCGACCCGCGGCAGCGAC          650
 E  A  F  E  S  A  G  I  T  P  D  S  T  R  G  S  D

ACCGGCGTGTTCGTCGGCGCCTTCTCCTACGGTTACGGCACCGGTGCGGA          700
   T  G  V  F  V  G  A  F  S  Y  G  Y  G  T  G  A  D

CACCGACGGCTTCGGCGCGACCGGCTCGCAGACCAGTGTGCTCTCCGGCC          750
   T  D  G  F  G  A  T  G  S  Q  T  S  V  L  S  G

GGCTGTCGTACTTCTACGGTCTGGAGGGTCCGGCGGTCACGGTCGACACG          800
 R  L  S  Y  F  Y  G  L  E  G  P  A  V  T  V  D  T

GCGTGTTCGTCGTCGCTGGTGGCGCTGCACCAGGCCGGGCAGTCGCTGCG          850
 A  C  S  S  S  L  V  A  L  H  Q  A  G  Q  S  L  R

CTCCGGCGAATGCTCGCTCGCCCTGGTCGGCGGCGTCACGGTGATGGCGT          900
   S  G  E  C  S  L  A  L  V  G  G  V  T  V  M  A

CTCCCGGCGGCTTCGTGGAGTTCTCCCGGCAGCGCGGCCTCGCGCCGGAC          950
 S  P  G  G  F  V  E  F  S  R  Q  R  G  L  A  P  D

GGCCGGGCGAAGGCGTTCGGCGCGGGTGCGGACGGCACGAGCTTCGCCGA          1000
   G  R  A  K  A  F  G  A  G  A  D  G  T  S  F  A  E

GGGTGCCGGTGTGCTGATCGTCGAGAGGCTCTCCGACGCCGAACGCAACG          1050
   G  A  G  V  L  I  V  E  R  L  S  D  A  E  R  N

GTCACACCGTCCTGGCGGTCGTCCGTGGTTCGGCGGTCAACCAGGATGGT          1100
 G  H  T  V  L  A  V  V  R  G  S  A  V  N  Q  D  G

GCCTCCAACGGGCTGTCGGCGCCGAACGGGCCGTCGCAGGAGCGGGTGAT          1150
 A  S  N  G  L  S  A  P  N  G  P  S  Q  E  R  V  I

CCGGCAGGCCCTGGCCAACGCCGGGCTCACCCCGGCGGACGTGGACGCCG          1200
   R  Q  A  L  A  N  A  G  L  T  P  A  D  V  D  A

TCGAGGCCCACGGCACCGGCACCAGGCTGGGCGACCCCATCGAGGCACAG          1250
 V  E  A  H  G  T  G  T  R  L  G  D  P  I  E  A  Q

GCGGTACTGGCCACCTACGGACAGGAGCGCGCCACCCCCCTGCTGCTGGG          1300
   A  V  L  A  T  Y  G  Q  E  R  A  T  P  L  L  L  G

CTCGCTGAAGTCCAACATCGGCCACGCCCAGGCCGCGTCCGGCGTCGCCG          1350
   S  L  K  S  N  I  G  H  A  Q  A  A  S  G  V  A

GCATCATCAAGATGGTGCAGGCCCTCCGGCACGGGGAGCTGCCGCCGACG          1400
 G  I  I  K  M  V  Q  A  L  R  H  G  E  L  P  P  T

CTGCACGCCGACGAGCCGTCGCCGCACGTCGACTGGACGGCCGGCGCCGT          1450
 L  H  A  D  E  P  S  P  H  V  D  W  T  A  G  A  V
```

-continued

```
CGAACTGCTGACGTCGGCCCGGCCGTGGCCCGAGACCGACCGGCCACGGC      1500
 E  L  L  T  S  A  R  P  W  P  E  T  D  R  P  R

GTGCCGCCGTCTCCTCGTTCGGGGTGAGCGGCACCAACGCCCACGTCATC      1550
 R  A  A  V  S  S  F  G  V  S  G  T  N  A  H  V  I

CTGGAGGCCGGACCGGTAACGGAGACGCCCGCGGCATCGCCTTCCGGTGA      1600
 L  E  A  G  P  V  T  E  T  P  A  A  S  P  S  G  D

CCTTCCCCTGCTGGTGTCGGCACGCTCACCGGAAGCGCTCGACGAGCAGA      1650
 L  P  L  L  V  S  A  R  S  P  E  A  L  D  E  Q

TCCGCCGACTGCGCGCCTACCTGGACACCACCCCGGACGTCGACCGGGTG      1700
 I  R  R  L  R  A  Y  L  D  T  T  P  D  V  D  R  V

GCCGTGGCACAGACGCTGGCCCGGCGCACACACTTCGCCCACCGCGCCGT      1750
 A  V  A  Q  T  L  A  R  R  T  H  F  A  H  R  A  V

GCTGCTCGGTGACACCGTCATCACCACACCCCCGCGGACCGGCCCGACG       1800
 L  L  G  D  T  V  I  T  T  P  P  A  D  R  P  D

AACTCGTCTTCGTCTACTCCGGCCAGGGCACCCAGCATCCCGCGATGGGC      1850
 E  L  V  F  V  Y  S  G  Q  G  T  Q  H  P  A  M  G

GAGCAGCTAGCCGCCGCGTTCCCCGTCTTCGCGCGGATCCATCAGCAGGT      1900
 E  Q  L  A  A  A  F  P  V  F  A  R  I  H  Q  Q  V

GTGGGACCTGCTCGATGTGCCCGATCTGGAGGTGAACGAGACCGGTTACG      1950
 W  D  L  L  D  V  P  D  L  E  V  N  E  T  G  Y

CCCAGCCGGCCCTGTTCGCAATGCAGGTGGCTCTGTTCGGGCTGCTGGAA      2000
 A  Q  P  A  L  F  A  M  Q  V  A  L  F  G  L  L  E

TCGTGGGGTGTACGACCGGACGCGGTGATCGGCCATTCGGTGGGTGAGCT      2050
 S  W  G  V  R  P  D  A  V  I  G  H  S  V  G  E  L

TGCGGCTGCGTATGTGTCCGGGGTGTGGTCGTTGGAGGATGCCTGCACTT      2100
 A  A  A  Y  V  S  G  V  W  S  L  E  D  A  C  T

TGGTGTCGGCGCGGGCTCGTCTGATGCAGGCTCTGCCCGCGGGTGGGGTG      2150
 L  V  S  A  R  A  R  L  M  Q  A  L  P  A  G  G  V

ATGGTCGCTGTCCCGGTCTCGGAGGATGAGGCCCGGGCCGTGCTGGGTGA      2200
 M  V  A  V  P  V  S  E  D  E  A  R  A  V  L  G  E

GGGTGTGGAGATCGCCGCGGTCAACGGCCCGTCGTCGGTGGTTCTCTCCG      2250
 G  V  E  I  A  A  V  N  G  O  S  S  V  V  L  S

GTGATGAGGCCGCCGTGCTGCAGGCCGCGGAGGGGCTGGGGAAGTGGACG      2300
 G  D  E  A  A  V  L  Q  A  A  E  G  L  G  K  W  T

CGGCTGGCGACCAGCCACGCGTTCCATTCCGCCCGTATGGAACCCATGCT      2350
 R  L  A  T  S  H  A  F  H  S  A  R  M  E  P  M  L

GGAGGAGTTCCGGGCGGTCGCCGAAGGCCTGACCTACCGGACGCCGCAGG      2400
 E  E  F  R  A  V  A  E  G  L  T  Y  R  T  P  Q

TCTCCATGGCCGTTGGTGATCAGGTGACCACCGCTGAGTACTGGGTGCGG      2450
 V  S  M  A  V  G  D  Q  V  T  T  A  E  Y  W  V  R

CAGGTCCGGGACACGGTCCGGTTCGGCGAGCAGGTGGCCTCGTACGAGGA      2500
 Q  V  R  D  T  V  R  F  G  E  Q  V  A  S  Y  E  D

CGCCGTGTTCGTCGAGCTGGGTGCCGACCGGTCACTGGCCCGCCTGGTCG      2550
 A  V  F  V  E  L  G  A  D  R  S  L  A  R  L  V

ACGGTGTCGCGATGCTGCACGGCGACCACGAAATCCAGGCCGCGATCGGC      2600
 D  G  V  A  M  L  H  G  D  H  E  I  Q  A  A  I  G

GCCCTGGCCCACCTGTATGTCAACGGCGTCACGGTCGACTGGCCCGCGCT      2650
 A  L  A  H  L  Y  V  N  G  V  T  V  D  W  P  A  L

CCTGGGCGATGCTCCGGCAACACGGGTGCTGGACCTTCCGACATACGCCT      2700
 L  G  D  A  P  A  T  R  V  L  D  L  P  T  Y  A

TCCAGCACCAGCGCTACTGGCTCGAGTCGGCACGCCCGGCCGCATCCGAC      2750
 F  Q  H  Q  R  Y  W  L  E  S  A  R  P  A  A  S  D
```

```
GCGGGCCACCCCGTGCTGGGCTCCGGTATCGCCCTCGCCGGGTCGCCGGG         2800
  A  G  H  P  V  L  G  S  G  I  A  L  A  G  S  P  G

CCGGGTGTTCACGGGTTCCGTGCCGACCGGTGCGGACCGCGCGGTGTTCG         2850
  R  V  F  T  G  S  V  P  T  G  A  D  R  A  V  F

TCGCCGAGCTGGCGCTGGCCGCCGCGGACGCGGTCGACTGCGCCACGGTC         2900
 V  A  E  L  A  L  A  A  A  D  A  V  D  C  A  T  V

GAGCGGCTCGACATCGCCTCCGTGCCCGGCCGGCCGGGCCATGGCCGGAC         2950
 E  R  L  D  I  A  S  V  P  G  R  P  G  H  G  R  T

GACCGTACAGACCTGGGTCGACGAGCCGGCGGACGACGGCCGGCGCCGGT         3000
  T  V  Q  T  W  V  D  E  P  A  D  D  G  R  R  R

TCACCGTGCACACCCGCACCGGCGACGCCCCGTGGACGCTGCACGCCGAG         3050
 F  T  V  H  T  R  T  G  D  A  P  W  T  L  H  A  E

GGGGTGCTGCGCCCCCATGGCACGGCCCTGCCCGATGCGGCCGACGCCGA         3100
  G  V  L  R  P  H  G  T  A  L  P  D  A  A  D  A  E

GTGGCCCCCACCGGGCGCGGTGCCCGGGACGGGCTGCCGGGTGTGTGGC          3150
  W  P  P  P  G  A  V  P  A  D  G  L  P  G  V  W

GCCGGGGGACCAGGTCTTCGCCGAGGCCGAGGTGGACGGACCGGACGGT          3200
 R  R  G  D  Q  V  F  A  E  A  E  V  D  G  P  D  G

TTCGTGGTGCACCCCGACCTGCTCGACGCGGTCTTCTCCGCGGTCGGCGA         3250
 F  V  V  H  P  D  L  L  D  A  V  F  S  A  V  G  D

CGGAAGCCGCCAGCCGGCCGGATGGCGCGACCTGACGGTGCACGCGTCGG         3300
  G  S  R  Q  P  A  G  W  R  D  L  T  V  H  A  S

ACGCCACCGTACTGCGCGCCTGCCTCACCCGGCGCACCGACGGAGCCATG         3350
 D  A  T  V  L  R  A  C  L  T  R  R  T  D  G  A  M

GGATTCGCCGCCTTCGACGGCGCCGGCCTGCCGGTACTCACCGCGGAGGC         3400
  G  F  A  A  F  D  G  A  G  L  P  V  L  T  A  E  A

GGTGACGCTGCGGGAGGTGGCGTCACCGTCCGGCTCCGAGGAGTCGGACG         3450
  V  T  L  R  E  V  A  S  P  S  G  S  E  E  S  D

GCCTGCACCGGTTGGAGTGGCTCGCGGTCGCCGAGGCGGTCTACGACGGT         3500
  G  L  H  R  L  E  W  L  A  V  A  E  A  V  Y  D  G

GACCTGCCCGAGGGACATGTCCTGATCACCGCCGCCCACCCCGACGACCC         3550
  D  L  P  E  G  H  V  L  I  T  A  A  H  P  D  D  P

CGAGGACATACCCACCCGCGCCCACACCCGCGCCACCCGCGTCCTGACCG         3600
  E  D  I  P  T  R  A  H  T  R  A  T  R  V  L  T

CCCTGCAACACCACCTCACCACCACCGACCACACCCTCATCGTCCACACC         3650
 A  L  Q  H  H  L  T  T  T  D  H  T  L  I  V  H  T

ACCACCGACCCCGCCGGCGCCACCGTCACCGGCCTCACCCGCACCGCCCA         3700
  T  T  D  P  A  G  A  T  V  T  G  L  T  R  T  A  Q

GAACGAACACCCCCACCGCATCCGCCTCATCGAAACCGACCACCCCCACA         3750
  N  E  H  P  H  R  I  R  L  I  E  T  D  H  P  H

CCCCCCTCCCCCTGGCCCAACTCGCCACCCTCGACCACCCCCACCTCCGC         3800
  T  P  L  P  L  A  Q  L  A  T  L  D  H  P  H  L  R

CTCACCCACCACACCCTCCACCACCCCCACCTCACCCCCCTCCACACCAC         3850
  L  T  H  H  T  L  H  H  P  H  L  T  P  L  H  T  T

CACCCCACCCACCACCACCCCCCTCAACCCCGAACACGCCATCATCATCA         3900
   T  P  P  T  T  T  P  L  N  P  E  H  A  I  I  I

CCGGCGGCTCCGGCACCCTCGCCGGCATCCTCGCCCGCCACCTGAACCAC         3950
  T  G  G  S  G  T  L  A  G  I  L  A  R  H  L  N  H

CCCCACACCTACCTCCTCTCCCGCACCCCCACCCCCCGACGCCACCCCCGG        4000
  P  H  T  Y  L  L  S  R  T  P  P  P  D  A  T  P  G

CACCCACCTCCCCTGCGACGTCGGCGACCCCCACCAACTCGCCACCACCC         4050
  T  H  L  P  C  D  V  G  D  P  H  Q  L  A  T  T
```

```
TCACCCACATCCCCCAACCCCTCACCGCCATCTTCCACACCGCCGCCACC          4100
 L  T  H  I  P  Q  P  L  T  A  I  F  H  T  A  A  T

CTCGACGACGGCATCCTCCACGCCCTCACCCCCGACCGCCTCACCACCGT          4150
 L  D  D  G  I  L  H  A  L  T  P  D  R  L  T  T  V

CCTCCACCCCAAAGCCAACGCCGCCTGGCACCTGCACCACCTCACCCAAA          4200
  L  H  P  K  A  N  A  A  W  H  L  H  H  L  T  Q

ACCAACCCCTCACCCACTTCGTCCTCTACTCCAGCGCCGCCGCCGTCCTC          4250
 N  Q  P  L  T  H  F  V  L  Y  S  S  A  A  A  V  L

GGCAGCCCCGGACAAGGAAACTACGCCGCCGCCAACGCCTTCCTCGACGC          4300
  G  S  P  G  Q  G  N  Y  A  A  A  N  A  F  L  D  A

CCTCGCCACCCACCGCCACACCCTCGGCCAACCCGCCACCTCCATCGCCT          4350
   L  A  T  H  R  H  T  L  G  Q  P  A  T  S  I  A

GGGGCATGTGGCACACCACCAGCACCCTCACCGGACAACTCGACGACGCC          4400
 W  G  M  W  H  T  T  S  T  L  T  G  Q  L  D  D  A

GACCGGGACCGCATCCGCCGCGGCGGTTTCCTCCCGATCACGGACGACGA          4450
 D  R  D  R  I  R  R  G  G  F  L  P  I  T  D  D  E

GGGCATGGGGATGCAT
 G
```

The NheII-XhoI restriction fragment that encodes module 8 of the FK-520 PKS with the endogenous AT domain replaced by the AT domain of module 13 (specific for methylmalonyl CoA) of the rapamycin PKS has the DNA sequence and encodes the amino acid sequence shown below (SEQ ID NOS:22-23).

```
AGATCTGGCAGCTCGCCGAAGCGCTGCTGACGCTCGTCCGGGAGAGCACC          50
  Q  L  A  E  A  L  L  T  L  V  R  E  S  T

GCCGCCGTGCTCGGCCACGTGGGTGGCGAGGACATCCCCGCGACGGCGGC          100
 A  A  V  L  G  H  V  G  G  E  D  I  P  A  T  A  A

GTTCAAGGACCTCGGCATCGACTCGCTCACCGCGGTCCAGCTGCGCAACG          150
  F  K  D  L  G  I  D  S  L  T  A  V  Q  L  R  N

CCCTCACCGAGGCGACCGGTGTGCGGCTGAACGCCACGGCGGTCTTCGAC          200
 A  L  T  E  A  T  G  V  R  L  N  A  T  A  V  F  D

TTCCCGACCCCGCACGTGCTCGCCGGGAAGCTCGGCGACGAACTGACCGG          250
 F  P  T  P  H  V  L  A  G  K  L  G  D  E  L  T  G

CACCCGCGCGCCCGTCGTGCCCCGGACCGCGGCCACGGCCGGTGCGCACG          300
   T  R  A  P  V  V  P  R  T  A  A  T  A  G  A  H

ACGAGCCGCTGGCGATCGTGGGAATGGCCTGCCGGCTGCCCGGCGGGGTC          350
 D  E  P  L  A  I  V  G  M  A  C  R  L  P  G  G  V

GCGTCACCCGAGGAGCTGTGGCACCTCGTGGCATCCGGCACCGACGCCAT          400
  A  S  P  E  E  L  W  H  L  V  A  S  G  T  D  A  I

CACGGAGTTCCCGACGGACCGCGGCTGGGACGTCGACGCGATCTACGACC          450
   T  E  F  P  T  D  R  G  W  D  V  D  A  I  Y  D

CGGACCCCGACGCGATCGGCAAGACCTTCGTCCGGCACGGTGGCTTCCTC          500
 P  D  P  D  A  I  G  K  T  F  V  R  H  G  G  F  L

ACCGGCGCGACAGGCTTCGACGCGGCGTTCTTCGGCATCAGCCCGCGCGA          550
  T  G  A  T  G  F  D  A  A  F  F  G  I  S  P  R  E

GGCCCTCGCGATGGACCCGCAGCAGCGGGTGCTCCTGGAGACGTCGTGGG          600
   A  L  A  M  D  P  Q  Q  R  V  L  L  E  T  S  W

AGGCGTTCGAAAGCGCCGGCATCACCCCGGACTCGACCCGCGGCAGCGAC          650
 E  A  F  E  S  A  G  I  T  P  D  S  T  R  G  S  D

ACCGGCGTGTTCGTCGGCGCCTTCTCCTACGGTTACGGCACCGGTGCGGA          700
  T  G  V  F  V  G  A  F  S  Y  G  Y  G  T  G  A  D

CACCGACGGCTTCGGCGCGACCGGCTCGCAGACCAGTGTGCTCTCCGGCC          750
   T  D  G  F  G  A  T  G  S  Q  T  S  V  L  S  G
```

```
GGCTGTCGTACTTCTACGGTCTGGAGGGTCCGGCGGTCACGGTCGACACG         800
 R  L  S  Y  F  Y  G  L  E  G  P  A  V  T  V  D  T

GCGTGTTCGTCGTCGCTGGTGGCGCTGCACCAGGCCGGGCAGTCGCTGCG         850
 A  C  S  S  S  L  V  A  L  H  Q  A  G  Q  S  L  R

CTCCGGCGAATGCTCGCTCGCCCTGGTCGGCGGCGTCACGGTGATGGCGT         900
  S  G  E  C  S  L  A  L  V  G  G  V  T  V  M  A

CTCCCGGCGGCTTCGTGGAGTTCTCCCGGCAGCGCGGCCTCGCGCCGGAC         950
 S  P  G  G  F  V  E  F  S  R  Q  R  G  L  A  P  D

GGCCGGGCGAAGGCGTTCGGCGCGGGTGCGGACGGCACGAGCTTCGCCGA        1000
 G  R  A  K  A  F  G  A  G  A  D  G  T  S  F  A  E

GGGTGCCGGTGTGCTGATCGTCGAGAGGCTCTCCGACGCCAACGCAACG         1050
  G  A  G  V  L  I  V  E  R  L  S  D  A  E  R  N

GTCACACCGTCCTGGCGGTCGTCCGTGGTTCGGCGGTCAACCAGGATGGT        1100
 G  H  T  V  L  A  V  V  R  G  S  A  V  N  Q  D  G

GCCTCCAACGGGCTGTCGGCGCCGAACGGGCCGTCGCAGGAGCGGGTGAT        1150
  A  S  N  G  L  S  A  P  N  G  P  S  Q  E  R  V  I

CCGGCAGGCCCTGGCCAACGCCGGGCTCACCCCGGCGGACGTGGACGCCG        1200
  R  Q  A  L  A  N  A  G  L  T  P  A  D  V  D  A

TCGAGGCCCACGGCACCGGCACCAGGCTGGGCGACCCCATCGAGGCACAG        1250
 V  E  A  H  G  T  G  T  R  L  G  D  P  I  E  A  Q

GCGGTACTGGCCACCTACGGACAGGAGCGCGCCACCCCCCTGCTGCTGGG        1300
  A  V  L  A  T  Y  G  Q  E  R  A  T  P  L  L  L  G

CTCGCTGAAGTCCAACATCGGCCACGCCCAGGCCGCGTCCGGCGTCGCCG        1350
  S  L  K  S  N  I  G  H  A  Q  A  A  S  G  V  A

GCATCATCAAGATGGTGCAGGCCCTCCGGCACGGGGAGCTGCCGCCGACG        1400
 G  I  I  K  M  V  Q  A  L  R  H  G  E  L  P  P  T

CTGCACGCCGACGAGCCGTCGCCGCACGTCGACTGGACGGCCGGCGCCGT        1450
 L  H  A  D  E  P  S  P  H  V  D  W  T  A  G  A  V

CGAACTGCTGACGTCGGCCCGGCCGTGGCCCGAGACCGACCGGCCACGGC        1500
  E  L  L  T  S  A  R  P  W  P  E  T  D  R  P  R

GTGCCGCCGTCTCCTCGTTCGGGGTGAGCGGCACCAACGCCCACGTCATC        1550
 R  A  A  V  S  S  F  G  V  S  G  T  N  A  H  V  I

CTGGAGGCCGGACCGGTAACGGAGACGCCCGCGGCATCGCCTTCCGGTGA        1600
  L  E  A  G  P  V  T  E  T  P  A  A  S  P  S  G  D

CCTTCCCCTGCTGGTGTCGGCACGCTCACCGGAAGCGCTCGACGAGCAGA        1650
  L  P  L  L  V  S  A  R  S  P  E  A  L  D  E  Q

TCCGCCGACTGCGCGCCTACCTGGACACCACCCCGGACGTCGACCGGGTG        1700
 I  R  R  L  R  A  Y  L  D  T  T  P  D  V  D  R  V

GCCGTGGCACAGACGCTGGCCCGGCGCACACACTTCGCCCACCGCGCCGT        1750
 A  V  A  Q  T  L  A  R  R  T  H  F  A  H  R  A  V

GCTGCTCGGTGACACCGTCATCACCACACCCCCCGCGGACCGGCCCGACG        1800
  L  L  G  D  T  V  I  T  T  P  P  A  D  R  P  D

AACTCGTCTTCGTCTACTCCGGCCAGGGCACCCAGCATCCCGCGATGGGC        1850
 E  L  V  F  V  Y  S  G  Q  G  T  Q  H  P  A  M  G

GAGCAGCTAGCCGATTCGTCGGTGGTGTTCGCCGAGCGGATGGCCGAGTG        1900
 E  Q  L  A  D  S  S  V  V  F  A  E  R  M  A  E  C

TGCGGCGGCGTTGCGCGAGTTCGTGGACTGGGATCTGTTCACGGTTCTGG        1950
  A  A  A  L  R  E  F  V  D  W  D  L  F  T  V  L

ATGATCCGGCGGTGGTGGACCGGGTTGATGTGGTCCAGCCCGCTTCCTGG        2000
 D  D  P  A  V  V  D  R  V  D  V  V  Q  P  A  S  W

GCGATGATGGTTTCCCTGGCCGCGGTGTGGCAGGCGGCCGGTGTGCGGCC        2050
 A  M  M  V  S  L  A  A  V  W  Q  A  A  G  V  R  P
```

```
                                      -continued
GGATGCGGTGATCGGCCATTCGCAGGGTGAGATCGCCGCAGCTTGTGTGG      2100
  D  A  V  I  G  H  S  Q  G  E  I  A  A  A  C  V CGGGTGCGGTGTCACTACGCGATGCCGCCCGGATCGTGACCTTGCGCAGC      2150
A  G  A  V  S  L  R  D  A  A  R  I  V  T  L  R  S CAGGCGATCGCCCGGGGCCTGGCGGGCCGGGGCGCGATGGCATCCGTCGC      2200
  Q  A  I  A  R  G  L  A  G  R  G  A  M  A  S  V  A CCTGCCCGCGCAGGATGTCGAGCTGGTCGACGGGGCCTGGATCGCCGCCC      2250
  L  P  A  Q  D  V  E  L  V  D  G  A  W  I  A  A ACAACGGGCCCGCCTCCACCGTGATCGCGGGCACCCCGGAAGCGGTCGAC      2300
H  N  G  P  A  S  T  V  I  A  G  T  P  E  A  V  D CATGTCCTCACCGCTCATGAGGCACAAGGGGTGCGGGTGCGGCGGATCAC      2350
  H  V  L  T  A  H  E  A  Q  G  V  R  V  R  R  I  T CGTCGACTATGCCTCGCACACCCCGCACGTCGAGCTGATCCGCGACGAAC      2400
  V  D  Y  A  S  H  T  P  H  V  E  L  I  R  D  E TACTCGACATCACTAGCGACAGCAGCTCGCAGACCCCGCTCGTGCCGTGG      2450
L  L  D  I  T  S  D  S  S  S  Q  T  P  L  V  P  W CTGTCGACCGTGGACGGCACCTGGGTCGACAGCCCGCTGGACGGGGAGTA      2500
  L  S  T  V  D  G  T  W  V  D  S  P  L  D  G  E  Y CTGGTACCGGAACCTGCGTGAACCGGTCGGTTTCCACCCCGCCGTCAGCC      2550
  W  Y  R  N  L  R  E  P  V  G  F  H  P  A  V  S AGTTGCAGGCCCAGGGCGACACCGTGTTCGTCGAGGTCAGCGCCAGCCCG      2600
  Q  L  Q  A  Q  G  D  T  V  F  V  E  V  S  A  S  P GTGTTGTTGCAGGCGATGGACGACGATGTCGTCACGGTTGCCACGCTGCG      2650
  V  L  L  Q  A  M  D  D  D  V  V  T  V  A  T  L  R TCGTGACGACGGCGACGCCACCCGGATGCTCACCGCCCTGGCACAGGCCT      2700
  R  D  D  G  D  A  T  R  M  L  T  A  L  A  Q  A ATGTCCACGGCGTCACCGTCGACTGGCCCGCCATCCTCGGCACCACCACA      2750
Y  V  H  G  V  T  V  D  W  P  A  I  L  G  T  T  T ACCCGGGTACTGGACCTTCCGACCTACGCCTTCCAACACCAGCGGTACTG      2800
  T  R  V  L  D  L  P  T  Y  A  F  Q  H  Q  R  Y  W GCTCGAGTCGGCACGCCCGGCCGCATCCGACGCGGGCCACCCCGTGCTGG      2850
  L  E  S  A  R  P  A  A  S  D  A  G  H  P  V  L GCTCCGGTATCGCCCTCGCCGGGTCGCCGGGCCGGGTGTTCACGGGTTCC      2900
  G  S  G  I  A  L  A  G  S  P  G  R  V  F  T  G  S GTGCCGACCGGTGCGGACCGCGCGGTGTTCGTCGCCGAGCTGGCGCTGGC      2950
  V  P  T  G  A  D  R  A  V  F  V  A  E  L  A  L  A CGCCGCGGACGCGGTCGACTGCGCCACGGTCGAGCGGCTCGACATCGCCT      3000
  A  A  D  A  V  D  C  A  T  V  E  R  L  D  I  A CCGTGCCCGGCCGGCCGGGCCATGGCCGGACGACCGTACAGACCTGGGTC      3050
S  V  P  G  R  P  G  H  G  R  T  T  V  Q  T  W  V GACGAGCCGGCGGACGACGGCCGGCGCCGGTTCACCGTGCACACCCGCAC      3100
  D  E  P  A  D  D  G  R  R  R  F  T  V  H  T  R  T CGGCGACGCCCCGTGGACGCTGCACGCCGAGGGGGTGCTGCGCCCCCATG      3150
  G  D  A  P  W  T  L  H  A  E  G  V  L  R  P  H GCACGGCCCTGCCCGATGCGGCCGACGCCGAGTGGCCCCACCGGGCGCG       3200
  G  T  A  L  P  D  A  A  D  A  E  W  P  P  P  G  A GTGCCCGCGGACGGGCTGCCGGGTGTGTGGCGCCGGGGGGACCAGGTCTT      3250
  V  P  A  D  G  L  P  G  V  W  R  R  G  D  Q  V  F CGCCGAGGCCGAGGTGGACGGACCGGACGGTTTCGTGGTGCACCCCGACC      3300
  A  E  A  E  V  D  G  P  D  G  F  V  V  H  P  D TGCTCGACGCGGTCTTCTCCGCGGTCGGCGACGGAAGCCGCCAGCCGGCC      3350
  L  L  D  A  V  F  S  A  V  G  D  G  S  R  Q  P  A
```

```
GGATGGCGCGACCTGACGGTGCACGCGTCGGACGCCACCGTACTGCGCGC        3400
 G  W  R  D  L  T  V  H  A  S  D  A  T  V  L  R  A

CTGCCTCACCCGGCGCACCGACGGAGCCATGGGATTCGCCGCCTTCGACG        3450
 C  L  T  R  R  T  D  G  A  M  G  F  A  A  F  D

GCGCCGGCCTGCCGGTACTCACCGCGGAGGCGGTGACGCTGCGGGAGGTG        3500
 G  A  G  L  P  V  L  T  A  E  A  V  T  L  R  E  V

GCGTCACCGTCCGGCTCCGAGGAGTCGGACGGCCTGCACCGGTTGGAGTG        3550
 A  S  P  S  G  S  E  E  S  D  G  L  H  R  L  E  W

GCTCGCGGTCGCCGAGGCGGTCTACGACGGTGACCTGCCCGAGGGACATG        3600
 L  A  V  A  E  A  V  Y  D  G  D  L  P  E  G  H

TCCTGATCACCGCCGCCCACCCCGACGACCCCGAGGACATACCCACCCGC        3650
 V  L  I  T  A  A  H  P  D  D  P  E  D  I  P  T  R

GCCCACACCCGCGCCACCCGCGTCCTGACCGCCCTGCAACACCACCTCAC        3700
 A  H  T  R  A  T  R  V  L  T  A  L  Q  H  H  L  T

CACCACCGACCACACCCTCATCGTCCACACCACCACCGACCCCGCCGGCG        3750
 T  T  D  H  T  L  I  V  H  T  T  T  D  P  A  G

CCACCGTCACCGGCCTCACCCGCACCGCCCAGAACGAACACCCCCACCGC        3800
 A  T  V  T  G  L  T  R  T  A  Q  N  E  H  P  H  R

ATCCGCCTCATCGAAACCGACCACCCCCACACCCCCCTCCCCCTGGCCCA        3850
 I  R  L  I  E  T  D  H  P  H  T  P  L  P  L  A  Q

ACTCGCCACCCTCGACCACCCCCACCTCCGCCTCACCCACCACACCCTCC        3900
 L  A  T  L  D  H  P  H  L  R  L  T  H  H  T  L

ACCACCCCCACCTCACCCCCCTCCACACCACCACCCCACCCACCACCACC  3950
 H  H  P  H  L  T  P  L  H  T  T  T  P  P  T  T  T

CCCCTCAACCCCGAACACGCCATCATCATCACCGGCGGCTCCGGCACCCT        4000
 P  L  N  P  E  H  A  I  I  I  T  G  G  S  G  T  L

CGCCGGCATCCTCGCCCGCCACCTGAACCACCCCCACACCTACCTCCTCT        4050
 A  G  I  L  A  R  H  L  N  H  P  H  T  Y  L  L

CCCGCACCCCACCCCCCGACGCCACCCCCGGCACCCACCTCCCCTGCGAC        4100
 S  R  T  P  P  P  D  A  T  P  G  T  H  L  P  C  D

GTCGGCGACCCCCACCAACTCGCCACCACCCTCACCCACATCCCCCAACC        4150
 V  G  D  P  H  Q  L  A  T  T  L  T  H  I  P  Q  P

CCTCACCGCCATCTTCCACACCGCCGCCACCCTCGACGACGGCATCCTCC        4200
 L  T  A  I  F  H  T  A  A  T  L  D  D  G  I  L

ACGCCCTCACCCCCGACCGCCTCACCACCGTCCTCCACCCCAAAGCCAAC        4250
 H  A  L  T  P  D  R  L  T  T  V  L  H  P  K  A  N

GCCGCCTGGCACCTGCACCACCTCACCCAAAACCAACCCCTCACCCACTT        4300
 A  A  W  H  L  H  H  L  T  Q  N  Q  P  L  T  H  F

CGTCCTCTACTCCAGCGCCGCCGCCGTCCTCGGCAGCCCCGGACAAGGAA        4350
 V  L  Y  S  S  A  A  A  V  L  G  S  P  G  Q  G

ACTACGCCGCCGCCAACGCCTTCCTCGACGCCCTCGCCACCCACCGCCAC        4400
 N  Y  A  A  A  N  A  F  L  D  A  L  A  T  H  R  H

ACCCTCGGCCAACCCGCCACCTCCATCGCCTGGGGCATGTGGCACACCAC        4450
 T  L  G  Q  P  A  T  S  I  A  W  G  M  W  H  T  T

CAGCACCCTCACCGGACAACTCGACGACGCCGACCGGGACCGCATCCGCC        4500
 S  T  L  T  G  Q  L  D  D  A  D  R  D  R  I  R

GCGGCGGTTTCCTCCCCGATCACGGACGACGAGGGCATGGGGATGCAT
 R  G  G  F  L  P  I  T  D  D  E  G
```

Phage KC515 DNA was prepared using the procedure described in Genetic Manipulation of Streptomyces, A Laboratory Manual, edited by D. Hopwood et al. A phage suspension prepared from 10 plates (100 mm) of confluent plaques of KC515 on S. lividans TK24 generally gave about 3 μg of phage DNA. The DNA was ligated to circularize at the cos site, subsequently digested with restriction enzymes BamHI and PstI, and dephosphorylated with SAP.

Each module 8 cassette described above was excised with restriction enzymes BglII and NsiI and ligated into the compatible BamHI and PstI sites of KC515 phage DNA prepared as described above. The ligation mixture containing KC515 and various cassettes was transfected into protoplasts of Streptomyces lividans TK24 using the procedure described in Genetic Manipulation of Streptomyces, A Laboratory Manual edited by D. Hopwood et al. and overlaid with TK24 spores. After 16-24 hr, the plaques were restreaked on plates overlaid with TK24 spores. Single plaques were picked and resuspended in 200 μL of nutrient broth. Phage DNA was prepared by the boiling method (Hopwood et al., supra). The PCR with primers spanning the left and right boundaries of the recombinant phage was used to verify the correct phage had been isolated. In most cases, at least 80% of the plaques contained the expected insert. To confirm the presence of the resistance marker (thiostrepton), a spot test is used, as described in Lomovskaya et al. (1997), in which a plate with spots of phage is overlaid with mixture of spores of TK24 and phiC31 TK24 lysogen. After overnight incubation, the plate is overlaid with antibiotic in soft agar. A working stock is made of all phage containing desired constructs.

Streptomyces hygroscopicus ATCC 14891 (see U.S. Pat. No. 3,244,592, issued 5 Apr. 1966, incorporated herein by reference) mycelia were infected with the recombinant phage by mixing the spores and phage ($1\times10^8$ of each), and incubating on R2YE agar (Genetic Manipulation of Streptomyces, A Laboratory Manual, edited by D. Hopwood et al.) at 30° C. for 10 days. Recombinant clones were selected and plated on minimal medium containing thiostrepton (50 μg/ml) to select for the thiostrepton resistance-conferring gene. Primary thiostrepton resistant clones were isolated and purified through a second round of single colony isolation, as necessary. To obtain thiostrepton-sensitive revertants that underwent a second recombination event to evict the phage genome, primary recombinants were propagated in liquid media for two to three days in the absence of thiostrepton and then spread on agar medium without thiostrepton to obtain spores. Spores were plated to obtain about 50 colonies per plate, and thiostrepton sensitive colonies were identified by replica plating onto thiostrepton containing agar medium. The PCR was used to determine which of the thiostrepton sensitive colonies reverted to the wild type (reversal of the initial integration event), and which contain the desired AT swap at module 8 in the ATCC 14891-derived cells. The PCR primers used amplified either the KS/AT junction or the AT/DH junction of the wild-type and the desired recombinant strains. Fermentation of the recombinant strains, followed by isolation of the metabolites and analysis by LCMS, and NMR is used to characterize the novel polyketide compounds.

Example 2

Replacement of Methoxyl with Hydrogen or Methyl at C-13 of FK-506

The present invention also provides the 13-desmethoxy derivatives of FK-506 and the novel PKS enzymes that produce them. A variety of Streptomyces strains that produce FK-506 are known in the art, including S. tsukubaensis No. 9993 (FERM BP-927), described in U.S. Pat. No. 5,624,852, incorporated herein by reference; S. hygroscopicus subsp. yakushimaensis No. 7238, described in U.S. Pat. No. 4,894,366, incorporated herein by reference; S. sp. MA6858 (ATCC 55098), described in U.S. Pat. No. 5,116,756, incorporated herein by reference; and S. sp. MA 6548, described in Motamedi et al., 1998, "The biosynthetic gene cluster for the macrolactone ring of the immunosuppressant FK-506," Eur. J. Biochem. 256: 528-534, and Motamedi et al., 1997, "Structural organization of a multifunctional polyketide synthase involved in the biosynthesis of the macrolide immunosuppressant FK-506," Eur. J. Biochem. 244: 74-80, each of which is incorporated herein by reference.

The complete sequence of the FK-506 gene cluster from Streptomyces sp. MA6548 is known, and the sequences of the corresponding gene clusters from other FK-506-producing organisms is highly homologous thereto. The novel FK-506 recombinant gene clusters of the present invention differ from the naturally occurring gene clusters in that the AT domain of module 8 of the naturally occurring PKSs is replaced by an AT domain specific for malonyl CoA or methylmalonyl CoA. These AT domain replacements are made at the DNA level, following the methodology described in Example 1.

The naturally occurring module 8 sequence for the MA6548 strain is shown below, followed by the illustrative hybrid module 8 sequences for the MA6548 strains (SEQ ID NOS:24-25).

```
GCATGCGGCTGTACGAGGCGGCACGGCGCACCGGAAGTCCCGTGGTGGTG         50
   M  R  L  Y  E  A  A  R  R  T  G  S  P  V  V  V

GCGGCCGCGCTCGACGACGCGCCGGACGTGCCGCTGCTGCGCGGGCTGCG        100
 A  A  A  L  D  D  A  P  D  V  P  L  L  R  G  L  R

GCGTACGACCGTCCGGCGTGCCGCCGTCCGGGAACGCTCTCTCGCCGACC        150
  R  T  T  V  R  R  A  A  V  R  E  R  S  L  A  D

GCTCGCCGTGCTGCCCGACGACGAGCGCGCCGACGCCTCCCTCGCGTTCG        200
 R  S  P  C  C  P  T  T  S  A  P  T  P  P  S  R  S

TCCTGGAACAGCACCGCCACCGTGCTCGGCCACCTGGGCGCCGAAGACAT        250
  S  W  N  S  T  A  T  V  L  G  H  L  G  A  E  D  I

CCCGGCGACGACGACGTTCAAGGAACTCGGCATCGACTCGCTCACCGCGG        300
   P  A  T  T  T  F  K  E  L  G  I  D  S  L  T  A

TCCAGCTGCGCAACGCGCTGACCACGGCGACCGGCGTACGCCTCAACGCC        350
   V  Q  L  R  N  A  L  T  T  A  T  G  V  R  L  N  A
```

-continued

```
ACAGCGGTCTTCGACTTTCCGACGCCGCGCGCGCTCGCCGCGAGACTCGG      400
 T  A  V  F  D  F  P  T  P  R  A  L  A  A  R  L  G

CGACGAGCTGGCCGGTACCCGCGCGCCCGTCGCGGCCCGGACCGCGGCCA      450
  D  E  L  A  G  T  R  A  P  V  A  A  R  T  A  A

CCGCGGCCGCGCACGACGAACCGCTGGCGATCGTGGGCATGGCCTGCCGT      500
 T  A  A  A  H  D  E  P  L  A  I  V  G  M  A  C  R

CTGCCGGGCGGGGTCGCGTCGCCACAGGAGCTGTGGCGTCTCGTCGCGTC      550
  L  P  G  G  V  A  S  P  Q  E  L  W  R  L  V  A  S

CGGCACCGACGCCATCACGGAGTTCCCCGCGGACCGCGGCTGGGACGTGG      600
  G  T  D  A  I  T  E  F  P  A  D  R  G  W  D  V

ACGCGCTCTACGACCCGGACCCCGACGCGATCGGCAAGACCTTCGTCCGG      650
  D  A  L  Y  D  P  D  P  D  A  I  G  K  T  F  V  R

CACGGCGGCTTCCTCGACGGTGCGACCGGCTTCGACGCGGCGTTCTTCGG      700
  H  G  G  F  L  D  G  A  T  G  F  D  A  A  F  F  G

GATCAGCCCGCGCGAGGCCCTGGCCATGGACCCGCAGCAACGGGTGCTCC      750
  I  S  P  R  E  A  L  A  M  D  P  Q  Q  R  V  L

TGGAGACGTCCTGGGAGGCGTTCGAAAGCGCGGGCATCACCCCGGACGCG      800
 L  E  T  S  W  E  A  F  E  S  A  G  I  T  P  D  A

GCGCGGGGCAGCGACACCGGCGTGTTCATCGGCGCGTTCTCCTACGGGTA      850
 A  R  G  S  D  T  G  V  F  I  G  A  F  S  Y  G  Y

CGGCACGGGTGCGGATACCAACGGCTTCGGCGCGACAGGGTCGCAGACCA      900
  G  T  G  A  D  T  N  G  F  G  A  T  G  S  Q  T

GCGTGCTCTCCGGCCGCCTCTCGTACTTCTACGGTCTGGAGGGCCCTTCG      950
 S  V  L  S  G  R  L  S  Y  F  Y  G  L  E  G  P  S

GTCACGGTCGACACCGCCTGCTCGTCGTCACTGGTCGCCCTGCACCAGGC      1000
 V  T  V  D  T  A  C  S  S  S  L  V  A  L  H  Q  A

AGGGCAGTCCCTGCGCTCGGGCGAATGCTCGCTCGCCCTGGTCGGCGGTG      1050
  G  Q  S  L  R  S  G  E  C  S  L  A  L  V  G  G

TCACGGTGATGGCGTCGCCCGGCGGATTCGTCGAGTTCTCCCGGCAGCGC      1100
 V  T  V  M  A  S  P  G  G  F  V  E  F  S  R  Q  R

GGGCTCGCGCCGGACGGGCGGGCGAAGGCGTTCGGCGCGGGCGCGGACGG      1150
  G  L  A  P  D  G  R  A  K  A  F  G  A  G  A  D  G

TACGAGCTTCGCCGAGGGCGCCGGTGCCCTGGTGGTCGAGCGGCTCTCCG      1200
  T  S  F  A  E  G  A  G  A  L  V  V  E  R  L  S

ACGCGGAGCGCCACGGCCACACCGTCCTCGCCCTCGTACGCGGCTCCGCG      1250
 D  A  E  R  H  G  H  T  V  L  A  L  V  R  G  S  A

GCTAACTCCGACGGCGCGTCGAACGGTCTGTCGGCGCCGAACGGCCCCTC      1300
 A  N  S  D  G  A  S  N  G  L  S  A  P  N  G  P  S

CCAGGAACGCGTCATCCACCAGGCCCTCGCGAACGCGAAACTCACCCCCG      1350
  Q  E  R  V  I  H  Q  A  L  A  N  A  K  L  T  P

CCGATGTCGACGCGGTCGAGGCGCACGGCACCGGCACCCGCCTCGGCGAC      1400
 A  D  V  D  A  V  E  A  H  G  T  G  T  R  L  G  D

CCCATCGAGGCGCAGGCGCTGCTCGCGACGTACGGACAGGACCGGGCGAC      1450
  P  I  E  A  Q  A  L  L  A  T  Y  G  Q  D  R  A  T

GCCCCTGCTGCTCGGCTCGCTGAAGTCGAACATCGGGCACGCCCAGGCCG      1500
  P  L  L  L  G  S  L  K  S  N  I  G  H  A  Q  A

CGTCAGGGGTCGCCGGGATCATCAAGATGGTGCAGGCCATCCGGCACGGG      1550
 A  S  G  V  A  G  I  I  K  M  V  Q  A  I  R  H  G

GAACTGCCGCCGACACTGCACGCGGACGAGCCGTCGCCGCACGTCGACTG      1600
  E  L  P  P  T  L  H  A  D  E  P  S  P  H  V  D  W

GACGGCCGGTGCCGTCGAGCTCCTGACGTCGGCCCGGCCGTGGCCGGGGA      1650
  T  A  G  A  V  E  L  L  T  S  A  R  P  W  P  G
```

```
CCGGTCGCCCGCGCCGCGCTGCCGTCTCGTCGTTCGGCGTGAGCGGCACG    1700
 T  G  R  P  R  R  A  A  V  S  S  F  G  V  S  G  T

AACGCCCACATCATCCTTGAGGCAGGACCGGTCAAAACGGGACCGGTCGA    1750
 N  A  H  I  I  L  E  A  G  P  V  K  T  G  P  V  E

GGCAGGAGCGATCGAGGCAGGACCGGTCGAAGTAGGACCGGTCGAGGCTG    1800
 A  G  A  I  E  A  G  P  V  E  V  G  P  V  E  A

GACCGCTCCCCGCGGCGCCGCCGTCAGCACCGGGCGAAGACCTTCCGCTG    1850
 G  P  L  P  A  A  P  P  S  A  P  G  E  D  L  P  L

CTCGTGTCGGCGCGTTCCCCGGAGGCACTCGACGAGCAGATCGGGCGCCT    1900
 L  V  S  A  R  S  P  E  A  L  D  E  Q  I  G  R  L

GCGCGCCTATCTCGACACCGGCCCGGGCGTCGACCGGGCGGCCGTGGCGC    1950
 R  A  Y  L  D  T  G  P  G  V  D  R  A  A  V  A

AGACACTGGCCCGGCGTACGCACTTCACCCACCGGGCCGTACTGCTCGGG    2000
 Q  T  L  A  R  R  T  H  F  T  H  R  A  V  L  L  G

GACACCGTCATCGGCGCTCCCCCCGCGGACCAGGCCGACGAACTCGTCTT    2050
 D  T  V  I  G  A  P  P  A  D  Q  A  D  E  L  V  F

CGTCTACTCCGGTCAGGGCACCCAGCATCCCGCGATGGGCGAGCAACTCG    2100
 V  Y  S  G  Q  G  T  Q  H  P  A  M  G  E  Q  L

CGGCCGCGTTCCCCGTGTTCGCCGATGCCTGGCACGACGCGCTCCGACGG    2150
 A  A  A  F  P  V  F  A  D  A  W  H  D  A  L  R  R

CTCGACGACCCCGACCCGCACGACCCCACACGGAGCCAGCACACGCTCTT    2200
 L  D  D  P  D  P  H  D  P  T  R  S  Q  H  T  L  F

CGCCCACCAGGCGGCGTTCACCGCCCTCCTGAGGTCCTGGGACATCACGC    2250
 L  D  V  A  Q  R  L  G  I  H  H  R  L  P  A  P

CGCACGCCGTCATCGGCCACTCGCTCGGCGAGATCACCGCCGCGTACGCC    2300
 P  H  A  V  I  G  H  S  L  G  E  I  T  A  A  Y  A

GCCGGGATCCTGTCGCTCGACGACGCCTGCACCCTGATCACCACGCGTGC    2350
 A  G  I  L  S  L  D  D  A  C  T  L  I  T  T  R  A

CCGCCTCATGCACACGCTTCCGCCGCCCGGCGCCATGGTCACCGTGCTGA    2400
 R  L  M  H  T  L  P  P  P  G  A  M  V  T  V  L

CCAGCGAGGAGGAGGCCCGTCAGGCGCTGCGGCCGGGCGTGGAGATCGCC    2450
 T  S  E  E  E  A  R  Q  A  L  R  P  G  V  E  I  A

GCGGTCTTCGGCCCGCACTCCGTCGTGCTCTCGGGCGACGAGGACGCCGT    2500
 A  V  F  G  P  H  S  V  V  L  S  G  D  E  D  A  V

GCTCGACGTCGCACAGCGGCTCGGCATCCACCACCGTCTGCCCGCGCCGC    2550
 L  D  V  A  Q  R  L  G  I  H  H  R  L  P  A  P

ACGCGGGCCACTCCGCGCACATGGAACCCGTGGCCGCCGAGCTGCTCGCC    2600
 H  A  G  H  S  A  H  M  E  P  V  A  A  E  L  L  A

ACCACTCGCGAGCTCCGTTACGACCGGCCCCACACCGCCATCCCGAACGA    2650
 T  T  R  E  L  R  Y  D  R  P  H  T  A  I  P  N  D

CCCCACCACCGCCGAGTACTGGGCCGAGCAGGTCCGCAACCCCGTGCTGT    2700
 P  T  T  A  E  Y  W  A  E  Q  V  R  N  P  V  L

TCCACGCCCACACCCAGCGGTACCCCGACGCCGTGTTCGTCGAGATCGGC    2750
 F  H  A  H  T  Q  R  Y  P  D  A  V  F  V  E  I  G

CCCGGCCAGGACCTCTCACCGCTGGTCGACGGCATCGCCCTGCAGAACGG    2800
 P  G  Q  D  L  S  P  L  V  D  G  I  A  L  Q  N  G

CACGGCGGACGAGGTGCACGCGCTGCACACCGCGCTCGCCCGCCTCTTCA    2850
 T  A  D  E  V  H  A  L  H  T  A  L  A  R  L  F

CACGCGGCGCCACGCTCGACTGGTCCCGCATCCTCGGCGGTGCTTCGCGG    2900
 T  R  G  A  T  L  D  W  S  R  I  L  G  G  A  S  R

CACGACCCTGACGTCCCCTCGTACGCGTTCCAGCGGCGTCCCTACTGGAT    2950
 H  D  P  D  V  P  S  Y  A  F  Q  R  R  P  Y  W  I
```

```
                                                   -continued
CGAGTCGGCTCCCCCGGCCACGGCCGACTCGGGCCACCCCGTCCTCGGCA            3000
 E  S  A  P  P  A  T  A  D  S  G  H  P  V  L  G CCGGAGTCGCCGTCGCCGGGTCGCCGGGCCGGGTGTTCACGGGTCCCGTG            3050
 T  G  V  A  V  A  G  S  P  G  R  V  F  T  G  P  V CCCGCCGGTGCGGACCGCGCGGTGTTCATCGCCGAACTGGCGCTCGCCGC            3100
 P  A  G  A  D  R  A  V  F  I  A  E  L  A  L  A  A CGCCGACGCCACCGACTGCGCCACGGTCGAACAGCTCGACGTCACCTCCG            3150
 A  D  A  T  D  C  A  T  V  E  Q  L  D  V  T  S TGCCCGGCGGATCCGCCCGCGGCAGGGCCACCGCGCAGACCTGGGTCGAT            3200
 V  P  G  G  S  A  R  G  R  A  T  A  Q  T  W  V  D GAACCCGCCGCCGACGGGCGGCGCCGCTTCACCGTCCACACCCGCGTCGG            3250
 E  P  A  A  D  G  R  R  R  G  T  V  H  T  R  V  G CGACGCCCCGTGGACGCTGCACGCCGAGGGGTTCTCCGCCCCGGCCGCG            3300
 D  A  P  W  T  L  H  A  E  G  V  L  R  P  G  R TGCCCCAGCCCGAAGCCGTCGACACCGCCTGGCCCCCGCCGGGCGCGGTG            3350
 V  P  Q  P  E  A  V  D  T  A  W  P  P  P  G  A  V CCCGCGGACGGGCTGCCCGGGGCGTGGCGACGCGCGGACCAGGTCTTCGT            3400
 P  A  D  G  L  P  G  A  W  R  R  A  D  Q  V  F  V CGAAGCCGAAGTCGACAGCCCTGACGGCTTCGTGGCACACCCCGACCTGC            3450
 E  A  E  V  D  S  P  D  G  F  V  A  H  P  D  L TCGACGCGGTCTTCTCCGCGGTCGGCGACGGGAGCCGCCAGCCGACCGGA            3500
 L  D  A  V  F  S  A  V  G  D  G  S  R  Q  O  T  G TGGCGCGACCTCGCGGTGCACGCGTCGGACGCCACCGTGCTGCGCGCCTG            3550
 W  R  D  L  A  V  H  A  S  D  A  T  V  L  R  A  C CCTCACCCGCCGCGACAGTGGTGTCGTGGAGCTCGCCGCCTTCGACGGTG            3600
 L  T  R  R  D  S  G  V  V  E  L  A  A  F  D  G CCGGAATGCCGGTGCTCACCGCGGAGTCGGTGACGCTGGGCGAGGTCGCG            3650
 A  G  M  P  V  L  T  A  E  S  V  T  L  G  E  V  A TCGGCAGGCGGATCCGACGAGTCGGACGGTCTGCTTCGGCTTGAGTGGTT            3700
 S  A  G  G  S  D  E  S  D  G  L  L  R  L  E  W  L GCCGGTGGCGGAGGCCCACTACGACGGTGCCGACGAGCTGCCCGAGGGCT            3750
 P  V  A  E  A  H  Y  D  G  A  D  E  L  P  E  G ACACCCTCATCACCGCCACACACCCCGACGACCCCGACGACCCCACCAAC            3800
 Y  T  L  I  T  A  T  H  P  D  D  P  D  D  P  T  N CCCCACAACACACCCACACGCACCCACACACAAACCACACGCGTCCTCAC            3850
 P  H  N  T  P  T  R  T  H  T  Q  T  T  R  V  L  T CGCCCTCCAACACCACCTCATCACCACCAACCACACCCTCATCGTCCACA            3900
 A  L  Q  H  H  L  I  T  T  N  H  T  L  I  V  H CCACCACCGACCCCCCAGGCGCCGCCGTCACCGGCCTCACCCGCACCGCA            3950
 T  T  T  D  P  P  G  A  A  V  T  G  L  T  R  T  A CAAAACGAACACCCCGGCCGCATCCACCTCATCGAAACCCACCACCCCCA            4000
 Q  N  E  H  P  G  R  I  H  L  I  E  T  H  H  P  H CACCCCACTCCCCCTCACCCAACTCACCACCCTCCACCAACCCCACCTAC            4050
 T  P  L  P  L  T  Q  L  T  T  L  H  Q  P  H  L GCCTCACCAACAACACCCTCCACACCCCCCACCTCACCCCCATCACCACC            4100
 R  L  T  N  N  T  L  H  T  P  H  L  T  P  I  T  T CACCACAACACCACCACAACCACCCCCAACACCCCACCCCTCAACCCCAA            4150
 H  H  N  T  T  T  T  T  P  N  T  P  P  L  N  P  N CCACGCCATCCTCATCACCGGCGGCTCCGGCACCCTCGCCGGCATCCTCG            4200
 H  A  I  L  I  T  G  G  S  G  T  L  A  G  I  L CCCGCCACCTCAACCACCCCCACACCTACCTCCTCTCCCGCACACCACCA            4250
 A  R  H  L  N  H  P  H  T  Y  L  L  S  R  T  P  P
```

```
CCCCCCACCACACCCGGCACCCACATCCCCTGCGACCTCACCGACCCCAC      4300
 P  P  T  T  P  H  T  H  I  P  C  D  L  T  D  P  T

CCAAATCACCCAAGCCCTCACCCACATACCACAACCCCTCACCGGCATCT      4350
 Q  I  T  Q  A  L  T  H  I  P  Q  P  L  T  G  I

TCCACACCGCCGCCACCCTCGACGACGCCACCCTCACCAACCTCACCCCC      4400
 F  H  T  A  A  T  L  D  D  A  T  L  T  N  L  T  P

CAACACCTCACCACCACCCTCCAACCCAAAGCCGACGCCGCCTGGCACCT      4450
 Q  H  L  T  T  T  L  Q  P  K  A  D  A  A  W  H  L

CCACCACCACACCCAAAACCAACCCCTCACCCACTTCGTCCTCTACTCCA      4500
 H  H  H  T  Q  N  Q  P  L  T  H  F  V  L  Y  S

GCGCCGCCGCCACCCTCGGCAGCCCCGGCCAAGCCAACTACGCCGCCGCC      4550
 S  A  A  A  T  L  G  S  P  G  Q  A  N  Y  A  A  A

AACGCCTTCCTCGACGCCCTCGCCACCCACCGCCACACCCAAGGACAACC      4600
 N  A  F  L  D  A  L  A  T  H  R  H  T  Q  G  Q  P

CGCCACCACCATCGCCTGGGGCATGTGGCACACCACCACCACACTCACCA      4650
 A  T  T  I  A  W  G  M  W  H  T  T  T  T  L  T

GCCAACTCACCGACAGCGACCGCGACCGCATCCGCCGCGGCGGCTTCCTG      4700
 S  Q  L  T  D  S  D  R  D  R  I  R  R  G  G  F  L

CCGATCTCGGACGACGAGGGCATGC
 P  I  S  D  D  E  G  M
```

The AvrII-XhoI hybrid FK-506 PKS module 8 containing the AT domain of module 12 of rapamycin is shown below (SEQ ID NOS:26-27).

```
GCATGCGGCTGTACGAGGCGGCACGGCGCACCGGAAGTCCCGTGGTGGTG       50
  M  R  L  Y  E  A  A  R  R  T  G  S  P  V  V  V

GCGGCCGCGCTCGACGACGCGCCGGACGTGCCGCTGCTGCGCGGGCTGCG      100
 A  A  A  L  D  D  A  P  D  V  P  L  L  R  G  L  R

GCGTACGACCGTCCGGCGTGCCGCCGTCCGGGAACGCTCTCTCGCCGACC      150
  R  T  T  V  R  R  A  A  V  R  E  R  S  L  A  D

GCTCGCCGTGCTGCCCGACGACGAGCGCGCCGACGCCTCCCTCGCGTTCG      200
 R  S  P  C  C  P  T  T  S  A  P  T  P  P  S  R  S

TCCTGGAACAGCACCGCCACCGTGCTCGGCCACCTGGGCGCCGAAGACAT      250
 S  W  N  S  T  A  T  V  L  G  H  L  G  A  E  D  I

CCCGGCGACGACGACGTTCAAGGAACTCGGCATCGACTCGCTCACCGCGG      300
  P  A  T  T  T  F  K  E  L  G  I  D  S  L  T  A

TCCAGCTGCGCAACGCGCTGACCACGGCGACCGGCGTACGCCTCAACGCC      350
 V  Q  L  R  N  A  L  T  T  A  T  G  V  R  L  N  A

ACAGCGGTCTTCGACTTTCCGACGCCGCGCGCGCTCGCCGCGAGACTCGG      400
  T  A  V  F  D  F  P  T  P  R  A  L  A  A  R  L  G

CGACGAGCTGGCCGGTACCCGCGCGCCCGTCGCGGCCCGGACCGCGGCCA      450
  D  E  L  A  G  T  R  A  P  V  A  A  R  T  A  A

CCGCGGCCGCGCACGACGAACCGCTGGCGATCGTGGGCATGGCCTGCCGT      500
 T  A  A  A  H  D  E  P  L  A  I  V  G  M  A  C  R

CTGCCGGGCGGGGTCGCGTCGCCACAGGAGCTGTGGCGTCTCGTCGCGTC      550
 L  P  G  G  V  A  S  P  Q  E  L  W  R  L  V  A  S

CGGCACCGACGCCATCACGGAGTTCCCCGCGGACCGCGGCTGGGACGTGG      600
  G  T  D  A  I  T  E  F  P  A  D  R  G  W  D  V

ACGCGCTCTACGACCCGGACCCCGACGCGATCGGCAAGACCTTCGTCCGG      650
 D  A  L  Y  D  P  D  P  D  A  I  G  K  T  F  V  R

CACGGCGGCTTCCTCGACGGTGCGACCGGCTTCGACGCGGCGTTCTTCGG      700
 H  G  G  F  L  D  G  A  T  G  F  D  A  A  F  F  G
```

```
GATCAGCCCGCGCGAGGCCCTGGCCATGGACCCGCAGCAACGGGTGCTCC          750
  I  S  P  R  E  A  L  A  M  D  P  Q  Q  R  V  L

TGGAGACGTCCTGGGAGGCGTTCGAAAGCGCGGGCATCACCCCGGACGCG          800
L  E  T  S  W  E  A  F  E  S  A  G  I  T  P  D  A

GCGCGGGCAGCGACACCGGCGTGTTCATCGGCGCGTTCTCCTACGGGTA           850
A  R  G  S  D  T  G  V  F  I  G  A  F  S  Y  G  Y

CGGCACGGGTGCGGATACCAACGGCTTCGGCGCGACAGGGTCGCAGACCA          900
  G  T  G  A  D  T  N  G  F  G  A  T  G  S  Q  T

GCGTGCTCTCCGGCCGCCTCTCGTACTTCTACGGTCTGGAGGGCCCTTCG          950
S  V  L  S  G  R  L  S  Y  F  Y  G  L  E  G  P  S

GTCACGGTCGACACCGCCTGCTCGTCGTCACTGGTCGCCCTGCACCAGGC         1000
V  T  V  D  T  A  C  S  S  S  L  V  A  L  H  Q  A

AGGGCAGTCCCTGCGCTCGGGCGAATGCTCGCTCGCCCTGGTCGGCGGTG         1050
  G  Q  S  L  R  S  G  E  C  S  L  A  L  V  G  G

TCACGGTGATGGCGTCGCCCGGCGGATTCGTCGAGTTCTCCCGGCAGCGC         1100
V  T  V  M  A  S  P  G  G  F  V  E  F  S  R  Q  R

GGGCTCGCGCCGGACGGGCGGGCGAAGGCGTTCGGCGCGGGCGCGGACGG         1150
G  L  A  P  D  G  R  A  K  A  F  G  A  G  A  D  G

TACGAGCTTCGCCGAGGGCGCCGGTGCCCTGGTGGTCGAGCGGCTCTCCG         1200
  T  S  F  A  E  G  A  G  A  L  V  V  E  R  L  S

ACGCGGAGCGCCACGGCCACACCGTCCTCGCCCTCGTACGCGGCTCCGCG         1250
D  A  E  R  H  G  H  T  V  L  A  L  V  R  G  S  A

GCTAACTCCGACGGCGCGTCGAACGGTCTGTCGGCGCCGAACGGCCCCTC         1300
A  N  S  D  G  A  S  N  G  L  S  A  P  N  G  P  S

CCAGGAACGCGTCATCCACCAGGCCCTCGCGAACGCGAAACTCACCCCCG         1350
  Q  E  R  V  I  H  Q  A  L  A  N  A  K  L  T  P

CCGATGTCGACGCGGTCGAGGCGCACGGCACCGGCACCCGCCTCGGCGAC         1400
A  D  V  D  A  V  E  A  H  G  T  G  T  R  L  G  D

CCCATCGAGGCGCAGGCGCTGCTCGCGACGTACGGACAGGACCGGGCGAC         1450
  P  I  E  A  Q  A  L  L  A  T  Y  G  Q  D  R  A  T

GCCCCTGCTGCTCGGCTCGCTGAAGTCGAACATCGGGCACGCCCAGGCCG         1500
  P  L  L  L  G  S  L  K  S  N  I  G  H  A  Q  A

CGTCAGGGGTCGCCGGGATCATCAAGATGGTGCAGGCCATCCGGCACGGG         1550
A  S  G  V  A  G  I  I  K  M  V  Q  A  I  R  H  G

GAACTGCCGCCGACACTGCACGCGGACGAGCCGTCGCCGCACGTCGACTG         1600
E  L  P  P  T  L  H  A  D  E  P  S  P  H  V  D  W

GACGGCCGGTGCCGTCGAGCTCCTGACGTCGGCCCGGCCGTGGCCGGGGA         1650
  T  A  G  A  V  E  L  L  T  S  A  R  P  W  P  G

CCGGTCGCCCTAGGCGGGCAGGCGTGTCGTCCTTCGGGATCAGTGGCACC         1700
T  G  R  P  R  R  A  A  V  S  S  F  G  V  S  G  T

AACGCCCACGTCATCCTGGAAAGCGCACCCCCCACTCAGCCTGCGGACAA         1750
N  A  H  V  I  L  E  S  A  P  P  T  Q  P  A  D  N

CGCGGTGATCGAGCGGGCACCGGAGTGGGTGCCGTTGGTGATTTCGGCCA         1800
  A  V  I  E  R  A  P  E  W  V  P  L  V  I  S  A

GGACCCAGTCGGCTTTGACTGAGCACGAGGGCCGGTTGCGTGCGTATCTG         1850
R  T  Q  S  A  L  T  E  H  E  G  R  L  R  A  Y  L

GCGGCGTCGCCCGGGGTGGATATGCGGGCTGTGGCATCGACGCTGGCGAT         1900
A  A  S  P  G  V  D  M  R  A  V  A  S  T  L  A  M

GACACGGTCGGTGTTCGAGCACCGTGCCGTGCTGCTGGGAGATGACACCG         1950
  T  R  S  V  F  E  H  R  A  V  L  L  G  D  D  T

TCACCGGCACCGCTGTGTCTGACCCTCGGGCGGTGTTCGTCTTCCCGGGA         2000
V  T  F  T  A  V  S  D  P  R  A  V  F  V  F  P  G
```

```
CAGGGGTCGCAGCGTGCTGGCATGGGTGAGGAACTGGCCGCCGCGTTCCC          2050
 Q  G  S  Q  R  A  G  M  G  E  E  L  A  A  A  F  P

CGTCTTCGCGCGGATCCATCAGCAGGTGTGGGACCTGCTCGATGTGCCCG          2100
 V  F  A  R  I  H  Q  Q  V  W  D  L  L  D  V  P

ATCTGGAGGTGAACGAGACCGGTTACGCCCAGCCGGCCCTGTTCGCAATG          2150
 D  L  E  V  N  E  T  G  Y  A  Q  P  A  L  F  A  M

CAGGTGGCTCTGTTCGGGCTGCTGGAATCGTGGGGTGTACGACCGGACGC          2200
 Q  V  A  L  F  G  L  L  E  S  W  G  V  R  P  D  A

GGTGATCGGCCATTCGGTGGGTGAGCTTGCGGCTGCGTATGTGTCCGGGG          2250
 V  I  G  H  S  V  G  E  L  A  A  A  Y  V  S  G

TGTGGTCGTTGGAGGATGCCTGCACTTTGGTGTCGGCGCGGGCTCGTCTG          2300
 V  W  S  L  E  D  A  C  T  L  V  S  A  R  A  R  L

ATGCAGGCTCTGCCCGCGGGTGGGGTGATGGTCGCTGTCCCGGTCTCGGA          2350
 M  Q  A  L  P  A  G  G  V  M  V  A  V  F  V  S  E

GGATGAGGCCCGGGCCGTGCTGGGTGAGGGTGTGGAGATCGCCGCGGTCA          2400
 D  E  A  R  A  V  L  G  E  G  V  E  I  A  A  V

ACGGCCCGTCGTCGGTGGTTCTCTCCGGTGATGAGGCCGCCGTGCTGCAG          2450
 N  G  P  S  S  V  V  L  S  G  D  E  A  A  V  L  Q

GCCGCGGAGGGGCTGGGGAAGTGGACGCGGCTGGCGACCAGCCACGCGTT          2500
 A  A  E  G  L  G  K  W  T  R  L  A  T  S  H  A  F

CCATTCCGCCCGTATGGAACCCATGCTGGAGGAGTTCCGGGCGGTCGCCG          2550
 H  S  A  R  M  E  P  M  L  E  E  F  R  A  V  A

AAGGCCTGACCTACCGGACGCCGCAGGTCTCCATGGCCGTTGGTGATCAG          2600
 E  G  L  T  Y  R  T  P  Q  V  S  M  A  V  G  D  Q

GTGACCACCGCTGAGTACTGGGTGCGGCAGGTCCGGGACACGGTCCGGTT          2650
 V  T  T  A  E  Y  W  V  R  Q  V  R  D  T  V  R  F

CGGCGAGCAGGTGGCCTCGTACGAGGACGCCGTGTTCGTCGAGCTGGGTG          2700
 G  E  Q  V  A  S  Y  E  D  A  V  F  V  E  L  G

CCGACCGGTCACTGGCCCGCCTGGTCGACGGTGTCGCGATGCTGCACGGC          2750
 A  D  R  S  L  A  R  L  V  D  G  V  A  M  L  H  G

GACCACGAAATCCAGGCCGCGATCGGCGCCCTGGCCCACCTGTATGTCAA          2800
 D  H  E  I  Q  A  A  I  G  A  L  A  H  L  Y  V  N

CGGCGTCACGGTCGACTGGCCCGCGCTCCTGGGCGATGCTCCGGCAAcAC          2850
 G  V  T  V  D  W  P  A  L  L  G  D  A  P  A  T

GGGTGCTGGACCTTCCGACATACGCCTTCCAGCACCAGCGCTACTGGCTC          2900
 R  V  L  D  L  P  T  Y  A  F  Q  H  Q  R  Y  W  L

GAGTCGGCTCCCCCGGCCACGGCCGACTCGGGCCACCCCGTCCTCGGCAC          2950
 E  S  A  P  P  A  T  A  D  S  G  H  P  V  L  G  T

CGGAGTCGCCGTCGCCGGGTCGCCGGGCCGGGTGTTCACGGGTCCCGTGC          3000
 G  V  A  U  A  G  S  P  G  R  V  F  T  G  P  V

CCGCCGGTGCGGACCGCGCGGTGTTCATCGCCGAACTGGCGCTCGCCGCC          3050
 P  A  G  A  D  R  A  V  F  I  A  E  L  A  L  A  A

GCCGACGCCACCGACTGCGCCACGGTCGAACAGCTCGACGTCACCTCCGT          3100
 A  D  A  T  D  C  A  T  V  E  Q  L  D  V  T  S  V

GCCCGGCGGATCCGCCCGCGGCAGGGCCACCGCGCAGACCTGGGTCGATG          3150
 P  G  G  S  A  R  G  R  A  T  A  Q  T  W  V  D

AACCCGCCGCCGACGGGCGGCGCCGCTTCACCGTCCACACCCGCGTCGGC          3200
 E  P  A  A  D  G  R  R  R  F  T  V  H  T  R  V  G

GACGCCCCGTGGACGCTGCACGCCGAGGGGGTTCTCCGCCCCGGCCGCGT          3250
 D  A  P  W  T  L  H  A  E  G  V  L  R  P  G  R  V

GCCCCAGCCCGAAGCCGTCGACACCGCCTGGCCCCCGCCGGGCGCGGTGC          3300
 P  Q  P  E  A  V  D  T  A  W  P  P  P  G  A  V
```

```
CCGCGGACGGGCTGCCCGGGGCGTGGCGACGCGCGGACCAGGTCTTCGTC    3350
 P   A   D   G   L   P   G   A   W   R   R   A   D   Q   V   F   V

GAAGCCGAAGTCGACAGCCCTGACGGCTTCGTGGCACACCCCGACCTGCT    3400
 E   A   E   V   D   S   P   D   G   F   V   A   H   P   D   L   L

CGACGCGGTCTTCTCCGCGGTCGGCGACGGGAGCCGCCAGCCGACCGGAT    3450
   D   A   V   F   S   A   V   G   D   G   S   R   Q   P   T   G

GGCGCGACCTCGCGGTGCACGCGTCGGACGCCACCGTGCTGCGCGCCTGC    3500
 W   R   D   L   A   V   H   A   S   D   A   T   V   L   R   A   C

CTCACCCGCCGCGACAGTGGTGTCGTGGAGCTCGCCGCCTTCGACGGTGC    3550
 L   T   R   R   D   S   G   V   V   E   L   A   A   F   D   G   A

CGGAATGCCGGTGCTCACCGCGGAGTCGGTGACGCTGGGCGAGGTCGCGT    3600
   G   M   P   V   L   T   A   E   S   V   T   L   G   E   V   A

CGGCAGGCGGATCCGACGAGTCGGACGGTCTGCTTCGGCTTGAGTGGTTG    3650
 S   A   G   G   S   D   E   S   D   G   L   L   R   L   E   W   L

CCGGTGGCGGAGGCCCACTACGACGGTGCCGACGAGCTGCCCGAGGGCTA    3700
   P   V   A   E   A   H   Y   D   G   A   D   E   L   P   E   G   Y

CACCCTCATCACCGCCACACACCCCGACGACCCCGACGACCCCACCAACC    3750
   T   L   I   T   A   T   H   P   D   D   P   D   D   P   T   N

CCCACAACACACCCACACGCACCCACACACAAACCACACGCGTCCTCACC    3800
 P   H   N   T   P   T   R   H   T   Q   T   T   R   V   L   T

GCCCTCCAACACCACCTCATCACCACCAACCACACCCTCATCGTCCACAC    3850
 A   L   Q   H   H   L   I   T   T   N   H   T   L   I   V   H   T

CACCACCGACCCCCAGGCGCCGCCGTCACCGGCCTCACCCGCACCGCAC    3900
   T   T   D   P   P   G   A   A   V   T   G   L   T   R   T   A

AAAACGAACACCCCGGCCGCATCCACCTCATCGAAACCCACCACCCCCAC    3950
 Q   N   E   H   P   G   R   I   H   L   I   E   T   H   H   P   H

ACCCCACTCCCCCTCACCCAACTCACCACCCTCCACCAACCCCACCTACG    4000
   T   P   L   P   L   T   Q   L   T   T   L   H   Q   P   H   L   R

CCTCACCAACAACACCCTCCACACCCCCCACCTCACCCCCATCACCACCC    4050
   L   T   N   N   T   L   H   T   P   H   L   T   P   I   T   T

ACCACAACACCACCACAACCACCCCCAACACCCCACCCCTCAACCCCAAC    4100
 H   H   N   T   T   T   T   T   P   N   T   P   P   L   N   P   N

CACGCCATCCTCATCACCGGCGGCTCCGGCACCCTCGCCGGCATCCTCGC    4150
   H   A   I   L   I   T   G   G   S   G   T   L   A   G   I   L   A

CCGCCACCTCAACCACCCCCACACCTACCTCCTCTCCCGCACACCACCAC    4200
   R   H   L   N   H   P   H   T   Y   L   L   S   R   T   P   P

CCCCCACCACACCCGGCACCCACATCCCCTGCGACCTCACCGACCCCACC    4250
 P   P   T   T   P   G   T   H   I   P   C   D   L   T   D   P   T

CAAATCACCCAAGCCCTCACCCACATACCACAACCCCTCACCGGCATCTT    4300
   Q   I   T   Q   A   L   T   H   I   P   Q   P   L   T   G   I   F

CCACACCGCCGCCACCCTCGACGACGCCACCCTCACCAACCTCACCCCCC    4350
   H   T   A   A   T   L   D   D   A   T   L   T   N   L   T   P

AACACCTCACCACCACCCTCCAACCCAAAGCCGACGCCGCCTGGCACCTC    4400
 A   H   L   T   T   T   L   Q   P   K   A   D   A   A   W   H   L

CACCACCACACCCAAAACCAACCCCTCACCCACTTCGTCCTCTACTCCAG    4450
 H   H   H   T   Q   N   Q   P   L   T   H   F   V   L   Y   S   S

CGCCGCCGCCACCCTCGGCAGCCCCGGCCAAGCCAACTACGCCGCCGCCA    4500
   A   A   A   T   L   G   S   P   G   Q   A   N   Y   A   A   A

ACGCCTTCCTCGACGCCCTCGCCACCCACCGCCACACCCAAGGACAACCC    4550
 N   A   F   L   D   A   L   A   T   H   R   H   T   Q   G   Q   P

GCCACCACCATCGCCTGGGGCATGTGGCACACCACCACCACACTCACCAG    4600
   A   T   T   I   A   W   G   M   W   H   T   T   T   T   L   T   S
```

-continued

```
CCAACTCACCGACAGCGACCGCGACCGCATCCGCCGCGGCGGCTTCCTGC        4650
  Q  L  T  D  S  D  R  D  R  I  R  R  G  G  F  L

CGATCTCGGACGACGAGGGCATGC
  P  I  S  D  D  E  G  M
```

The AvrII-XhoI hybrid FK-506 PKS module 8 containing the AT domain of module 13 of rapamycin is shown below (SEQ ID NOS:28-29).

```
GCATGCGGCTGTACGAGGCGGCACGGCGCACCGGAAGTCCCGTGGTGGTG          50
  M  R  L  Y  E  A  A  R  R  T  G  S  P  V  V  V

GCGGCCGCGCTCGACGACGCGCCGGACGTGCCGCTGCTGCGCGGGCTGCG         100
  A  A  A  L  D  D  A  P  D  V  P  L  L  R  G  L  R

GCGTACGACCGTCCGGCGTGCCGCCGTCCGGGAACGCTCTCTCGCCGACC         150
  R  T  T  V  R  R  A  A  V  R  E  R  S  L  A  D

GCTCGCCGTGCTGCCCGACGACGAGCGCGCCGACGCCTCCCTCGCGTTCG         200
  R  S  P  C  C  P  T  T  S  A  P  T  P  P  S  R  S

TCCTGGAACAGCACCGCCACCGTGCTCGGCCACCTGGGCGCCGAAGACAT         250
  S  W  N  S  T  A  T  V  L  G  H  L  G  A  E  D  I

CCCGGCGACGACGACGTTCAAGGAACTCGGCATCGACTCGCTCACCGCGG         300
  P  A  T  T  T  F  K  E  L  G  I  D  S  L  T  A

TCCAGCTGCGCAACGCGCTGACCACGGCGACCGGCGTACGCCTCAACGCC         350
  V  Q  L  R  N  A  L  T  T  A  T  G  V  R  L  N  A

ACAGCGGTCTTCGACTTTCCGACGCCGCGCGCGCTCGCCGCGAGACTCGG         400
  T  A  V  F  D  F  P  T  P  R  A  L  A  A  R  L  G

CGACGAGCTGGCCGGTACCCGCGCGCCCGTCGCGGCCCGGACCGCGGCCA         450
  D  E  L  A  G  T  R  A  P  V  A  A  R  T  A  A

CCGCGGCCGCGCACGACGAACCGCTGGCGATCGTGGGCATGGCCTGCCGT         500
  T  A  A  A  H  D  E  P  L  A  I  V  G  M  A  C  R

CTGCCGGGCGGGGTCGCGTCGCCACAGGAGCTGTGGCGTCTCGTCGCGTC         550
  L  P  G  G  V  A  S  P  O  E  L  W  R  L  V  A  S

CGGCACCGACGCCATCACGGAGTTCCCCGCGGACCGCGGCTGGGACGTGG         600
  G  T  D  A  I  T  E  F  P  A  D  R  G  W  D  V

ACGCGCTCTACGACCCGGACCCCGACGCGATCGGCAAGACCTTCGTCCGG         650
  D  A  L  Y  D  P  D  P  D  A  I  G  K  T  F  V  R

CACGGCGGCTTCCTCGACGGTGCGACCGGCTTCGACGCGGCGTTCTTCGG         700
  H  G  G  F  L  D  G  A  T  G  F  D  A  A  F  F  G

GATCAGCCCGCGCGAGGCCCTGGCCATGGACCCGCAGCAACGGGTGCTCC         750
  I  S  P  R  E  A  L  A  M  D  P  Q  Q  R  V  L

TGGAGACGTCCTGGGAGGCGTTCGAAAGCGCGGGCATCACCCCGGACGCG         800
  L  E  T  S  W  E  A  F  E  S  A  G  I  T  P  D  A

GCGCGGGGCAGCGACACCGGCGTGTTCATCGGCGCGTTCTCCTACGGGTA         850
  A  R  G  S  D  T  G  V  F  I  G  A  F  S  Y  G  Y

CGGCACGGGTGCGGATACCAACGGCTTCGGCGCGACAGGGTCGCAGACCA         900
  G  T  G  A  D  T  N  G  F  G  A  T  G  S  Q  T

GCGTGCTCTCCGGCCGCCTCTCGTACTTCTACGGTCTGGAGGGCCCTTCG         950
  S  V  L  S  G  R  L  S  Y  F  Y  G  L  E  G  P  S

GTCACGGTCGACACCGCCTGCTCGTCGTCACTGGTCGCCCTGCACCAGGC        1000
  V  T  V  D  T  A  C  S  S  S  L  V  A  L  H  Q  A

AGGGCAGTCCCTGCGCTCGGGCGAATGCTCGCTCGCCCTGGTCGGCGGTG        1050
  G  Q  S  L  R  S  G  E  C  S  L  A  L  V  G  G

TCACGGTGATGGCGTCGCCCGGCGGATTCGTCGAGTTCTCCCGGCAGCGC        1100
  V  T  V  M  A  S  P  G  G  F  V  E  F  S  R  Q  R
```

-continued

```
GGGCTCGCGCCGGACGGGCGGGCGAAGGCGTTCGGCGCGGGCGCGGACGG        1150
 G  L  A  P  D  G  R  A  K  A  F  G  A  G  A  D  G

TACGAGCTTCGCCGAGGGCGCCGGTGCCCTGGTGGTCGAGCGGCTCTCCG        1200
 T  S  F  A  E  G  A  G  A  L  V  V  E  R  L  S

ACGCGGAGCGCCACGGCCACACCGTCCTCGCCCTCGTACGCGGCTCCGCG        1250
 D  A  E  R  H  G  H  T  V  L  A  L  V  R  G  S  A

GCTAACTCCGACGGCGCGTCGAACGGTCTGTCGGCGCCGAACGGCCCCTC        1300
 A  N  S  D  G  A  S  N  G  L  S  A  P  N  G  P  S

CCAGGAACGCGTCATCCACCAGGCCCTCGCGAACGCGAAACTCACCCCCG        1350
 Q  E  R  V  I  H  Q  A  L  A  N  A  K  L  T  P

CCGATGTCGACGCGGTCGAGGCGCACGGCACCGGCACCCGCCTCGGCGAC        1400
 A  D  V  D  A  V  E  A  H  G  T  G  T  R  L  G  D

CCCATCGAGGCGCAGGCGCTGCTCGCGACGTACGGACAGGACCGGGCGAC        1450
 P  I  E  A  Q  A  L  L  A  T  Y  G  Q  D  R  A  T

GCCCCTGCTGCTCGGCTCGCTGAAGTCGAACATCGGGCACGCCCAGGCCG        1500
 P  L  L  L  G  S  L  K  S  N  I  G  H  A  Q  A

CGTCAGGGGTCGCCGGGATCATCAAGATGGTGCAGGCCATCCGGCACGGG        1550
 A  S  G  V  A  G  I  I  K  M  V  Q  A  I  R  H  G

GAACTGCCGCCGACACTGCACGCGGACGAGCCGTCGCCGCACGTCGACTG        1600
 E  L  P  P  T  L  H  A  D  E  P  S  P  H  V  D  W

GACGGCCGGTGCCGTCGAGCTCCTGACGTCGGCCCGGCCGTGGCCGGGGA        1650
 T  A  G  A  V  E  L  L  T  S  A  R  P  W  P  G

CCGGTCGCCCTAGGCGGGCAGGCGTGTCGTCCTTCGGGATCAGTGGCACC        1700
 T  G  R  P  R  R  A  A  V  S  S  F  G  V  S  G  T

AACGCCCACGTCATCCTGGAGAGCGCACCCCCCGCTCAGCCCGCGGAGGA        1750
 N  A  H  V  I  L  E  S  A  P  P  A  Q  P  A  E  E

GGCGCAGCCTGTTGAGACGCCGGTGGTGGCCTCGGATGTGCTGCCGCTGG        1800
 A  Q  P  V  E  T  P  V  V  A  S  D  V  L  P  L

TGATATCGGCCAAGACCCAGCCCGCCCTGACCGAACACGAAGACCGGCTG        1850
 V  I  S  A  K  T  Q  P  A  L  T  E  H  E  D  R  L

CGCGCCTACCTGGCGGCGTCGCCCGGGGCGGATATACGGGCTGTGGCATC        1900
 R  A  Y  L  A  A  S  P  G  A  D  I  R  A  V  A  S

GACGCTGGCGGTGACACGGTCGGTGTTCGAGCACCGCGCCGTACTCCTTG        1950
 T  L  A  V  T  R  S  V  F  E  H  R  A  V  L  L

GAGATGACACCGTCACCGGCACCGCGGTGACCGACCCCAGGATCGTGTTT        2000
 G  D  D  T  V  T  G  T  A  V  T  D  P  R  I  V  F

GTCTTTCCCGGGCAGGGGTGGCAGTGGCTGGGGATGGGCAGTGCACTGCG        2050
 V  F  P  G  Q  G  W  Q  W  L  G  M  G  S  A  L  R

CGATTCGTCGGTGGTGTTCGCCGAGCGGATGGCCGAGTGTGCGGCGGCGT        2100
 D  S  S  V  V  F  A  E  R  M  A  E  C  A  A  A

TGCGCGAGTTCGTGGACTGGGATCTGTTCACGGTTCTGGATGATCCGGCG        2150
 L  R  E  F  V  D  W  D  L  F  T  V  L  D  D  P  A

GTGGTGGACCGGGTTGATGTGGTCCAGCCCGCTTCCTGGGCGATGATGGT        2200
 V  V  D  R  V  D  V  V  Q  P  A  S  W  A  M  M  V

TTCCCTGGCCGCGGTGTGGCAGGCGGCCGGTGTGCGGCCGGATGCGGTGA        2250
 S  L  A  A  V  W  Q  A  A  G  V  R  P  D  A  V

TCGGCCATTCGCAGGGTGAGATCGCCGCAGCTTGTGTGGCGGGTGCGGTG        2300
 I  G  H  S  Q  G  E  I  A  A  A  C  V  A  G  A  V

TCACTACGCGATGCCGCCCGGATCGTGACCTTGCGCAGCCAGGCGATCGC        2350
 S  L  R  D  A  A  R  I  V  T  L  R  S  Q  A  I  A

CCGGGGCCTGGCGGGCCGGGGCGCGATGGCATCCGTCGCCCTGCCCGCGC        2400
 R  G  L  A  G  R  G  A  M  A  S  V  A  L  P  A
```

```
AGGATGTCGAGCTGGTCGACGGGCCTGGATCGCCGCCCACAACGGGCCC        2450
 Q  D  V  E  L  V  D  G  A  W  I  A  A  H  N  G  P

GCCTCCACCGTGATCGCGGGCACCCCGGAAGCGGTCGACCATGTCCTCAC        2500
 A  S  T  V  I  A  G  T  P  E  A  V  D  H  V  L  T

CGCTCATGAGGCACAAGGGGTGCGGGTGCGGCGGATCACCGTCGACTATG        2550
 A  H  E  A  Q  G  V  R  V  R  R  I  T  V  D  Y

CCTCGCACACCCCGCACGTCGAGCTGATCCGCGACGAACTACTCGACATC        2600
 A  S  H  T  P  H  V  E  L  I  R  D  E  L  L  D  I

ACTAGCGACAGCAGCTCGCAGACCCCGCTCGTGCCGTGGCTGTCGACCGT        2650
 T  S  D  S  S  S  Q  T  P  L  V  P  W  L  S  T  V

GGACGGCACCTGGGTCGACAGCCCGCTGGACGGGGAGTACTGGTACCGGA        2700
 D  G  T  W  V  D  S  P  L  D  G  E  Y  W  Y  R

ACCTGCGTGAACCGGTCGGTTTCCACCCCGCCGTCAGCCAGTTGCAGGCC        2750
 N  L  R  E  P  V  G  F  H  P  A  V  S  Q  L  Q  A

CAGGGCGACACCGTGTTCGTCGAGGTCAGCGCCAGCCCGGTGTTGTTGCA        2800
 Q  G  D  T  V  F  V  E  V  S  A  S  P  V  L  L  Q

GGCGATGGACGACGATGTCGTCACGGTTGCCACGCTGCGTCGTGACGACG        2850
 A  M  D  D  D  V  V  T  V  A  T  L  R  R  D  D

GCGACGCCACCCGGATGCTCACCGCCCTGGCACAGGCCTATGTCCACGGC        2900
 G  D  A  T  R  M  L  T  A  L  A  Q  A  Y  V  H  G

GTCACCGTCGACTGGCCCGCCATCCTCGGCACCACCACAACCCGGGTACT        2950
 V  T  V  D  W  P  A  I  L  G  T  T  T  T  R  V  L

GGACCTTCCGACCTACGCCTTCCAACACCAGCGGTACTGGCTCGAGTCGG        3000
 D  L  P  T  Y  A  F  Q  H  Q  R  Y  W  L  E  S

CTCCCCCGGCCACGGCCGACTCGGGCCACCCCGTCCTCGGCACCGGAGTC        3050
 A  P  P  A  T  A  D  S  G  H  P  V  L  G  T  G  V

GCCGTCGCCGGGTCGCCGGGCCGGGTGTTCACGGGTCCCGTGCCCGCCGG        3100
 A  V  A  G  S  P  G  R  V  F  T  G  P  V  P  A  G

TGCGGACCGCGCGGTGTTCATCGCCGAACTGGCGCTCGCCGCCGCCGACG        3150
 A  D  R  A  V  F  I  A  E  L  A  L  A  A  A  D

CCACCGACTGCGCCACGGTCGAACAGCTCGACGTCACCTCCGTGCCCGGC        3200
 A  T  D  C  A  T  V  E  Q  L  D  V  T  S  V  P  G

GGATCCGCCCGCGGCAGGGCCACCGCGCAGACCTGGGTCGATGAACCCGC        3250
 G  S  A  R  G  R  A  T  A  Q  T  W  V  D  E  P  A

CGCCGACGGGCGGCGCCGCTTCACCGTCCACACCCGCGTCGGCGACGCCC        3300
 A  D  G  R  R  R  F  T  V  H  T  R  V  G  D  A

CGTGGACGCTGCACGCCGAGGGGGTTCTCCGCCCCGGCCGCGTGCCCCAG        3350
 P  W  T  L  H  A  E  G  V  L  R  P  G  R  V  P  Q

CCCGAAGCCGTCGACACCGCCTGGCCCCCGCCGGGCGCGGTGCCCGCGGA        3400
 P  E  A  V  D  T  A  W  P  P  P  G  A  V  P  A  D

CGGGCTGCCCGGGGCGTGGCGACGCGCGGACCAGGTCTTCGTCGAAGCCG        3450
 G  L  P  G  A  W  R  R  A  D  Q  V  F  V  E  A

AAGTCGACAGCCCTGACGGCTTCGTGGCACACCCCGACCTGCTCGACGCG        3500
 E  V  D  S  P  D  G  F  V  A  H  P  D  L  L  D  A

GTCTTCTCCGCGGTCGGCGACGGGAGCCGCCAGCCGACCGGATGGCGCGA        3550
 V  F  S  A  V  G  D  G  S  R  Q  P  T  G  W  R  D

CCTCGCGGTGCACGCGTCGGACGCCACCGTGCTGCGCGCCTGCCTCACCC        3600
 L  A  V  H  A  S  D  A  T  V  L  R  A  C  L  T

GCCGCGACAGTGGTGTCGTGGAGCTCGCCGCCTTCGACGGTGCCGGAATG        3650
 R  R  D  S  G  V  V  E  L  A  A  F  D  G  A  G  M

CCGGTGCTCACCGCGGAGTCGGTGACGCTGGGCGAGGTCGCGTCGGCAGG        3700
 P  V  L  T  A  E  S  V  T  L  G  E  V  A  S  A  G
```

```
CGGATCCGACGAGTCGGACGGTCTGCTTCGGCTTGAGTGGTTGCCGGTGG        3750
  G  S  D  E  S  D  G  L  L  R  L  E  L  P  V

CGGAGGCCCACTACGACGGTGCCGACGAGCTGCCCGAGGGCTACACCCTC        3800
  A  E  A  H  Y  D  G  A  D  E  L  P  E  G  Y  T  L

ATCACCGCCACACACCCCGACGACCCCGACGACCCCACCAACCCCCACAA        3850
  I  T  A  T  H  P  D  D  P  D  D  P  T  N  P  H  N

CACACCCACACGCACCCACACACAAACCACACGCGTCCTCACCGCCCTCC        3900
  T  P  T  R  T  H  T  Q  T  T  R  V  L  T  A  L

AACACCACCTCATCACCACCAACCACACCCTCATCGTCCACACCACCACC        3950
  Q  H  H  L  I  T  T  N  H  T  L  I  V  H  T  T  T

GACCCCCCAGGCGCCGCCGTCACCGGCCTCACCCGCACCGCACAAAACGA        4000
  D  P  P  G  A  A  V  T  G  L  T  R  T  A  Q  N  E

ACACCCCGGCCGCATCCACCTCATCGAAACCCACCACCCCCACACCCCAC        4050
  H  P  G  R  I  H  L  I  E  T  H  H  P  H  T  P

TCCCCCTCACCCAACTCACCACCCTCCACCAACCCCACCTACGCCTCACC        4100
  L  P  L  T  Q  L  T  T  L  H  Q  P  H  L  R  L  T

AACAACACCCTCCACACCCCCCACCTCACCCCCATCACCACCCACCACAA        4150
  N  N  T  L  H  T  P  H  L  T  P  I  T  T  H  H  N

CACCACCACAACCACCCCCAACACCCCACCCCTCAACCCCAACCACGCCA        4200
  T  T  T  T  P  N  T  P  P  L  N  P  N  H  A

TCCTCATCACCGGCGGCTCCGGCACCCTCGCCGGCATCCTCGCCCGCCAC        4250
  I  L  I  T  G  G  S  G  T  L  A  G  I  L  A  R  H

CTCAACCACCCCCACACCTACCTCCTCTCCCGCACACCACCACCCCCCAC        4300
  L  N  H  P  H  T  Y  L  L  S  R  T  P  P  P  P  T

CACACCCGGCACCCACATCCCCTGCGACCTCACCGACCCCACCCAAATCA        4350
  T  P  G  T  H  I  P  C  D  L  T  D  P  T  Q  I

CCCAAGCCCTCACCCACATACCACAACCCCTCACCGGCATCTTCCACACC        4400
  T  Q  A  L  T  H  I  P  Q  P  L  T  G  I  F  H  T

GCCGCCACCCTCGACGACGCCACCCTCACCAACCTCACCCCGCAACACCT        4450
  A  A  T  L  D  D  A  T  L  T  N  L  T  P  Q  H  L

CACCACCACCCTCCAACCCAAAGCCGACGCCGCCTGGCACCTCCACCACC        4500
  T  T  T  L  Q  P  K  A  D  A  A  W  H  L  H  H

ACACCCAAAACCAACCCCTCACCCACTTCGTCCTCTACTCCAGCGCCGCC        4550
  H  T  Q  N  Q  P  L  T  H  F  V  L  Y  S  S  A  A

GCCACCCTCGGCAGCCCCGGCCAAGCCAACTACGCCGCCGCCAACGCCTT        4600
  A  T  L  G  S  P  G  Q  A  N  Y  A  A  A  N  A  F

CCTCGACGCCCTCGCCACCCACCGCCACACCCAAGGACAACCCGCCACCA        4600
  L  D  A  L  A  T  H  R  H  T  Q  G  G  P  A  T

CCATCGCCTGGGGCATGTGGCACACCACCACCACACTCACCAGCCAACTC        4700
  T  I  A  W  G  M  W  H  T  T  T  T  L  T  S  Q  L

ACCGACAGCGACCGCGACCGCATCCGCCGCGGCGGCTTCCTGCCGATCTC        4750
  T  D  S  D  R  D  R  I  R  R  G  G  F  L  P  I  S

GGACGACGAGGGCATGC
  D  D  E  G  M
```

The NheI-XhoI hybrid FK-506 PKS module 8 containing the AT domain of module 12 of rapamycin is shown below (SEQ ID NOS:30-31).

```
GCATGCGGCTGTACGAGGCGGCACGGCGCACCGGAAGTCCCGTGGTGGTG         50
  M  R  L  Y  E  A  A  R  R  T  G  S  P  V  V  V

GCGGCCGCGCTCGACGACGCGCCGGACGTGCCGCTGCTGCGCGGGCTGCG        100
  A  A  A  L  D  D  A  P  D  V  P  L  L  R  G  L  R
```

-continued

```
GCGTACGACCGTCCGGCGTGCCGCCGTCCGGGAACGCTCTCTCGCCGACC          150
  R  T  T  V  R  R  A  A  V  R  E  R  S  L  A  D

GCTCGCCGTGCTGCCCGACGACGAGCGCGCCGACGCCTCCCTCGCGTTCG          200
  R  S  P  C  C  P  T  T  S  A  P  T  P  P  S  R  S

TCCTGGAACAGCACCGCCACCGTGCTCGGCCACCTGGGCGCCGAAGACAT          250
  S  W  N  S  T  A  T  V  L  G  H  L  G  A  E  D  I

CCCGGCGACGACACGTTCAAGGAACTCGGCATCGACTCGCTCACCGCGG           300
  P  A  T  T  T  F  K  E  L  G  I  D  S  L  T  A

TCCAGCTGCGCAACGCGCTGACCACGGCGACCGGCGTACGCCTCAACGCC          350
  V  Q  L  R  N  A  L  T  T  A  T  G  V  R  L  N  A

ACAGCGGTCTTCGACTTTCCGACGCCGCGCGCGCTCGCCGCGAGACTCGG          400
  T  A  V  F  D  F  P  T  P  R  A  L  A  A  R  L  G

CGACGAGCTGGCCGGTACCCGCGCGCCCGTCGCGGCCCGGACCGCGGCCA          450
  D  E  L  A  G  T  R  A  P  V  A  A  R  T  A  A

CCGCGGCCGCGCACGACGAACCGCTGGCGATCGTGGGCATGGCCTGCCGT          500
  T  A  A  A  H  D  E  P  L  A  I  V  G  M  A  C  R

CTGCCGGGCGGGGTCGCGTCGCCACAGGAGCTGTGGCGTCTCGTCGCGTC          550
  L  P  G  G  V  A  S  P  O  E  L  W  R  L  V  A  S

CGGCACCGACGCCATCACGGAGTTCCCCGCGGACCGCGGCTGGGACGTGG         600
  G  T  D  A  I  T  E  F  P  A  D  R  G  W  D  V

ACGCGCTCTACGACCCGGACCCCGACGCGATCGGCAAGACCTTCGTCCGG         650
  D  A  L  Y  D  P  D  P  D  A  I  G  K  T  F  V  R

CACGGCGGCTTCCTCGACGGTGCGACCGGCTTCGACGCGGCGTTCTTCGG         700
  H  G  G  F  L  D  G  A  T  G  F  D  A  A  F  F  G

GATCAGCCCGCGCGAGGCCCTGGCCATGGACCCGCAGCAACGGGTGCTCC         750
  I  S  P  R  E  A  L  A  M  D  P  Q  Q  R  V  L

TGGAGACGTCCTGGGAGGCGTTCGAAAGCGCGGGCATCACCCCGGACGCG         800
  L  E  T  S  W  E  A  F  E  S  A  G  I  T  P  D  A

GCGCGGGGCAGCGACACCGGCGTGTTCATCGGCGCGTTCTCCTACGGGTA         850
  A  R  G  S  D  T  G  V  F  I  G  A  F  S  Y  G  Y

CGGCACGGGTGCGGATACCAACGGCTTCGGCGCGACAGGGTCGCAGACCA         900
  G  T  G  A  D  T  N  G  F  G  A  T  G  S  Q  T

GCGTGCTCTCCGGCCGCCTCTCGTACTTCTACGGTCTGGAGGGCCCTTCG         950
  S  V  L  S  G  R  L  S  Y  F  Y  G  L  E  G  P  S

GTCACGGTCGACACCGCCTGCTCGTCGTCACTGGTCGCCCTGCACCAGGC        1000
  V  T  V  D  T  A  C  S  S  S  L  V  A  L  H  Q  A

AGGGCAGTCCCTGCGCTCGGGCGAATGCTCGCTCGCCCTGGTCGGCGGTG        1050
  G  Q  S  L  R  S  G  E  C  S  L  A  L  V  G  G

TCACGGTGATGGCGTCGCCCGGCGGATTCGTCGAGTTCTCCCGGCAGCGC        1100
  V  T  V  M  A  S  P  G  G  F  V  E  F  S  R  Q  R

GGGCTCGCGCCGGACGGGCGGGCGAAGGCGTTCGGCGCGGGCGCGGACGG        1150
  G  L  A  P  D  G  R  A  K  A  F  G  A  G  A  D  G

TACGAGCTTCGCCGAGGGCGCCGGTGCCCTGGTGGTCGAGCGGCTCTCCG        1200
  T  S  F  A  E  G  A  G  A  L  V  V  E  R  L  S

ACGCGGAGCGCCACGGCCACACCGTCCTCGCCCTCGTACGCGGCTCCGCG        1250
  D  A  E  R  H  G  H  T  V  L  A  L  V  R  G  S  A

GCTAACTCCGACGGCGCGTCGAACGGTCTGTCGGCGCCGAACGGCCCCTC        1300
  A  N  S  D  G  A  S  N  G  L  S  A  P  N  G  P  S

CCAGGAACGCGTCATCCACCAGGCCCTCGCGAACGCGAAACTCACCCCCG        1350
  Q  E  R  V  I  H  Q  A  L  A  N  A  K  L  T  P

CCGATGTCGACGCGGTCGAGGCGCACGGCACCGGCACCCGCCTCGGCGAC        1400
  A  D  V  D  A  V  E  A  H  G  T  G  T  R  L  G  D
```

```
CCCATCGAGGCGCAGGCGCTGCTCGCGACGTACGGACAGGACCGGGCGAC          1450
 P   I   E   A   Q   A   L   L   A   T   Y   G   Q   D   R   A   T

GCCCCTGCTGCTCGGCTCGCTGAAGTCGAACATCGGGCACGCCCAGGCCG          1500
   P   L   L   L   G   S   L   K   S   N   I   G   H   A   Q   A

CGTCAGGGGTCGCCGGGATCATCAAGATGGTGCAGGCCATCCGGCACGGG          1550
 A   S   G   V   A   G   I   I   K   M   V   Q   A   I   R   H   G

GAACTGCCGCCGACACTGCACGCGGACGAGCCGTCGCCGCACGTCGACTG          1600
   E   L   P   P   T   L   H   A   D   E   P   S   P   H   V   D   W

GACGGCCGGTGCCGTCGAGCTCCTGACGTCGGCCCGGCCGTGGCCGGGGA          1650
   T   A   G   A   V   E   L   L   T   S   A   R   P   W   P   G

CCGGTCGCCCGCCGCGCTGCCGTCTCGTCGTTCGGCGTGAGCGGCACG            1700
 T   G   R   P   R   R   A   A   V   S   S   F   G   V   S   G   T

AACGCCCACATCATCCTTGAGGCAGGACCGGTCAAAACGGGACCGGTCGA          1750
 N   A   H   I   I   L   E   A   G   P   V   K   T   G   P   V   E

GGCAGGAGCGATCGAGGCAGGACCGGTCGAAGTAGGACCGGTCGAGGCTG          1800
   A   G   A   I   E   A   G   P   V   E   V   G   P   V   E   A

GACCGCTCCCCGCGGCGCCGCCGTCAGCACCGGGCGAAGACCTTCCGCTG          1850
 G   P   L   P   A   A   P   P   S   A   P   G   E   D   L   P   L

CTCGTGTCGGCGCGTTCCCCGGAGGCACTCGACGAGCAGATCGGGCGCCT          1900
 L   V   S   A   R   S   P   E   A   L   D   E   Q   I   G   R   L

GCGCGCCTATCTCGACACCGGCCCGGGCGTCGACCGGGCGGCCGTGGCGC          1950
   R   A   Y   L   D   T   G   P   G   V   D   R   A   A   V   A

AGACACTGGCCCGGCGTACGCACTTCACCCACCGGGCCGTACTGCTCGGG          2000
 Q   T   L   A   R   R   T   H   F   T   H   R   A   V   L   L   G

GACACCGTCATCGGCGCTCCCCCCGCGGACCAGGCCGACGAACTCGTCTT          2050
   D   T   V   I   G   A   P   P   A   D   Q   A   D   E   L   V   F

CGTCTACTCCGGTCAGGGCACCCAGCATCCCGCGATGGGCGAGCAGCTAG          2100
 V   Y   S   G   Q   G   T   Q   H   P   A   M   G   E   Q   L

CCGCCGCGTTCCCCGTCTTCGCGCGGATCCATCAGCAGGTGTGGGACCTG        2150
   A   A   A   F   P   V   F   A   R   I   H   Q   Q   V   W   D   L

CTCGATGTGCCCGATCTGGAGGTGAACGAGACCGGTTACGCCCAGCCGGC          2200
 L   D   V   P   D   L   E   V   N   E   T   G   Y   A   Q   P   A

CCTGTTCGCAATGCAGGTGGCTCTGTTCGGGCTGCTGGAATCGTGGGGTG        2250
   L   F   A   M   Q   V   A   L   F   G   L   L   E   S   W   G

TACGACCGGACGCGGTGATCGGCCATTCGGTGGGTGAGCTTGCGGCTGCG        2300
 V   R   P   D   A   V   I   G   H   S   V   G   E   L   A   A   A

TATGTGTCCGGGGTGTGGTCGTTGGAGGATGCCTGCACTTTGGTGTCGGC          2350
   Y   V   S   G   V   W   S   L   E   D   A   C   T   L   V   S   A

GCGGGCTCGTCTGATGCAGGCTCTGCCCGCGGGTGGGGTGATGGTCGCTG        2400
 R   A   R   L   M   Q   A   L   P   A   G   G   V   M   V   A

TCCCGGTCTCGGAGGATGAGGCCCGGGCCGTGCTGGGTGAGGGTGTGGAG        2450
   V   P   V   S   E   D   E   A   R   A   V   L   G   E   G   V   E

ATCGCCGCGGTCAACGGCCCGTCGTCGGTGGTTCTCTCCGGTGATGAGGC          2500
 I   A   A   V   N   G   P   S   S   V   V   L   S   G   D   E   A

CGCCGTGCTGCAGGCCGCGGAGGGGCTGGGGAAGTGGACGCGGCTGGCGA        2550
   A   V   L   Q   A   A   E   G   L   G   K   W   T   R   L   A

CCAGCCACGCGTTCCATTCCGCCCGTATGGAACCCATGCTGGAGGAGTTC          2600
 T   S   H   A   F   H   S   A   R   M   E   P   M   L   E   E   F

CGGGCGGTCGCCGAAGGCCTGACCTACCGGACGCCGCAGGTCTCCATGGC        2650
   R   A   V   A   E   G   L   T   Y   R   T   P   Q   V   S   M   A

CGTTGGTGATCAGGTGACCACCGCTGAGTACTGGGTGCGGCAGGTCCGGG          2700
 V   G   D   Q   V   T   T   A   E   Y   W   V   R   Q   V   R
```

-continued

```
ACACGGTCCGGTTCGGCGAGCAGGTGGCCTCGTACGAGGACGCCGTGTTC    2750
 D  T  V  R  F  G  E  Q  V  A  S  Y  E  D  A  V  F

GTCGAGCTGGGTGCCGACCGGTCACTGGCCCGCCTGGTCGACGGTGTCGC    2800
 V  E  L  G  A  D  R  S  L  A  R  L  V  D  G  V  A

GATGCTGCACGGCGACCACGAAATCCAGGCCGCGATCGGCGCCCTGGCCC    2850
  M  L  H  G  D  H  E  I  Q  A  A  I  G  A  L  A

ACCTGTATGTCAACGGCGTCACGGTCGACTGGCCCGCGCTCCTGGGCGAT    2900
  H  L  Y  V  N  G  V  T  V  D  W  P  A  L  L  G  D

GCTCCGGCAACACGGGTGCTGGACCTTCCGACATACGCCTTCCAGCACCA    2950
  A  P  A  T  R  V  L  D  L  P  T  Y  A  F  Q  H  Q

GCGCTACTGGCTCGAGTCGGCTCCCCCGGCCACGGCCGACTCGGGCCACC    3000
   R  Y  W  L  E  S  A  P  P  A  T  A  D  S  G  H

CCGTCCTCGGCACCGGAGTCGCCGTCGCCGGGTCGCCGGGCCGGGTGTTC    3050
  P  V  L  G  T  G  V  A  V  A  G  S  P  G  R  V  F

ACGGGTCCCGTGCCCGCCGGTGCGGACCGCGCGGTGTTCATCGCCGAACT    3100
   T  G  P  V  P  A  G  A  D  R  A  V  F  I  A  E  L

GGCGCTCGCCGCCGCCGACGCCACCGACTGCGCCACGGTCGAACAGCTCG    3150
   A  L  A  A  A  D  A  T  D  C  A  T  V  E  Q  L

ACGTCACCTCCGTGCCCGGCGGATCCGCCCGCGGCAGGGCCACCGCGCAG    3200
  D  V  T  S  V  P  G  G  S  A  R  G  R  A  T  A  Q

ACCTGGGTCGATGAACCCGCCGCCGACGGGCGGCGCCGCTTCACCGTCCA    3250
  T  W  V  D  E  P  A  A  D  G  R  R  R  F  T  V  H

CACCCGCGTCGGCGACGCCCCGTGGACGCTGCACGCCGAGGGGGTTCTCC    3300
   T  R  V  G  D  A  P  W  T  L  H  A  E  G  V  L

GCCCCGGCCGCGTGCCCCAGCCCGAAGCCGTCGACACCGCCTGGCCCCCG    3350
  R  P  G  R  V  P  Q  P  E  A  V  D  T  A  W  P  P

CCGGGCGCGGTGCCCGCGGACGGGCTGCCCGGGGCGTGGCGACGCGCGGA    3400
  P  G  A  V  P  A  D  G  L  P  G  A  W  R  R  A  D

CCAGGTCTTCGTCGAAGCCGAAGTCGACAGCCCTGACGGCTTCGTGGCAC    3450
   Q  V  F  V  E  A  E  V  D  S  P  D  G  F  V  A

ACCCCGACCTGCTCGACGCGGTCTTCTCCGCGGTCGGCGACGGGAGCCGC    3500
  H  P  D  L  L  D  A  V  F  S  A  V  G  D  G  S  R

CAGCCGACCGGATGGCGCGACCTCGCGGTGCACGCGTCGGACGCCACCGT    3550
  Q  P  T  G  W  R  D  L  A  V  H  A  S  D  A  T  V

GCTGCGCGCCTGCCTCACCCGCCGCGACAGTGGTGTCGTGGAGCTCGCCG    3600
   L  R  A  C  L  T  R  R  D  S  G  V  V  E  L  A

CCTTCGACGGTGCCGGAATGCCGGTGCTCACCGCGGAGTCGGTGACGCTG    3650
  A  F  D  G  A  G  M  P  V  L  T  A  E  S  V  T  L

GGCGAGGTCGCGTCGGCAGGCGGATCCGACGAGTCGGACGGTCTGCTTCG    3700
   G  E  V  A  S  A  G  G  S  D  E  S  D  G  L  L  R

GCTTGAGTGGTTGCCGGTGGCGGAGGCCCACTACGACGGTGCCGACGAGC    3750
   L  E  W  L  P  V  A  E  A  H  Y  D  G  A  D  E

TGCCCGAGGGCTACACCCTCATCACCGCCACACACCCCGACGACCCCGAC    3800
  L  P  E  G  Y  T  L  I  T  A  T  H  P  D  D  P  D

GACCCCACCAACCCCCACAACACACCCACACGCACCCACACACAAACCAC    3850
  D  P  T  N  P  H  N  T  P  T  R  T  H  T  Q  T  T

ACGCGTCCTCACCGCCCTCCAACACCACCTCATCACCACCAACCACACCC    3900
   R  V  L  T  A  L  P  H  H  L  I  T  T  N  H  T

TCATCGTCCACACCACCACCGACCCCCCAGGCGCCGCCGTCACCGGCCTC    3950
  L  I  V  H  T  T  T  D  P  P  G  A  A  V  T  G  L

ACCCGCACCGCACAAAACGAACACCCCCGGCCGCATCCACCTCATCGAAAC    4000
  T  R  T  A  Q  N  E  H  P  G  R  I  H  L  I  E  T
```

```
CCACCACCCCCACACCCCACTCCCCCTCACCCAACTCACCACCCTCCACC        4050
  H  H  P  H  T  P  L  P  L  T  Q  L  T  T  L  H

AACCCCACCTACGCCTCACCAACAACACCCTCCACACCCCCCACCTCACC        4100
 Q  P  H  L  R  L  T  N  N  T  L  H  T  P  H  L  T

CCCATCACCACCCACCACAACACCACCACAACCACCCCCAACACCCCACC        4150
  P  I  T  T  H  H  N  T  T  T  T  P  N  T  P  P

CCTCAACCCCAACCACGCCATCCTCATCACCGGCGGCTCCGGCACCCTCG        4200
  L  N  P  N  H  A  I  L  I  T  G  G  S  G  T  L

CCGGCATCCTCGCCCGCCACCTCAACCACCCCCACACCTACCTCCTCTCC        4250
 A  G  I  L  A  R  H  L  N  H  P  H  T  Y  L  L  S

CGCACACCACCACCCCCACCACACCCGGCACCCACATCCCCTGCGACCT         4300
 R  T  P  P  P  T  T  P  G  T  H  I  P  C  D  L

CACCGACCCCACCCAAATCACCCAAGCCCTCACCCACATACCACAACCCC        4350
  T  D  P  T  Q  I  T  Q  A  L  T  H  I  P  Q  P

TCACCGGCATCTTCCACACCGCCGCCACCCTCGACGACGCCACCCTCACC        4400
 L  T  G  I  F  H  T  A  A  T  L  D  D  A  T  L  T

AACCTCACCCCCCAACACCTCACCACCACCCTCCAACCCAAAGCCGACGC        4450
 N  L  T  P  Q  H  L  T  T  T  L  Q  P  K  A  D  A

CGCCTGGCACCTCCACCACCACACCCAAAACCAACCCCTCACCCACTTCG        4500
  A  W  H  L  H  H  H  T  Q  N  Q  P  L  T  H  F

TCCTCTACTCCAGCGCCGCCGCCACCCTCGGCAGCCCCGGCCAAGCCAAC        4550
 V  L  Y  S  S  A  A  A  T  L  G  S  P  G  Q  A  N

TACGCCGCCGCCAACGCCTTCCTCGACGCCCTCGCCACCGACCGCCACAC        4600
  Y  A  A  A  N  A  F  L  D  A  L  A  T  H  R  H  T

CCAAGGACAACCCGCCACCACCATCGCCTGGGGCATGTGGCACACCACCA        4650
   Q  G  Q  P  A  T  T  I  A  W  G  M  W  H  T  T

CCACACTCACCAGCCAACTCACCGACAGCGACCGCGACCGCATCCGCCGC        4700
 T  T  L  T  S  Q  L  T  D  S  D  R  D  R  I  R  R

GGCGGCTTCCTGCCGATCTCGGACGACGAGGGCATGC
  G  G  F  L  P  I  S  D  D  E  G  M
```

The NheI-XhoI hybrid FK-506 PKS module 8 containing the AT domain of module 13 of rapamycin is shown below (SEQ ID NOS:32-33).

```
GCATGCGGCTGTACGAGGCGGCACGGCGCACCGGAAGTCCCGTGGTGGTG         50
  M  R  L  Y  E  A  A  R  R  T  G  S  P  V  V  V

GCGGCCGCGCTCGACGACGCGCCGGACGTGCCGCTGCTGCGCGGGCTGCG        100
 A  A  A  L  D  D  A  P  D  V  P  L  L  R  G  L  R

GCGTACGACCGTCCGGCGTGCCGCCGTCCGGGAACGCTCTCTCGCCGACC        150
  R  T  T  V  R  R  A  A  V  R  E  R  S  L  A  D

GCTCGCCGTGCTGCCCGACGACGAGCGCGCCGACGCCTCCCTCGCGTTCG        200
 R  S  P  C  C  P  T  T  S  A  P  T  P  P  S  R  S

TCCTGGAACAGCACCGCCACCGTGCTCGGCCACCTGGGCGCCGAAGACAT        250
 S  W  N  S  T  A  T  V  L  G  H  L  G  A  E  D  I

CCCGGCGACGACGACGTTCAAGGAACTCGGCATCGACTCGCTCACCGCGG        300
  P  A  T  T  T  F  K  E  L  G  I  D  S  L  T  A

TCCAGCTGCGCAACGCGCTGACCACGGCGACCGGCGTACGCCTCAACGCC        350
 V  Q  L  R  N  A  L  T  T  A  T  G  V  R  L  N  A

ACAGCGGTCTTCGACTTTCCGACGCCGCGCGCGCTCGCCGCGAGACTCGG        400
  T  A  V  F  D  F  P  T  P  R  A  L  A  A  R  L  G

CGACGAGCTGGCCGGTACCCGCGCGCCCGTCGCGGCCCGGACCGCGGCCA        450
  D  E  L  A  G  T  R  A  P  V  A  A  R  T  A  A
```

```
CCGCGGCCGCGCACGACGAACCGCTGGCGATCGTGGGCATGGCCTGCCGT        500
 T  A  A  A  H  D  E  P  L  A  I  V  G  M  A  C  R

CTGCCGGGCGGGTCGCGTCGCCACAGGAGCTGTGGCGTCTCGTCGCGTC         550
 L  P  G  G  V  A  S  P  O  E  L  W  R  L  V  A  S

CGGCACCGACGCCATCACGGAGTTCCCCGCGGACCGCGGCTGGGACGTGG        600
  G  T  D  A  I  T  E  F  P  A  D  R  G  W  D  V

ACGCGCTCTACGACCCGGACCCCGACGCGATCGGCAAGACCTTCGTCCGG        650
 D  A  L  Y  D  P  D  P  D  A  I  G  K  T  F  V  R

CACGGCGGCTTCCTCGACGGTGCGACCGGCTTCGACGCGGCGTTCTTCGG        700
 H  G  G  F  L  D  G  A  T  G  F  D  A  A  F  F  G

GATCAGCCCGCGCGAGGCCCTGGCCATGGACCCGCAGCAACGGGTGCTCC        750
  I  S  P  R  E  A  L  A  M  D  P  Q  Q  R  V  L

TGGAGACGTCCTGGGAGGCGTTCGAAAGCGCGGGCATCACCCCGGACGCG        800
 L  E  T  S  W  E  A  F  E  S  A  G  I  T  P  D  A

GCGCGGGGCAGCGACACCGGCGTGTTCATCGGCGCGTTCTCCTACGGGTA        850
  A  R  G  S  D  T  G  V  F  I  G  A  F  S  Y  G  Y

CGGCACGGGTGCGGATACCAACGGCTTCGGCGCGACAGGGTCGCAGACCA        900
  G  T  G  A  D  T  N  G  F  G  A  T  G  S  Q  T

GCGTGCTCTCCGGCCGCCTCTCGTACTTCTACGGTCTGGAGGGCCCTTCG       950
 S  V  L  S  G  R  L  S  Y  F  Y  G  L  E  G  P  S

GTCACGGTCGACACCGCCTGCTCGTCGTCACTGGTCGCCCTGCACCAGGC       1000
 V  T  V  D  T  A  C  S  S  S  L  V  A  L  H  Q  A

AGGGCAGTCCCTGCGCTCGGGCGAATGCTCGCTCGCCCTGGTCGGCGGTG       1050
  G  Q  S  L  R  S  G  E  C  S  L  A  L  V  G  G

TCACGGTGATGGCGTCGCCCGGCGGATTCGTCGAGTTCTCCCGGCAGCGC       1100
 V  T  V  M  A  S  P  G  G  F  V  E  F  S  R  Q  R

GGGCTCGCGCCGGACGGGCGGGCGAAGGCGTTCGGCGCGGGCGCGGACGG       1150
  G  L  A  P  D  G  R  A  K  A  F  G  A  G  A  D  G

TACGAGCTTCGCCGAGGGCGCCGGTGCCCTGGTGGTCGAGCGGCTCTCCG       1200
  T  S  F  A  E  G  A  G  A  L  V  V  E  R  L  S

ACGCGGAGCGCCACGGCCACACCGTCCTCGCCCTCGTACGCGGCTCCGCG       1250
 D  A  E  R  H  G  H  T  V  L  A  L  V  R  G  S  A

GCTAACTCCGACGGCGCGTCGAACGGTCTGTCGGCGCCGAACGGCCCCTC       1300
  A  N  S  D  G  A  S  N  G  L  S  A  P  N  G  P  S

CCAGGAACGCGTCATCCACCAGGCCCTCGCGAACGCGAAACTCACCCCCG       1350
  Q  E  R  V  I  H  Q  A  L  A  N  A  K  L  T  P

CCGATGTCGACGCGGTCGAGGCGCACGGCACCGGCACCCGCCTCGGCGAC       1400
 A  D  V  D  A  V  E  A  H  G  T  G  T  R  L  G  D

CCCATCGAGGCGCAGGCGCTGCTCGCGACGTACGGACAGGACCGGGCGAC       1450
  P  I  E  A  Q  A  L  L  A  T  Y  G  Q  D  R  A  T

GCCCCTGCTGCTCGGCTCGCTGAAGTCGAACATCGGGCACGCCCAGGCCG       1500
  P  L  L  L  G  S  L  K  S  N  I  G  H  A  Q  A

CGTCAGGGGTCGCCGGGATCATCAAGATGGTGCAGGCCATCCGGCACGGG       1550
  A  S  G  V  A  G  I  I  K  M  V  Q  A  I  R  H  G

GAACTGCCGCCGACACTGCACGCGGACGAGCCGTCGCCGCACGTCGACTG       1600
 E  L  P  P  T  L  H  A  D  E  P  S  P  H  V  D  W

GACGGCCGGTGCCGTCGAGCTCCTGACGTCGGCCCGGCCGTGGCCGGGGA       1650
  T  A  G  A  V  E  L  L  T  S  A  R  P  W  P  G

CCGGTCGCCCGCGCCGCGCTGCCGTCTCGTCGTTCGGCGTGAGCGGCACG       1700
 T  G  R  P  R  R  A  A  V  S  S  F  G  V  S  G  T

AACGCCCACATCATCCTTGAGGCAGGACCGGTCAAAACGGGACCGGTCGA       1750
  N  A  H  I  I  L  E  A  G  P  V  K  T  G  P  V  E
```

```
                                              -continued
GGCAGGAGCGATCGAGGCAGGACCGGTCGAAGTAGGACCGGTCGAGGCTG          1800
  A  G  A  I  E  A  G  P  V  E  V  G  P  V  E  A GACCGCTCCCCGCGGCGCCGCCGTCAGCACCGGGCGAAGACCTTCCGCTG          1850
 G  P  L  P  A  A  P  P  S  A  P  G  E  D  L  P  L CTCGTGTCGGCGCGTTCCCCGGAGGCACTCGACGAGCAGATCGGGCGCCT          1900
  L  V  S  A  R  S  P  E  A  L  D  E  Q  I  G  R  L GCGCGCCTATCTCGACACCGGCCCGGGCGTCGACCGGGCGGCCGTGGCGC          1950
   R  A  Y  L  D  T  G  P  G  V  D  R  A  A  V  A AGACACTGGCCCGGCGTACGCACTTCACCCACCGGGCCGTACTGCTCGGG          2000
  Q  T  L  A  R  R  T  H  F  T  H  R  A  V  L  L  G GACACCGTCATCGGCGCTCCCCCCGCGGACCAGGCCGACGAACTCGTCTT          2050
   D  T  V  I  G  A  P  P  A  D  Q  A  D  E  L  V  F CGTCTACTCCGGTCAGGGCACCCAGCATCCCGCGATGGGCGAGCAGCTAG          2100
  V  Y  S  G  Q  G  T  Q  H  P  A  M  G  E  Q  L CCGATTCGTCGGTGGTGTTCGCCGAGCGGATGGCCGAGTGTGCGGCGGCG          2150
  A  D  S  S  V  V  F  A  E  R  M  A  E  C  A  A  A TTGCGCGAGTTCGTGGACTGGGATCTGTTCACGGTTCTGGATGATCCGGC          2200
  L  R  E  F  V  D  W  D  L  F  T  V  L  D  D  P  A GGTGGTGGACCGGGTTGATGTGGTCCAGCCCGCTTCCTGGGCGATGATGG          2250
   V  V  D  R  V  D  V  V  Q  P  A  S  W  A  M  M TTTCCCTGGCCGCGGTGTGGCAGGCGGCCGGTGTGCGGCCGGATGCGGTG          2300
  V  S  L  A  A  V  W  Q  A  A  G  V  R  P  D  A  V ATCGGCCATTCGCAGGGTGAGATCGCCGCAGCTTGTGTGGCGGGTGCGGT          2350
  I  G  H  S  Q  G  E  I  A  A  A  C  V  A  G  A  V GTCACTACGCGATGCCGCCCGGATCGTGACCTTGCGCAGCCAGGCGATCG          2400
   S  L  R  D  A  A  R  I  V  T  L  R  S  Q  A  I CCCGGGGCCTGGCGGGCCGGGGCGCGATGGCATCCGTCGCCCTGCCCGCG          2450
  A  R  G  L  A  G  R  G  A  M  A  S  V  A  L  P  A CAGGATGTCGAGCTGGTCGACGGGGCCTGGATCGCCGCCCACAACGGGCC          2500
  Q  D  V  E  L  V  D  G  A  W  I  A  A  H  N  G  P CGCCTCCACCGTGATCGCGGGCACCCCGGAAGCGGTCGACCATGTCCTCA          2550
   A  S  T  V  I  A  G  T  P  E  A  V  D  H  V  L CCGCTCATGAGGCACAAGGGGTGCGGGTGCGGCGGATCACCGTCGACTAT          2600
  T  A  H  E  A  Q  G  V  R  V  R  R  I  T  V  D  Y GCCTCGCACACCCCGCACGTCGAGCTGATCCGCGACGAACTACTCGACAT          2650
  A  S  H  T  P  H  V  E  L  I  R  D  E  L  L  D  I CACTAGCGACAGCAGCTCGCAGACCCCGCTCGTGCCGTGGCTGTCGACCG          2700
   T  S  D  S  S  S  Q  T  P  L  V  P  W  L  S  T TGGACGGCACCTGGGTCGACAGCCCGCTGGACGGGGAGTACTGGTACCGG          2750
  V  D  G  T  W  V  D  S  P  L  D  G  E  Y  W  Y  R AACCTGCGTGAACCGGTCGGTTTCCACCCCGCCGTCAGCCAGTTGCAGGC          2800
  N  L  R  E  P  V  G  F  H  P  A  V  S  Q  L  Q  A CCAGGGCGACACCGTGTTCGTCGAGGTCAGCGCCAGCCCGGTGTTGTTGC          2850
   Q  G  D  T  V  F  V  E  V  S  A  S  P  V  L  L AGGCGATGGACGACGATGTCGTCACGGTTGCCACGCTGCGTCGTGACGAC          2900
  Q  A  M  D  D  D  V  V  T  V  A  T  L  R  R  D  D GGCGACGCCACCCGGATGCTCACCGCCCTGGCACAGGCCTATGTCCACGG          2950
   G  D  A  T  R  M  L  T  A  L  A  Q  A  Y  V  H  G CGTCACCGTCGACTGGCCCGCCATCCTCGGCACCACCACAACCCGGGTAC          3000
   V  T  V  D  W  P  A  I  L  G  T  T  T  T  R  V TGGACCTTCCGACCTACGCCTTCCAACACCAGCGGTACTGGCTCGAGTCG          3050
  L  D  L  P  T  Y  A  F  Q  H  Q  R  Y  W  L  E  S
```

```
GCTCCCCCGGCCACGGCCGACTCGGGCCACCCCGTCCTCGGCACCGGAGT      3100
 A  P  P  A  T  A  D  S  G  H  P  V  L  G  T  G  V

CGCCGTCGCCGGGTCGCCGGGCCGGGTGTTCACGGGTCCCGTGCCCGCCG      3150
  A  V  A  G  S  P  G  R  V  F  T  G  P  V  P  A

GTGCGGACCGCGCGGTGTTCATCGCCGAACTGGCGCTCGCCGCCGCCGAC      3200
 G  A  D  R  A  V  F  I  A  E  L  A  L  A  A  A  D

GCCACCGACTGCGCCACGGTCGAACAGCTCGACGTCACCTCCGTGCCCGG      3250
  A  T  D  C  A  T  V  E  Q  L  D  V  T  S  V  P  G

CGGATCCGCCCGCGGCAGGGCCACCGCGCAGACCTGGGTCGATGAACCCG      3300
  G  S  A  R  G  R  A  T  A  Q  T  W  V  D  E  P

CCGCCGACGGGCGGCGCCGCTTCACCGTCCACACCCGCGTCGGCGACGCC      3350
 A  A  D  G  R  R  R  F  T  V  H  T  R  V  G  D  A

CCGTGGACGCTGCACGCCGAGGGGGTTCTCCGCCCCGGCCGCGTGCCCCA      3400
 P  W  T  L  H  A  E  G  V  L  R  P  G  R  V  P  Q

GCCCGAAGCCGTCGACACCGCCTGGCCCCCGCCGGGCGCGGTGCCCGCGG      3450
  P  E  A  V  D  T  A  W  P  P  P  G  A  V  P  A

ACGGGCTGCCCGGGGCGTGGCGACGCGCGGACCAGGTCTTCGTCGAAGCC      3500
 D  G  L  P  G  A  W  R  R  A  D  Q  V  F  V  E  A

GAAGTCGACAGCCCTGACGGCTTCGTGGCACACCCCGACCTGCTCGACGC      3550
  E  V  D  S  P  D  G  F  V  A  H  P  D  L  L  D  A

GGTCTTCTCCGCGGTCGGCGACGGGAGCCGCCAGCCGACCGGATGGCGCG      3600
  V  F  S  A  V  G  D  G  S  R  Q  P  T  G  W  R

ACCTCGCGGTGCACGCGTCGGACGCCACCGTGCTGCGCGCCTGCCTCACC      3650
 D  L  A  V  H  A  S  D  A  T  V  L  R  A  C  L  T

CGCCGCGACAGTGGTGTCGTGGAGCTCGCCGCCTTCGACGGTGCCGGAAT      3700
  R  R  D  S  G  V  V  E  L  A  A  F  D  G  A  G  M

GCCGGTGCTCACCGCGGAGTCGGTGACGCTGGGCGAGGTCGCGTCGGCAG      3750
  P  V  L  T  A  E  S  V  T  L  G  E  V  A  S  A

GCGGATCCGACGAGTCGGACGGTCTGCTTCGGCTTGAGTGGTTGCCGGTG      3800
 G  G  S  D  E  S  D  G  L  L  R  L  E  W  L  P  V

GCGGAGGCCCACTACGACGGTGCCGACGAGCTGCCCGAGGGCTACACCCT      3850
 A  E  A  H  Y  D  G  A  D  E  L  P  E  G  Y  T  L

CATCACCGCCACACACCCCGACGACCCCGACGACCCCACCAACCCCCACA      3900
  I  T  A  T  H  P  D  D  P  D  D  P  T  N  P  H

ACACACCCACACGCACCCACACACAAACCACACGCGTCCTCACCGCCCTC      3950
 N  T  P  T  R  T  H  T  Q  T  T  R  V  L  T  A  L

CAACACCACCTCATCACCACCAACCACACCCTCATCGTCCACACCACCAC      4000
  Q  H  H  L  I  T  T  N  H  T  L  I  V  H  T  T  T

CGACCCCCCAGGCGCCGCCGTCACCGGCCTCACCCGCACCGCACAAAACG      4050
  D  P  P  G  A  A  V  T  G  L  T  R  T  A  Q  N

AACACCCCGGCCGCATCCACCTCATCGAAACCCACCACCCCCACACCCCA      4100
 E  H  P  G  R  I  H  L  I  E  T  H  H  P  H  T  P

CTCCCCCTCACCCAACTCACCACCCTCCACCAACCCCACCTACGCCTCAC      4150
  L  P  L  T  Q  L  T  T  L  H  Q  P  H  L  R  L  T

CAACAACACCCTCCACACCCCCCACCTCACCCCCATCACCACCCACCACA      4200
  N  N  T  L  H  T  P  H  L  T  P  I  T  T  H  H

ACACCACCACAACCACCCCCAACACCCCACCCCTCAACCCCAACCACGCC      4250
 N  T  T  T  T  T  P  N  T  P  P  L  N  P  N  H  A

ATCCTCATCACCGGCGGCTCCGGCACCCTCGCCGGCATCCTCGCCCGCCA      4300
  I  L  I  T  G  G  S  G  T  L  A  G  I  L  A  R  H

CCTCAACCACCCCCACACCTACCTCCTCTCCCGCACACCACCACCCCCCA      4350
  L  N  H  P  H  T  Y  L  L  S  R  T  P  P  P  P
```

-continued

```
CCACACCCGGCACCCACATCCCCTGCGACCTCACCGACCCCACCCAAATC         4400
 T  T  P  G  T  H  I  P  C  D  L  T  D  P  T  Q  I

ACCCAAGCCCTCACCCACATACCACAACCCCTCACCGGCATCTTCCACAC         4450
 T  Q  A  L  T  H  I  P  Q  P  L  T  G  I  F  H  T

CGCCGCCACCCTCGACGACGCCACCCTCACCAACCTCACCCCCCAACACC         4500
    A  A  T  L  D  D  A  T  L  T  N  L  T  P  Q  H

TCACCACCACCCTCCAACCCAAAGCCGACGCCGCCTGGCACCTCcACCAC         4550
 L  T  T  T  L  Q  P  K  A  D  A  A  W  H  L  H  H

CACACCCAAAACCAACCCCTCACCCACTTCGTCCTCTACTCCAGCGCCGC         4600
    H  T  Q  N  Q  P  L  T  H  F  V  L  Y  S  S  A  A

CGCCACCCTCGGCAGCCCCGGCCAAGCCAACTACGCCGCCGCCAACGCCT         4650
    A  T  L  G  S  P  G  Q  A  N  Y  A  A  A  N  A

TCCTCGACGCCCTCGCCACCCACCGCCACACCCAAGGACAACCCGCCACC         4700
 F  L  D  A  L  A  T  H  R  H  T  Q  G  Q  P  A  T

ACCATCGCCTGGGGCATGTGGCACACCACCACCACACTCACCAGCCAACT         4750
    T  I  A  W  G  M  W  H  T  T  T  L  T  S  Q  L

CACCGACAGCGACCGCGACCGCATCCGCCGCGGCGGCTTCCTGCCGATCT         4800
    T  D  S  D  R  D  R  I  R  R  G  G  F  L  P  I

CGGACGACGAGGGCATGC
 S  D  D  E  G  M
```

Example 3

Recombinant PKS Genes for 13-desmethoxy FK-506 and FK-520

The present invention provides a variety of recombinant PKS genes in addition to those described in Examples 1 and 2 for producing 13-desmethoxy FK-506 and FK-520 compounds. This Example provides the construction protocols for recombinant FK-520 and FK-506 (from *Streptomyces* sp. MA6858 (ATCC 55098), described in U.S. Pat. No. 5,116,756, incorporated herein by reference) PKS genes in which the module 8 AT coding sequences have been replaced by either the rapAT3 (the AT domain from module 3 of the rapamycin PKS), rapAT12, eryAT1 (the AT domain from module I of the erythromycin (DEBS) PKS), or eryAT2 coding sequences. Each of these constructs provides a PKS that produces the 13-desmethoxy-13-methyl derivative, except for the rapAT12 replacement, which provides the 13-desmethoxy derivative, i.e., it has a hydrogen where the other derivatives have methyl.

FIG. 7 shows the process used to generate the AT replacement constructs. First, a fragment of ~4.5 kb containing module 8 coding sequences from the FK-520 cluster of ATCC 14891 was cloned using the convenient restriction sites SacI and SphI (Step A in FIG. 7). The choice of restriction sites used to clone a 4.0-4.5 kb fragment comprising module 8 coding sequences from other FK-520 or FK-506 clusters can be different depending on the DNA sequence, but the overall scheme is identical. The unique SacI and SphI restriction sites at the ends of the FK-520 module 8 fragment were then changed to unique Bgl II and NsiI sites by ligation to synthetic linkers (described in the preceding Examples, see Step B of FIG. 7). Fragments containing sequences 5' and 3' of the AT8 sequences were then amplified using primers, described above, that introduced either an AvrII site or an NheI site at two different KS/AT boundaries and an XhoI site at the AT/DH boundary (Step C of FIG. 7). Heterologous AT domains from the rapamycin and erythromycin gene clusters were amplified using primers, as described above, that introduced the same sites as just described (Step D of FIG. 7). The fragments were ligated to give hybrid modules with in-frame fusions at the KS/AT and AT/DH boundaries (Step E of FIG. 7). Finally, these hybrid modules were ligated into the BamHI and PstI sites of the KC515 vector. The resulting recombinant phage were used to transform the FK-506 and FK-520 producer strains to yield the desired recombinant cells, as described in the preceding Examples.

The following table shows the location and sequences surrounding the engineered site of each of the heterologous AT domains employed (SEQ ID NOS:34-63, in order of appearance). The FK-506 hybrid construct was used as a control for the FK-520 recombinant cells produced, and a similar FK-520 hybrid construct was used as a control for the FK-506 recombinant cells.

```
Hetero-
logous AT  Enzyme  Location of Engineered Site

FK-506     AvrII   GGCCGTccgcgcCGTGCGGCGGTCTCGTCGTTC
AT8                 G  R  P  R  R  A  A  V  S  S  F
(hydroxy-  NheI    ACCCAGCATCCCGCGATGGGTGAGCGgctcgcC
malonyl)            T  Q  H  P  A  M  G  E  R  L  A
           XhoI    TACGCCTTCCAGCGGCGGCCCTACTGGatCgag
                    Y  A  F  Q  R  R  P  Y  W  I  E rapamycin  AvrII   GACCGGccccgtCGGGCGGGCGTGTCGTCCTTC
AT3                 D  R  P  R  R  A  G  V  S  S  F
(methyl-   NheI    TGGCAGTGGCTGGGGATGGGCAGTGCcctgcgG
malonyl)            W  Q  W  L  G  M  G  S  A  L  R
           XhoI    TACGCCTTCCAACACCAGCGGTACTGGgtcgag
                    Y  A  F  Q  H  Q  R  Y  W  V  E rapamycin  AvrII   GGCCGAgcgcgcCGGGCAGGCGTGTCGTCCTTC
AT12                G  R  A  R  R  A  G  V  S  S  F
(malonyl)  NheI    TCGCAGCGTGCTGGCATGGGTGAGGAactgcC
                    S  Q  R  A  G  M  G  E  E  L  A
           XhoI    TACGCCTTCCAGCACCAGCGCTACTGGctcgag
                    Y  A  F  Q  H  Q  R  Y  W  L  E
```

-continued

| Hetero-logous AT | Enzyme | Location of Engineered Site |
|---|---|---|
| DEBS AT1 (methyl-malonyl) | AvrII | GCGCGAccgcgcCGGGCGGGGGTCTCGTCGTTC<br>A R P R R A G V S S F |
| | NheI | TGGCAGTGGGCGGGCATGGCCGTCGAcctgctC<br>W Q W A G M A V D L L |
| | XhoI | TACCCGTTCCAGCGCGAGCGCGTCTGGctcgaa<br>Y P F Q R E R V W L E |
| DEBS AT2 (methyl- | AvrII | GACGGGgtgcgcCGGGCAGGTGTGTCGGCGTTC<br>D G V R R A G V S A F |

-continued

| Hetero-logous AT | Enzyme | Location of Engineered Site |
|---|---|---|
| malonyl) | NheI | GCCCAGTGGGAAGGCATGGCGCGGGAgttgttG<br>A Q W E G M A R E L L |
| | XhoI | TATCCTTTCCAGGGCAAGCGGTTCTGGctgctg<br>Y P F Q G K R F W L L |

The sequences shown below provide the location of the KS/AT boundaries chosen in the FK-520 module 8 coding sequences. Regions where AvrII and NheI sites were engineered are indicated by lower case and underlining (SEQ ID NOS:64-65).

```
CCGGCGCCGTCGAACTGCTGACGTCGGCCCGGCCGTGGCCCGAGACCGACCGGccacggC
 A  G  A  V  E  L  L  T  S  A  R  P  W  P  E  T  D  R  P  R GTGCCGCCGTCTCCTCGTTCGGGGTGAGCGGCACCAACGCCCACGTCATCCTGGAGGCCG
 R  A  A  V  S  S  F  G  V  S  G  T  N  A  H  V  I  L  E  A GACCGGTAACGGAGACGCCCGCGGCATCGCCTTCCGGTGACCTTCCCCTGCTGGTGTCGG
 G  P  V  T  E  T  P  A  A  S  P  S  G  D  L  P  L  L  V  S CACGCTCACCGGAAGCGCTCGACGAGCAGATCCGCCGACTGCGCGCCTACCTGGACACCA
 A  R  S  P  E  A  L  D  E  Q  I  R  R  L  R  A  Y  L  D  T CCCCGGACGTCGACCGGGTGGCCGTGGCACAGACGCTGGCCCGGCGCACACACTTCGCCC
 T  P  D  V  D  R  V  A  V  A  Q  T  L  A  R  R  T  H  F  A ACCGCGCCGTGCTGCTCGGTGACACCGTCATCACCACACCCCCCGCGGACCGGCCCGACG
 H  R  A  V  L  L  G  D  T  V  I  T  T  P  P  A  D  R  P  D AACTCGTCTTCGTCTACTCCGGCCAGGGCACCCAGCATCCCGCGATGGGCGAGCAgctcg
 E  L  V  F  V  Y  S  G  Q  G  T  Q  H  P  A  M  G  E  Q  L cCGCCGCCCATCCCGTGTTCGCCGACGCCTGGCATGAAGCGCTCCGCCGCCTTGACAACC
 A  A  A  H  P  V  F  A  D  A  W  H  E  A  L  R  R  L  D  N
```

The sequences shown below provide the location of the AT/DH boundary chosen in the FK-520 module 8 coding sequences. The region where an XhoI site was engineered is indicated by lower case and underlining (SEQ ID NOS:66-67).

```
TCCTCGGGGCTGGGTCACGGCACGACGCGGATGTGCCCGCGTACGCGTTCCAACGGCGGC
 I  L  G  A  G  S  R  H  D  A  D  V  P  A  Y  A  F  Q  R  R

ACTACTGGatcgagTCGGCACGCCCGGCCGCATCCGACGCGGGCCACCCCGTGCTGGGCT
 H  Y  W  I  E  S  A  R  P  A  A  S  D  A  G  H  P  V  L  G
```

The sequences shown below provide the location of the KS/AT boundaries chosen in the FK-506 module 8 coding sequences. Regions where AvrII and NheI sites were engineered are indicated by lower case and underlining (SEQ ID NOS:68-69).

```
TCGGCCAGGCCGTGGCCGCGGACCGGCCGTccgcgcCGTGCGGCGGTCTCGTCGTTCGGG
 S   A   R   P   W   P   R   T   G   R   P   R   R   A   A   V   S   S   F   G GTGAGCGGCACCAACGCCCACATCATCCTGGAGGCCGGACCCGACCAGGAGGAGCCGTCG
 V   S   G   T   N   A   H   I   I   L   E   A   G   P   D   Q   E   E   P   S GCAGAACCGGCCGGTGACCTCCCGCTGCTCGTGTCGGCACGGTCCCCGGAGGCACTGGAC
 A   E   P   A   G   D   L   P   L   L   V   S   A   R   S   P   E   A   L   D GAGCAGATCGGGCGCCTGCGCGACTATCTCGAOGCCGCCCCCGGCGTGGACCTGGCGGCC
 E   Q   I   G   R   L   R   D   Y   L   D   A   A   P   G   V   D   L   A   A GTGGCGCGGACACTGGCCACGCGTACGCACTTCTCCCACCGCGCCGTACTGCTCGGTGAC
 V   A   R   T   L   A   T   R   T   H   F   S   H   R   A   V   L   L   G   D ACCGTCATCACCGCTCCCCCCGTGGAACAGCCGGGCGAGCTCGTCTTCGTCTACTCGGGA
 T   V   I   T   A   P   P   V   E   Q   P   G   E   L   V   F   V   Y   S   G CAGGGCACCCAGCATCCCGCGATGGGTGAGCGgctCgcCGCAGCCTTCCCCGTGTTCGCC
 Q   G   T   Q   H   P   A   M   G   E   R   L   A   A   A   F   P   V   F   A GACCCGGACGTACCCGCCTACGCCTTCCAGCGGCGGCCCTACTGGATCGAGTCCGCGCCG
 D   P   D   V   P   A   Y   A   F   Q   R   R   P   Y   W   I   E   S   A   P
```

The sequences shown below provide the location of the AT/DH boundary chosen in the FK-506 module 8 coding sequences. The region where an XhoI site was engineered is indicated by lower case and underlining (SEQ ID NOS:70-71).

```
GACCCGGACGTACCCGCCTACGCCTTCCAGCGGCGGCCCTACTGGatcgagTCCGCGCCG
 D   P   D   V   P   A   Y   A   F   Q   R   R   P   Y   W   I   E   S   A   P
```

Example 4

Replacement of Methoxyl with Hydrogen or Methyl at C-15 of FK-506 and FK-520

The methods and reagents of the present invention also provide novel FK-506 and FK-520 derivatives in which the methoxy group at C-15 is replaced by a hydrogen or methyl. These derivatives are produced in recombinant host cells of the invention that express recombinant PKS enzymes the produce the derivatives. These recombinant PKS enzymes are prepared in accordance with the methodology of Examples 1 and 2, with the exception that AT domain of module 7, instead of module 8, is replaced. Moreover, the present invention provides recombinant PKS enzymes in which the AT domains of both modules 7 and 8 have been changed. The table below summarizes the various compounds provided by the present invention.

| Compound | C-13 | C-15 | Derivative Provided |
|---|---|---|---|
| FK-506 | hydrogen | hydrogen | 13,15-didesmethoxy-FK-506 |
| FK-506 | hydrogen | methoxy | 13-desmethoxy-FK-506 |
| FK-506 | hydrogen | methyl | 13,15-didesmethoxy-15-methyl-FK-506 |
| FK-506 | methoxy | hydrogen | 15-desmethoxy-FK-506 |
| FK-506 | methoxy | methoxy | Original Compound -- FK-506 |
| FK-506 | methoxy | methyl | 15-desmethoxy-15-methyl-FK-506 |
| FK-506 | methyl | hydrogen | 13,15-didesmethoxy-13-methyl-FK-506 |
| FK-506 | methyl | methoxy | 13-desmethoxy-13-methyl-FK-506 |
| FK-506 | methyl | methyl | 13,15-didesmethoxy-13,15-dimethyl-FK-506 |
| FK-520 | hydrogen | hydrogen | 13,15-didesmethoxy FK-520 |
| FK-520 | hydrogen | methoxy | 13-desmethoxy FK-520 |
| FK-520 | hydrogen | methyl | 13,15-didesmethoxy-15-methyl-FK-520 |
| FK-520 | methoxy | hydrogen | 15-desmethoxy-FK-520 |
| FK-520 | methoxy | methoxy | Original Compound -- FK-520 |
| FK-520 | methoxy | methyl | 15-desmethoxy-15-methyl-FK-520 |
| FK-520 | methyl | hydrogen | 13,15-didesmethoxy-13-methyl-FK-520 |
| FK-520 | methyl | methoxy | 13-desmethoxy-13-methyl-FK-520 |
| FK-520 | methyl | methyl | 13,15-didesmethoxy-13,15-dimethyl-FK-520 |

Example 5

Replacement of Methoxyl with Ethyl at C-13 and/or C-15 of FK-506 and FK-520

The present invention also provides novel FK-506 and FK-520 derivative compounds in which the methoxy groups at either or both the C-13 and C-15 positions are instead ethyl groups. These compounds are produced by novel PKS enzymes of the invention in which the AT domains of modules 8 and/or 7 are converted to ethylmalonyl specific AT domains by modification of the PKS gene that encodes the module.

Ethylmalonyl specific AT domain coding sequences can be obtained from, for example, the FK-520 PKS genes, the niddamycin PKS genes, and the tylosin PKS genes. The novel PKS genes of the invention include not only those in which either or both of the AT domains of modules 7 and 8 have been converted to ethylmalonyl specific AT domains but also those in which one of the modules is converted to an ethylmalonyl specific AT domain and the other is converted to a malonyl specific or a methylmalonyl specific AT domain.

Example 6

Neurotrophic Compounds

The compounds described in Examples 1-4, inclusive have immunosuppressant activity and can be employed as immunosuppressants in a manner and in formulations similar to those employed for FK-506. The compounds of the invention are generally effective for the prevention of organ rejection in patients receiving organ transplants and in particular can be used for immunosuppression following orthotopic liver transplantation. These compounds also have pharmacokinetic properties and metabolism that are more advantageous for certain applications relative to those of FK-506 or FK-520. These compounds are also neurotrophic; however, for use as neurotrophins, it is desirable to modify the compounds to diminish or abolish their immunosuppressant activity. This can be readily accomplished by hydroxylating the compounds at the C-18 position using established chemical methodology or novel FK-520 PKS genes provided by the present invention.

Thus, in one aspect, the present invention provides a method for stimulating nerve growth that comprises administering a therapeutically effective dose of 18-hydroxy-FK-520. In another embodiment, the compound administered is a C-18,20-dihydroxy-FK-520 derivative. In another embodiment, the compound administered is a C-13-desmethoxy and/or C-15-desmethoxy 18-hydroxy-FK-520 derivative. In another embodiment, the compound administered is a C-13-desmethoxy and/or C-15-desmethoxy 18,20-dihydroxy-FK-520 derivative. In other embodiments, the compounds are the corresponding analogs of FK-506. The 18-hydroxy compounds of the invention can be prepared chemically, as described in U.S. Pat. No. 5,189,042, incorporated herein by reference, or by fermentation of a recombinant host cell provided by the present invention that expresses a recombinant PKS in which the module 5 DH domain has been deleted or rendered non-functional.

The chemical methodology is as follows. A compound of the invention (~200 mg) is dissolved in 3 mL of dry methylene chloride and added to 45 µL of 2,6-lutidine, and the mixture stirred at room temperature. After 10 minutes, tert-butyldimethylsilyl trifluoromethanesulfonate (64 µL) is added by syringe. After 15 minutes, the reaction mixture is diluted with ethyl acetate, washed with saturated bicarbonate, washed with brine, and the organic phase dried over magnesium sulfate. Removal of solvent in vacuo and flash chromatography on silica gel (ethyl acetate:hexane (1:2) plus 1% methanol) gives the protected compound, which is dissolved in 95% ethanol (2.2 mL) and to which is added 53 µL of pyridine, followed by selenium dioxide (58 mg). The flask is fitted with a water condenser and heated to 70° C. on a mantle. After 20 hours, the mixture is cooled to room temperature, filtered through diatomaceous earth, and the filtrate poured into a saturated sodium bicarbonate solution. This is extracted with ethyl acetate, and the organic phase is washed with brine and dried over magnesium sulfate. The solution is concentrated and purified by flash chromatography on silica gel (ethyl acetate:hexane (1:2) plus 1% methanol) to give the protected 18-hydroxy compound. This compound is dissolved in acetonitrile and treated with aqueous HF to remove the protecting groups. After dilution with ethyl acetate, the mixture is washed with saturated bicarbonate and brine, dried over magnesium sulfate, filtered, and evaporated to yield the 18-hydroxy compound. Thus, the present invention provides the C-18-hydroxyl derivatives of the compounds described in Examples 1-4.

Those of skill in the art will recognize that other suitable chemical procedures can be used to prepare the novel 18-hydroxy compounds of the invention. See, e.g., Kawai et al., January 1993, Structure-activity profiles of macrolactam immunosuppressant FK-506 analogues, *FEBS Letters* 316 (2): 107-113, incorporated herein by reference. These methods can be used to prepare both the C18-[S]-OH and C18-[R]-OH enantiomers, with the R enantiomer showing a somewhat lower $IC_{50}$, which may be preferred in some applications. See Kawai et al., supra. Another preferred protocol is described in Umbreit and Sharpless, 1977, JACS 99(16): 1526-28, although it may be preferable to use 30 equivalents each of $SeO_2$ and t-BuOOH rather than the 0.02 and 3-4 equivalents, respectively, described in that reference.

All scientific and patent publications referenced herein are hereby incorporated by reference. The invention having now been described by way of written description and example, those of skill in the art will recognize that the invention can be practiced in a variety of embodiments, that the foregoing description and example is for purposes of illustration and not limitation of the following claims.

The invention claimed is:

1. An isolated nucleic acid comprising a nucleotide sequence encoding the CoA ligase domain of the loading module of an fkbB polypeptide, wherein the CoA ligase-encoding nucleotide sequence is selected from the group consisting of (a) the complement of the sequence of nucleotides 44974-46573 of SEQ ID NO:1 and (b) a nucleotide sequence encoding the amino acid sequence identical to that encoded by the sequence complementary to the sequence of nucleotides 44974-46573 of SEQ ID NO:1.

2. The isolated nucleic acid of claim 1, wherein said nucleic acid further comprises a coding sequence complementary to a sequence selected from the group consisting of;

nucleotides 43777-44629 of SEQ ID NO:1;
nucleotides 43144-43660 of SEQ ID NO:1; nucleotides 41842-43093 of SEQ ID NO:1;
nucleotides 40609-41842 of SEQ ID NO:1; nucleotides 39442-40609 of SEQ ID NO:1;
nucleotides 38677-39307 of SEQ ID NO:1; nucleotides 38371-38581 of SEQ ID NO:1;
nucleotides 37145-38296 of SEQ ID NO:1; nucleotides 35749-37144 of SEQ ID NO:1;
nucleotides 34606-35749 of SEQ ID NO:1; nucleotides 33823-34480 of SEQ ID NO:1;
nucleotides 33505-33715 of SEQ ID NO:1; nucleotides 32185-33439 of SEQ ID NO:1;
nucleotides 31018-32185 of SEQ ID NO:1; nucleotides 29869-31018 of SEQ ID NO:1;
nucleotides 29092-29740 of SEQ ID NO:1; nucleotides 28750-28960 of SEQ ID NO:1;
nucleotides 27430-28684 of SEQ ID NO:1; nucleotides 26146-27430 of SEQ ID NO:1;
nucleotides 24997-26146 of SEQ ID NO:1; nucleotides 24163-24373 of SEQ ID NO:1;
and a sequence that encodes the amino acid sequence identical to that encoded by any of the foregoing sequences.

3. The isolated nucleic acid of claim 1, wherein the nucleotide sequence further encodes an extender module, said module comprising a ketosynthase domain, an acyl transferase domain, and an acyl carrier protein domain.

4. The isolated nucleic acid of claim 3, wherein at least one of the ketosynthase domain, the acyl transferase domain or the acyl carrier protein domain is a domain of a module of a non-FK-520 polyketide synthase.

5. The isolated nucleic acid of claim 4, wherein said non-FK-520 polyketide synthase is rapamycin polyketide synthase, FK-506 polyketide synthase, or erythromycin polyketide synthase.

6. The isolated nucleic acid of claim 1, wherein the nucleotide sequence further encodes an open reading frame, said open reading frame comprising coding sequences for two or more extender modules, each extender module comprising a ketosynthase domain, an acyl transferase domain, and an acyl carrier protein domain.

7. The isolated nucleic acid of claim 1, wherein the nucleotide sequence is a gene cluster, said gene cluster comprising two or more open reading frames, each of said open reading frames comprising coding sequences for two or more extender modules, each of said extender modules comprising a ketosynthase domain, an acyl transferase domain, and an acyl carrier protein domain.

8. The isolated nucleic acid of claim 1, wherein the nucleic acid further encodes at least one further loading module domain selected from the group of the CoA ligase, the enoyl-reductase (ER) domain, and the acyl carrier protein (ACP) domain.

9. The isolated nucleic acid of claim 1, wherein said nucleic acid is contained in a recombinant vector capable of replication in or integration into the chromosome of a host cell.

10. The isolated nucleic acid of claim 9, that is selected from the group consisting of cosmid pKOS034-120(ATCC Deposit No. PTA-728) and cosmid pKOS034-124 (ATCC Deposit No. PTA-729).

11. A recombinant DNA vector capable of homologous recombination with the FK-520 polyketide synthase gene in a Streptomyces host cell that produces FK-520, wherein said vector comprises a nucleic acid sequence encoding at least the CoA ligase domain of the loading module of the fkbB polypeptide, wherein the amino acid sequence of the fkbB polypeptide is set forth as SEQ ID NO:73.

12. The recombinant vector of claim 11, wherein the nucleic acid sequence further encodes at least one domain selected from the group consisting of the ER domain of the loading module, the ACP domain of the loading module, the KS domain of the first extender module, the AT domain of the first extender module, the DH domain of the first extender module, the KR domain of the first extender module, the ACP domain of the first extender module, the KS domain of the second extender module, the AT domain of the second extender module, the DH domain of the second extender module, the ER domain of the second extender module, the ACP domain of the second extender module, the KS domain of the third extender module, the AT domain of the third extender module, the DH domain of the third extender module, the KR domain of the third extender module, the ACP domain of the third extender module, the KS domain of the fourth extender module, the AT domain of the fourth extender module, the DH domain of the fourth extender module, and ACP domain of the fourth extender module.

13. The recombinant vector of claim 11, wherein the nucleic acid sequence encodes at least one domain of an extender module of the fkbB polypeptide and at least one domain of a non-FK-520 polyketide synthase.

14. The recombinant vector of claim 13, wherein the non-FK-520 polyketide synthase is rapamycin polyketide synthase, FK-506 polyketide synthase, or erythromycin polyketide synthase.

15. The recombinant vector of claim 13, wherein the non-FK-520 synthase domain is the AT domain of extender module 3, 12, or 13 of the rapamycin polyketide synthase.

16. The recombinant vector of claim 13, wherein the non-FK-520 synthase domain is the AT domain of extender module 1 or 2 of the erythromycin polyketide synthase.

17. A method of preparing a polyketide, said method comprising transforming a host cell with the recombinant DNA vector defined in claim 11, and culturing said host cell under conditions such that a polyketide synthase is produced and catalyzes the synthesis of said polyketide.

18. The method of claim 17, wherein said host cell is a *Streptomyces* host cell.

19. A recombinant host cell that expresses a modular recombinant polyketide synthase comprising the CoA ligase domain of the loading module of the fkbB polypeptide either encoded by a nucleotide sequence complementary to the nucleotide sequence of SEQ ID NO:1, or encoded by a nucleic acid sequence encoding an amino acid sequence identical to that encoded by the complement of nucleotides 44974-46573 of SEQ ID NO:1, said modular polyketide synthase further comprising either or both of: (i) a FK-520 polyketide synthase in which at least one acyl transferase (AT) domain of the fkbB polypeptide is replaced by an AT domain of a non-FK-520 modular polyketide synthase; and (ii) a FK-520 polyketide synthase in which at least one dehydratase (DH) domain of the fkbB polypeptide has been deleted, wherein the amino acid sequence of the fkbB polypeptide is set forth as SEQ ID NO:73.

* * * * *